United States Patent
Nelson et al.

(10) Patent No.: US 9,278,911 B2
(45) Date of Patent: Mar. 8, 2016

(54) 4-DEDIMETHYLAMINO TETRACYCLINE COMPOUNDS

(71) Applicant: Paratek Pharmaceuticals, Inc., Boston, MA (US)

(72) Inventors: Mark L. Nelson, Norfolk, MA (US); Kwasi Ohemeng, West Haven, CT (US)

(73) Assignee: Paratek Pharmaceuticals, Inc., Boston, MA (US)

(*) Notice: Subject to any disclaimer, the term of this patent is extended or adjusted under 35 U.S.C. 154(b) by 0 days.

(21) Appl. No.: 14/176,923

(22) Filed: Feb. 10, 2014

(65) Prior Publication Data

US 2015/0105355 A1    Apr. 16, 2015

Related U.S. Application Data

(63) Continuation of application No. 11/283,571, filed on Nov. 18, 2005, now abandoned, which is a continuation of application No. 10/337,914, filed on Jan. 6, 2003, now Pat. No. 7,056,902.

(60) Provisional application No. 60/367,049, filed on Mar. 21, 2002, provisional application No. 60/346,930, filed on Jan. 8, 2002, provisional application No. 60/346,929, filed on Jan. 8, 2002, provisional application No. 60/347,065, filed on Jan. 8, 2002, provisional application No. 60/346,956, filed on Jan. 8, 2002.

(51) Int. Cl.
| | | |
|---|---|---|
| *A61K 31/65* | (2006.01) | |
| *C07C 237/26* | (2006.01) | |
| *C07C 235/70* | (2006.01) | |
| *C07C 251/48* | (2006.01) | |
| *C07C 255/41* | (2006.01) | |
| *C07C 271/22* | (2006.01) | |
| *C07C 271/54* | (2006.01) | |
| *C07C 271/58* | (2006.01) | |
| *C07C 275/42* | (2006.01) | |
| *C07C 275/54* | (2006.01) | |
| *C07C 279/18* | (2006.01) | |
| *C07C 311/06* | (2006.01) | |
| *C07C 311/08* | (2006.01) | |
| *C07C 333/08* | (2006.01) | |
| *C07C 335/22* | (2006.01) | |
| *C07C 381/10* | (2006.01) | |
| *C07D 295/155* | (2006.01) | |
| *C07D 295/185* | (2006.01) | |
| *C07D 317/60* | (2006.01) | |
| *C07F 9/24* | (2006.01) | |
| *C07F 9/40* | (2006.01) | |

(52) U.S. Cl.
CPC .............. *C07C 237/26* (2013.01); *C07C 235/70* (2013.01); *C07C 251/48* (2013.01); *C07C 255/41* (2013.01); *C07C 271/22* (2013.01); *C07C 271/54* (2013.01); *C07C 271/58* (2013.01); *C07C 275/42* (2013.01); *C07C 275/54* (2013.01); *C07C 279/18* (2013.01); *C07C 311/06* (2013.01); *C07C 311/08* (2013.01); *C07C 333/08* (2013.01); *C07C 335/22* (2013.01); *C07C 381/10* (2013.01); *C07D 295/155* (2013.01); *C07D 295/185* (2013.01); *C07D 317/60* (2013.01); *C07F 9/2475* (2013.01); *C07F 9/4006* (2013.01); *C07C 2101/08* (2013.01); *C07C 2101/10* (2013.01); *C07C 2101/16* (2013.01); *C07C 2103/46* (2013.01)

(58) Field of Classification Search
CPC ....................................................... A61K 31/65
USPC ......................................................... 514/152
See application file for complete search history.

(56) References Cited

PUBLICATIONS

Alarcon, "Tetracyclines for the Treatment of Rheumatoid Arthritis", Exp. Opin. Invest. Drugs, vol. 9(7), 1491-1498, 2000.*
Langevitz et al., "Benefits and Risks of Minocycline in Rheumatoid Arthritis", Drug Safety, vol. 22(5), 405-414, 2000.*

* cited by examiner

*Primary Examiner* — Barbara P Badio
(74) *Attorney, Agent, or Firm* — McCarter & English, LLP; Elizabeth A. Hanley

(57) ABSTRACT

The present invention pertains, at least in part, to novel substituted 4-dedimethylamino tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

14 Claims, No Drawings

4-DEDIMETHYLAMINO TETRACYCLINE COMPOUNDS

RELATED APPLICATIONS

This application is a continuation of U.S. patent application Ser. No. 11/283,571, filed on Nov. 18, 2005; which is a continuation of U.S. patent application Ser. No. 10/337,914, filed on Jan. 6, 2003, now U.S. Pat. No. 7,056,902, issued on Jun. 6, 2006; which claims the benefit of U.S. Provisional Patent Application No. 60/367,049, filed on Mar. 21, 2002; U.S. Provisional Patent Application Ser. No. 60/346,930, filed on Jan. 8, 2002; U.S. Provisional Patent Application Ser. No. 60/346,929, filed on Jan. 8, 2002; U.S. Provisional Patent Application Ser. No. 60/347,065, filed on Jan. 8, 2002; and U.S. Provisional Patent Application Ser. No. 60/346,956, filed on Jan. 8, 2002. The entire contents of each of these applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454, 697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

The invention pertains, at least in part, to 7-substituted 4-dedimethylamino tetracycline compound of Formula I:

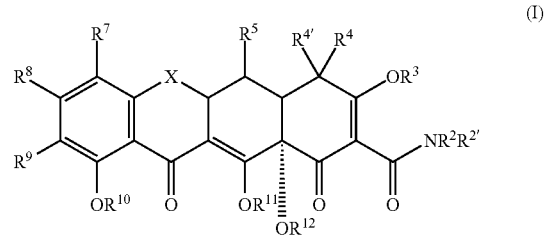

wherein:

X is CHC($R^{13}$Y'Y), CR$^6$'R$^6$, C=CR$^6$'R$^6$, S, NR$^6$, or O;

$R^2$ and $R^{2'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each independently alkyl, alkenyl, alkynyl, hydroxyl, halogen, hydrogen, or when taken together the oxygen of a carbonyl group;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkyl sulfonyl, alkylamino, or an arylalkyl;

$R^7$ is hydrogen, nitro, alkyl, alkenyl, alkynyl, aryl, heterocyclic, alkoxy, alkylthio, alkylsulfinyl, alkylsulfonyl, arylalkyl, amino, amido, arylalkenyl, arylalkynyl, or —$(CH_2)_{0-3}$NR$^{7c}$C(=W')WR$^{7a}$;

$R^9$ is hydrogen, nitro, alkyl, alkenyl, alkynyl, aryl, alkoxy, alkylthio, alkylsulfinyl, alkylsulfonyl, arylalkyl, amino, amido, arylalkenyl, arylalkynyl, thionitroso (e.g., —N=S), or —$(CH_2)_{0-3}$NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains to 7-substituted 4-dedimethylamino sancycline compounds of the formula:

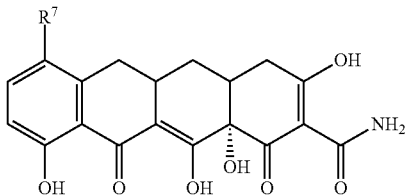

(II)

wherein:
$R^7$ is a fused ring moiety of the formula

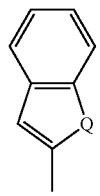

where Q is C or a heteroatom; an acylfuranyl group; a tri-, tetra- or penta-halo substituted phenyl group; an aminomethylphenyl group; an acylaminomethyl group; an alkylesterphenyl group; an acylphenyl group; an acylalkynyl group; an acylalkoxyphenyl group; a methylphenyl group; a dimethylphenyl group; a carboxyphenyl group; a carboxyalkynyl group; a thiophene group; a halothiophene group; an alkoxycarbonylphenyl group; an alkoxyphenyl group; an alkoxyphenylalkynyl group; an alkoxypyridyl group; an alkylenepyridine group; a cyclopentyl or cyclopentenyl group; a cyclohexylalkynyl group; a cyclohexenylalkynyl group; a cyclohexenylhaloalkenyl group; a hydroxycyclohexylalkynyl group; a phenylalkynyl group; a phenylalkenyl group; an aminoalkynyl group; a cyclobutylalkenyl group; a pyridylalkynyl group; a pyridylalkenyl group; a nitrophenylalkynyl group; a nitrophenylalkenyl group; a cyanoalkynyl group; an alkynyl group; a cyanoalkenyl group; a cyanophenyl group; a dialkylamidoalkenyl group; a dialkylamidophenyl group; an aminophenylethyl group; an aminophenylethynyl group; a haloethenyl group; a halophenylalkynyl group; or an alkylester-substituted pentenyl group; and pharmaceutically acceptable salts thereof.

In an embodiment, the invention pertains to 7,9-substituted 4-dedimethylamino tetracycline compounds of Formula III:

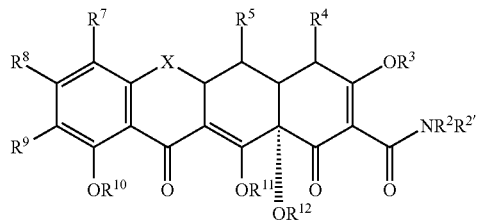

(III)

wherein:
X is $CHC(R^{13}Y'Y)$, $CR^{6'}R^6$, S, $NR^6$, or O;
$R^2$ and $R^{2'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each independently alkyl, alkenyl, alkynyl, hydroxyl, halogen, hydrogen, or when taken together the oxygen of a carbonyl group;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is nitro, alkyl, alkenyl, alkynyl, aryl, alkoxy, alkylthio, alkylsulfinyl, alkylsulfonyl, arylalkyl, amino, arylalkenyl, arylalkynyl, or $-(CH_2)_{0-3}NR^{7c}C(=W')WR^{7a}$;
$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;
Z is $CR^{9d}R^{9e}$, S, $NR^{9b}$ or O;
Z' is O, S, or $NR^{9f}$;
W is $CR^{7d}R^{7e}$, S, $NR^{7b}$ or O;
W' is O, $NR^{7f}$S;
$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The invention pertains, at least in part, to 4-dedimethylamino tetracycline compounds of formula IV:

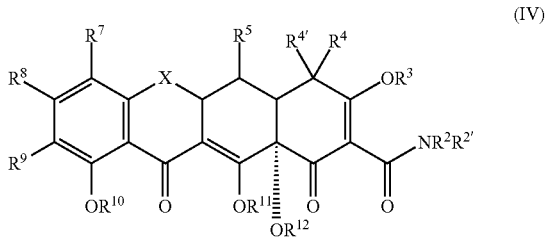

(IV)

wherein:
X is $CHC(R^{13}Y'Y)$, $CR^{6'}R^6$, S, $NR^6$, or O;
$R^2$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ and $R^{4'}$ are each independently alkyl, alkenyl, alkynyl, aryl, hydroxyl, alkoxy halogen, hydrogen, or taken together to form the oxygen of a carbonyl;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is $NR^{7'}R^{7''}$, alkyl, alkenyl, alkynyl, aryl, hydroxyl, halogen, or hydrogen;

$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}NR^{9c}C(=Z')ZR^{9a}$;

Z is $CR^{9d}R^{9e}$, S, $NR^{9b}$ or O;

Z' is $NR^{9f}$, O or S;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The invention also pertains, at least in part, to 9-substituted 4-dedimethylamino tetracycline compounds of the formula (V):

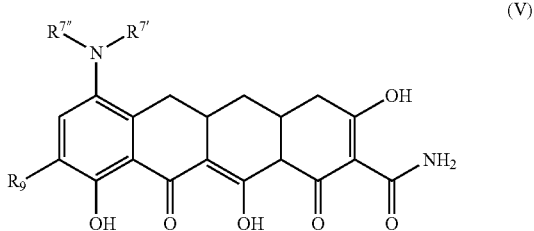

(V)

wherein:

$R^{7'}$ and $R^{7''}$ are each alkyl; and $R^9$ is a pyridylethynyl group; an alkenylcarbamate group; a halo group; an alkylacrylate group; a naphthyl group; a haloacetyl group; an alkyl carbamate group; a cyclopentyl or cyclopentenyl group; a benzofuranyl group; a phenylpropiononeamino group; a tosylamino group; a methoxypyridyl group; an alkeneamino group; an N-t-butyl group; a t-butylamide group; a hydroxybutylimino group; a hydroxypropylamino group; a phenyl group; a nitrophenyl group; a nitrophenyl alkynyl group; an aminophenyl group; an alkoxyphenyl group; a halophenyl urea group; a cyanophenyl group; a carboxyphenyl group; an acylphenyl group; an alkylphenyl group; a halophenyl group; an alkoxyphenyl group; a carboxyalkylphenyl group; a phenylalkynyl group; an alkynyl group; an alkylglycineethylester group; a styrene group; a thiophene group; and an alkylaminophospho group; and pharmaceutically acceptable salts, esters and prodrugs thereof.

In another embodiment, the invention pertains to 13-substituted tetracycline compounds of the formula (VI):

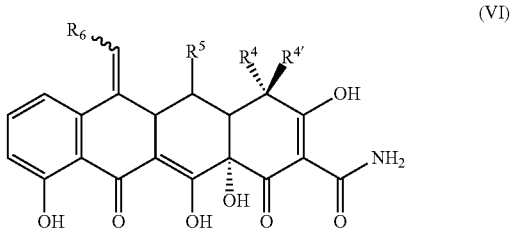

(VI)

wherein:

$R^4$ and $R^{4'}$ are each independently alkyl, alkenyl, alkynyl, hydroxyl, halogen, hydrogen, or when taken together the oxygen of a carbonyl group;

$R^5$ is hydrogen, hydroxyl, or a prodrug moiety;

$R^6$ is an alkyl or an aryl group, and pharmaceutically acceptable salts, esters, and prodrugs thereof.

In a further embodiment, $R^6$ is a phenyl group, i.e., an alkoxyphenyl group, a halophenyl group, a carboxyphenyl group, an acylphenyl group, a cyanophenyl group, a nitrophenyl group, a naphthyl group, a dialkylphenyl group, or an alkylphenyl group; a t-butyl group; or an aminoalkanethio group.

In another embodiment, the invention pertains, at least in part, to 8-substituted 4-dedimethylamino tetracycline compound of Formula VII:

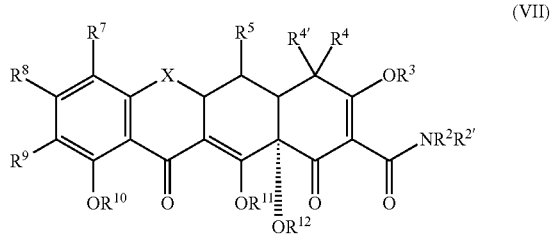

(VII)

wherein:

X is $CHC(R^{13}Y'Y)$, $CR^{6'}R^6$, $C=CR^{6'}R^6$, S, $NR^6$, or O;

$R^2$ and $R^{2'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each independently alkyl, alkenyl, alkynyl, hydroxyl, halogen, hydrogen, or when taken together the oxygen of a carbonyl group;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is nitro, alkyl, alkenyl, alkynyl, aryl, alkoxy, alkylthio, alkylsulfonyl, arylalkyl, amino, arylalkenyl, arylalkynyl, or —$(CH_2)_{0-3}NR^{7c}C(=W')WR^{7a}$;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., —N=S), or —(CH$_2$)$_{0-3}$ NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$S;

R$^{7a}$, R$^{7b}$, R$^{7c}$, R$^{7d}$, R$^{7e}$, R$^{9a}$, R$^{9b}$, R$^{9c}$, R$^{9d}$ and R$^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, prodrugs and esters thereof.

In another embodiment, the invention pertains, at least in part, to 8-substituted 4-dedimethylamino tetracycline compounds of the formula:

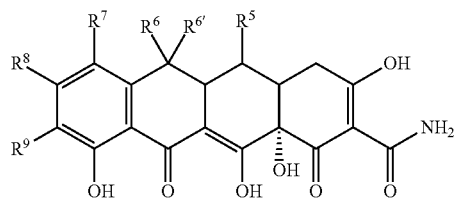

(VIII)

wherein:

R$^5$ is hydrogen or hydroxyl;

R$^6$ and R$^{6'}$ are each independently hydrogen, methyl, or hydroxyl;

R$^7$ is hydrogen,

R$^8$ is phenyl, nitrophenyl, halo, or lower alkynyl; and

R$^9$ is hydrogen or amino, and pharmaceutically acceptable salts, prodrugs and esters thereof.

The invention also pertains to a method for treating a tetracycline responsive state in a subject, by administering to the subject a 4-dedimethylamino tetracycline compound of the invention (e.g., of Formula I, II, III, IV, V, VI, VII, VIII or Table 2), such that the tetracycline responsive state is treated. In an embodiment, the tetracycline responsive state is not a bacterial infection.

The invention also includes pharmaceutical compositions comprising an effective amount of a 4-dedimethylamino tetracycline compound of the invention (e.g., of Formula I, II, III, IV, V, VI, VII, VIII or Table 2), and, optionally, a pharmaceutically acceptable carrier.

DETAILED DESCRIPTION OF THE INVENTION

The present invention pertains, at least in part, to novel 4-dedimethylamino tetracycline compounds. These tetracycline compounds can be used to treat numerous tetracycline compound-responsive states, such as, but not limited to, bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline. Other derivatives and analogues comprising a similar four ring structure are also included. The term also includes 4-dedimethylamino tetracycline compounds. Table 1 depicts tetracycline and several known tetracycline derivatives.

TABLE I

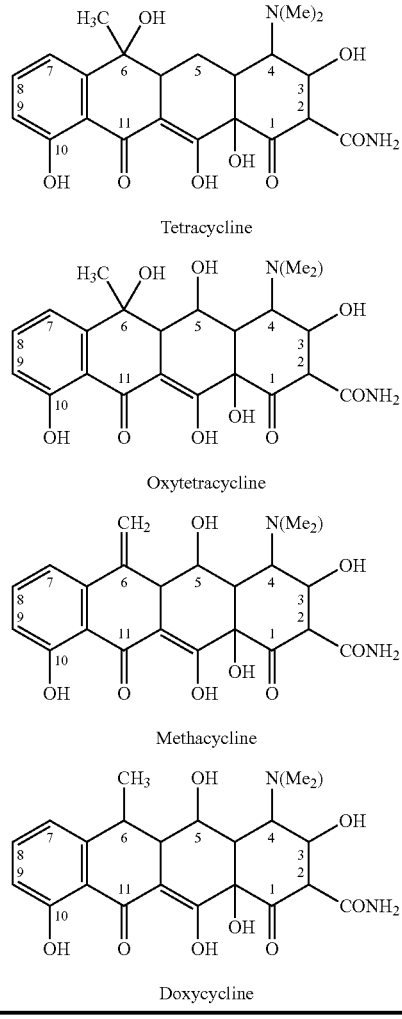

I. 7-Substituted 4-Dedimethylamino Tetracycline Compounds

The term "7-substituted 4-dedimethylamino tetracycline compounds" includes tetracycline compounds with substitution at the 7 position. In one embodiment, the substitution at the 7-position enhances the ability of the tetracycline compound to perform its intended function, e.g., treat tetracycline responsive states. In an embodiment, the 7-substituted tetracycline compound is 7-substituted 4-dedimethylamino tetracycline (e.g., wherein R$^4$ and R$^{4'}$ are hydrogen, R$^5$ is hydrogen and X is CR$^6$R$^{6'}$, wherein R$^6$ is methyl and R$^{6'}$ is hydroxy); 7-substituted 4-dedimethylamino doxycycline (e.g., wherein R$^4$ and R$^{4'}$ are hydrogen, R$^5$ is hydroxyl and X is CR$^6$R$^{6'}$, wherein R⁶ is methyl and R⁶' is hydrogen); 7-substituted dedimethylamino tetracycline compounds, wherein X is CR⁶R⁶', R⁴, R⁴', R⁵, R⁶', and R⁶ are hydrogen; or 7-substituted 4-dedimethylamino sancycline (wherein R⁴ and R⁴' are hydrogen; R⁵ is hydrogen and X is CR⁶R⁶' wherein R⁶ and R⁶' are hydrogen atoms.

The invention pertains, at least in part, to 7-substituted 4-dedimethylamino tetracycline compound of Formula I:

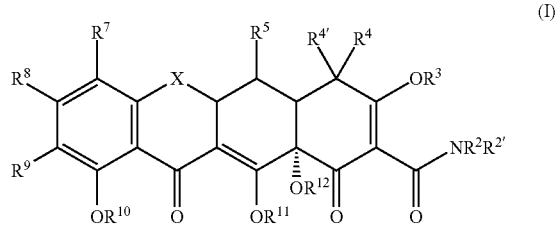

wherein:

X is CHC(R¹³Y'Y), CR⁶R⁶', C=CR⁶'R⁶, S, NR⁶, or O;

R² and R²' are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R⁴ and R⁴' are each independently alkyl, alkenyl, alkynyl, hydroxyl, halogen, hydrogen, or when taken together the oxygen of a carbonyl group;

R²', R³, R¹⁰, R¹¹ and R¹² are each hydrogen or a pro-drug moiety;

R⁵ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R⁷ is hydrogen, nitro, alkyl, alkenyl, alkynyl, aryl, heterocyclic, alkoxy, alkylthio, alkylsulfinyl, alkylsulfonyl, arylalkyl, amino, amido, arylalkenyl, arylalkynyl, or —(CH₂)₀₋₃NR⁷ᶜC(=W')WR⁷ᵃ;

R⁹ is hydrogen, nitro, alkyl, alkenyl, alkynyl, aryl, alkoxy, alkylthio, alkylsulfinyl, alkylsulfonyl, arylalkyl, amino, amido, arylalkenyl, arylalkynyl, thionitroso (e.g., —N=S), or —(CH₂)₀₋₃NR⁹ᶜC(=Z')ZR⁹ᵃ;

Z is CR⁹ᵈR⁹ᵉ, S, NR⁹ᵇ or O;

Z' is O, S, or NR⁹ᶠ;

W is CR⁷ᵈR⁷ᵉ, S, NR⁷ᵇ or O;

W' is O, NR⁷ᶠS;

R⁷ᵃ, R⁷ᵇ, R⁷ᶜ, R⁷ᵈ, R⁷ᵉ, R⁹ᵃ, R⁹ᵇ, R⁹ᶜ, R⁹ᵈ, and R⁹ᵉ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R⁸ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R¹³ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In certain embodiment, R⁷ is not nitro or amino.

In an embodiment, X is CR⁶R⁶'; R², R²', R⁶, R⁶', R⁹, R¹⁰, R¹¹, and R¹² are each hydrogen; R⁴ and R⁴' are hydrogen, halogen (e.g., chlorine, fluorine, bromine, iodine, etc.), hydroxy, or when taken together the oxygen of a carbonyl group; and R⁵ is hydroxy or hydrogen.

In an embodiment, R⁷ is aryl. Examples of aryl R⁷ groups include substituted or unsubstituted phenyl. The phenyl R⁷ group can be substituted with any substituent which allow the tetracycline compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the phenyl R⁷ group is substituted with substituted or unsubstituted alkyl. Examples of substituents of the alkyl include heterocycles such as, morpholine, piperidine, and pyrrolidine. In another further embodiment, the phenyl R⁷ group is substituted with an amino group. The amino group also may be further substituted e.g., with an alkyl, alkenyl, alkynyl, carbonyl, alkoxy or aryl (e.g., substituted or unsubstituted, heteroaryl, phenyl, etc.) group. The phenyl amino substituent may be substituted with any substituent or combination of substituents which allow it to perform its intended function. Examples of such substituents include halogens (e.g., fluorine, chlorine, bromine, iodine, etc.), amino (e.g., which can in turn be substituted with an alkyl, carbonyl, alkenyl, alkynyl, or aryl moiety), and arylamino (e.g., phenylamino).

The R⁷ phenyl group may also be substituted with alkoxy groups. Examples of alkoxy groups include, but are not limited to, methoxy, ethoxy, propoxy, butoxy, perfluoromethoxy, perchloromethoxy, methylenedioxy, etc. The phenyl group may also be substituted with an amide group such as a carbamate moiety (e.g., an alkoxycarbonylamino group).

The aryl R⁷ group also may be substituted or unsubstituted biaryl, e.g., naphthyl, fluorenyl, etc. The biaryl R⁷ group can be substituted with any substituent which allow it to perform its intended function. Examples of substituents include but are not limited to, alkyl, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, the substituent is amino or formyl.

The aryl R⁷ group also may be heteroaryl. Examples of heteroaryl R⁷ moieties include, but are not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In certain embodiments, the heteroaryl $R^7$ group is thiazolyl, thiophenyl, or furanyl.

$R^7$ also may be substituted or unsubstituted alkyl. The alkyl group can be a straight or branched chain, e.g., methyl, ethyl, i-propyl, n-propyl, n-butyl, i-butyl, t-butyl, pentyl, hexyl. etc. The alkyl group may also comprise a ring, e.g., a cycloalkyl (e.g., cyclopentyl, cyclohexyl, cyclopropyl, or cyclobutyl). The alkyl $R^7$ group may be substituted with any substituent or combination of substituents which allows the compound to perform its intended function. Examples of substituents include, but are not limited to, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In certain embodiments, the alkyl group is substituted with an amino, hydroxy, carboxy, carbonyl (e.g., substituted carbonyl, e.g., morpholinyl carbonyl), heterocyclic or aryl groups. Examples heterocyclic groups include, for example, furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, and deazapurinyl. In a further embodiment, the aryl group is pyridinyl.

In a further embodiment, the aralkyl $R^7$ group comprises substituted or unsubstituted phenyl. This phenyl group also may be substituted with any substituent which allows it to perform its intended function. Examples of substituents include, but are not limited to, sulfonamido, alkyl, and the other substituents listed supra for alkyl $R^7$ groups.

$R^7$ also may be substituted or unsubstituted alkenyl. Examples of substituents include those which allow the compound to perform its intended function. Examples of substituents include but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In a further embodiment, the alkenyl $R^7$ group is substituted with an aminocarbonyl (e.g., alkylaminocarbonyl, dialkylaminocarbonyl, dimethylaminocarbonyl) or alkoxycarbonyl. The alkenyl $R^7$ group also may be substituted with one or more halogens (e.g., fluorine, chlorine, bromine, iodine, etc.), hydroxy groups, heteroaryl groups (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, deazapurinyl, etc.). In an embodiment, the heteroaryl substituent s thiazolyl.

In a further embodiment, the alkenyl $R^7$ group is substituted with a substituted or unsubstituted phenyl. The phenyl can be substituted with any substituent which allows it to perform its intended function. Examples of substituents include those listed supra for other phenyl moieties. Other examples of substituents include, but are not limited to, halogens (e.g., fluorine, chlorine, bromine, iodine, etc.), alkoxy (e.g., methoxy, ethoxy, propoxy, perfluoromethyl, perchloromethyl, etc.), hydroxy, or alkyl (e.g., methyl, ethyl, propyl, butyl, pentyl, hexyl, etc.) groups.

Another example of $R^7$ include substituted and unsubstituted alkynyls. The alkynyl moieties can be substituted with any substituent or combination of substituents which allow the tetracycline compound of the invention to perform its intended function. Examples of the substituents include, but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In an embodiment, the alkynyl $R^7$ moiety is substituted with an aryl, e.g., substituted or unsubstituted heteroaryl, phenyl, etc. This aryl moiety may be substituted with any substituent or combinations of substituents listed supra for the alkynyl $R^7$ moiety. Examples of advantageous substituents include, but are not limited to, carbonylamino (e.g., alkylcarbonylamino, dialkylcarbonylamino, arylcarbonylamino, etc.) and sulphonamido groups.

In another embodiment, the alkynyl $R^7$ group is substituted with a tetracycline moiety. The term "tetracycline moiety" includes a four ring tetracycline ring system as described above. This may be connected to the alkynyl $R^7$ group through a linker of 1-20 atoms. The linker may be attached to the tetracycline moiety at any position on that ring system which is convenient or allows the compound to perform its intended function. In a certain embodiment, the tetracycline moiety is attached to the linker at its 7 position.

Other examples of $R^7$ moieties include substituted and unsubstituted alkylcarbonyl amino, sulfonamido, imino and carbonyl moieties. The carbonyl moieties may be substituted with a substituted or unsubstituted alkyl group. Examples of possible substituents of the alkyl group include, but are not limited to, aryl moieties such as phenyl and heteroaryls (e.g., pyridinyl, etc.). Examples of substituents of the imino group include, but are not limited to, hydroxy and alkoxy groups.

In another embodiment, $R^7$ is $NR^{7c}(C{=}W')WR^{7a}$. Examples of tetracycline compounds of the invention include compounds wherein $R^{7c}$ is hydrogen, W' is oxygen and W is oxygen. In certain embodiments, $R^{7a}$ is substituted or unsubstituted phenyl. Examples of substituents include, but are not limited to, alkyl, halogen, hydroxyl, alkoxy, alkylcarbonyloxy, alkyloxycarbonyl, carboxy, alkylcarbonylamino, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano; amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In a further embodiment, $R^{7a}$ is substituted or unsubstituted alkyl.

The invention also pertains to 7-substituted 4-dedimethylamino sancycline compounds of the formula:

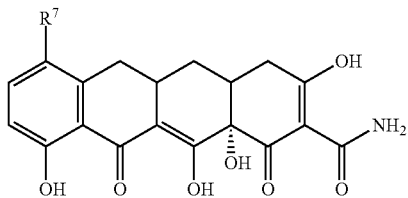

(II)

wherein:
$R^7$ is a fused ring moiety of the formula

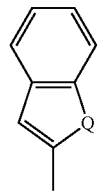

where Q is C or a heteroatom; an acylfuranyl group; a tri-, tetra- or penta-halo substituted phenyl group; an aminomethylphenyl group; an acylaminomethyl group; an alkylesterphenyl group; an acylphenyl group; an acylalkynyl group; an acylalkoxyphenyl group; a methylphenyl group; a dimethylphenyl group; a carboxyphenyl group; a carboxyalkynyl group; a thiophene group; a halothiophene group; an alkoxycarbonylphenyl group; an alkoxyphenyl group; an alkoxyphenylalkynyl group; an alkoxypyridyl group; an alkylenepyridine group; a cyclopentyl or cyclopentenyl group; a cyclohexylalkynyl group; a cyclohexenylalkynyl group; a cyclohexenylhaloalkenyl group; a hydroxycyclohexylalkynyl group; a phenylalkynyl group; a phenylalkenyl group; an aminoallynyl group; a cyclobutylalkenyl group; a pyridylalkynyl group; a pyridylalkenyl group; a nitrophenylalkynyl group; a nitrophenylalkenyl group; a cyanoalkynyl group; an alkynyl group; a cyanoalkenyl group; a cyanophenyl group; a dialkylamidoalkenyl group; a dialkylamidophenyl group; an aminophenylethyl group; an aminophenylethynyl group; a haloethenyl group; a halophenylalkynyl group; or an alkylester-substituted pentenyl group; and pharmaceutically acceptable salts thereof.

The term "7-substituted 4-dedimethylamino sancycline compounds" includes sancycline compounds with a substituent at the 7 position, as described in formula I and a substituent other than dimethylamino at the 4 position In a further embodiment, $R^7$ is a fused ring moiety of the formula

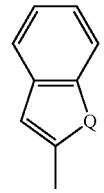

where Q is C or a heteroatom. Examples of 4-dedimethylamino sancycline compounds with this $R^7$ substituent include 7-(2'-benzofuran) 4-dedimethylamino sancycline.

In yet another embodiment, $R^7$ is an acylfuranyl group. Examples of 4-dedimethylamino sancycline compounds with this $R^7$ substituent include 7-(3'-formylfuranyl) 4-dedimethylamino sancycline.

In yet another embodiment, $R^7$ is a tri-, tetra- or penta-halo substituted phenyl group. Examples of 4-dedimethylamino sancycline compounds with this $R^7$ substituent include 7-(2',3',4',5',6'-pentafluorophenyl) 4-dedimethylamino sancycline.

In yet another embodiment, $R^7$ is an aminomethylphenyl 4-dedimethylamino group. Examples of sancycline compounds with this $R^7$ substituent include 7-(4'-aminomethylphenyl) 4-dedimethylamino sancycline.

In yet another embodiment, $R^7$ is an acylaminomethyl group. Examples of 4-dedimethylamino sancycline compounds with this $R^7$ substituent include 7-(4'-formylaminomethylphenyl) 4-dedimethylamino sancycline.

In yet another embodiment, $R^7$ is an alkylesterphenyl group. Examples of 4-dedimethylamino sancycline compounds with this $R^7$ substituent include 7-(4'-carboxyphenyl methylester) 4-dedimethylamino sancycline and 7-(2'-carboxyphenylethylester) 4-dedimethylamino sancycline.

In yet another embodiment, $R^7$ is an alkylphenyl group. Examples of 4-dedimethylamino sancycline compounds with this $R^7$ substituent include 7-(4'-tolyl) 4-dedimethylamino sancycline.

In yet another embodiment, $R^7$ is an acylphenyl group. Examples of 4-dedimethylamino sancycline compounds with this $R^7$ substituent include 7-(3'-formylphenyl) 4-dedimethylamino sancycline, 7-(4'-formylphenyl) 4-dedimethylamino sancycline, 7-(3'-acetylphenyl) 4-dedimethylamino sancycline, 7-(2'-acetylphenyl) 4-dedimethylamino sancycline, 7-(3'-acetylphenyl) 4-dedimethylamino sancycline, and 7-(4'-acetylphenyl) 4-dedimethylamino sancycline.

In yet another embodiment, $R^7$ is an acylalkoxyphenyl group. Examples of 4-dedimethylamino sancycline compounds with this $R^7$ substituent include 7-(3'-formyl-6'-methoxyphenyl) 4-dedimethylamino sancycline.

In yet another embodiment, $R^7$ is a methylphenyl group. Examples of sancycline compounds with this $R^7$ substituent include 7-(4'-methylphenyl) 4-dedimethylamino sancycline.

In yet another embodiment, $R^7$ is a dimethylphenyl group. Examples of sancycline compounds with this $R^7$ substituent include 7-(3',5'-dimethylphenyl) 4-dedimethylamino sancycline.

In yet another embodiment, $R^7$ is a carboxyphenyl group. Examples of 4-dedimethylamino sancycline compounds with this $R^7$ substituent include 7-(3'-carboxyphenyl) 4-dedimethylamino sancycline.

In yet another embodiment, $R^7$ is a carboxyalkynyl group. Examples of 4-dedimethylamino sancycline compounds with this $R^7$ substituent include 7-(carboxyethynyl) 4-dedimethylamino sancycline.

In yet another embodiment, $R^7$ is a thiophene group. Examples of 4-dedimethylamino sancycline compounds with this $R^7$ substituent include 7-(3-thiophene) 4-dedimethylamino sancycline, 7-(3'-methyl-2'-thiophene) 4-dedimethylamino sancycline, and 7-(3-methyl-5-thiophene) 4-dedimethylamino sancycline.

In yet another embodiment, $R^7$ is a halothiophene group. Examples of 4-dedimethylamino sancycline compounds with this $R^7$ substituent include 7-(3'-chloro-2'-thiophene) 4-dedimethylamino sancycline and 7-(4'-chloro-2'-thiophene) 4-dedimethylamino sancycline.

In yet another embodiment, $R^7$ is an alkoxycarbonylphenyl group. Examples of 4-dedimethylamino sancycline compounds with this $R^7$ substituent include 7-(2'-ethoxycarbonylphenyl) 4-dedimethylamino sancycline.

In yet another embodiment, $R^7$ is an alkoxyphenyl group. Examples of 4-dedimethylamino sancycline compounds with this $R^7$ substituent include 7-(2'-ethoxyphenyl) 4-dedimethylamino sancycline, 7-(3'-ethoxyphenyl) 4-dedimethylamino sancycline, 7-(4'-methoxyphenyl) 4-dedimethylamino sancycline, and 7-(2',5'-dimethoxyphenyl) 4-dedimethylamino sancycline.

In yet another embodiment, $R^7$ is an alkoxyphenylalkynyl group. Examples of 4-dedimethylamino sancycline compounds with this $R^7$ substituent include 7-(4'-methoxyphenylethynyl) 4-dedimethylamino sancycline.

In yet another embodiment, $R^7$ is an alkoxypyridyl group. Examples of 4-dedimethylamino sancycline compounds with this $R^7$ substituent include 7-(4'-methoxy-5'-pyridyl) 4-dedimethylamino sancycline.

In yet another embodiment, $R^7$ is a cyclopentyl or cyclopentenyl group. Examples of 4-dedimethylamino sancycline compounds with this $R^7$ substituent include 7-(cyclopentenyl) 4-dedimethylamino sancycline.

In yet another embodiment, $R^7$ is a cyclohexylalkynyl group. Examples of 4-dedimethylamino sancycline compounds with this $R^7$ substituent include 7-(cyclohexylethynyl) 4-dedimethylamino sancycline.

In yet another embodiment, $R^7$ is a cyclohexenylalkynyl group. Examples of 4-dedimethylamino sancycline compounds with this $R^7$ substituent include 7-(1-ethynyl-1-cyclohexyl) 4-dedimethylamino sancycline.

In yet another embodiment, $R^7$ is a cyclohexenylhaloalkenyl group. Examples of 4-dedimethylamino sancycline compounds with this $R^7$ substituent include 7-(1-chlorovinyl-1-cyclohexyl) 4-dedimethylamino sancycline.

In yet another embodiment, $R^7$ is a hydroxycyclohexylalkynyl group. Examples of 4-dedimethylamino sancycline compounds with this $R^7$ substituent include 7-(1-ethynyl-1-hydroxycyclohexyl) 4-dedimethylamino sancycline.

In yet another embodiment, $R^7$ is a phenylalkynyl group. Examples of 4-dedimethylamino sancycline compounds with this $R^7$ substituent include 7-(phenylethynyl) 4-dedimethylamino sancycline, 7-(tolylethynyl) 4-dedimethylamino sancycline, and 7-(4-methoxyphenylethynyl) 4-dedimethylamino sancycline.

In yet another embodiment, $R^7$ is a phenylalkenyl group. Examples of 4-dedimethylamino sancycline compounds with this $R^7$ substituent include 7-(2-vinylpyridyl) 4-dedimethylamino sancycline and 7-(vinylphenyl) 4-dedimethylamino sancycline.

In yet another embodiment, $R^7$ is an aminoalkynyl group. Examples of 4-dedimethylamino sancycline compounds with this $R^7$ substituent include 7-(dimethylaminoethynyl) 4-dedimethylamino sancycline.

In yet another embodiment, $R^7$ is a cyclobutylalkenyl group. Examples of 4-dedimethylamino sancycline compounds with this $R^7$ substituent include 7-(cyclobutylmethenyl) 4-dedimethylamino sancycline.

In yet another embodiment, $R^7$ is a pyridylalkynyl group. Examples of 4-dedimethylamino sancycline compounds with this $R^7$ substituent include 7-(2-pyridylethynyl) 4-dedimethylamino sancycline and 7-(3-pyridylethynyl) 4-dedimethylamino sancycline.

In yet another embodiment, $R^7$ is a pyridylalkenyl group. Examples of 4-dedimethylamino sancycline compounds with this $R^7$ substituent include 7-(4-pyridylethenyl) 4-dedimethylamino sancycline.

In yet another embodiment, $R^7$ is a nitrophenylalkynyl group. Examples of 4-dedimethylamino sancycline compounds with this $R^7$ substituent include 7-(4-nitrophenylethynyl) 4-dedimethylamino sancycline.

In yet another embodiment, $R^7$ is a nitrophenylalkenyl group. Examples of 4-dedimethylamino sancycline compounds with this $R^7$ substituent include 7-(4-nitrostyryl) 4-dedimethylamino sancycline.

In yet another embodiment, $R^7$ is an alkynyl group. Examples of 4-dedimethylamino sancycline compounds with this $R^7$ substituent include 7-(ethynyl) 4-dedimethylamino sancycline.

In yet another embodiment, $R^7$ is a cyanoalkynyl group. Examples of 4-dedimethylamino sancycline compounds with this $R^7$ substituent include 7-(cyano-1-pentynyl) 4-dedimethylamino sancycline.

In yet another embodiment, $R^7$ is a cyanoalkenyl group. Examples of 4-dedimethylamino sancycline compounds with this $R^7$ substituent include and 7-(cyanohexenyl) 4-dedimethylamino sancycline.

In yet another embodiment, $R^7$ is a cyanophenyl group. Examples of 4-dedimethylamino sancycline compounds with this $R^7$ substituent include 7-(3-cyanophenyl) 4-dedimethylamino sancycline and 7-(4-cyanophenyl) 4-dedimethylamino sancycline.

In yet another embodiment, $R^7$ is a hydroxylphenylethynyl group. Examples of 4-dedimethylamino sancycline compounds with this $R^7$ substituent include 7-(3-hydroxylphenylethynyl) 4-dedimethylamino sancycline.

In yet another embodiment, $R^7$ is a dialkylamidoalkenyl group. Examples of 4-dedimethylamino sancycline compounds with this $R^7$ substituent include 7-(N,N-dimethylacrylamide) 4-dedimethylamino sancycline and 7-(dimethylamidoethenyl) 4-dedimethylamino sancycline.

In yet another embodiment, $R^7$ is a dialkylamidophenyl group. Examples of 4-dedimethylamino sancycline compounds with this $R^7$ substituent include 7-(3-dimethylamidophenyl) 4-dedimethylamino sancycline.

In yet another embodiment, $R^7$ is an aminophenylethyl group. Examples of 4-dedimethylamino sancycline compounds with this $R^7$ substituent include 7-(4-aminophenylethyl) 4-dedimethylamino sancycline.

In yet another embodiment, $R^7$ is an aminophenylethynyl group. Examples of 4-dedimethylamino sancycline compounds with this $R^7$ substituent include 7-(4-aminophenylethynyl) 4-dedimethylamino sancycline.

In yet another embodiment, $R^7$ is a haloethenyl group. Examples of 4-dedimethylamino sancycline compounds with this $R^7$ substituent include 7-(2-chloroethenyl) 4-dedimethylamino sancycline.

In yet another embodiment, $R^7$ is a halophenylalkynyl group. Examples of 4-dedimethylamino sancycline compounds with this $R^7$ substituent include 7-(2-fluorophenylethenyl) 4-dedimethylamino sancycline.

In yet another embodiment, $R^7$ is an alkylester-substituted pentenyl group. Examples of 4-dedimethylamino sancycline compounds with this R[7] substituent include 7-(1-iodo-1,3-dicarboethoxy-1,3-butadiene) 4-dedimethylamino sancycline.

In yet another embodiment, R[7] is an aminophenylalkynyl group. Examples of 4-dedimethylamino sancycline compounds with this R[7] substituent include 7-(4-aminophenylvinyl) 4-dedimethylamino sancycline.

The invention also pertains to the tetracycline compounds shown below:

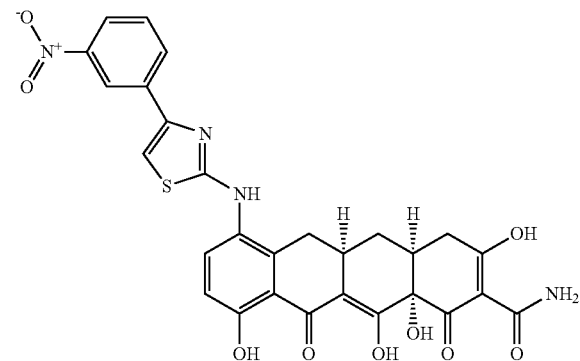

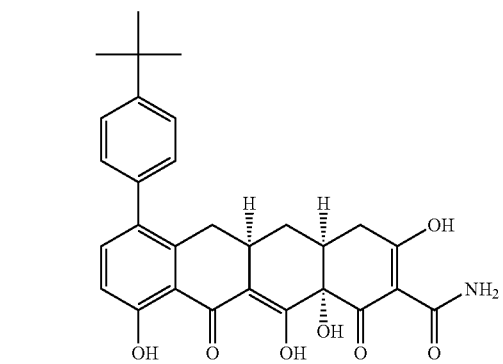

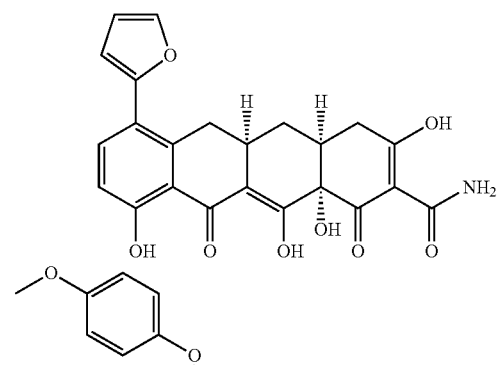

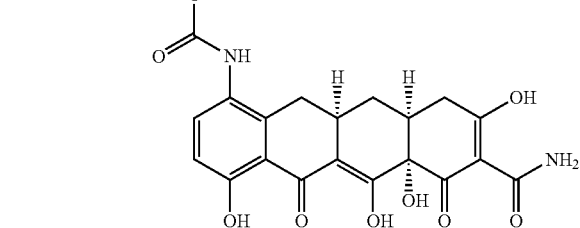

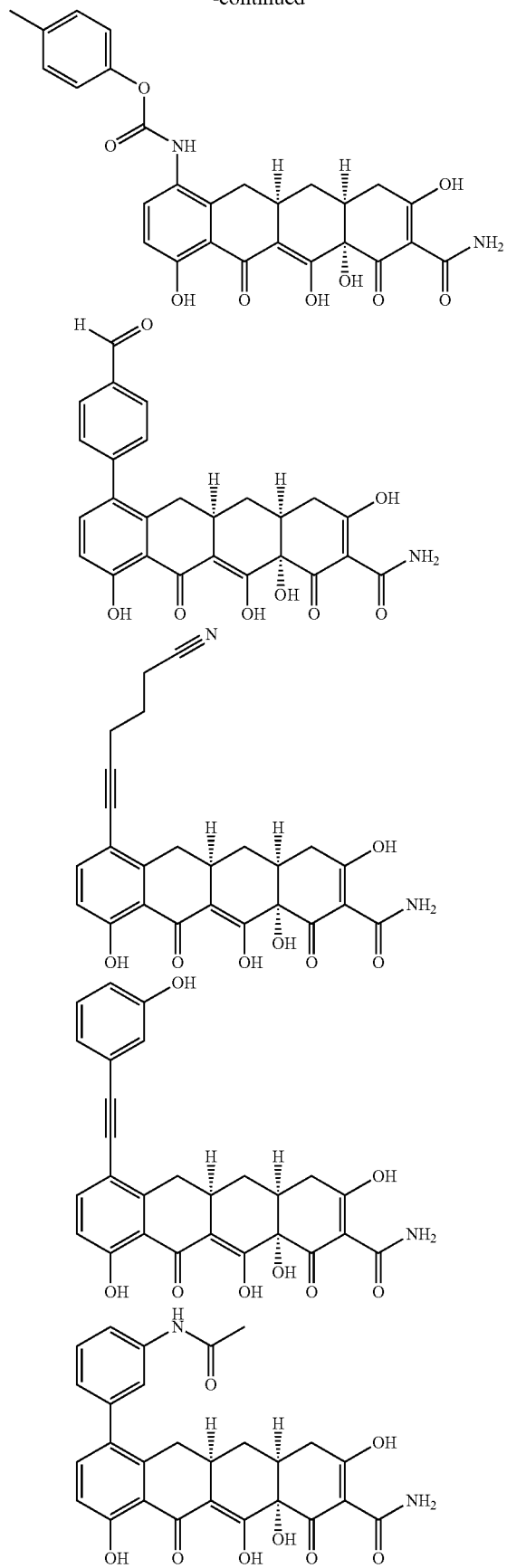

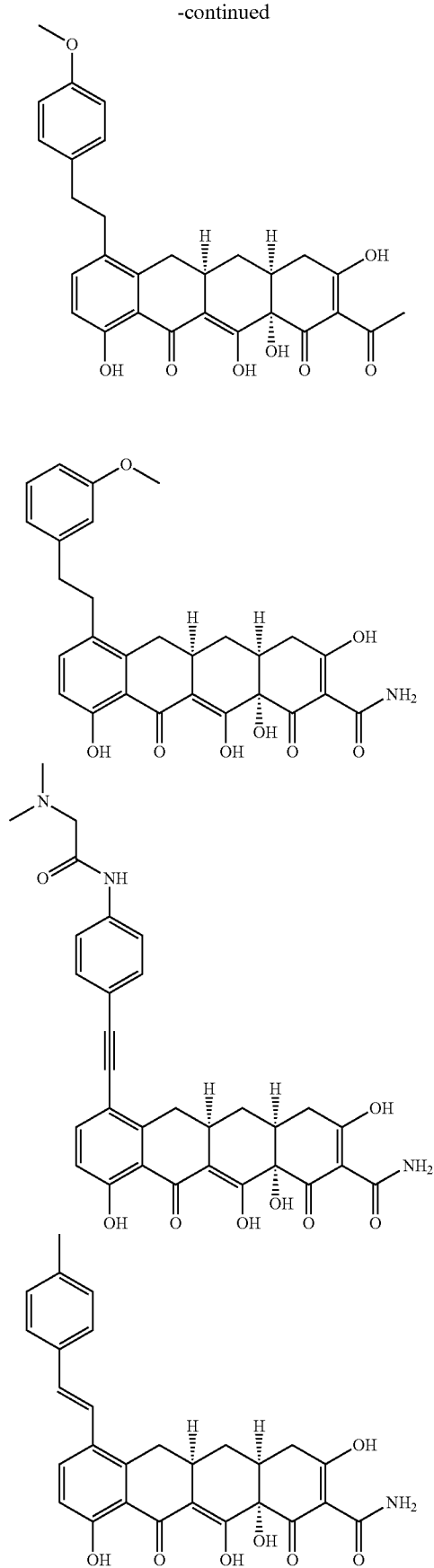
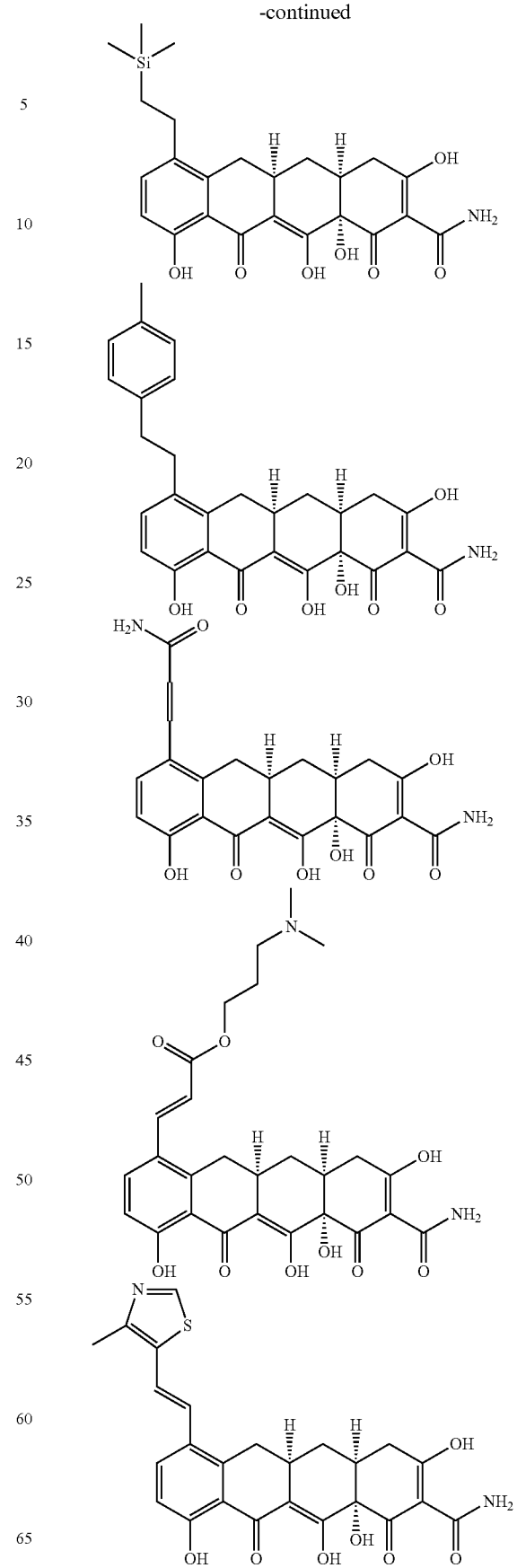

21
-continued
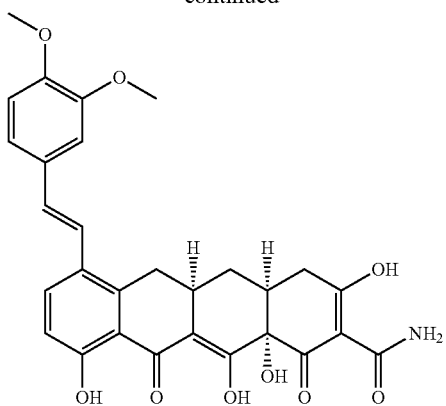
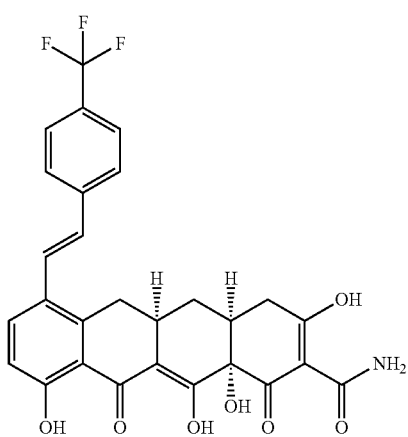
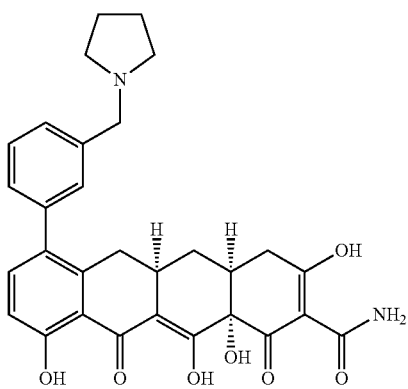
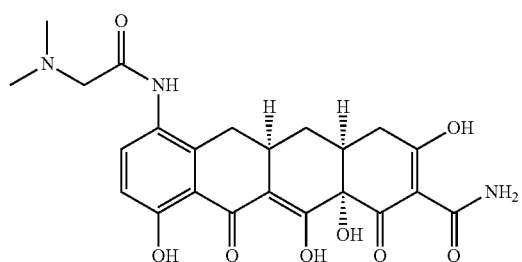
22
-continued
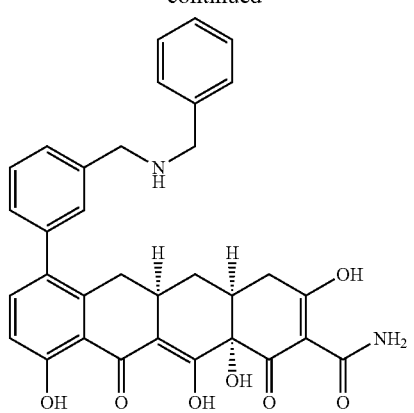
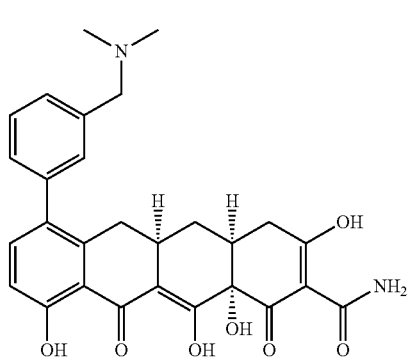
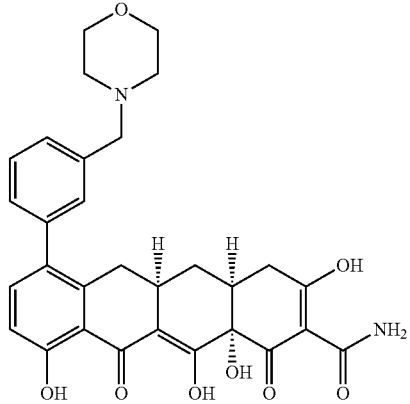
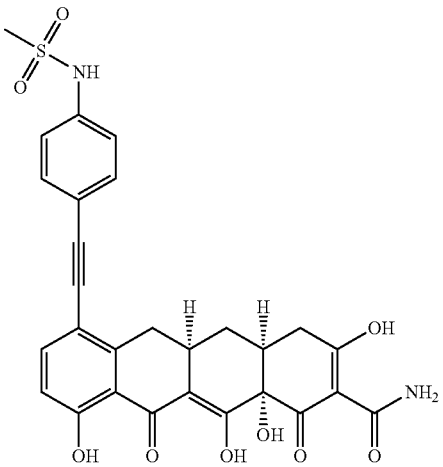

-continued
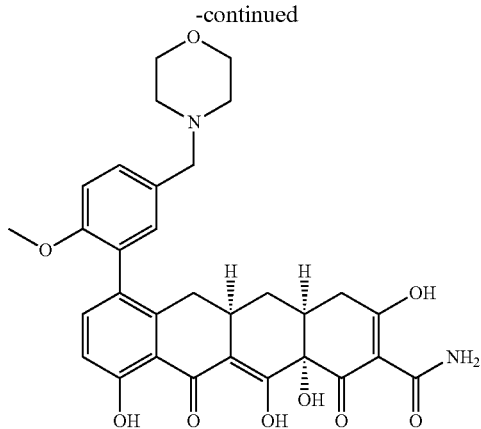
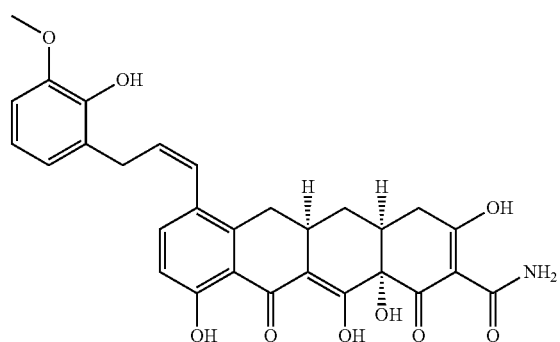
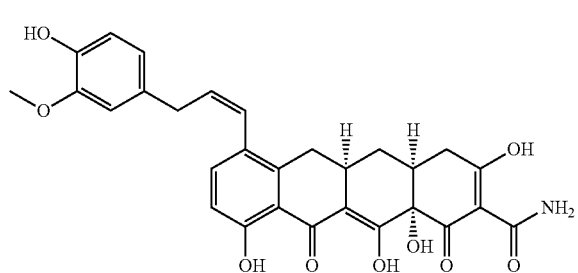
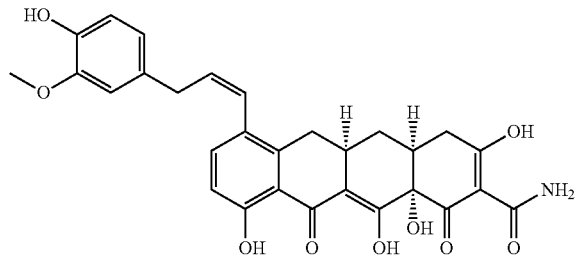
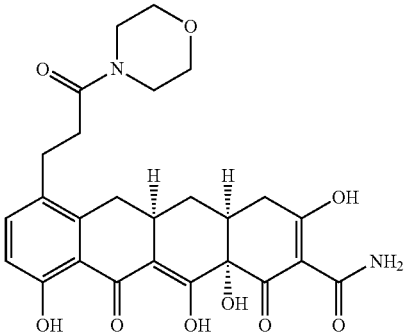
-continued
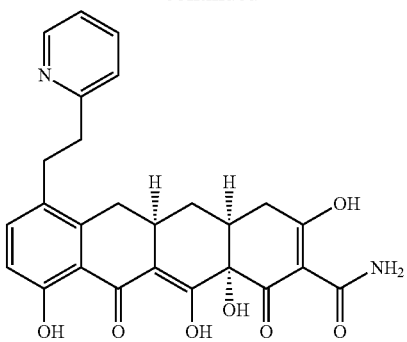
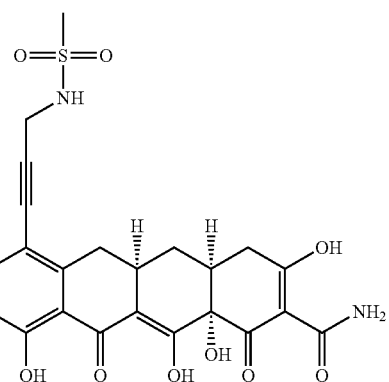
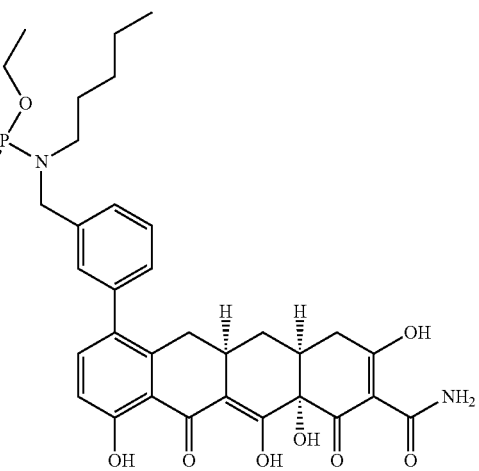
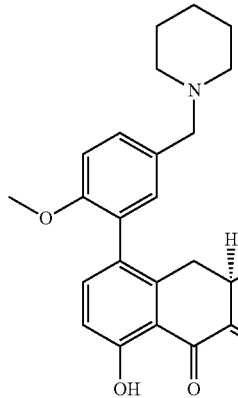

25
-continued
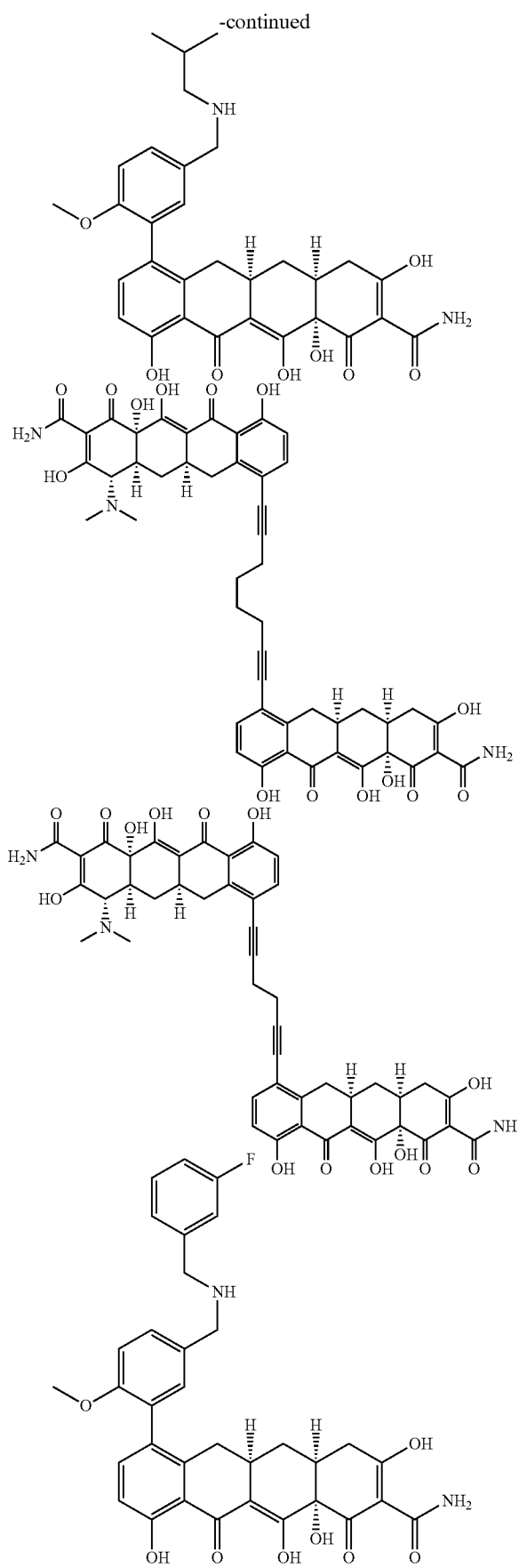
26
-continued
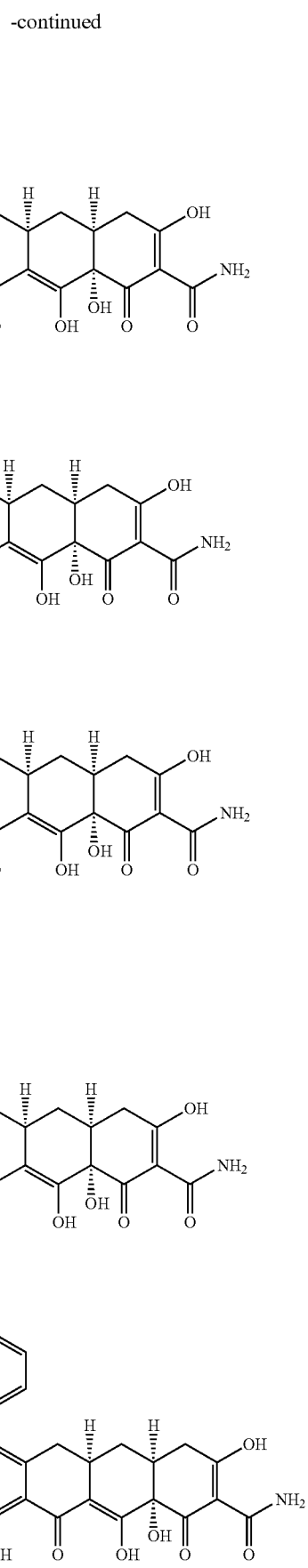

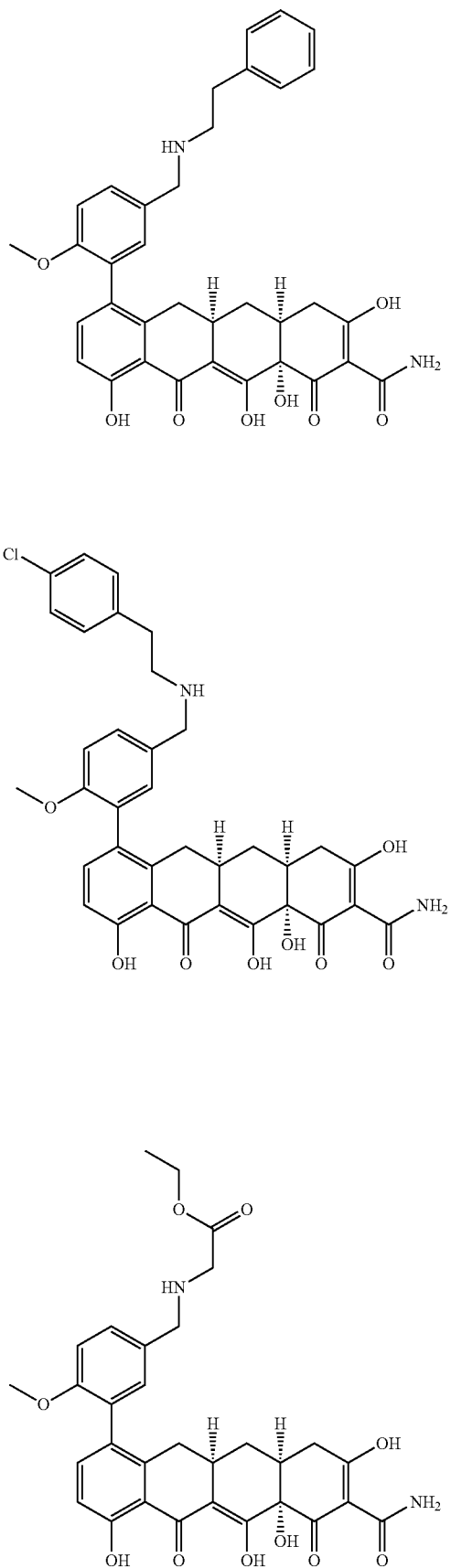
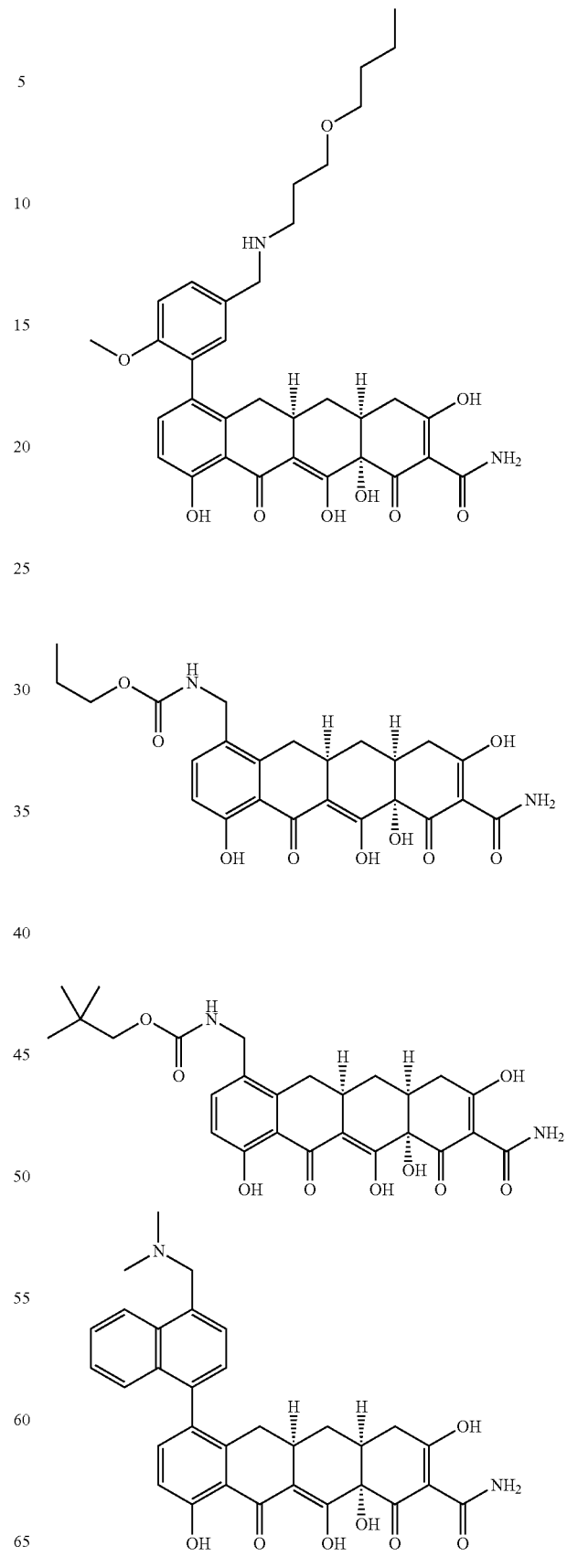

-continued
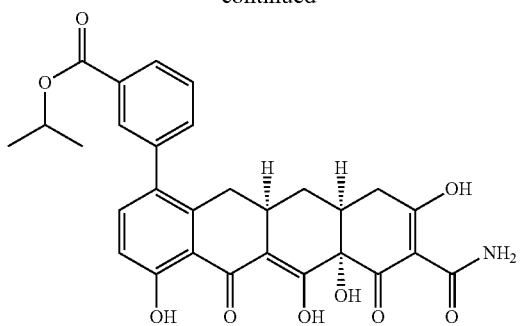
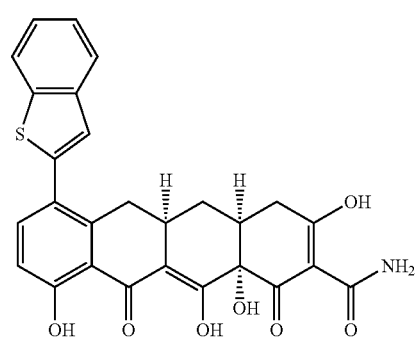
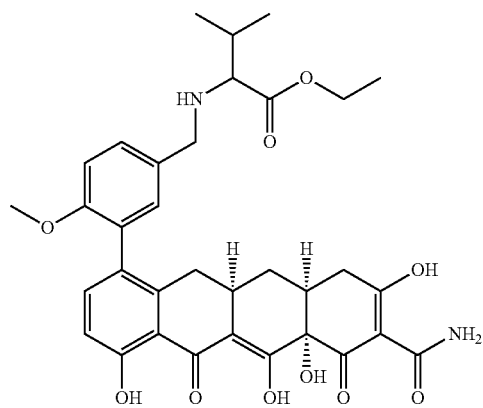
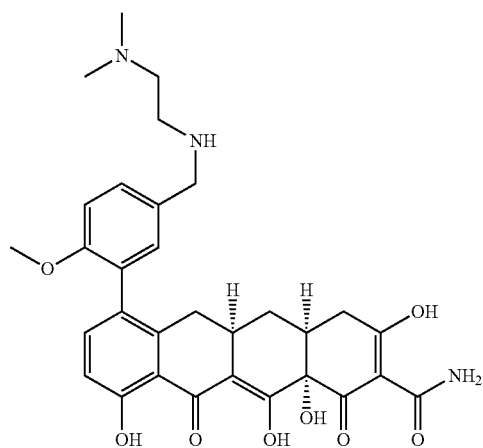
-continued
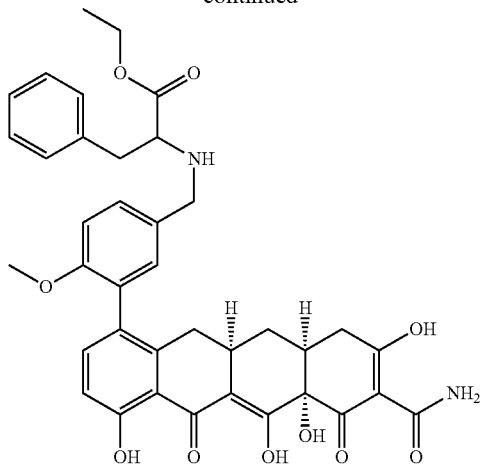
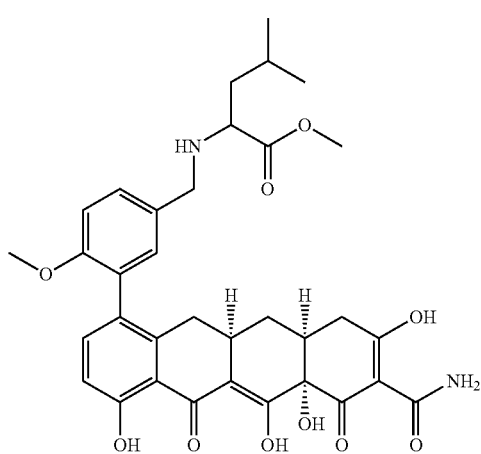
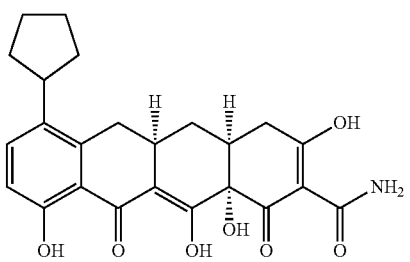
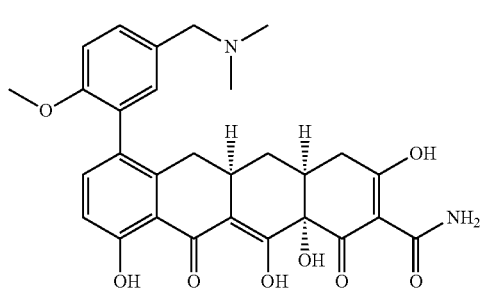

31
-continued

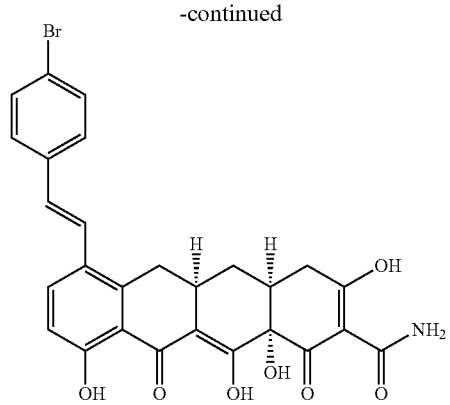

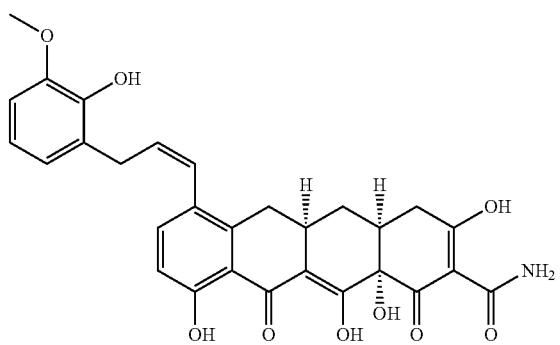

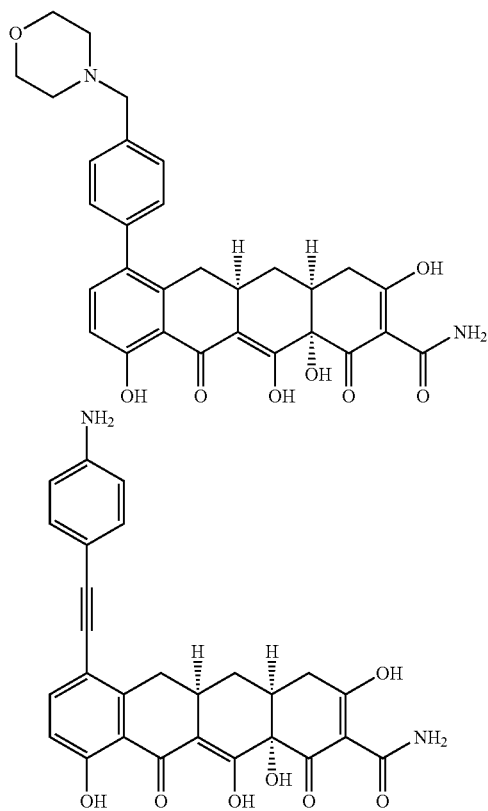

32
-continued

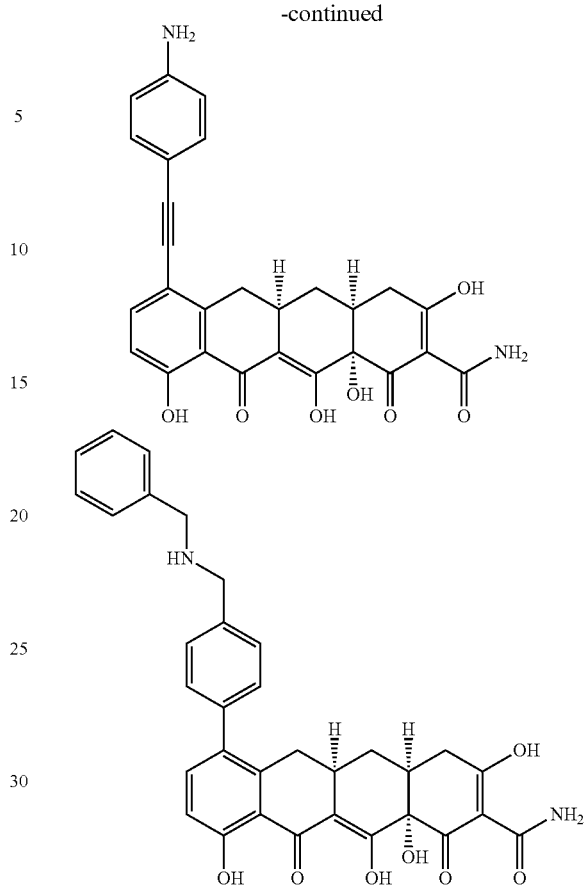

Also included are salts, esters and prodrugs of the compounds shown above and in Table 2.

II. 7,9-Substituted 4-Dedimethylamino Tetracycline Compounds

The present invention pertains, at least in part, to novel 7,9-substituted 4-dedimethylamino tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "7,9-substituted 4-dedimethylamino tetracycline compounds" includes tetracycline compounds with substitution at the 7 and 9-positions and a substituent other than dimethylamino at the 4 position. In one embodiment, the substitution at the 7- and 9-positions enhances the ability of the tetracycline compound to perform its intended function, e.g., treat tetracycline responsive states. In an embodiment, the 7,9-substituted tetracycline compound is 7,9-substituted tetracycline (e.g., wherein $R^4$ is $NR^{4'}R^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 7,9-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 7,9-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 7,9-substituted tetracycline compound is not chlorine or trimethylamino. In one embodiment, $R^4$ and $R^{4'}$ are each hydrogen or the oxygen of a carbonyl group.

The 7,9-substituted 4-dedimethylamino tetracycline compounds of the invention include compounds of Formula I:

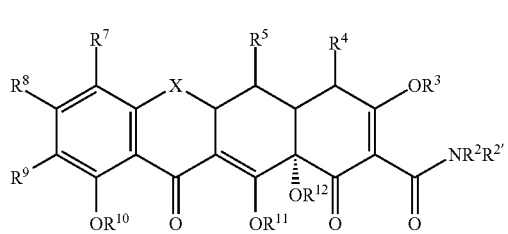
(III)

wherein:

X is $CHC(R^{13}Y'Y)$, $CR^{6'}R^{6}$, S, $NR^{6}$, or O;

$R^{2}$ and $R^{2'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{4}$ and $R^{4'}$ are each independently alkyl, alkenyl, alkynyl, hydroxyl, halogen, hydrogen, or when taken together the oxygen of a carbonyl group;

$R^{2'}$, $R^{3}$, $R^{10}$, $R^{11}$ and $R^{12}$ are each hydrogen or a pro-drug moiety;

$R^{5}$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^{6}$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7}$ is nitro, alkyl, alkenyl, alkynyl, aryl, alkoxy, alkylthio, alkylsulfinyl, alkylsulfonyl, arylalkyl, amino, arylalkenyl, arylalkynyl, or $—(CH_{2})_{0-3}NR^{7c}C(=W')WR^{7a}$;

$R^{9}$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $—(CH_{2})_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{8}$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The tetracycline compounds of the invention include, for example, compounds wherein X is $CR^{6}R^{6'}$; $R^{4}$ and $R^{4'}$ are hydrogen or the oxygen of a carbonyl group; $R^{2}$, $R^{2'}$, $R^{6}$, $R^{6'}$, $R^{8}$, $R^{10}$, $R^{11}$, and $R^{12}$ are each hydrogen; $R^{4}$ and $R^{4''}$ are lower alkyl; and $R^{5}$ is hydroxy or hydrogen. In an embodiment, $R^{4}$ and $R^{4'}$ are each methyl and $R^{5}$ is hydrogen. The tetracycline compounds of the invention include each possible combination of $R^{7}$ and $R^{9}$ substituents discussed below.

In an embodiment, $R^{7}$ is aryl (e.g., heteroaryl or substituted or unsubstituted phenyl). The phenyl $R^{7}$ group may be substituted with one or more substituents. Examples of substituents of phenyl $R^{7}$ groups include alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituent is substituted or unsubstituted alkyl (e.g., methyl, ethyl, propyl, butyl, etc.), nitro, halogen (e.g., fluorine, bromine, chlorine, iodine, etc.), amino (e.g., unsubstituted amino, alkyl amino, dialkylamino (e.g., dimethylamino), or alkoxy (methylenedioxy or methoxy).

$R^{7}$ also may be substituted or unsubstituted alkyl(e.g., methyl, ethyl, i-propyl, n-propyl, t-butyl, i-butyl, n-butyl, pentyl, n-pentyl, n-hexyl, or hexyl). The alkyl may be branched or straight chain and may comprise a ring, e.g., a cycloalkyl ring, e.g., cyclohexyl ring.

The alkyl $R^{7}$ group may be substituted with any substituent which allows the tetracycline compound to perform its intended function. Examples of substituents include, but are not limited to, alkenyl, halogen (e.g., fluorine, chlorine, bromine, iodine, etc.), hydroxyl, alkoxy (e.g., methoxy, ethoxy, perchloromethoxy, perfluoromethoxy, etc.), alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Examples of heterocyclic substituents include N-isoindole-[1,3]-dione (e.g., phthalimide). In an embodiment, the substituent is arylcarbonylamino, e.g., heteroaryl carbonyl amino. The heteroaryl group may be, for example, pyridinyl. Other examples of substituents include amino or carboxylate.

In another embodiment, $R^{7}$ is acyl, e.g., acetyl.

In yet another embodiment, $R^{7}$ is substituted or unsubstituted alkynyl. Examples of substituents include those which allow the tetracycline compound to perform its intended function. Examples of substituents include, but are not limited to, alkyl (e.g., methyl, ethyl, propyl, butyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituent is substituted or unsubstituted phenyl. The phenyl also may be further substituted with one or more substituents which allow the compound to perform its intended function. Examples of phenyl substituents include, but are not limited to, alkoxy (e.g., methoxy).

The tetracycline compounds of the invention include compounds wherein $R^9$ is substituted or unsubstituted aryl (e.g., carbocyclic or heteroaryl). In an embodiment, $R^9$ is substituted or unsubstituted phenyl. The substituted phenyl group can be substituted with any substituent or combination of substituents which allows the compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the phenyl $R^9$ substituent is substituted or unsubstituted alkyl, nitro, halogen, amino, or alkoxy (e.g., methylenedioxy).

The invention also includes compounds wherein $R^9$ is substituted or unsubstituted alkyl (e.g., methyl, ethyl, i-propyl, n-propyl, i-butyl, t-butyl, n-butyl, pentyl, hexyl, etc.). The alkyl group may be substituted with any substituent that allows the compound to perform its intended function. Examples of the substituents include, but are not limited to, alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, alkylcarbonylamino, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, wherein said substituent is unsubstituted amino. In a further embodiment, the $R^9$ group is aminomethyl. In another, the alkyl $R^9$ group is substituted with arylcarbonylamino (e.g., heteroarylcarbonylamino, e.g., pyridinylcarboynlamino) or alkylcarbonylamino.

In another further embodiment, the $R^9$ alkyl group is substituted with a heterocyclic substituent, such as isoindole-[1,3]-dione (e.g., phthalimide).

In an embodiment, $R^7$ is acyl, e.g., acetyl.

In yet another embodiment, $R^9$ is substituted or unsubstituted alkynyl. The alkynyl $R^9$ group can be substituted with any substituent which allows the tetracycline compound of the invention to perform its intended function. Examples of substituents include, but are not limited to, alkyl (e.g., methyl, ethyl, propyl, butyl, pentyl, hexyl, heptyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituted alkynyl $R^9$ moiety is, for example, substituted or unsubstituted phenyl. The phenyl may be substituted with, for example, alkoxy, e.g., methoxy. Examples of alkenyl substituents include cycloalkenes such as, cyclohexene.

In one embodiment, $R^9$ is not unsubstituted phenyl when $R^7$ is unsubstituted phenyl.

Examples of 7,9-substituted 4-dedimethylamino tetracycline compounds of the invention include those listed below and in Table 2:

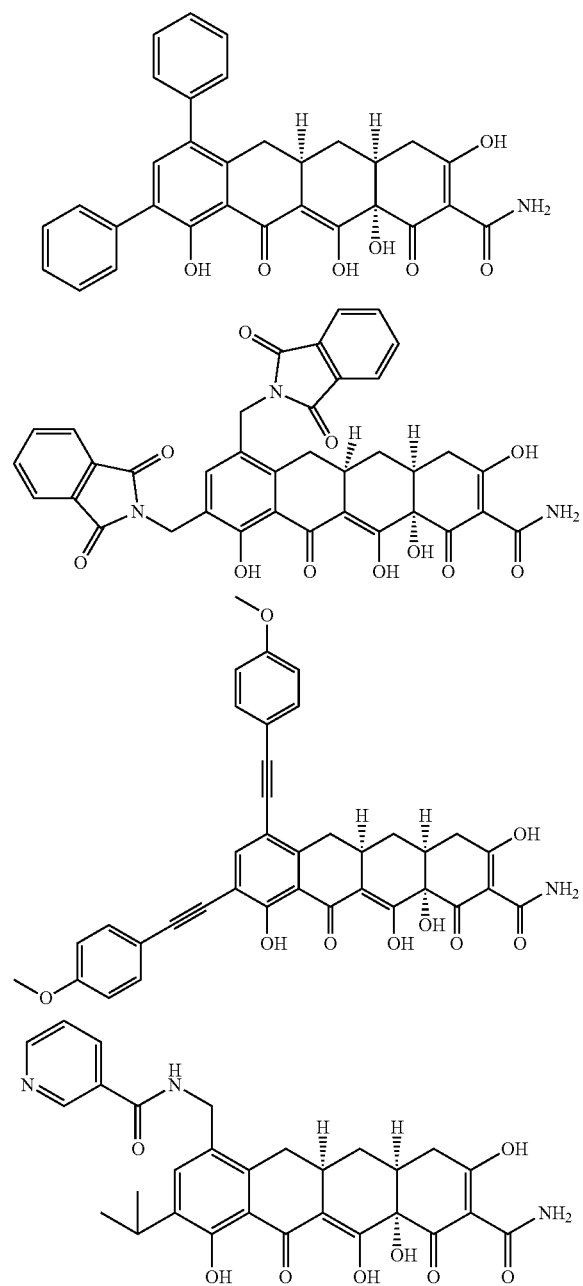

37
-continued
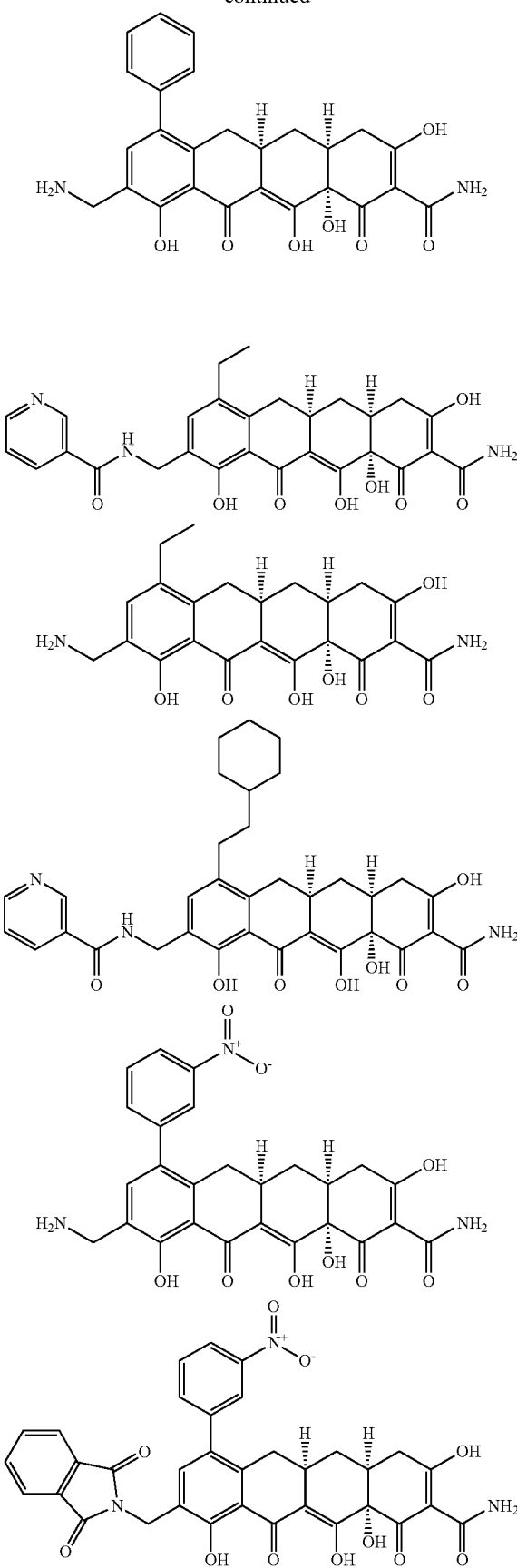
38
-continued
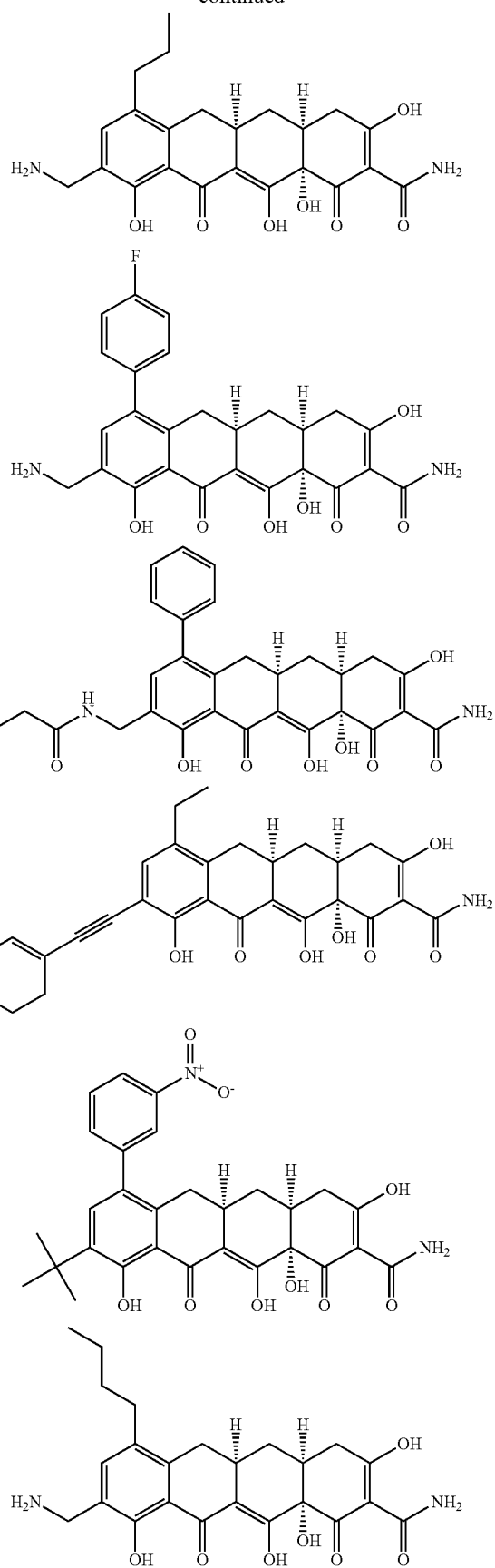

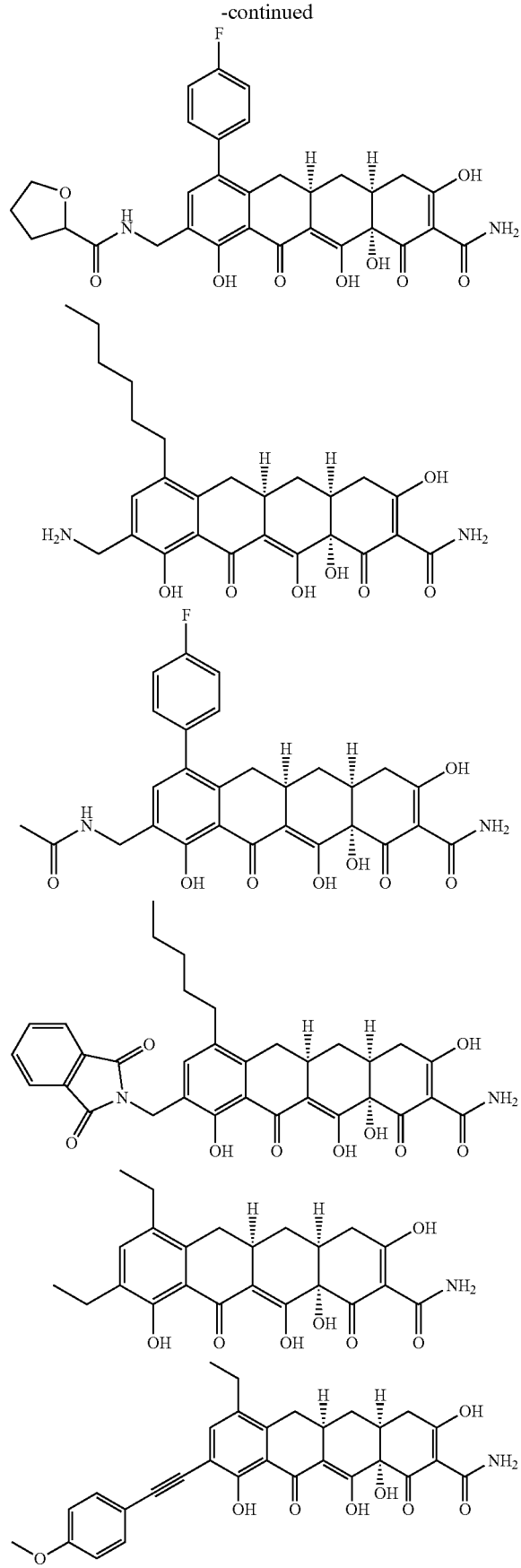

-continued

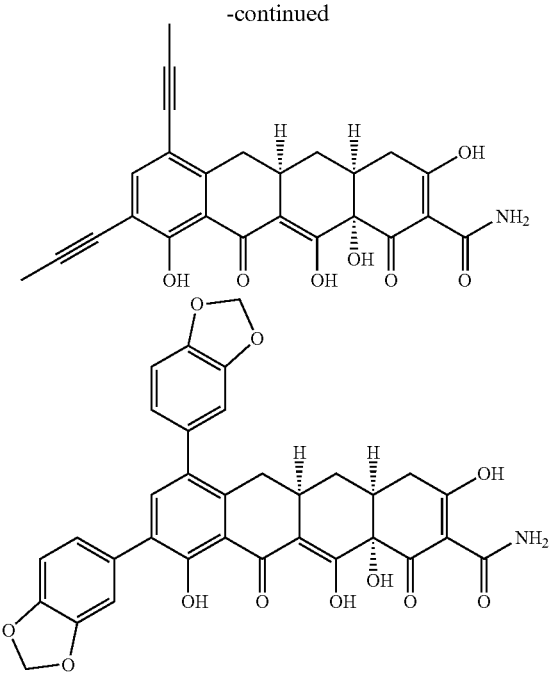

The invention also pertains to each of the 4-dedimethylamino tetracycline compounds shown in Table 2, as well as their pharmaceutically acceptable salts, esters, and prodrugs.

III. 9-Substituted 4-Dedimethylamino Tetracycline Compounds

The present invention pertains, at least in part, to novel 9-substituted 4-dedimethylamino tetracycline compounds. These tetracycline compounds can be used to treat numerous tetracycline compound-responsive states, such as bacterial infections and neoplasms, as well as other known applications for tetracycline compounds, such as blocking tetracycline efflux and modulation of gene expression.

The term "9-substituted 4-dedimethylamino tetracycline compounds" includes tetracycline compounds with substitution at the 9 position. In one embodiment, the substitution at the 9-position enhances the ability of the tetracycline compound to perform its intended function, e.g., treat tetracycline responsive states. In an embodiment, the 9-substituted tetracycline compound is 9-substituted 4-dedimethylamino tetracycline (e.g., wherein $R^4$ and $R^{4'}$ are hydrogen, $R^5$ is hydrogen and X is $CR^6R^{6'}$, wherein $R^6$ is methyl and $R^{6'}$ is hydroxy); 9-substituted 4-dedimethylamino doxycycline (e.g., wherein $R^4$ and $R^{4'}$ are hydrogen, $R^5$ is hydroxyl and X is $CR^6R^{6'}$, wherein $R^6$ is methyl and $R^{6'}$ is hydrogen); 9-substituted dedimethylamino minocycline compounds, wherein X is $CR^6R^{6'}$, $R^4$, $R^{4'}$, $R^5$, $R^{6'}$, and $R^6$ are hydrogen, and $R^7$ is dimethylamino; or 9-substituted 4-dedimethylamino sancycline (wherein $R^4$ and $R^{4'}$ are hydrogen; $R^5$ and $R^7$ are hydrogen and X is $CR^6R^{6'}$ wherein $R^6$ and $R^{6'}$ are hydrogen atoms).

The invention pertains, at least in part, to tetracycline compounds of Formula IV:

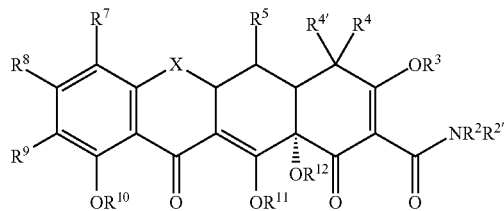

(IV)

wherein:
X is $CHC(R^{13}Y'Y)$, $CR^6R^{6'}$, S, $NR^6$, or O;
$R^2$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ and $R^{4'}$ are each independently alkyl, alkenyl, alkynyl, aryl, hydroxyl, alkoxy halogen, hydrogen, or taken together to form the oxygen of a carbonyl;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is $NR^{7'}R^{7''}$, alkyl, alkenyl, alkynyl, aryl, hydroxyl, halogen, or hydrogen;
$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;
Z is $CR^{9d}R^{9e}$, S, $NR^{9b}$ or O;
Z' is $NR^{9f}$, O or S;
$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The term tetracycline compounds refers to compounds of formula (I) above. In an embodiment, the term minocycline compounds include compounds wherein X is $CR^6R^{6'}$; $R^2$, $R^{2'}$, $R^5$, $R^6$, $R^{6'}$, $R^8$, $R^9$, $R^{10}$, $R^{11}$, and $R^{12}$ are each hydrogen; $R^7$ is $NR^{7'}R^{7''}$; $R^4$ and $R^{4'}$ are each hydrogen or taken together to form the oxygen of a carbonyl group; and $R^{7'}$, and $R^{7''}$ are each lower alkyl, e.g., methyl.

Examples of $R^9$ include substituted and unsubstituted aryl groups. The aryl groups include substituted and unsubstituted heteroaryls (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, or deazapurinyl), substituted or unsubstituted phenyl, and groups with more than one aromatic ring, such as naphthyl.

Examples of substituents of $R^9$ include, but are not limited to, alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aralkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl $R^9$ group is substituted with one or more substituents such as, for example, carboxylate, alkyl, alkenyl, alkynyl, aryl, heterocyclic, cyano, amino, halogen, alkoxy, alkoxycarbonyl, amido, alkylcarbonyl, or nitro.

In another embodiment, $R^9$ is substituted or unsubstituted alkynyl. The alkynyl $R^9$ group may be substituted with a substituted or unsubstituted aryl group, such as, for example, phenyl. The possible substituents for the substituted phenyl group include, for example, those listed supra, for the aryl $R^9$ group. Furthermore, the substituted alkynyl $R^9$ group may be substituted with a heteroaryl (e.g., pyridinyl), alkyl (e.g., methyl, ethyl, propyl, butyl, pentyl, hexyl, cyclopropyl, cyclobutyl, cyclopentyl, cyclohexyl, etc.), alkenyl (e.g., ethenyl, propenyl, butenyl, pentenyl, hexenyl, etc.), carboxylate, silyl (e.g., trialkylsilyl, e.g., trimethylsilyl), aralkyl, or a alkyloxycarbonyl group.

Each of these groups may also be further substituted, with such substituents as alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the alkynyl $R^9$ group is substituted with an aminoalkyl group. The aminoalkyl group may then also be substituted with, for example, an alkyl, alkenyl, alkynyl, acyl, carbonyl, or alkylsulfone group.

In another further embodiment, the alkynyl $R^9$ group is substituted with a cycloalkenyl group, such as, for example, cyclopentene.

In another embodiment, $R^9$ is alkyl. The alkyl group may be substituted or unsubstituted. Examples of alkyl groups include, for example, both straight chain, branched and cyclic alkyl groups. For example, alkyl groups include methyl, ethyl, i-propyl, n-propyl, i-butyl, n-butyl, t-butyl, pentyl, hexyl, heptyl, octyl, nonyl, decyl, etc. Cyclic alkyl groups include groups with one or more rings, such as, for example, cyclopropane, cyclobutane, cyclopentane, cyclohexane, cycloheptane, etc. In an embodiment, the alkyl $R^9$ group is 2-cyclopentylethyl.

Examples of substituents of alkyl groups include, for example, halogens (e.g., fluorine, chlorine, bromine, iodine, etc.), hydroxyl, alkoxy (e.g., methoxy, ethoxy, propoxy, butoxy, pentoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, carboxy, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, alkenyl, sulfonato, sulfamoyl, sulfonamido, nitro, alkenyl, cyano, azido, heterocyclyl, alkylaryl, aryl and heteroaryl.

In another embodiment, the minocycline compound of the invention is a compound wherein $R^9$ is —$NR^{9c}C(=Z')ZR^{9a}$, —$CH_2NR^{9c}C(=Z')ZR^{9a}$, —$(CH_2)_2NR^{9c}C(=Z')ZR^{9a}$, or —$(CH_2)_3NR^{9c}C(=Z')ZR^{9a}$. In certain embodiments, $R^9$ is —$NR^{9c}C(=Z')ZR^{9a}$ or —$CH_2NR^{9c}C(=Z')ZR^{9a}$. Examples of $R^{9c}$ include hydrogen. Z' may be, for example, S, NH, or O.

Examples of Z include $NR^{9b}$ (e.g., when $R^{9b}$ is hydrogen, alkyl, etc.), O or S.

Examples of $R^{9a}$ groups include aryl groups such as substituted and unsubstituted phenyl. Examples of possible substituents of aryl $R^{9a}$ groups include, but are not limited to, alkyl (e.g., methyl, ethyl, propyl, butyl, pentyl, hexyl, perfluoromethyl, perchloroethyl, etc.), alkenyl, halogen (e.g., fluorine, chlorine, bromine, iodine, etc.), hydroxyl, alkoxy (e.g., methoxy, ethoxy, propoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, sulfonato, sulfamoyl, sulfonamido, nitro, acetyl, alkyl, cyano, azido, heterocyclyl, alkylaryl, aryl and heteroaryl groups.

In certain embodiments, at least one of the substituents of the substituted phenyl is nitro, alkoxy (e.g., methoxy, methylenedioxy, perfluoromethoxy) alkyl (e.g., methyl, ethyl, propyl, butyl, or pentyl), acetyl, halogen (e.g., fluorine, chlorine, bromine, or iodine), or amino (e.g., dialkylamino). In certain embodiments, the alkoxy group is perhalogenated, e.g., perfluoromethoxy.

Examples of aryl $R^{9a}$ groups include, but are not limited to, unsubstituted phenyl, para-nitrophenyl, para-methoxy phenyl, para-perfluoromethoxy phenyl, para-acetyl phenyl, 3,5-methylenedioxyphenyl, 3,5-diperfluoromethyl phenyl, para-bromo phenyl, para-chloro phenyl, and para-fluoro phenyl.

Other examples of aryl $R^{9a}$ groups include substituted and unsubstituted heterocycles (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, pyrrolidinyl, oxazolyl, isooxazolyl, naphthridinyl, thiazolyl, isothiazolyl, or deazapurinyl) and substituted and unsubstituted biaryl groups, such as naphthyl and fluorene.

$R^{9a}$ also may be substituted or unsubstituted alkyl, e.g., methyl, ethyl, propyl, butyl, pentyl, etc. Examples of substituents include but are not limited to halogens (e.g., fluorine, bromine, chlorine, iodine, etc.), hydroxyl, alkoxy (e.g., methoxy, ethoxy, propoxy, butoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, alkenyl, heterocyclyl, alkylaryl, aryl and heteroaryl.

$R^{9a}$ also can be substituted or unsubstituted alkenyl. Examples of substituents for alkenyl $R^{9a}$ groups include those listed above for alkyl $R^{9a}$ groups. Examples of alkenyl $R^{9a}$ groups include pent-1-enyl.

In an embodiment, Z' is NH, Z is NH, and $R^{9a}$ is alkyl.

The invention also pertains to compounds wherein $R^9$ is aminoalkyl (e.g., aminomethyl). Aminoalkyl $R^9$ groups may be further substituted. Examples of substituents include aryl groups, such as, for example substituted or unsubstituted phenyl (e.g., methylenedioxyphenyl or para-perfluoromethoxyphenyl), or heteroaromatic groups which allows the compound of the invention to perform its intended function.

Examples of tetracycline compounds of the invention include those listed in Table 2, as well as the ones listed below:

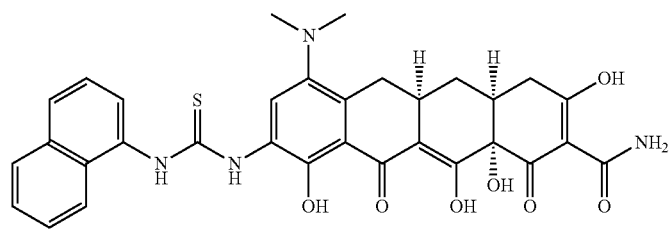
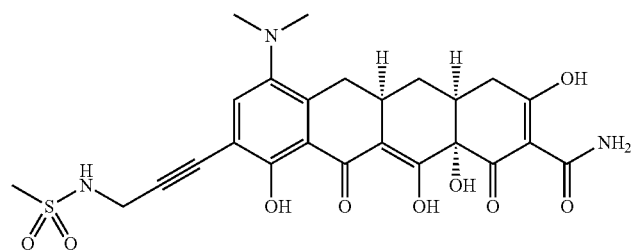
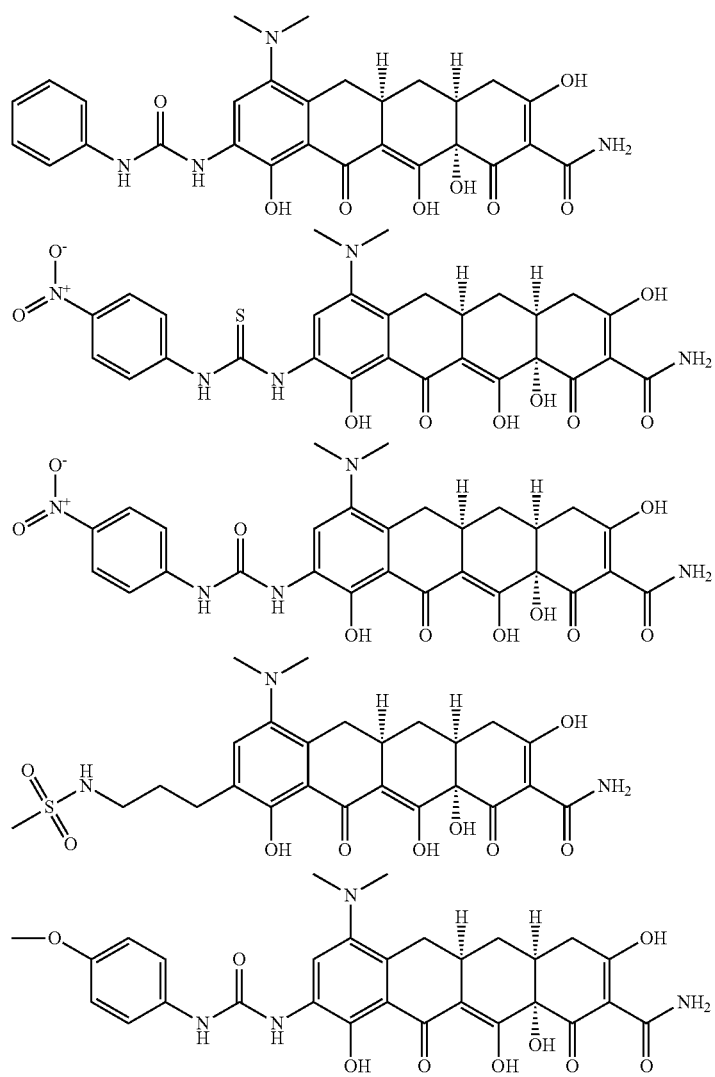

-continued
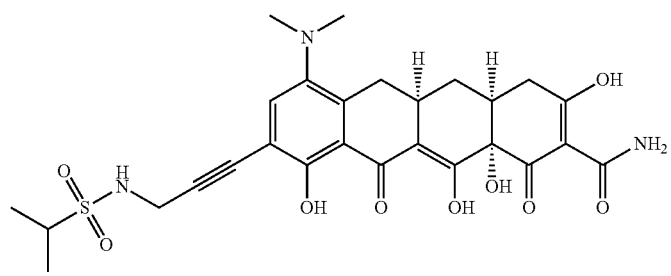
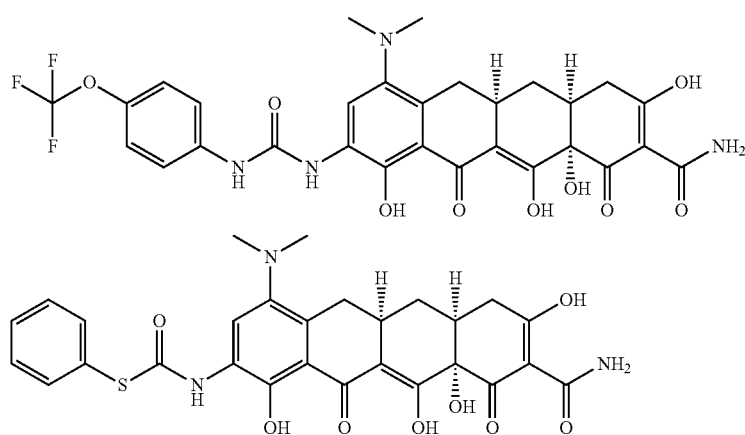
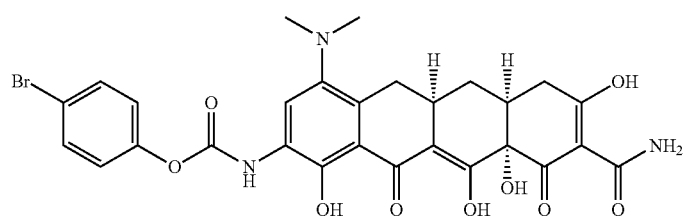
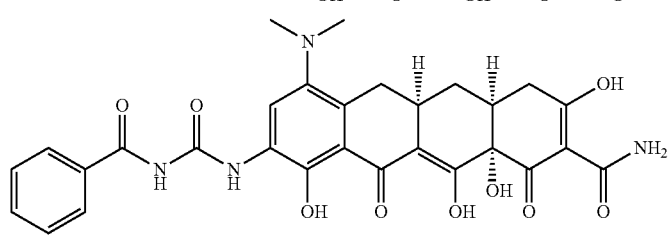
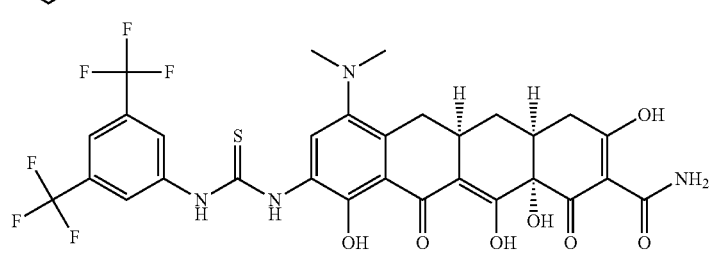
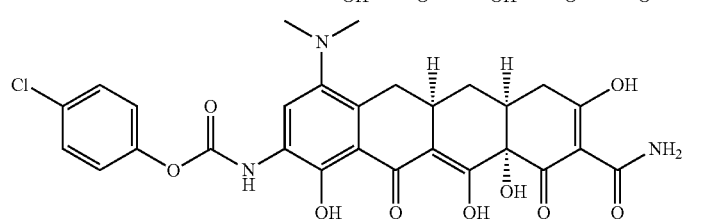
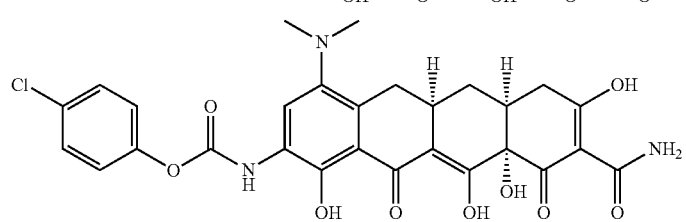

-continued
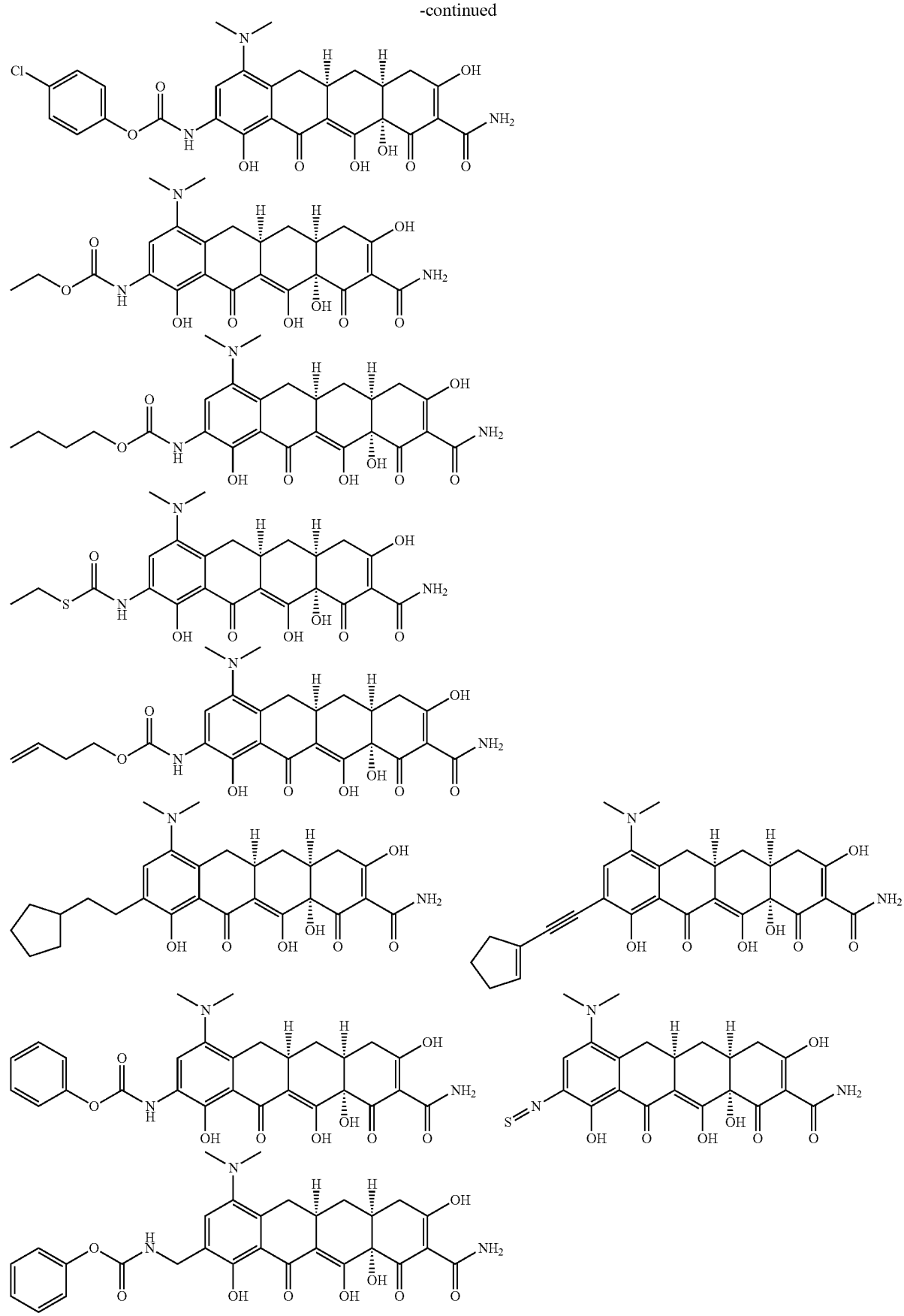

-continued
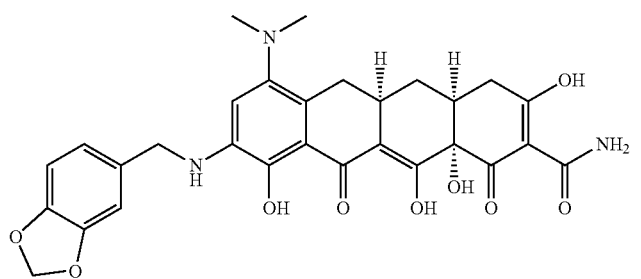
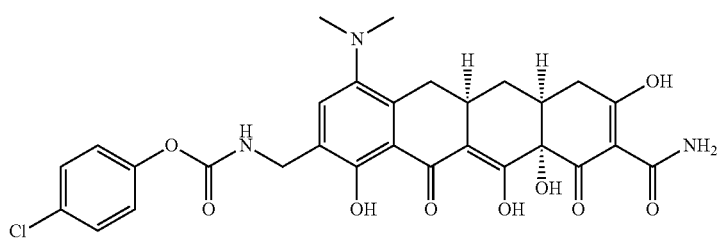
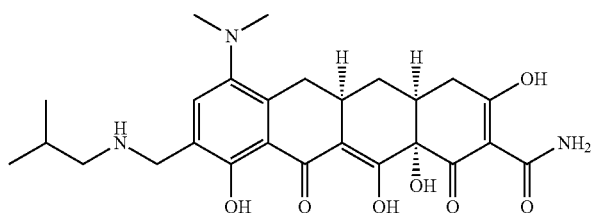
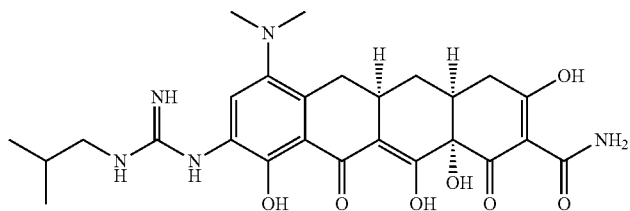
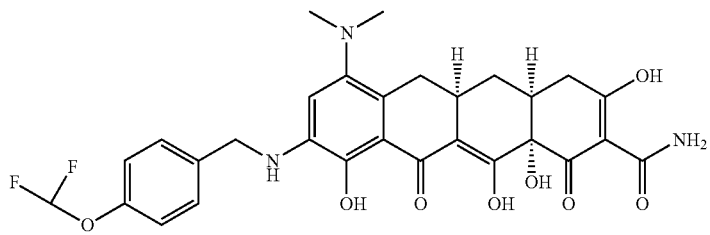
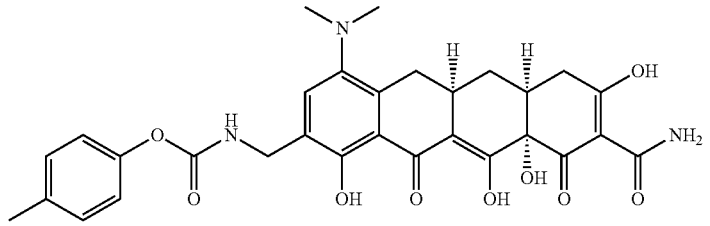
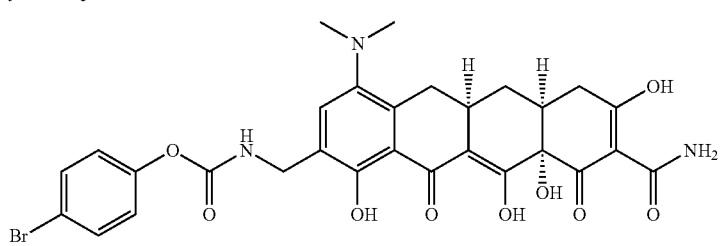

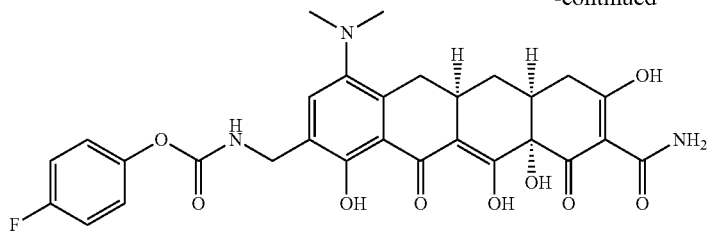
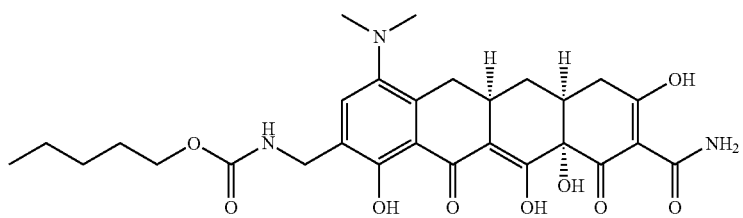
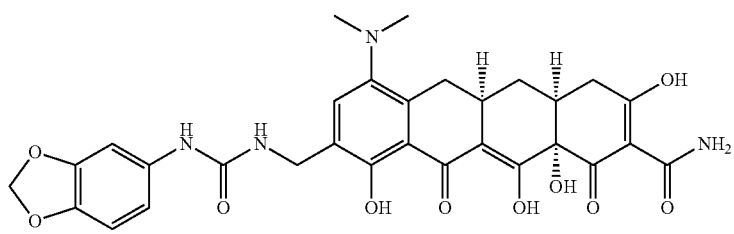
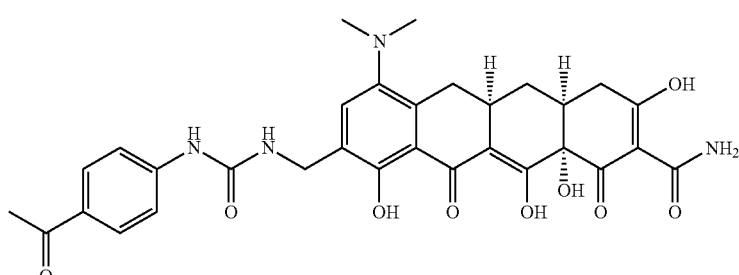
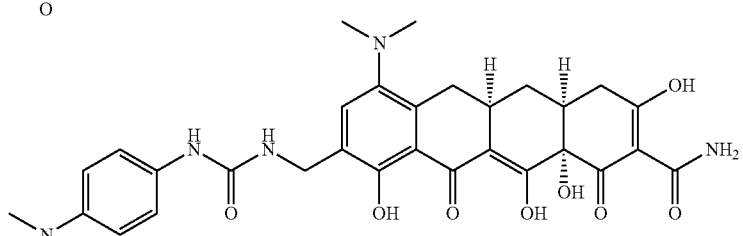
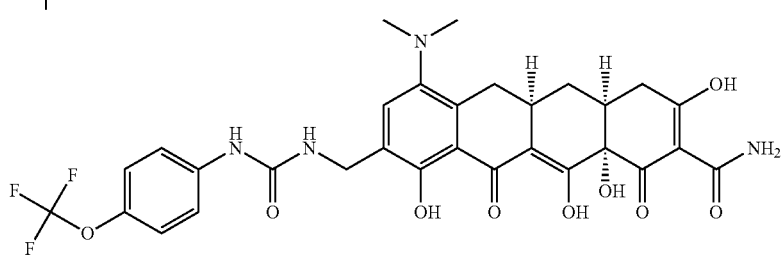

Pharmaceutically acceptable salts of these compounds are also included. Other compound of the invention are listed in Table 2.

The invention also relates, at least in part, to 9-substituted 4-dedimethylamino minocycline compounds of the formula:

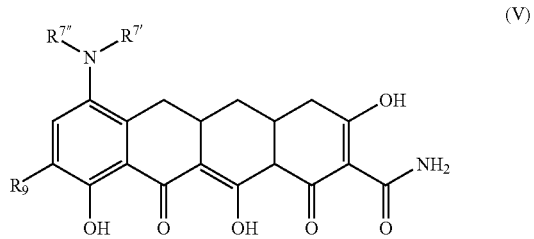

(V)

wherein:

$R^7$, and $R^{7''}$ are each alkyl; and $R^9$ is a pyridylethynyl group; an alkenylcarbamate group; a halo group; an alkylacrylate group; a naphthyl urea group; a haloacetyl group; an alkyl carbamate group; a cyclopentyl or cyclopentenyl group; a benzofuranyl group; a phenylpropiononeamino group; a tosylamino group; a methoxypyridyl group; an alkeneamino group; an N-t-butyl group; a t-butylamide group; a hydroxybutylamino group; a hydroxypropylamino group; a phenyl group; a nitrophenyl group; a nitrophenyl alkynyl group; an aminophenyl group; a halophenyl urea group; an alkoxyphenyl group; a cyanophenyl group; a carboxyphenyl group; an acylphenyl group; an alkylphenyl group; a halophenyl group; an alkoxyphenyl group; a carboxyalkylphenyl group; a phenylalkynyl group; an alkynyl group; an alkylglycineethylester group; a styrene group; a thiophene group; an alkylaminophospho group; and pharmaceutically acceptable salts thereof.

The term "9-substituted 4-dedimethylamino minocycline compound" includes minocycline compounds with a substituent at the 9 position and a substituent other than dimethylamino at the 4 position. In another embodiment, the compound is a derivative of minocycline.

In an embodiment, $R^9$ is an alkenylcarbamate group. Examples of minocycline compounds with this $R^9$ substituent include 9-isopropenyl carbamate 4-dedimethylamino minocycline.

In an embodiment, $R^9$ is a pyridylethynyl group. Examples of minocycline compounds with this $R^9$ substituent include 9-(2-pyridylethynyl) 4-dedimethylamino minocycline.

In an embodiment, $R^9$ is a halo group. Examples of minocycline compounds with this $R^9$ substituent include 9-iodo 4-dedimethylamino minocycline.

In an embodiment, $R^9$ is an alkylacrylate group. Examples of minocycline compounds with this $R^9$ substituent include 9-butylacrylate 4-dedimethylamino minocycline.

In an embodiment, $R^9$ is a naphthyl urea group. Examples of minocycline compounds with this $R^9$ substituent include 9-naphthyl 4-dedimethylamino minocycline urea.

In an embodiment, $R^9$ is a haloacetyl group. Examples of minocycline compounds with this $R^9$ substituent include 9-chloroacetyl 4-dedimethylamino minocycline urea.

In an embodiment, $R^9$ is an alkyl carbamate group. Examples of minocycline compounds with this $R^9$ substituent include 9-neopentyl 4-dedimethylamino minocycline carbamate.

In an embodiment, $R^9$ is a cyclopentyl or cyclopentenyl group. Examples of minocycline compounds with this $R^9$ substituent include 9-cyclopentene 4-dedimethylamino minocycline.

In an embodiment, $R^9$ is a benzofuranyl group. Examples of minocycline compounds with this $R^5$ substituent include 9-benzofuranyl 4-dedimethylamino minocycline.

In an embodiment, $R^9$ is a phenylpropiononeamino group. Examples of minocycline compounds with this $R^9$ substituent include 9-(phenylpropiononeamino) 4-dedimethylamino minocycline.

In an embodiment, $R^9$ is a tosylamino group. Examples of minocycline compounds with this $R^9$ substituent include 9-tosylamino 4-dedimethylamino minocycline.

In an embodiment, $R^9$ is a methoxypyridyl group. Examples of minocycline compounds with this $R^5$ substituent include 9-(2-methoxy-3-pyridyl) 4-dedimethylamino minocycline.

In an embodiment, $R^9$ is a t-butylamide group. Examples of minocycline compounds with this $R^9$ substituent include 9-BOC-NH 4-dedimethylamino minocycline.

In an embodiment, $R^9$ is a hydroxybutylamino group. Examples of minocycline compounds with this $R^9$ substituent include 9-(N-2'-hydroxybutylamino) 4-dedimethylamino minocycline.

In an embodiment, $R^9$ is a hydroxypropylamino group. Examples of minocycline compounds with this $R^9$ substituent include 9-(N-3-chloro, 2-hydroxylpropylamino) 4-dedimethylamino minocycline. In an embodiment, $R^9$ is a phenyl group. Examples of minocycline compounds with this $R^9$ substituent include 9-phenyl 4-dedimethylamino minocycline HCl and 9-p-tolyl 4-dedimethylamino minocycline.

In an embodiment, $R^9$ is a nitrophenyl group. Examples of minocycline compounds with this $R^9$ substituent include 9-(3'-nitrophenyl) 4-dedimethylamino minocycline.

In an embodiment, $R^9$ is a nitrophenyl alkynyl group. Examples of minocycline compounds with this $R^9$ substituent include 9-(4'-nitrophenylethynyl) 4-dedimethylamino minocycline.

In an embodiment, $R^9$ is an aminophenyl group. Examples of minocycline compounds with this $R^9$ substituent include 9-(3-aminophenyl) 4-dedimethylamino minocycline.

In an embodiment, $R^9$ is a halophenyl urea group. Examples of minocycline compounds with this $R^9$ substituent include 9-(4-chloro,2-trifluoromethylphenyl) 4-dedimethylamino minocycline urea.

In an embodiment, $R^9$ is an alkoxyphenyl group. Examples of minocycline compounds with this $R^9$ substituent include 9-(p-methoxyphenyl) 4-dedimethylamino minocycline, 9-(4'-methoxyphenyl) 4-dedimethylamino minocycline, and 9-(3,4-methylenedioxyphenyl) 4-dedimethylamino minocycline.

In an embodiment, $R^9$ is a cyanophenyl group. Examples of minocycline compounds with this $R^9$ substituent include 9-(4'-cyanophenyl) 4-dedimethylamino minocycline.

In an embodiment, $R^9$ is a carboxyalkylphenyl group. Examples of minocycline compounds with this $R^9$ substituent include 9-(4'-carboxyphenyl) 4-dedimethylamino minocycline.

In an embodiment, $R^9$ is an acylphenyl group. Examples of minocycline compounds with this $R^9$ substituent include 9-(3-formylphenyl) 4-dedimethylamino minocycline.

In an embodiment, $R^9$ is a carboxyalkylphenyl group. Examples of minocycline compounds with this $R^9$ substituent include 9-(4'-carboxyphenyl) 4-dedimethylamino minocycline.

In an embodiment, $R^9$ is an acylphenyl group. Examples of minocycline compounds with this $R^9$ substituent include 9-(3-formylphenyl) 4-dedimethylamino minocycline.

In an embodiment, $R^9$ is an alkylphenyl group. Examples of minocycline compounds with this $R^9$ substituent include 9-(4'-t-butylphenyl) 4-dedimethylamino minocycline.

In an embodiment, $R^9$ is a halophenyl group. Examples of minocycline compounds with this $R^9$ substituent include 9-(3-chlorophenyl) 4-dedimethylamino minocycline, 9-(2',4'-difluorophenyl) 4-dedimethylamino minocycline, 9-(3,4-difluorophenyl) 4-dedimethylamino minocycline, 9-(4'-chlorophenyl) 4-dedimethylamino minocycline, 9-(3,4-dichlorophenyl) 4-dedimethylamino minocycline, and 9-(4'-trifluoromethylphenyl) 4-dedimethylamino minocycline.

In an embodiment, $R^9$ is an alkoxyphenyl group. Examples of minocycline compounds with this $R^9$ substituent include 9-(3-ethoxyphenyl) 4-dedimethylamino minocycline.

In an embodiment, $R^9$ is a carboxyalkylphenyl group. Examples of minocycline compounds with this $R^9$ substituent include 9-(4-carboxymethylphenyl) 4-dedimethylamino minocycline.

In an embodiment, $R^9$ is a phenylalkynyl group. Examples of minocycline compounds with this $R^9$ substituent include 9-(phenylethynyl) 4-dedimethylamino minocycline, 9-(3-hydroxyphenylethynyl) 4-dedimethylamino minocycline, 9-(p-tolylethynyl) 4-dedimethylamino minocycline, and 9-(p-methoxyphenylethynyl) 4-dedimethylamino minocycline.

In an embodiment, $R^9$ is an alkynyl group. Examples of minocycline compounds with this $R^9$ substituent include 9-ethynyl 4-dedimethylamino minocycline, 9-(p-fluoroethynyl) 4-dedimethylamino minocycline, 9-(trimethylsilylethynyl) 4-dedimethylamino minocycline, 9-(propionyl) 4-dedimethylamino minocycline, 9-(cyclohexenylethynyl) 4-dedimethylamino minocycline, and 9-(1-cyclohexyl-1-hydroxyethynyl) 4-dedimethylamino minocycline.

In an embodiment, $R^9$ is an alkylglycineethylester group. Examples of minocycline compounds with this $R^9$ substituent include 9-propylglycineethylester 4-dedimethylamino minocycline HCl, and 9-methylglycineethylester 4-dedimethylamino minocycline.

In an embodiment, $R^9$ is a styrene group. Examples of minocycline compounds with this $R^9$ substituent include 9-(styrene) 4-dedimethylamino minocycline, 9-(4'-fluorostyrene) 4-dedimethylamino minocycline.

In an embodiment, $R^9$ is a thiophene group. Examples of minocycline compounds with this $R^9$ substituent include 9-(2-thiophene) 4-dedimethylamino minocycline, and 9-(5'-chloro-2'-thiophene) 4-dedimethylamino minocycline.

In an embodiment, $R^9$ is an alkylaminophospho group. Examples of minocycline compounds with this $R^9$ substituent include 9-(p-methoxyphenylaminophospho) 4-dedimethylamino minocycline, and 9-(phenylaminophospho) 4-dedimethylamino minocycline.

IV. 13-Substituted 4-Dedimethylamino Tetracycline Compounds

The invention pertains to 13-substituted 4-dedimethylamino tetracycline compounds of the formula:

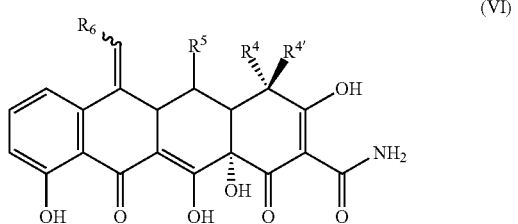

(VI)

wherein:

$R^4$ and $R^{4'}$ are each independently alkyl, alkenyl, alkynyl, hydroxyl, halogen, hydrogen, or when taken together the oxygen of a carbonyl group;

$R^5$ is hydrogen, hydroxyl, or a prodrug moiety;

$R^6$ is an alkyl or an aryl group, and pharmaceutically acceptable salts, esters, and prodrugs thereof.

The term "13-substituted 4-dedimethylamino tetracycline compounds" includes 4-dedimethylamino methacycline compounds with a substituent at the 13 position (e.g., a compound of formula I with a substituent at the $R^6$ position). In an embodiment, the 13-substituted 4-dedimethylamino methacycline compound is 13-substituted 4-dedimethylamino methacycline (e.g., wherein $R^4$ and $R^{4'}$ are hydrogen, and $R^5$ is hydroxyl). In another embodiment, $R^4$ and $R^{4'}$ taken together are the oxygen of a carbonyl group.

In a further embodiment, $R^6$ is a phenyl group, i.e., an alkoxyphenyl group, a halophenyl group, a carboxyphenyl group, an acylphenyl group, a cyanophenyl group, a nitrophenyl group, a naphthyl group, a dialkylphenyl group, or an alkylphenyl group; a t-butyl group; or an aminoalkanethio group.

In yet another embodiment, $R^6$ is a phenyl group, i.e., an alkoxyphenyl group, an halophenyl group, a carboxyphenyl group, an acylphenyl group, a cyanophenyl group, a nitrophenyl group, a naphthyl group or an alkylphenyl group; a t-butyl group; an aminoalkanethio group. Examples of compounds where $R^6$ is a phenyl group include 13-(phenyl) 4-dedimethylamino methacycline and 13-(4'-chlorophenyl-5-cyclohexanoate) 4-dedimethylamino methacycline.

In an embodiment, $R^6$ is an alkoxyphenyl group. Examples of such compounds include 13-(4'-methoxyphenyl) 4-dedimethylamino methacycline, 13-(methylenedioxyphenyl) 4-dedimethylamino methacycline, 13-(4'-ethoxyphenyl) 4-dedimethylamino methacycline, 13-(p-carbomethoxyphenyl) 4-dedimethylamino methacycline, and 13-(3',4'-methylenedioxyphenyl) 4-dedimethylamino methacycline.

In an embodiment, $R^6$ is a halophenyl group. Examples of such compounds include 13-(4'-fluorophenyl) 4-dedimethylamino methacycline, 13-(4'-chlorophenyl) 4-dedimethylamino methacycline, 13-(3'-chlorophenyl) 4-dedimethylamino methacycline, 13-(methylenedioxyphenyl) 4-dedimethylamino methacycline, 13-(3'-carboxylphenyl) 4-dedimethylamino methacycline, 13-(3'-4'-dichlorophenyl) 4-dedimethylamino methacycline, 13-(4'-acetylphenyl) 4-dedimethylamino methacycline, 13-(4'-ethoxyphenyl) 4-dedimethylamino methacycline, 13-(4'-chlorophenyl-5-cyclohexanoate) 4-dedimethylamino methacycline, 13-(3,5-difluorophenyl) 4-dedimethylamino methacycline, 13-(3'-acetylphenyl) 4-dedimethylamino methacycline, 13-(4'-bromophenyl) 4-dedimethylamino methacycline, 13-(2,4-difluorophenyl) 4-dedimethylamino methacycline, 13-(2-chlorophenyl) 4-dedimethylamino methacycline, 13-(p-carbomethoxyphenyl) 4-dedimethylamino methacycline, and 13-(trifluoromethylphenyl) 4-dedimethylamino methacycline.

In an embodiment, $R^6$ is a carboxyphenyl group. Examples of such compounds include 13-(3'-carboxylphenyl) 4-dedimethylamino methacycline.

In an embodiment, $R^6$ is an acylphenyl group. Examples of such compounds include 13-(3'-acetylphenyl) 4-dedimethylamino methacycline, 13-(4'-acetylphenyl) 4-dedimethylamino methacycline, and 13-(3'-formyl) 4-dedimethylamino methacycline.

In an embodiment, $R^6$ is a cyanophenyl group. Examples of such compounds include 13-(p-cyanophenyl) 4-dedimethylamino methacycline.

In an embodiment, $R^6$ is a nitrophenyl group. Examples of such compounds include 13-(4'-nitrophenyl) 4-dedimethylamino methacycline.

In an embodiment, $R^6$ is a naphthyl group. Examples of such compounds include 13-(naphthyl) 4-dedimethylamino methacycline.

In an embodiment, $R^6$ is an dialkylphenyl group. Examples of such compounds include 13-(3,5-dimethylphenyl) 4-dedimethylamino methacycline.

In an embodiment, $R^6$ is an alkylphenyl group. Examples of such compounds include 13-(p-t-butylphenyl) 4-dedimethylamino methacycline and 13-(p-tolyl) 4-dedimethylamino methacycline.

In an embodiment, $R^6$ is a t-butyl group. Examples of such compounds include 9,13-di-t-butyl) 4-dedimethylamino methacycline.

In an embodiment, $R^6$ is an aminoalkanethio group. Examples of such compounds include 13-(dimethylaminoethanethio) 4-dedimethylamino methacycline.

Examples of 13-substituted methacycline compounds include 13-(phenyl) 4-dedimethylamino methacycline, 13-(4'-chlorophenyl-5-cyclohexanoate) 4-dedimethylamino methacycline, 13-(4'-methoxyphenyl) 4-dedimethylamino methacycline, 13-(methylenedioxyphenyl) 4-dedimethylamino methacycline, 13-(4'-ethoxyphenyl) 4-dedimethylamino methacycline, 13-(p-carbomethoxyphenyl) 4-dedimethylamino ethylamino methacycline, 13-(3',4'-methylenedioxyphenyl) 4-dedimethylamino methacycline, 13-(4'-fluorophenyl) 4-dedimethylamino methacycline, 13-(4'-chlorophenyl) 4-dedimethylamino methacycline, 13-(3'-chlorophenyl) 4-dedimethylamino methacycline, 13-(methylenedioxyphenyl) 4-dedimethylamino methacycline, 13-(3'-carboxylphenyl) 4-dedimethylamino methacycline, 13-(3'-4'-dichlorophenyl) 4-dedimethylamino methacycline, 13-(4'-acetylphenyl) 4-dedimethylamino methacycline, 13-(4'-ethoxyphenyl) 4-dedimethylamino methacycline, 13-(4'-chlorophenyl-5-cyclohexanoate) 4-dedimethylamino methacycline, 13-(3,5-difluorophenyl) 4-dedimethylamino methacycline, 13-(3'-acetylphenyl) 4-dedimethylamino methacycline, 13-(4'-bromophenyl) 4-dedimethylamino methacycline, 13-(2,4-difluorophenyl) 4-dedimethylamino methacycline, 13-(2-chlorophenyl) 4-dedimethylamino methacycline, 13-(p-carbomethoxyphenyl) 4-dedimethylamino methacycline, 13-(trifluoromethylphenyl) 4-dedimethylamino methacycline, 13-(3'-carboxylphenyl) 4-dedimethylamino methacycline, 13-(3'-acetylphenyl) 4-dedimethylamino methacycline, 13-(4'-acetylphenyl) 4-dedimethylamino methacycline, 13-(3'-formyl) 4-dedimethylamino methacycline, 13-(p-cyanophenyl) 4-dedimethylamino methacycline, 13-(4'-nitrophenyl) 4-dedimethylamino methacycline, 13-(naphthyl) 4-dedimethylamino methacycline, 13-(p-t-butylphenyl) 4-dedimethylamino methacycline, 13-((3,5-dimethylphenyl) 4-dedimethylamino methacycline, 13-(p-tolyl) 4-dedimethylamino methacycline, 9,13-(di-t-butyl) 4-dedimethylamino methacycline, 13-(dimethylaminoethanethio) 4-dedimethylamino methacycline, and pharmaceutically acceptable esters, prodrugs, and salts thereof.

Other examples of compounds include:

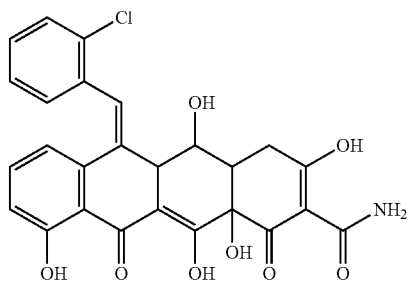

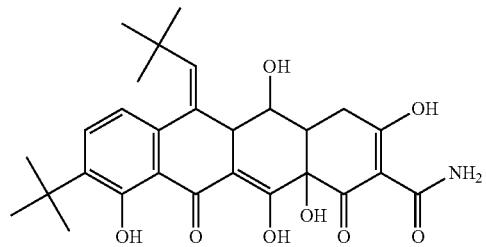

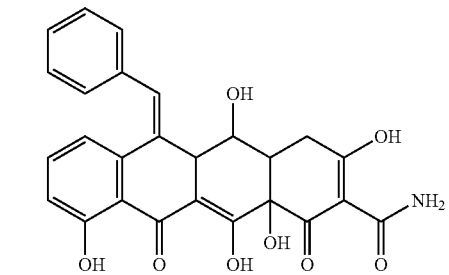

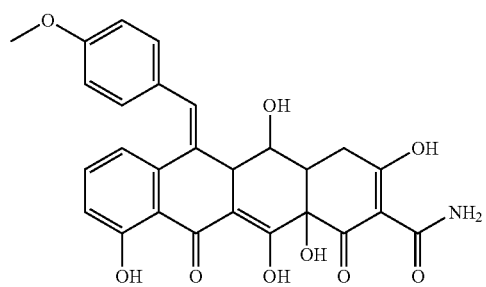

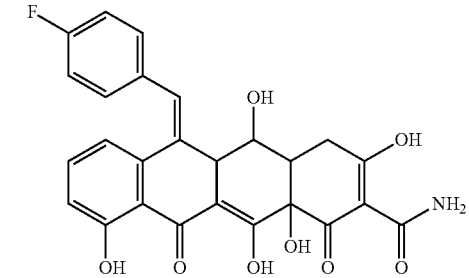

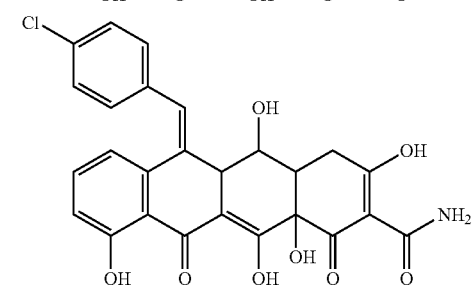

61
-continued
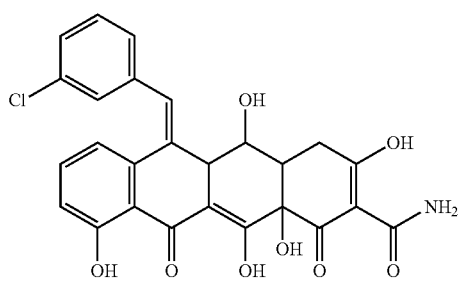
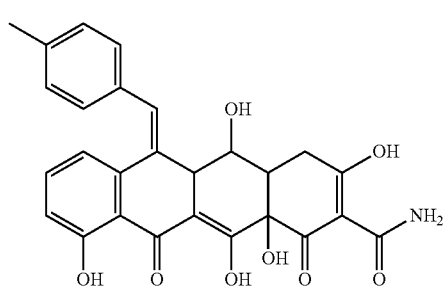
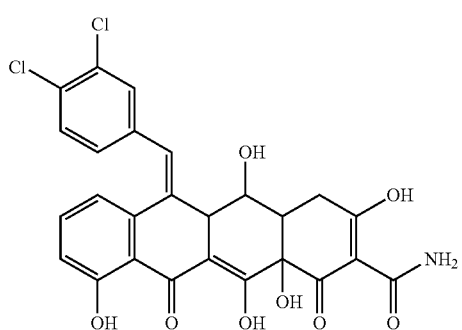
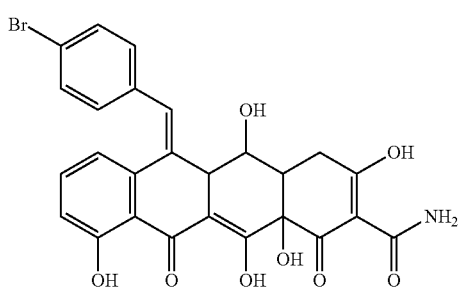
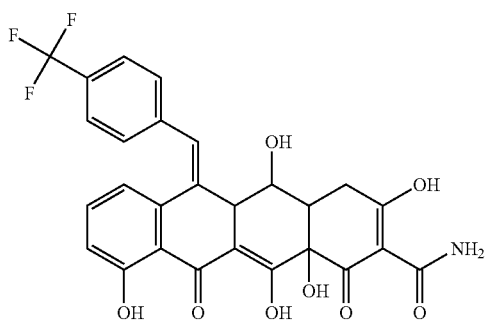
62
-continued
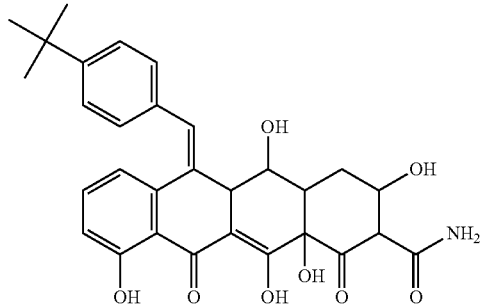
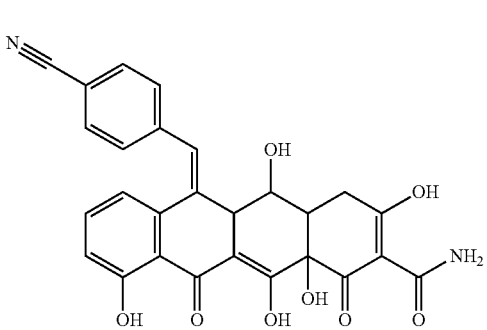
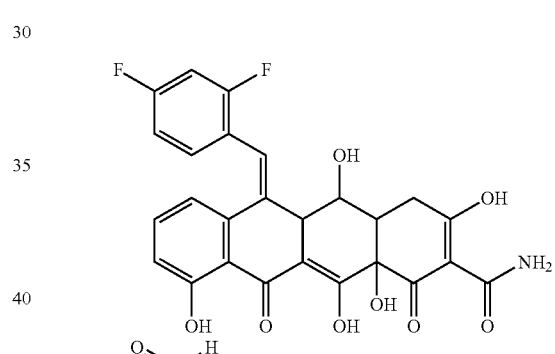
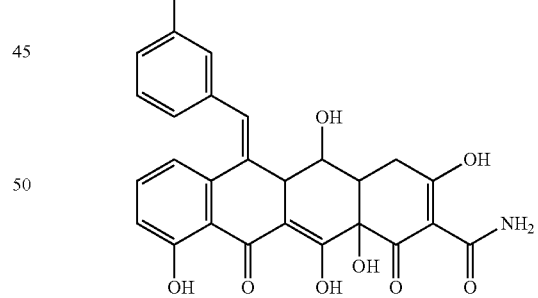
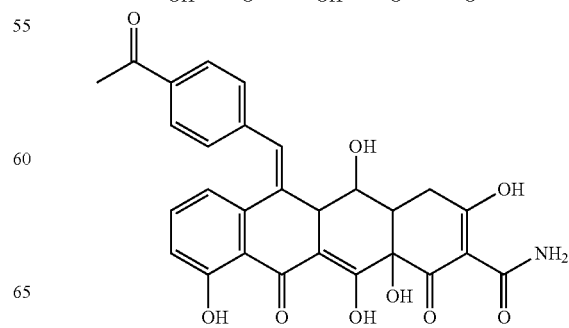

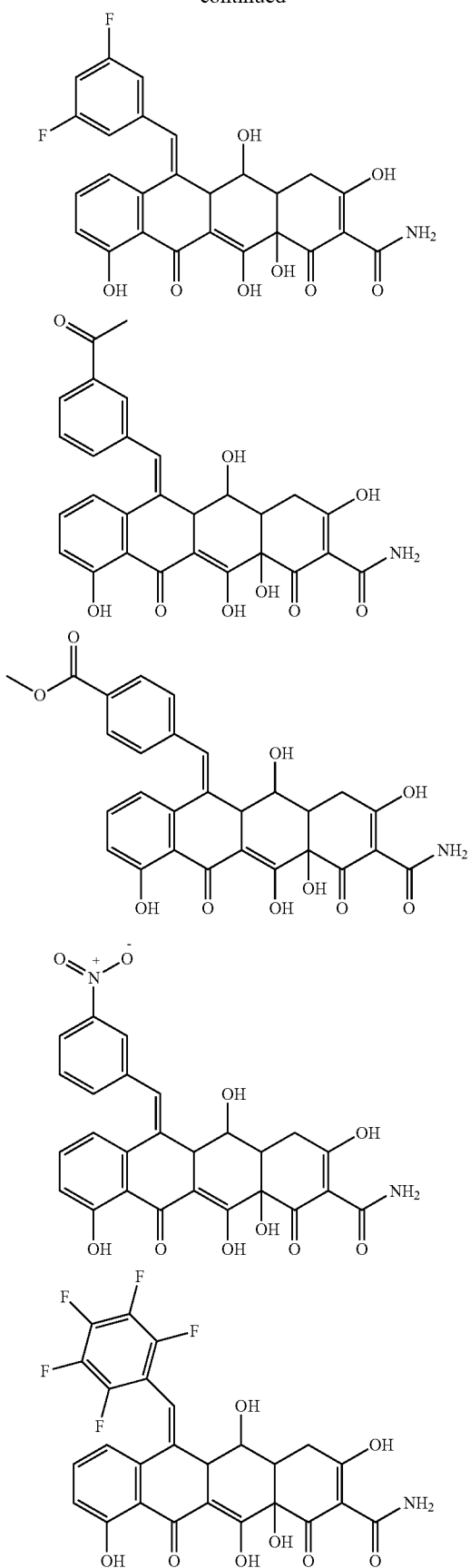

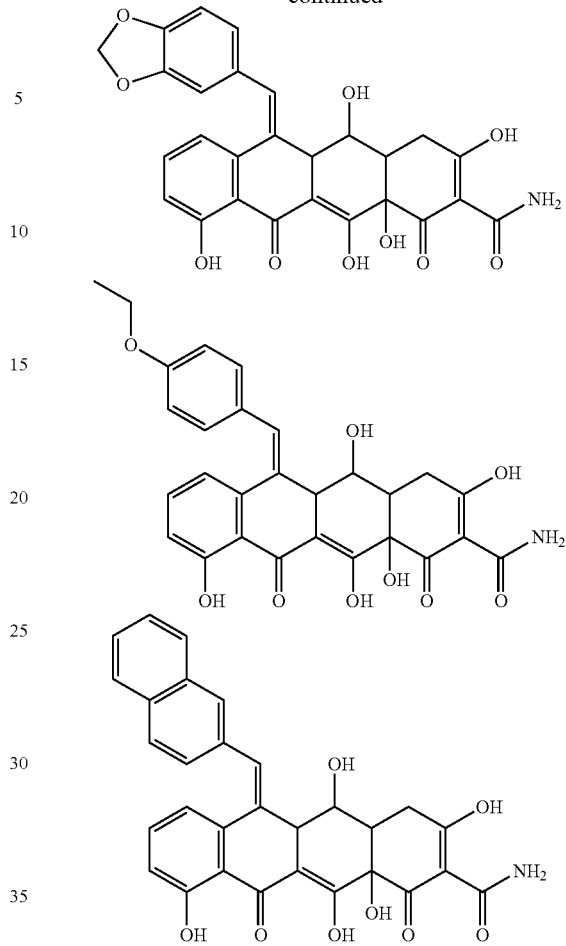

and pharmaceutically acceptable esters, salts, and prodrugs thereof.

VI. 8-Substituted 4-Dedimethylamino Tetracycline Compounds

The term "8-substituted 4-dedimethylamino tetracycline compounds" includes tetracycline compounds with a substituent at the 8 position, as described in formula I, and a substituent other than dimethylamino at the 8 position. In an embodiment, the substituted tetracycline compound is a substituted 4-dedimethylamino doxycycline derivative (e.g., wherein $R^4$ and $R^{4'}$ are hydrogen, $R^5$ is hydroxyl, $R^6$ is methyl, and $R^{6'}$ is hydrogen).

In an embodiment, the invention pertains, at least in part, to 8-substituted 4-dedimethylamino tetracycline compound of formula VII:

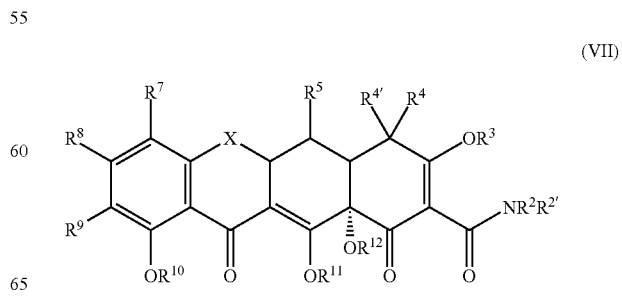

(VII)

wherein:

X is CHC($R^{13}$Y'Y), C$R^6R^6$, C=C$R^{6'}R^6$, S, N$R^6$, or O;

$R^2$ and $R^{2'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each independently alkyl, alkenyl, alkynyl, hydroxyl, halogen, hydrogen, or when taken together the oxygen of a carbonyl group;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is nitro, alkyl, alkenyl, alkynyl, aryl, alkoxy, alkylthio, alkylsulfinyl, alkylsulfonyl, arylalkyl, amino, arylalkenyl, arylalkynyl, or —$(CH_2)_{0-3}NR^{7c}C(=W')WR^{7a}$;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., —N=S), or —$(CH_2)_{0-3}NR^{9c}C(=Z')ZR^{9a}$;

Z is C$R^{9d}R^{9e}$, S, N$R^{9b}$ or O;

Z' is O, S, or N$R^{9f}$;

W is C$R^{7d}R^{7e}$, S, N$R^{7b}$ or O;

W' is O, N$R^{7f}$S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, prodrugs and esters thereof.

In an embodiment, X is C$R^6R^{6'}$; $R^2$, $R^{2'}$, $R^6$, $R^{6'}$, $R^8$, $R^9$, $R^{10}$, $R^{11}$, and $R^{12}$ are each hydrogen; $R^4$ and $R^{4'}$ are hydrogen, halogen (e.g., chlorine, fluorine, bromine, iodine, etc.), hydroxy, or when taken together the oxygen of a carbonyl group; and $R^5$ is hydroxy or hydrogen. In a further embodiment, $R^4$, $R^{4'}$, and $R^5$ are each hydrogen; $R^7$ is hydrogen; and $R^9$ is hydrogen or amino.

In another embodiment, $R^8$ is halogen, alkyl, alkenyl, alkynyl, aryl or heteroaryl. $R^8$ may be further substituted or unsubstituted.

In a further embodiment, $R^8$ is aryl. Examples of aryl $R^8$ groups include substituted or unsubstituted phenyl. The phenyl $R^8$ group can be substituted with any substituent which allow the tetracycline compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

The aryl $R^8$ group also may be heteroaryl. Examples of heteroaryl $R^8$ moieties include, but are not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In certain embodiments, the heteroaryl $R^7$ group is thiazolyl, thiophenyl, or furanyl.

$R^8$ also may be substituted or unsubstituted alkyl. The alkyl group can be a straight or branched chain, e.g., methyl, ethyl, i-propyl, n-propyl, n-butyl, i-butyl, t-butyl, pentyl, hexyl. etc. The alkyl group may also comprise a ring, e.g., a cycloalkyl (e.g., cyclopentyl, cyclohexyl, cyclopropyl, or cyclobutyl). The alkyl $R^8$ group may be substituted with any substituent or combination of substituents which allows the compound to perform its intended function. Examples of substituents include, but are not limited to, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

$R^8$ also may be substituted or unsubstituted alkenyl. Examples of substituents include those which allow the compound to perform its intended function. Examples of substituents include but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

Another example of $R^8$ include substituted and unsubstituted alkynyls. The alkynyl moieties can be substituted with any substituent or combination of substituents which allow the tetracycline compound of the invention to perform its intended function. Examples of the substituents include, but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

The invention pertains to, at least in part, to 8-substituted tetracycline compounds of the formula (VIII):

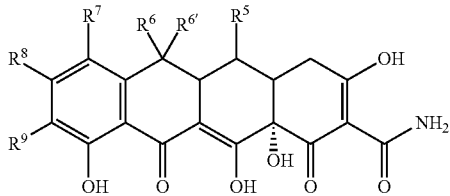

wherein:
$R^5$ is hydrogen or hydroxyl;
$R^6$ and $R^{6'}$ are each independently hydrogen, methyl, or hydroxyl;
$R^7$ is hydrogen,
$R^8$ is phenyl, nitrophenyl, halo, or lower alkynyl; and
$R^9$ is hydrogen or amino, and pharmaceutically acceptable salts, prodrugs and esters thereof.

In an embodiment, doxycycline derivatives of tetracycline compounds of the invention include compounds wherein $R^7$ is hydrogen, $R^8$ is halo, phenyl, or nitrophenyl, and $R^9$ is hydrogen. In an alternate embodiment, $R^7$ is hydrogen, $R^8$ is phenyl or lower alkynyl (e.g., ethynyl), and $R^9$ is amino.

Examples of such tetracycline compounds which are doxycycline derivatives include 8-phenyl 4-dedimethylamino doxycycline, 8-bromo 4-dedimethylamino doxycycline, 8-(p-nitrophenyl) 4-dedimethylamino doxycycline, 8-ethynyl-9-amino 4-dedimethylamino doxycycline, and 8-phenyl-9-amino 4-dedimethylamino doxycycline.

Other compounds of the invention are shown in Table 2, below.

TABLE 2

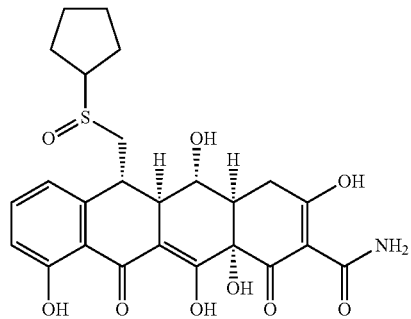 [SMILES: NC(=O)C1=C(O)C[C@@H]2[C@@H](O)[C@H]3C(=C(O)[C@]2(O)C1=O)C(=O)c1c(O)cccc1[C@@H]3CS(=O)C1CCCC1]

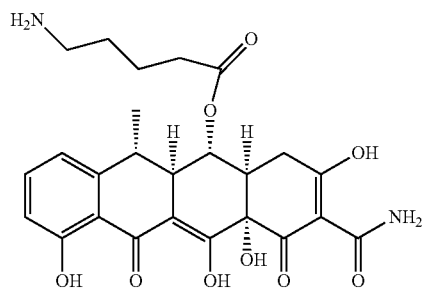 [SMILES: C[C@H]1c2cccc(O)c2C(=O)C2=C(O)[C@]3(O)C(=O)C(C(N)=O)=C(O)C[C@@H]3[C@@H](OC(=O)CCCCN)[C@@H]21]

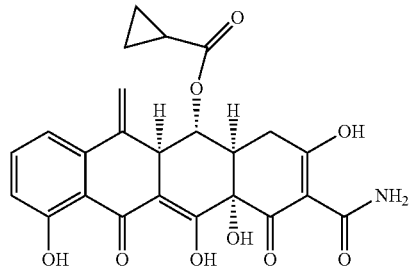 [SMILES: C=C1c2cccc(O)c2C(=O)C2=C(O)[C@]3(O)C(=O)C(C(N)=O)=C(O)C[C@@H]3[C@@H](OC(=O)C3CC3)[C@H]12]

TABLE 2-continued
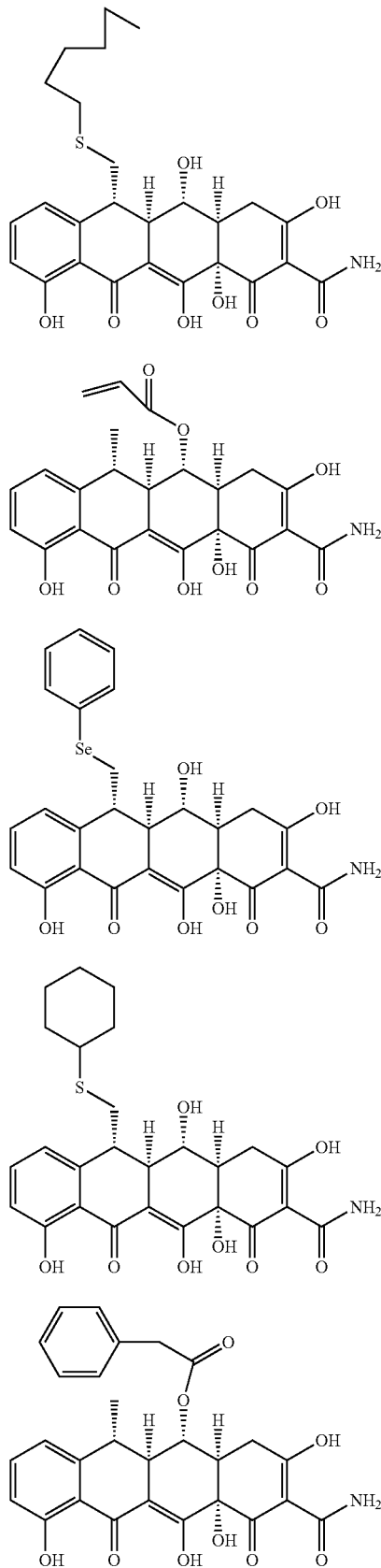

TABLE 2-continued
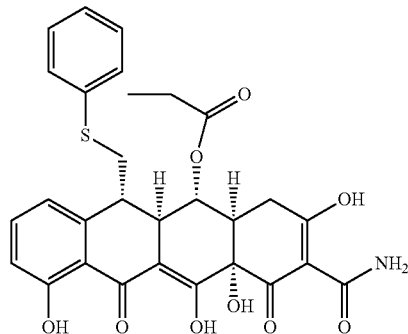 [SMILES: CCC(=O)O[C@H]1[C@H]2C(=C(O)[C@]3(O)C(=O)C(C(N)=O)=C(O)C[C@H]13)C(=O)c1c(O)cccc1[C@@H]2CSc1ccccc1]
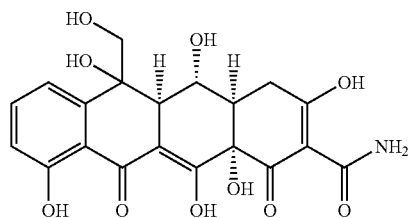 [SMILES: NC(=O)C1=C(O)C[C@@H]2[C@@H](O)[C@H]3C(=C(O)[C@]2(O)C1=O)C(=O)c1c(O)cccc1C3(O)CO]
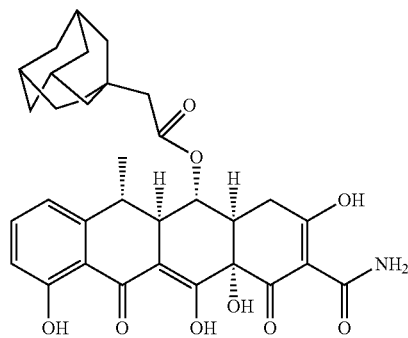 [SMILES: C[C@H]1c2cccc(O)c2C(=O)C2=C(O)[C@]3(O)C(=O)C(C(N)=O)=C(O)C[C@@H]3[C@@H](OC(=O)CC34CCC5CC(CC(C5)C3)C4)[C@@H]21]
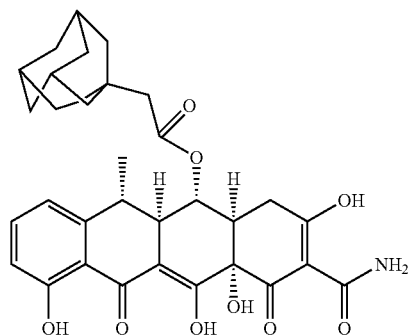 [SMILES: C[C@H]1c2cccc(O)c2C(=O)C2=C(O)[C@]3(O)C(=O)C(C(N)=O)=C(O)C[C@@H]3[C@@H](OC(=O)CC34CCC5CC(CC(C5)C3)C4)[C@@H]21]
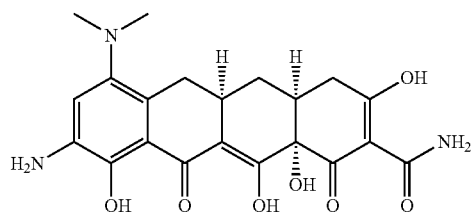 [SMILES: CN(C)c1cc(N)c(O)c2c1C[C@H]1C[C@H]3CC(O)=C(C(N)=O)C(=O)[C@@]3(O)C(O)=C1C2=O]

TABLE 2-continued
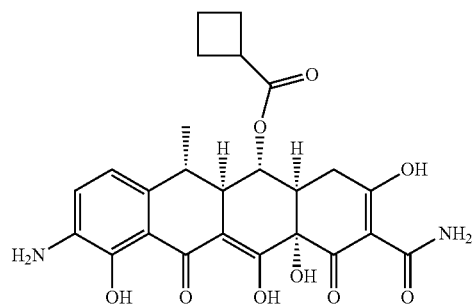 [SMILES: C[C@H]1c2ccc(N)c(O)c2C(=O)C2=C(O)[C@]3(O)C(=O)C(C(N)=O)=C(O)C[C@@H]3[C@@H](OC(=O)C3CCC3)[C@@H]21]
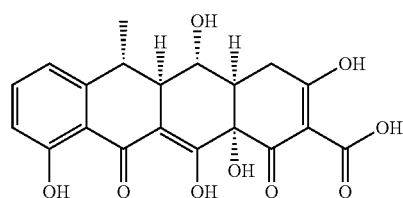 [SMILES: C[C@H]1c2cccc(O)c2C(=O)C2=C(O)[C@]3(O)C(=O)C(C(=O)O)=C(O)C[C@@H]3[C@@H](O)[C@@H]21]
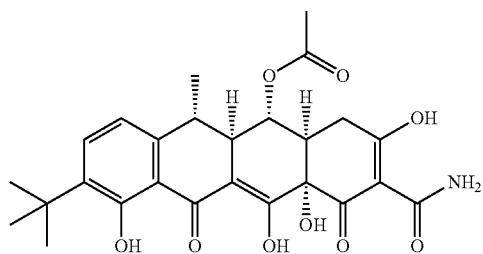 [SMILES: CC(=O)O[C@H]1[C@H]2C(=C(O)[C@]3(O)C(=O)C(C(N)=O)=C(O)C[C@H]13)C(=O)c1c(ccc(C(C)(C)C)c1O)[C@@H]2C]
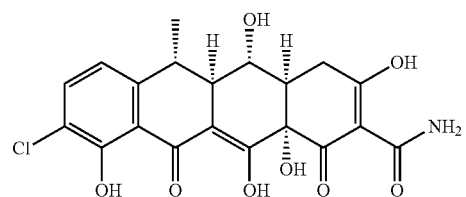 [SMILES: C[C@H]1c2ccc(Cl)c(O)c2C(=O)C2=C(O)[C@]3(O)C(=O)C(C(N)=O)=C(O)C[C@@H]3[C@@H](O)[C@@H]21]
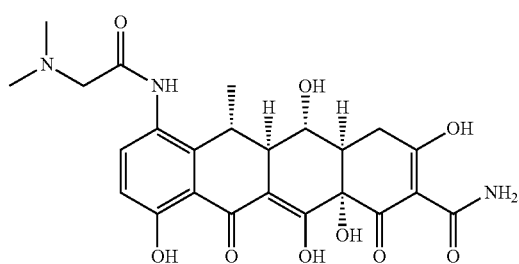 [SMILES: C[C@H]1c2c(NC(=O)CN(C)C)ccc(O)c2C(=O)C2=C(O)[C@]3(O)C(=O)C(C(N)=O)=C(O)C[C@@H]3[C@@H](O)[C@@H]21]
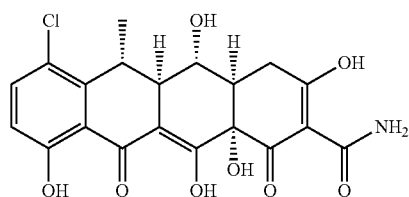 [SMILES: C[C@H]1c2c(Cl)ccc(O)c2C(=O)C2=C(O)[C@]3(O)C(=O)C(C(N)=O)=C(O)C[C@@H]3[C@@H](O)[C@@H]21]

TABLE 2-continued
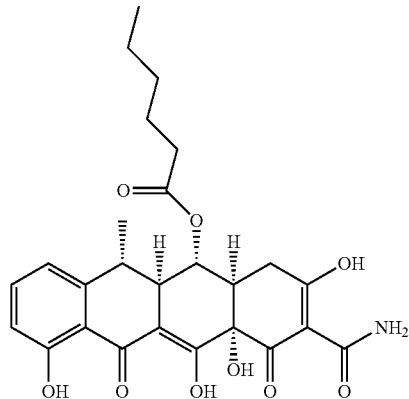 [SMILES: CCCCCC(=O)O[C@H]1[C@H]2C(=C(O)[C@]3(O)C(=O)C(C(N)=O)=C(O)C[C@H]13)C(=O)c1c(O)cccc1[C@@H]2C]
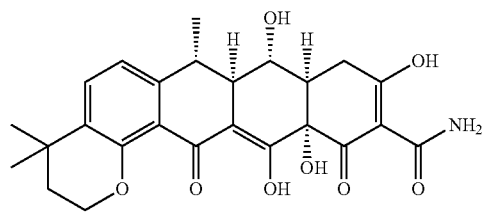 [SMILES: C[C@H]1c2ccc3c(c2C(=O)C2=C(O)[C@]4(O)C(=O)C(C(N)=O)=C(O)C[C@@H]4[C@@H](O)[C@@H]21)OCCC3(C)C]
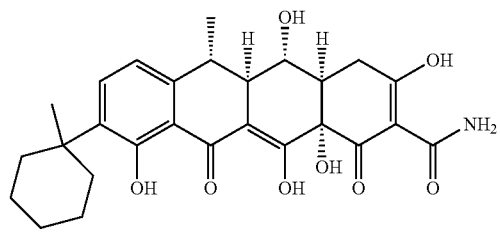 [SMILES: C[C@H]1c2ccc(C3(C)CCCCC3)c(O)c2C(=O)C2=C(O)[C@]3(O)C(=O)C(C(N)=O)=C(O)C[C@@H]3[C@@H](O)[C@@H]21]
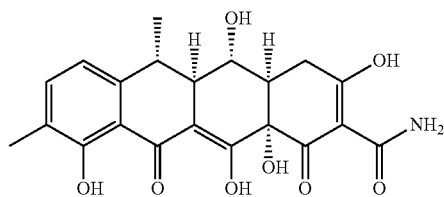 [SMILES: Cc1ccc2c(c1O)C(=O)C1=C(O)[C@]3(O)C(=O)C(C(N)=O)=C(O)C[C@@H]3[C@@H](O)[C@@H]1[C@H]2C]
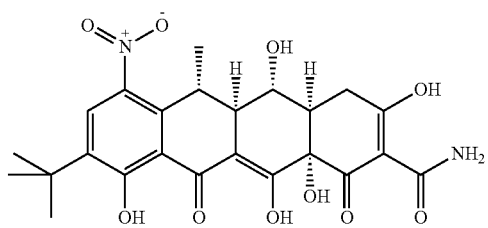
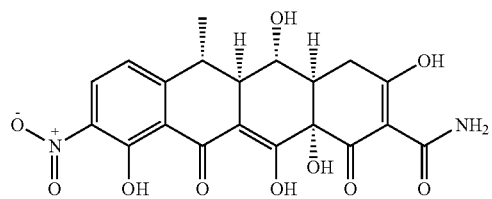

TABLE 2-continued
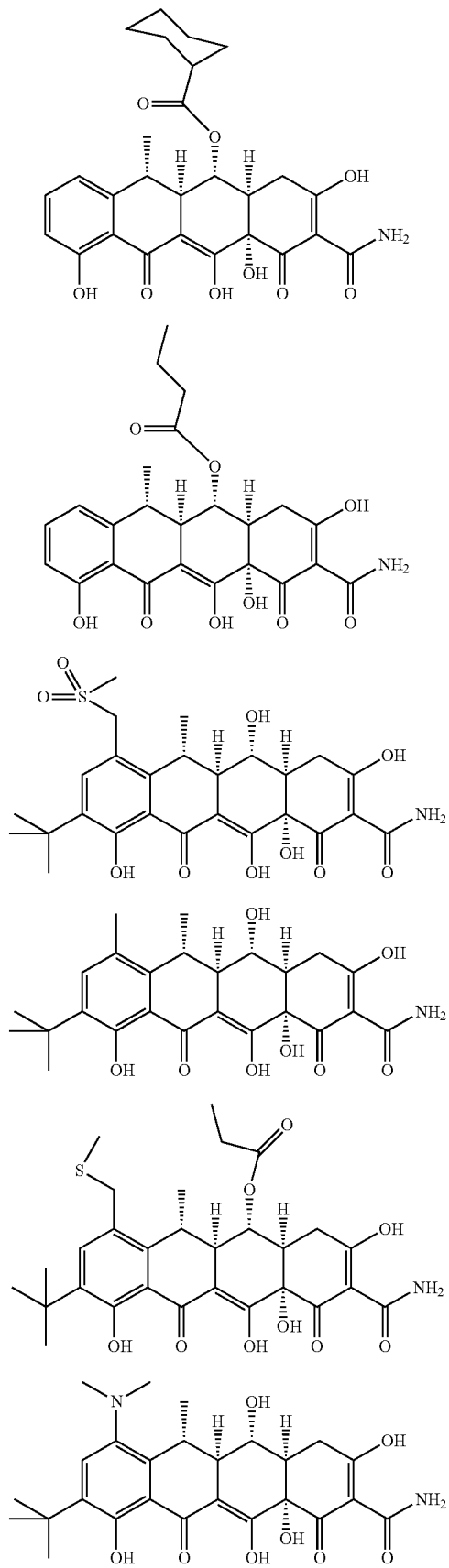

TABLE 2-continued
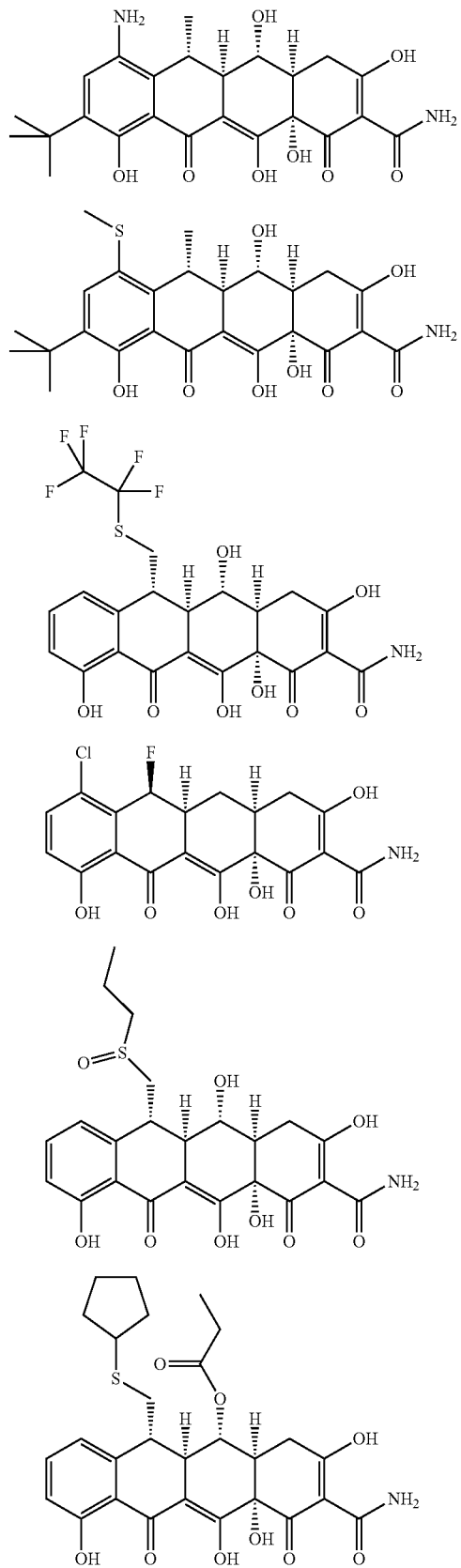

TABLE 2-continued
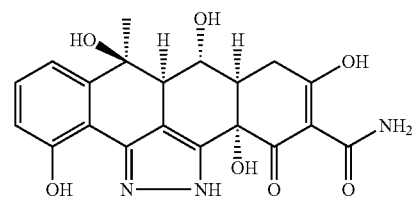 [SMILES: C[C@@]1(O)c2cccc(O)c2-c2n[nH]c3c2[C@@H]1[C@H](O)[C@H]1CC(O)=C(C(N)=O)C(=O)[C@@]31O]
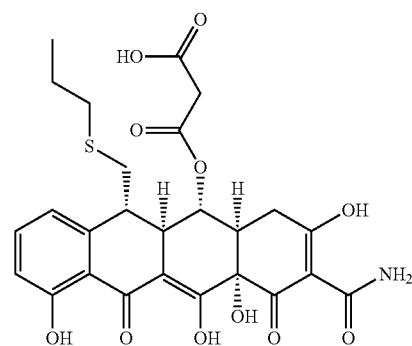 [SMILES: CCCSC[C@H]1c2cccc(O)c2C(=O)C2=C(O)[C@]3(O)C(=O)C(C(N)=O)=C(O)C[C@@H]3[C@@H](OC(=O)CC(=O)O)[C@@H]21]
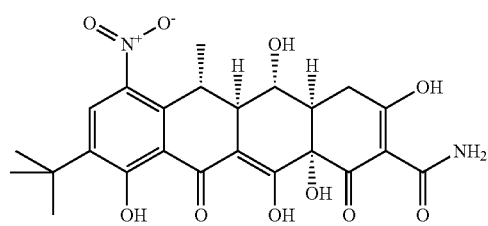 [SMILES: C[C@H]1c2c([N+](=O)[O-])cc(C(C)(C)C)c(O)c2C(=O)C2=C(O)[C@]3(O)C(=O)C(C(N)=O)=C(O)C[C@@H]3[C@@H](O)[C@@H]21]
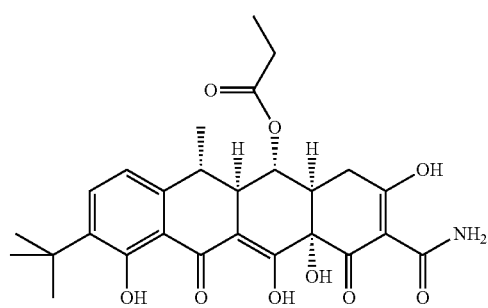 [SMILES: CCC(=O)O[C@H]1[C@H]2C(=C(O)[C@]3(O)C(=O)C(C(N)=O)=C(O)C[C@H]13)C(=O)c1c(ccc(C(C)(C)C)c1O)[C@@H]2C]
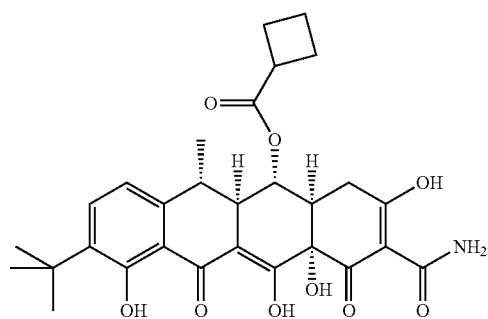 [SMILES: C[C@H]1c2ccc(C(C)(C)C)c(O)c2C(=O)C2=C(O)[C@]3(O)C(=O)C(C(N)=O)=C(O)C[C@@H]3[C@@H](OC(=O)C3CCC3)[C@@H]21]

TABLE 2-continued
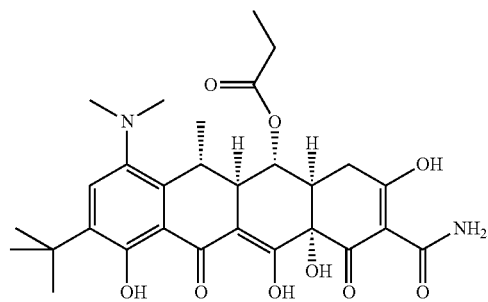 [SMILES: CCC(=O)O[C@H]1[C@H]2C(=C(O)[C@]3(O)C(=O)C(C(N)=O)=C(O)C[C@H]13)C(=O)c1c(O)c(C(C)(C)C)cc(N(C)C)c1[C@@H]2C]
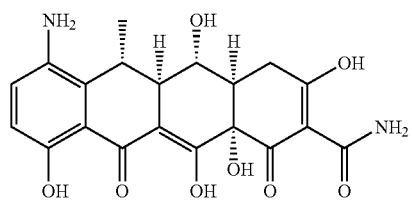 [SMILES: C[C@H]1c2c(N)ccc(O)c2C(=O)C2=C(O)[C@]3(O)C(=O)C(C(N)=O)=C(O)C[C@@H]3[C@@H](O)[C@@H]21]
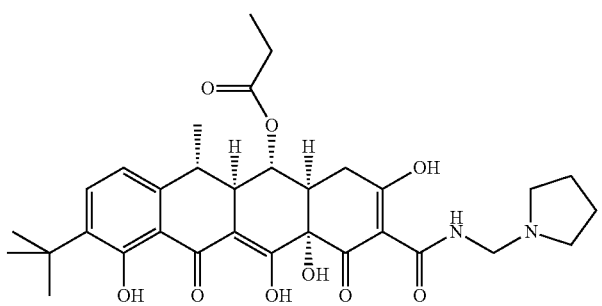 [SMILES: CCC(=O)O[C@H]1[C@H]2C(=C(O)[C@]3(O)C(=O)C(C(=O)NCN4CCCC4)=C(O)C[C@H]13)C(=O)c1c(ccc(C(C)(C)C)c1O)[C@@H]2C]
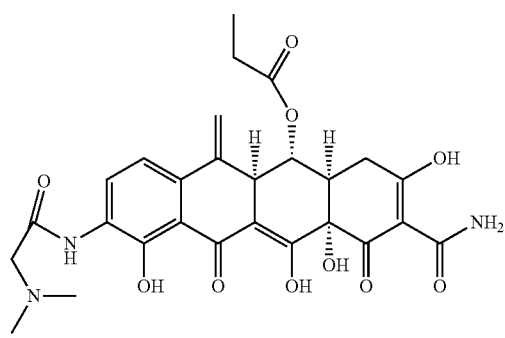 [SMILES: C=C1c2ccc(NC(=O)CN(C)C)c(O)c2C(=O)C2=C(O)[C@]3(O)C(=O)C(C(N)=O)=C(O)C[C@@H]3[C@@H](OC(=O)CC)[C@H]12]
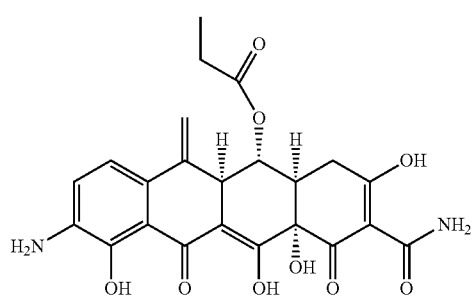 [SMILES: C=C1c2ccc(N)c(O)c2C(=O)C2=C(O)[C@]3(O)C(=O)C(C(N)=O)=C(O)C[C@@H]3[C@@H](OC(=O)CC)[C@H]12]

TABLE 2-continued
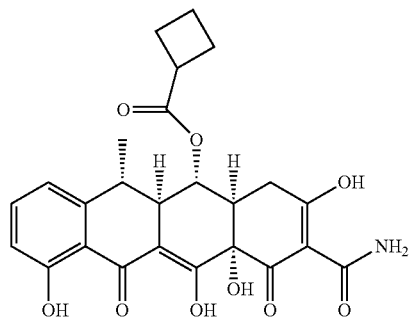 [SMILES: C[C@H]1c2cccc(O)c2C(=O)C2=C(O)[C@]3(O)C(=O)C(C(N)=O)=C(O)C[C@@H]3[C@@H](OC(=O)C3CCC3)[C@@H]21]
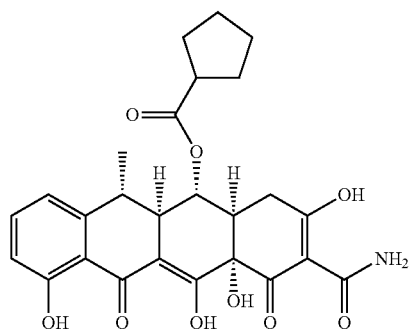 [SMILES: C[C@H]1c2cccc(O)c2C(=O)C2=C(O)[C@]3(O)C(=O)C(C(N)=O)=C(O)C[C@@H]3[C@@H](OC(=O)C3CCCC3)[C@@H]21]
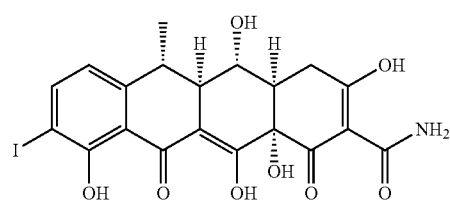 [SMILES: C[C@H]1c2ccc(I)c(O)c2C(=O)C2=C(O)[C@]3(O)C(=O)C(C(N)=O)=C(O)C[C@@H]3[C@@H](O)[C@@H]21]
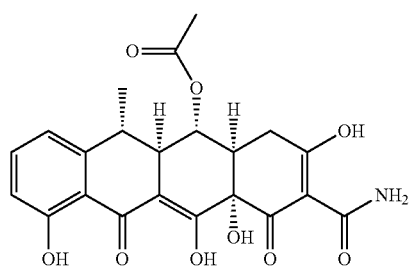 [SMILES: CC(=O)O[C@H]1[C@H]2C(=C(O)[C@]3(O)C(=O)C(C(N)=O)=C(O)C[C@H]13)C(=O)c1c(O)cccc1[C@@H]2C]
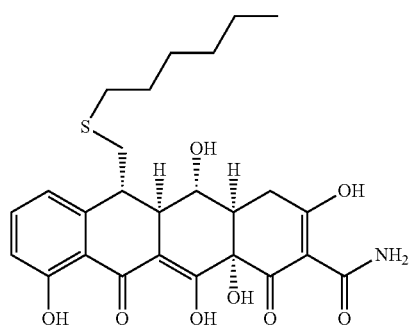 [SMILES: CCCCCCSC[C@H]1c2cccc(O)c2C(=O)C2=C(O)[C@]3(O)C(=O)C(C(N)=O)=C(O)C[C@@H]3[C@@H](O)[C@@H]21]

TABLE 2-continued
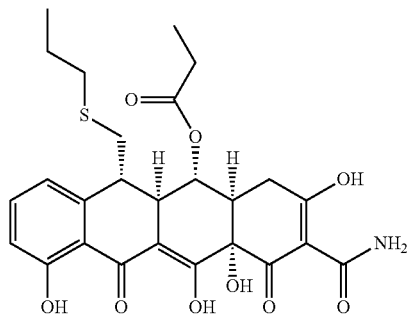 [SMILES: CCCSC[C@H]1c2cccc(O)c2C(=O)C2=C(O)[C@]3(O)C(=O)C(C(N)=O)=C(O)C[C@@H]3[C@@H](OC(=O)CC)[C@@H]21]
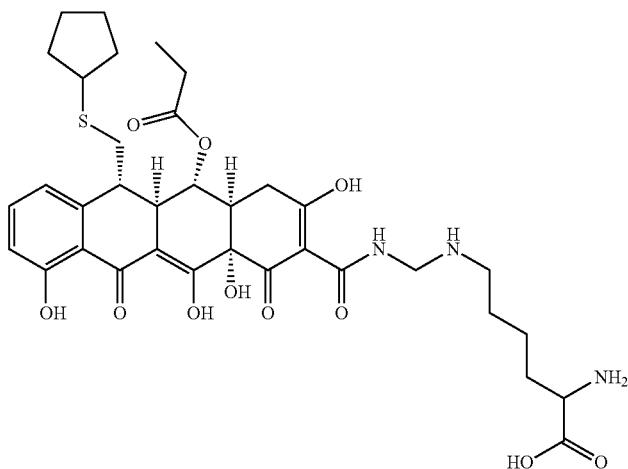 [SMILES: CCC(=O)O[C@H]1[C@H]2C(=C(O)[C@]3(O)C(=O)C(C(=O)NCNCCCCC(N)C(=O)O)=C(O)C[C@H]13)C(=O)c1c(O)cccc1[C@@H]2CSC1CCCC1]
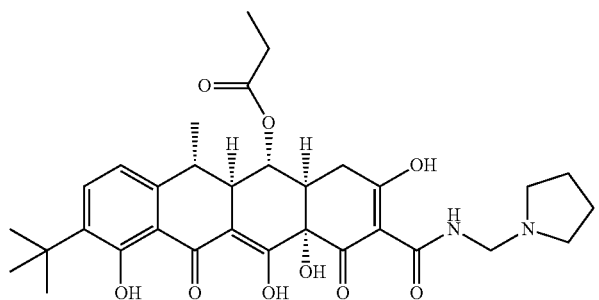 [SMILES: CCC(=O)O[C@H]1[C@H]2C(=C(O)[C@]3(O)C(=O)C(C(=O)NCN4CCCC4)=C(O)C[C@H]13)C(=O)c1c(ccc(C(C)(C)C)c1O)[C@@H]2C]
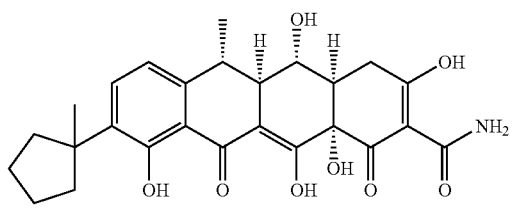 [SMILES: C[C@H]1c2ccc(C3(C)CCCC3)c(O)c2C(=O)C2=C(O)[C@]3(O)C(=O)C(C(N)=O)=C(O)C[C@@H]3[C@@H](O)[C@@H]21]
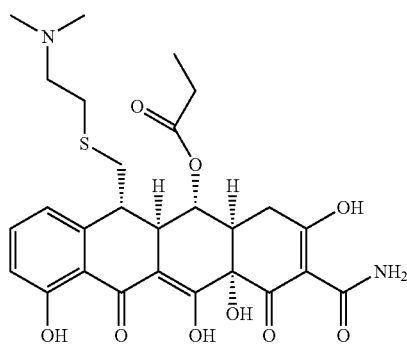 [SMILES: CCC(=O)O[C@H]1[C@H]2C(=C(O)[C@]3(O)C(=O)C(C(N)=O)=C(O)C[C@H]13)C(=O)c1c(O)cccc1[C@@H]2CSCCN(C)C]

TABLE 2-continued
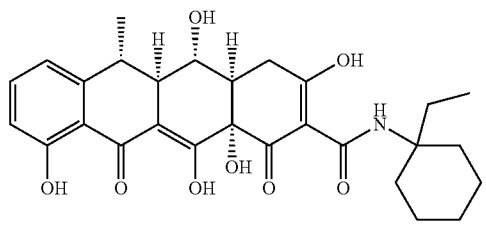 [SMILES: CCC1(NC(=O)C2=C(O)C[C@@H]3[C@@H](O)[C@H]4C(=C(O)[C@]3(O)C2=O)C(=O)c2c(O)cccc2[C@@H]4C)CCCCC1]
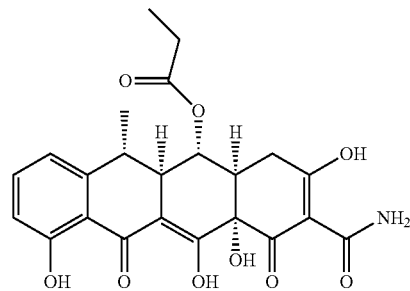 [SMILES: CCC(=O)O[C@H]1[C@H]2C(=C(O)[C@]3(O)C(=O)C(C(N)=O)=C(O)C[C@H]13)C(=O)c1c(O)cccc1[C@@H]2C]
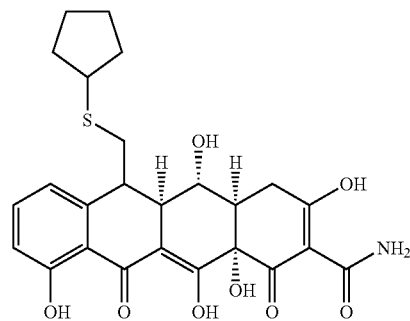 [SMILES: NC(=O)C1=C(O)C[C@@H]2[C@@H](O)[C@H]3C(=C(O)[C@]2(O)C1=O)C(=O)c1c(O)cccc1C3CSC1CCCC1]
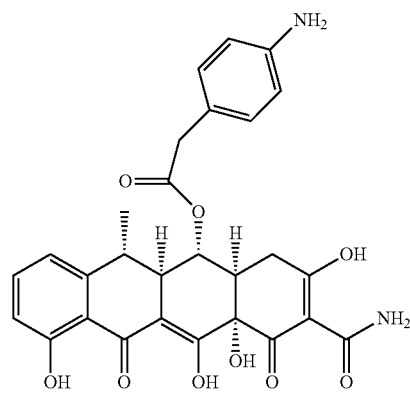 [SMILES: C[C@H]1c2cccc(O)c2C(=O)C2=C(O)[C@]3(O)C(=O)C(C(N)=O)=C(O)C[C@@H]3[C@@H](OC(=O)Cc3ccc(N)cc3)[C@@H]21]
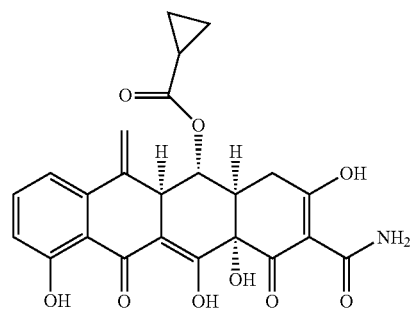 [SMILES: C=C1c2cccc(O)c2C(=O)C2=C(O)[C@]3(O)C(=O)C(C(N)=O)=C(O)C[C@@H]3[C@@H](OC(=O)C3CC3)[C@H]12]

TABLE 2-continued
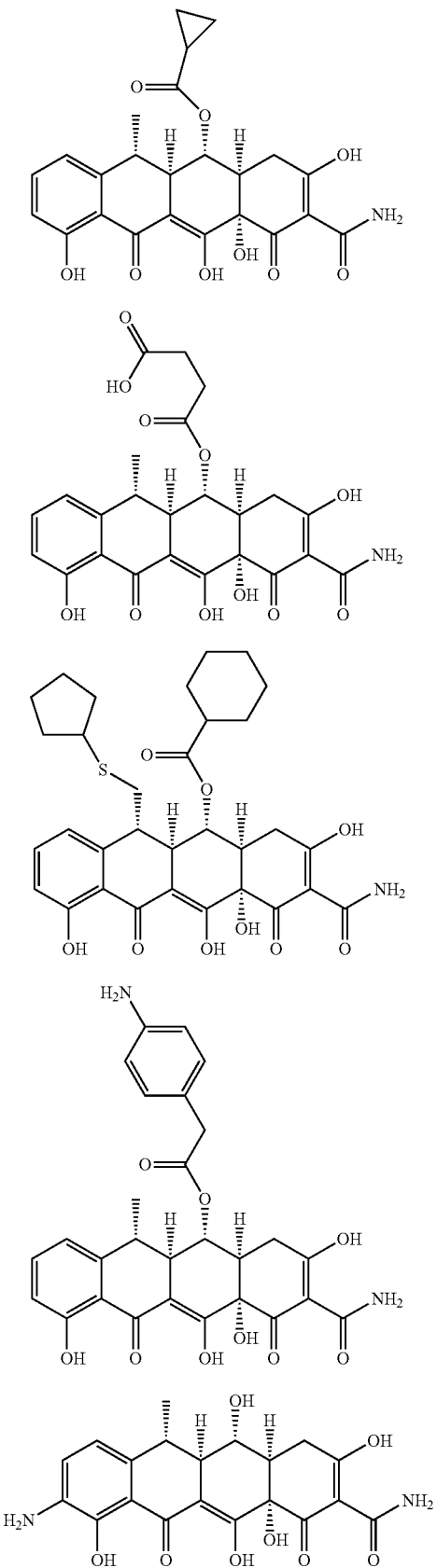

TABLE 2-continued
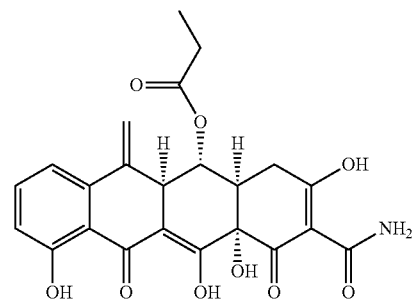 [SMILES: C=C1c2cccc(O)c2C(=O)C2=C(O)[C@]3(O)C(=O)C(C(N)=O)=C(O)C[C@@H]3[C@@H](OC(=O)CC)[C@H]12]
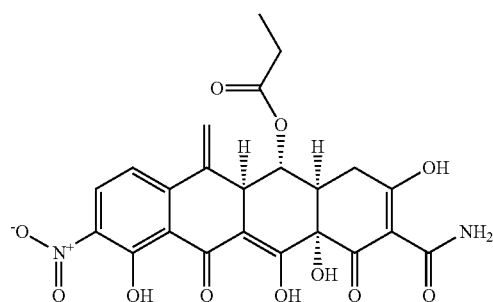
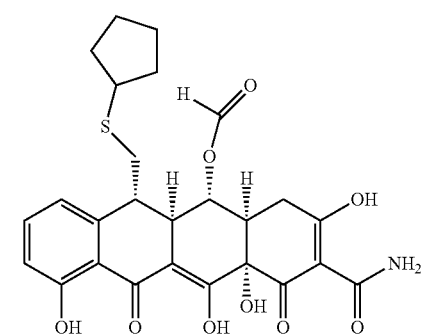 [SMILES: NC(=O)C1=C(O)C[C@@H]2[C@@H](OC=O)[C@H]3C(=C(O)[C@]2(O)C1=O)C(=O)c1c(O)cccc1[C@@H]3CSC1CCCC1]
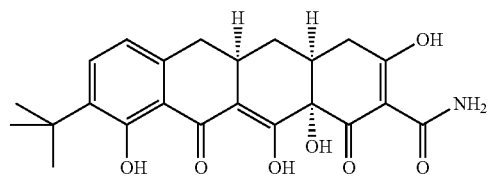 [SMILES: CC(C)(C)c1ccc2c(c1O)C(=O)C1=C(O)[C@]3(O)C(=O)C(C(N)=O)=C(O)C[C@@H]3C[C@@H]1C2]
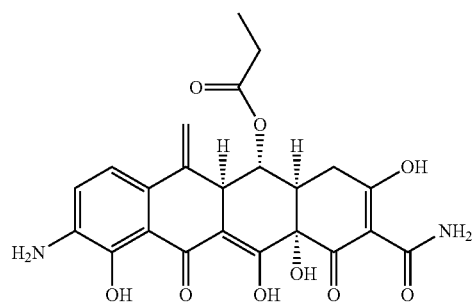 [SMILES: C=C1c2ccc(N)c(O)c2C(=O)C2=C(O)[C@]3(O)C(=O)C(C(N)=O)=C(O)C[C@@H]3[C@@H](OC(=O)CC)[C@H]12]

TABLE 2-continued
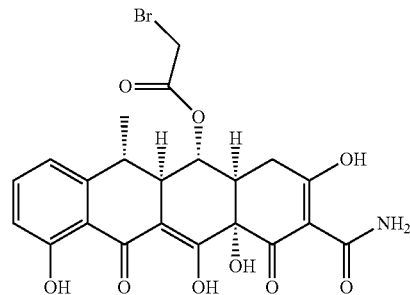 [SMILES: C[C@H]1c2cccc(O)c2C(=O)C2=C(O)[C@]3(O)C(=O)C(C(N)=O)=C(O)C[C@@H]3[C@@H](OC(=O)CBr)[C@@H]21]
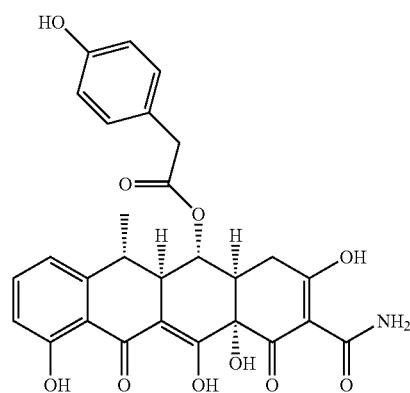 [SMILES: C[C@H]1c2cccc(O)c2C(=O)C2=C(O)[C@]3(O)C(=O)C(C(N)=O)=C(O)C[C@@H]3[C@@H](OC(=O)Cc3ccc(O)cc3)[C@@H]21]
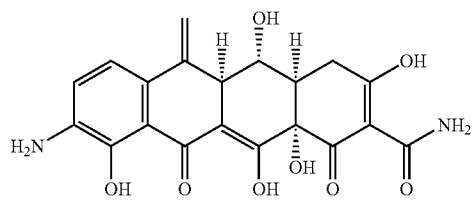 [SMILES: C=C1c2ccc(N)c(O)c2C(=O)C2=C(O)[C@]3(O)C(=O)C(C(N)=O)=C(O)C[C@@H]3[C@@H](O)[C@H]12]
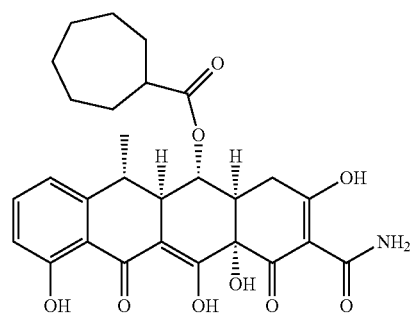 [SMILES: C[C@H]1c2cccc(O)c2C(=O)C2=C(O)[C@]3(O)C(=O)C(C(N)=O)=C(O)C[C@@H]3[C@@H](OC(=O)C3CCCCCC3)[C@@H]21]
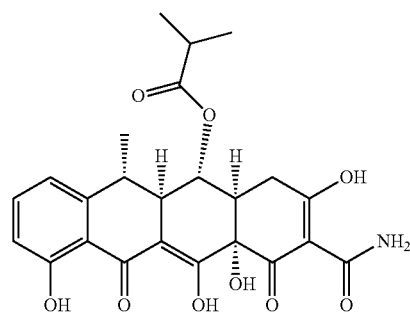 [SMILES: CC(C)C(=O)O[C@H]1[C@H]2C(=C(O)[C@]3(O)C(=O)C(C(N)=O)=C(O)C[C@H]13)C(=O)c1c(O)cccc1[C@@H]2C]

TABLE 2-continued
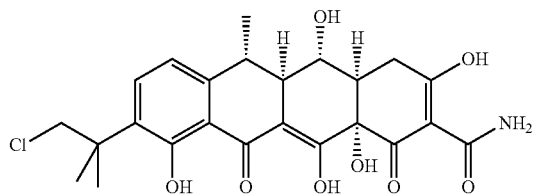 [SMILES: C[C@H]1c2ccc(C(C)(C)CCl)c(O)c2C(=O)C2=C(O)[C@]3(O)C(=O)C(C(N)=O)=C(O)C[C@@H]3[C@@H](O)[C@@H]21]
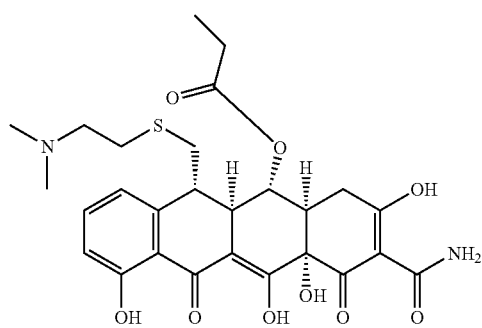 [SMILES: CCC(=O)O[C@H]1[C@H]2C(=C(O)[C@]3(O)C(=O)C(C(N)=O)=C(O)C[C@H]13)C(=O)c1c(O)cccc1[C@@H]2CSCCN(C)C]
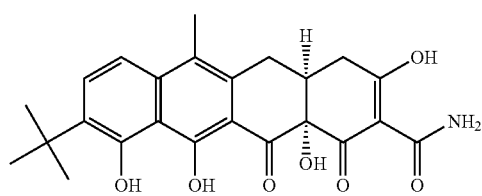 [SMILES: Cc1c2c(c(O)c3c(O)c(C(C)(C)C)ccc13)C(=O)[C@]1(O)C(=O)C(C(N)=O)=C(O)C[C@@H]1C2]
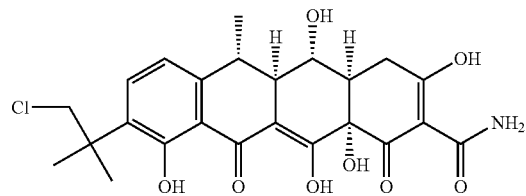 [SMILES: C[C@H]1c2ccc(C(C)(C)CCl)c(O)c2C(=O)C2=C(O)[C@]3(O)C(=O)C(C(N)=O)=C(O)C[C@@H]3[C@@H](O)[C@@H]21]
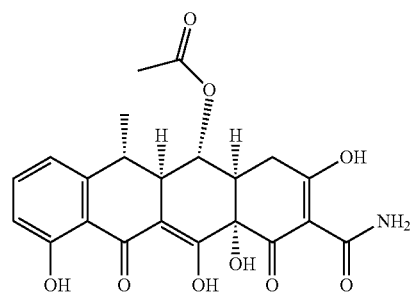 [SMILES: CC(=O)O[C@H]1[C@H]2C(=C(O)[C@]3(O)C(=O)C(C(N)=O)=C(O)C[C@H]13)C(=O)c1c(O)cccc1[C@@H]2C]
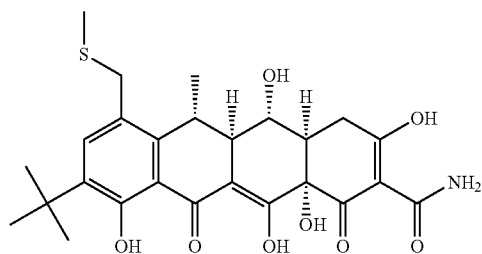 [SMILES: CSCc1cc(C(C)(C)C)c(O)c2c1[C@H](C)[C@@H]1C(=C(O)[C@]3(O)C(=O)C(C(N)=O)=C(O)C[C@@H]3[C@H]1O)C2=O]

TABLE 2-continued
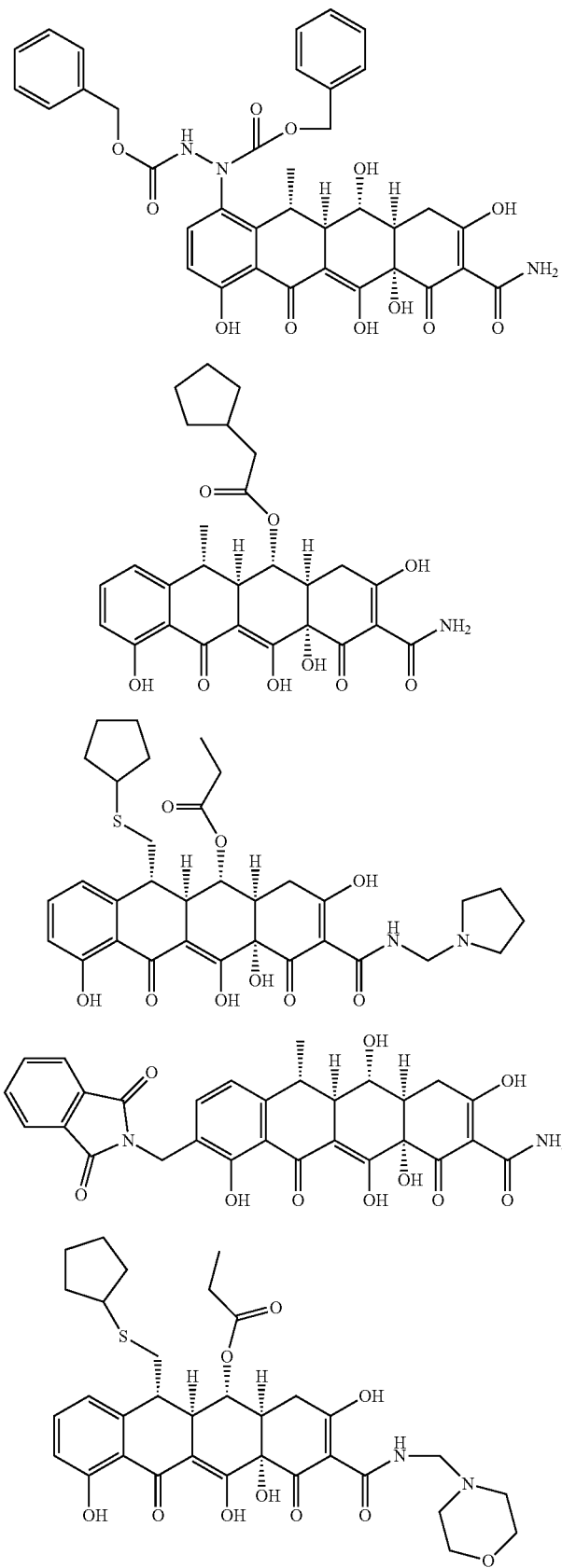

TABLE 2-continued
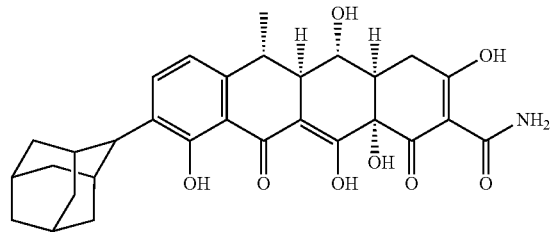 [SMILES: C[C@H]1c2ccc(C3C4CC5CC(C4)CC3C5)c(O)c2C(=O)C2=C(O)[C@]3(O)C(=O)C(C(N)=O)=C(O)C[C@@H]3[C@@H](O)[C@@H]21]
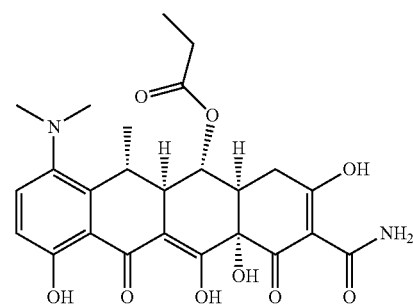 [SMILES: CCC(=O)O[C@H]1[C@H]2C(=C(O)[C@]3(O)C(=O)C(C(N)=O)=C(O)C[C@H]13)C(=O)c1c(O)ccc(N(C)C)c1[C@@H]2C]
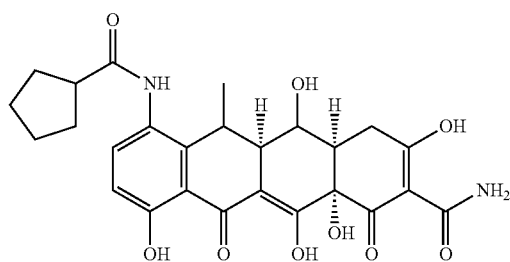 [SMILES: CC1c2c(NC(=O)C3CCCC3)ccc(O)c2C(=O)C2=C(O)[C@]3(O)C(=O)C(C(N)=O)=C(O)C[C@@H]3C(O)[C@@H]21]
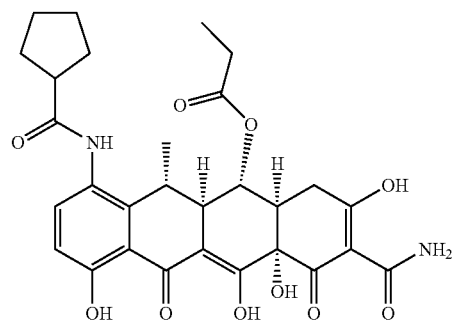 [SMILES: CCC(=O)O[C@H]1[C@H]2C(=C(O)[C@]3(O)C(=O)C(C(N)=O)=C(O)C[C@H]13)C(=O)c1c(O)ccc(NC(=O)C3CCCC3)c1[C@@H]2C]
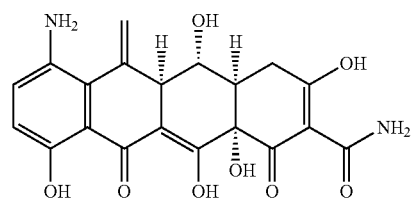 [SMILES: C=C1c2c(N)ccc(O)c2C(=O)C2=C(O)[C@]3(O)C(=O)C(C(N)=O)=C(O)C[C@@H]3[C@@H](O)[C@H]12]

TABLE 2-continued
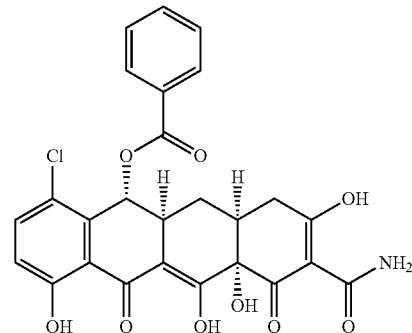 [SMILES: NC(=O)C1=C(O)C[C@@H]2C[C@H]3C(=C(O)[C@]2(O)C1=O)C(=O)c1c(O)ccc(Cl)c1[C@@H]3OC(=O)c1ccccc1]
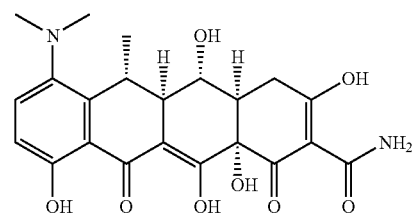 [SMILES: C[C@H]1c2c(N(C)C)ccc(O)c2C(=O)C2=C(O)[C@]3(O)C(=O)C(C(N)=O)=C(O)C[C@@H]3[C@@H](O)[C@@H]21]
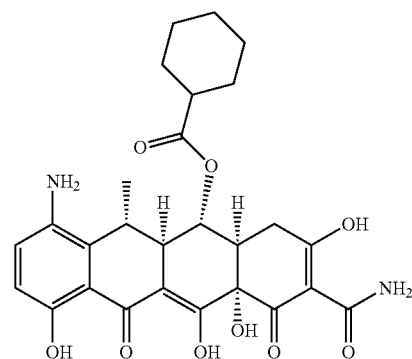 [SMILES: C[C@H]1c2c(N)ccc(O)c2C(=O)C2=C(O)[C@]3(O)C(=O)C(C(N)=O)=C(O)C[C@@H]3[C@@H](OC(=O)C3CCCCC3)[C@@H]21]
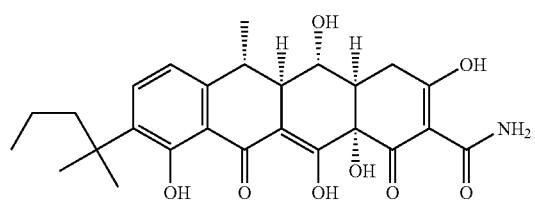 [SMILES: CCCC(C)(C)c1ccc2c(c1O)C(=O)C1=C(O)[C@]3(O)C(=O)C(C(N)=O)=C(O)C[C@@H]3[C@@H](O)[C@@H]1[C@H]2C]
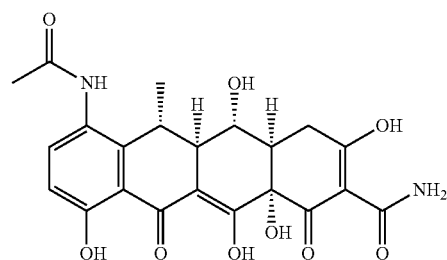 [SMILES: CC(=O)Nc1ccc(O)c2c1[C@H](C)[C@@H]1C(=C(O)[C@]3(O)C(=O)C(C(N)=O)=C(O)C[C@@H]3[C@H]1O)C2=O]

TABLE 2-continued
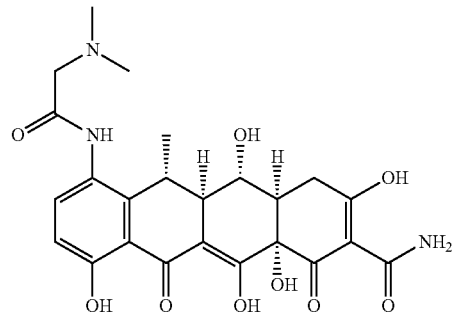 [SMILES: C[C@H]1c2c(NC(=O)CN(C)C)ccc(O)c2C(=O)C2=C(O)[C@]3(O)C(=O)C(C(N)=O)=C(O)C[C@@H]3[C@@H](O)[C@@H]21]
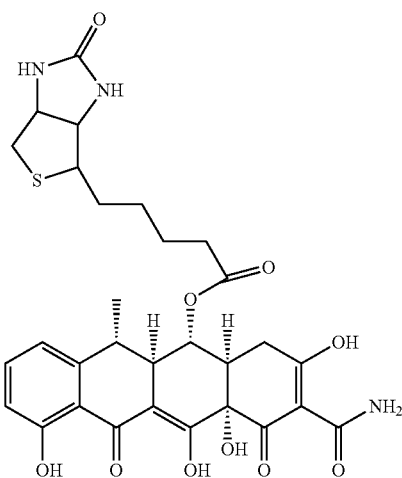 [SMILES: C[C@H]1c2cccc(O)c2C(=O)C2=C(O)[C@]3(O)C(=O)C(C(N)=O)=C(O)C[C@@H]3[C@@H](OC(=O)CCCCC3SCC4NC(=O)NC43)[C@@H]21]
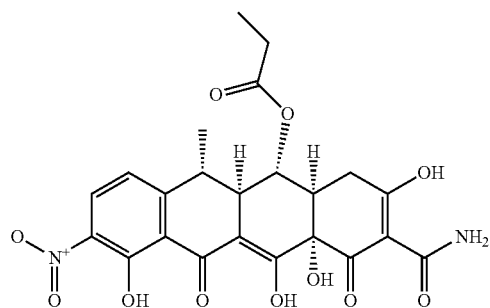
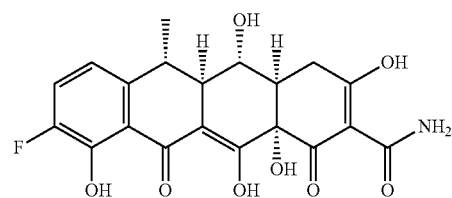 [SMILES: C[C@H]1c2ccc(F)c(O)c2C(=O)C2=C(O)[C@]3(O)C(=O)C(C(N)=O)=C(O)C[C@@H]3[C@@H](O)[C@@H]21]
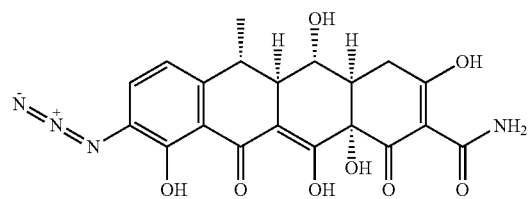

TABLE 2-continued
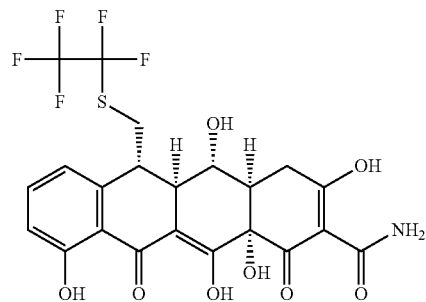 [SMILES: NC(=O)C1=C(O)C[C@@H]2[C@@H](O)[C@H]3C(=C(O)[C@]2(O)C1=O)C(=O)c1c(O)cccc1[C@@H]3CSC(F)(F)C(F)(F)F]
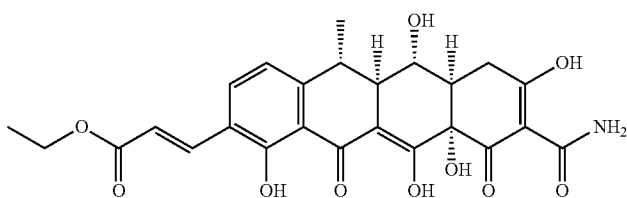 [SMILES: CCOC(=O)/C=C/c1ccc2c(c1O)C(=O)C1=C(O)[C@]3(O)C(=O)C(C(N)=O)=C(O)C[C@@H]3[C@@H](O)[C@@H]1[C@H]2C]
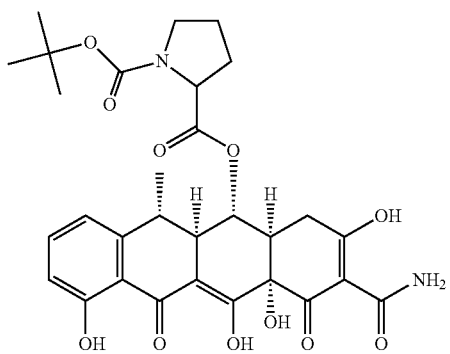 [SMILES: C[C@H]1c2cccc(O)c2C(=O)C2=C(O)[C@]3(O)C(=O)C(C(N)=O)=C(O)C[C@@H]3[C@@H](OC(=O)C3CCCN3C(=O)OC(C)(C)C)[C@@H]21]
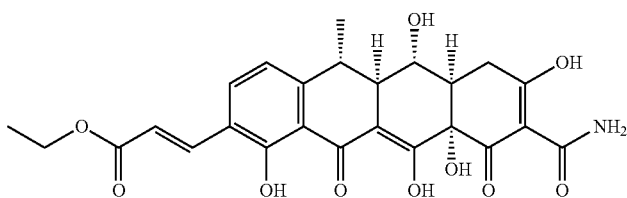 [SMILES: CCOC(=O)/C=C/c1ccc2c(c1O)C(=O)C1=C(O)[C@]3(O)C(=O)C(C(N)=O)=C(O)C[C@@H]3[C@@H](O)[C@@H]1[C@H]2C]
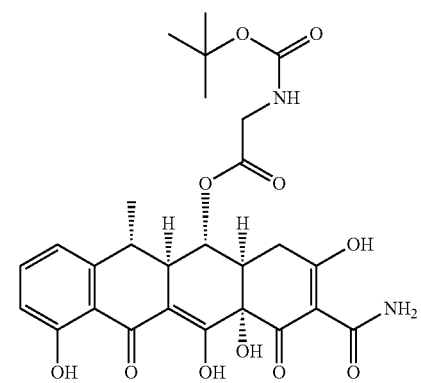 [SMILES: C[C@H]1c2cccc(O)c2C(=O)C2=C(O)[C@]3(O)C(=O)C(C(N)=O)=C(O)C[C@@H]3[C@@H](OC(=O)CNC(=O)OC(C)(C)C)[C@@H]21]

TABLE 2-continued
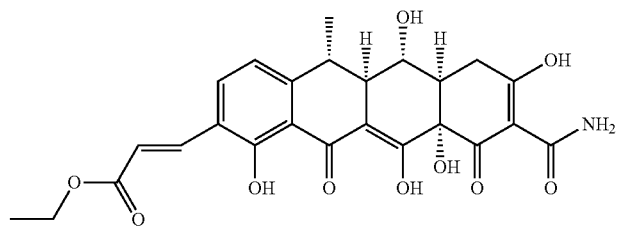 [SMILES: CCOC(=O)/C=C/c1ccc2c(c1O)C(=O)C1=C(O)[C@]3(O)C(=O)C(C(N)=O)=C(O)C[C@@H]3[C@@H](O)[C@@H]1[C@H]2C]
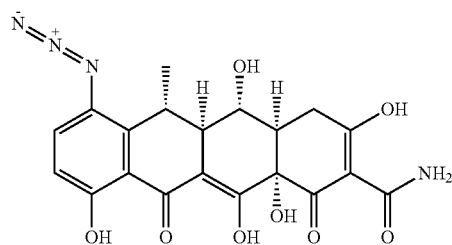
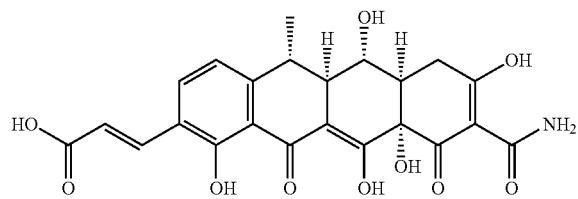 [SMILES: C[C@H]1c2ccc(/C=C/C(=O)O)c(O)c2C(=O)C2=C(O)[C@]3(O)C(=O)C(C(N)=O)=C(O)C[C@@H]3[C@@H](O)[C@@H]21]
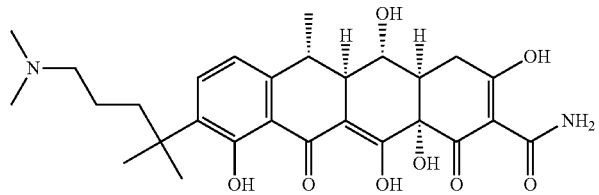 [SMILES: C[C@H]1c2ccc(C(C)(C)CCCN(C)C)c(O)c2C(=O)C2=C(O)[C@]3(O)C(=O)C(C(N)=O)=C(O)C[C@@H]3[C@@H](O)[C@@H]21]
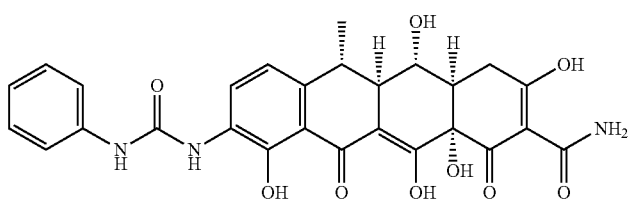 [SMILES: C[C@H]1c2ccc(NC(=O)Nc3ccccc3)c(O)c2C(=O)C2=C(O)[C@]3(O)C(=O)C(C(N)=O)=C(O)C[C@@H]3[C@@H](O)[C@@H]21]
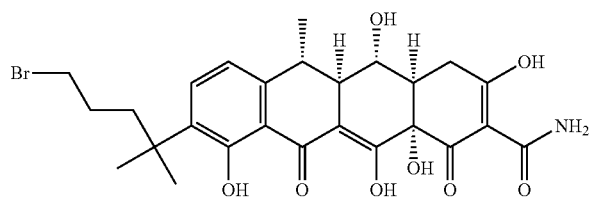 [SMILES: C[C@H]1c2ccc(C(C)(C)CCCBr)c(O)c2C(=O)C2=C(O)[C@]3(O)C(=O)C(C(N)=O)=C(O)C[C@@H]3[C@@H](O)[C@@H]21]
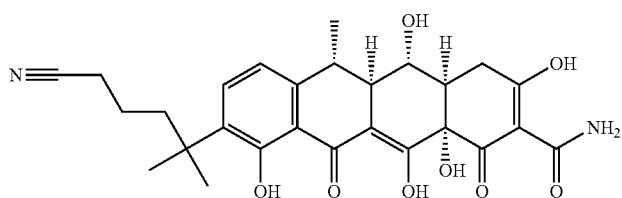 [SMILES: C[C@H]1c2ccc(C(C)(C)CCCC#N)c(O)c2C(=O)C2=C(O)[C@]3(O)C(=O)C(C(N)=O)=C(O)C[C@@H]3[C@@H](O)[C@@H]21]

TABLE 2-continued
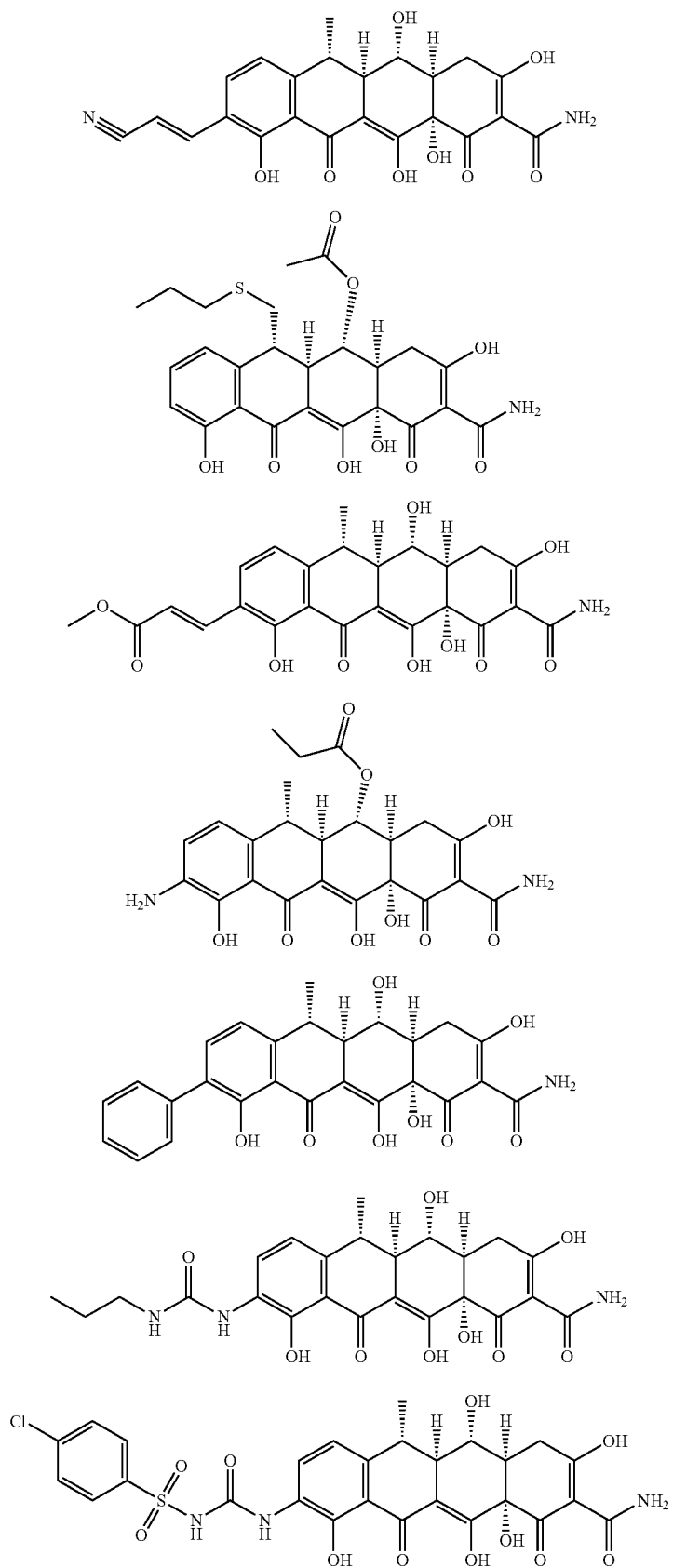

TABLE 2-continued
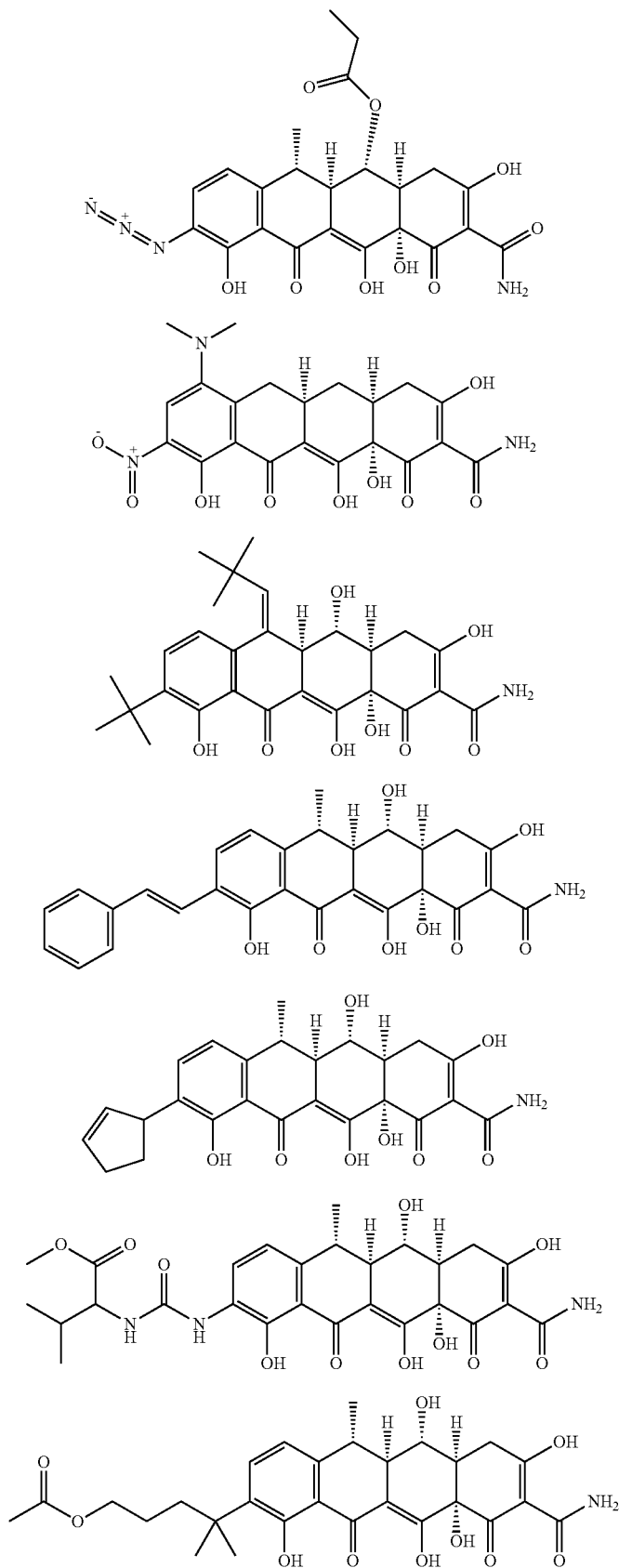

TABLE 2-continued
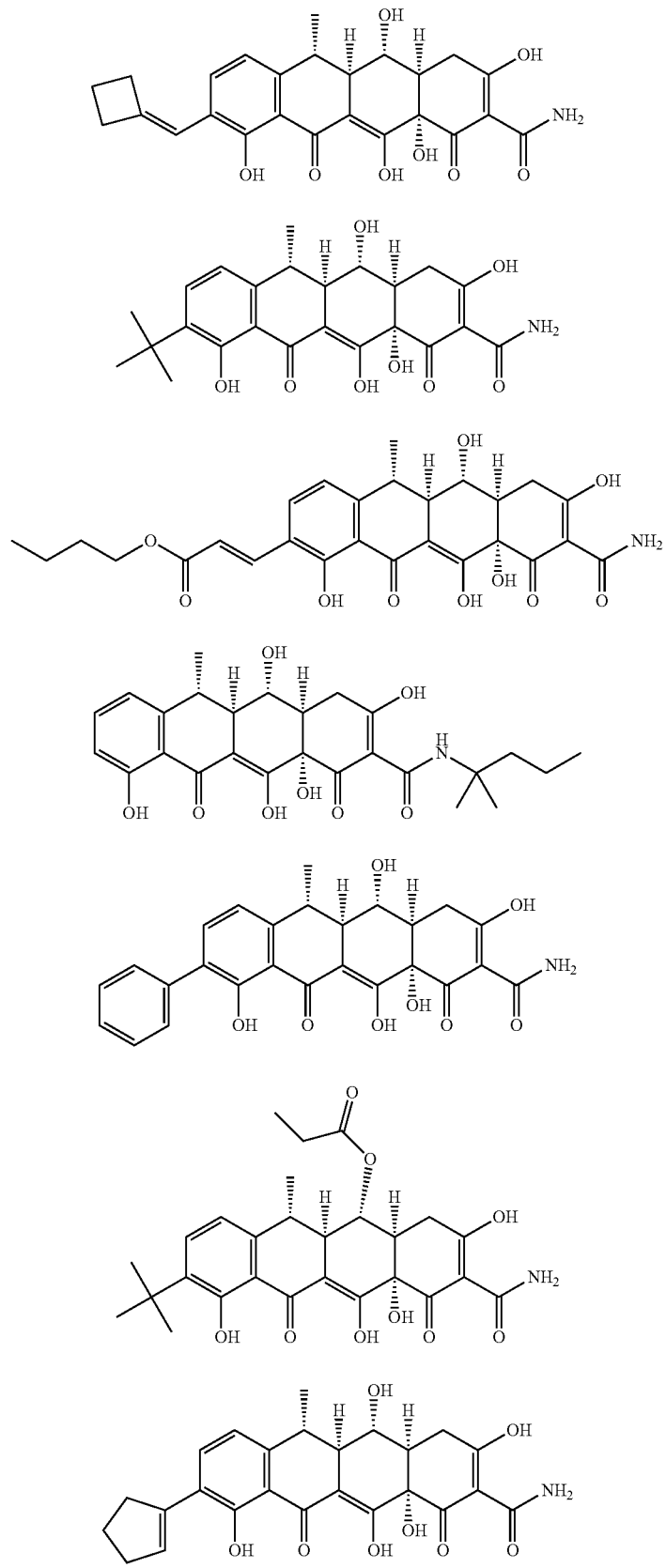

TABLE 2-continued
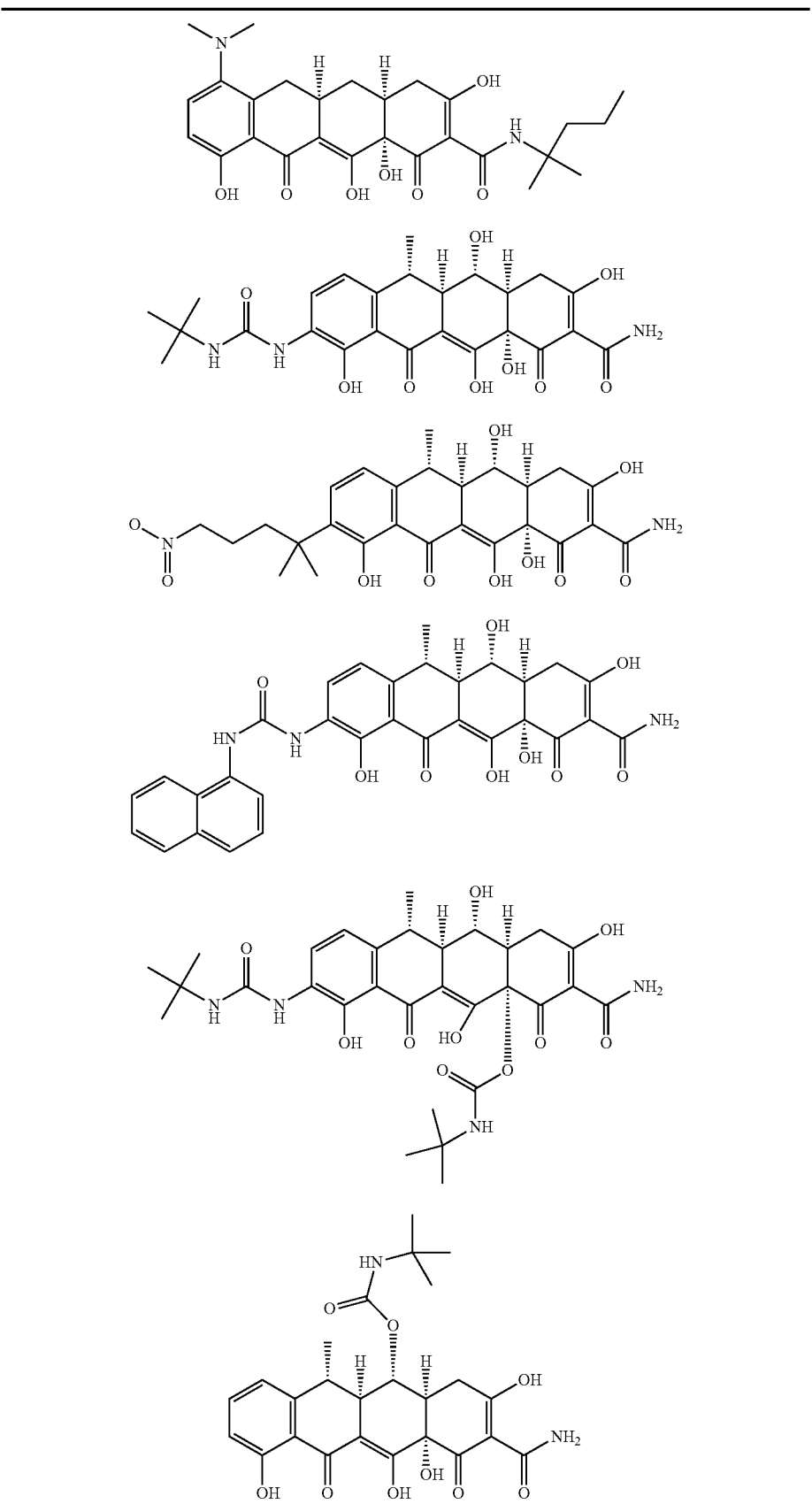

TABLE 2-continued
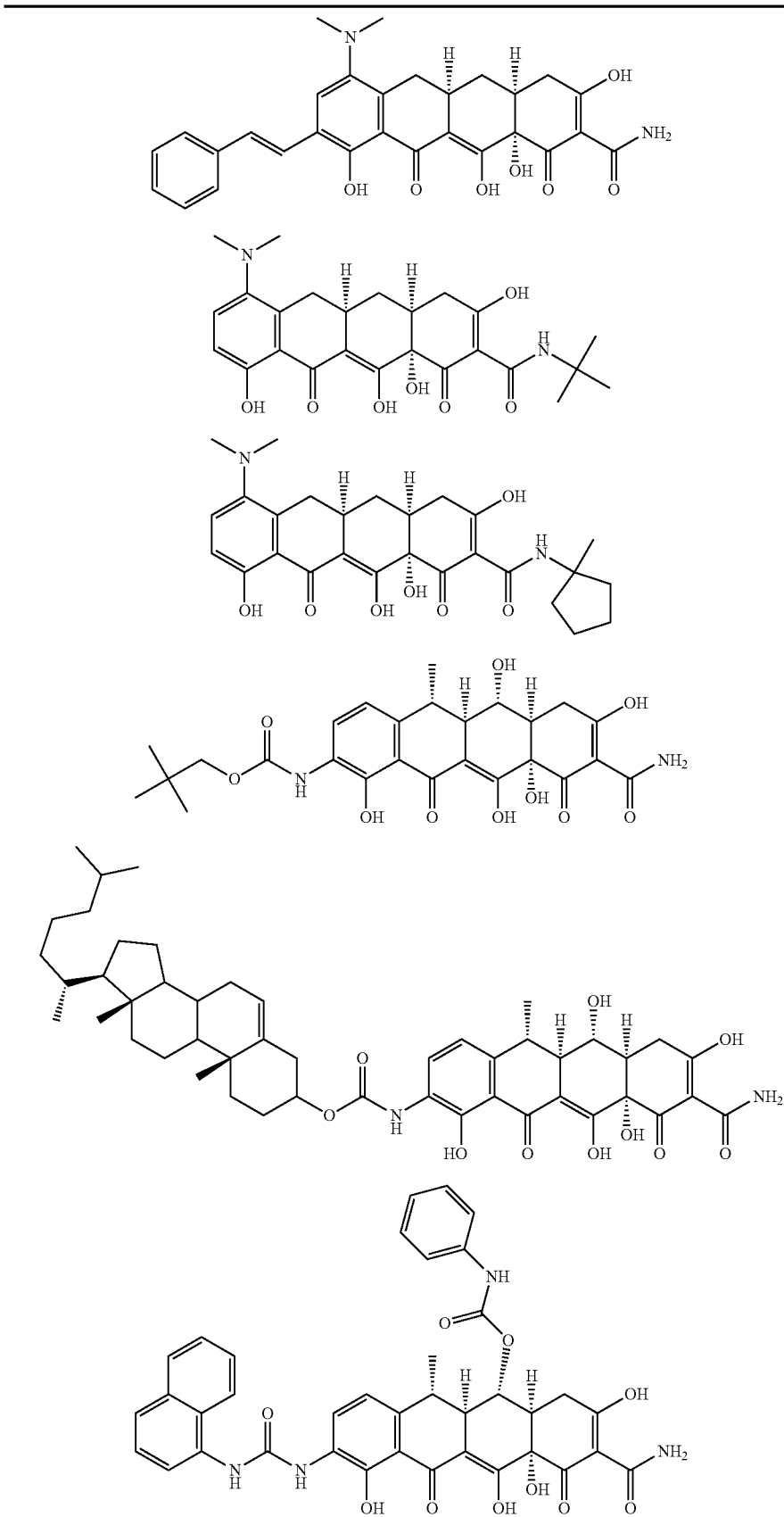

TABLE 2-continued
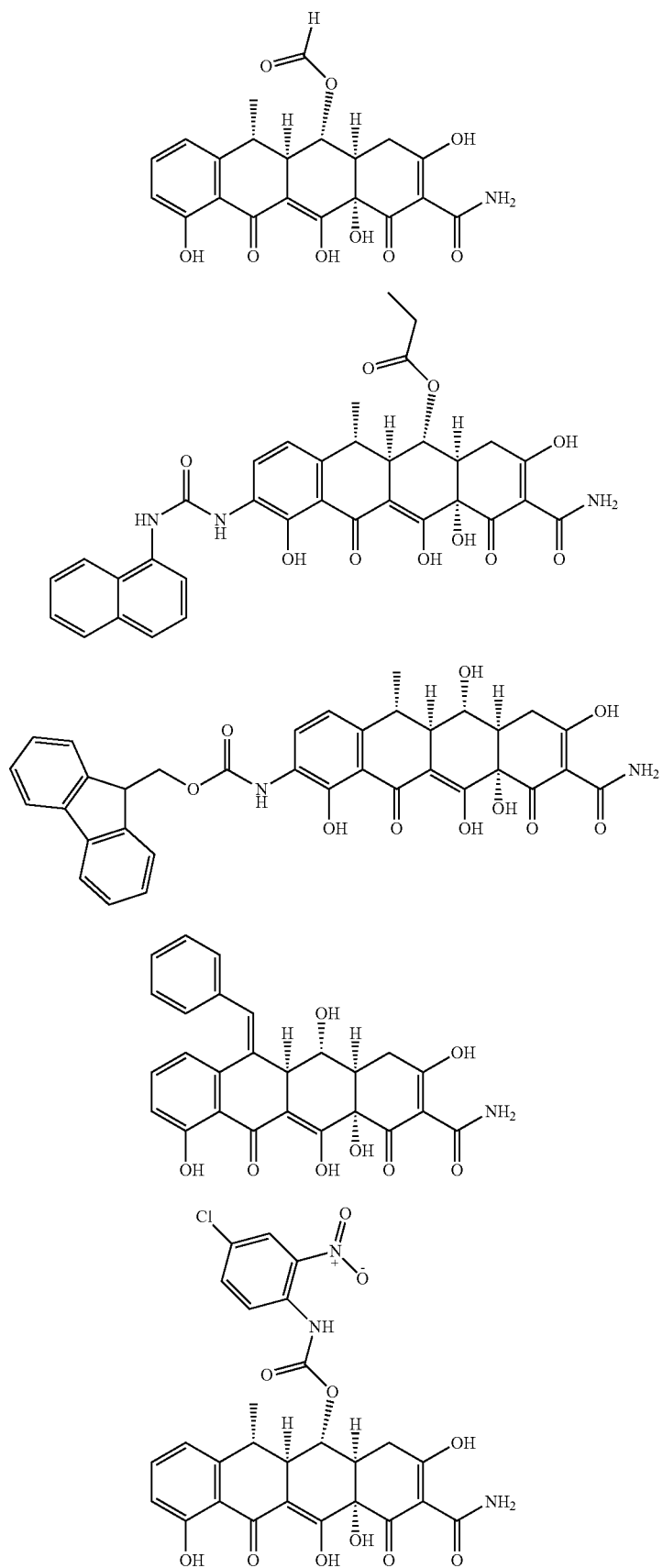

TABLE 2-continued
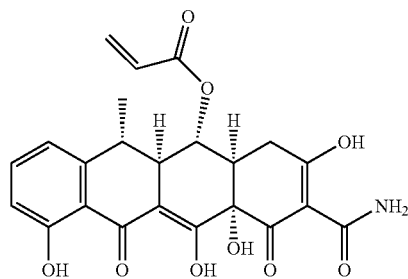 [SMILES: C=CC(=O)O[C@H]1[C@H]2C(=C(O)[C@]3(O)C(=O)C(C(N)=O)=C(O)C[C@H]13)C(=O)c1c(O)cccc1[C@@H]2C]
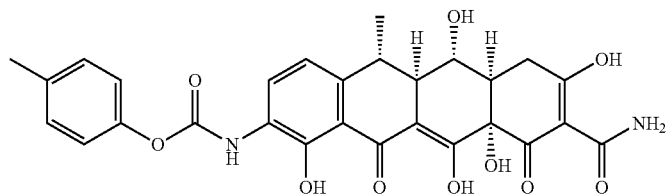 [SMILES: Cc1ccc(OC(=O)Nc2ccc3c(c2O)C(=O)C2=C(O)[C@]4(O)C(=O)C(C(N)=O)=C(O)C[C@@H]4[C@@H](O)[C@@H]2[C@H]3C)cc1]
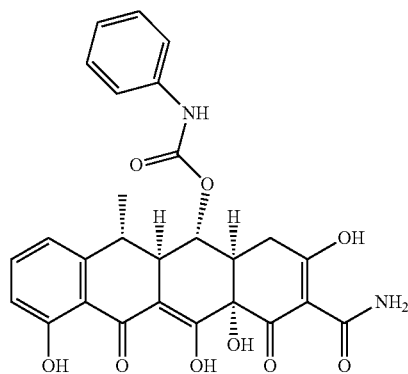 [SMILES: C[C@H]1c2cccc(O)c2C(=O)C2=C(O)[C@]3(O)C(=O)C(C(N)=O)=C(O)C[C@@H]3[C@@H](OC(=O)Nc3ccccc3)[C@@H]21]
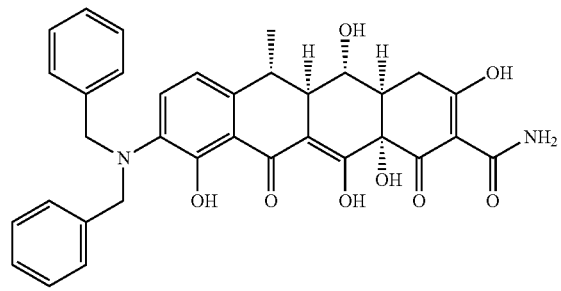 [SMILES: C[C@H]1c2ccc(N(Cc3ccccc3)Cc3ccccc3)c(O)c2C(=O)C2=C(O)[C@]3(O)C(=O)C(C(N)=O)=C(O)C[C@@H]3[C@@H](O)[C@@H]21]
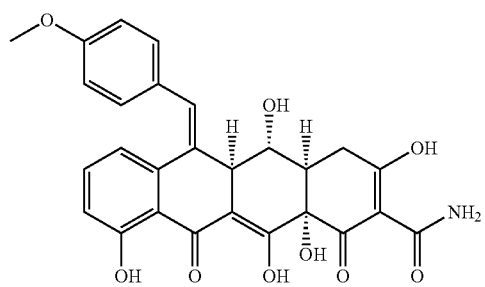 [SMILES: COc1ccc(/C=C2\c3cccc(O)c3C(=O)C3=C(O)[C@]4(O)C(=O)C(C(N)=O)=C(O)C[C@@H]4[C@@H](O)[C@@H]32)cc1]

TABLE 2-continued
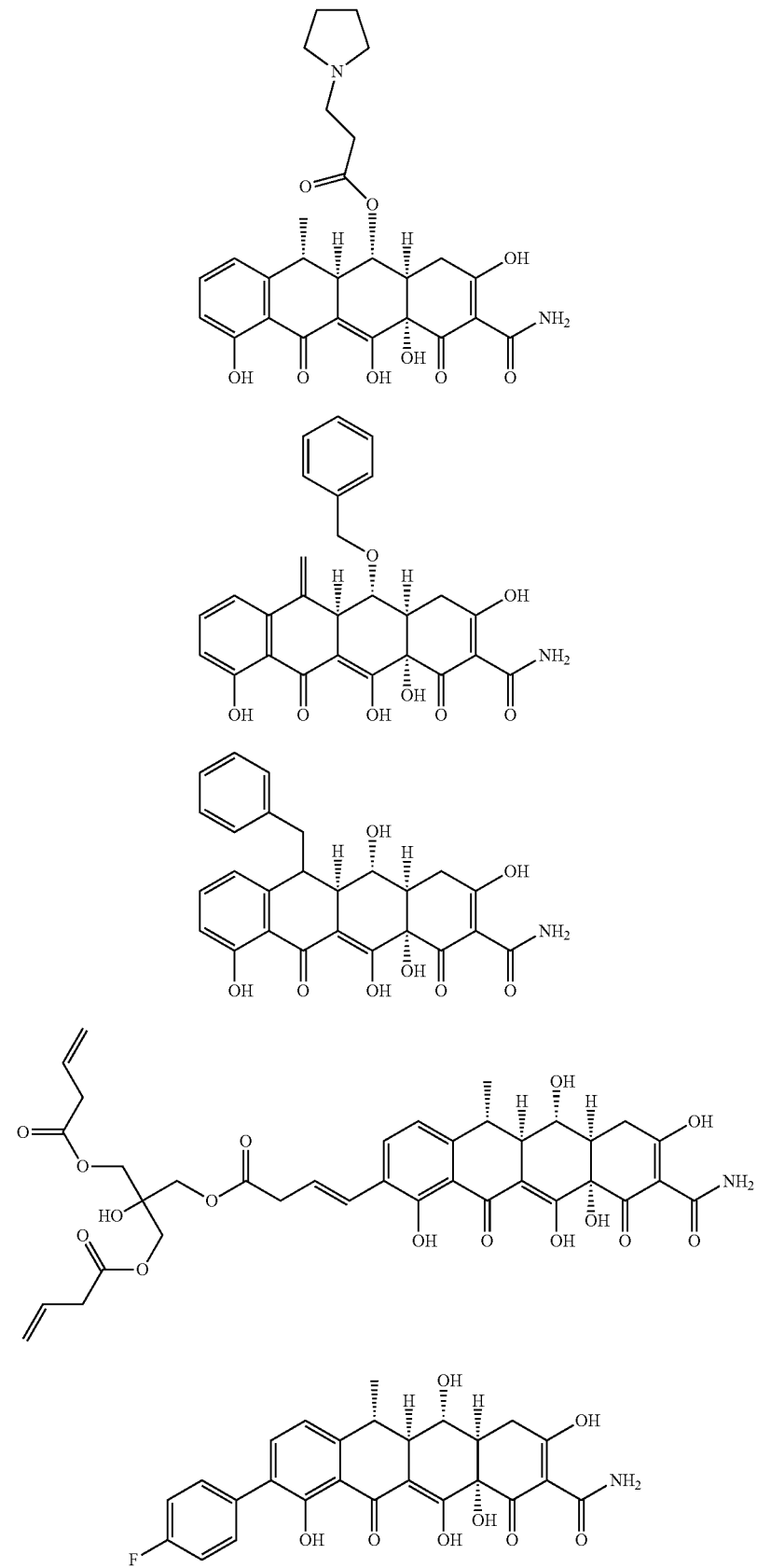

TABLE 2-continued
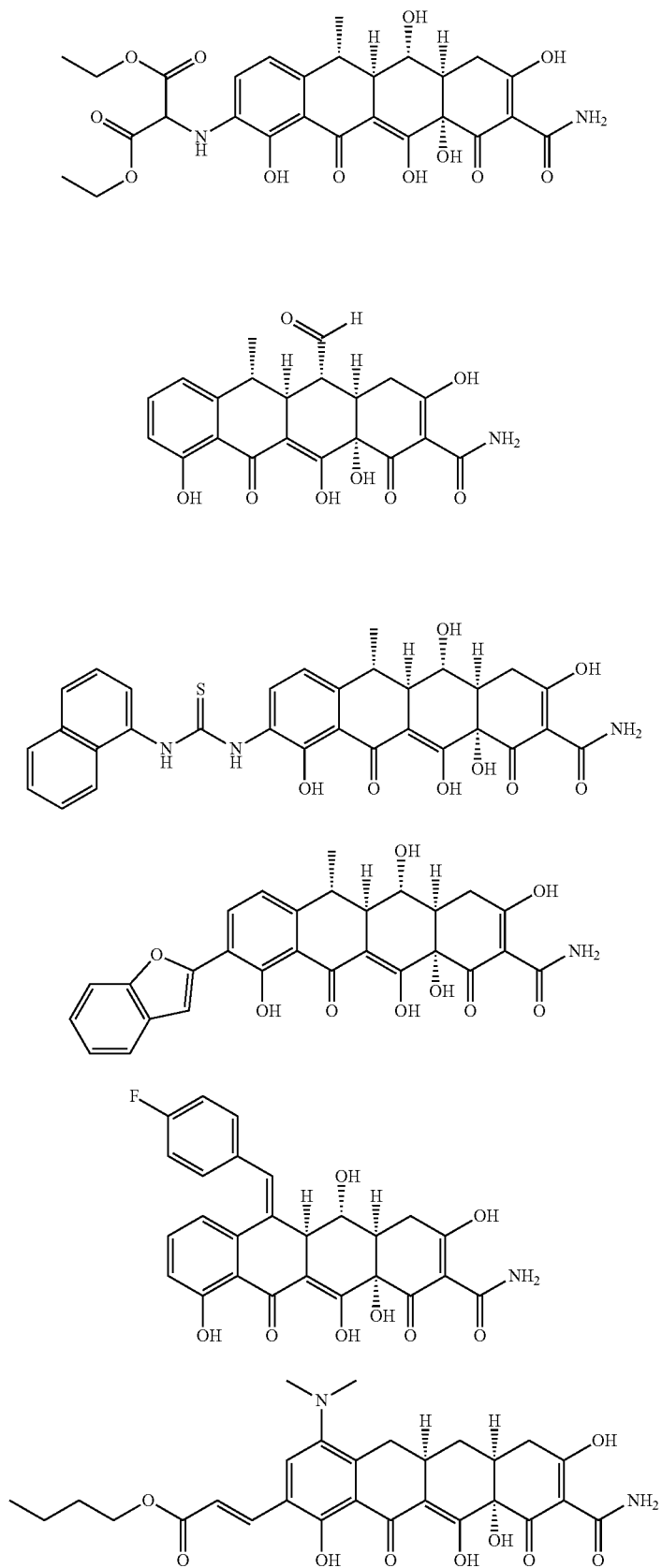

TABLE 2-continued
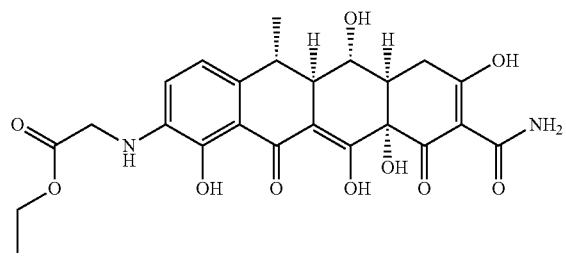 [SMILES: CCOC(=O)CNc1ccc2c(c1O)C(=O)C1=C(O)[C@]3(O)C(=O)C(C(N)=O)=C(O)C[C@@H]3[C@@H](O)[C@@H]1[C@H]2C]
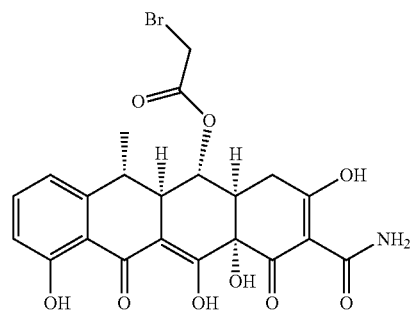 [SMILES: C[C@H]1c2cccc(O)c2C(=O)C2=C(O)[C@]3(O)C(=O)C(C(N)=O)=C(O)C[C@@H]3[C@@H](OC(=O)CBr)[C@@H]21]
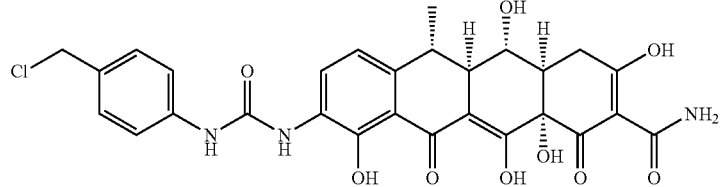 [SMILES: C[C@H]1c2ccc(NC(=O)Nc3ccc(CCl)cc3)c(O)c2C(=O)C2=C(O)[C@]3(O)C(=O)C(C(N)=O)=C(O)C[C@@H]3[C@@H](O)[C@@H]21]
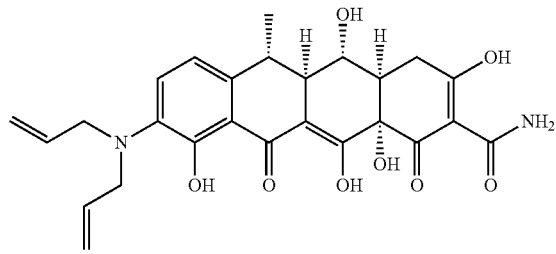 [SMILES: C=CCN(CC=C)c1ccc2c(c1O)C(=O)C1=C(O)[C@]3(O)C(=O)C(C(N)=O)=C(O)C[C@@H]3[C@@H](O)[C@@H]1[C@H]2C]
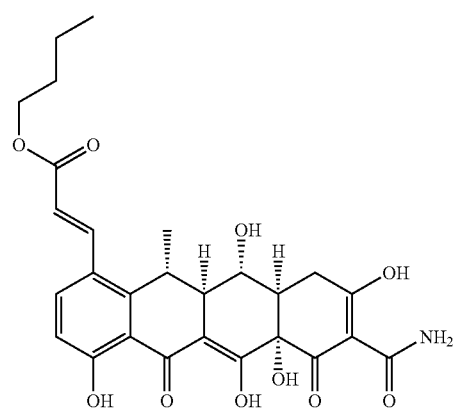 [SMILES: CCCCOC(=O)/C=C/c1ccc(O)c2c1[C@H](C)[C@@H]1C(=C(O)[C@]3(O)C(=O)C(C(N)=O)=C(O)C[C@@H]3[C@H]1O)C2=O]

TABLE 2-continued
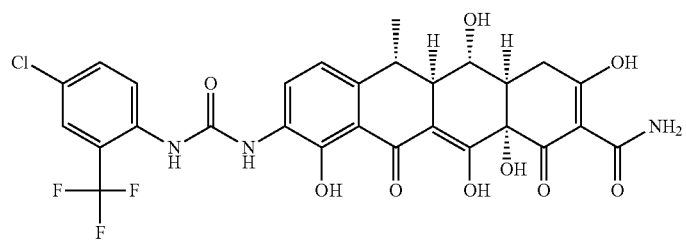 [SMILES: C[C@H]1c2ccc(NC(=O)Nc3ccc(Cl)cc3C(F)(F)F)c(O)c2C(=O)C2=C(O)[C@]3(O)C(=O)C(C(N)=O)=C(O)C[C@@H]3[C@@H](O)[C@@H]21]
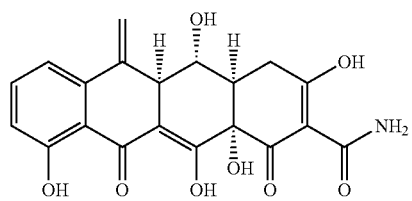 [SMILES: C=C1c2cccc(O)c2C(=O)C2=C(O)[C@]3(O)C(=O)C(C(N)=O)=C(O)C[C@@H]3[C@@H](O)[C@H]12]
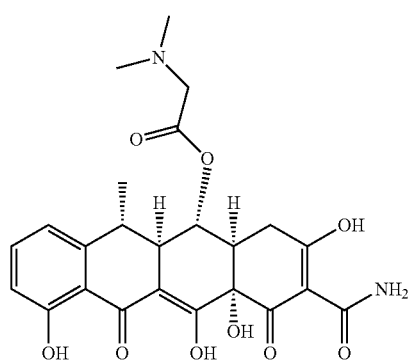 [SMILES: C[C@H]1c2cccc(O)c2C(=O)C2=C(O)[C@]3(O)C(=O)C(C(N)=O)=C(O)C[C@@H]3[C@@H](OC(=O)CN(C)C)[C@@H]21]
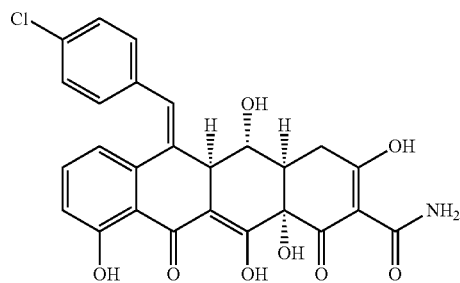 [SMILES: NC(=O)C1=C(O)C[C@@H]2[C@@H](O)[C@H]3C(=C(O)[C@]2(O)C1=O)C(=O)c1c(O)cccc1/C3=C\c1ccc(Cl)cc1]
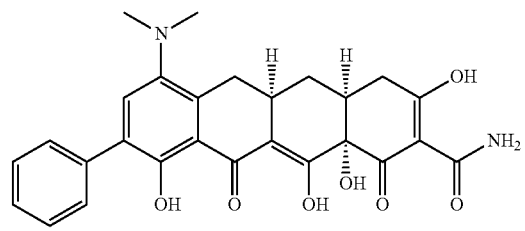 [SMILES: CN(C)c1cc(-c2ccccc2)c(O)c2c1C[C@H]1C[C@H]3CC(O)=C(C(N)=O)C(=O)[C@@]3(O)C(O)=C1C2=O]
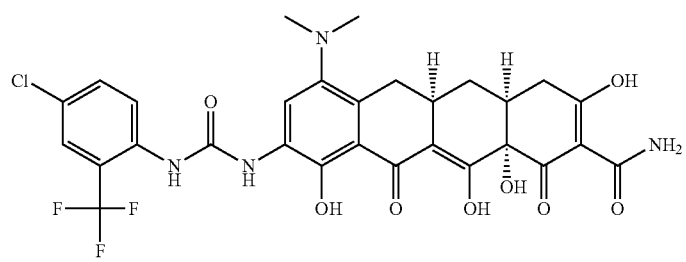 [SMILES: CN(C)c1cc(NC(=O)Nc2ccc(Cl)cc2C(F)(F)F)c(O)c2c1C[C@H]1C[C@H]3CC(O)=C(C(N)=O)C(=O)[C@@]3(O)C(O)=C1C2=O]

TABLE 2-continued
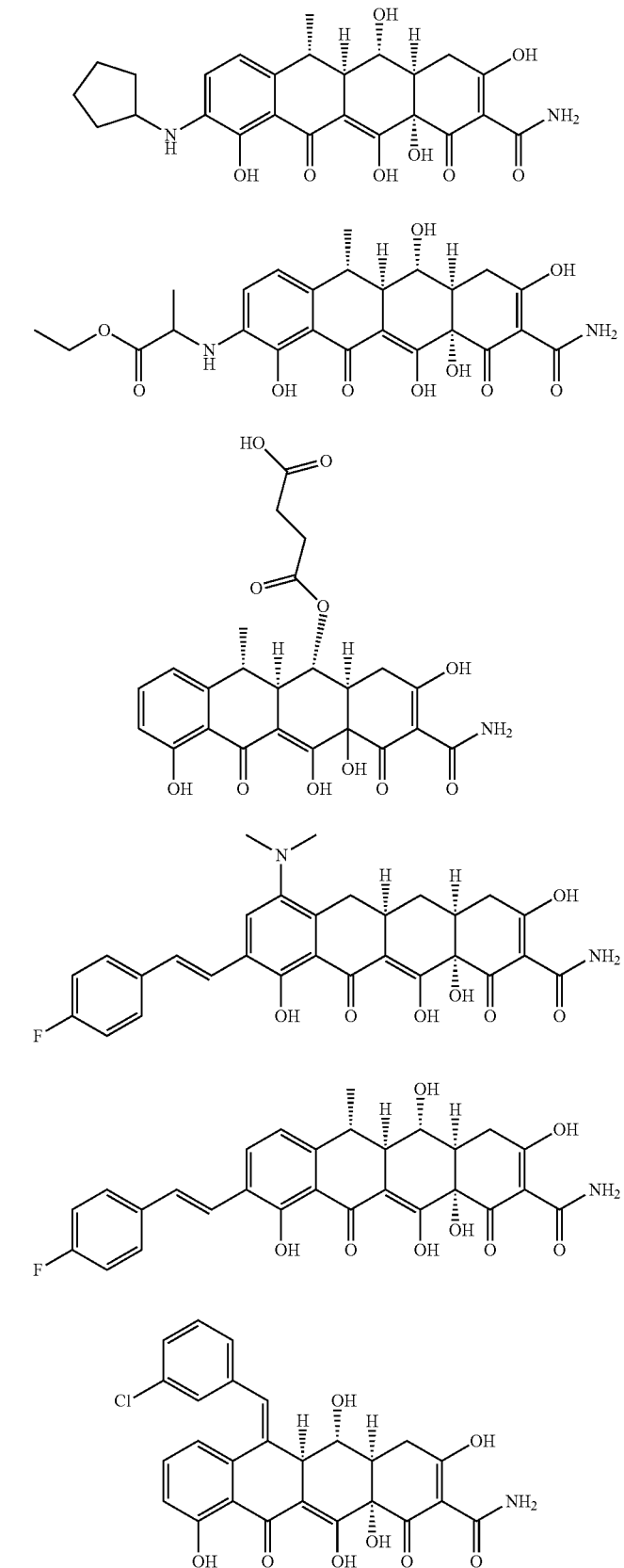

TABLE 2-continued
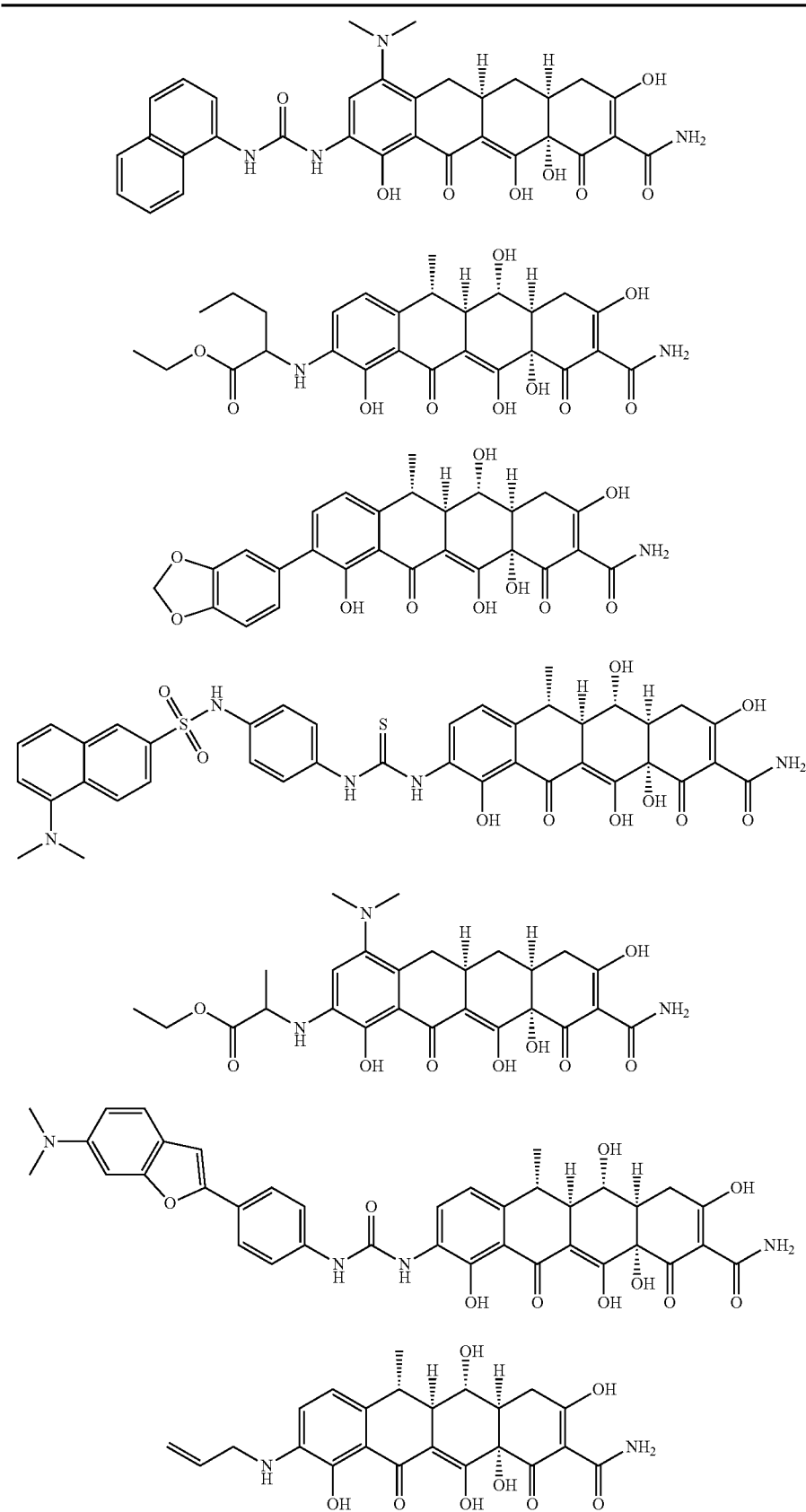

TABLE 2-continued
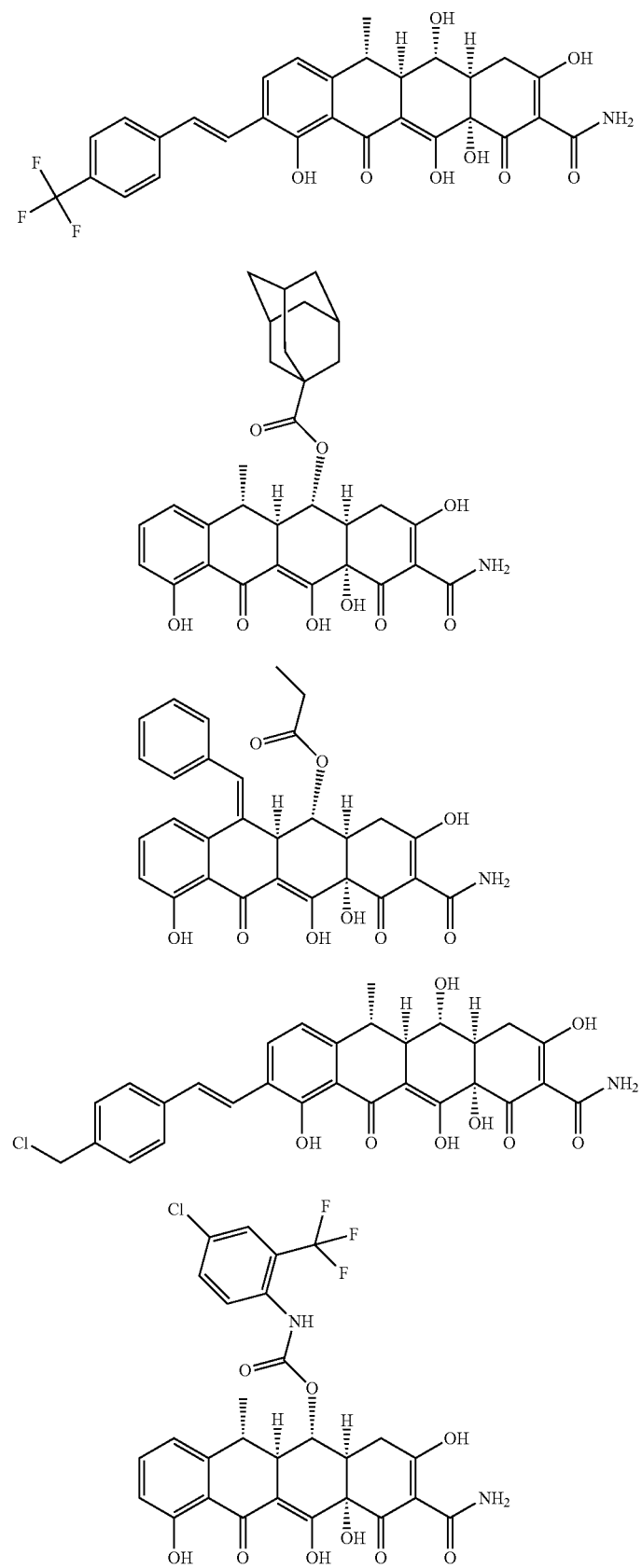

TABLE 2-continued
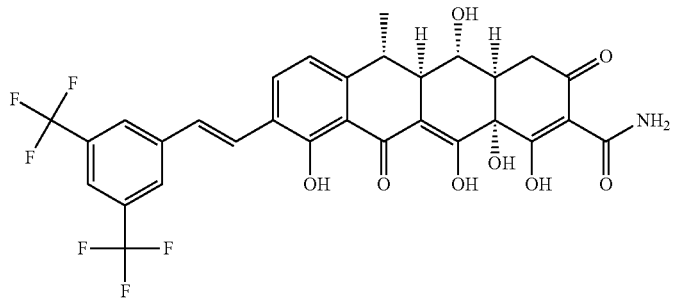 [SMILES: C[C@H]1c2ccc(/C=C/c3cc(C(F)(F)F)cc(C(F)(F)F)c3)c(O)c2C(=O)C2=C(O)[C@]3(O)C(O)=C(C(N)=O)C(=O)C[C@@H]3[C@@H](O)[C@@H]21]
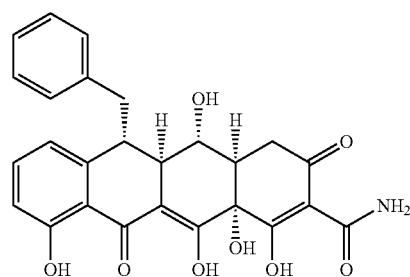 [SMILES: NC(=O)C1=C(O)[C@@]2(O)C(O)=C3C(=O)c4c(O)cccc4[C@H](Cc4ccccc4)[C@H]3[C@H](O)[C@H]2CC1=O]
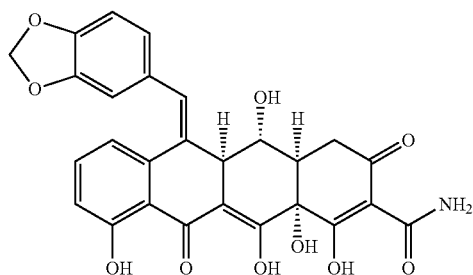 [SMILES: NC(=O)C1=C(O)[C@@]2(O)C(O)=C3C(=O)c4c(O)cccc4/C(=C\c4ccc5c(c4)OCO5)[C@H]3[C@H](O)[C@H]2CC1=O]
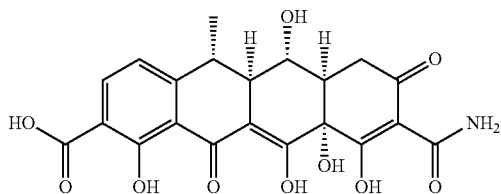 [SMILES: C[C@H]1c2ccc(C(=O)O)c(O)c2C(=O)C2=C(O)[C@]3(O)C(O)=C(C(N)=O)C(=O)C[C@@H]3[C@@H](O)[C@@H]21]
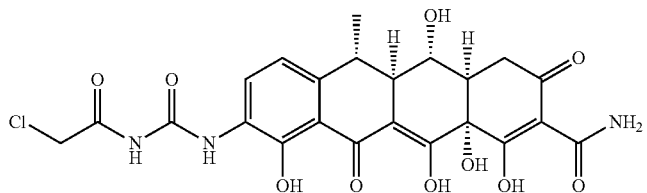 [SMILES: C[C@H]1c2ccc(NC(=O)NC(=O)CCl)c(O)c2C(=O)C2=C(O)[C@]3(O)C(O)=C(C(N)=O)C(=O)C[C@@H]3[C@@H](O)[C@@H]21]
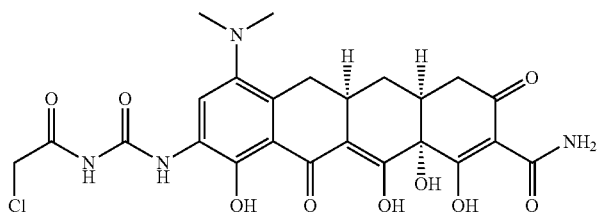 [SMILES: CN(C)c1cc(NC(=O)NC(=O)CCl)c(O)c2c1C[C@H]1C[C@H]3CC(=O)C(C(N)=O)=C(O)[C@@]3(O)C(O)=C1C2=O]

TABLE 2-continued
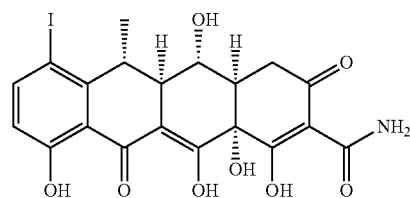 [SMILES: C[C@H]1c2c(I)ccc(O)c2C(=O)C2=C(O)[C@]3(O)C(O)=C(C(N)=O)C(=O)C[C@@H]3[C@@H](O)[C@@H]21]
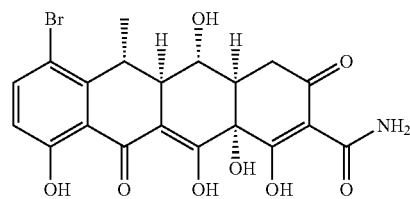 [SMILES: C[C@H]1c2c(Br)ccc(O)c2C(=O)C2=C(O)[C@]3(O)C(O)=C(C(N)=O)C(=O)C[C@@H]3[C@@H](O)[C@@H]21]
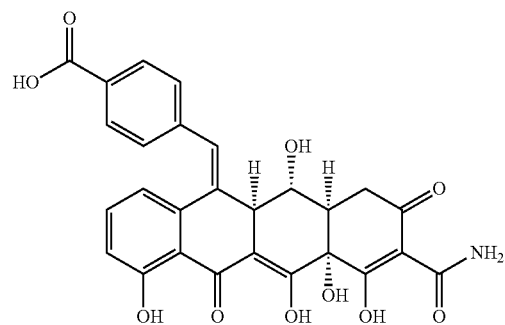 [SMILES: NC(=O)C1=C(O)[C@@]2(O)C(O)=C3C(=O)c4c(O)cccc4/C(=C\c4ccc(C(=O)O)cc4)[C@H]3[C@H](O)[C@H]2CC1=O]
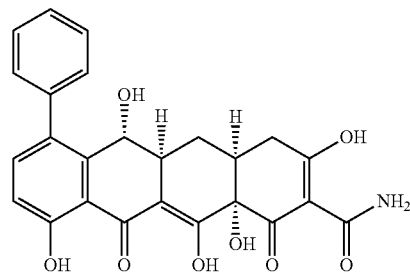 [SMILES: NC(=O)C1=C(O)C[C@@H]2C[C@H]3C(=C(O)[C@]2(O)C1=O)C(=O)c1c(O)ccc(-c2ccccc2)c1[C@@H]3O]
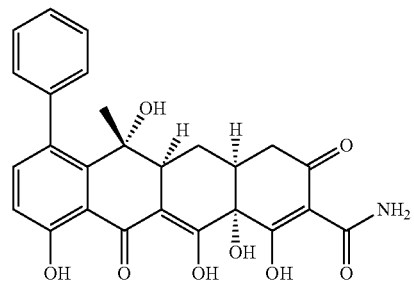 [SMILES: C[C@]1(O)c2c(-c3ccccc3)ccc(O)c2C(=O)C2=C(O)[C@]3(O)C(O)=C(C(N)=O)C(=O)C[C@@H]3C[C@@H]21]
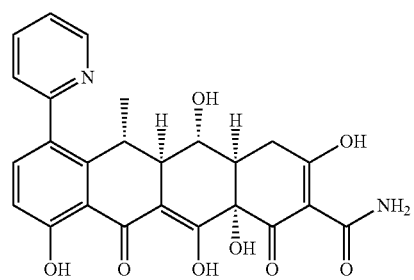

TABLE 2-continued
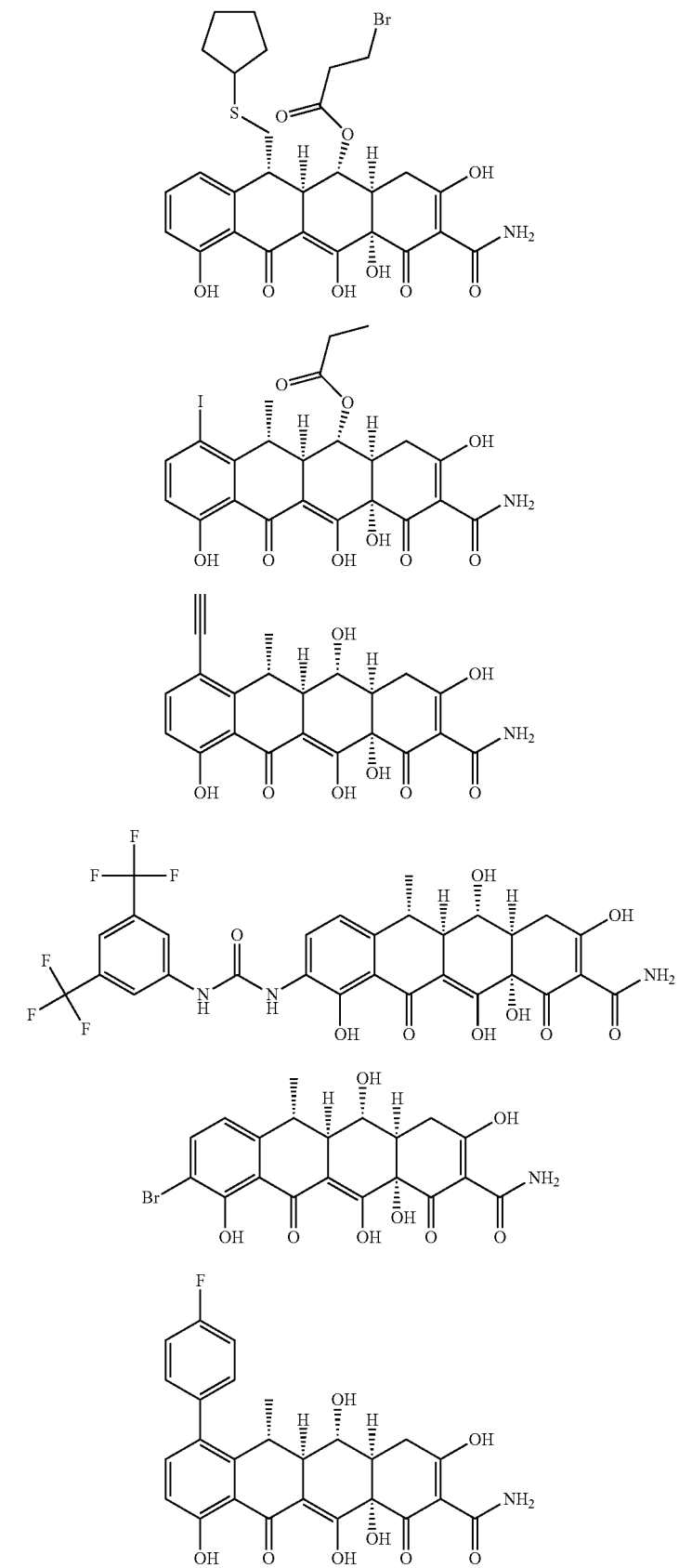

TABLE 2-continued
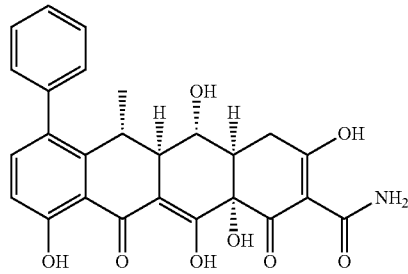 [SMILES: C[C@H]1c2c(-c3ccccc3)ccc(O)c2C(=O)C2=C(O)[C@]3(O)C(=O)C(C(N)=O)=C(O)C[C@@H]3[C@@H](O)[C@@H]21]
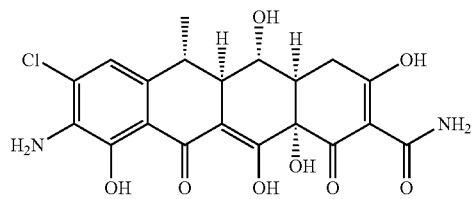 [SMILES: C[C@H]1c2cc(Cl)c(N)c(O)c2C(=O)C2=C(O)[C@]3(O)C(=O)C(C(N)=O)=C(O)C[C@@H]3[C@@H](O)[C@@H]21]
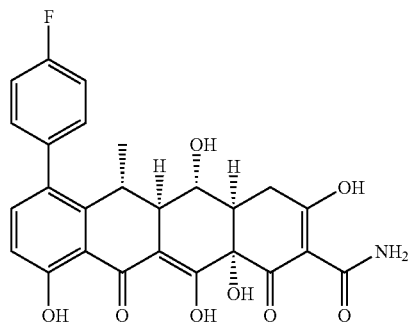 [SMILES: C[C@H]1c2c(-c3ccc(F)cc3)ccc(O)c2C(=O)C2=C(O)[C@]3(O)C(=O)C(C(N)=O)=C(O)C[C@@H]3[C@@H](O)[C@@H]21]
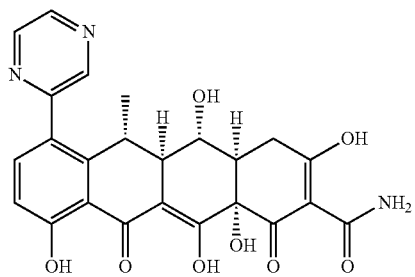 [SMILES: C[C@H]1c2c(-c3cnccn3)ccc(O)c2C(=O)C2=C(O)[C@]3(O)C(=O)C(C(N)=O)=C(O)C[C@@H]3[C@@H](O)[C@@H]21]
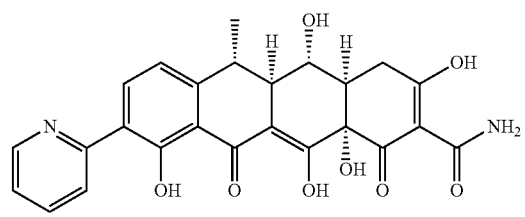 [SMILES: C[C@H]1c2ccc(-c3ccccn3)c(O)c2C(=O)C2=C(O)[C@]3(O)C(=O)C(C(N)=O)=C(O)C[C@@H]3[C@@H](O)[C@@H]21]
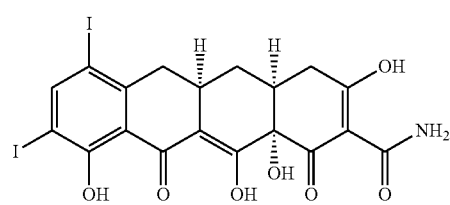 [SMILES: NC(=O)C1=C(O)C[C@@H]2C[C@@H]3Cc4c(I)cc(I)c(O)c4C(=O)C3=C(O)[C@]2(O)C1=O]

TABLE 2-continued
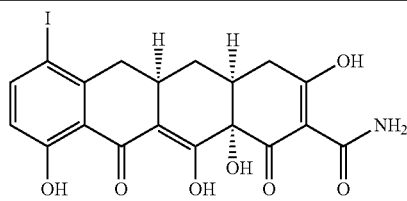
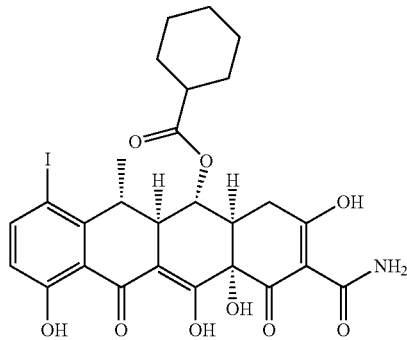 [SMILES: C[C@H]1c2c(I)ccc(O)c2C(=O)C2=C(O)[C@]3(O)C(=O)C(C(N)=O)=C(O)C[C@@H]3[C@@H](OC(=O)C3CCCCC3)[C@@H]21]
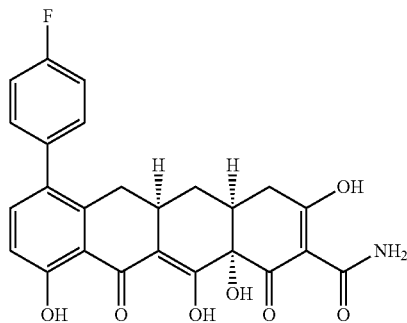 [SMILES: NC(=O)C1=C(O)C[C@@H]2C[C@@H]3Cc4c(-c5ccc(F)cc5)ccc(O)c4C(=O)C3=C(O)[C@]2(O)C1=O]
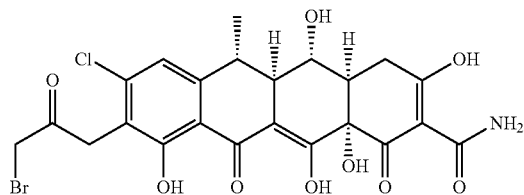 [SMILES: C[C@H]1c2cc(Cl)c(CC(=O)CBr)c(O)c2C(=O)C2=C(O)[C@]3(O)C(=O)C(C(N)=O)=C(O)C[C@@H]3[C@@H](O)[C@@H]21]
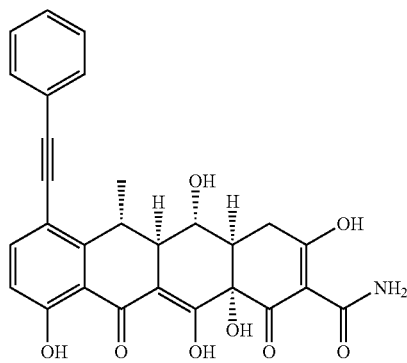 [SMILES: C[C@H]1c2c(C#Cc3ccccc3)ccc(O)c2C(=O)C2=C(O)[C@]3(O)C(=O)C(C(N)=O)=C(O)C[C@@H]3[C@@H](O)[C@@H]21]
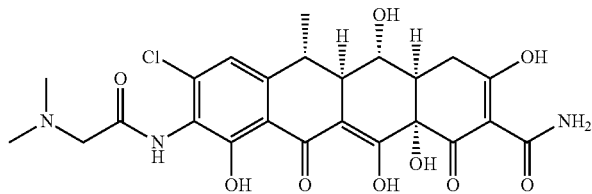 [SMILES: C[C@H]1c2cc(Cl)c(NC(=O)CN(C)C)c(O)c2C(=O)C2=C(O)[C@]3(O)C(=O)C(C(N)=O)=C(O)C[C@@H]3[C@@H](O)[C@@H]21]

TABLE 2-continued
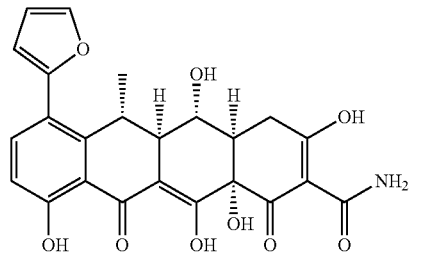 [SMILES: C[C@H]1c2c(-c3ccco3)ccc(O)c2C(=O)C2=C(O)[C@]3(O)C(=O)C(C(N)=O)=C(O)C[C@@H]3[C@@H](O)[C@@H]21]
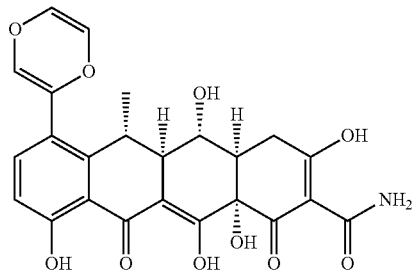 [SMILES: C[C@H]1c2c(C3=COC=CO3)ccc(O)c2C(=O)C2=C(O)[C@]3(O)C(=O)C(C(N)=O)=C(O)C[C@@H]3[C@@H](O)[C@@H]21]
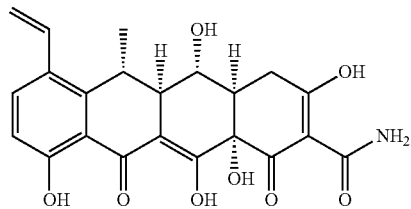 [SMILES: C=Cc1ccc(O)c2c1[C@H](C)[C@@H]1C(=C(O)[C@]3(O)C(=O)C(C(N)=O)=C(O)C[C@@H]3[C@H]1O)C2=O]
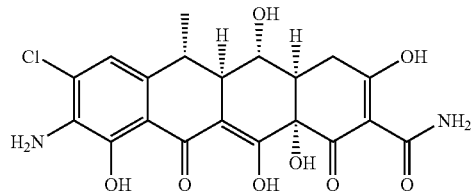 [SMILES: C[C@H]1c2cc(Cl)c(N)c(O)c2C(=O)C2=C(O)[C@]3(O)C(=O)C(C(N)=O)=C(O)C[C@@H]3[C@@H](O)[C@@H]21]
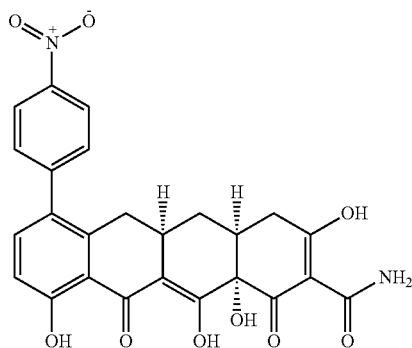
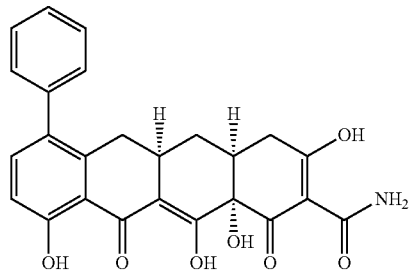 [SMILES: NC(=O)C1=C(O)C[C@@H]2C[C@@H]3Cc4c(-c5ccccc5)ccc(O)c4C(=O)C3=C(O)[C@]2(O)C1=O]

TABLE 2-continued
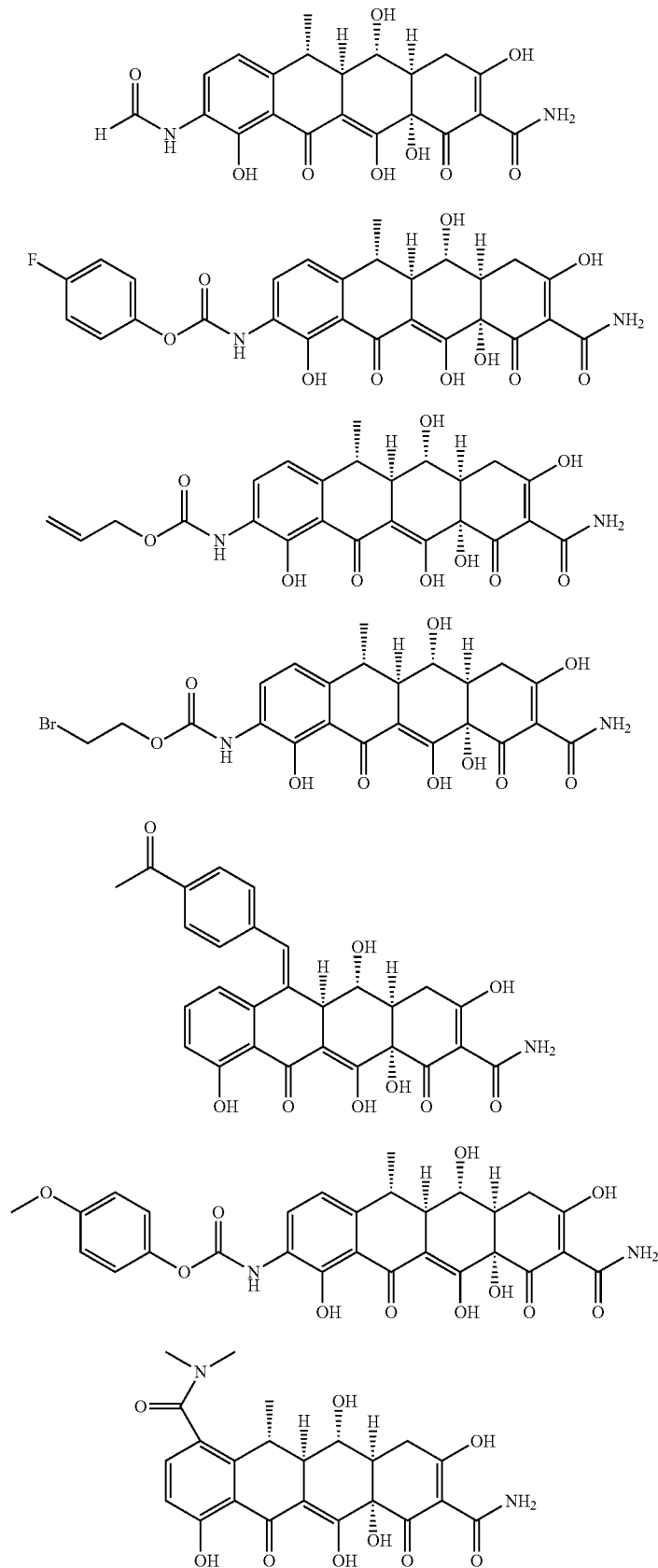

TABLE 2-continued
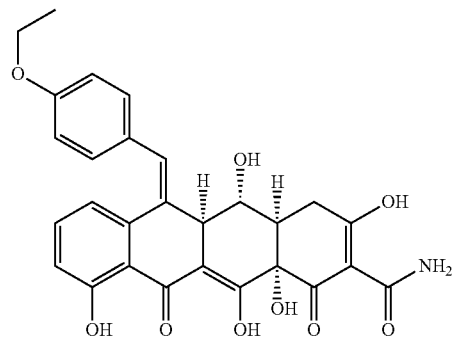 [SMILES: CCOc1ccc(/C=C2\c3cccc(O)c3C(=O)C3=C(O)[C@]4(O)C(=O)C(C(N)=O)=C(O)C[C@@H]4[C@@H](O)[C@@H]32)cc1]
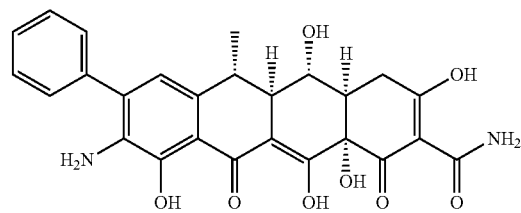 [SMILES: C[C@H]1c2cc(-c3ccccc3)c(N)c(O)c2C(=O)C2=C(O)[C@]3(O)C(=O)C(C(N)=O)=C(O)C[C@@H]3[C@@H](O)[C@@H]21]
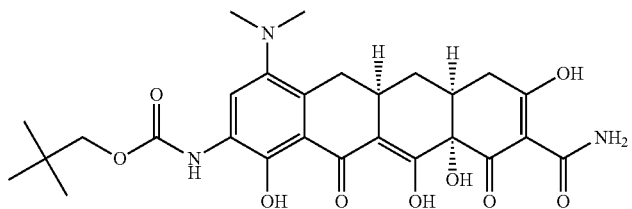 [SMILES: CN(C)c1cc(NC(=O)OCC(C)(C)C)c(O)c2c1C[C@H]1C[C@H]3CC(O)=C(C(N)=O)C(=O)[C@@]3(O)C(O)=C1C2=O]
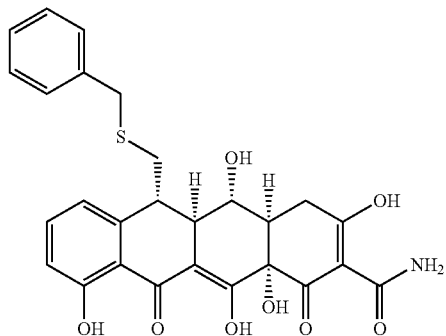 [SMILES: NC(=O)C1=C(O)C[C@@H]2[C@@H](O)[C@H]3C(=C(O)[C@]2(O)C1=O)C(=O)c1c(O)cccc1[C@@H]3CSCc1ccccc1]
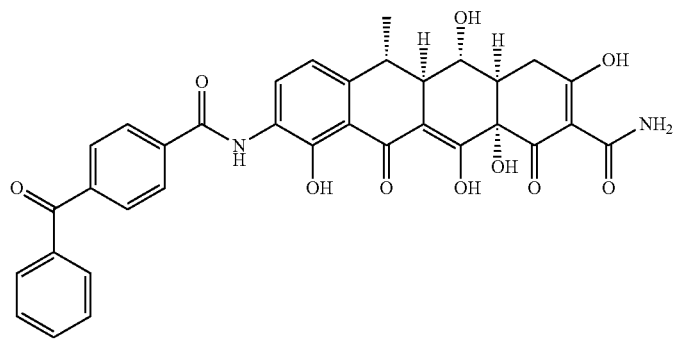 [SMILES: C[C@H]1c2ccc(NC(=O)c3ccc(C(=O)c4ccccc4)cc3)c(O)c2C(=O)C2=C(O)[C@]3(O)C(=O)C(C(N)=O)=C(O)C[C@@H]3[C@@H](O)[C@@H]21]

TABLE 2-continued
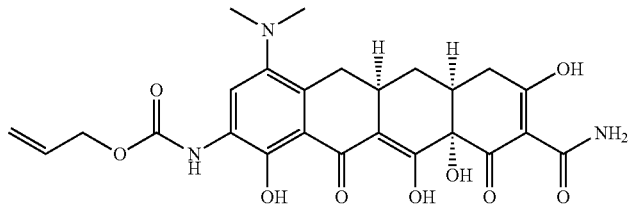 [SMILES: C=CCOC(=O)Nc1cc(N(C)C)c2c(c1O)C(=O)C1=C(O)[C@]3(O)C(=O)C(C(N)=O)=C(O)C[C@@H]3C[C@@H]1C2]
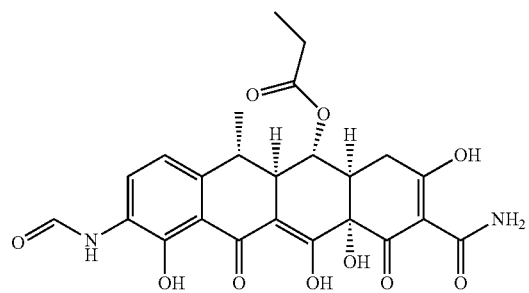 [SMILES: CCC(=O)O[C@H]1[C@H]2C(=C(O)[C@]3(O)C(=O)C(C(N)=O)=C(O)C[C@H]13)C(=O)c1c(ccc(NC=O)c1O)[C@@H]2C]
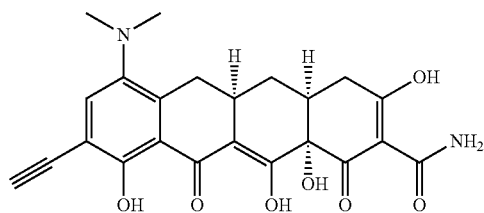 [SMILES: C#Cc1cc(N(C)C)c2c(c1O)C(=O)C1=C(O)[C@]3(O)C(=O)C(C(N)=O)=C(O)C[C@@H]3C[C@@H]1C2]
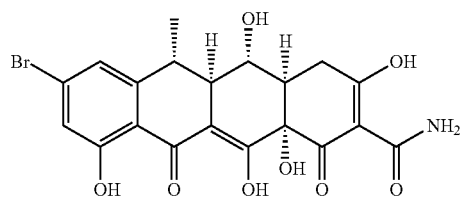 [SMILES: C[C@H]1c2cc(Br)cc(O)c2C(=O)C2=C(O)[C@]3(O)C(=O)C(C(N)=O)=C(O)C[C@@H]3[C@@H](O)[C@@H]21]
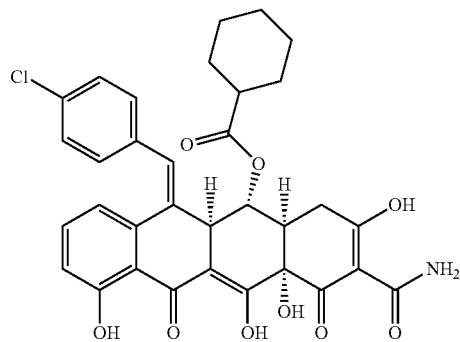 [SMILES: NC(=O)C1=C(O)C[C@@H]2[C@@H](OC(=O)C3CCCCC3)[C@H]3C(=C(O)[C@]2(O)C1=O)C(=O)c1c(O)cccc1/C3=C\c1ccc(Cl)cc1]
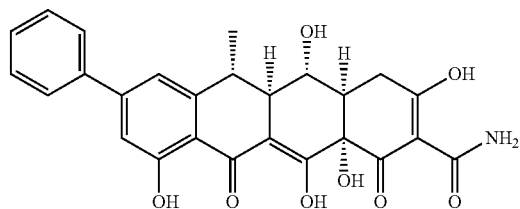 [SMILES: C[C@H]1c2cc(-c3ccccc3)cc(O)c2C(=O)C2=C(O)[C@]3(O)C(=O)C(C(N)=O)=C(O)C[C@@H]3[C@@H](O)[C@@H]21]

TABLE 2-continued
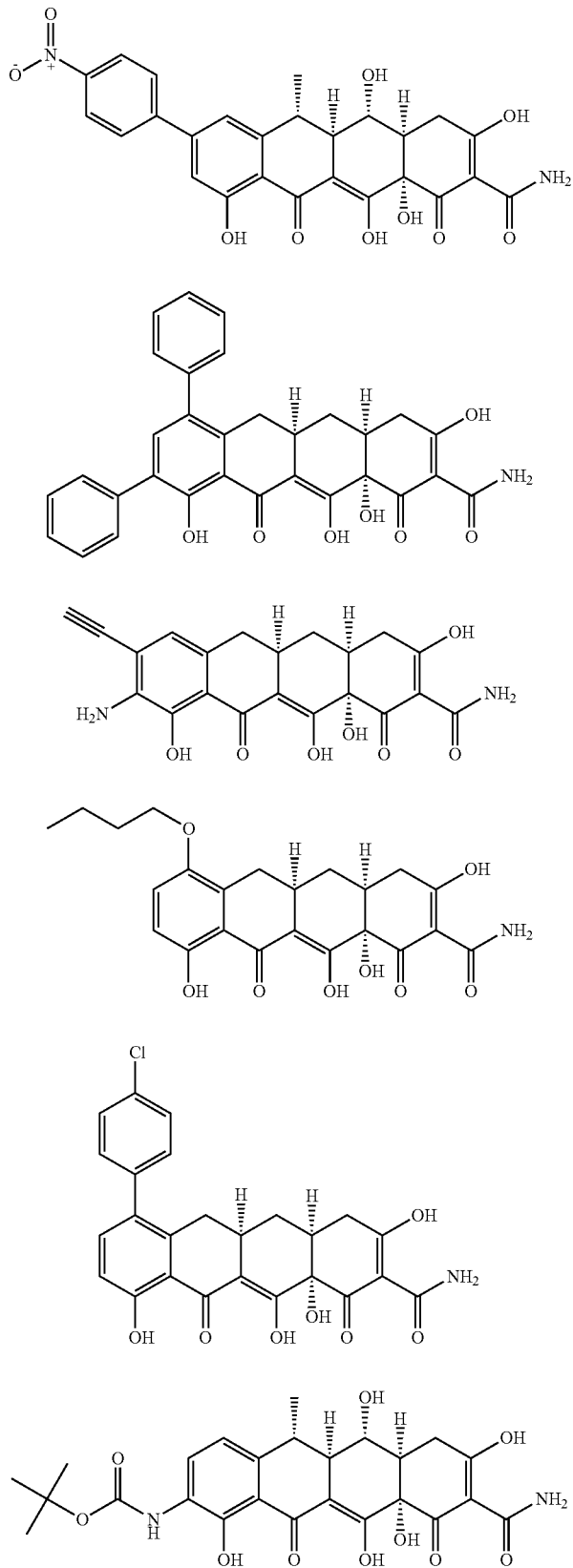

TABLE 2-continued
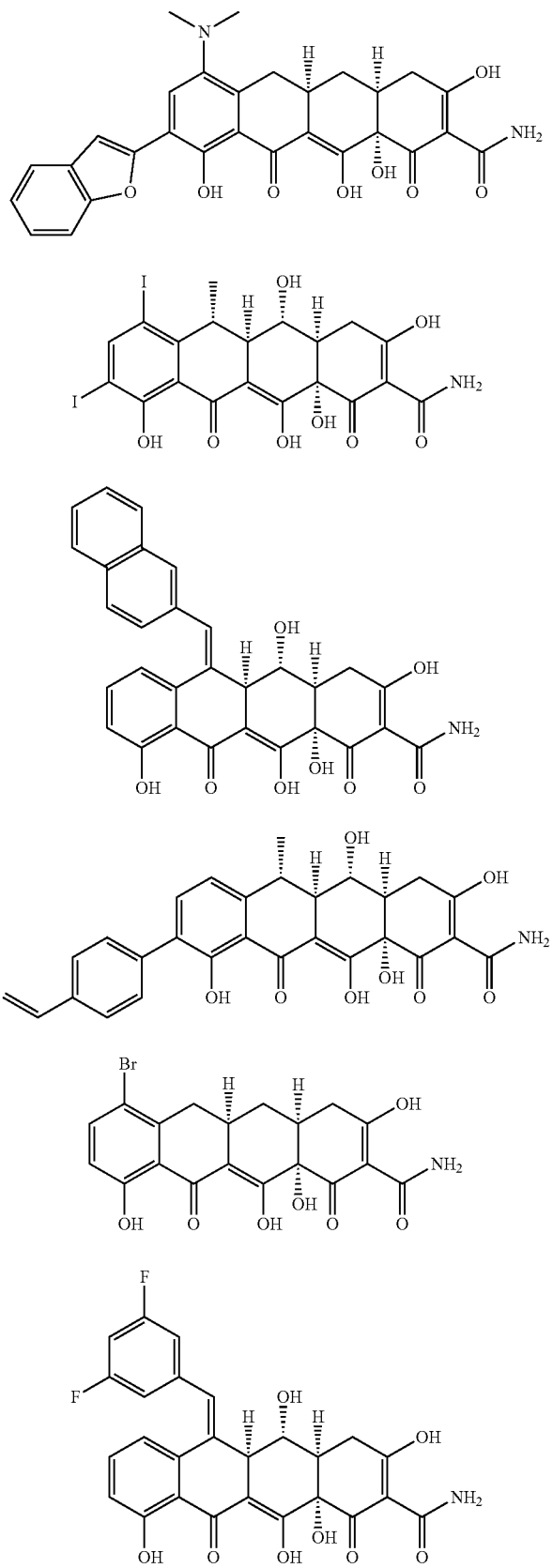

TABLE 2-continued
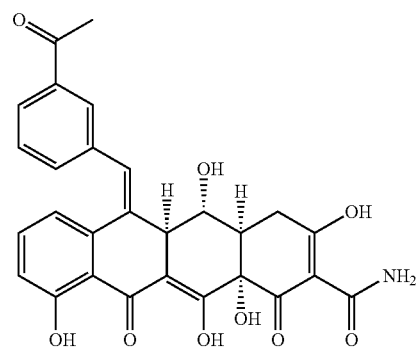 [SMILES: CC(=O)c1cccc(/C=C2\c3cccc(O)c3C(=O)C3=C(O)[C@]4(O)C(=O)C(C(N)=O)=C(O)C[C@@H]4[C@@H](O)[C@@H]32)c1]
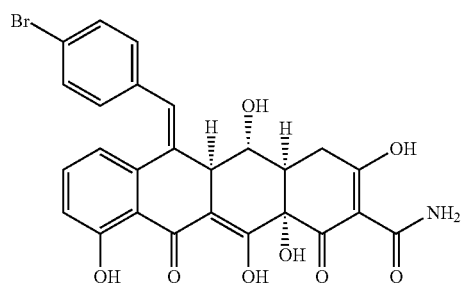 [SMILES: NC(=O)C1=C(O)C[C@@H]2[C@@H](O)[C@H]3C(=C(O)[C@]2(O)C1=O)C(=O)c1c(O)cccc1/C3=C\c1ccc(Br)cc1]
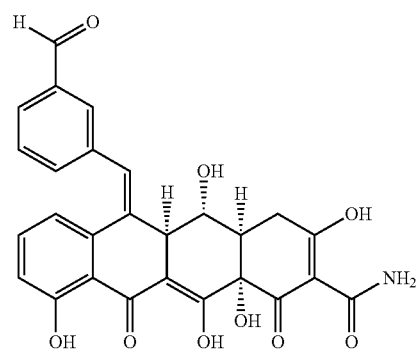 [SMILES: NC(=O)C1=C(O)C[C@@H]2[C@@H](O)[C@H]3C(=C(O)[C@]2(O)C1=O)C(=O)c1c(O)cccc1/C3=C\c1cccc(C=O)c1]
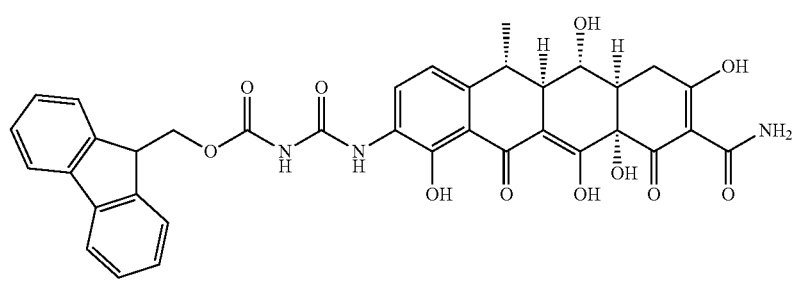 [SMILES: C[C@H]1c2ccc(NC(=O)NC(=O)OCC3c4ccccc4-c4ccccc43)c(O)c2C(=O)C2=C(O)[C@]3(O)C(=O)C(C(N)=O)=C(O)C[C@@H]3[C@@H](O)[C@@H]21]
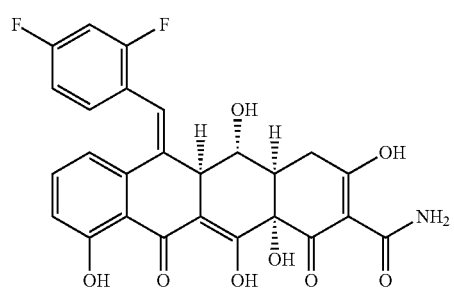 [SMILES: NC(=O)C1=C(O)C[C@@H]2[C@@H](O)[C@H]3C(=C(O)[C@]2(O)C1=O)C(=O)c1c(O)cccc1/C3=C\c1ccc(F)cc1F]

TABLE 2-continued
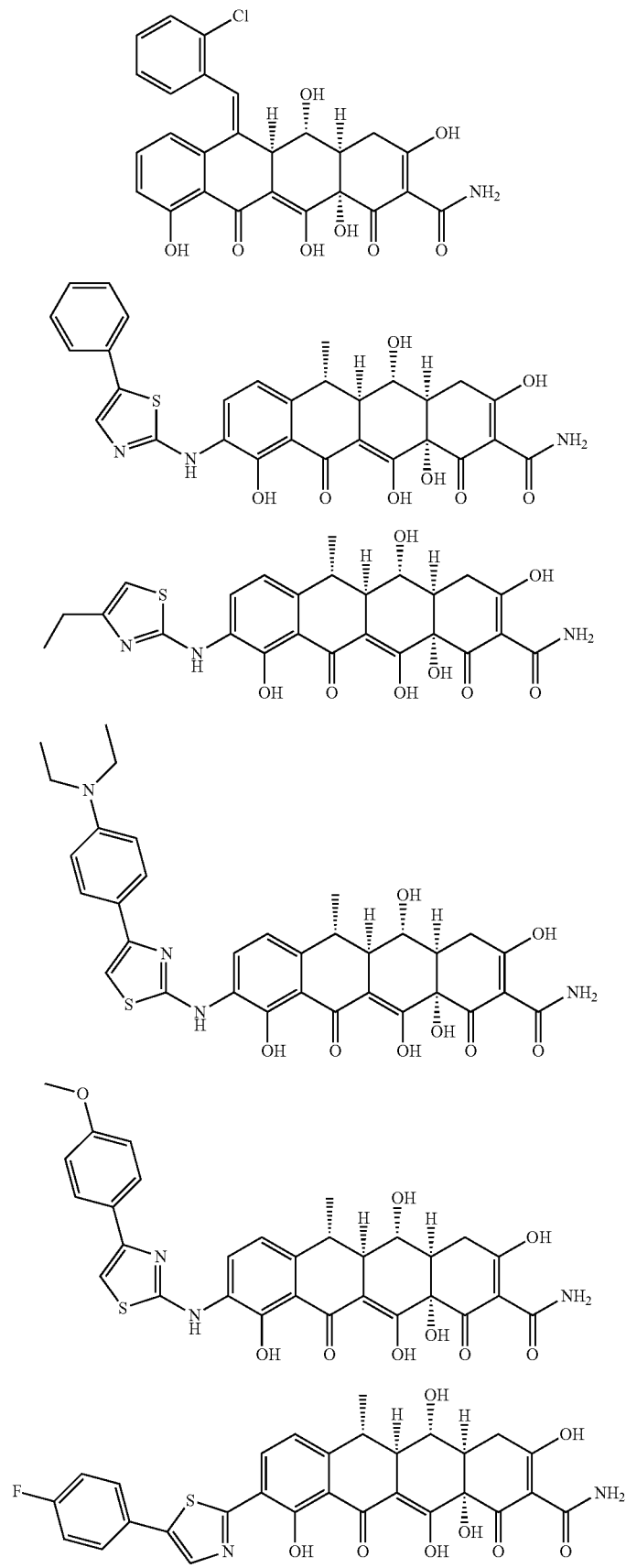

TABLE 2-continued
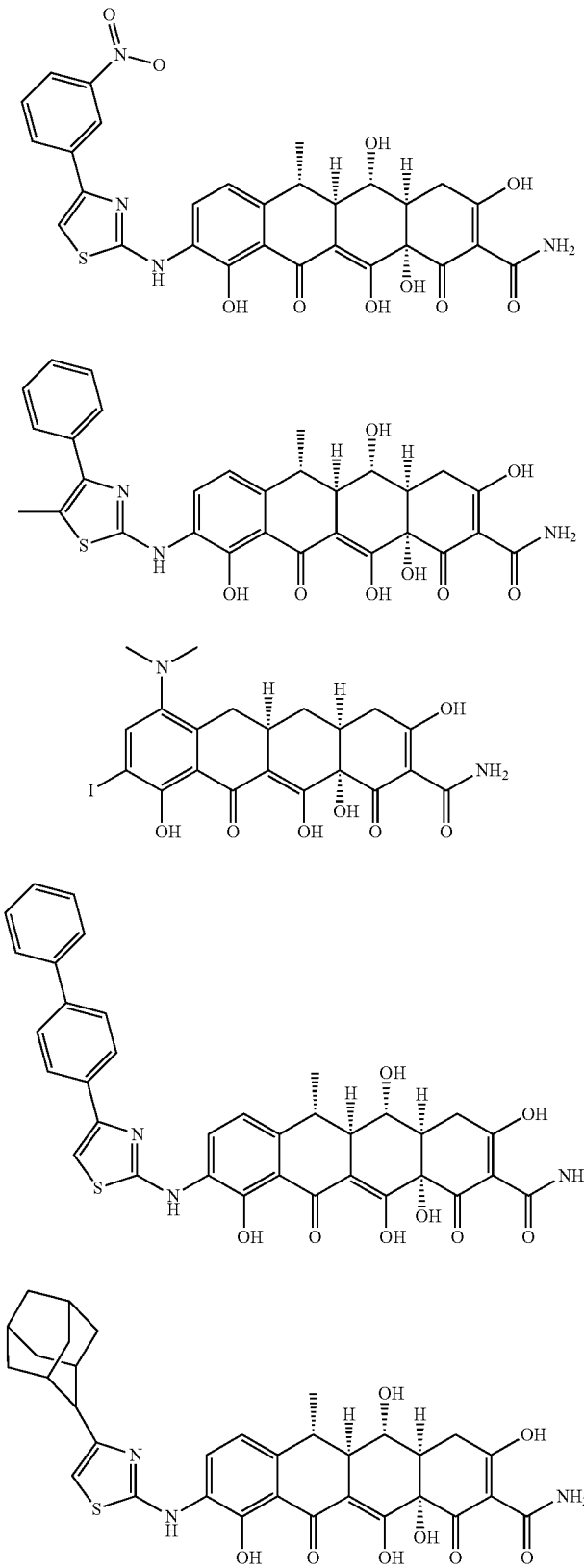

TABLE 2-continued
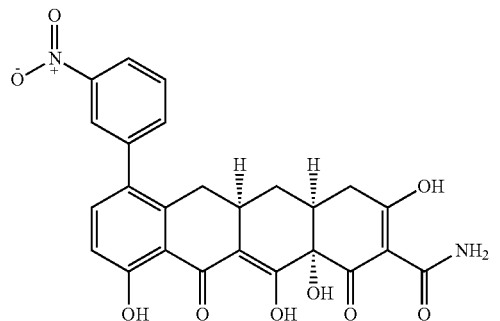
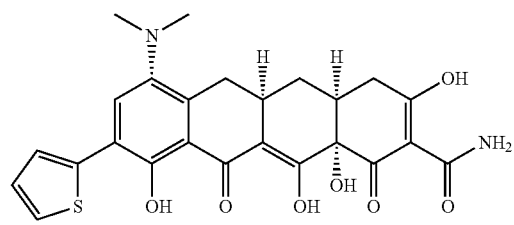
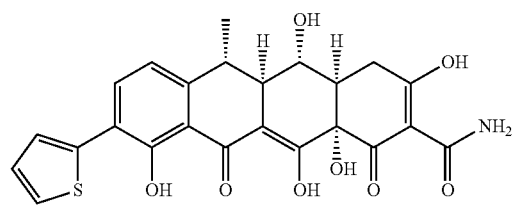 [SMILES: C[C@H]1c2ccc(-c3cccs3)c(O)c2C(=O)C2=C(O)[C@]3(O)C(=O)C(C(N)=O)=C(O)C[C@@H]3[C@@H](O)[C@@H]21]
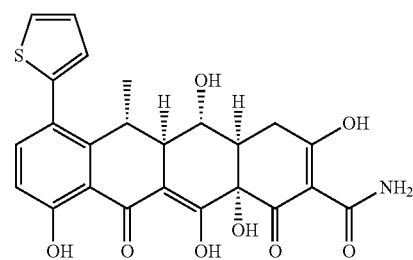 [SMILES: C[C@H]1c2c(-c3cccs3)ccc(O)c2C(=O)C2=C(O)[C@]3(O)C(=O)C(C(N)=O)=C(O)C[C@@H]3[C@@H](O)[C@@H]21]
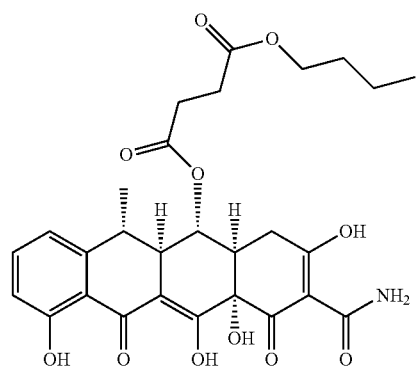 [SMILES: CCCCOC(=O)CCC(=O)O[C@H]1[C@H]2C(=C(O)[C@]3(O)C(=O)C(C(N)=O)=C(O)C[C@H]13)C(=O)c1c(O)cccc1[C@@H]2C]
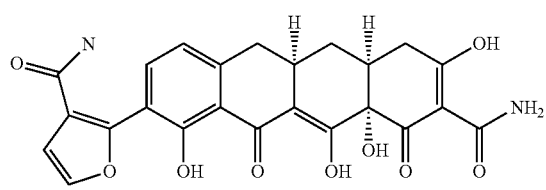 [SMILES: NC(=O)C1=C(O)C[C@@H]2C[C@@H]3Cc4ccc(-c5occc5C(N)=O)c(O)c4C(=O)C3=C(O)[C@]2(O)C1=O]

TABLE 2-continued
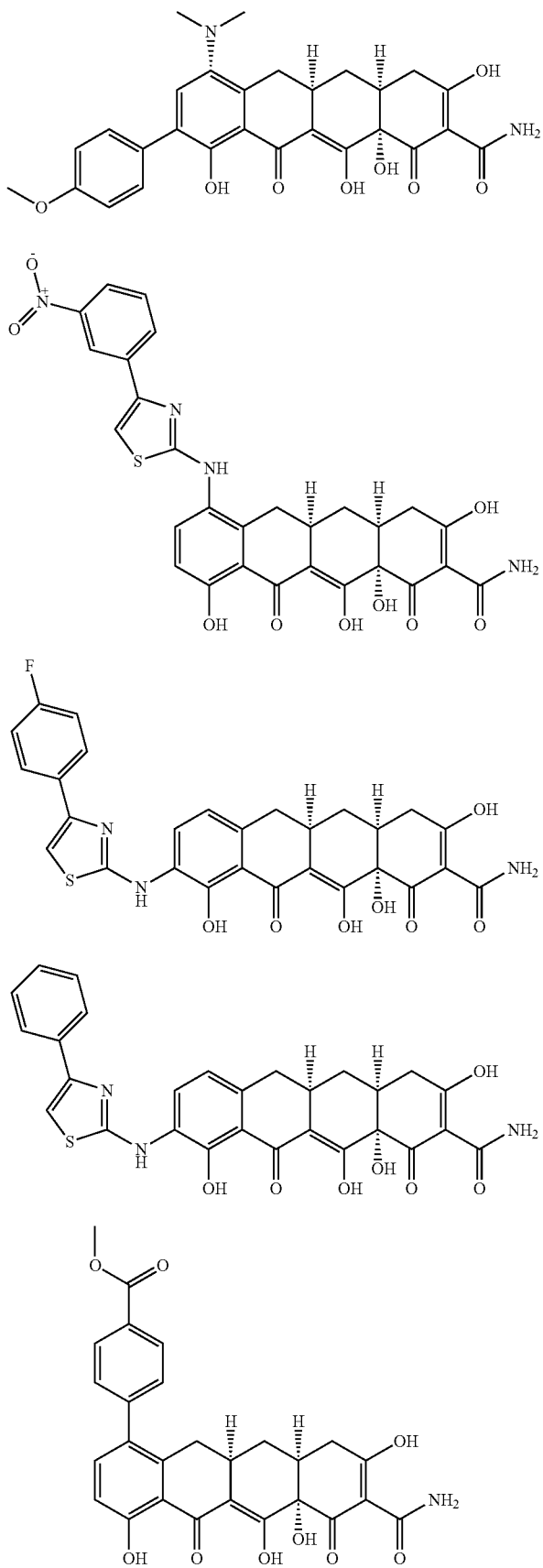

TABLE 2-continued
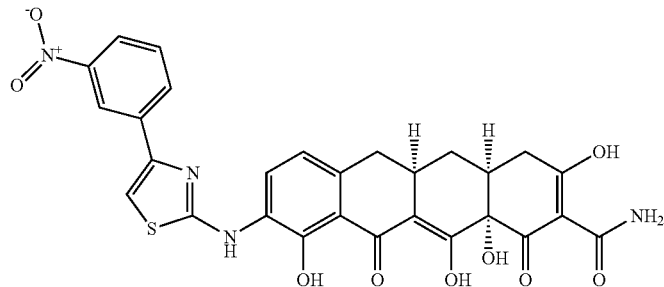
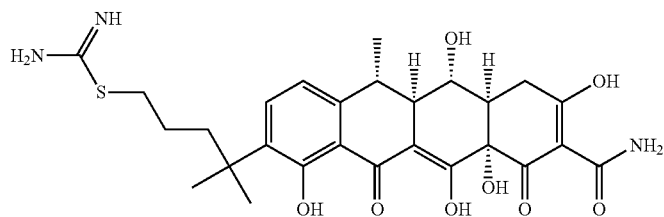 [SMILES: C[C@H]1c2ccc(C(C)(C)CCCSC(=N)N)c(O)c2C(=O)C2=C(O)[C@]3(O)C(=O)C(C(N)=O)=C(O)C[C@@H]3[C@@H](O)[C@@H]21]
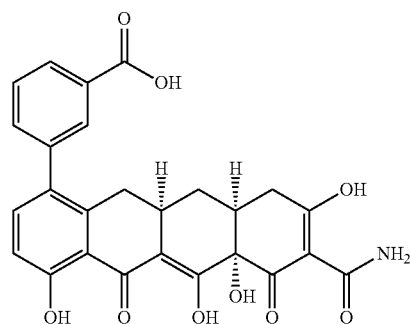 [SMILES: NC(=O)C1=C(O)C[C@@H]2C[C@@H]3Cc4c(-c5cccc(C(=O)O)c5)ccc(O)c4C(=O)C3=C(O)[C@]2(O)C1=O]
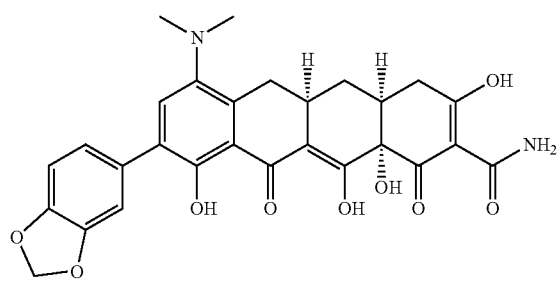 [SMILES: CN(C)c1cc(-c2ccc3c(c2)OCO3)c(O)c2c1C[C@H]1C[C@H]3CC(O)=C(C(N)=O)C(=O)[C@@]3(O)C(O)=C1C2=O]
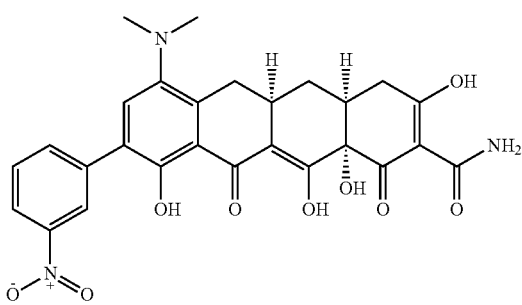

TABLE 2-continued
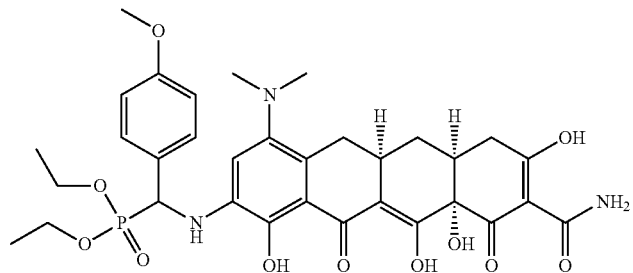 [SMILES: CCOP(=O)(OCC)C(Nc1cc(N(C)C)c2c(c1O)C(=O)C1=C(O)[C@]3(O)C(=O)C(C(N)=O)=C(O)C[C@@H]3C[C@@H]1C2)c1ccc(OC)cc1]
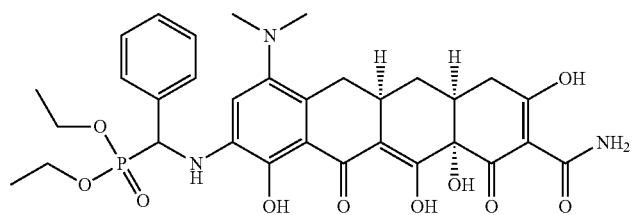 [SMILES: CCOP(=O)(OCC)C(Nc1cc(N(C)C)c2c(c1O)C(=O)C1=C(O)[C@]3(O)C(=O)C(C(N)=O)=C(O)C[C@@H]3C[C@@H]1C2)c1ccccc1]
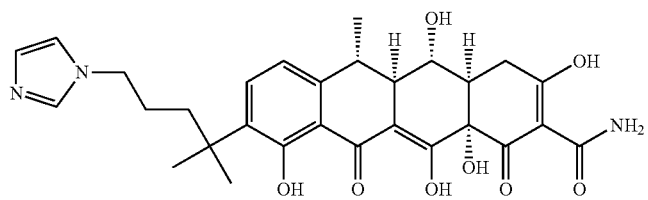 [SMILES: C[C@H]1c2ccc(C(C)(C)CCCn3ccnc3)c(O)c2C(=O)C2=C(O)[C@]3(O)C(=O)C(C(N)=O)=C(O)C[C@@H]3[C@@H](O)[C@@H]21]
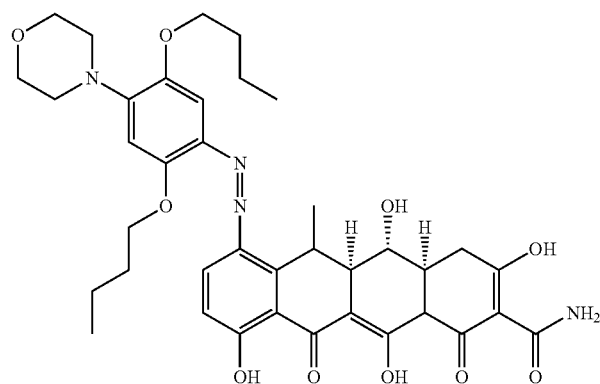 [SMILES: CCCCOc1cc(N2CCOCC2)c(OCCCC)cc1N=Nc1ccc(O)c2c1C(C)[C@@H]1C(=C(O)C3C(=O)C(C(N)=O)=C(O)C[C@@H]3[C@H]1O)C2=O]
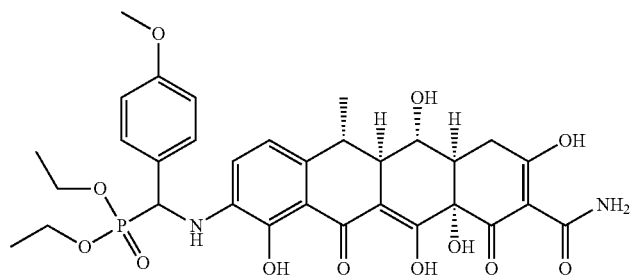 [SMILES: CCOP(=O)(OCC)C(Nc1ccc2c(c1O)C(=O)C1=C(O)[C@]3(O)C(=O)C(C(N)=O)=C(O)C[C@@H]3[C@@H](O)[C@@H]1[C@H]2C)c1ccc(OC)cc1]
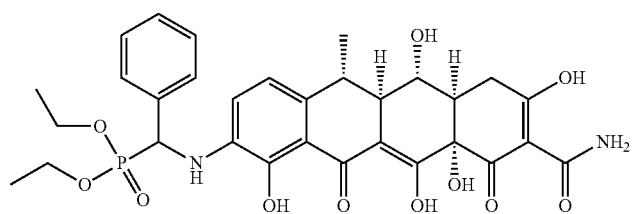 [SMILES: CCOP(=O)(OCC)C(Nc1ccc2c(c1O)C(=O)C1=C(O)[C@]3(O)C(=O)C(C(N)=O)=C(O)C[C@@H]3[C@@H](O)[C@@H]1[C@H]2C)c1ccccc1]

TABLE 2-continued
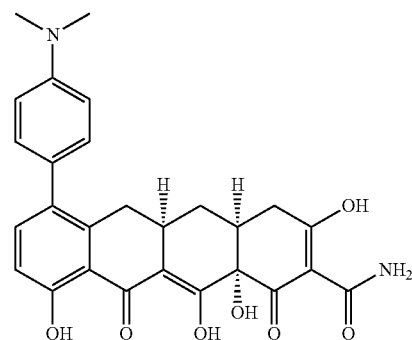 [SMILES: CN(C)c1ccc(-c2ccc(O)c3c2C[C@H]2C[C@H]4CC(O)=C(C(N)=O)C(=O)[C@@]4(O)C(O)=C2C3=O)cc1]
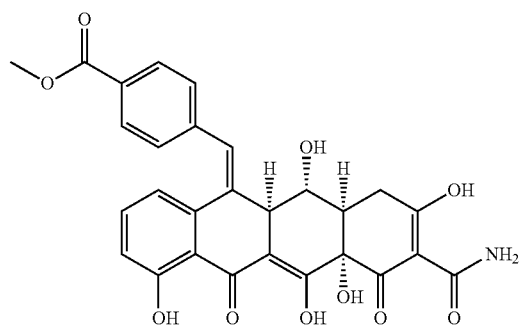 [SMILES: COC(=O)c1ccc(/C=C2\c3cccc(O)c3C(=O)C3=C(O)[C@]4(O)C(=O)C(C(N)=O)=C(O)C[C@@H]4[C@@H](O)[C@@H]32)cc1]
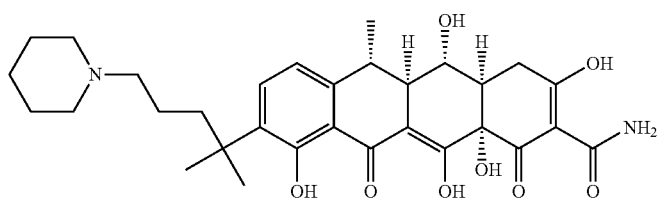 [SMILES: C[C@H]1c2ccc(C(C)(C)CCCN3CCCCC3)c(O)c2C(=O)C2=C(O)[C@]3(O)C(=O)C(C(N)=O)=C(O)C[C@@H]3[C@@H](O)[C@@H]21]
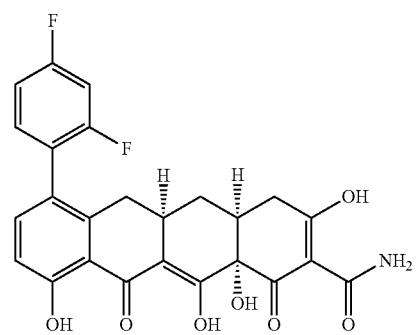 [SMILES: NC(=O)C1=C(O)C[C@@H]2C[C@@H]3Cc4c(-c5ccc(F)cc5F)ccc(O)c4C(=O)C3=C(O)[C@]2(O)C1=O]
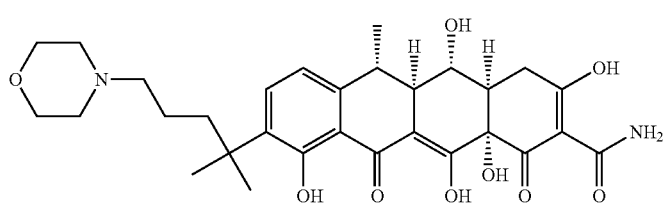 [SMILES: C[C@H]1c2ccc(C(C)(C)CCCN3CCOCC3)c(O)c2C(=O)C2=C(O)[C@]3(O)C(=O)C(C(N)=O)=C(O)C[C@@H]3[C@@H](O)[C@@H]21]

TABLE 2-continued
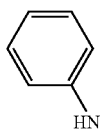
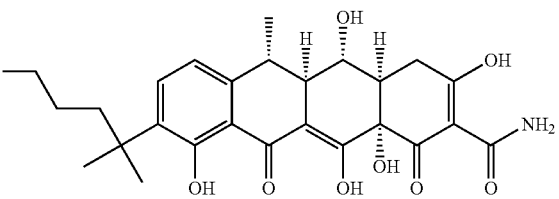
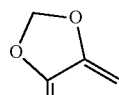
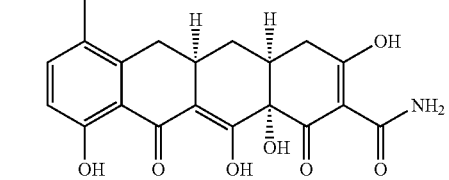
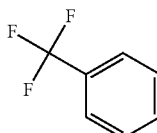
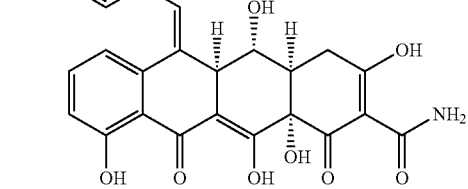
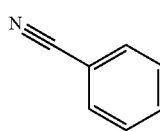
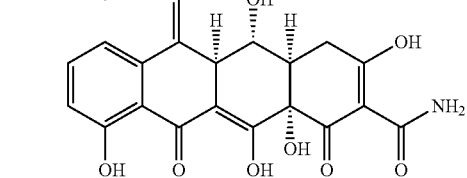
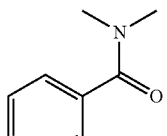
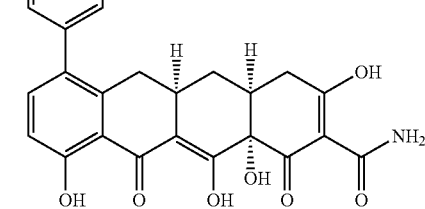

TABLE 2-continued
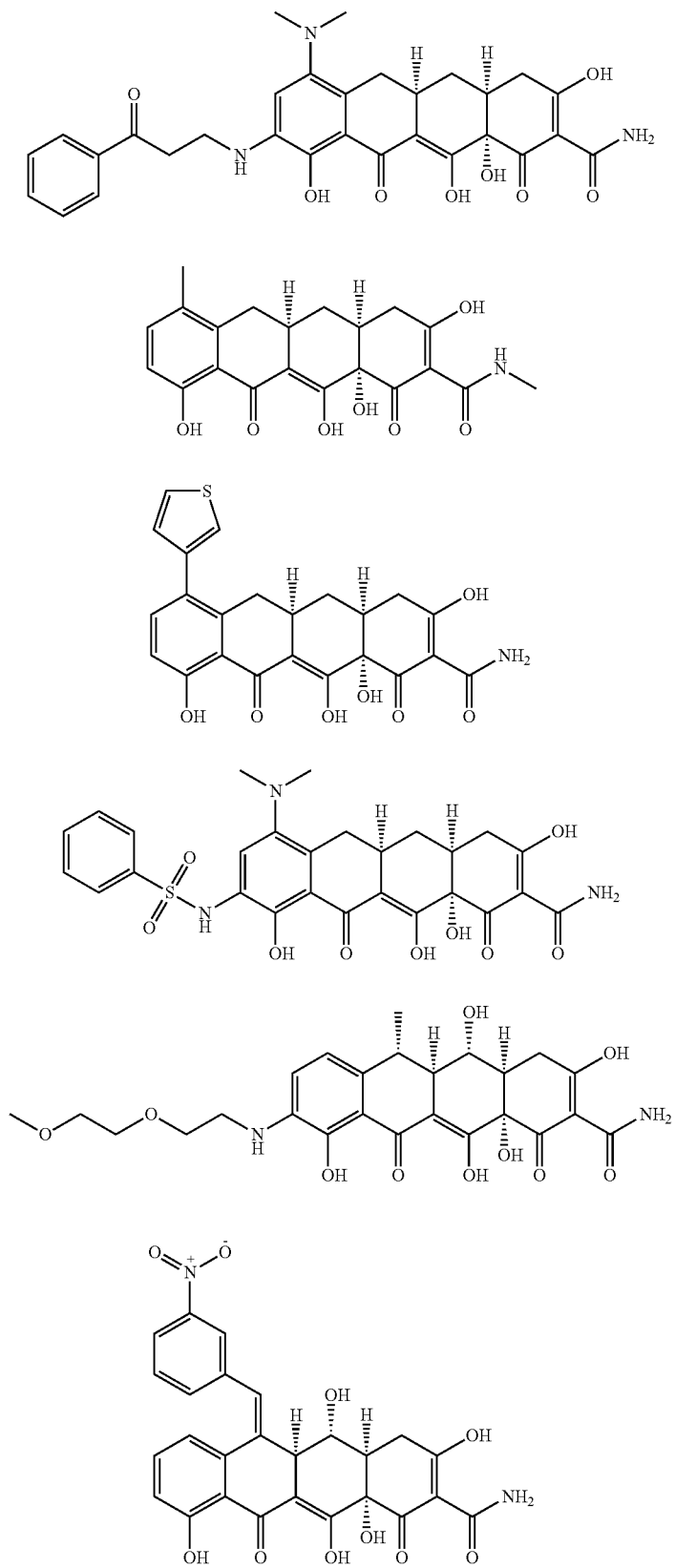

TABLE 2-continued
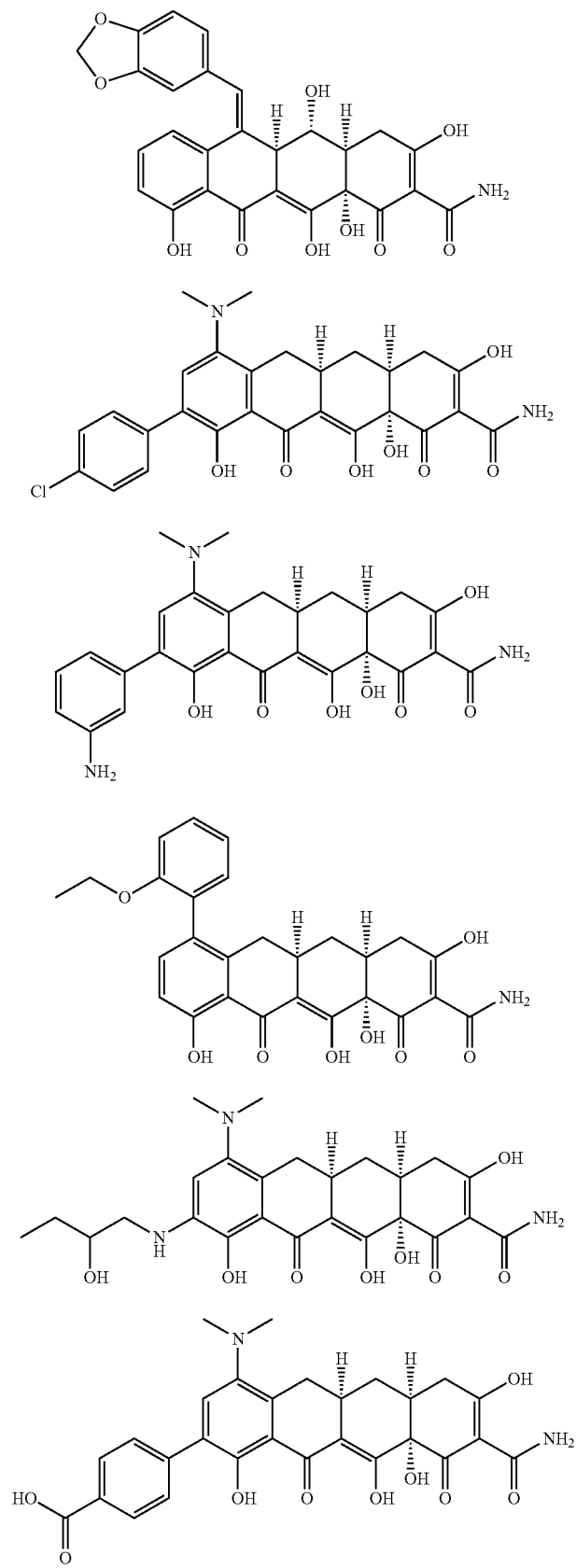

TABLE 2-continued
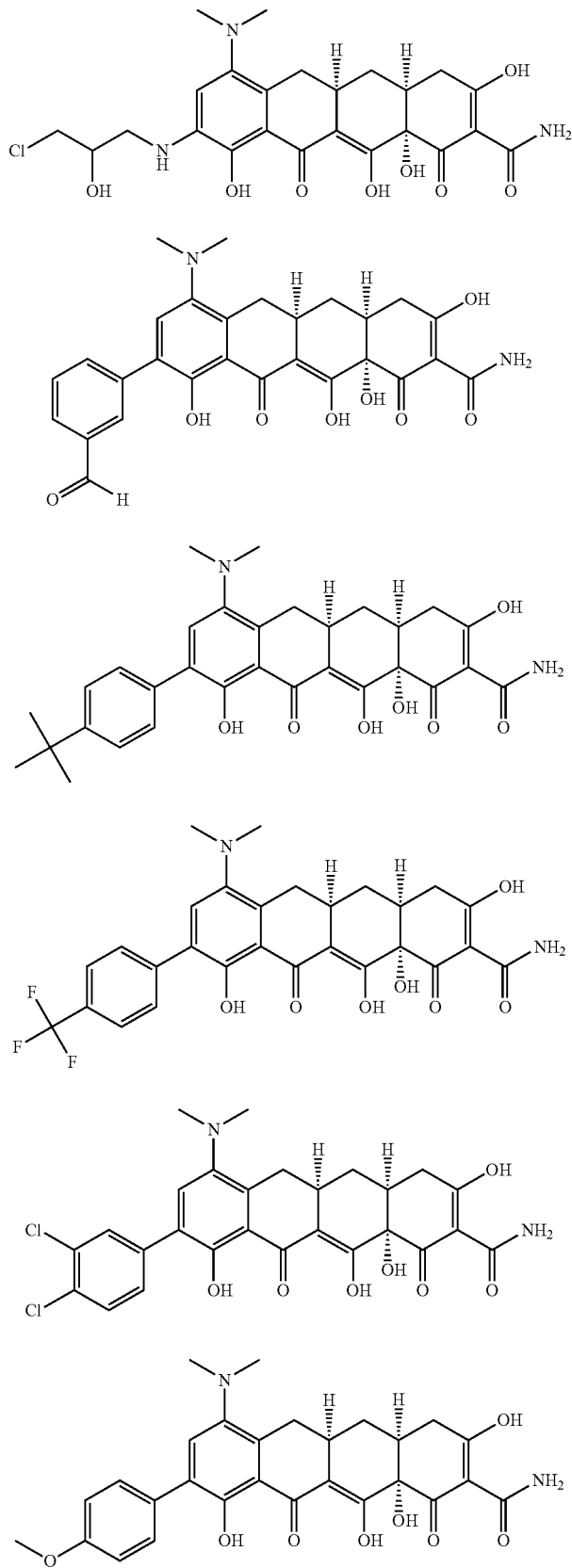

TABLE 2-continued
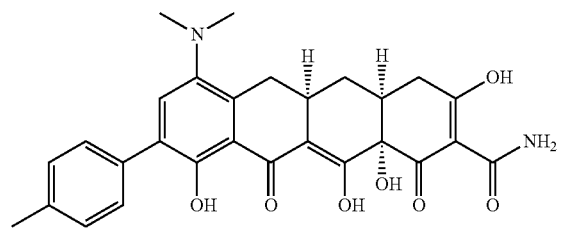 [SMILES: Cc1ccc(-c2cc(N(C)C)c3c(c2O)C(=O)C2=C(O)[C@]4(O)C(=O)C(C(N)=O)=C(O)C[C@@H]4C[C@@H]2C3)cc1]
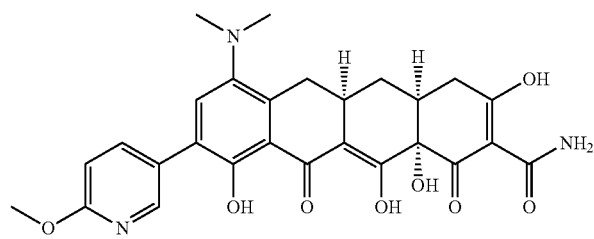
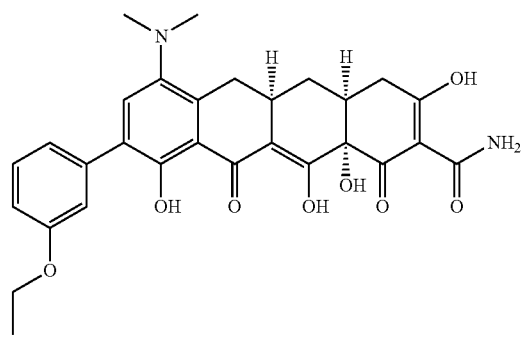 [SMILES: CCOc1cccc(-c2cc(N(C)C)c3c(c2O)C(=O)C2=C(O)[C@]4(O)C(=O)C(C(N)=O)=C(O)C[C@@H]4C[C@@H]2C3)c1]
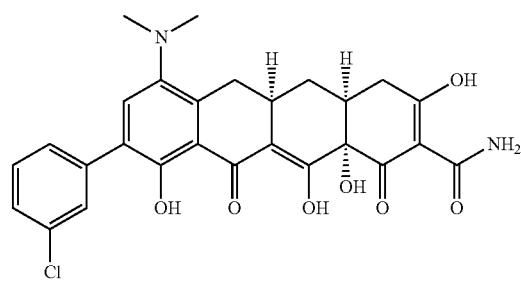 [SMILES: CN(C)c1cc(-c2cccc(Cl)c2)c(O)c2c1C[C@H]1C[C@H]3CC(O)=C(C(N)=O)C(=O)[C@@]3(O)C(O)=C1C2=O]
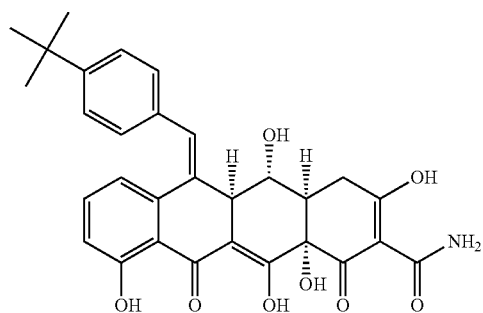 [SMILES: CC(C)(C)c1ccc(/C=C2\c3cccc(O)c3C(=O)C3=C(O)[C@]4(O)C(=O)C(C(N)=O)=C(O)C[C@@H]4[C@@H](O)[C@@H]32)cc1]

TABLE 2-continued
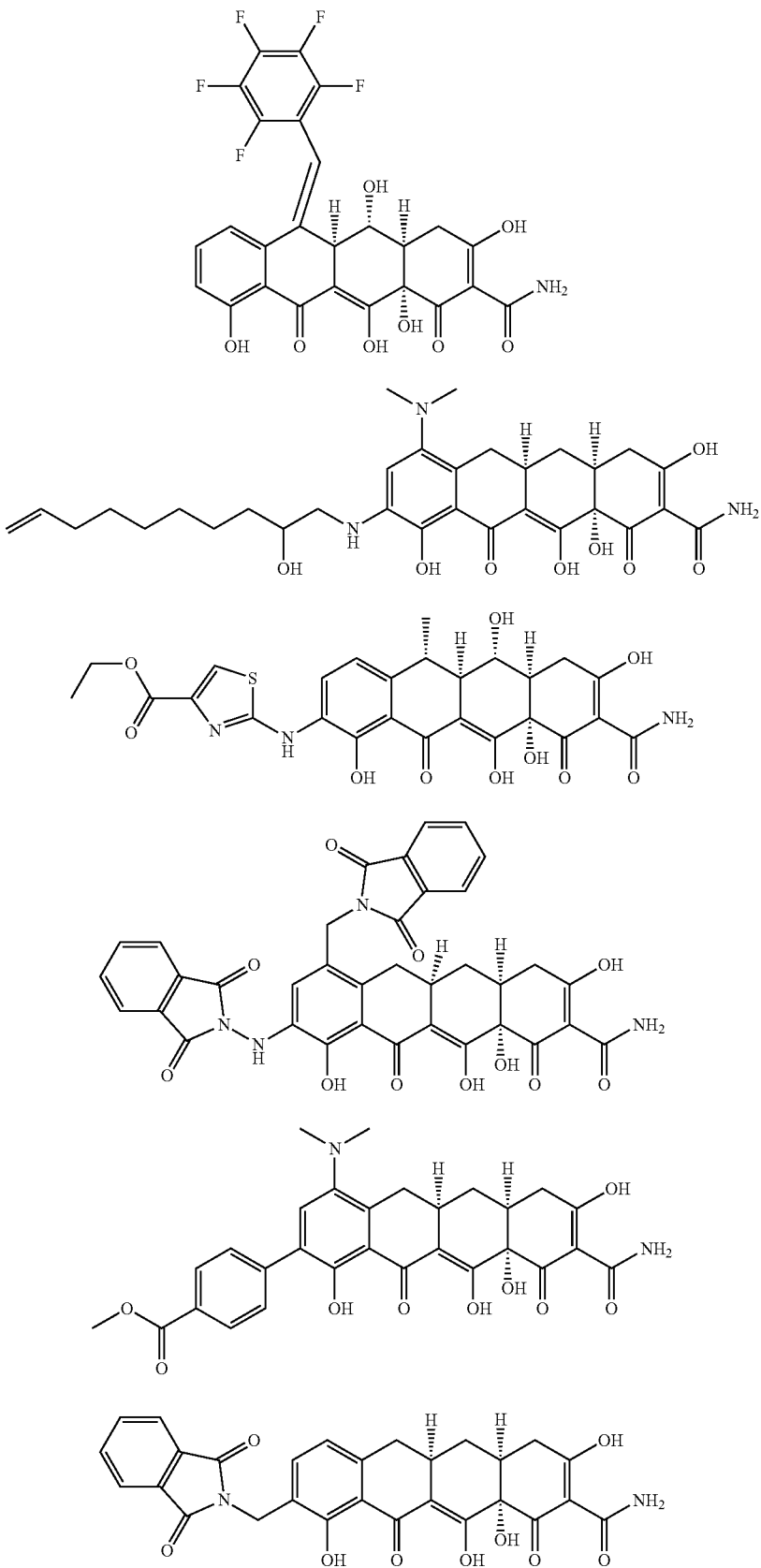

TABLE 2-continued
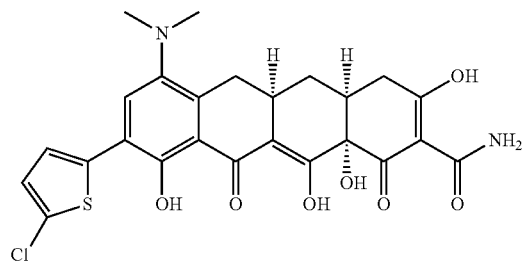 [SMILES: CN(C)c1cc(-c2ccc(Cl)s2)c(O)c2c1C[C@H]1C[C@H]3CC(O)=C(C(N)=O)C(=O)[C@@]3(O)C(O)=C1C2=O]
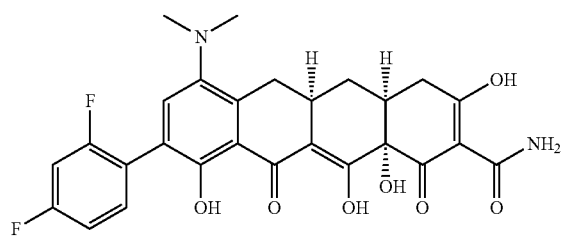 [SMILES: CN(C)c1cc(-c2ccc(F)cc2F)c(O)c2c1C[C@H]1C[C@H]3CC(O)=C(C(N)=O)C(=O)[C@@]3(O)C(O)=C1C2=O]
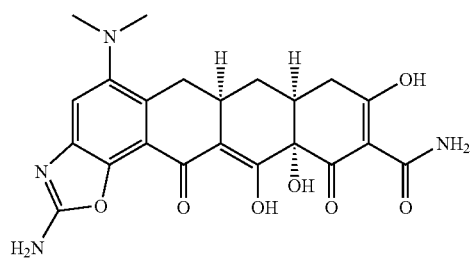 [SMILES: CN(C)c1cc2nc(N)oc2c2c1C[C@H]1C[C@H]3CC(O)=C(C(N)=O)C(=O)[C@@]3(O)C(O)=C1C2=O]
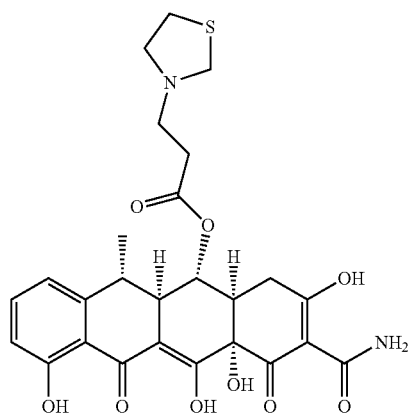 [SMILES: C[C@H]1c2cccc(O)c2C(=O)C2=C(O)[C@]3(O)C(=O)C(C(N)=O)=C(O)C[C@@H]3[C@@H](OC(=O)CCN3CCSC3)[C@@H]21]
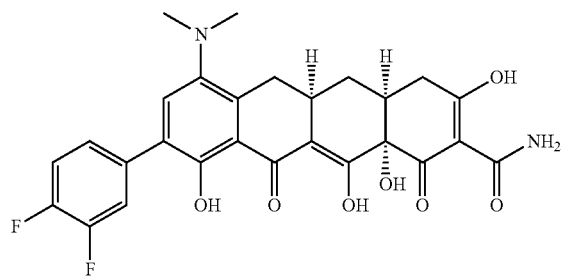 [SMILES: CN(C)c1cc(-c2ccc(F)c(F)c2)c(O)c2c1C[C@H]1C[C@H]3CC(O)=C(C(N)=O)C(=O)[C@@]3(O)C(O)=C1C2=O]

TABLE 2-continued
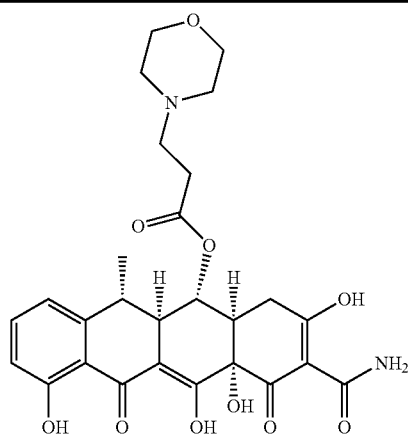
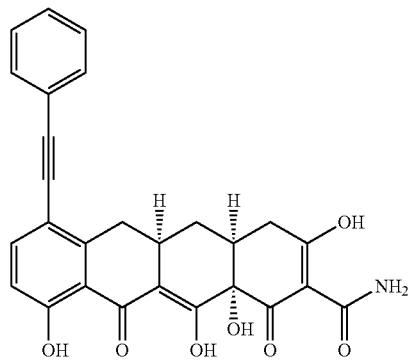 [SMILES: NC(=O)C1=C(O)C[C@@H]2C[C@@H]3Cc4c(C#Cc5ccccc5)ccc(O)c4C(=O)C3=C(O)[C@]2(O)C1=O]
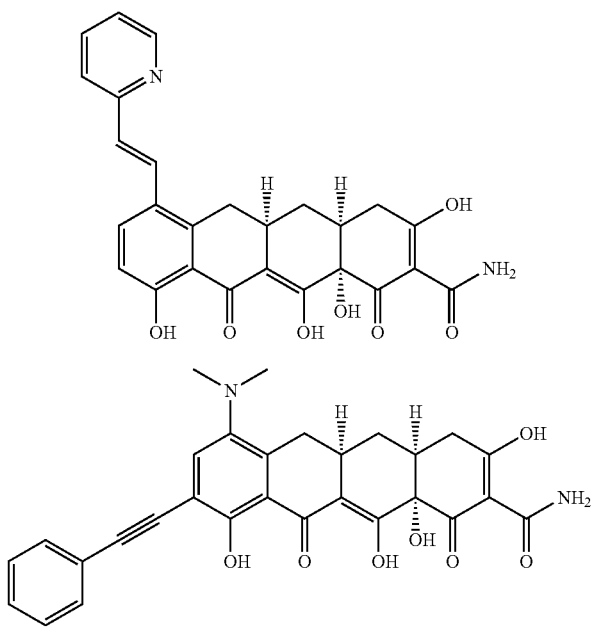
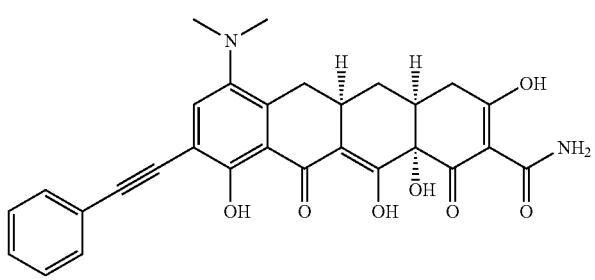 [SMILES: CN(C)c1cc(C#Cc2ccccc2)c(O)c2c1C[C@H]1C[C@H]3CC(O)=C(C(N)=O)C(=O)[C@@]3(O)C(O)=C1C2=O]

TABLE 2-continued
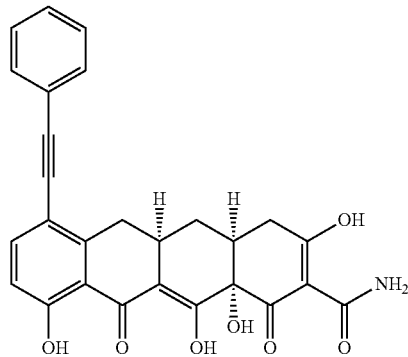 [SMILES: NC(=O)C1=C(O)C[C@@H]2C[C@@H]3Cc4c(C#Cc5ccccc5)ccc(O)c4C(=O)C3=C(O)[C@]2(O)C1=O]
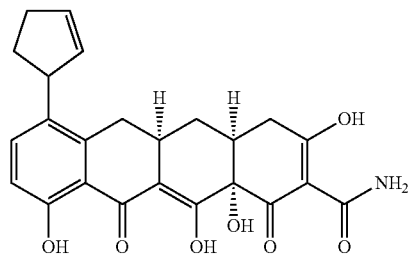 [SMILES: NC(=O)C1=C(O)C[C@@H]2C[C@@H]3Cc4c(C5C=CCC5)ccc(O)c4C(=O)C3=C(O)[C@]2(O)C1=O]
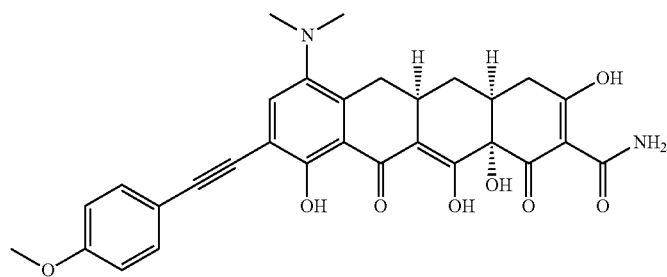 [SMILES: COc1ccc(C#Cc2cc(N(C)C)c3c(c2O)C(=O)C2=C(O)[C@]4(O)C(=O)C(C(N)=O)=C(O)C[C@@H]4C[C@@H]2C3)cc1]
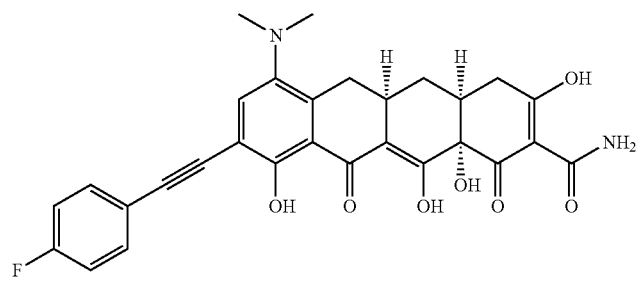 [SMILES: CN(C)c1cc(C#Cc2ccc(F)cc2)c(O)c2c1C[C@H]1C[C@H]3CC(O)=C(C(N)=O)C(=O)[C@@]3(O)C(O)=C1C2=O]
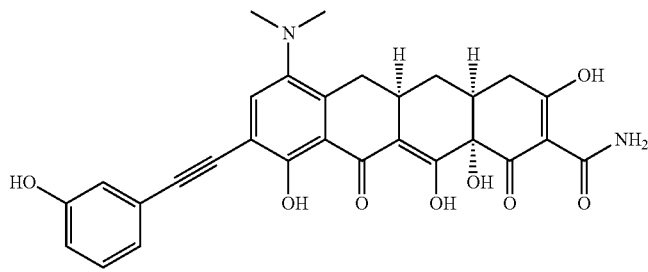 [SMILES: CN(C)c1cc(C#Cc2cccc(O)c2)c(O)c2c1C[C@H]1C[C@H]3CC(O)=C(C(N)=O)C(=O)[C@@]3(O)C(O)=C1C2=O]

TABLE 2-continued
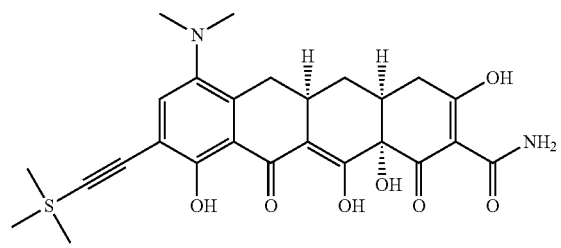 [SMILES: CN(C)c1cc(C#CS(C)(C)C)c(O)c2c1C[C@H]1C[C@H]3CC(O)=C(C(N)=O)C(=O)[C@@]3(O)C(O)=C1C2=O]
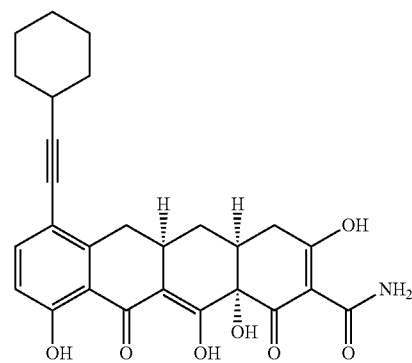 [SMILES: NC(=O)C1=C(O)C[C@@H]2C[C@@H]3Cc4c(C#CC5CCCCC5)ccc(O)c4C(=O)C3=C(O)[C@]2(O)C1=O]
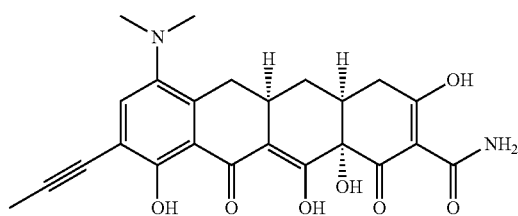 [SMILES: CC#Cc1cc(N(C)C)c2c(c1O)C(=O)C1=C(O)[C@]3(O)C(=O)C(C(N)=O)=C(O)C[C@@H]3C[C@@H]1C2]
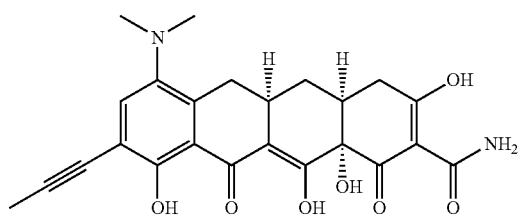 [SMILES: CC#Cc1cc(N(C)C)c2c(c1O)C(=O)C1=C(O)[C@]3(O)C(=O)C(C(N)=O)=C(O)C[C@@H]3C[C@@H]1C2]
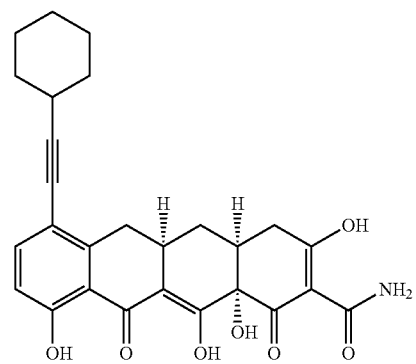 [SMILES: NC(=O)C1=C(O)C[C@@H]2C[C@@H]3Cc4c(C#CC5CCCCC5)ccc(O)c4C(=O)C3=C(O)[C@]2(O)C1=O]

TABLE 2-continued
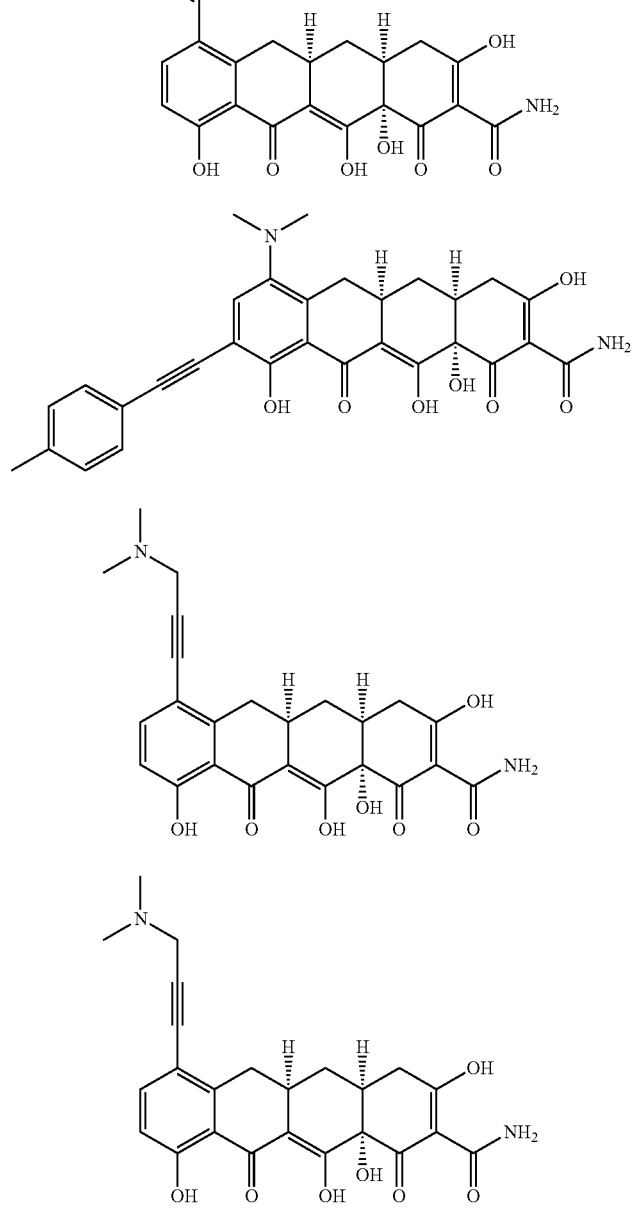
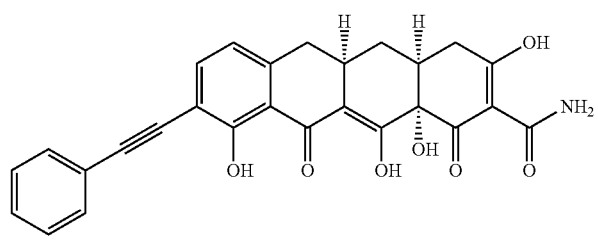 [SMILES: NC(=O)C1=C(O)C[C@@H]2C[C@@H]3Cc4ccc(C#Cc5ccccc5)c(O)c4C(=O)C3=C(O)[C@]2(O)C1=O]

TABLE 2-continued
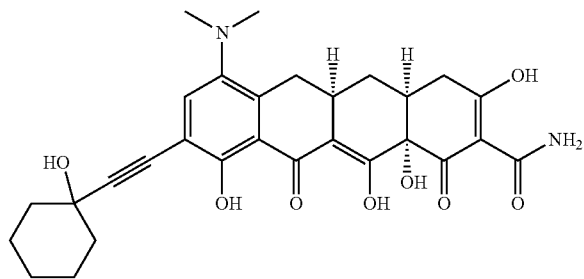 [SMILES: CN(C)c1cc(C#CC2(O)CCCCC2)c(O)c2c1C[C@H]1C[C@H]3CC(O)=C(C(N)=O)C(=O)[C@@]3(O)C(O)=C1C2=O]
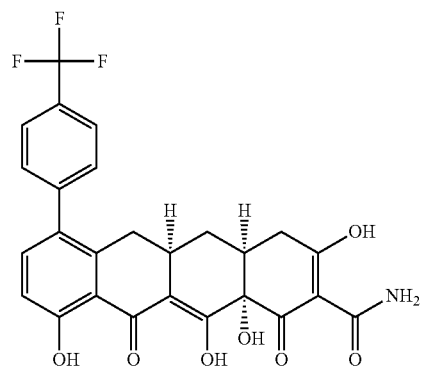
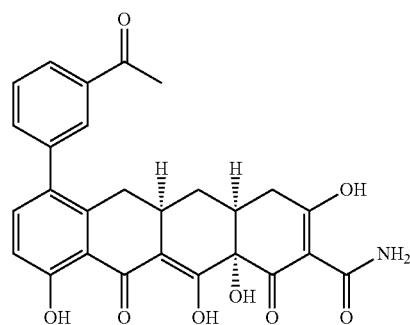 [SMILES: CC(=O)c1cccc(-c2ccc(O)c3c2C[C@H]2C[C@H]4CC(O)=C(C(N)=O)C(=O)[C@@]4(O)C(O)=C2C3=O)c1]
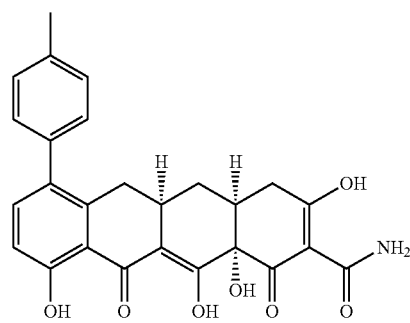 [SMILES: Cc1ccc(-c2ccc(O)c3c2C[C@H]2C[C@H]4CC(O)=C(C(N)=O)C(=O)[C@@]4(O)C(O)=C2C3=O)cc1]

TABLE 2-continued
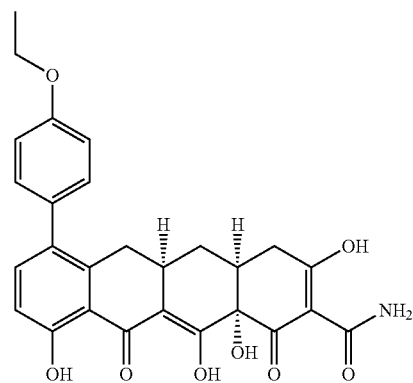 [SMILES: CCOc1ccc(-c2ccc(O)c3c2C[C@H]2C[C@H]4CC(O)=C(C(N)=O)C(=O)[C@@]4(O)C(O)=C2C3=O)cc1]
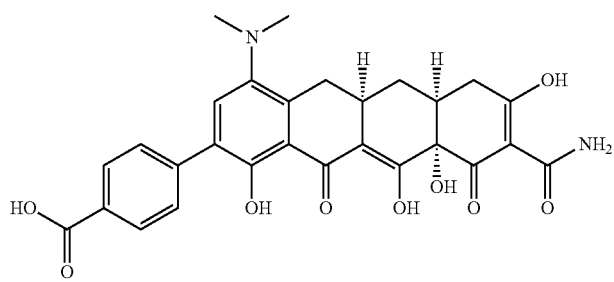 [SMILES: CN(C)c1cc(-c2ccc(C(=O)O)cc2)c(O)c2c1C[C@H]1C[C@H]3CC(O)=C(C(N)=O)C(=O)[C@@]3(O)C(O)=C1C2=O]
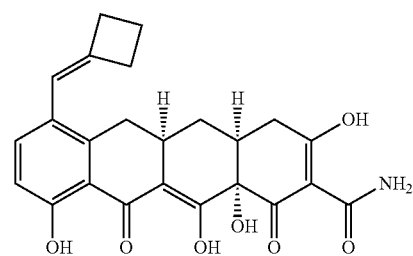 [SMILES: NC(=O)C1=C(O)C[C@@H]2C[C@@H]3Cc4c(C=C5CCC5)ccc(O)c4C(=O)C3=C(O)[C@]2(O)C1=O]
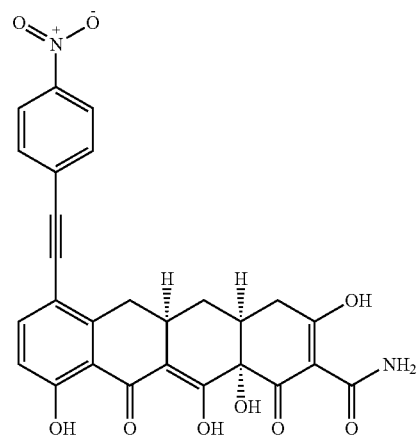

TABLE 2-continued
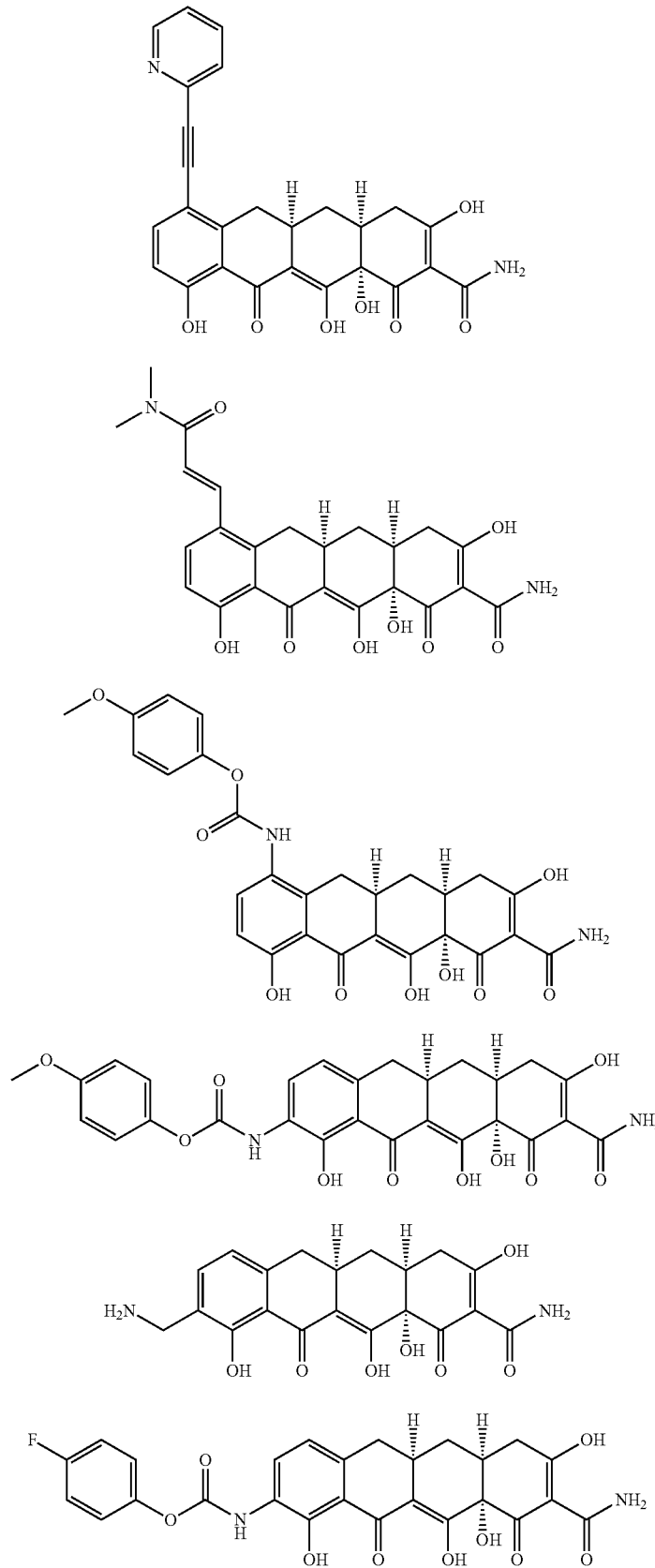

TABLE 2-continued
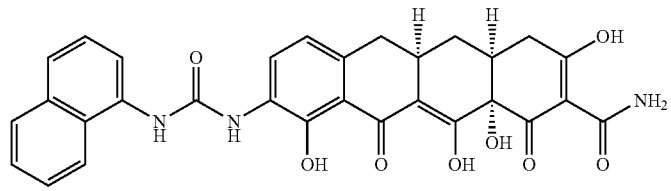 [SMILES: NC(=O)C1=C(O)C[C@@H]2C[C@@H]3Cc4ccc(NC(=O)Nc5cccc6ccccc56)c(O)c4C(=O)C3=C(O)[C@]2(O)C1=O]
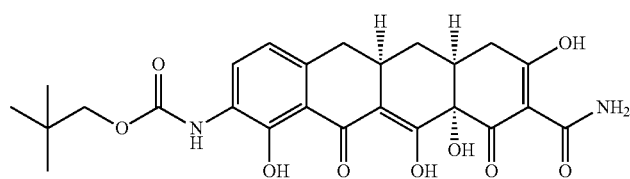 [SMILES: CC(C)(C)COC(=O)Nc1ccc2c(c1O)C(=O)C1=C(O)[C@]3(O)C(=O)C(C(N)=O)=C(O)C[C@@H]3C[C@@H]1C2]
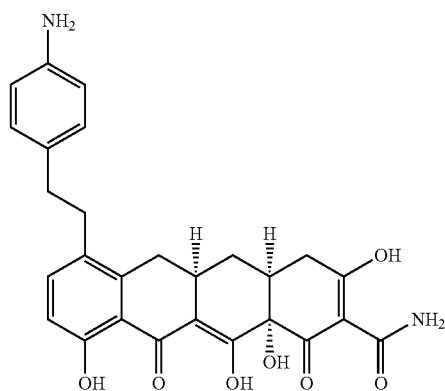 [SMILES: NC(=O)C1=C(O)C[C@@H]2C[C@@H]3Cc4c(CCc5ccc(N)cc5)ccc(O)c4C(=O)C3=C(O)[C@]2(O)C1=O]
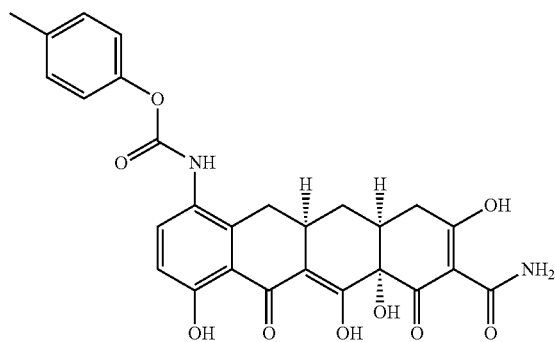 [SMILES: Cc1ccc(OC(=O)Nc2ccc(O)c3c2C[C@H]2C[C@H]4CC(O)=C(C(N)=O)C(=O)[C@@]4(O)C(O)=C2C3=O)cc1]
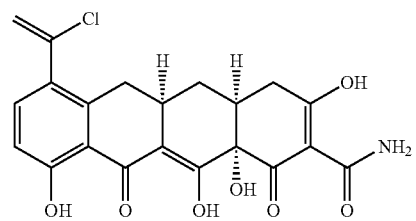 [SMILES: C=C(Cl)c1ccc(O)c2c1C[C@H]1C[C@H]3CC(O)=C(C(N)=O)C(=O)[C@@]3(O)C(O)=C1C2=O]

TABLE 2-continued
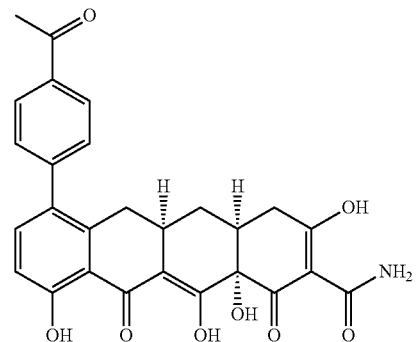 [SMILES: CC(=O)c1ccc(-c2ccc(O)c3c2C[C@H]2C[C@H]4CC(O)=C(C(N)=O)C(=O)[C@@]4(O)C(O)=C2C3=O)cc1]
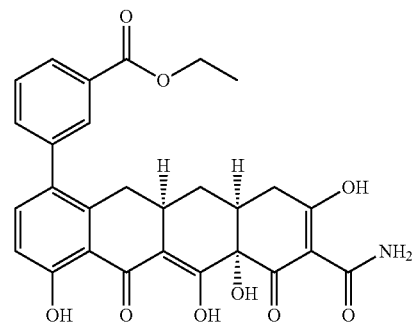
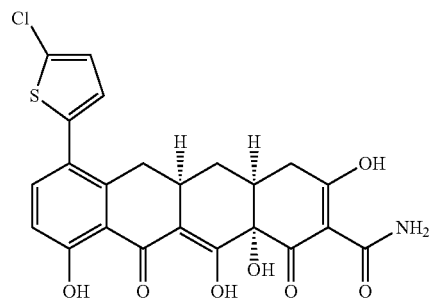 [SMILES: NC(=O)C1=C(O)C[C@@H]2C[C@@H]3Cc4c(-c5ccc(Cl)s5)ccc(O)c4C(=O)C3=C(O)[C@]2(O)C1=O]
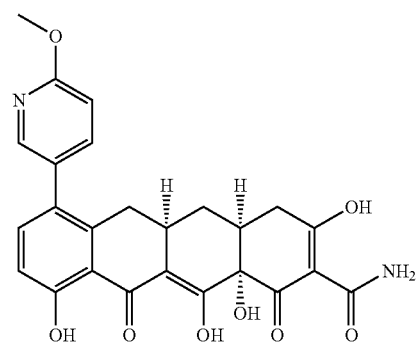 [SMILES: COc1ccc(-c2ccc(O)c3c2C[C@H]2C[C@H]4CC(O)=C(C(N)=O)C(=O)[C@@]4(O)C(O)=C2C3=O)cn1]
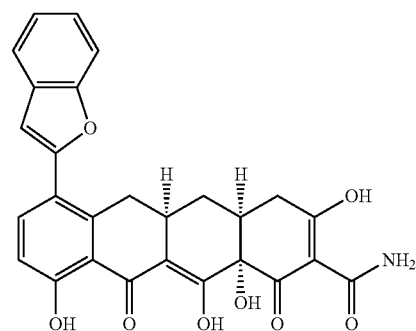 [SMILES: NC(=O)C1=C(O)C[C@@H]2C[C@@H]3Cc4c(-c5cc6ccccc6o5)ccc(O)c4C(=O)C3=C(O)[C@]2(O)C1=O]

TABLE 2-continued
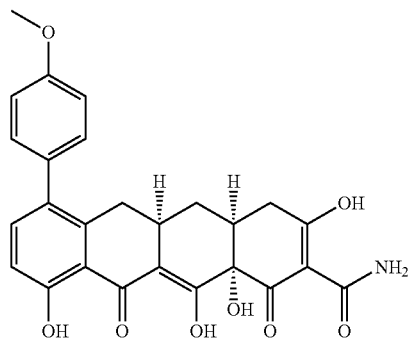 [SMILES: COc1ccc(-c2ccc(O)c3c2C[C@H]2C[C@H]4CC(O)=C(C(N)=O)C(=O)[C@@]4(O)C(O)=C2C3=O)cc1]
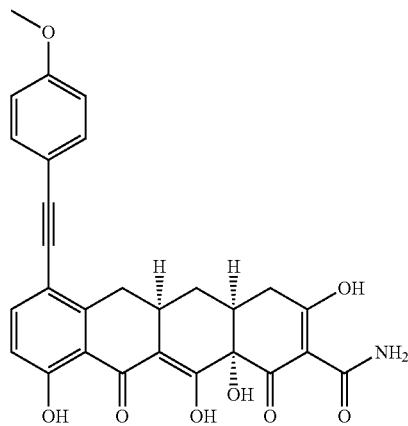 [SMILES: COc1ccc(C#Cc2ccc(O)c3c2C[C@H]2C[C@H]4CC(O)=C(C(N)=O)C(=O)[C@@]4(O)C(O)=C2C3=O)cc1]
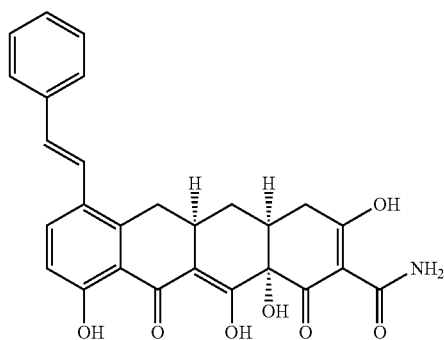 [SMILES: NC(=O)C1=C(O)C[C@@H]2C[C@@H]3Cc4c(/C=C/c5ccccc5)ccc(O)c4C(=O)C3=C(O)[C@]2(O)C1=O]
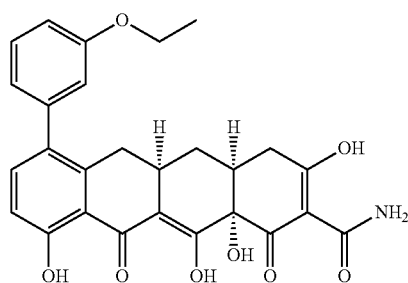 [SMILES: CCOc1cccc(-c2ccc(O)c3c2C[C@H]2C[C@H]4CC(O)=C(C(N)=O)C(=O)[C@@]4(O)C(O)=C2C3=O)c1]

TABLE 2-continued
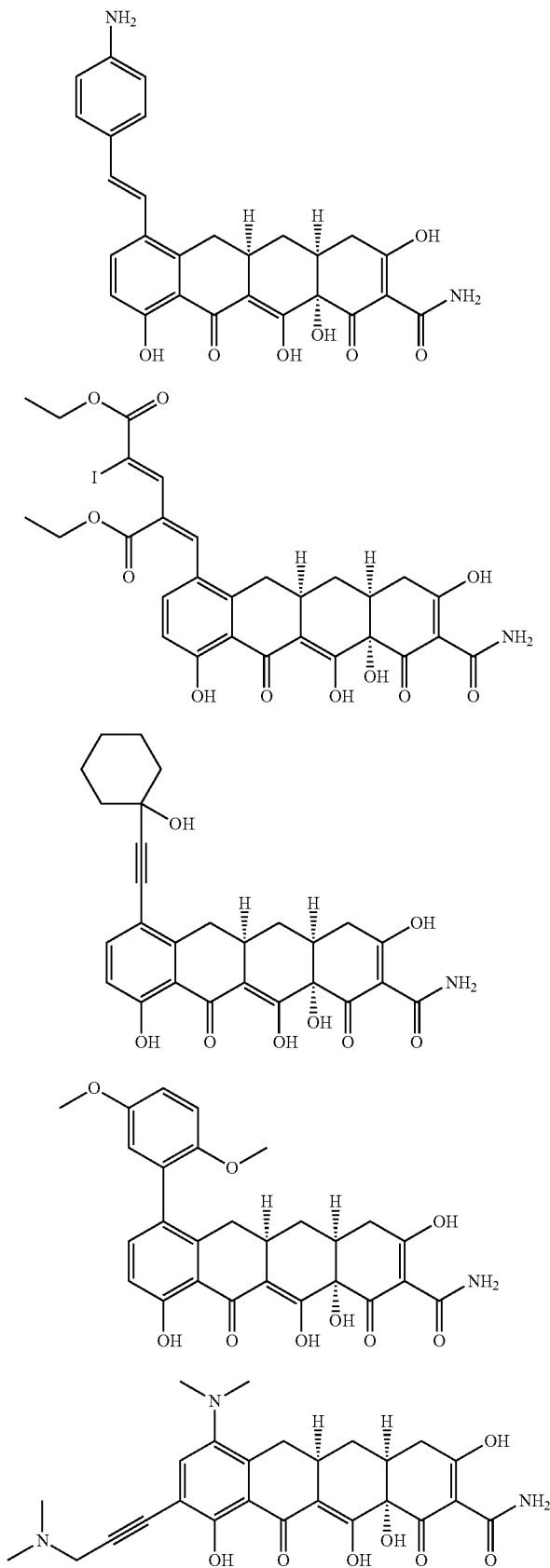

TABLE 2-continued
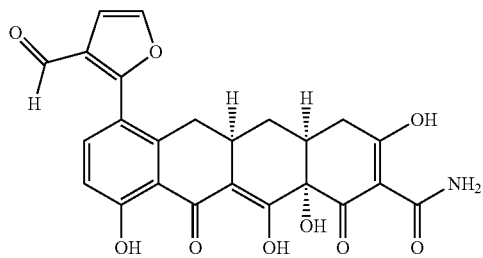 [SMILES: NC(=O)C1=C(O)C[C@@H]2C[C@@H]3Cc4c(-c5occc5C=O)ccc(O)c4C(=O)C3=C(O)[C@]2(O)C1=O]
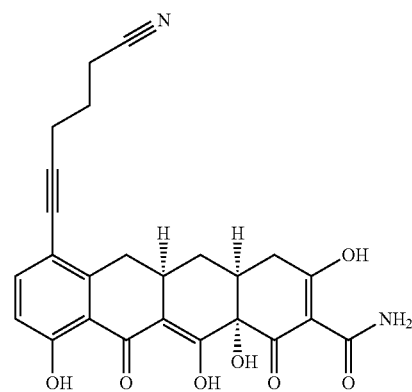 [SMILES: N#CCCCC#Cc1ccc(O)c2c1C[C@H]1C[C@H]3CC(O)=C(C(N)=O)C(=O)[C@@]3(O)C(O)=C1C2=O]
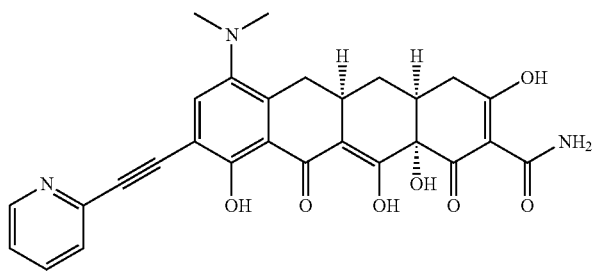 [SMILES: CN(C)c1cc(C#Cc2ccccn2)c(O)c2c1C[C@H]1C[C@H]3CC(O)=C(C(N)=O)C(=O)[C@@]3(O)C(O)=C1C2=O]
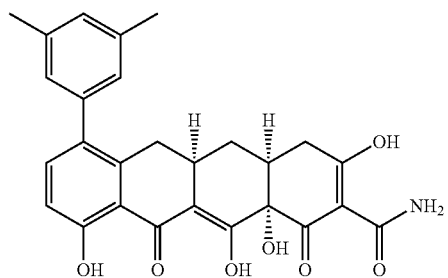 [SMILES: Cc1cc(C)cc(-c2ccc(O)c3c2C[C@H]2C[C@H]4CC(O)=C(C(N)=O)C(=O)[C@@]4(O)C(O)=C2C3=O)c1]
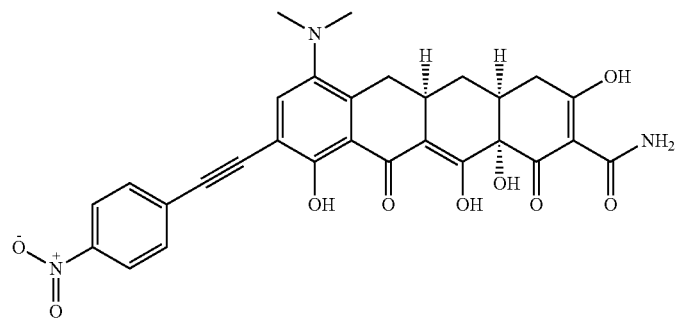

TABLE 2-continued
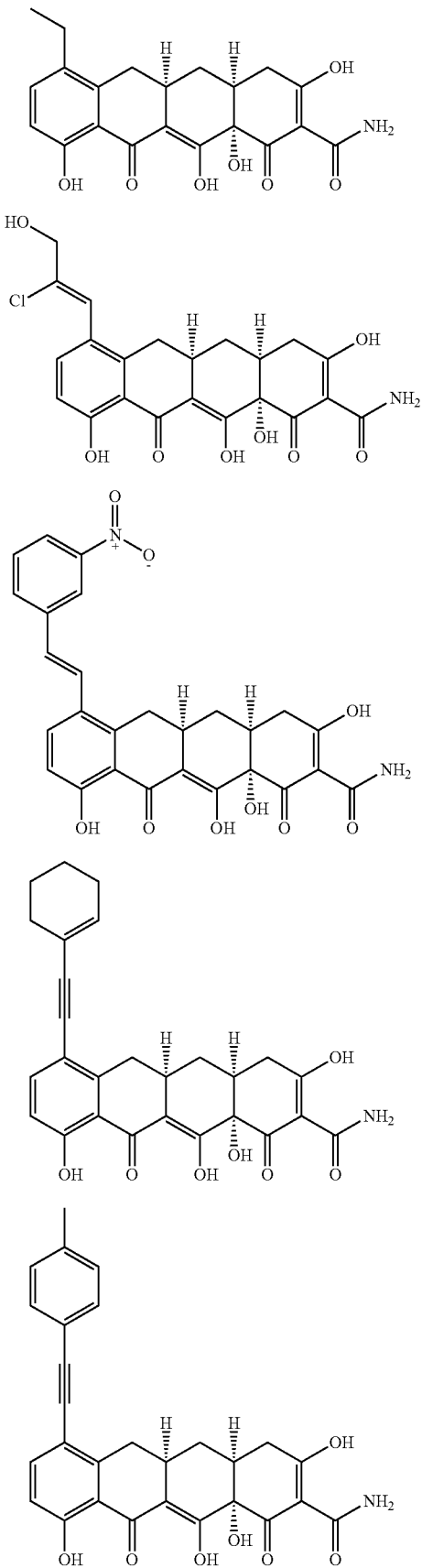

TABLE 2-continued
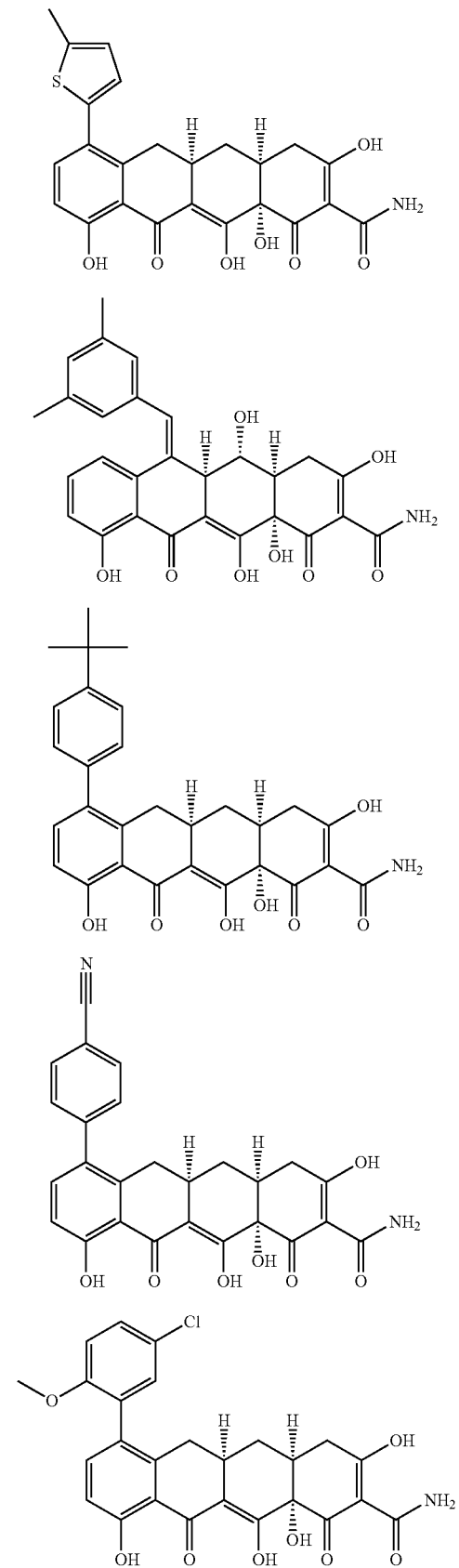

TABLE 2-continued
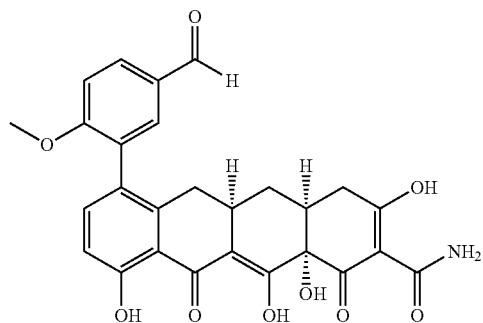 [SMILES: COc1ccc(C=O)cc1-c1ccc(O)c2c1C[C@H]1C[C@H]3CC(O)=C(C(N)=O)C(=O)[C@@]3(O)C(O)=C1C2=O]
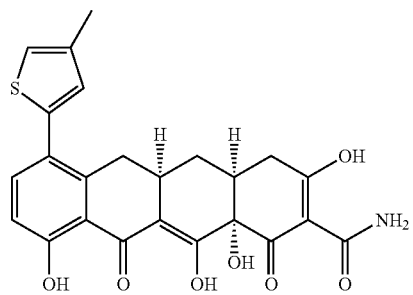 [SMILES: Cc1csc(-c2ccc(O)c3c2C[C@H]2C[C@H]4CC(O)=C(C(N)=O)C(=O)[C@@]4(O)C(O)=C2C3=O)c1]
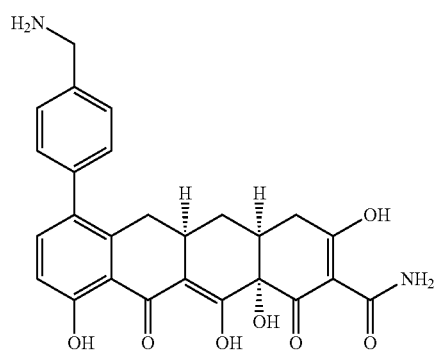 [SMILES: NCc1ccc(-c2ccc(O)c3c2C[C@H]2C[C@H]4CC(O)=C(C(N)=O)C(=O)[C@@]4(O)C(O)=C2C3=O)cc1]
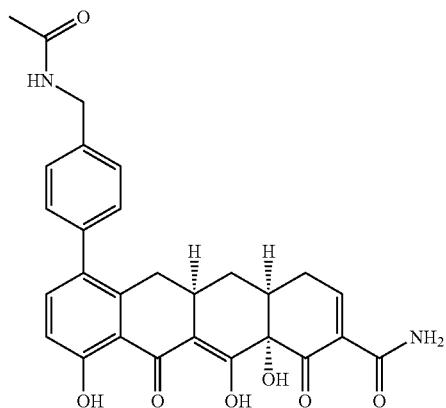 [SMILES: CC(=O)NCc1ccc(-c2ccc(O)c3c2C[C@H]2C[C@H]4CC=C(C(N)=O)C(=O)[C@@]4(O)C(O)=C2C3=O)cc1]

TABLE 2-continued
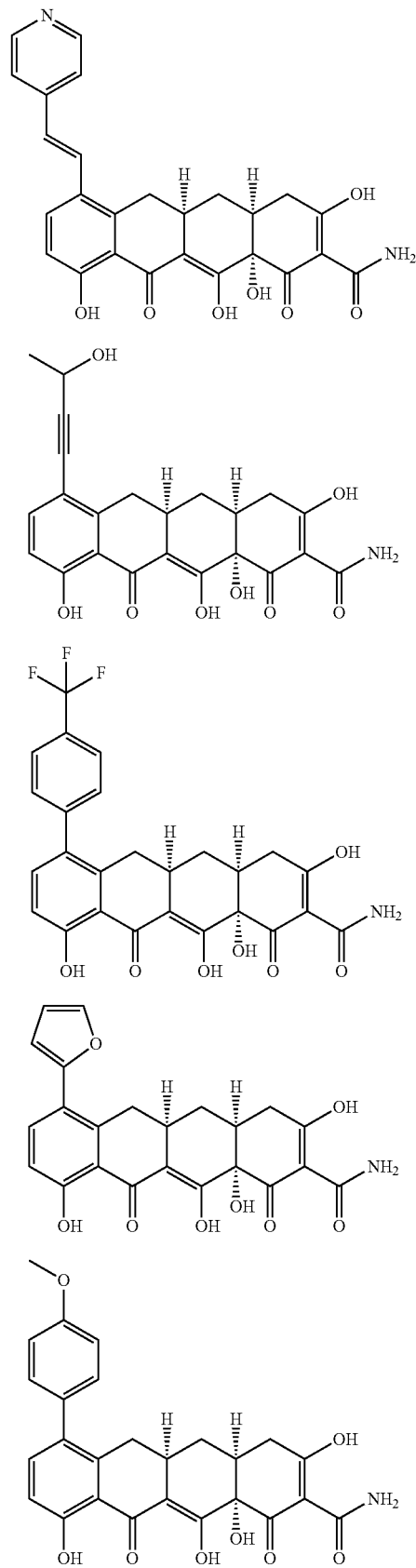

TABLE 2-continued
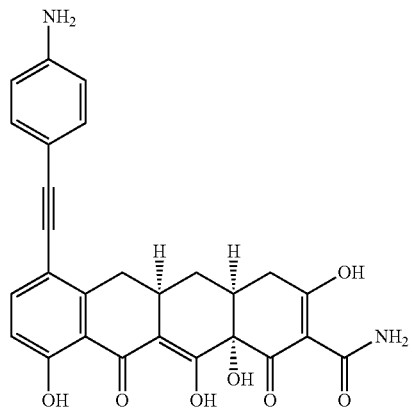 [SMILES: NC(=O)C1=C(O)C[C@@H]2C[C@@H]3Cc4c(C#Cc5ccc(N)cc5)ccc(O)c4C(=O)C3=C(O)[C@]2(O)C1=O]
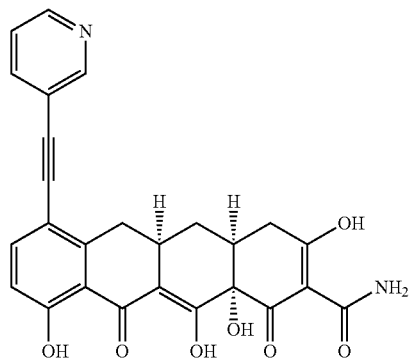 [SMILES: NC(=O)C1=C(O)C[C@@H]2C[C@@H]3Cc4c(C#Cc5cccnc5)ccc(O)c4C(=O)C3=C(O)[C@]2(O)C1=O]
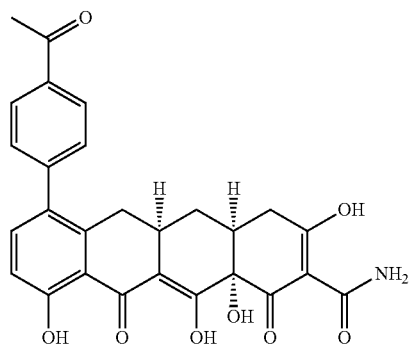 [SMILES: CC(=O)c1ccc(-c2ccc(O)c3c2C[C@H]2C[C@H]4CC(O)=C(C(N)=O)C(=O)[C@@]4(O)C(O)=C2C3=O)cc1]
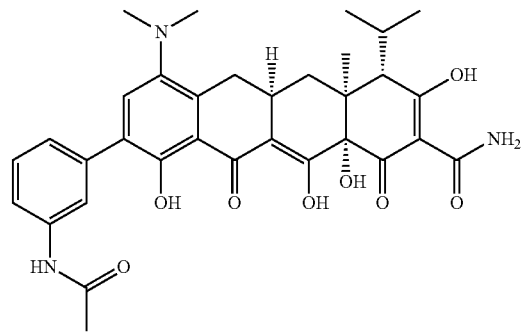 [SMILES: CC(=O)Nc1cccc(-c2cc(N(C)C)c3c(c2O)C(=O)C2=C(O)[C@]4(O)C(=O)C(C(N)=O)=C(O)[C@@H](C(C)C)[C@]4(C)C[C@@H]2C3)c1]

TABLE 2-continued
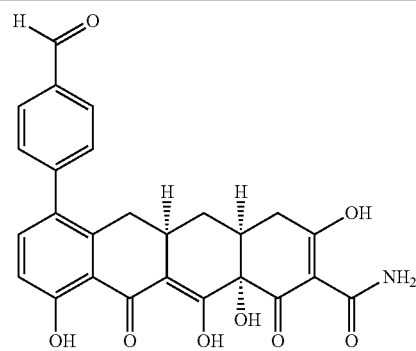 [SMILES: NC(=O)C1=C(O)C[C@@H]2C[C@@H]3Cc4c(-c5ccc(C=O)cc5)ccc(O)c4C(=O)C3=C(O)[C@]2(O)C1=O]
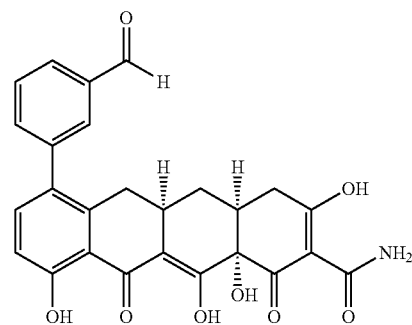 [SMILES: NC(=O)C1=C(O)C[C@@H]2C[C@@H]3Cc4c(-c5cccc(C=O)c5)ccc(O)c4C(=O)C3=C(O)[C@]2(O)C1=O]
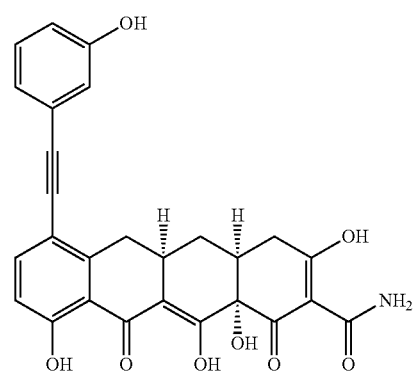 [SMILES: NC(=O)C1=C(O)C[C@@H]2C[C@@H]3Cc4c(C#Cc5cccc(O)c5)ccc(O)c4C(=O)C3=C(O)[C@]2(O)C1=O]
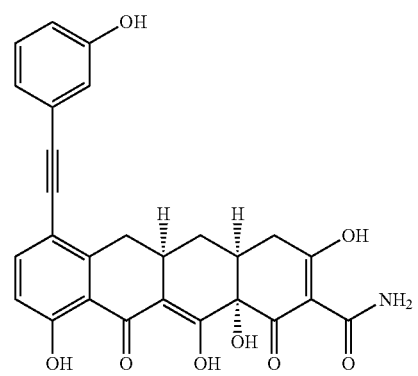 [SMILES: NC(=O)C1=C(O)C[C@@H]2C[C@@H]3Cc4c(C#Cc5cccc(O)c5)ccc(O)c4C(=O)C3=C(O)[C@]2(O)C1=O]

TABLE 2-continued
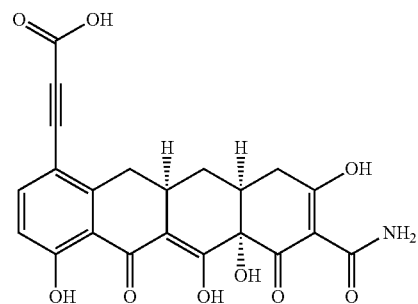 [SMILES: NC(=O)C1=C(O)C[C@@H]2C[C@@H]3Cc4c(C#CC(=O)O)ccc(O)c4C(=O)C3=C(O)[C@]2(O)C1=O]
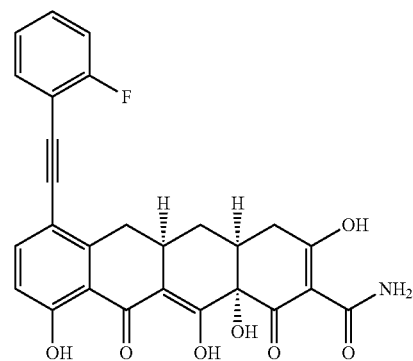 [SMILES: NC(=O)C1=C(O)C[C@@H]2C[C@@H]3Cc4c(C#Cc5ccccc5F)ccc(O)c4C(=O)C3=C(O)[C@]2(O)C1=O]
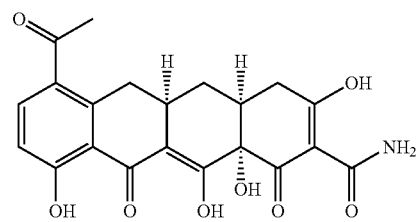 [SMILES: CC(=O)c1ccc(O)c2c1C[C@H]1C[C@H]3CC(O)=C(C(N)=O)C(=O)[C@@]3(O)C(O)=C1C2=O]
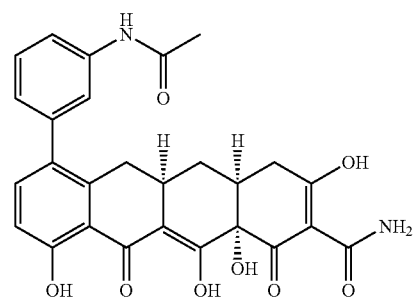 [SMILES: CC(=O)Nc1cccc(-c2ccc(O)c3c2C[C@H]2C[C@H]4CC(O)=C(C(N)=O)C(=O)[C@@]4(O)C(O)=C2C3=O)c1]
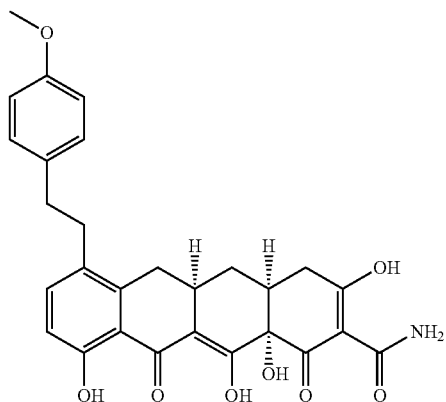 [SMILES: COc1ccc(CCc2ccc(O)c3c2C[C@H]2C[C@H]4CC(O)=C(C(N)=O)C(=O)[C@@]4(O)C(O)=C2C3=O)cc1]

TABLE 2-continued
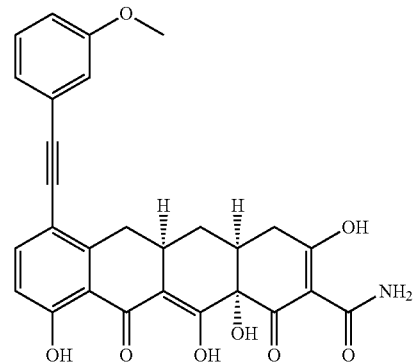 [SMILES: COc1cccc(C#Cc2ccc(O)c3c2C[C@H]2C[C@H]4CC(O)=C(C(N)=O)C(=O)[C@@]4(O)C(O)=C2C3=O)c1]
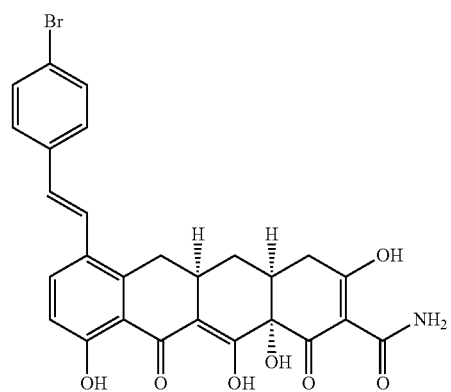 [SMILES: NC(=O)C1=C(O)C[C@@H]2C[C@@H]3Cc4c(/C=C/c5ccc(Br)cc5)ccc(O)c4C(=O)C3=C(O)[C@]2(O)C1=O]
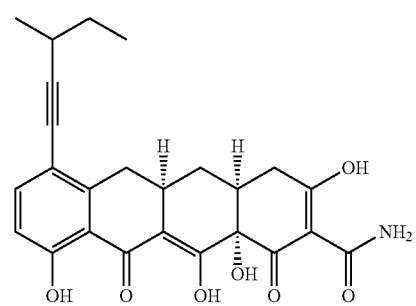 [SMILES: CCC(C)C#Cc1ccc(O)c2c1C[C@H]1C[C@H]3CC(O)=C(C(N)=O)C(=O)[C@@]3(O)C(O)=C1C2=O]
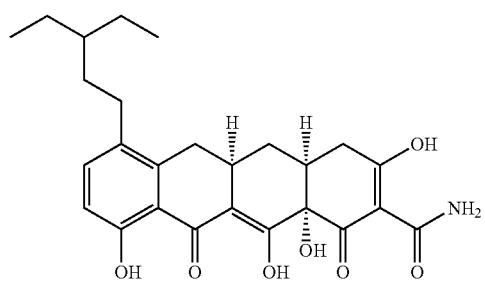 [SMILES: CCC(CC)CCc1ccc(O)c2c1C[C@H]1C[C@H]3CC(O)=C(C(N)=O)C(=O)[C@@]3(O)C(O)=C1C2=O]

TABLE 2-continued
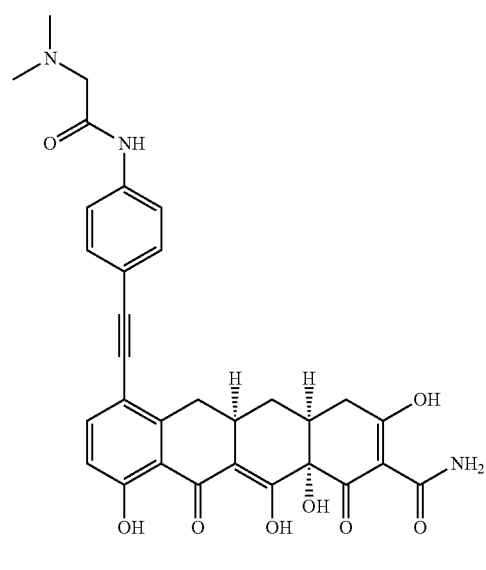 [SMILES: CN(C)CC(=O)Nc1ccc(C#Cc2ccc(O)c3c2C[C@H]2C[C@H]4CC(O)=C(C(N)=O)C(=O)[C@@]4(O)C(O)=C2C3=O)cc1]
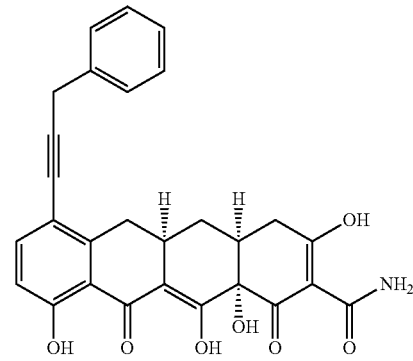 [SMILES: NC(=O)C1=C(O)C[C@@H]2C[C@@H]3Cc4c(C#CCc5ccccc5)ccc(O)c4C(=O)C3=C(O)[C@]2(O)C1=O]
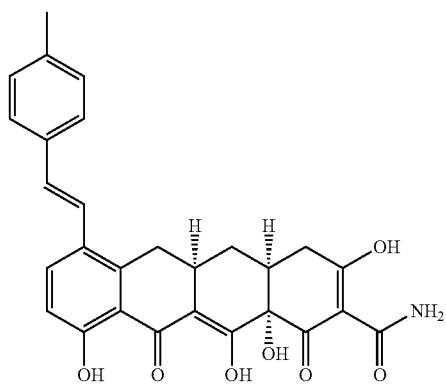 [SMILES: Cc1ccc(/C=C/c2ccc(O)c3c2C[C@H]2C[C@H]4CC(O)=C(C(N)=O)C(=O)[C@@]4(O)C(O)=C2C3=O)cc1]
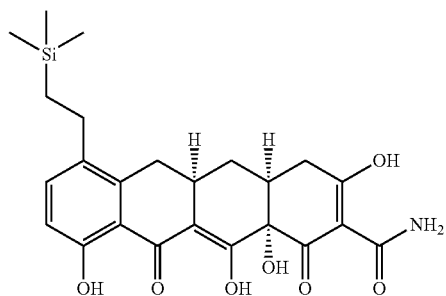 [SMILES: C[Si](C)(C)CCc1ccc(O)c2c1C[C@H]1C[C@H]3CC(O)=C(C(N)=O)C(=O)[C@@]3(O)C(O)=C1C2=O]

TABLE 2-continued
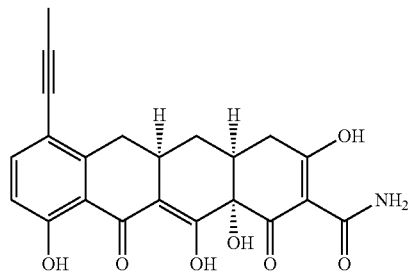 [SMILES: CC#Cc1ccc(O)c2c1C[C@H]1C[C@H]3CC(O)=C(C(N)=O)C(=O)[C@@]3(O)C(O)=C1C2=O]
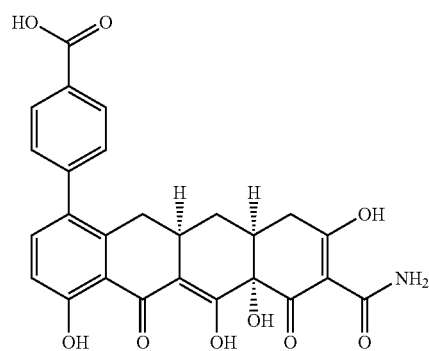 [SMILES: NC(=O)C1=C(O)C[C@@H]2C[C@@H]3Cc4c(-c5ccc(C(=O)O)cc5)ccc(O)c4C(=O)C3=C(O)[C@]2(O)C1=O]
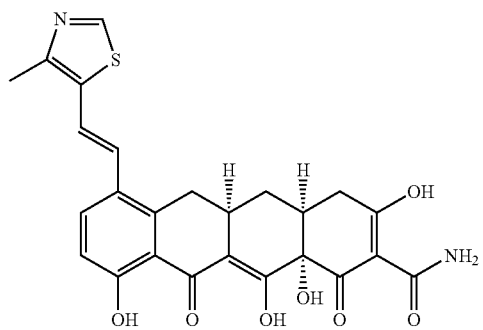 [SMILES: Cc1ncsc1/C=C/c1ccc(O)c2c1C[C@H]1C[C@H]3CC(O)=C(C(N)=O)C(=O)[C@@]3(O)C(O)=C1C2=O]
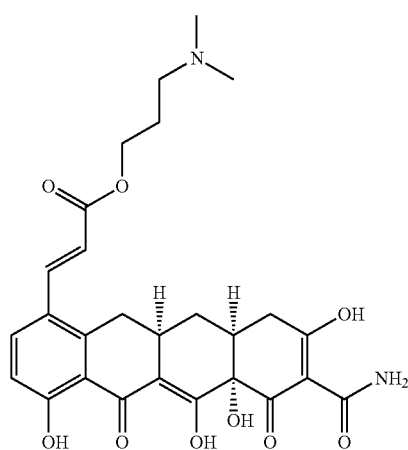 [SMILES: CN(C)CCCOC(=O)/C=C/c1ccc(O)c2c1C[C@H]1C[C@H]3CC(O)=C(C(N)=O)C(=O)[C@@]3(O)C(O)=C1C2=O]

TABLE 2-continued
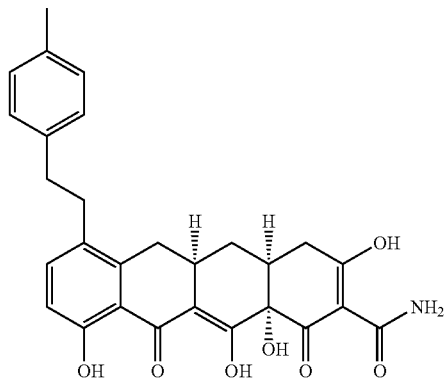 [SMILES: Cc1ccc(CCc2ccc(O)c3c2C[C@H]2C[C@H]4CC(O)=C(C(N)=O)C(=O)[C@@]4(O)C(O)=C2C3=O)cc1]
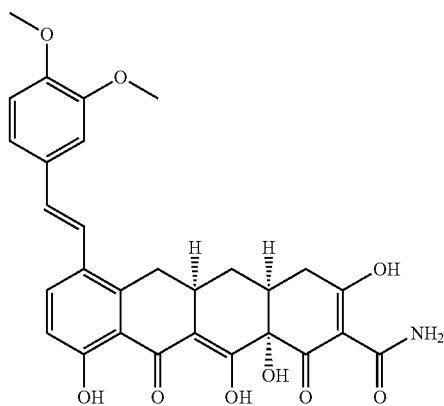 [SMILES: COc1ccc(/C=C/c2ccc(O)c3c2C[C@H]2C[C@H]4CC(O)=C(C(N)=O)C(=O)[C@@]4(O)C(O)=C2C3=O)cc1OC]
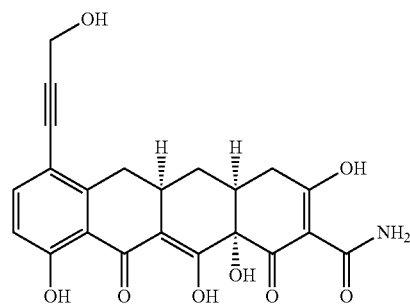 [SMILES: NC(=O)C1=C(O)C[C@@H]2C[C@@H]3Cc4c(C#CCO)ccc(O)c4C(=O)C3=C(O)[C@]2(O)C1=O]
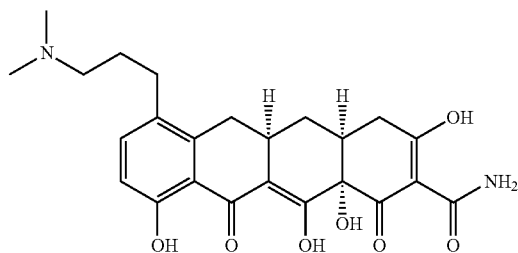 [SMILES: CN(C)CCCc1ccc(O)c2c1C[C@H]1C[C@H]3CC(O)=C(C(N)=O)C(=O)[C@@]3(O)C(O)=C1C2=O]

TABLE 2-continued
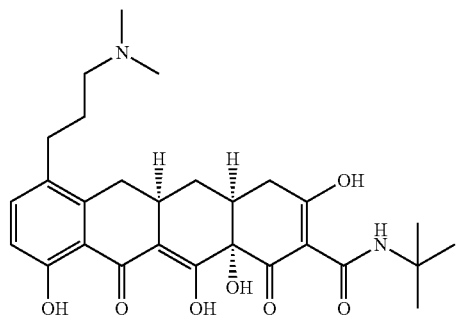 [SMILES: CN(C)CCCc1ccc(O)c2c1C[C@H]1C[C@H]3CC(O)=C(C(=O)NC(C)(C)C)C(=O)[C@@]3(O)C(O)=C1C2=O]
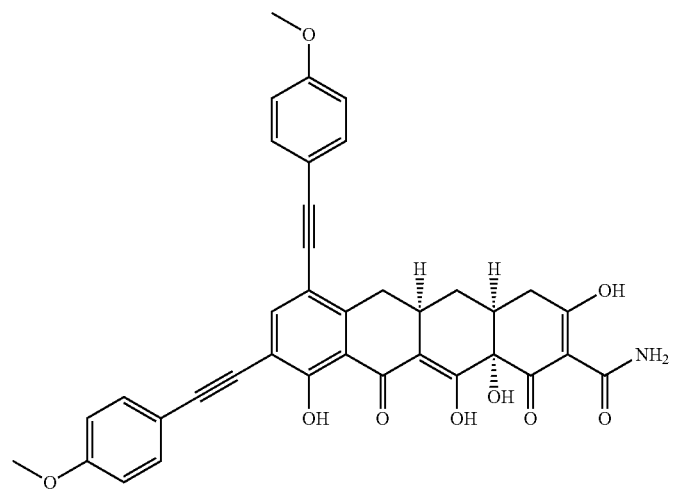 [SMILES: COc1ccc(C#Cc2cc(C#Cc3ccc(OC)cc3)c3c(c2O)C(=O)C2=C(O)[C@]4(O)C(=O)C(C(N)=O)=C(O)C[C@@H]4C[C@@H]2C3)cc1]
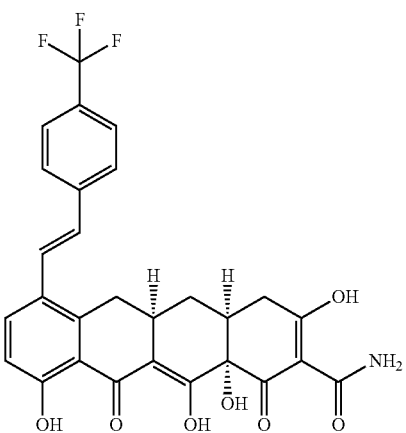 [SMILES: NC(=O)C1=C(O)C[C@@H]2C[C@@H]3Cc4c(/C=C/c5ccc(C(F)(F)F)cc5)ccc(O)c4C(=O)C3=C(O)[C@]2(O)C1=O]
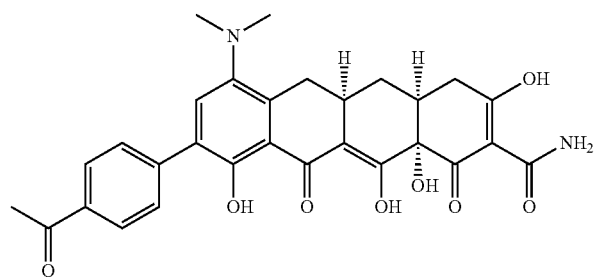 [SMILES: CC(=O)c1ccc(-c2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
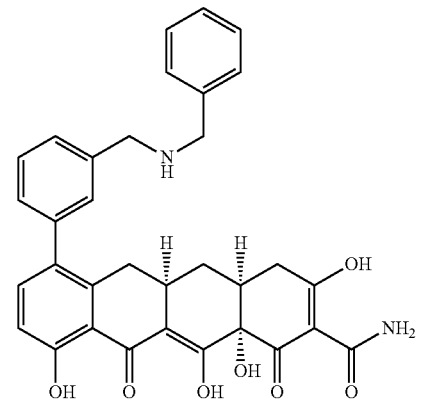 [SMILES: NC(=O)C1=C(O)C[C@@H]2C[C@@H]3Cc4c(-c5cccc(CNCc6ccccc6)c5)ccc(O)c4C(=O)C3=C(O)[C@]2(O)C1=O]
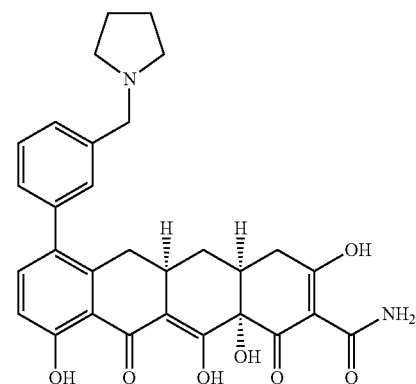 [SMILES: NC(=O)C1=C(O)C[C@@H]2C[C@@H]3Cc4c(-c5cccc(CN6CCCC6)c5)ccc(O)c4C(=O)C3=C(O)[C@]2(O)C1=O]
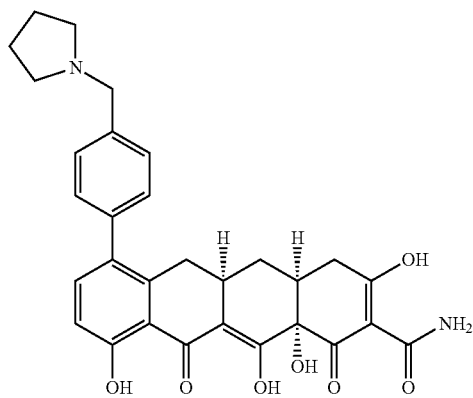 [SMILES: NC(=O)C1=C(O)C[C@@H]2C[C@@H]3Cc4c(-c5ccc(CN6CCCC6)cc5)ccc(O)c4C(=O)C3=C(O)[C@]2(O)C1=O]
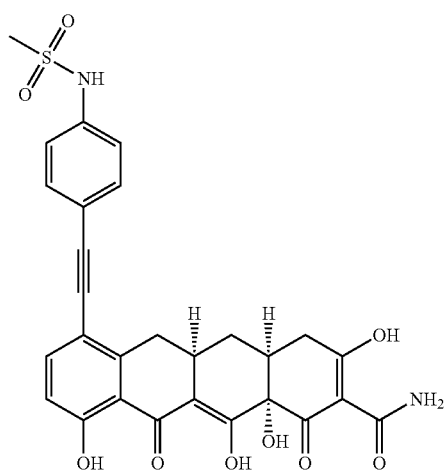 [SMILES: CS(=O)(=O)Nc1ccc(C#Cc2ccc(O)c3c2C[C@H]2C[C@H]4CC(O)=C(C(N)=O)C(=O)[C@@]4(O)C(O)=C2C3=O)cc1]

TABLE 2-continued
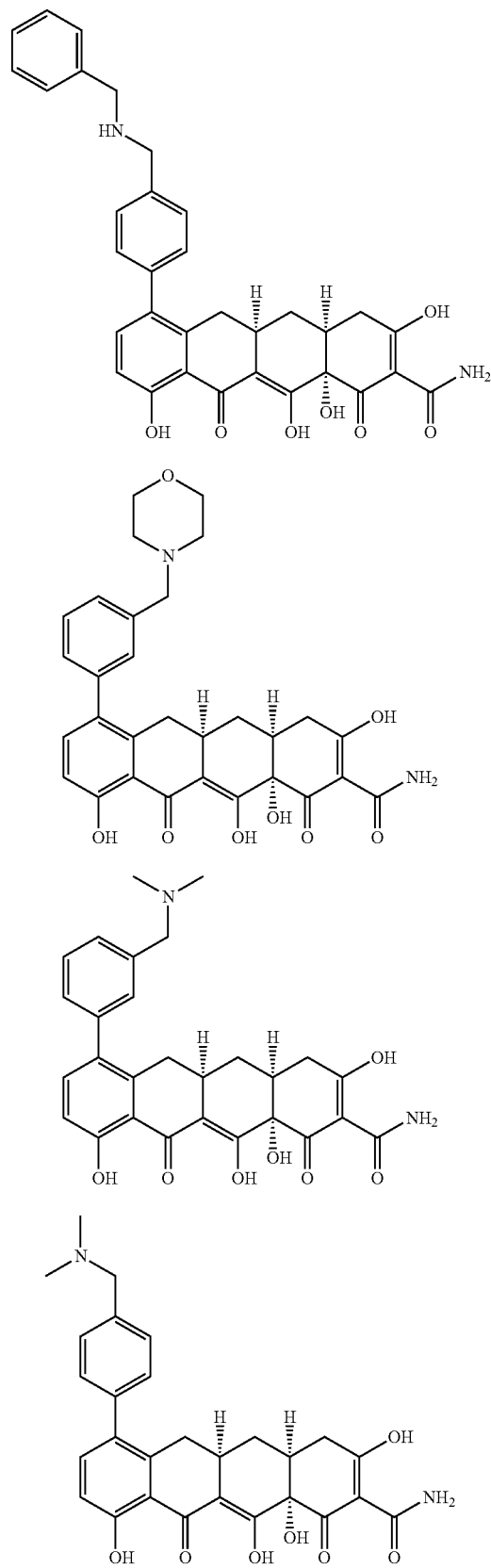

TABLE 2-continued
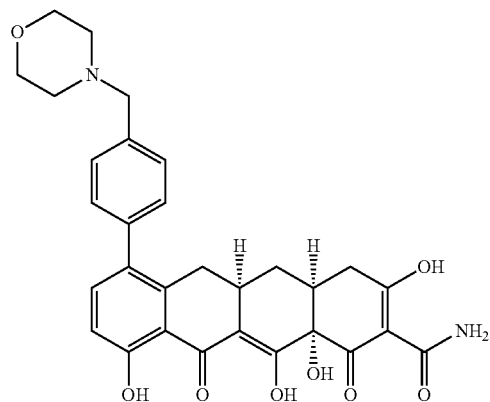 [SMILES: NC(=O)C1=C(O)C[C@@H]2C[C@@H]3Cc4c(-c5ccc(CN6CCOCC6)cc5)ccc(O)c4C(=O)C3=C(O)[C@]2(O)C1=O]
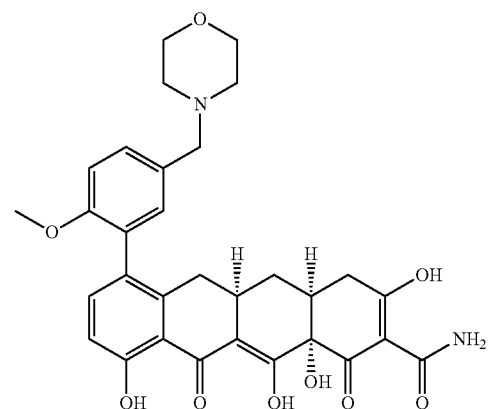 [SMILES: COc1ccc(CN2CCOCC2)cc1-c1ccc(O)c2c1C[C@H]1C[C@H]3CC(O)=C(C(N)=O)C(=O)[C@@]3(O)C(O)=C1C2=O]
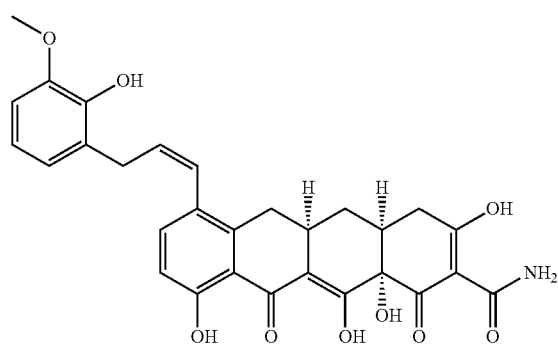 [SMILES: COc1cccc(C/C=C\c2ccc(O)c3c2C[C@H]2C[C@H]4CC(O)=C(C(N)=O)C(=O)[C@@]4(O)C(O)=C2C3=O)c1O]
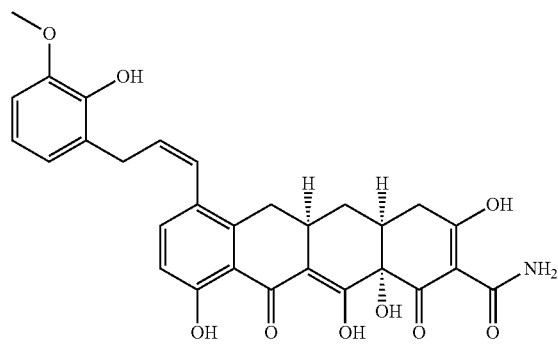 [SMILES: COc1cccc(C/C=C\c2ccc(O)c3c2C[C@H]2C[C@H]4CC(O)=C(C(N)=O)C(=O)[C@@]4(O)C(O)=C2C3=O)c1O]

TABLE 2-continued
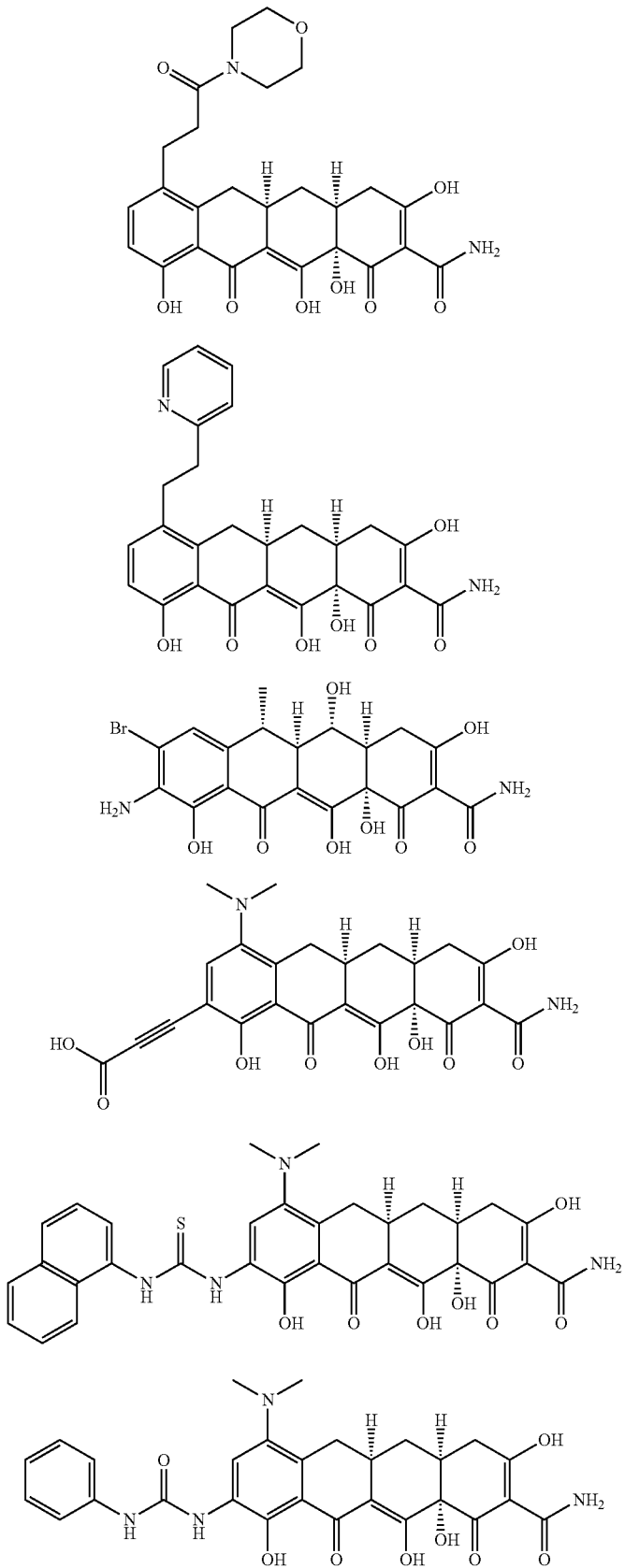

TABLE 2-continued
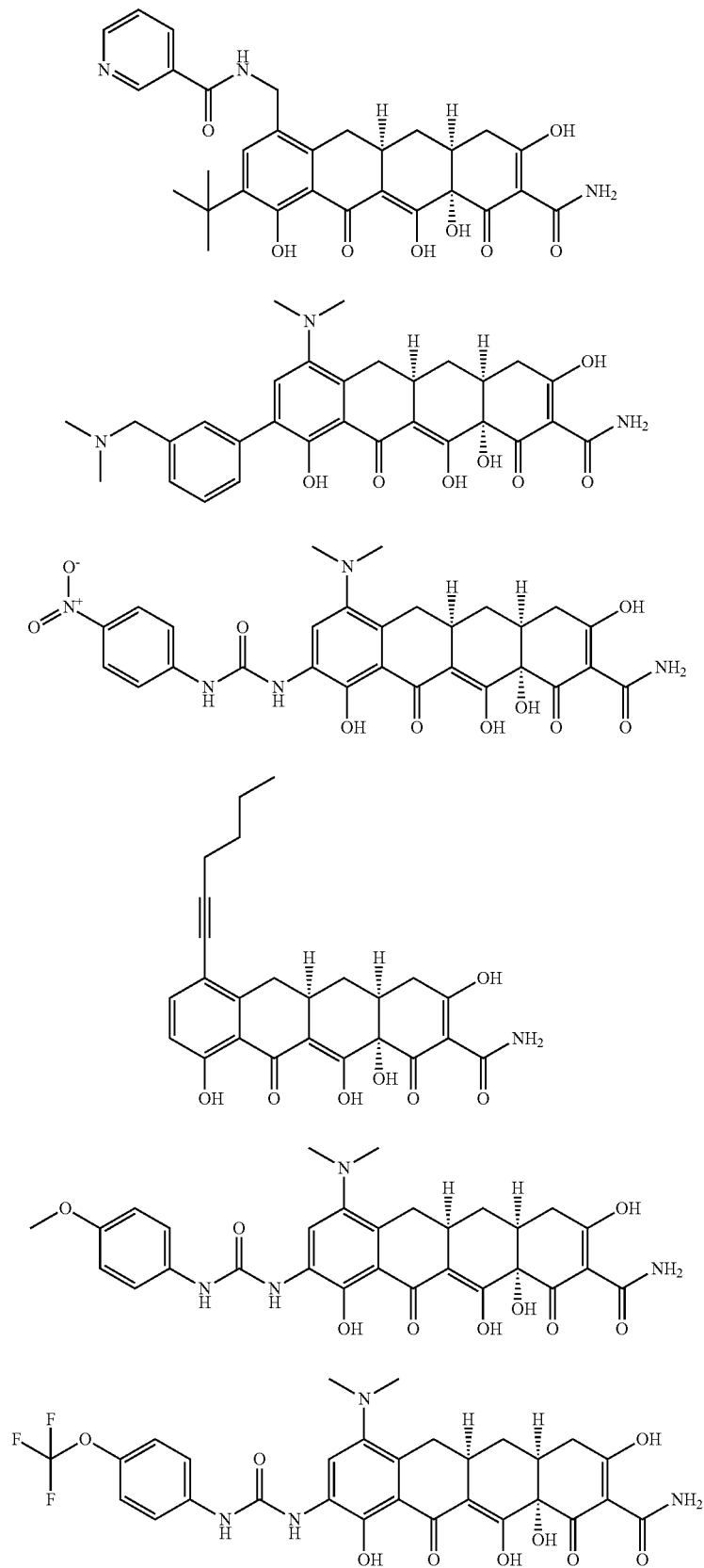

TABLE 2-continued
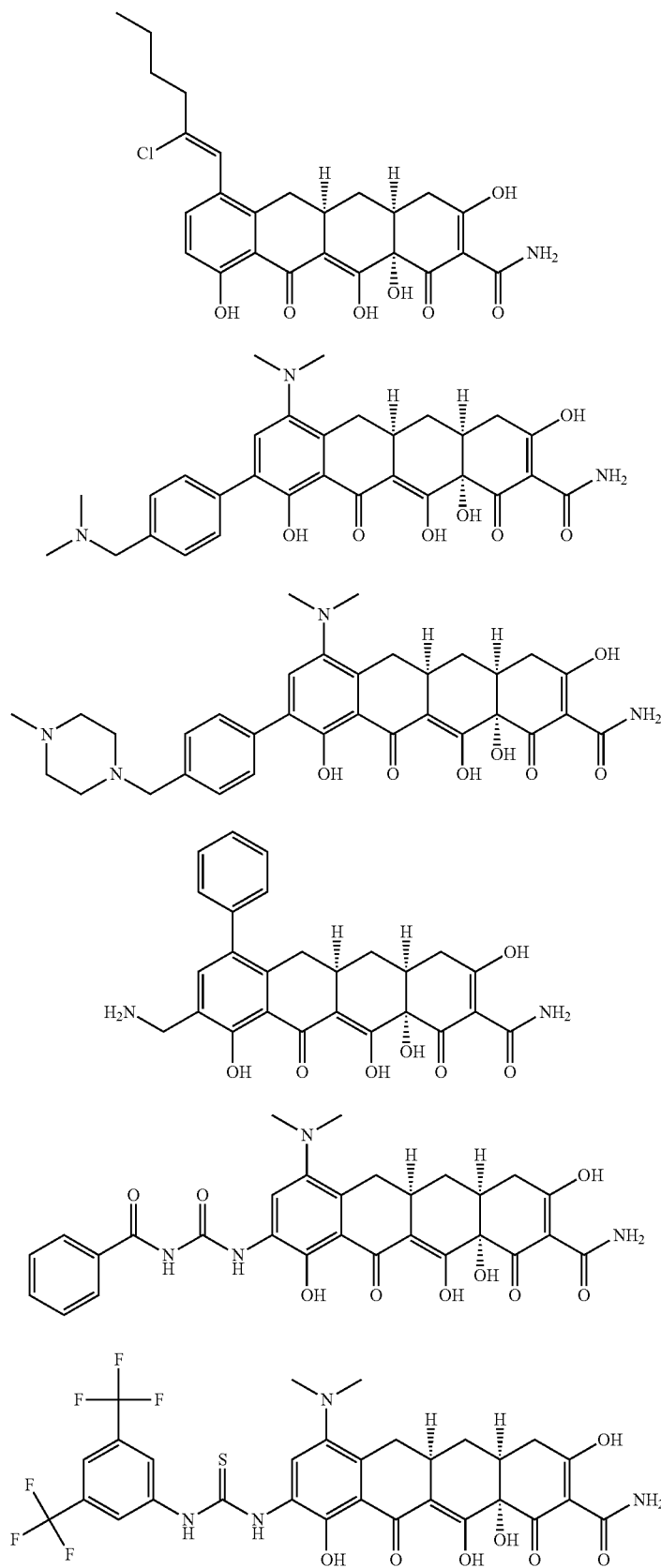

TABLE 2-continued
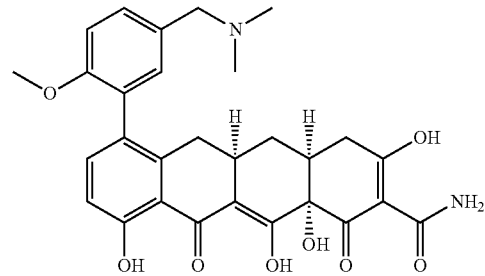 [SMILES: COc1ccc(CN(C)C)cc1-c1ccc(O)c2c1C[C@H]1C[C@H]3CC(O)=C(C(N)=O)C(=O)[C@@]3(O)C(O)=C1C2=O]
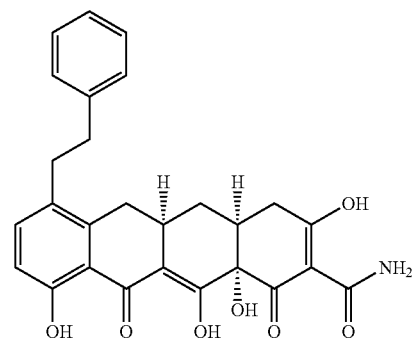 [SMILES: NC(=O)C1=C(O)C[C@@H]2C[C@@H]3Cc4c(CCc5ccccc5)ccc(O)c4C(=O)C3=C(O)[C@]2(O)C1=O]
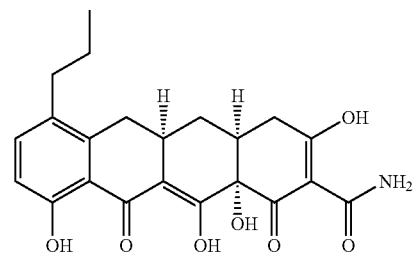 [SMILES: CCCc1ccc(O)c2c1C[C@H]1C[C@H]3CC(O)=C(C(N)=O)C(=O)[C@@]3(O)C(O)=C1C2=O]
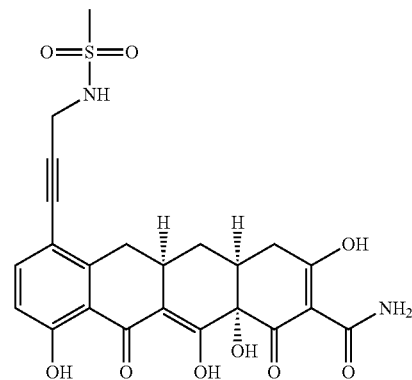 [SMILES: CS(=O)(=O)NCC#Cc1ccc(O)c2c1C[C@H]1C[C@H]3CC(O)=C(C(N)=O)C(=O)[C@@]3(O)C(O)=C1C2=O]
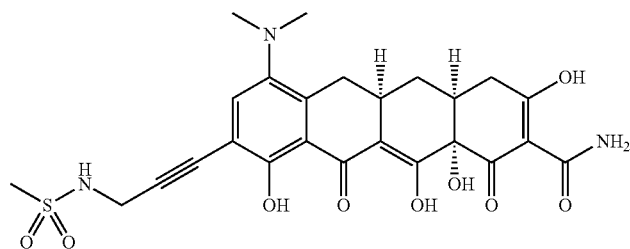 [SMILES: CN(C)c1cc(C#CCNS(C)(=O)=O)c(O)c2c1C[C@H]1C[C@H]3CC(O)=C(C(N)=O)C(=O)[C@@]3(O)C(O)=C1C2=O]

TABLE 2-continued
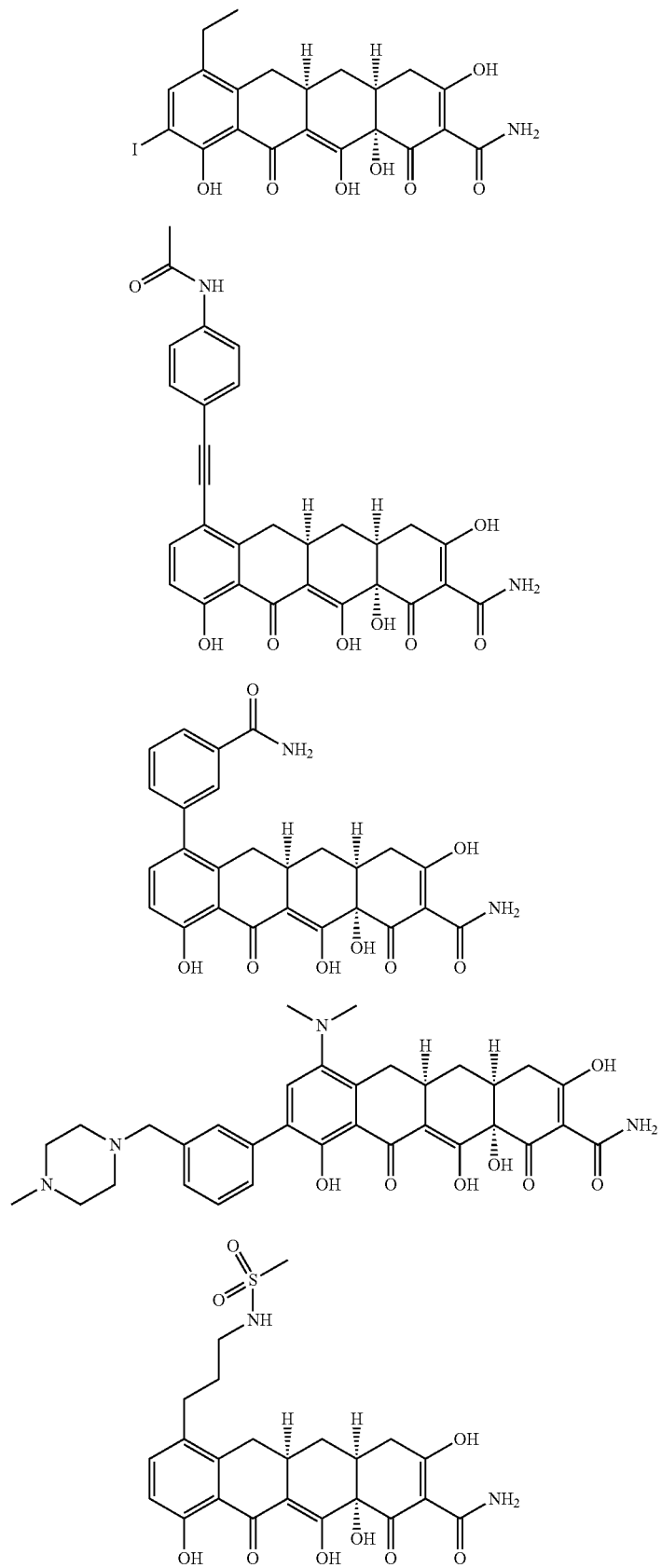

TABLE 2-continued
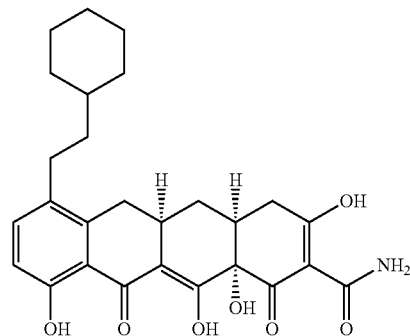 [SMILES: NC(=O)C1=C(O)C[C@@H]2C[C@@H]3Cc4c(CCC5CCCCC5)ccc(O)c4C(=O)C3=C(O)[C@]2(O)C1=O]
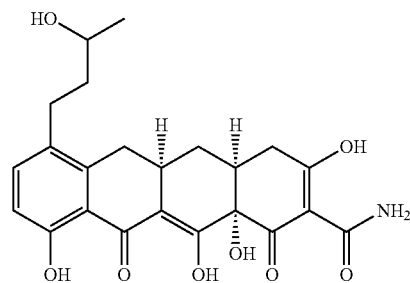 [SMILES: CC(O)CCc1ccc(O)c2c1C[C@H]1C[C@H]3CC(O)=C(C(N)=O)C(=O)[C@@]3(O)C(O)=C1C2=O]
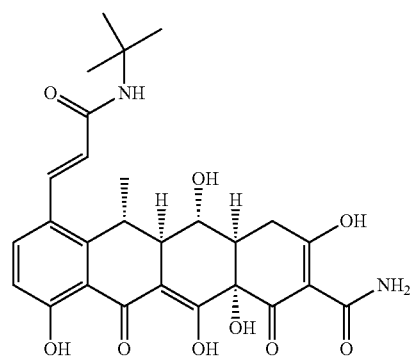 [SMILES: C[C@H]1c2c(/C=C/C(=O)NC(C)(C)C)ccc(O)c2C(=O)C2=C(O)[C@]3(O)C(=O)C(C(N)=O)=C(O)C[C@@H]3[C@@H](O)[C@@H]21]
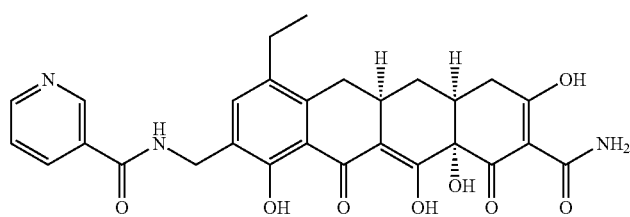 [SMILES: CCc1cc(CNC(=O)c2cccnc2)c(O)c2c1C[C@H]1C[C@H]3CC(O)=C(C(N)=O)C(=O)[C@@]3(O)C(O)=C1C2=O]
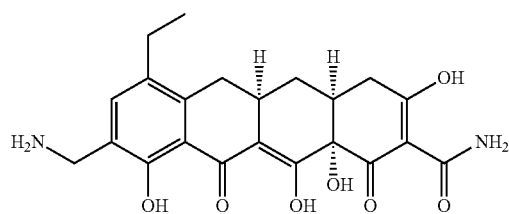 [SMILES: CCc1cc(CN)c(O)c2c1C[C@H]1C[C@H]3CC(O)=C(C(N)=O)C(=O)[C@@]3(O)C(O)=C1C2=O]

TABLE 2-continued
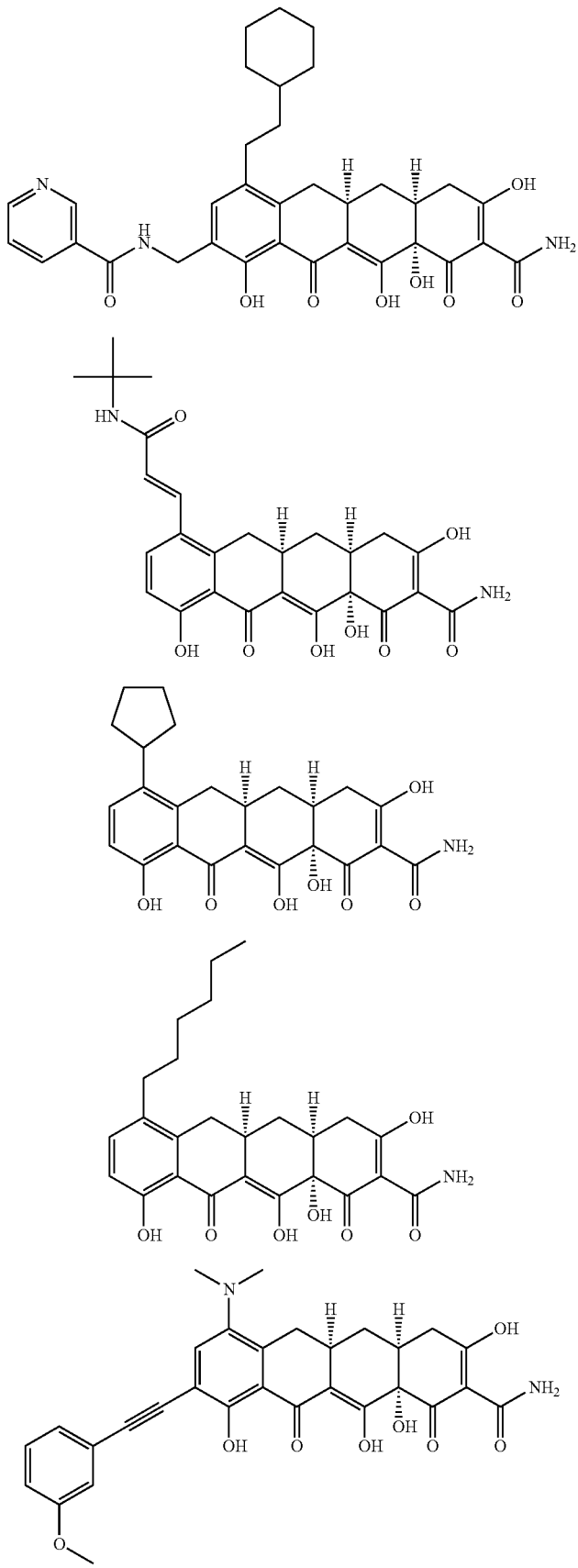

TABLE 2-continued
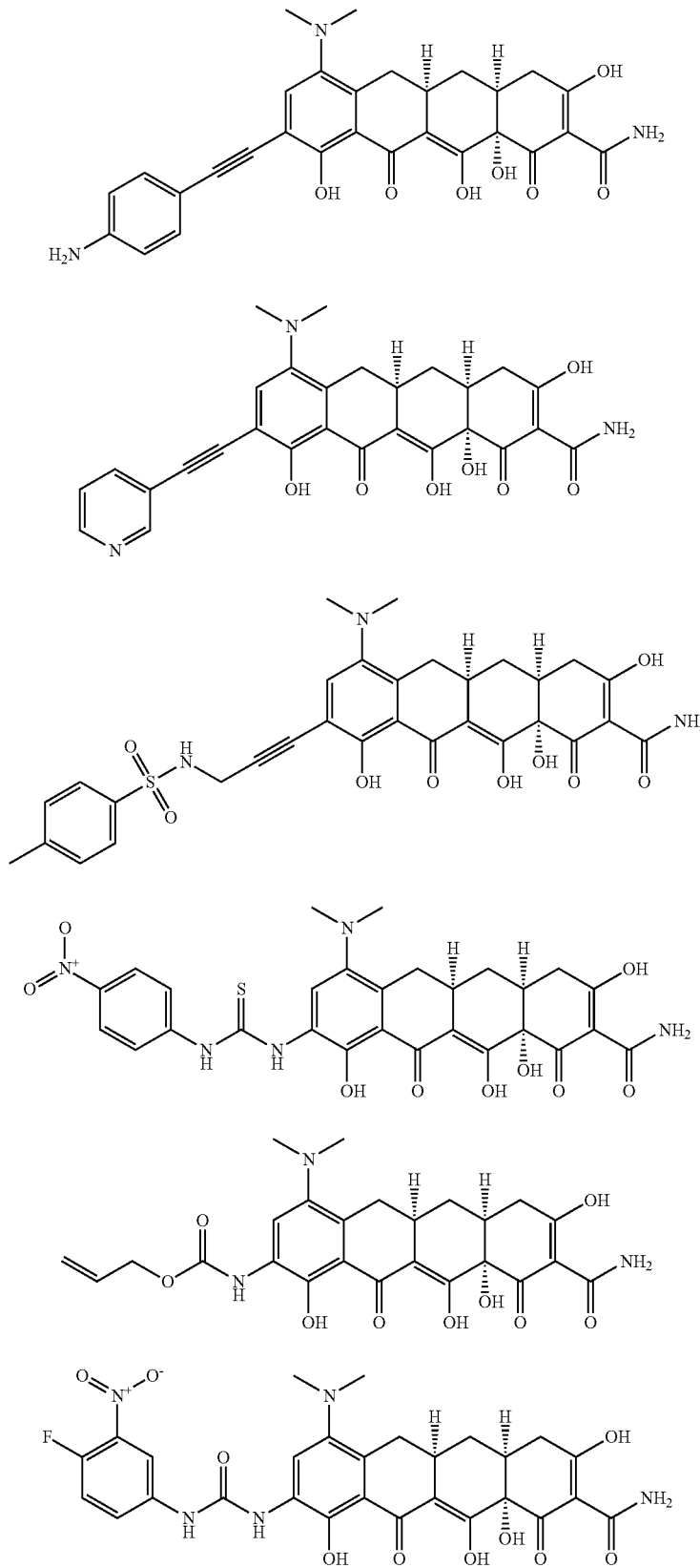

TABLE 2-continued
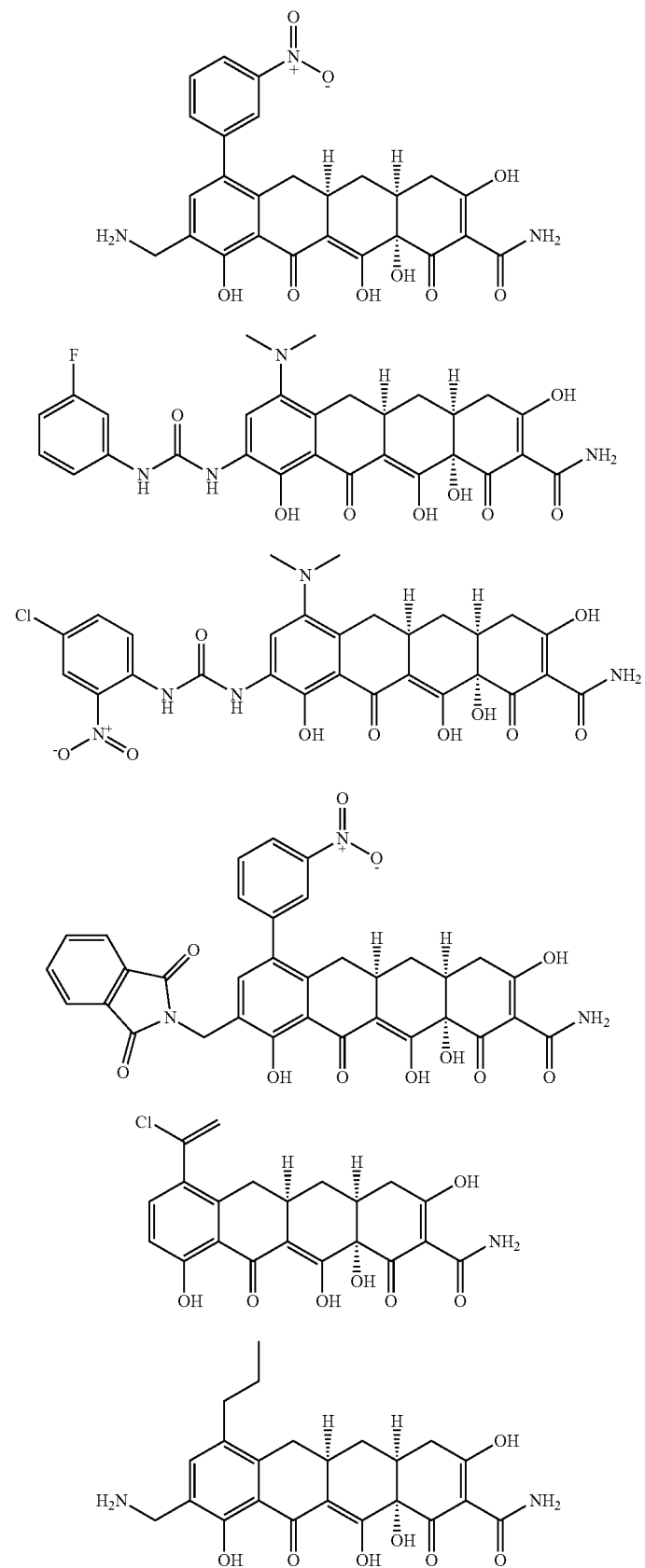

TABLE 2-continued
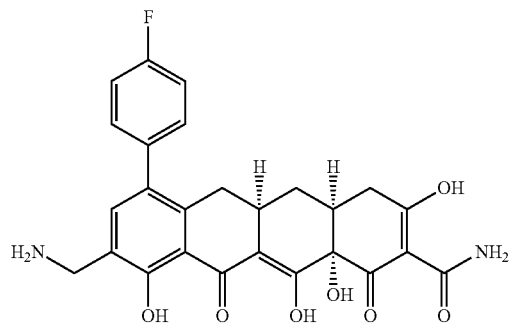 [SMILES: NCc1cc(-c2ccc(F)cc2)c2c(c1O)C(=O)C1=C(O)[C@]3(O)C(=O)C(C(N)=O)=C(O)C[C@@H]3C[C@@H]1C2]
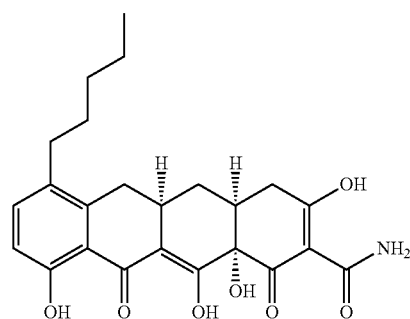 [SMILES: CCCCCc1ccc(O)c2c1C[C@H]1C[C@H]3CC(O)=C(C(N)=O)C(=O)[C@@]3(O)C(O)=C1C2=O]
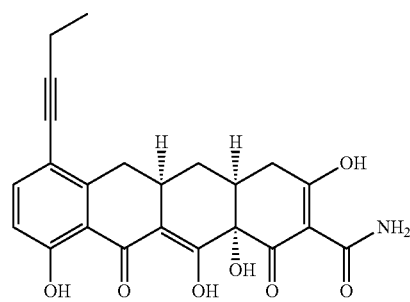 [SMILES: CCC#Cc1ccc(O)c2c1C[C@H]1C[C@H]3CC(O)=C(C(N)=O)C(=O)[C@@]3(O)C(O)=C1C2=O]
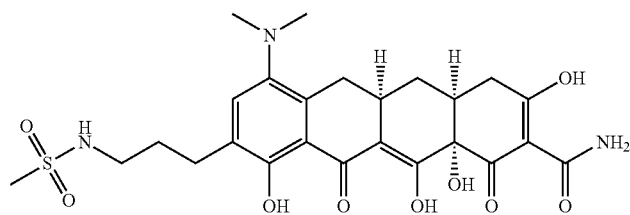 [SMILES: CN(C)c1cc(CCCNS(C)(=O)=O)c(O)c2c1C[C@H]1C[C@H]3CC(O)=C(C(N)=O)C(=O)[C@@]3(O)C(O)=C1C2=O]
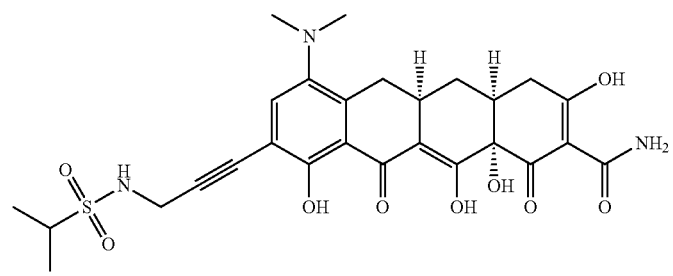 [SMILES: CC(C)S(=O)(=O)NCC#Cc1cc(N(C)C)c2c(c1O)C(=O)C1=C(O)[C@]3(O)C(=O)C(C(N)=O)=C(O)C[C@@H]3C[C@@H]1C2]

TABLE 2-continued
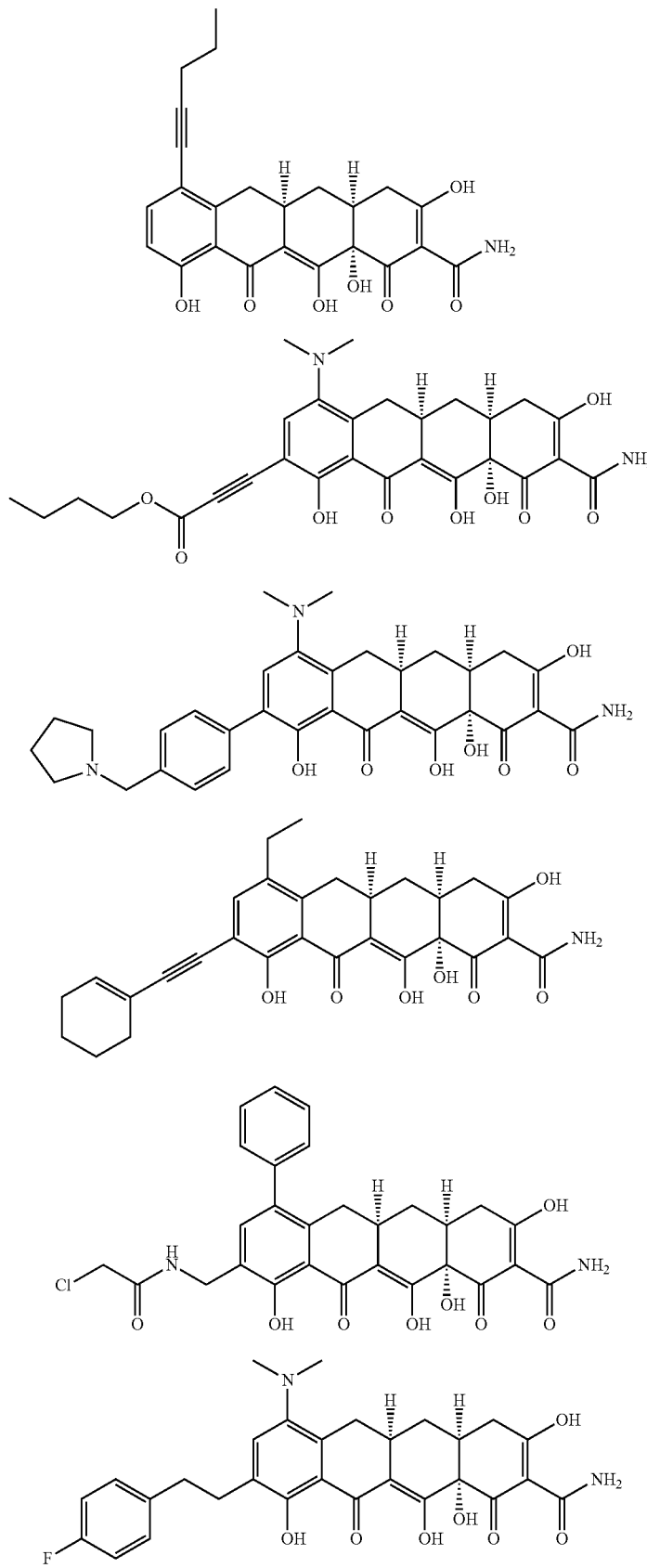

TABLE 2-continued
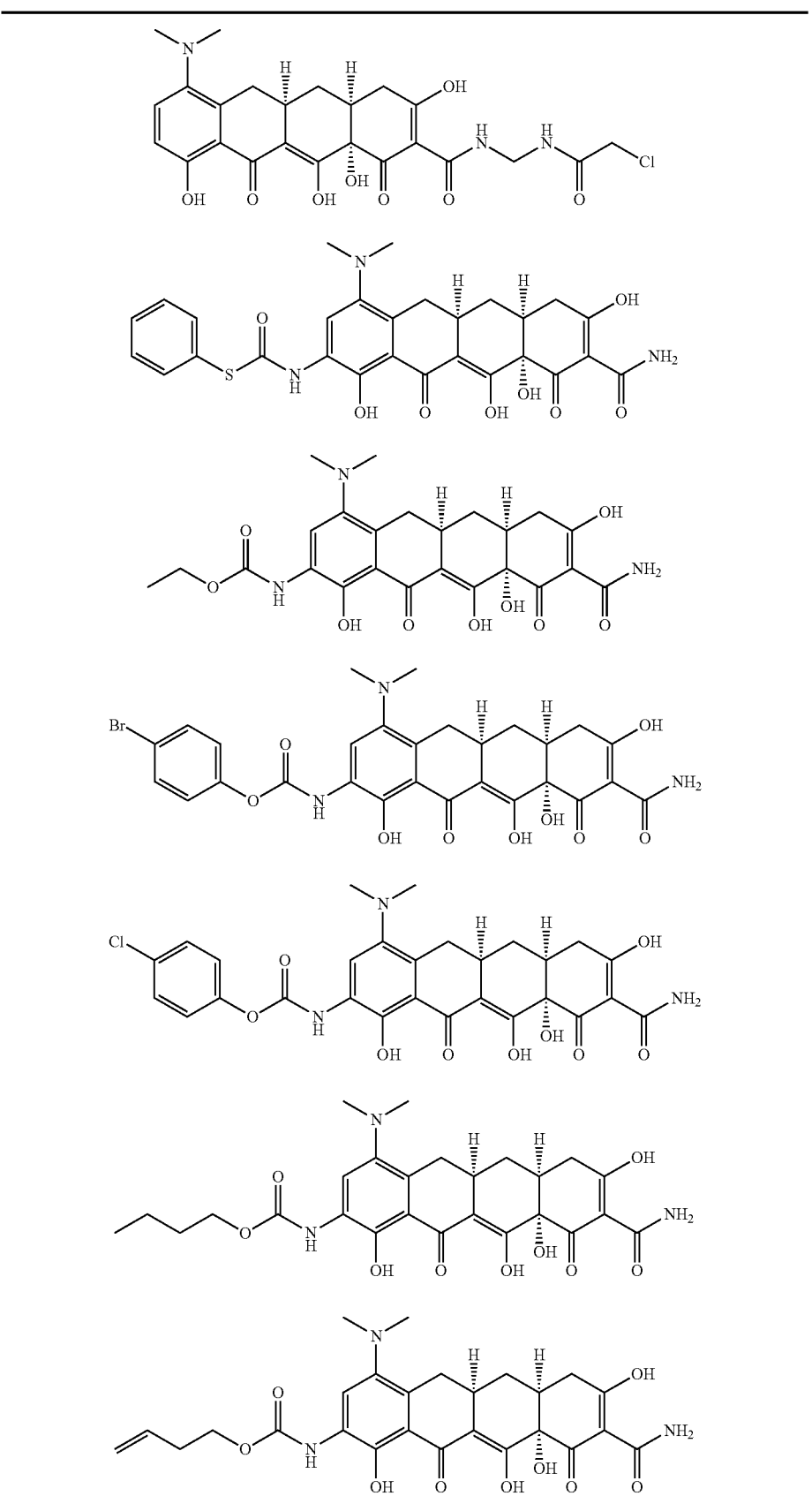

TABLE 2-continued
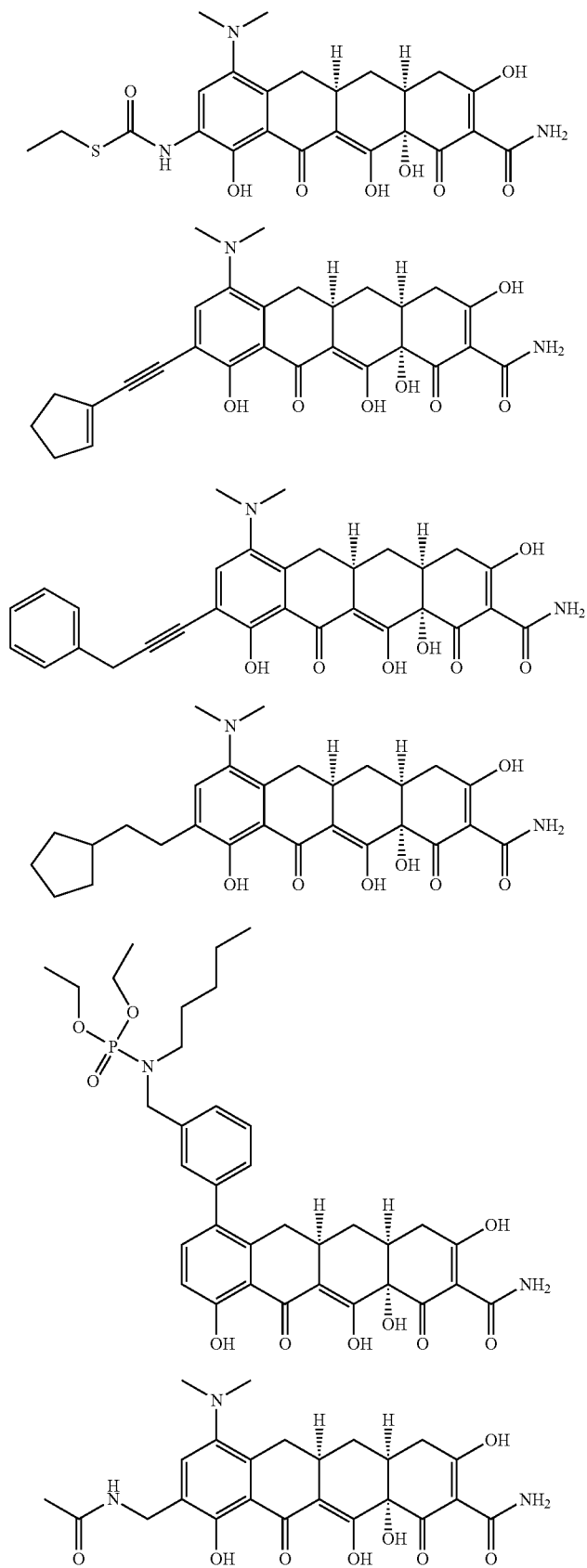

TABLE 2-continued
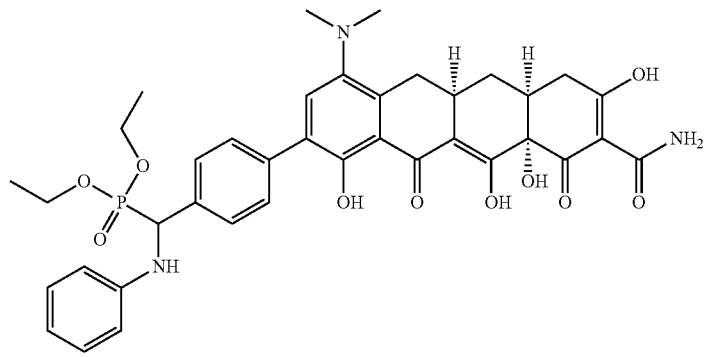 [SMILES: CCOP(=O)(OCC)C(Nc1ccccc1)c1ccc(-c2cc(N(C)C)c3c(c2O)C(=O)C2=C(O)[C@]4(O)C(=O)C(C(N)=O)=C(O)C[C@@H]4C[C@@H]2C3)cc1]
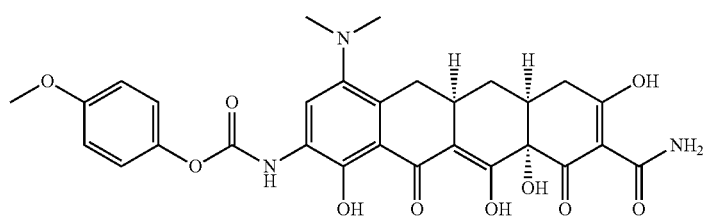 [SMILES: COc1ccc(OC(=O)Nc2cc(N(C)C)c3c(c2O)C(=O)C2=C(O)[C@]4(O)C(=O)C(C(N)=O)=C(O)C[C@@H]4C[C@@H]2C3)cc1]
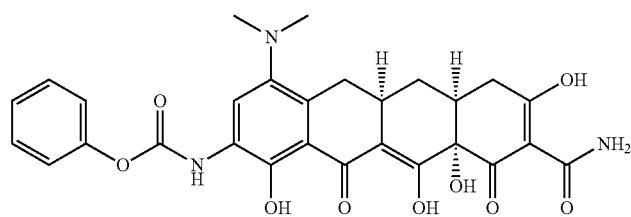
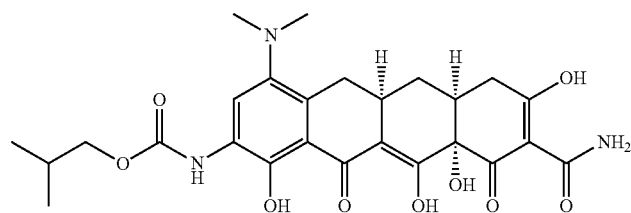 [SMILES: CC(C)COC(=O)Nc1cc(N(C)C)c2c(c1O)C(=O)C1=C(O)[C@]3(O)C(=O)C(C(N)=O)=C(O)C[C@@H]3C[C@@H]1C2]
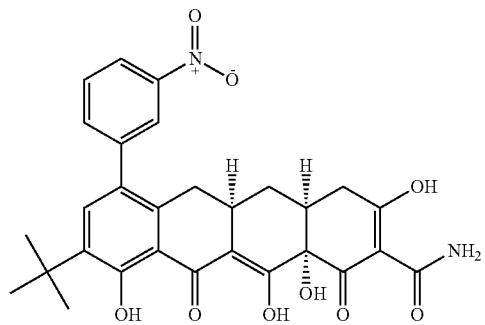

TABLE 2-continued
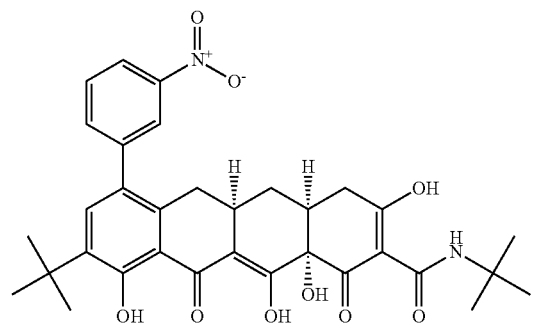 [SMILES: CC(C)(C)NC(=O)C1=C(O)C[C@@H]2C[C@@H]3Cc4c(-c5cccc([N+](=O)[O-])c5)cc(C(C)(C)C)c(O)c4C(=O)C3=C(O)[C@]2(O)C1=O]
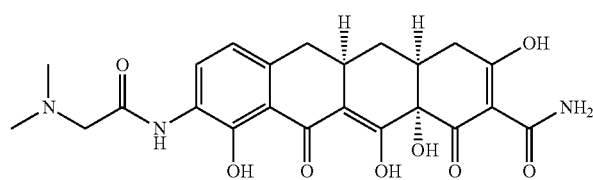 [SMILES: CN(C)CC(=O)Nc1ccc2c(c1O)C(=O)C1=C(O)[C@]3(O)C(=O)C(C(N)=O)=C(O)C[C@@H]3C[C@@H]1C2]
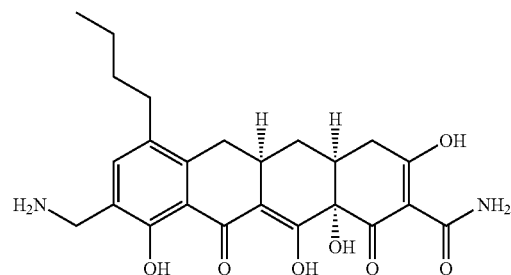 [SMILES: CCCCc1cc(CN)c(O)c2c1C[C@H]1C[C@H]3CC(O)=C(C(N)=O)C(=O)[C@@]3(O)C(O)=C1C2=O]
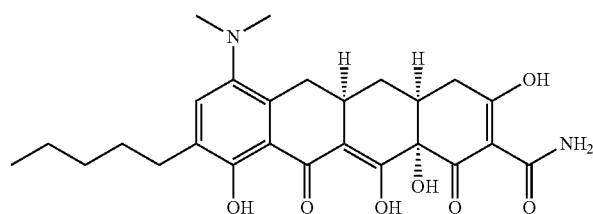 [SMILES: CCCCCc1cc(N(C)C)c2c(c1O)C(=O)C1=C(O)[C@]3(O)C(=O)C(C(N)=O)=C(O)C[C@@H]3C[C@@H]1C2]
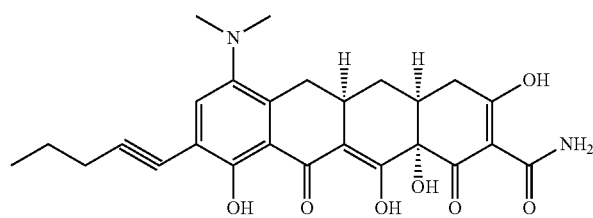 [SMILES: CCCC#Cc1cc(N(C)C)c2c(c1O)C(=O)C1=C(O)[C@]3(O)C(=O)C(C(N)=O)=C(O)C[C@@H]3C[C@@H]1C2]
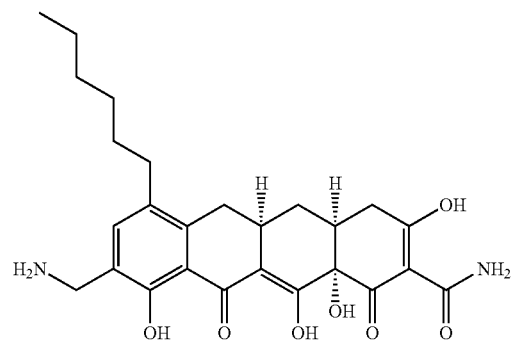 [SMILES: CCCCCCc1cc(CN)c(O)c2c1C[C@H]1C[C@H]3CC(O)=C(C(N)=O)C(=O)[C@@]3(O)C(O)=C1C2=O]

TABLE 2-continued
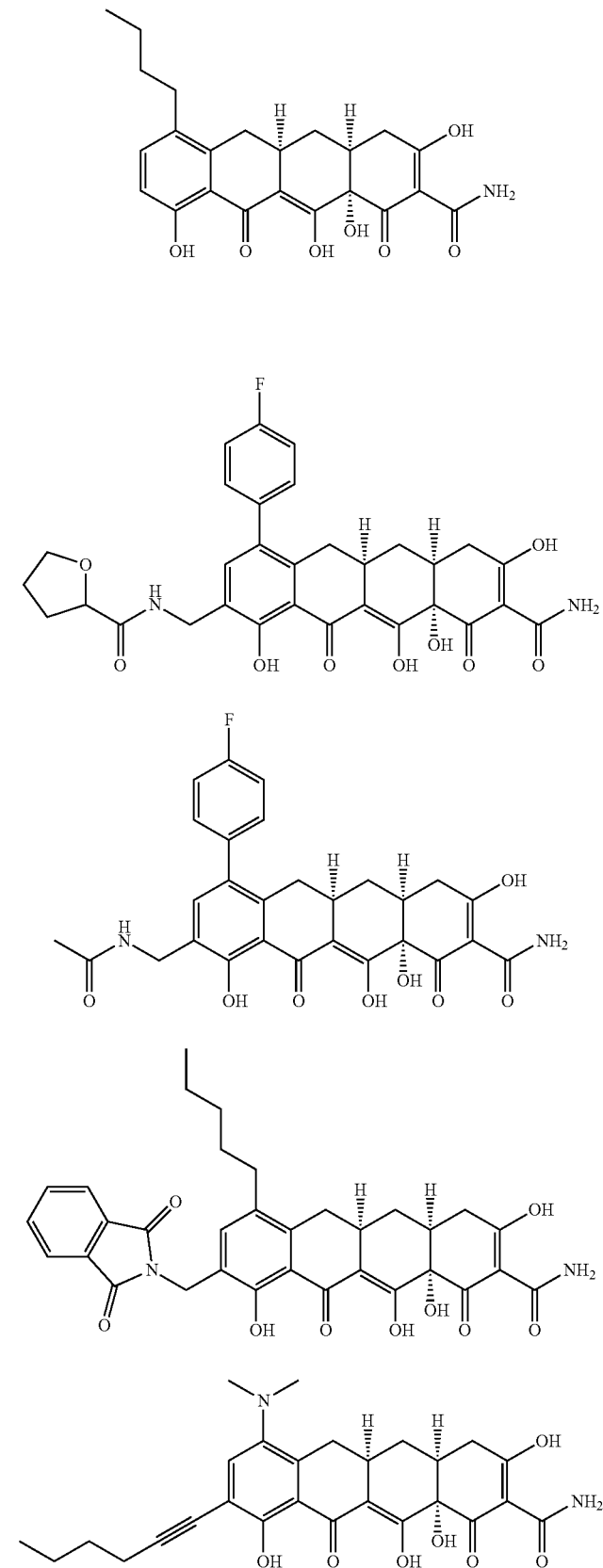

TABLE 2-continued
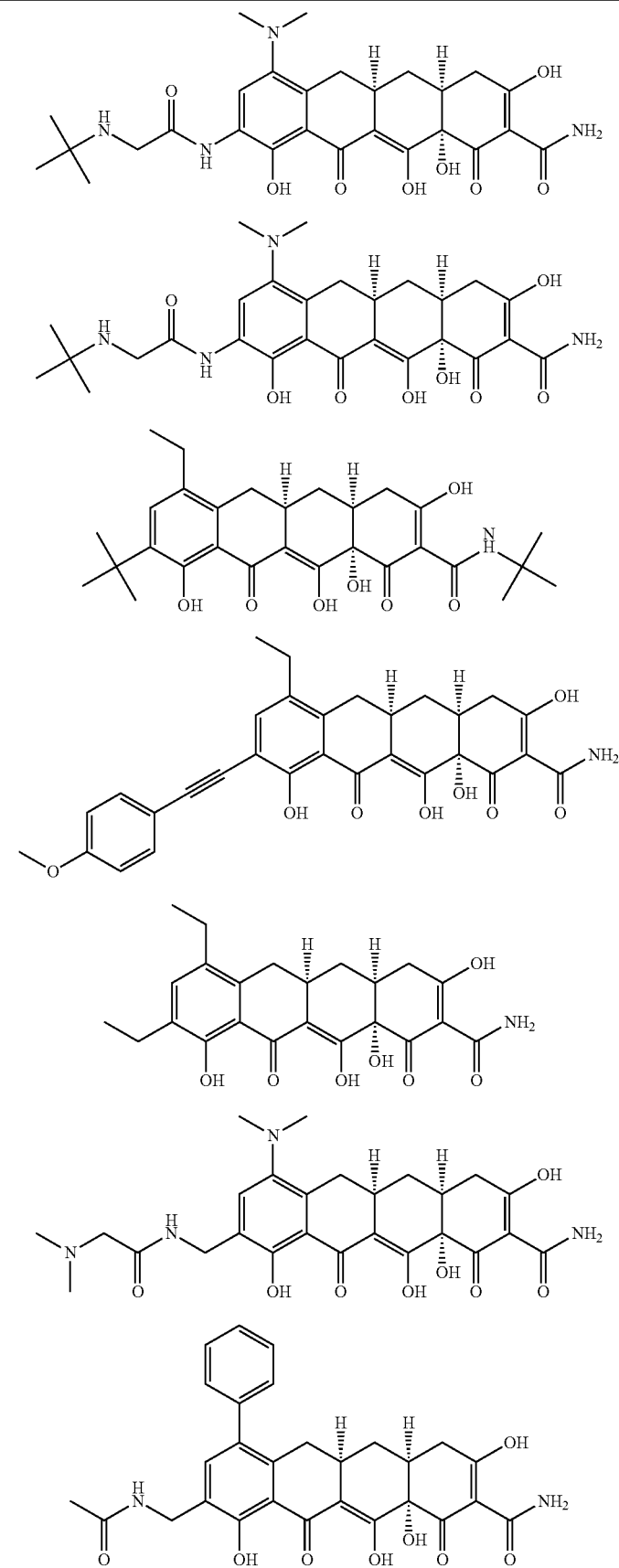

TABLE 2-continued
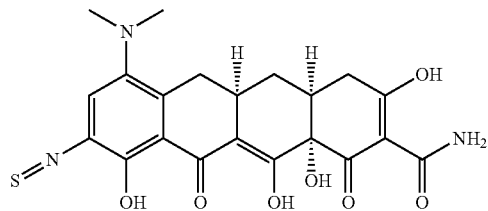 [SMILES: CN(C)c1cc(N=S)c(O)c2c1C[C@H]1C[C@H]3CC(O)=C(C(N)=O)C(=O)[C@@]3(O)C(O)=C1C2=O]
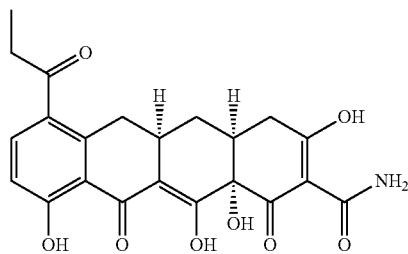 [SMILES: CCC(=O)c1ccc(O)c2c1C[C@H]1C[C@H]3CC(O)=C(C(N)=O)C(=O)[C@@]3(O)C(O)=C1C2=O]
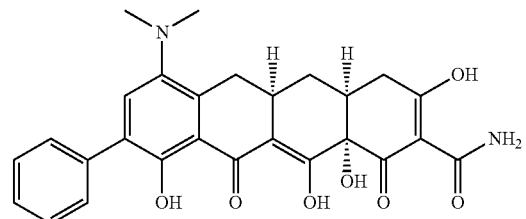
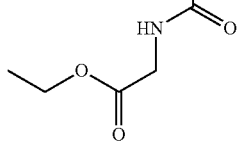
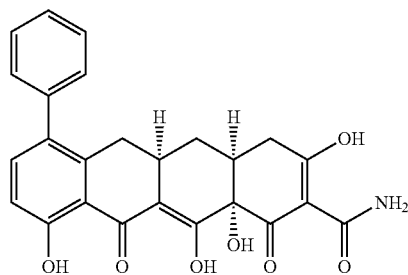 [SMILES: NC(=O)C1=C(O)C[C@@H]2C[C@@H]3Cc4c(-c5ccccc5)ccc(O)c4C(=O)C3=C(O)[C@]2(O)C1=O]
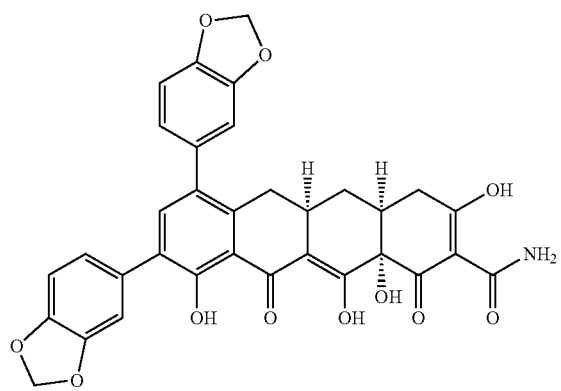 [SMILES: NC(=O)C1=C(O)C[C@@H]2C[C@@H]3Cc4c(-c5ccc6c(c5)OCO6)cc(-c5ccc6c(c5)OCO6)c(O)c4C(=O)C3=C(O)[C@]2(O)C1=O]

TABLE 2-continued
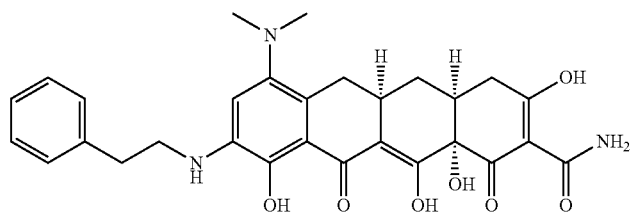 [SMILES: CN(C)c1cc(NCCc2ccccc2)c(O)c2c1C[C@H]1C[C@H]3CC(O)=C(C(N)=O)C(=O)[C@@]3(O)C(O)=C1C2=O]
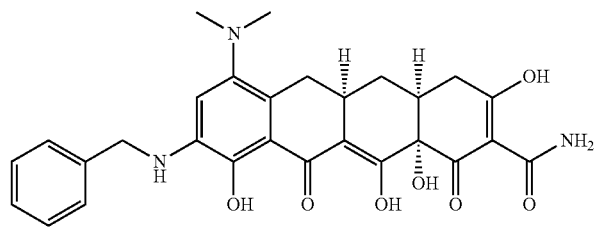 [SMILES: CN(C)c1cc(NCc2ccccc2)c(O)c2c1C[C@H]1C[C@H]3CC(O)=C(C(N)=O)C(=O)[C@@]3(O)C(O)=C1C2=O]
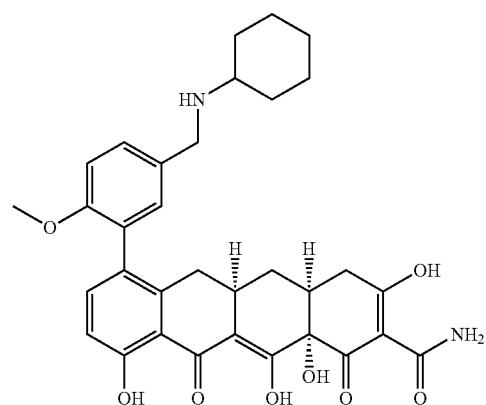 [SMILES: COc1ccc(CNC2CCCCC2)cc1-c1ccc(O)c2c1C[C@H]1C[C@H]3CC(O)=C(C(N)=O)C(=O)[C@@]3(O)C(O)=C1C2=O]
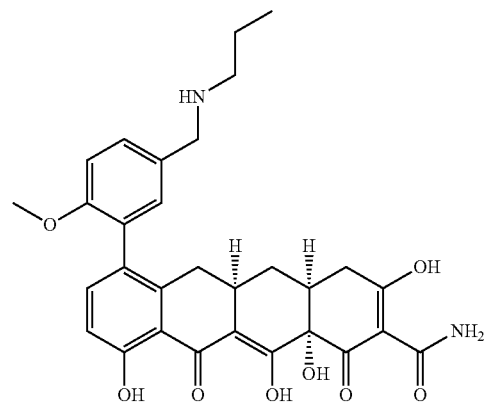 [SMILES: CCCNCc1ccc(OC)c(-c2ccc(O)c3c2C[C@H]2C[C@H]4CC(O)=C(C(N)=O)C(=O)[C@@]4(O)C(O)=C2C3=O)c1]
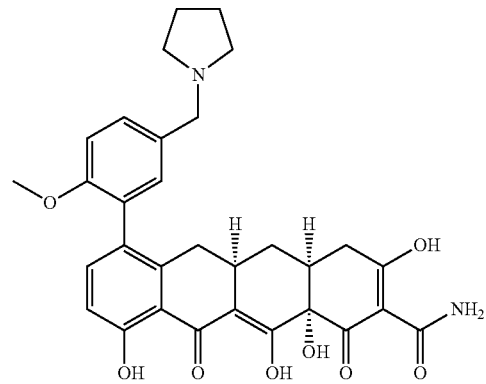 [SMILES: COc1ccc(CN2CCCC2)cc1-c1ccc(O)c2c1C[C@H]1C[C@H]3CC(O)=C(C(N)=O)C(=O)[C@@]3(O)C(O)=C1C2=O]

TABLE 2-continued
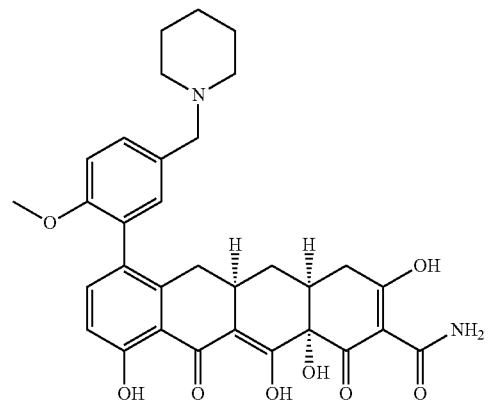 [SMILES: COc1ccc(CN2CCCCC2)cc1-c1ccc(O)c2c1C[C@H]1C[C@H]3CC(O)=C(C(N)=O)C(=O)[C@@]3(O)C(O)=C1C2=O]
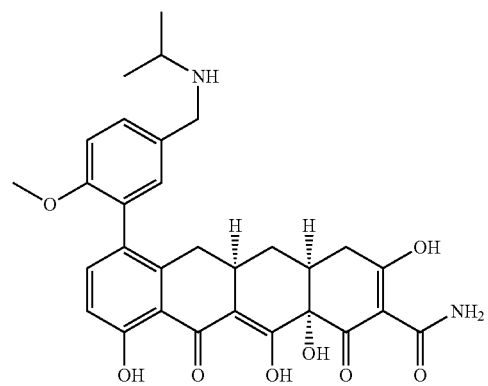 [SMILES: COc1ccc(CNC(C)C)cc1-c1ccc(O)c2c1C[C@H]1C[C@H]3CC(O)=C(C(N)=O)C(=O)[C@@]3(O)C(O)=C1C2=O]
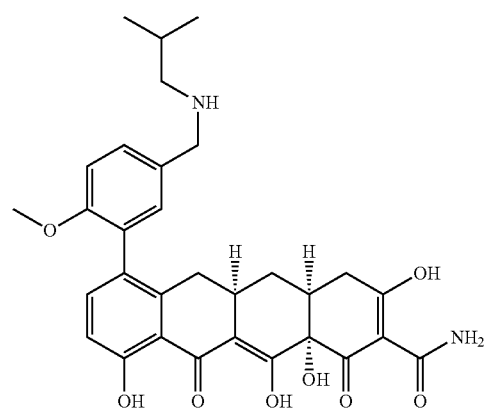 [SMILES: COc1ccc(CNCC(C)C)cc1-c1ccc(O)c2c1C[C@H]1C[C@H]3CC(O)=C(C(N)=O)C(=O)[C@@]3(O)C(O)=C1C2=O]
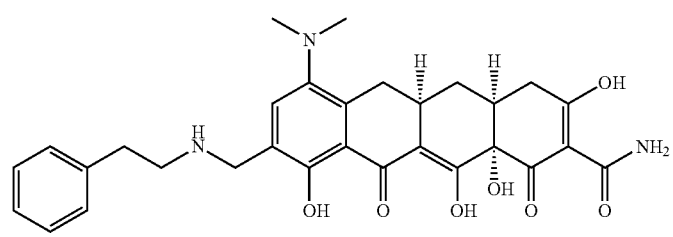 [SMILES: CN(C)c1cc(CNCCc2ccccc2)c(O)c2c1C[C@H]1C[C@H]3CC(O)=C(C(N)=O)C(=O)[C@@]3(O)C(O)=C1C2=O]

TABLE 2-continued
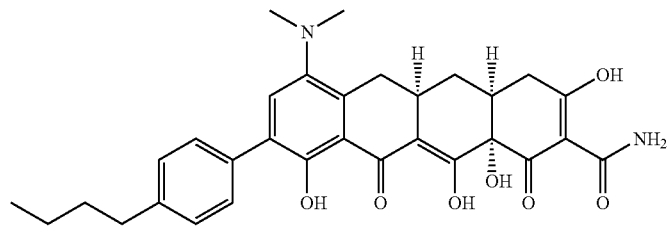 [SMILES: CCCCc1ccc(-c2cc(N(C)C)c3c(c2O)C(=O)C2=C(O)[C@]4(O)C(=O)C(C(N)=O)=C(O)C[C@@H]4C[C@@H]2C3)cc1]
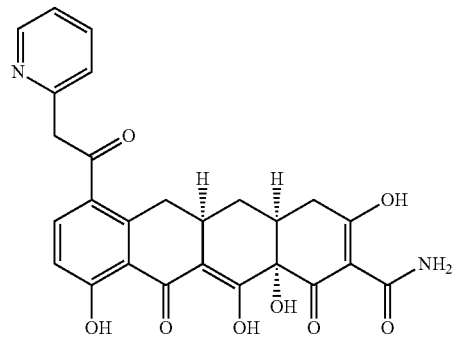 [SMILES: NC(=O)C1=C(O)C[C@@H]2C[C@@H]3Cc4c(C(=O)Cc5ccccn5)ccc(O)c4C(=O)C3=C(O)[C@]2(O)C1=O]
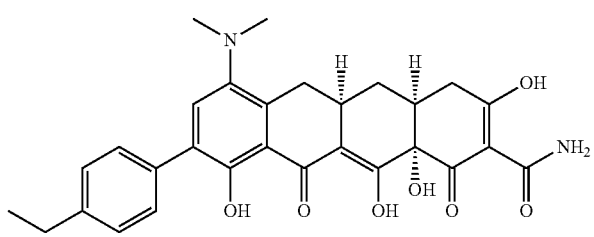 [SMILES: CCc1ccc(-c2cc(N(C)C)c3c(c2O)C(=O)C2=C(O)[C@]4(O)C(=O)C(C(N)=O)=C(O)C[C@@H]4C[C@@H]2C3)cc1]
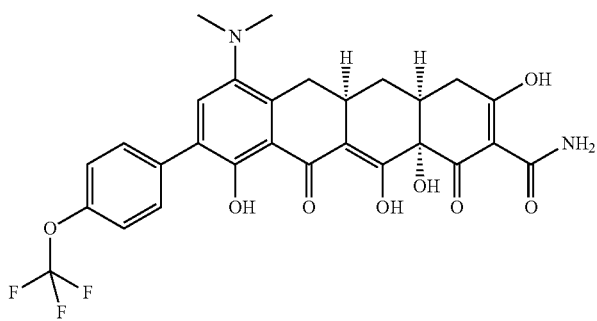 [SMILES: CN(C)c1cc(-c2ccc(OC(F)(F)F)cc2)c(O)c2c1C[C@H]1C[C@H]3CC(O)=C(C(N)=O)C(=O)[C@@]3(O)C(O)=C1C2=O]
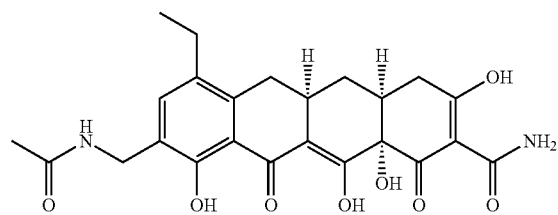 [SMILES: CCc1cc(CNC(C)=O)c(O)c2c1C[C@H]1C[C@H]3CC(O)=C(C(N)=O)C(=O)[C@@]3(O)C(O)=C1C2=O]
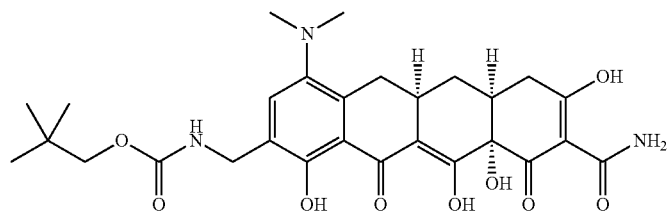 [SMILES: CN(C)c1cc(CNC(=O)OCC(C)(C)C)c(O)c2c1C[C@H]1C[C@H]3CC(O)=C(C(N)=O)C(=O)[C@@]3(O)C(O)=C1C2=O]

TABLE 2-continued
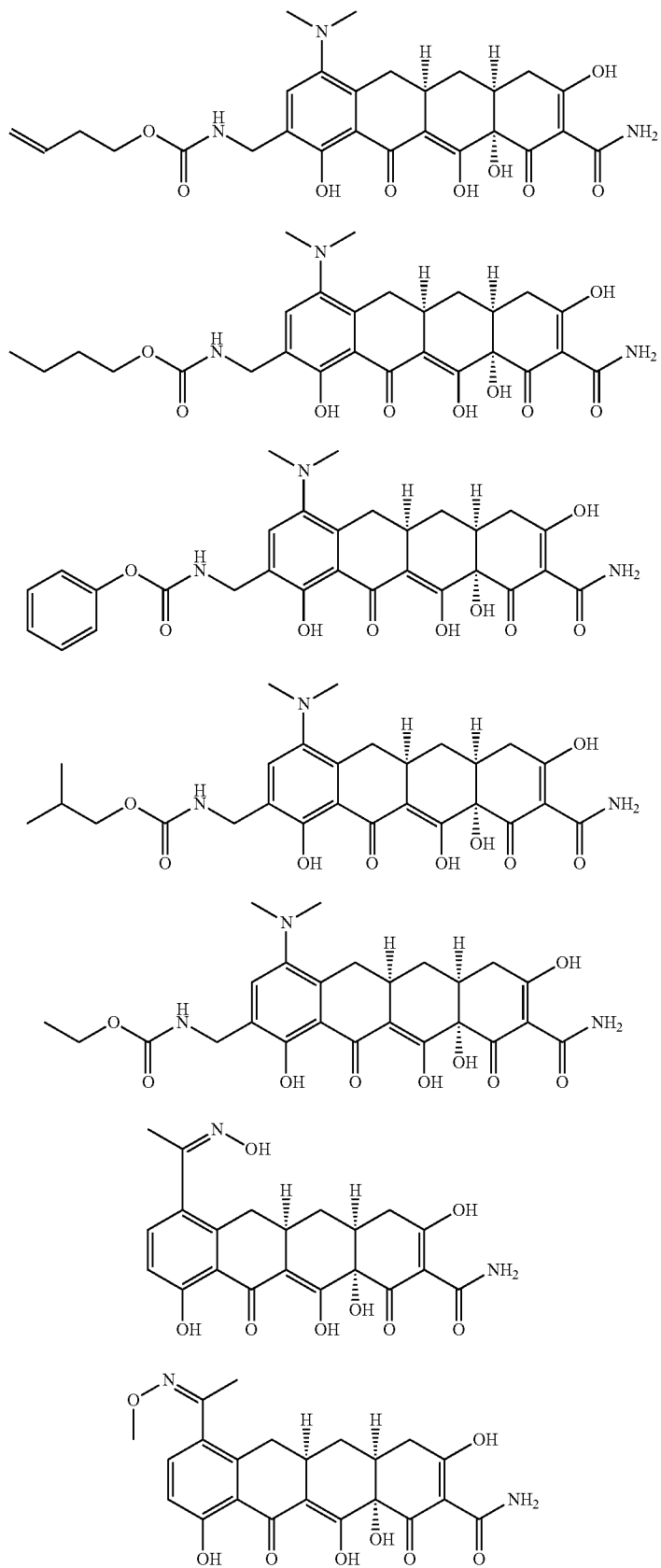

TABLE 2-continued
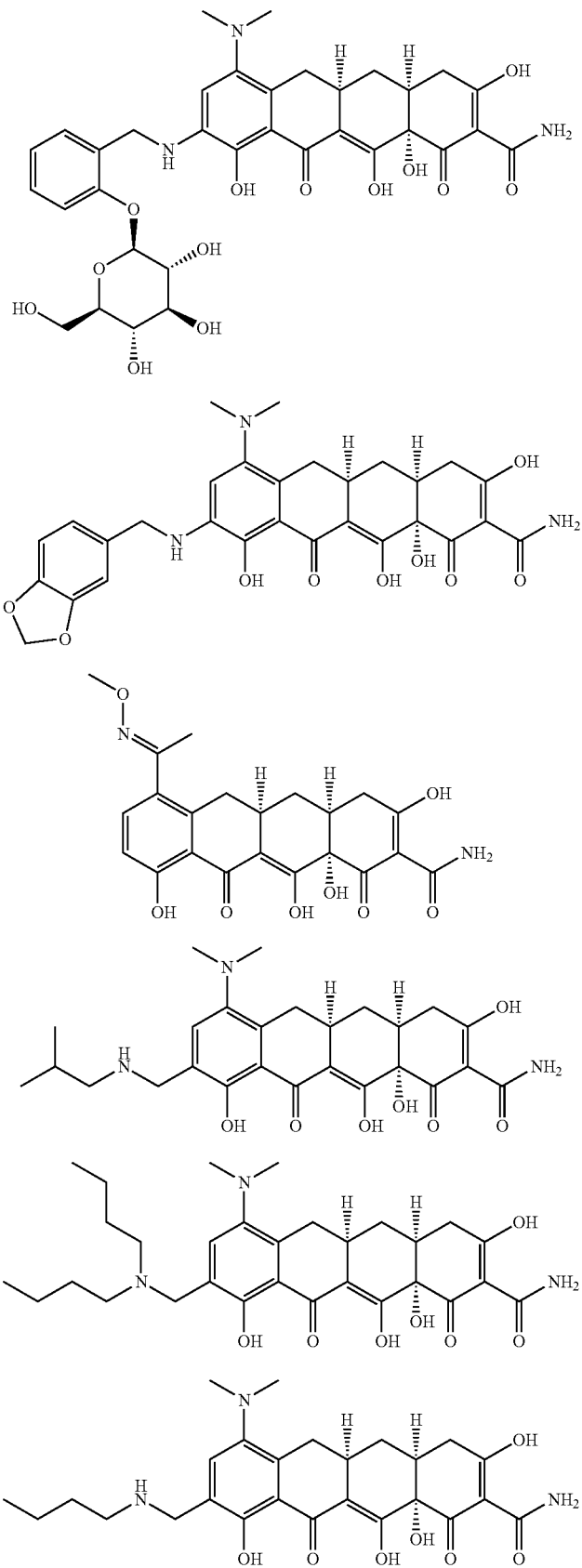

TABLE 2-continued
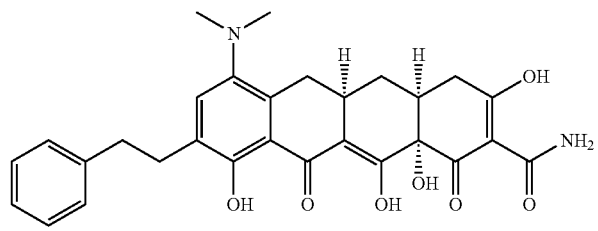 [SMILES: CN(C)c1cc(CCc2ccccc2)c(O)c2c1C[C@H]1C[C@H]3CC(O)=C(C(N)=O)C(=O)[C@@]3(O)C(O)=C1C2=O]
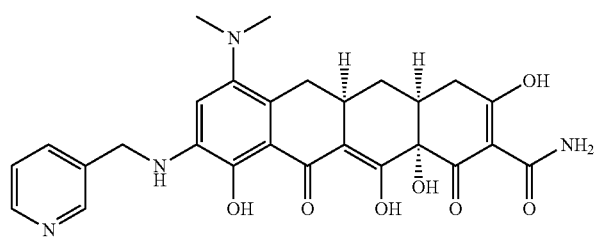 [SMILES: CN(C)c1cc(NCc2cccnc2)c(O)c2c1C[C@H]1C[C@H]3CC(O)=C(C(N)=O)C(=O)[C@@]3(O)C(O)=C1C2=O]
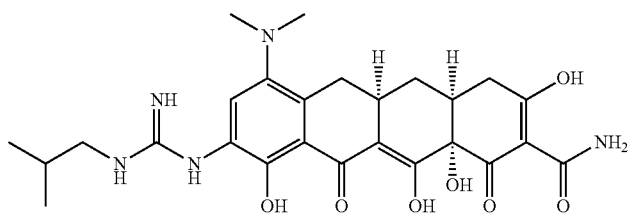 [SMILES: CC(C)CNC(=N)Nc1cc(N(C)C)c2c(c1O)C(=O)C1=C(O)[C@]3(O)C(=O)C(C(N)=O)=C(O)C[C@@H]3C[C@@H]1C2]
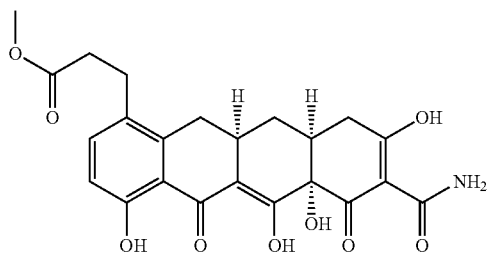 [SMILES: COC(=O)CCc1ccc(O)c2c1C[C@H]1C[C@H]3CC(O)=C(C(N)=O)C(=O)[C@@]3(O)C(O)=C1C2=O]
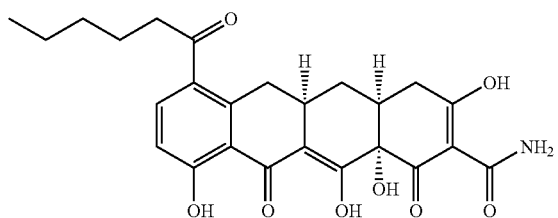 [SMILES: CCCCCC(=O)c1ccc(O)c2c1C[C@H]1C[C@H]3CC(O)=C(C(N)=O)C(=O)[C@@]3(O)C(O)=C1C2=O]
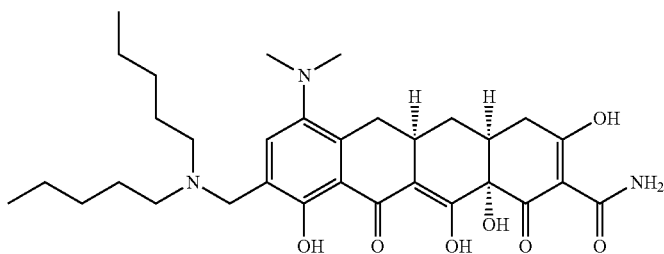 [SMILES: CCCCCN(CCCCC)Cc1cc(N(C)C)c2c(c1O)C(=O)C1=C(O)[C@]3(O)C(=O)C(C(N)=O)=C(O)C[C@@H]3C[C@@H]1C2]

TABLE 2-continued
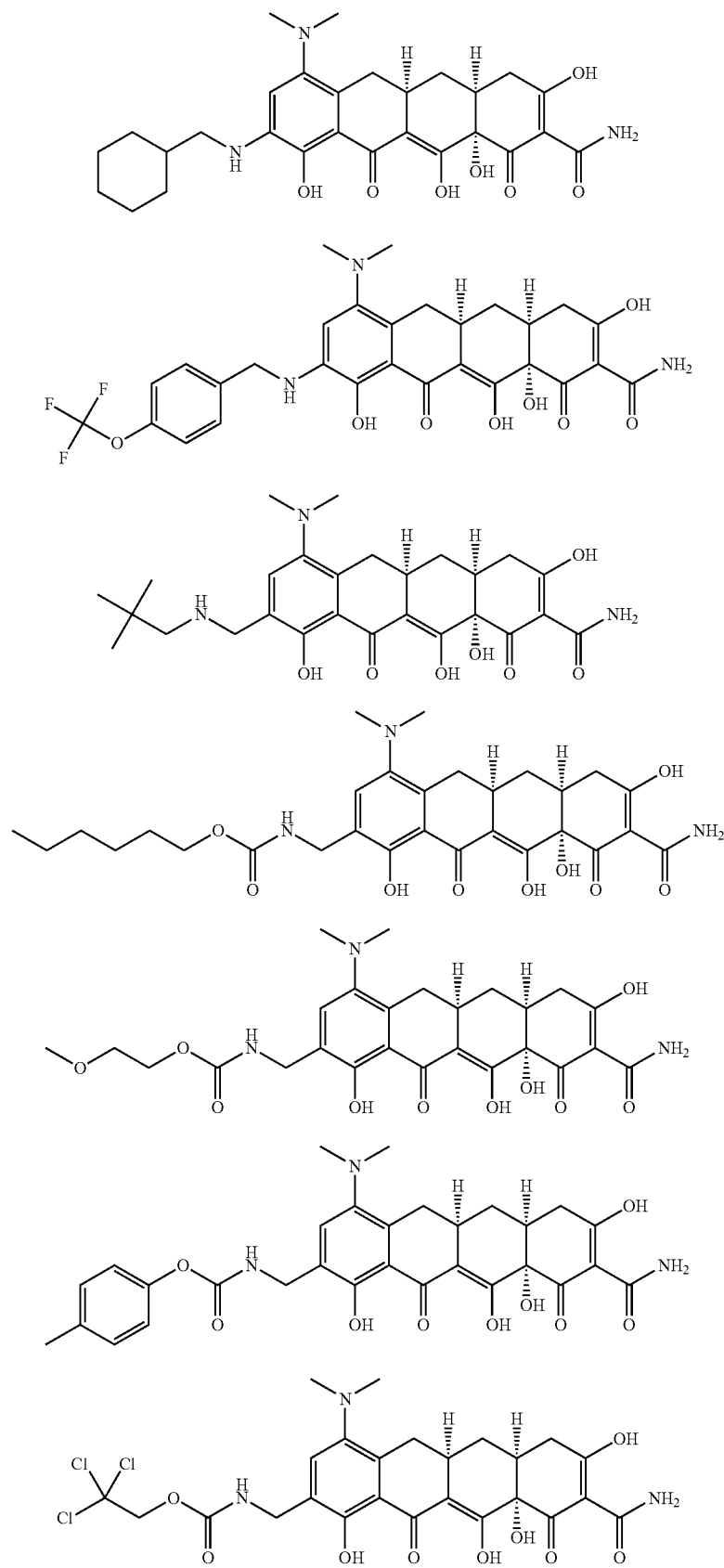

TABLE 2-continued
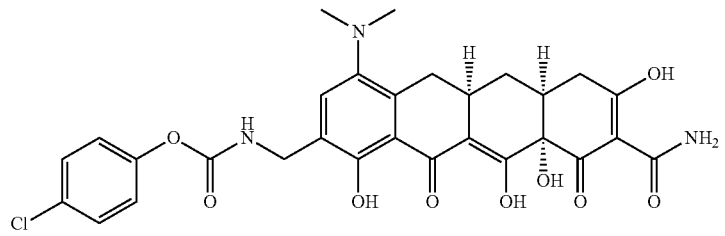 [SMILES: CN(C)c1cc(CNC(=O)Oc2ccc(Cl)cc2)c(O)c2c1C[C@H]1C[C@H]3CC(O)=C(C(N)=O)C(=O)[C@@]3(O)C(O)=C1C2=O]
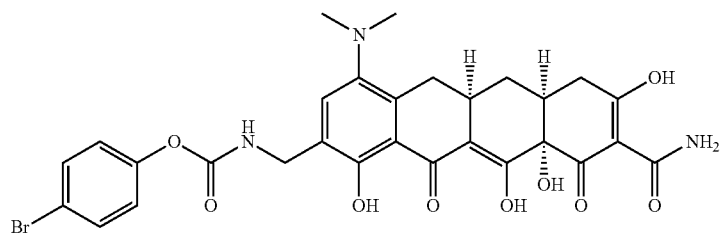
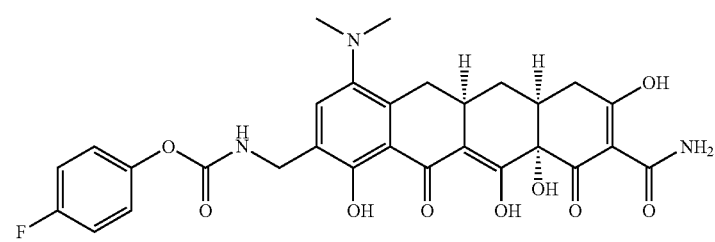 [SMILES: CN(C)c1cc(CNC(=O)Oc2ccc(F)cc2)c(O)c2c1C[C@H]1C[C@H]3CC(O)=C(C(N)=O)C(=O)[C@@]3(O)C(O)=C1C2=O]
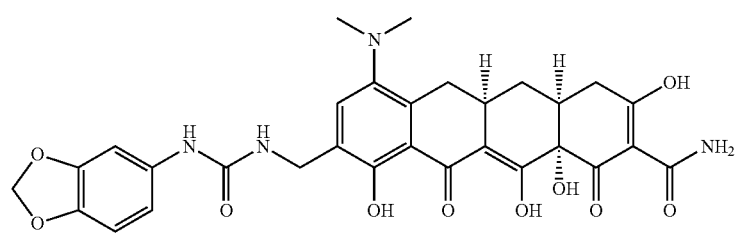 [SMILES: CN(C)c1cc(CNC(=O)Nc2ccc3c(c2)OCO3)c(O)c2c1C[C@H]1C[C@H]3CC(O)=C(C(N)=O)C(=O)[C@@]3(O)C(O)=C1C2=O]
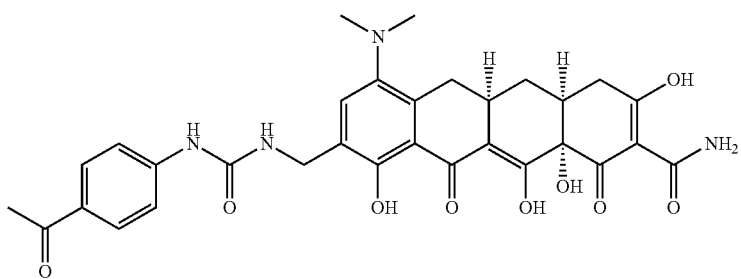 [SMILES: CC(=O)c1ccc(NC(=O)NCc2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
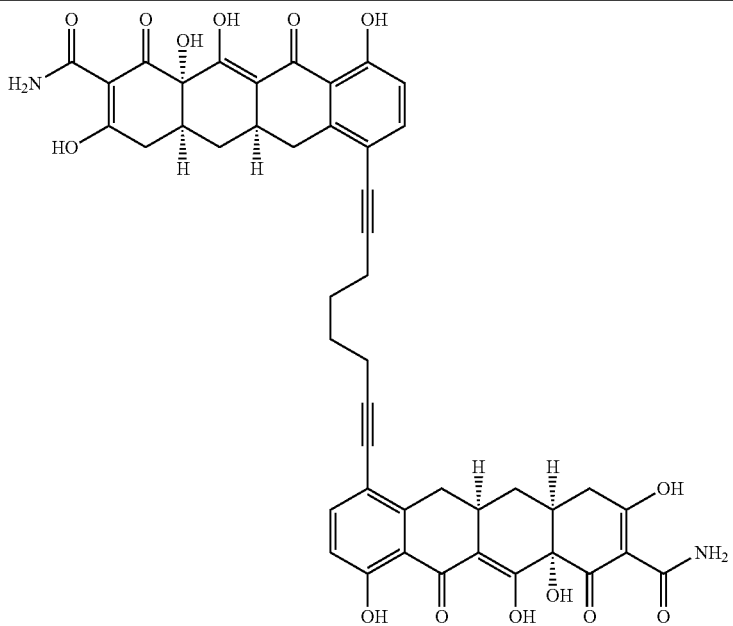
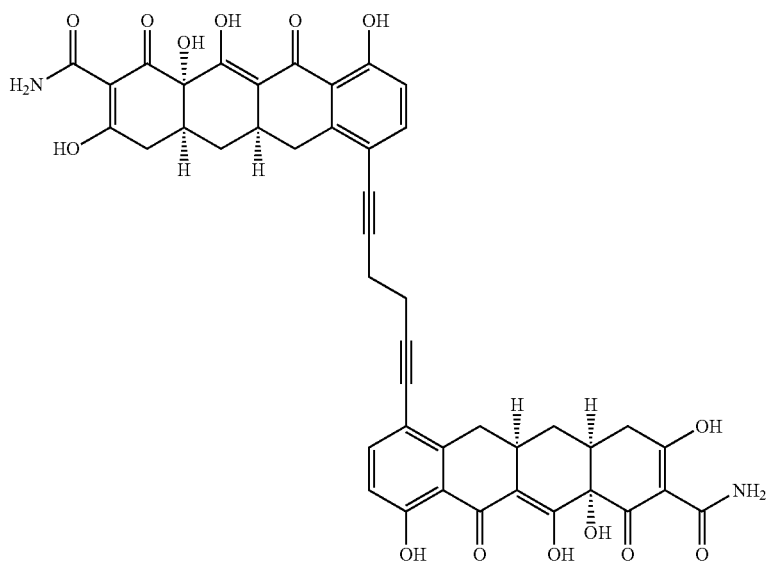 [SMILES: NC(=O)C1=C(O)C[C@@H]2C[C@@H]3Cc4c(C#CCCC#Cc5ccc(O)c6c5C[C@H]5C[C@H]7CC(O)=C(C(N)=O)C(=O)[C@@]7(O)C(O)=C5C6=O)ccc(O)c4C(=O)C3=C(O)[C@]2(O)C1=O]
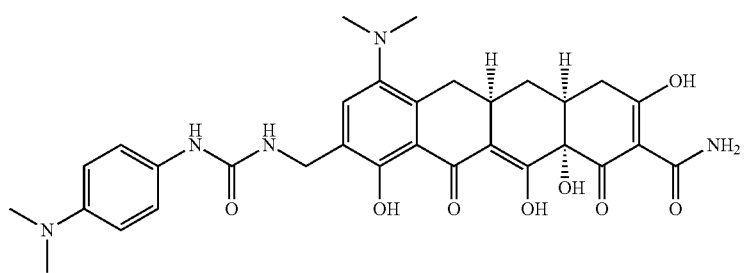 [SMILES: CN(C)c1ccc(NC(=O)NCc2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
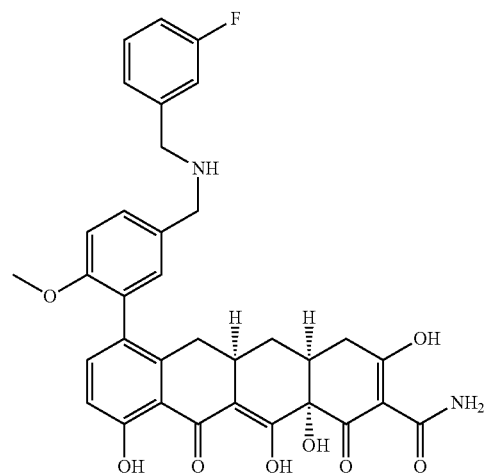 [SMILES: COc1ccc(CNCc2cccc(F)c2)cc1-c1ccc(O)c2c1C[C@H]1C[C@H]3CC(O)=C(C(N)=O)C(=O)[C@@]3(O)C(O)=C1C2=O]
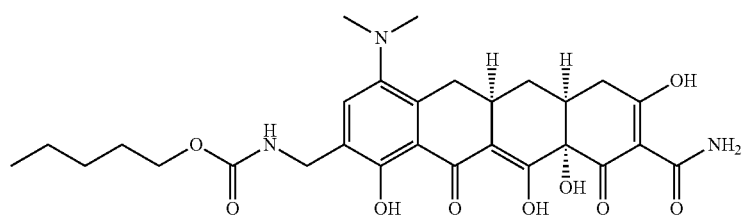 [SMILES: CCCCCOC(=O)NCc1cc(N(C)C)c2c(c1O)C(=O)C1=C(O)[C@]3(O)C(=O)C(C(N)=O)=C(O)C[C@@H]3C[C@@H]1C2]
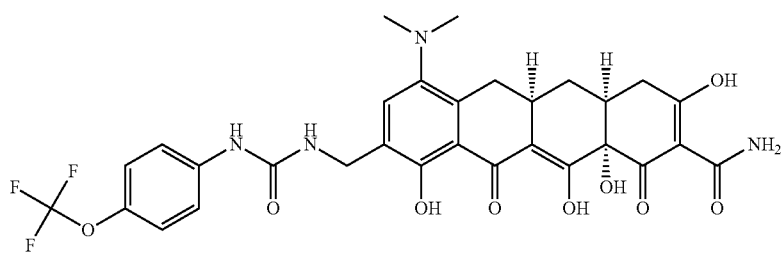 [SMILES: CN(C)c1cc(CNC(=O)Nc2ccc(OC(F)(F)F)cc2)c(O)c2c1C[C@H]1C[C@H]3CC(O)=C(C(N)=O)C(=O)[C@@]3(O)C(O)=C1C2=O]
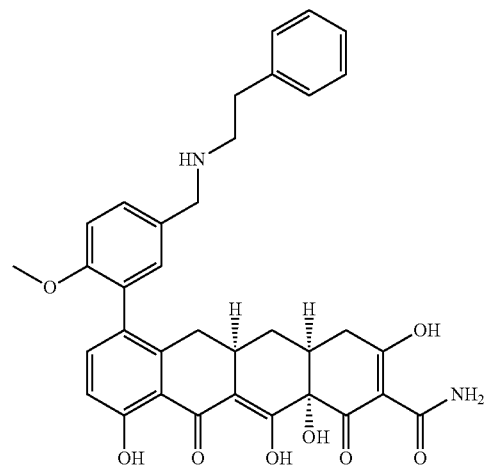 [SMILES: COc1ccc(CNCCc2ccccc2)cc1-c1ccc(O)c2c1C[C@H]1C[C@H]3CC(O)=C(C(N)=O)C(=O)[C@@]3(O)C(O)=C1C2=O]

TABLE 2-continued
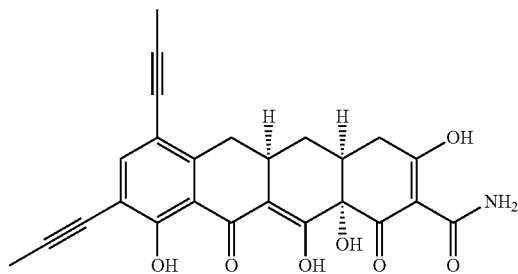 [SMILES: CC#Cc1cc(C#CC)c2c(c1O)C(=O)C1=C(O)[C@]3(O)C(=O)C(C(N)=O)=C(O)C[C@@H]3C[C@@H]1C2]
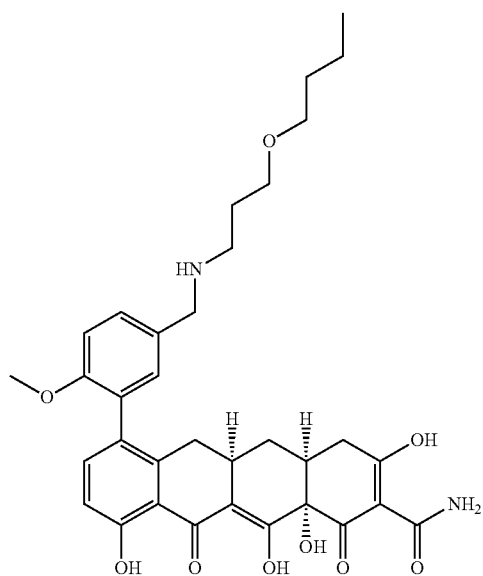 [SMILES: CCCCOCCCNCc1ccc(OC)c(-c2ccc(O)c3c2C[C@H]2C[C@H]4CC(O)=C(C(N)=O)C(=O)[C@@]4(O)C(O)=C2C3=O)c1]
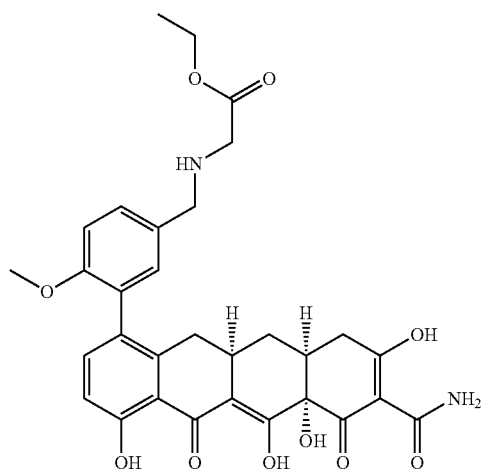 [SMILES: CCOC(=O)CNCc1ccc(OC)c(-c2ccc(O)c3c2C[C@H]2C[C@H]4CC(O)=C(C(N)=O)C(=O)[C@@]4(O)C(O)=C2C3=O)c1]
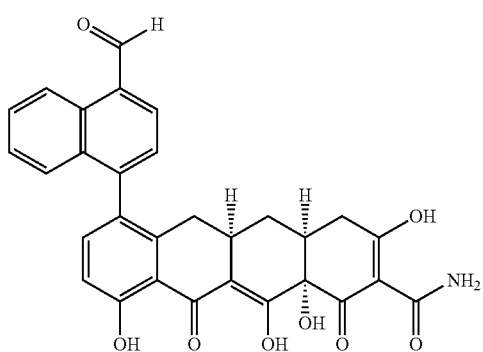 [SMILES: NC(=O)C1=C(O)C[C@@H]2C[C@@H]3Cc4c(-c5ccc(C=O)c6ccccc56)ccc(O)c4C(=O)C3=C(O)[C@]2(O)C1=O]

TABLE 2-continued
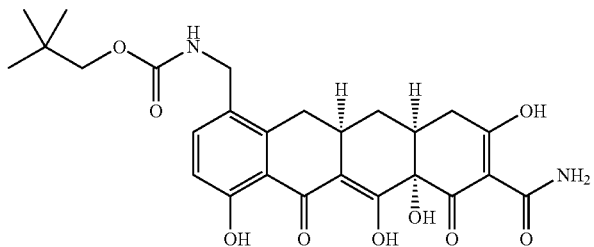 [SMILES: CC(C)(C)COC(=O)NCc1ccc(O)c2c1C[C@H]1C[C@H]3CC(O)=C(C(N)=O)C(=O)[C@@]3(O)C(O)=C1C2=O]
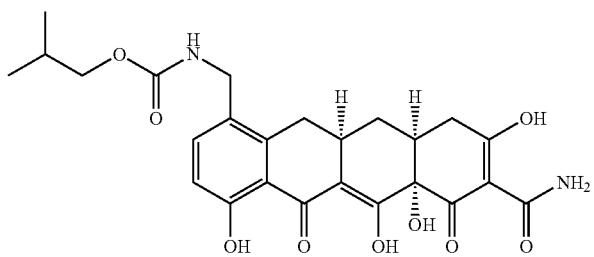 [SMILES: CC(C)COC(=O)NCc1ccc(O)c2c1C[C@H]1C[C@H]3CC(O)=C(C(N)=O)C(=O)[C@@]3(O)C(O)=C1C2=O]
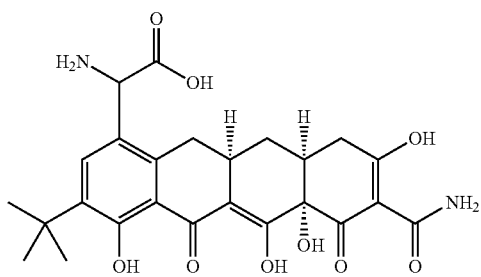 [SMILES: CC(C)(C)c1cc(C(N)C(=O)O)c2c(c1O)C(=O)C1=C(O)[C@]3(O)C(=O)C(C(N)=O)=C(O)C[C@@H]3C[C@@H]1C2]
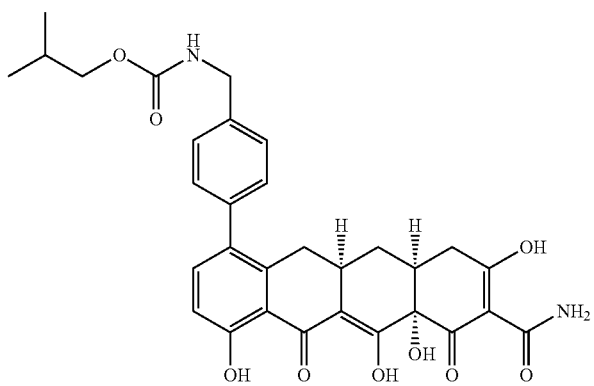 [SMILES: CC(C)COC(=O)NCc1ccc(-c2ccc(O)c3c2C[C@H]2C[C@H]4CC(O)=C(C(N)=O)C(=O)[C@@]4(O)C(O)=C2C3=O)cc1]
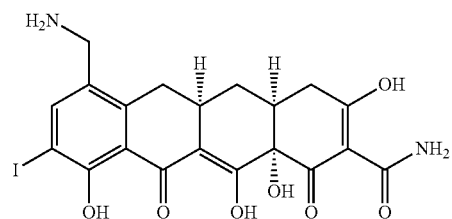 [SMILES: NCc1cc(I)c(O)c2c1C[C@H]1C[C@H]3CC(O)=C(C(N)=O)C(=O)[C@@]3(O)C(O)=C1C2=O]
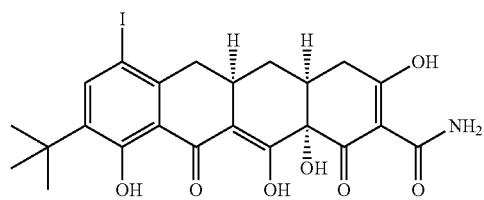 [SMILES: CC(C)(C)c1cc(I)c2c(c1O)C(=O)C1=C(O)[C@]3(O)C(=O)C(C(N)=O)=C(O)C[C@@H]3C[C@@H]1C2]

TABLE 2-continued
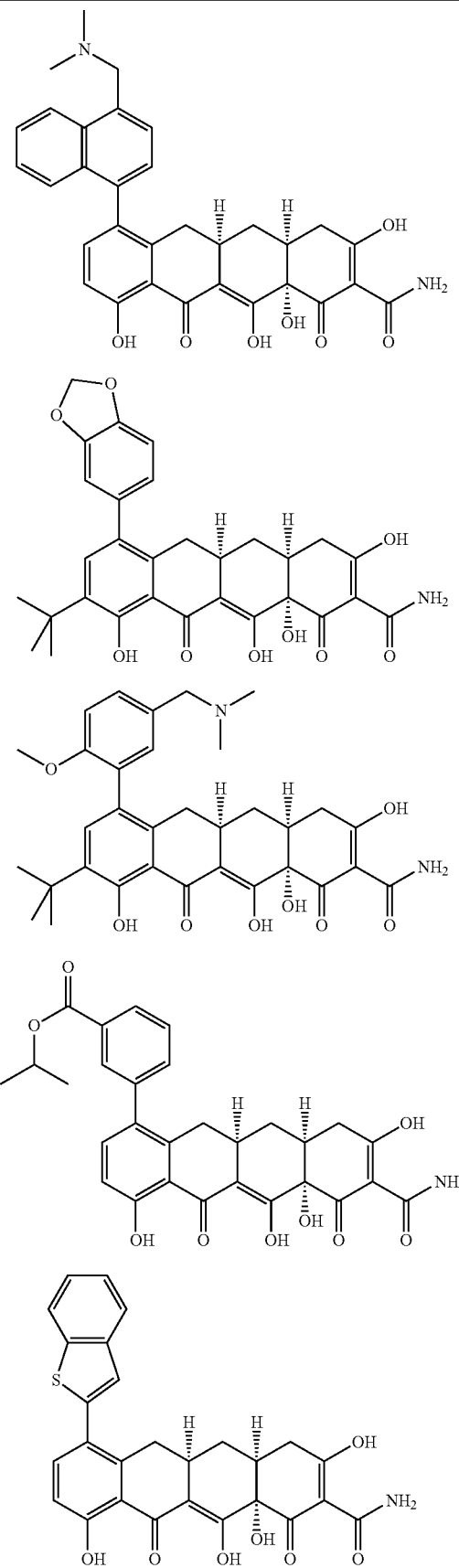

TABLE 2-continued
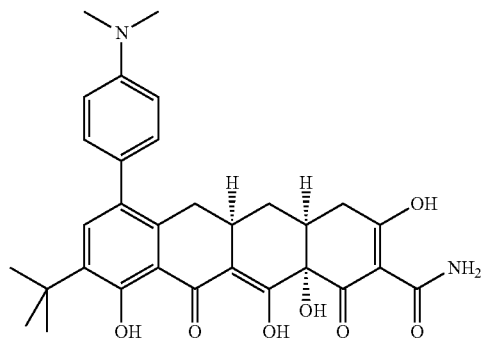 [SMILES: CN(C)c1ccc(-c2cc(C(C)(C)C)c(O)c3c2C[C@H]2C[C@H]4CC(O)=C(C(N)=O)C(=O)[C@@]4(O)C(O)=C2C3=O)cc1]
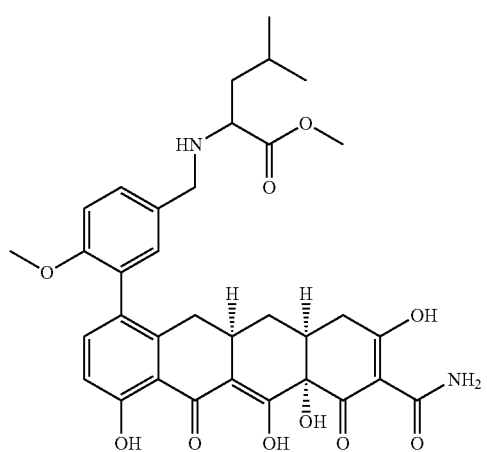 [SMILES: COC(=O)C(CC(C)C)NCc1ccc(OC)c(-c2ccc(O)c3c2C[C@H]2C[C@H]4CC(O)=C(C(N)=O)C(=O)[C@@]4(O)C(O)=C2C3=O)c1]
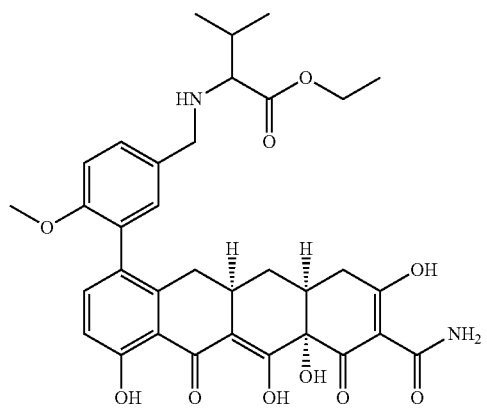 [SMILES: CCOC(=O)C(NCc1ccc(OC)c(-c2ccc(O)c3c2C[C@H]2C[C@H]4CC(O)=C(C(N)=O)C(=O)[C@@]4(O)C(O)=C2C3=O)c1)C(C)C]
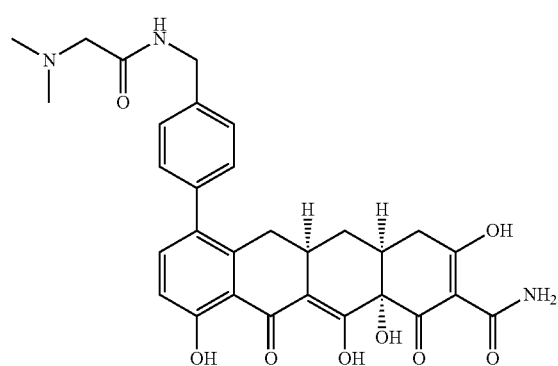 [SMILES: CN(C)CC(=O)NCc1ccc(-c2ccc(O)c3c2C[C@H]2C[C@H]4CC(O)=C(C(N)=O)C(=O)[C@@]4(O)C(O)=C2C3=O)cc1]

TABLE 2-continued
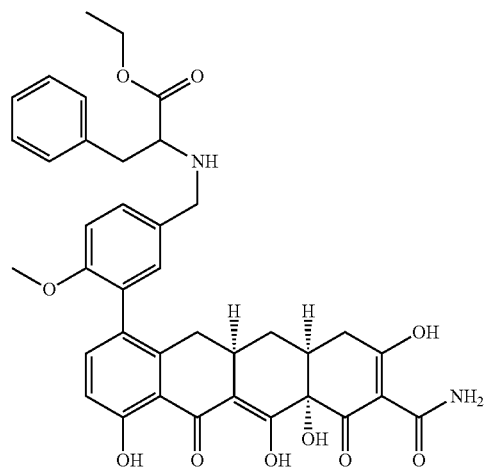 [SMILES: CCOC(=O)C(Cc1ccccc1)NCc1ccc(OC)c(-c2ccc(O)c3c2C[C@H]2C[C@H]4CC(O)=C(C(N)=O)C(=O)[C@@]4(O)C(O)=C2C3=O)c1]
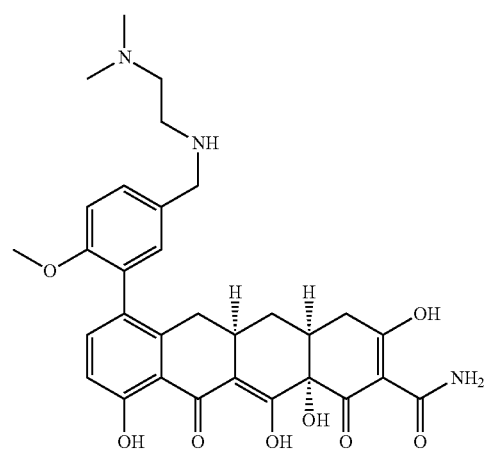 [SMILES: COc1ccc(CNCCN(C)C)cc1-c1ccc(O)c2c1C[C@H]1C[C@H]3CC(O)=C(C(N)=O)C(=O)[C@@]3(O)C(O)=C1C2=O]
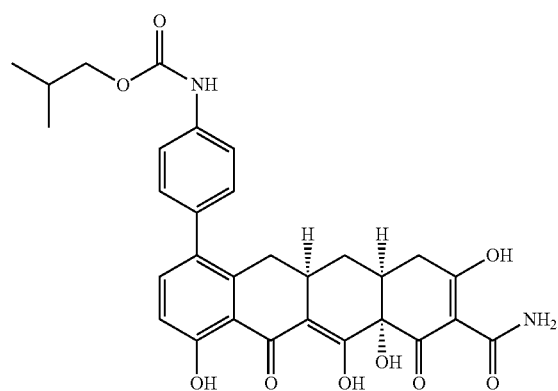

TABLE 2-continued
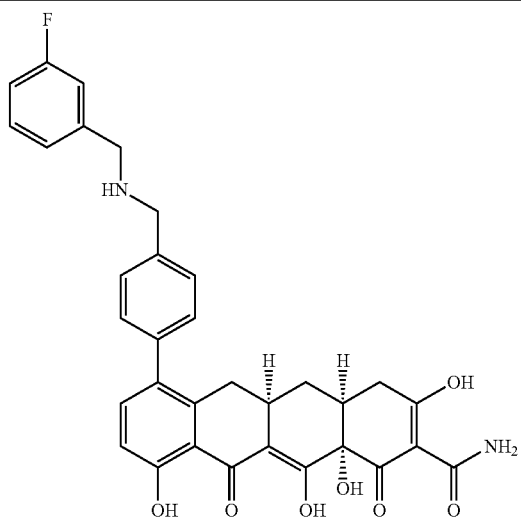
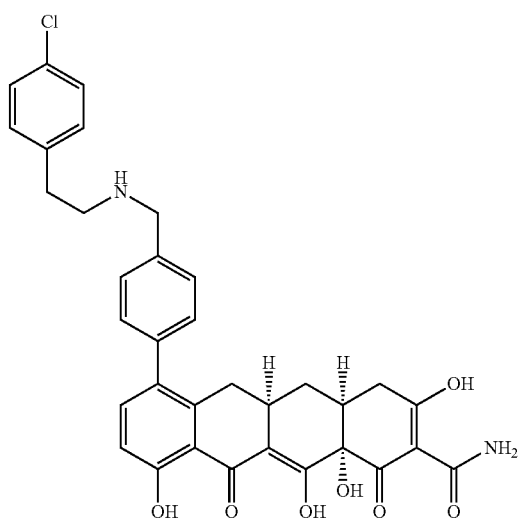 [SMILES: NC(=O)C1=C(O)C[C@@H]2C[C@@H]3Cc4c(-c5ccc(CNCCc6ccc(Cl)cc6)cc5)ccc(O)c4C(=O)C3=C(O)[C@]2(O)C1=O]
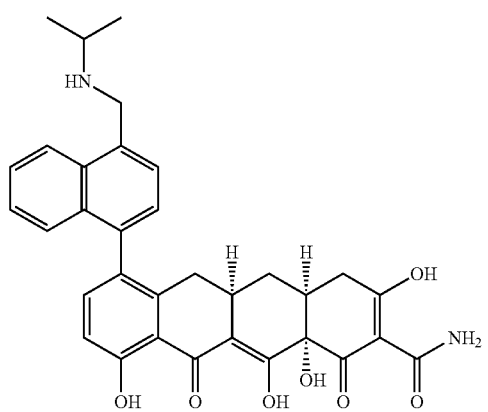 [SMILES: CC(C)NCc1ccc(-c2ccc(O)c3c2C[C@H]2C[C@H]4CC(O)=C(C(N)=O)C(=O)[C@@]4(O)C(O)=C2C3=O)c2ccccc12]

TABLE 2-continued
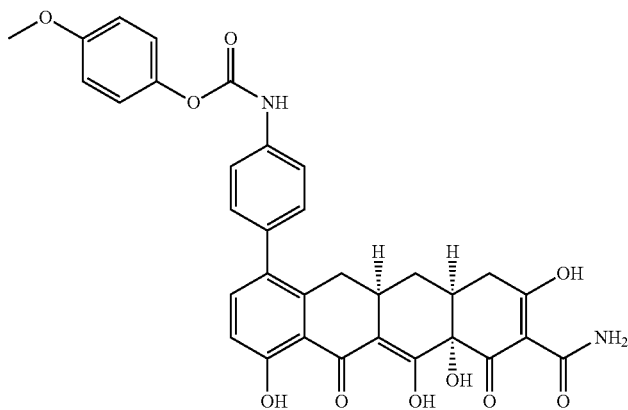 [SMILES: COc1ccc(OC(=O)Nc2ccc(-c3ccc(O)c4c3C[C@H]3C[C@H]5CC(O)=C(C(N)=O)C(=O)[C@@]5(O)C(O)=C3C4=O)cc2)cc1]
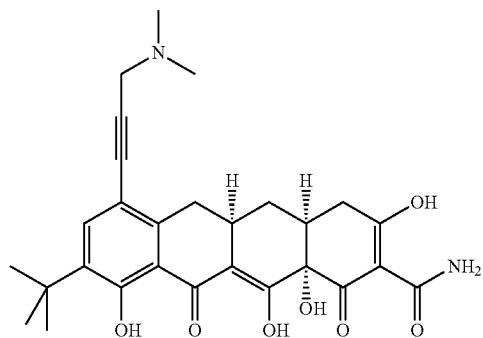 [SMILES: CN(C)CC#Cc1cc(C(C)(C)C)c(O)c2c1C[C@H]1C[C@H]3CC(O)=C(C(N)=O)C(=O)[C@@]3(O)C(O)=C1C2=O]
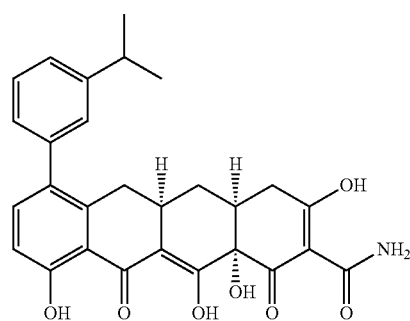 [SMILES: CC(C)c1cccc(-c2ccc(O)c3c2C[C@H]2C[C@H]4CC(O)=C(C(N)=O)C(=O)[C@@]4(O)C(O)=C2C3=O)c1]
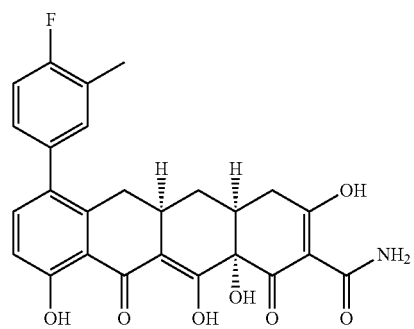

TABLE 2-continued
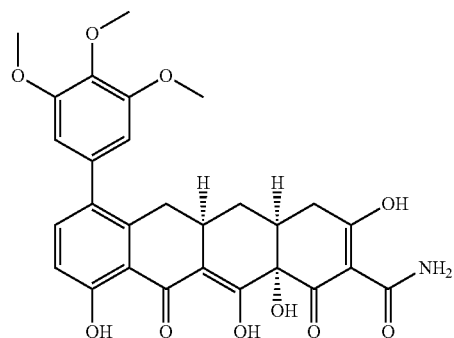 [SMILES: COc1cc(-c2ccc(O)c3c2C[C@H]2C[C@H]4CC(O)=C(C(N)=O)C(=O)[C@@]4(O)C(O)=C2C3=O)cc(OC)c1OC]
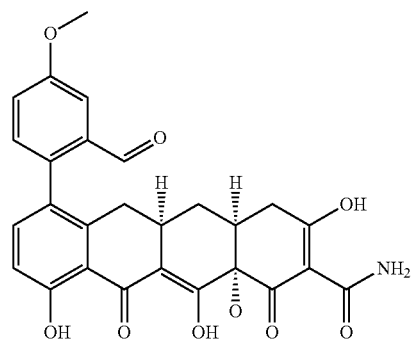 [SMILES: COc1ccc(-c2ccc(O)c3c2C[C@H]2C[C@H]4CC(O)=C(C(N)=O)C(=O)[C@@]4(O)C(O)=C2C3=O)c(C=O)c1]
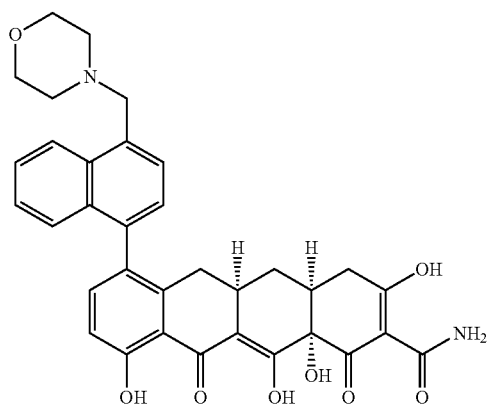 [SMILES: NC(=O)C1=C(O)C[C@@H]2C[C@@H]3Cc4c(-c5ccc(CN6CCOCC6)c6ccccc56)ccc(O)c4C(=O)C3=C(O)[C@]2(O)C1=O]
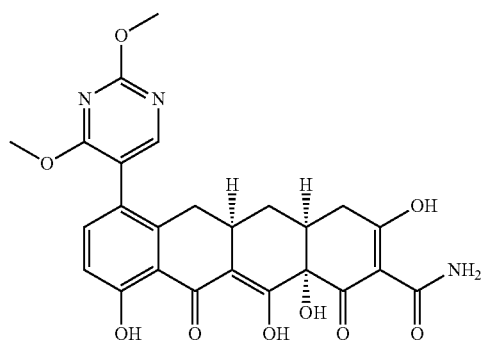 [SMILES: COc1ncc(-c2ccc(O)c3c2C[C@H]2C[C@H]4CC(O)=C(C(N)=O)C(=O)[C@@]4(O)C(O)=C2C3=O)c(OC)n1]

TABLE 2-continued
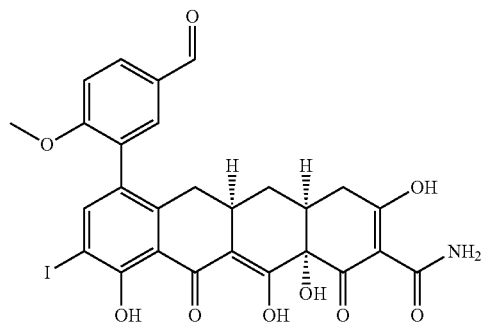 [SMILES: COc1ccc(C=O)cc1-c1cc(I)c(O)c2c1C[C@H]1C[C@H]3CC(O)=C(C(N)=O)C(=O)[C@@]3(O)C(O)=C1C2=O]
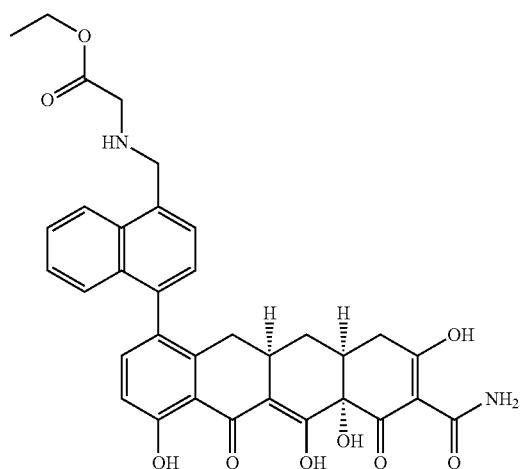 [SMILES: CCOC(=O)CNCc1ccc(-c2ccc(O)c3c2C[C@H]2C[C@H]4CC(O)=C(C(N)=O)C(=O)[C@@]4(O)C(O)=C2C3=O)c2ccccc12]
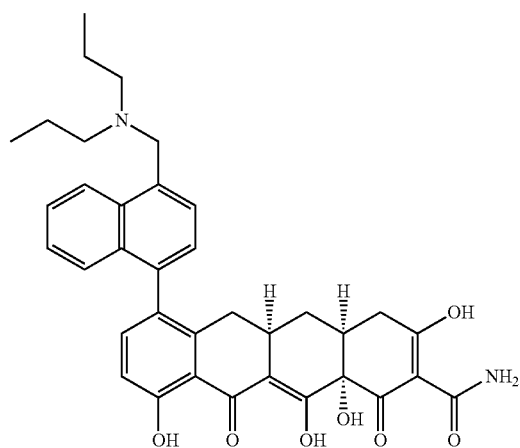 [SMILES: CCCN(CCC)Cc1ccc(-c2ccc(O)c3c2C[C@H]2C[C@H]4CC(O)=C(C(N)=O)C(=O)[C@@]4(O)C(O)=C2C3=O)c2ccccc12]
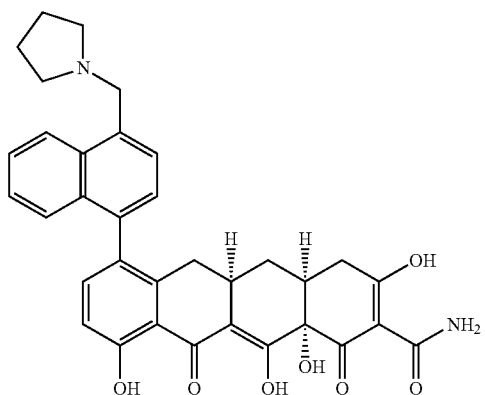 [SMILES: NC(=O)C1=C(O)C[C@@H]2C[C@@H]3Cc4c(-c5ccc(CN6CCCC6)c6ccccc56)ccc(O)c4C(=O)C3=C(O)[C@]2(O)C1=O]

TABLE 2-continued
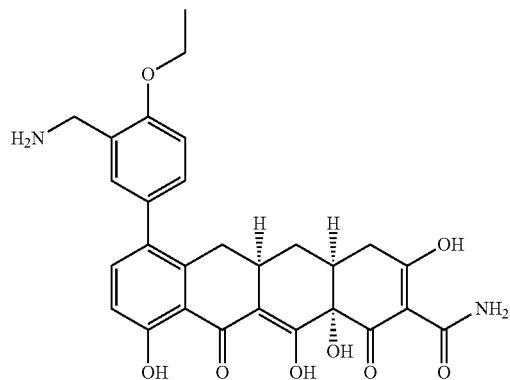 [SMILES: CCOc1ccc(-c2ccc(O)c3c2C[C@H]2C[C@H]4CC(O)=C(C(N)=O)C(=O)[C@@]4(O)C(O)=C2C3=O)cc1CN]
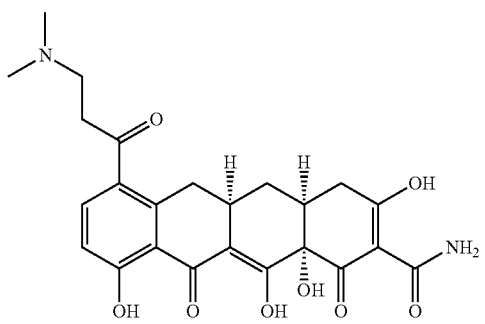 [SMILES: CN(C)CCC(=O)c1ccc(O)c2c1C[C@H]1C[C@H]3CC(O)=C(C(N)=O)C(=O)[C@@]3(O)C(O)=C1C2=O]
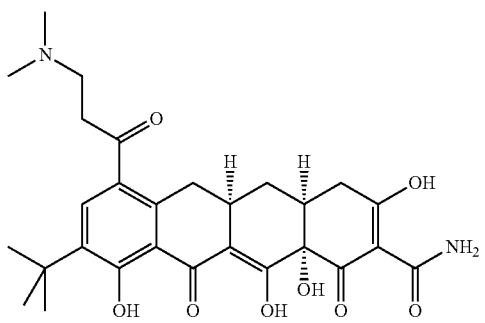 [SMILES: CN(C)CCC(=O)c1cc(C(C)(C)C)c(O)c2c1C[C@H]1C[C@H]3CC(O)=C(C(N)=O)C(=O)[C@@]3(O)C(O)=C1C2=O]
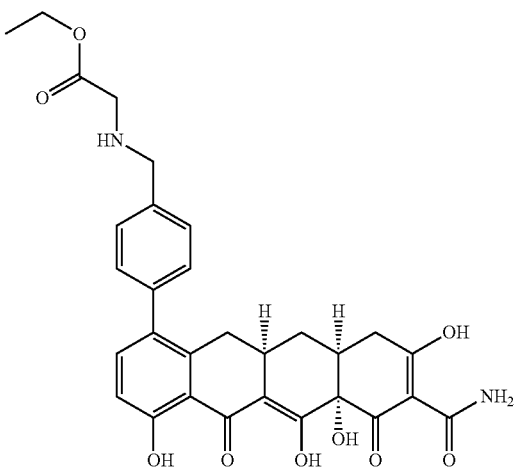 [SMILES: CCOC(=O)CNCc1ccc(-c2ccc(O)c3c2C[C@H]2C[C@H]4CC(O)=C(C(N)=O)C(=O)[C@@]4(O)C(O)=C2C3=O)cc1]

TABLE 2-continued
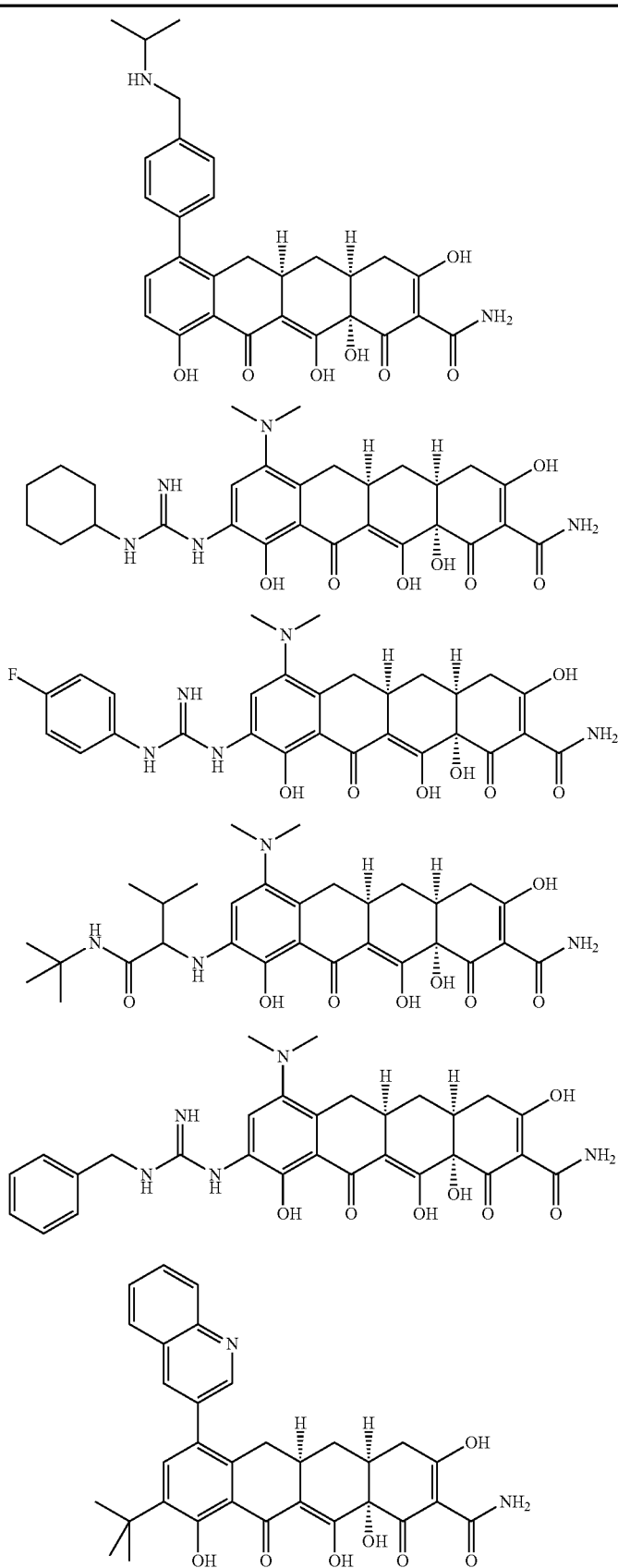

TABLE 2-continued
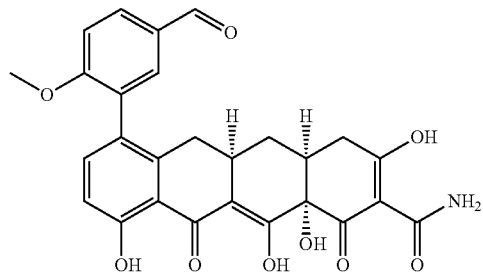 [SMILES: COc1ccc(C=O)cc1-c1ccc(O)c2c1C[C@H]1C[C@H]3CC(O)=C(C(N)=O)C(=O)[C@@]3(O)C(O)=C1C2=O]
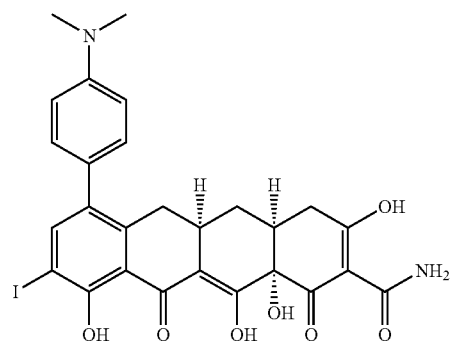 [SMILES: CN(C)c1ccc(-c2cc(I)c(O)c3c2C[C@H]2C[C@H]4CC(O)=C(C(N)=O)C(=O)[C@@]4(O)C(O)=C2C3=O)cc1]
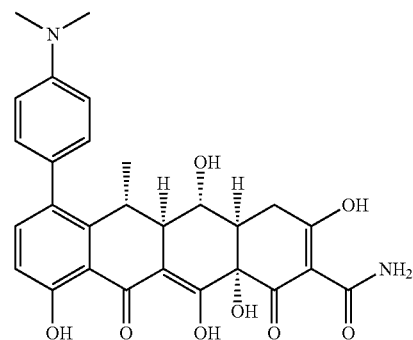 [SMILES: C[C@H]1c2c(-c3ccc(N(C)C)cc3)ccc(O)c2C(=O)C2=C(O)[C@]3(O)C(=O)C(C(N)=O)=C(O)C[C@@H]3[C@@H](O)[C@@H]21]
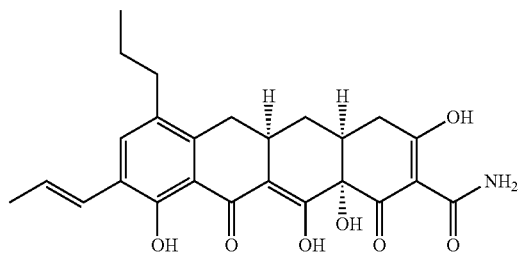 [SMILES: C/C=C/c1cc(CCC)c2c(c1O)C(=O)C1=C(O)[C@]3(O)C(=O)C(C(N)=O)=C(O)C[C@@H]3C[C@@H]1C2]
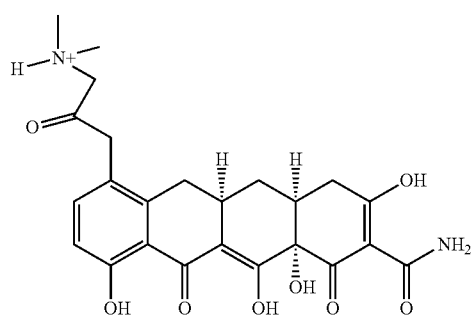 [SMILES: C[NH+](C)CC(=O)Cc1ccc(O)c2c1C[C@H]1C[C@H]3CC(O)=C(C(N)=O)C(=O)[C@@]3(O)C(O)=C1C2=O]

TABLE 2-continued
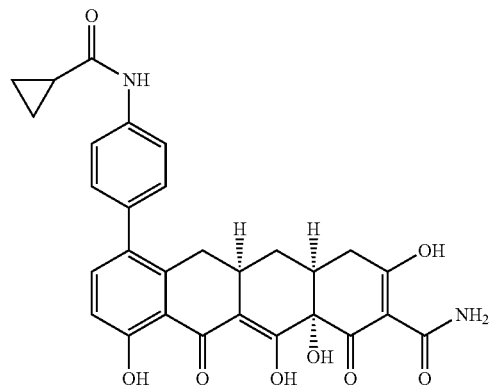 [SMILES: NC(=O)C1=C(O)C[C@@H]2C[C@@H]3Cc4c(-c5ccc(NC(=O)C6CC6)cc5)ccc(O)c4C(=O)C3=C(O)[C@]2(O)C1=O]
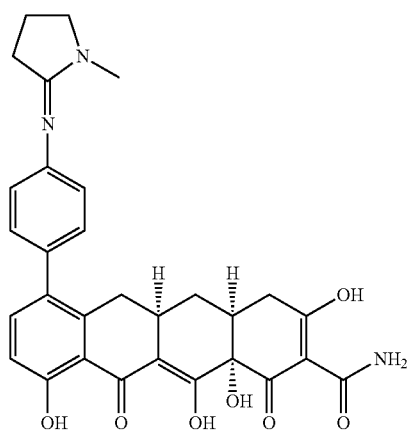 [SMILES: CN1CCCC1=Nc1ccc(-c2ccc(O)c3c2C[C@H]2C[C@H]4CC(O)=C(C(N)=O)C(=O)[C@@]4(O)C(O)=C2C3=O)cc1]
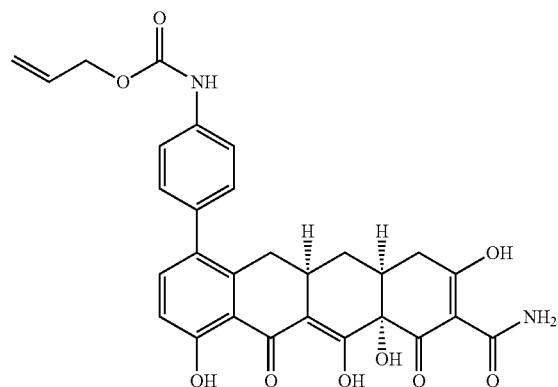 [SMILES: C=CCOC(=O)Nc1ccc(-c2ccc(O)c3c2C[C@H]2C[C@H]4CC(O)=C(C(N)=O)C(=O)[C@@]4(O)C(O)=C2C3=O)cc1]
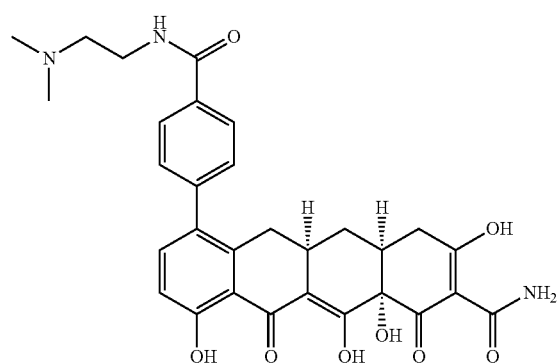 [SMILES: CN(C)CCNC(=O)c1ccc(-c2ccc(O)c3c2C[C@H]2C[C@H]4CC(O)=C(C(N)=O)C(=O)[C@@]4(O)C(O)=C2C3=O)cc1]

TABLE 2-continued
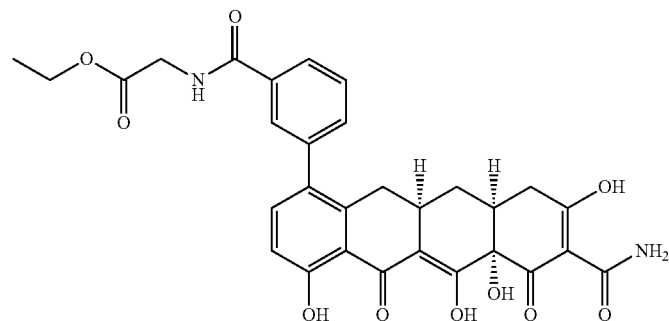 [SMILES: CCOC(=O)CNC(=O)c1cccc(-c2ccc(O)c3c2C[C@H]2C[C@H]4CC(O)=C(C(N)=O)C(=O)[C@@]4(O)C(O)=C2C3=O)c1]
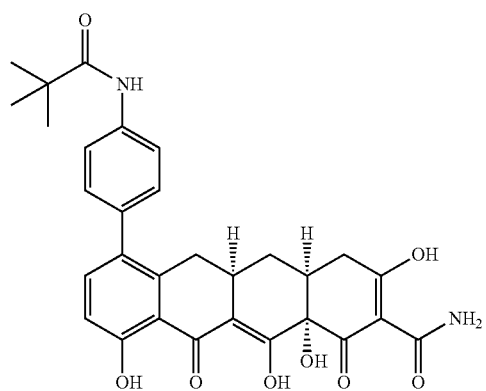 [SMILES: CC(C)(C)C(=O)Nc1ccc(-c2ccc(O)c3c2C[C@H]2C[C@H]4CC(O)=C(C(N)=O)C(=O)[C@@]4(O)C(O)=C2C3=O)cc1]
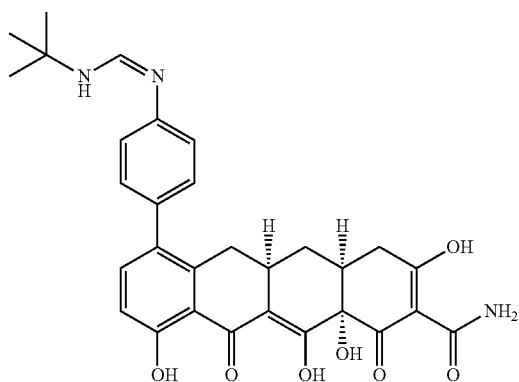 [SMILES: CC(C)(C)N/C=N\c1ccc(-c2ccc(O)c3c2C[C@H]2C[C@H]4CC(O)=C(C(N)=O)C(=O)[C@@]4(O)C(O)=C2C3=O)cc1]
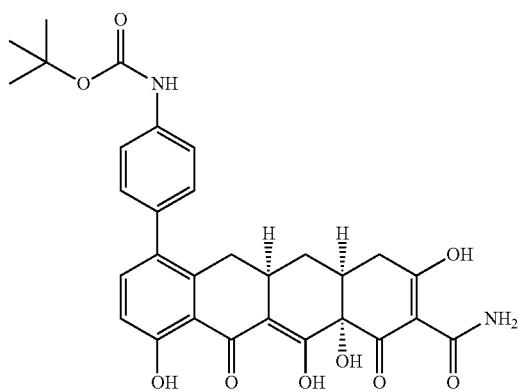 [SMILES: CC(C)(C)OC(=O)Nc1ccc(-c2ccc(O)c3c2C[C@H]2C[C@H]4CC(O)=C(C(N)=O)C(=O)[C@@]4(O)C(O)=C2C3=O)cc1]

TABLE 2-continued
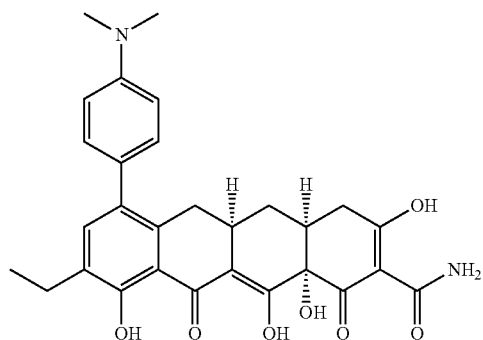 [SMILES: CCc1cc(-c2ccc(N(C)C)cc2)c2c(c1O)C(=O)C1=C(O)[C@]3(O)C(=O)C(C(N)=O)=C(O)C[C@@H]3C[C@@H]1C2]
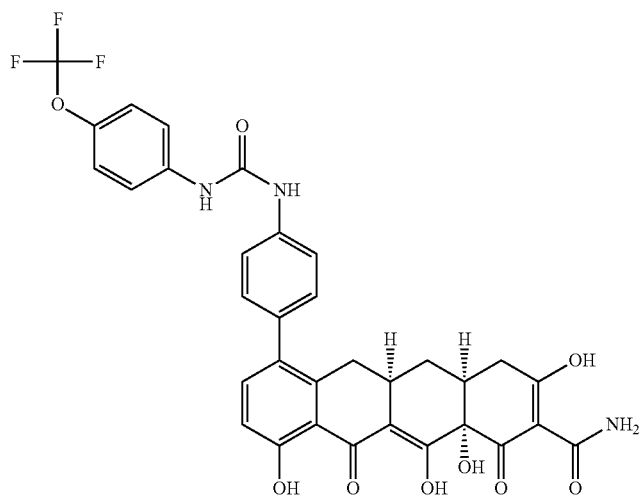 [SMILES: NC(=O)C1=C(O)C[C@@H]2C[C@@H]3Cc4c(-c5ccc(NC(=O)Nc6ccc(OC(F)(F)F)cc6)cc5)ccc(O)c4C(=O)C3=C(O)[C@]2(O)C1=O]
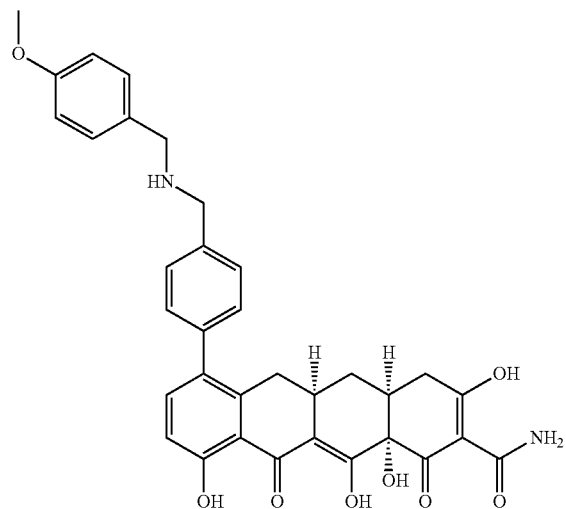 [SMILES: COc1ccc(CNCc2ccc(-c3ccc(O)c4c3C[C@H]3C[C@H]5CC(O)=C(C(N)=O)C(=O)[C@@]5(O)C(O)=C3C4=O)cc2)cc1]

TABLE 2-continued
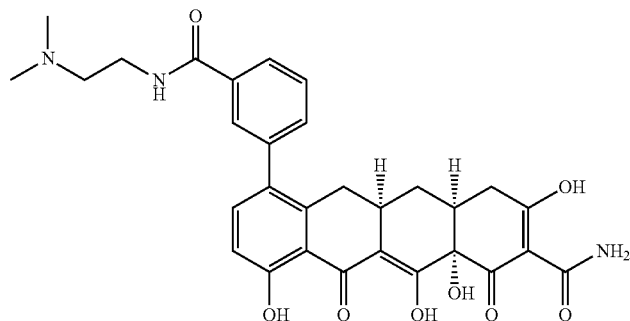 [SMILES: CN(C)CCNC(=O)c1cccc(-c2ccc(O)c3c2C[C@H]2C[C@H]4CC(O)=C(C(N)=O)C(=O)[C@@]4(O)C(O)=C2C3=O)c1]
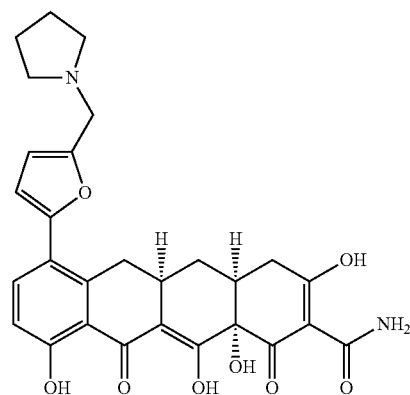 [SMILES: NC(=O)C1=C(O)C[C@@H]2C[C@@H]3Cc4c(-c5ccc(CN6CCCC6)o5)ccc(O)c4C(=O)C3=C(O)[C@]2(O)C1=O]
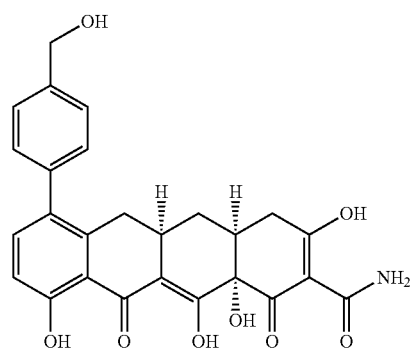 [SMILES: NC(=O)C1=C(O)C[C@@H]2C[C@@H]3Cc4c(-c5ccc(CO)cc5)ccc(O)c4C(=O)C3=C(O)[C@]2(O)C1=O]
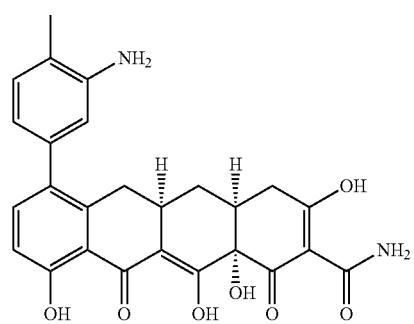 [SMILES: Cc1ccc(-c2ccc(O)c3c2C[C@H]2C[C@H]4CC(O)=C(C(N)=O)C(=O)[C@@]4(O)C(O)=C2C3=O)cc1N]

TABLE 2-continued
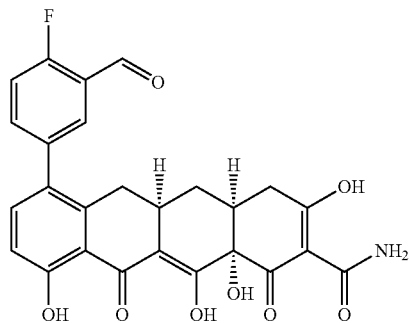 [SMILES: NC(=O)C1=C(O)C[C@@H]2C[C@@H]3Cc4c(-c5ccc(F)c(C=O)c5)ccc(O)c4C(=O)C3=C(O)[C@]2(O)C1=O]
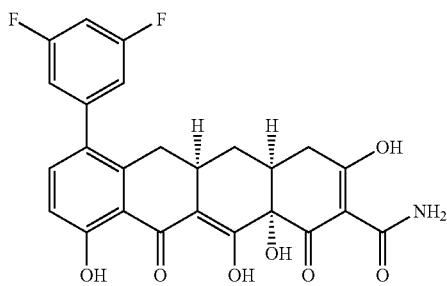 [SMILES: NC(=O)C1=C(O)C[C@@H]2C[C@@H]3Cc4c(-c5cc(F)cc(F)c5)ccc(O)c4C(=O)C3=C(O)[C@]2(O)C1=O]
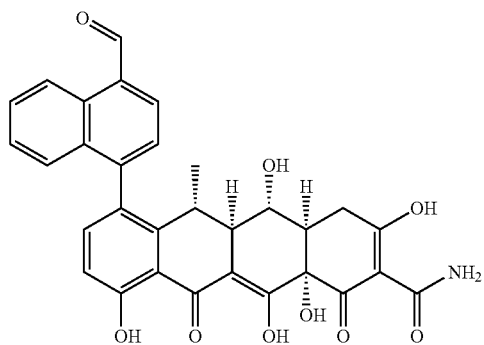 [SMILES: C[C@H]1c2c(-c3ccc(C=O)c4ccccc34)ccc(O)c2C(=O)C2=C(O)[C@]3(O)C(=O)C(C(N)=O)=C(O)C[C@@H]3[C@@H](O)[C@@H]21]
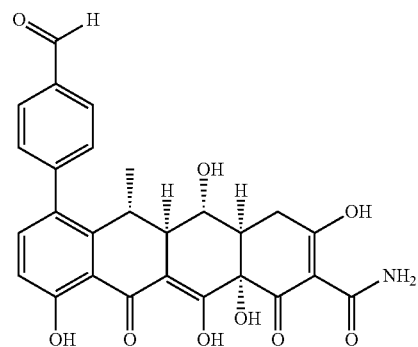 [SMILES: C[C@H]1c2c(-c3ccc(C=O)cc3)ccc(O)c2C(=O)C2=C(O)[C@]3(O)C(=O)C(C(N)=O)=C(O)C[C@@H]3[C@@H](O)[C@@H]21]
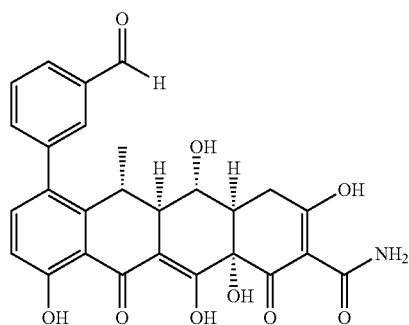 [SMILES: C[C@H]1c2c(-c3cccc(C=O)c3)ccc(O)c2C(=O)C2=C(O)[C@]3(O)C(=O)C(C(N)=O)=C(O)C[C@@H]3[C@@H](O)[C@@H]21]

TABLE 2-continued
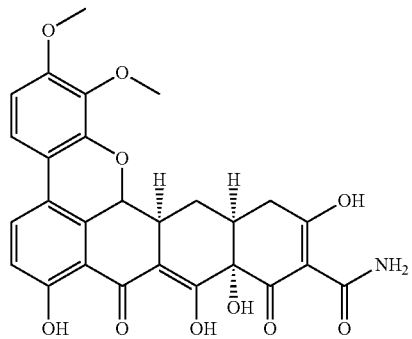 [SMILES: COc1ccc2c(c1OC)OC1c3c-2ccc(O)c3C(=O)C2=C(O)[C@]3(O)C(=O)C(C(N)=O)=C(O)C[C@@H]3C[C@@H]21]
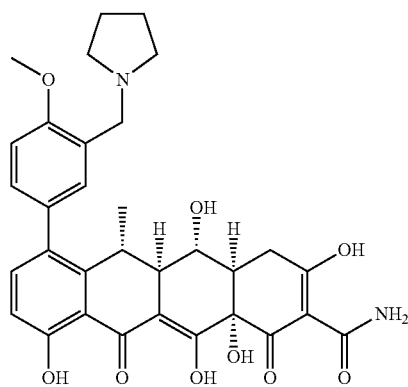 [SMILES: COc1ccc(-c2ccc(O)c3c2[C@H](C)[C@@H]2C(=C(O)[C@]4(O)C(=O)C(C(N)=O)=C(O)C[C@@H]4[C@H]2O)C3=O)cc1CN1CCCC1]
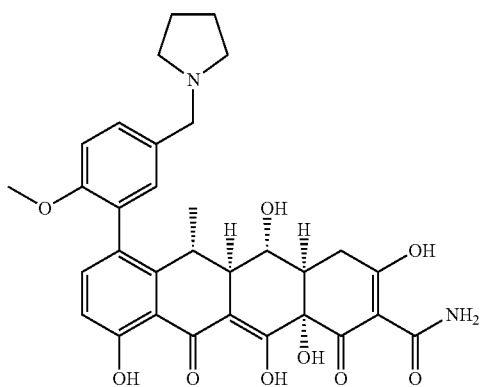 [SMILES: COc1ccc(CN2CCCC2)cc1-c1ccc(O)c2c1[C@H](C)[C@@H]1C(=C(O)[C@]3(O)C(=O)C(C(N)=O)=C(O)C[C@@H]3[C@H]1O)C2=O]
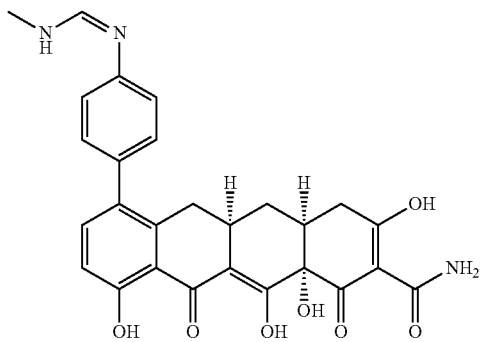 [SMILES: CN/C=N\c1ccc(-c2ccc(O)c3c2C[C@H]2C[C@H]4CC(O)=C(C(N)=O)C(=O)[C@@]4(O)C(O)=C2C3=O)cc1]

TABLE 2-continued
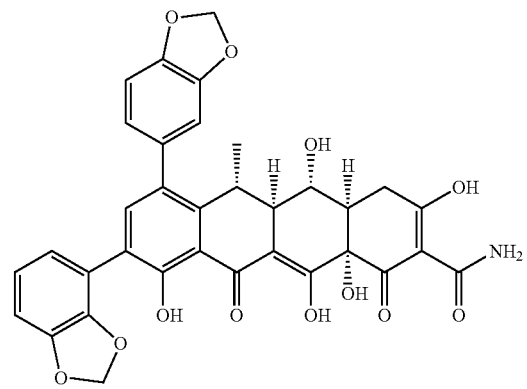 [SMILES: C[C@H]1c2c(-c3ccc4c(c3)OCO4)cc(-c3cccc4c3OCO4)c(O)c2C(=O)C2=C(O)[C@]3(O)C(=O)C(C(N)=O)=C(O)C[C@@H]3[C@@H](O)[C@@H]21]
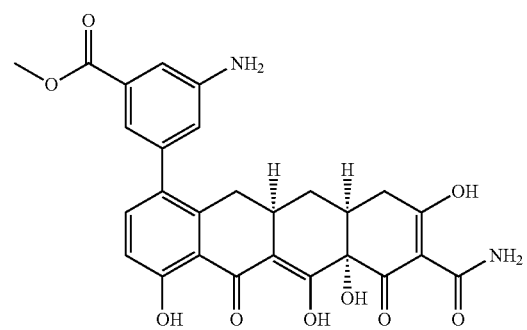 [SMILES: COC(=O)c1cc(N)cc(-c2ccc(O)c3c2C[C@H]2C[C@H]4CC(O)=C(C(N)=O)C(=O)[C@@]4(O)C(O)=C2C3=O)c1]
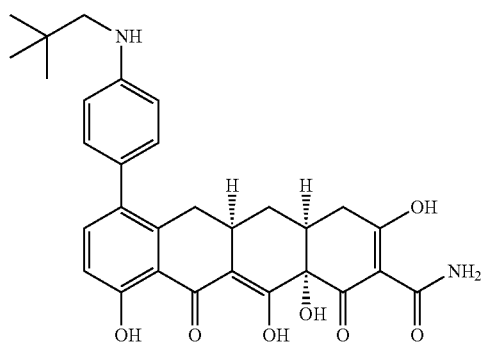 [SMILES: CC(C)(C)CNc1ccc(-c2ccc(O)c3c2C[C@H]2C[C@H]4CC(O)=C(C(N)=O)C(=O)[C@@]4(O)C(O)=C2C3=O)cc1]
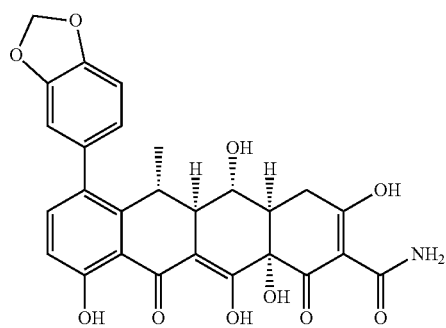 [SMILES: C[C@H]1c2c(-c3ccc4c(c3)OCO4)ccc(O)c2C(=O)C2=C(O)[C@]3(O)C(=O)C(C(N)=O)=C(O)C[C@@H]3[C@@H](O)[C@@H]21]
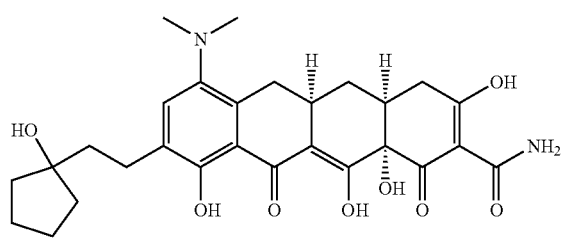 [SMILES: CN(C)c1cc(CCC2(O)CCCC2)c(O)c2c1C[C@H]1C[C@H]3CC(O)=C(C(N)=O)C(=O)[C@@]3(O)C(O)=C1C2=O]

TABLE 2-continued
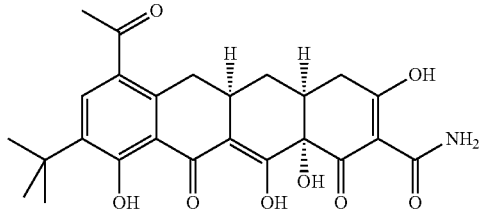 [SMILES: CC(=O)c1cc(C(C)(C)C)c(O)c2c1C[C@H]1C[C@H]3CC(O)=C(C(N)=O)C(=O)[C@@]3(O)C(O)=C1C2=O]
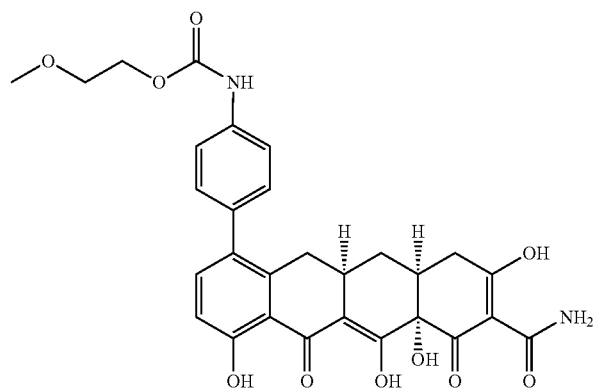 [SMILES: COCCOC(=O)Nc1ccc(-c2ccc(O)c3c2C[C@H]2C[C@H]4CC(O)=C(C(N)=O)C(=O)[C@@]4(O)C(O)=C2C3=O)cc1]
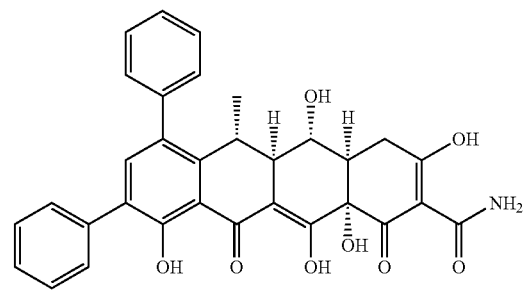 [SMILES: C[C@H]1c2c(-c3ccccc3)cc(-c3ccccc3)c(O)c2C(=O)C2=C(O)[C@]3(O)C(=O)C(C(N)=O)=C(O)C[C@@H]3[C@@H](O)[C@@H]21]
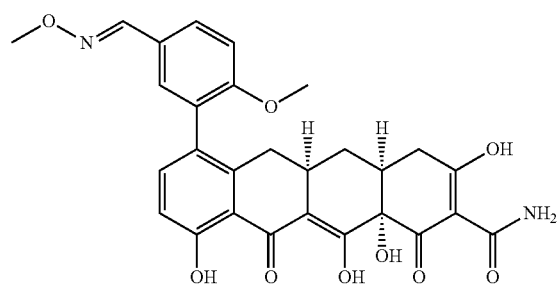 [SMILES: CO/N=C/c1ccc(OC)c(-c2ccc(O)c3c2C[C@H]2C[C@H]4CC(O)=C(C(N)=O)C(=O)[C@@]4(O)C(O)=C2C3=O)c1]
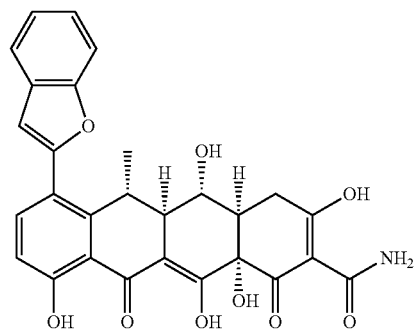 [SMILES: C[C@H]1c2c(-c3cc4ccccc4o3)ccc(O)c2C(=O)C2=C(O)[C@]3(O)C(=O)C(C(N)=O)=C(O)C[C@@H]3[C@@H](O)[C@@H]21]

TABLE 2-continued
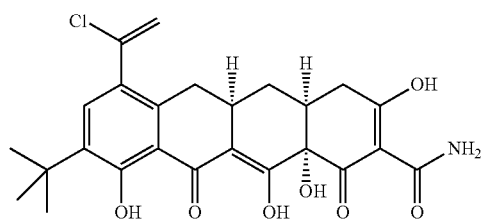 [SMILES: C=C(Cl)c1cc(C(C)(C)C)c(O)c2c1C[C@H]1C[C@H]3CC(O)=C(C(N)=O)C(=O)[C@@]3(O)C(O)=C1C2=O]
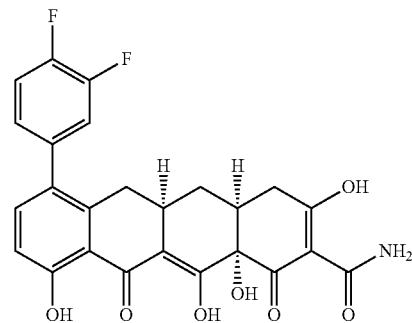
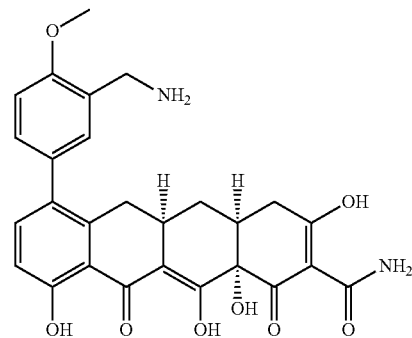 [SMILES: COc1ccc(-c2ccc(O)c3c2C[C@H]2C[C@H]4CC(O)=C(C(N)=O)C(=O)[C@@]4(O)C(O)=C2C3=O)cc1CN]
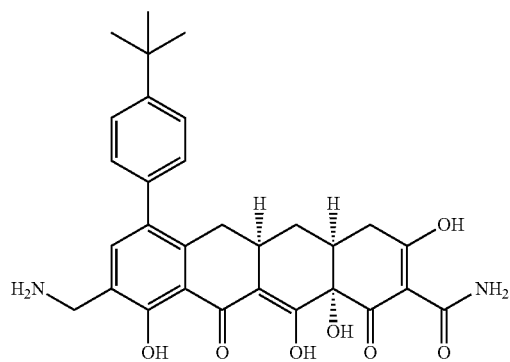 [SMILES: CC(C)(C)c1ccc(-c2cc(CN)c(O)c3c2C[C@H]2C[C@H]4CC(O)=C(C(N)=O)C(=O)[C@@]4(O)C(O)=C2C3=O)cc1]
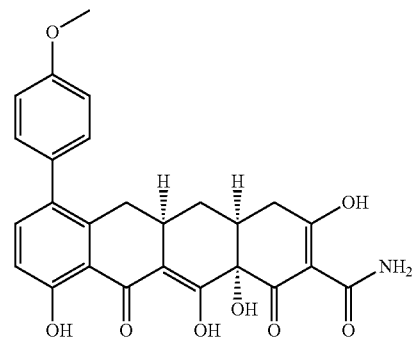 [SMILES: COc1ccc(-c2ccc(O)c3c2C[C@H]2C[C@H]4CC(O)=C(C(N)=O)C(=O)[C@@]4(O)C(O)=C2C3=O)cc1]

TABLE 2-continued
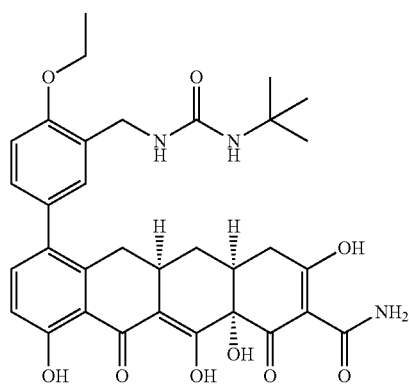 [SMILES: CCOc1ccc(-c2ccc(O)c3c2C[C@H]2C[C@H]4CC(O)=C(C(N)=O)C(=O)[C@@]4(O)C(O)=C2C3=O)cc1CNC(=O)NC(C)(C)C]
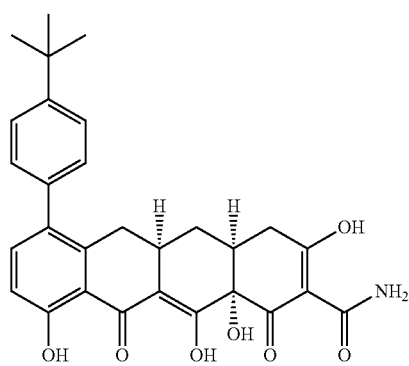 [SMILES: CC(C)(C)c1ccc(-c2ccc(O)c3c2C[C@H]2C[C@H]4CC(O)=C(C(N)=O)C(=O)[C@@]4(O)C(O)=C2C3=O)cc1]
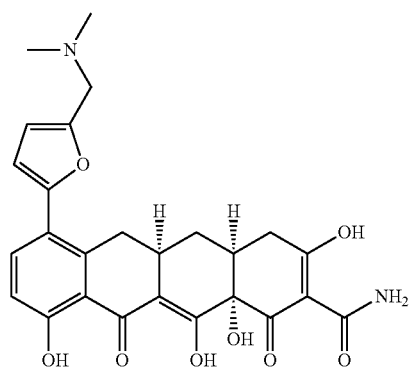 [SMILES: CN(C)Cc1ccc(-c2ccc(O)c3c2C[C@H]2C[C@H]4CC(O)=C(C(N)=O)C(=O)[C@@]4(O)C(O)=C2C3=O)o1]
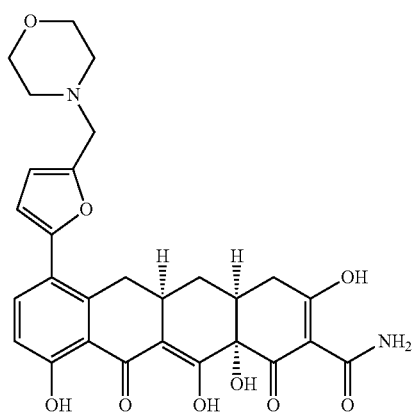 [SMILES: NC(=O)C1=C(O)C[C@@H]2C[C@@H]3Cc4c(-c5ccc(CN6CCOCC6)o5)ccc(O)c4C(=O)C3=C(O)[C@]2(O)C1=O]

TABLE 2-continued
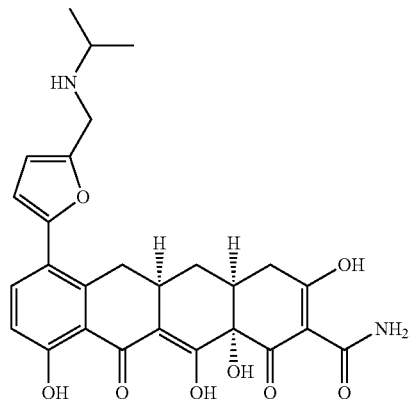 [SMILES: CC(C)NCc1ccc(-c2ccc(O)c3c2C[C@H]2C[C@H]4CC(O)=C(C(N)=O)C(=O)[C@@]4(O)C(O)=C2C3=O)o1]
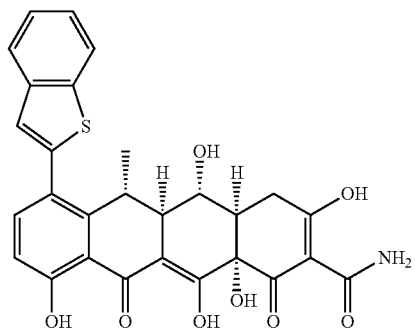
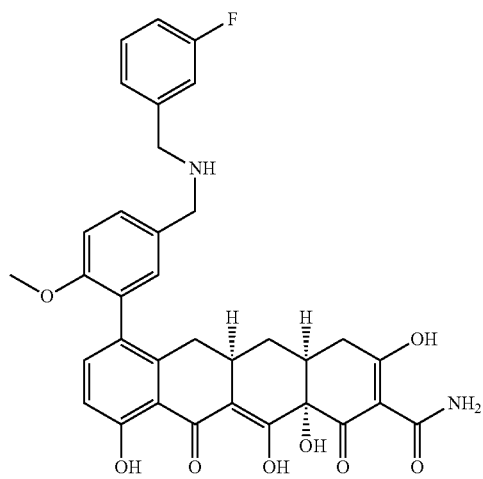 [SMILES: COc1ccc(CNCc2cccc(F)c2)cc1-c1ccc(O)c2c1C[C@H]1C[C@H]3CC(O)=C(C(N)=O)C(=O)[C@@]3(O)C(O)=C1C2=O]
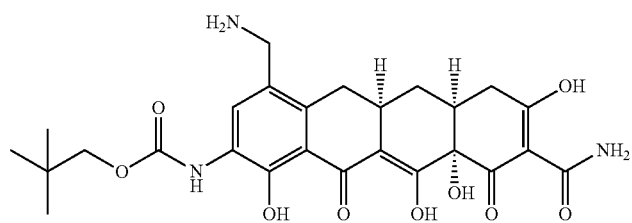 [SMILES: CC(C)(C)COC(=O)Nc1cc(CN)c2c(c1O)C(=O)C1=C(O)[C@]3(O)C(=O)C(C(N)=O)=C(O)C[C@@H]3C[C@@H]1C2]

TABLE 2-continued
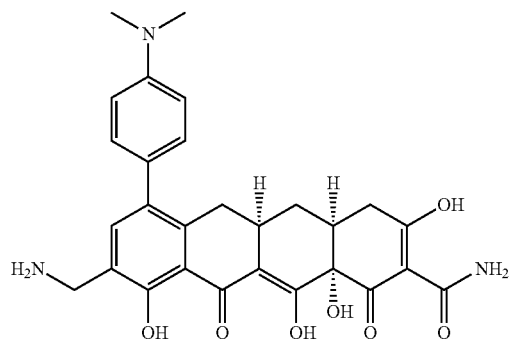 [SMILES: CN(C)c1ccc(-c2cc(CN)c(O)c3c2C[C@H]2C[C@H]4CC(O)=C(C(N)=O)C(=O)[C@@]4(O)C(O)=C2C3=O)cc1]
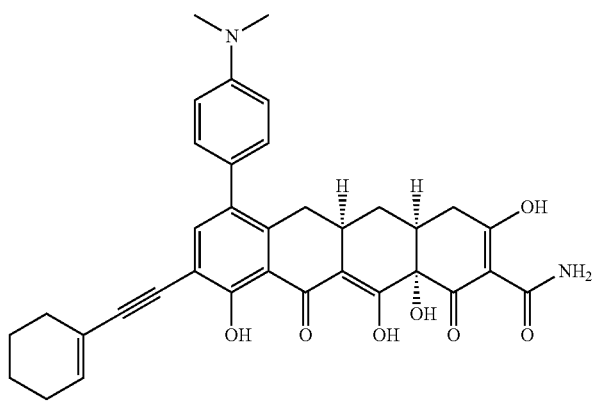 [SMILES: CN(C)c1ccc(-c2cc(C#CC3=CCCCC3)c(O)c3c2C[C@H]2C[C@H]4CC(O)=C(C(N)=O)C(=O)[C@@]4(O)C(O)=C2C3=O)cc1]
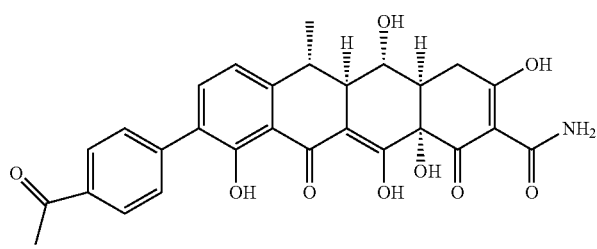 [SMILES: CC(=O)c1ccc(-c2ccc3c(c2O)C(=O)C2=C(O)[C@]4(O)C(=O)C(C(N)=O)=C(O)C[C@@H]4[C@@H](O)[C@@H]2[C@H]3C)cc1]
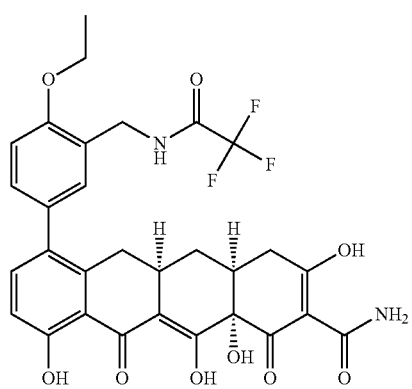 [SMILES: CCOc1ccc(-c2ccc(O)c3c2C[C@H]2C[C@H]4CC(O)=C(C(N)=O)C(=O)[C@@]4(O)C(O)=C2C3=O)cc1CNC(=O)C(F)(F)F]

TABLE 2-continued
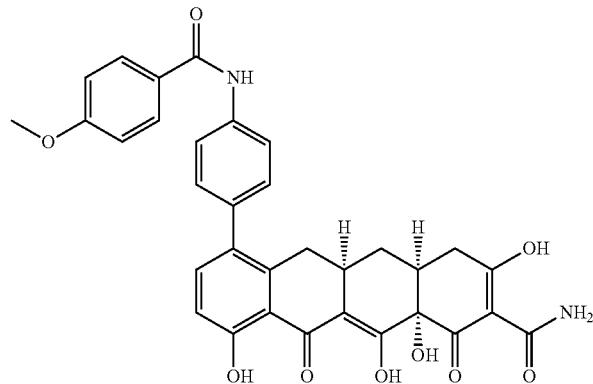 [SMILES: COc1ccc(C(=O)Nc2ccc(-c3ccc(O)c4c3C[C@H]3C[C@H]5CC(O)=C(C(N)=O)C(=O)[C@@]5(O)C(O)=C3C4=O)cc2)cc1]
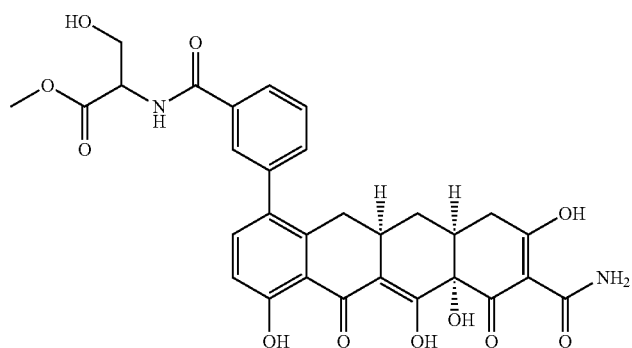 [SMILES: COC(=O)C(CO)NC(=O)c1cccc(-c2ccc(O)c3c2C[C@H]2C[C@H]4CC(O)=C(C(N)=O)C(=O)[C@@]4(O)C(O)=C2C3=O)c1]
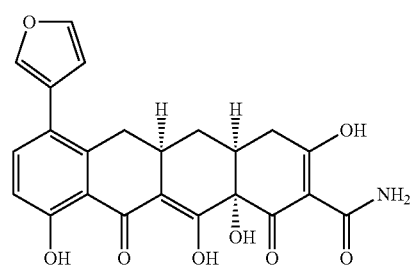 [SMILES: NC(=O)C1=C(O)C[C@@H]2C[C@@H]3Cc4c(-c5ccoc5)ccc(O)c4C(=O)C3=C(O)[C@]2(O)C1=O]
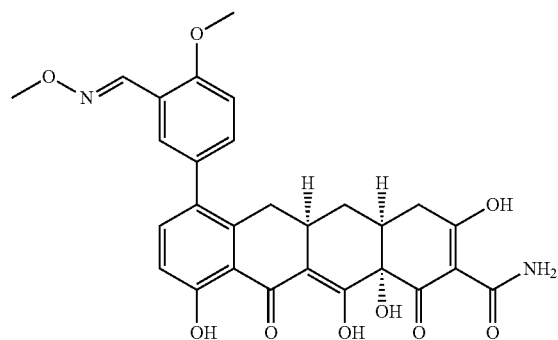 [SMILES: CO/N=C/c1cc(-c2ccc(O)c3c2C[C@H]2C[C@H]4CC(O)=C(C(N)=O)C(=O)[C@@]4(O)C(O)=C2C3=O)ccc1OC]

TABLE 2-continued
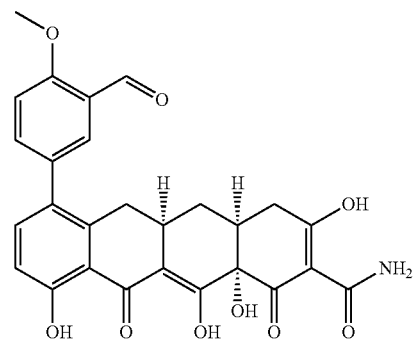 [SMILES: COc1ccc(-c2ccc(O)c3c2C[C@H]2C[C@H]4CC(O)=C(C(N)=O)C(=O)[C@@]4(O)C(O)=C2C3=O)cc1C=O]
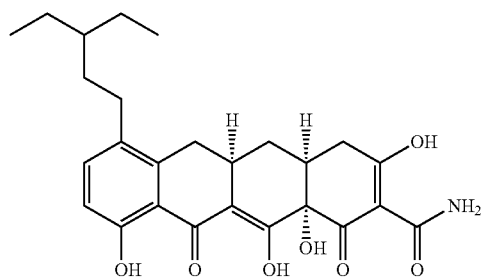 [SMILES: CCC(CC)CCc1ccc(O)c2c1C[C@H]1C[C@H]3CC(O)=C(C(N)=O)C(=O)[C@@]3(O)C(O)=C1C2=O]
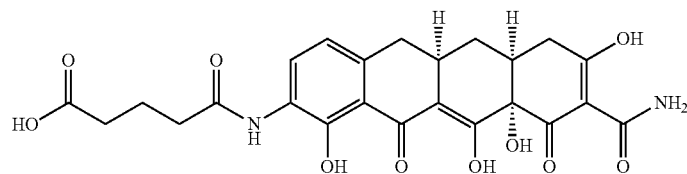 [SMILES: NC(=O)C1=C(O)C[C@@H]2C[C@@H]3Cc4ccc(NC(=O)CCCC(=O)O)c(O)c4C(=O)C3=C(O)[C@]2(O)C1=O]
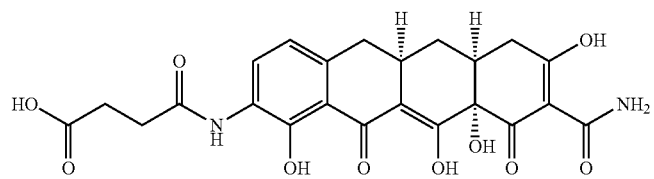 [SMILES: NC(=O)C1=C(O)C[C@@H]2C[C@@H]3Cc4ccc(NC(=O)CCC(=O)O)c(O)c4C(=O)C3=C(O)[C@]2(O)C1=O]
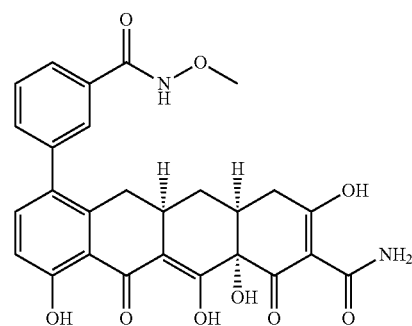
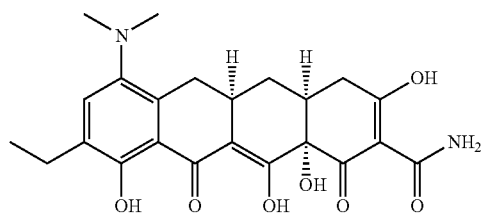 [SMILES: CCc1cc(N(C)C)c2c(c1O)C(=O)C1=C(O)[C@]3(O)C(=O)C(C(N)=O)=C(O)C[C@@H]3C[C@@H]1C2]

TABLE 2-continued
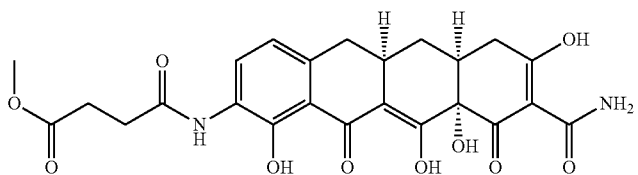 [SMILES: COC(=O)CCC(=O)Nc1ccc2c(c1O)C(=O)C1=C(O)[C@]3(O)C(=O)C(C(N)=O)=C(O)C[C@@H]3C[C@@H]1C2]
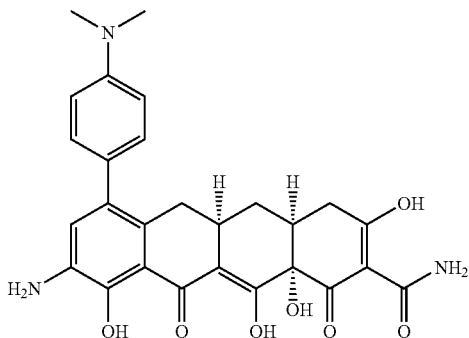 [SMILES: CN(C)c1ccc(-c2cc(N)c(O)c3c2C[C@H]2C[C@H]4CC(O)=C(C(N)=O)C(=O)[C@@]4(O)C(O)=C2C3=O)cc1]
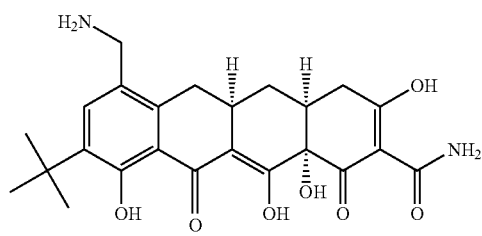
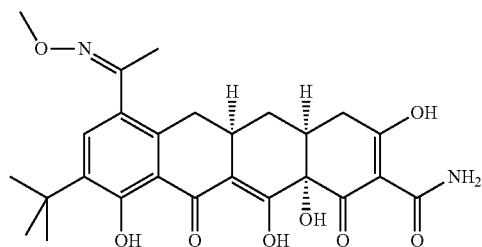 [SMILES: CO/N=C(/C)c1cc(C(C)(C)C)c(O)c2c1C[C@H]1C[C@H]3CC(O)=C(C(N)=O)C(=O)[C@@]3(O)C(O)=C1C2=O]
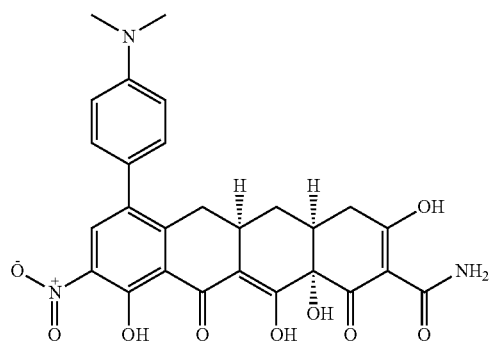
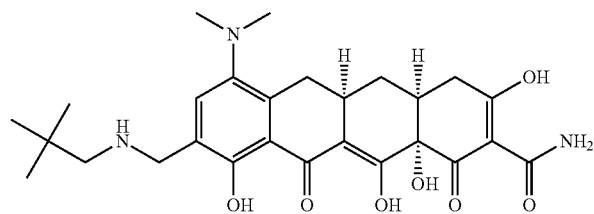 [SMILES: CN(C)c1cc(CNCC(C)(C)C)c(O)c2c1C[C@H]1C[C@H]3CC(O)=C(C(N)=O)C(=O)[C@@]3(O)C(O)=C1C2=O]

TABLE 2-continued
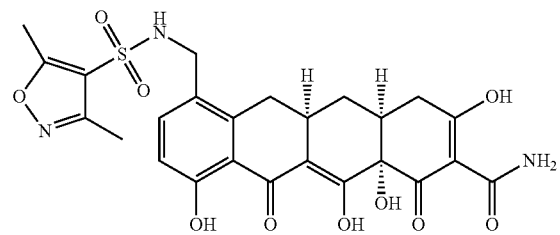 [SMILES: Cc1noc(C)c1S(=O)(=O)NCc1ccc(O)c2c1C[C@H]1C[C@H]3CC(O)=C(C(N)=O)C(=O)[C@@]3(O)C(O)=C1C2=O]
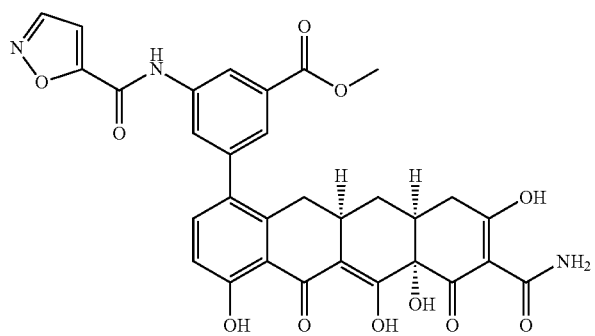 [SMILES: COC(=O)c1cc(NC(=O)c2ccno2)cc(-c2ccc(O)c3c2C[C@H]2C[C@H]4CC(O)=C(C(N)=O)C(=O)[C@@]4(O)C(O)=C2C3=O)c1]
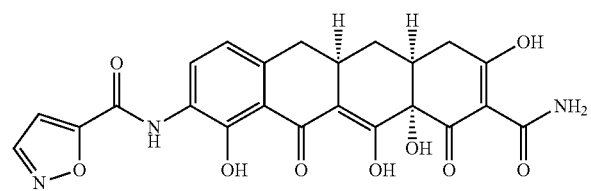 [SMILES: NC(=O)C1=C(O)C[C@@H]2C[C@@H]3Cc4ccc(NC(=O)c5ccno5)c(O)c4C(=O)C3=C(O)[C@]2(O)C1=O]
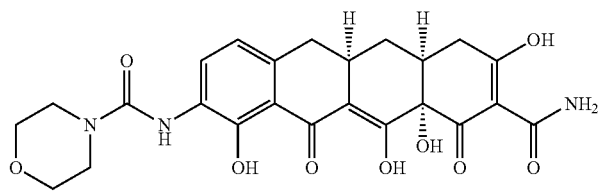 [SMILES: NC(=O)C1=C(O)C[C@@H]2C[C@@H]3Cc4ccc(NC(=O)N5CCOCC5)c(O)c4C(=O)C3=C(O)[C@]2(O)C1=O]
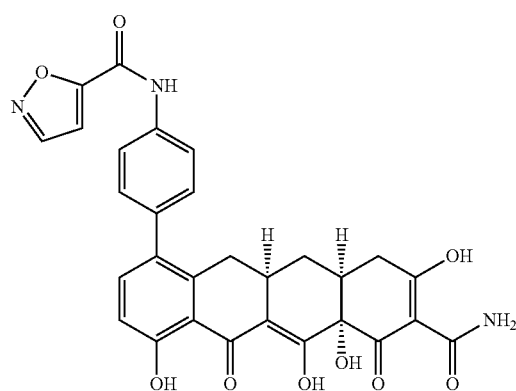 [SMILES: NC(=O)C1=C(O)C[C@@H]2C[C@@H]3Cc4c(-c5ccc(NC(=O)c6ccno6)cc5)ccc(O)c4C(=O)C3=C(O)[C@]2(O)C1=O]
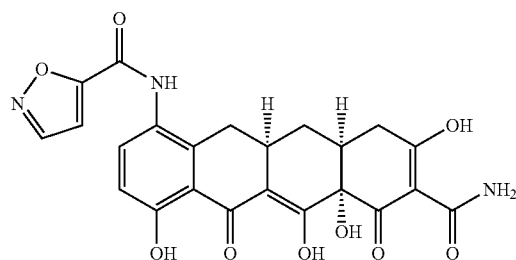 [SMILES: NC(=O)C1=C(O)C[C@@H]2C[C@@H]3Cc4c(NC(=O)c5ccno5)ccc(O)c4C(=O)C3=C(O)[C@]2(O)C1=O]

TABLE 2-continued
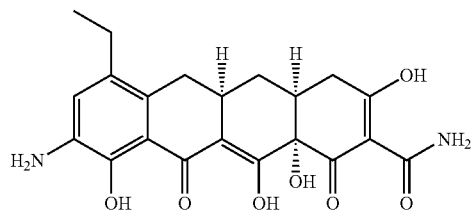 [SMILES: CCc1cc(N)c(O)c2c1C[C@H]1C[C@H]3CC(O)=C(C(N)=O)C(=O)[C@@]3(O)C(O)=C1C2=O]
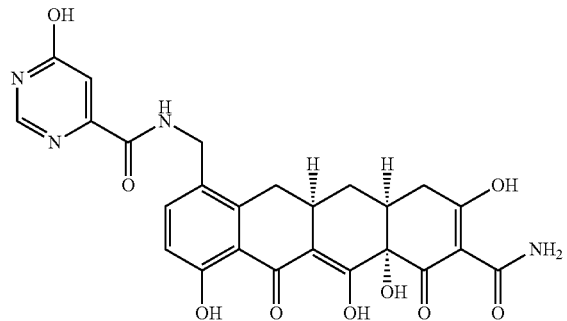 [SMILES: NC(=O)C1=C(O)C[C@@H]2C[C@@H]3Cc4c(CNC(=O)c5cc(O)ncn5)ccc(O)c4C(=O)C3=C(O)[C@]2(O)C1=O]
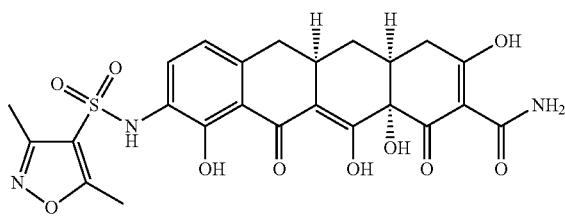 [SMILES: Cc1noc(C)c1S(=O)(=O)Nc1ccc2c(c1O)C(=O)C1=C(O)[C@]3(O)C(=O)C(C(N)=O)=C(O)C[C@@H]3C[C@@H]1C2]
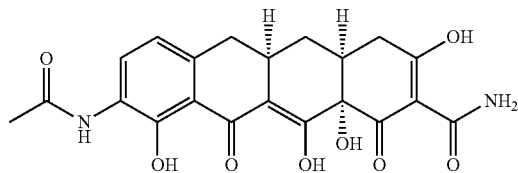 [SMILES: CC(=O)Nc1ccc2c(c1O)C(=O)C1=C(O)[C@]3(O)C(=O)C(C(N)=O)=C(O)C[C@@H]3C[C@@H]1C2]
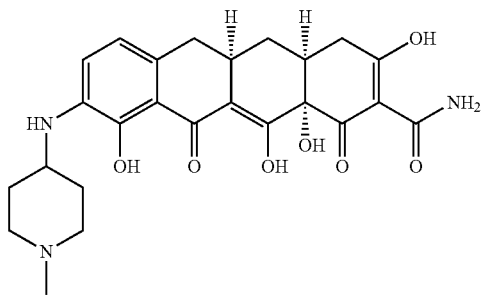 [SMILES: CN1CCC(Nc2ccc3c(c2O)C(=O)C2=C(O)[C@]4(O)C(=O)C(C(N)=O)=C(O)C[C@@H]4C[C@@H]2C3)CC1]
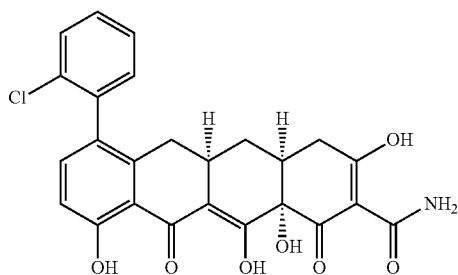 [SMILES: NC(=O)C1=C(O)C[C@@H]2C[C@@H]3Cc4c(-c5ccccc5Cl)ccc(O)c4C(=O)C3=C(O)[C@]2(O)C1=O]

TABLE 2-continued
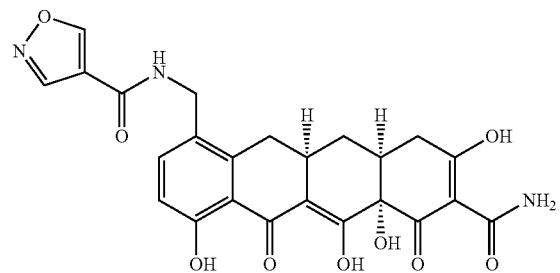 [SMILES: NC(=O)C1=C(O)C[C@@H]2C[C@@H]3Cc4c(CNC(=O)c5cnoc5)ccc(O)c4C(=O)C3=C(O)[C@]2(O)C1=O]
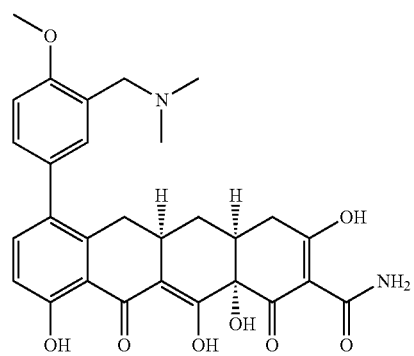 [SMILES: COc1ccc(-c2ccc(O)c3c2C[C@H]2C[C@H]4CC(O)=C(C(N)=O)C(=O)[C@@]4(O)C(O)=C2C3=O)cc1CN(C)C]
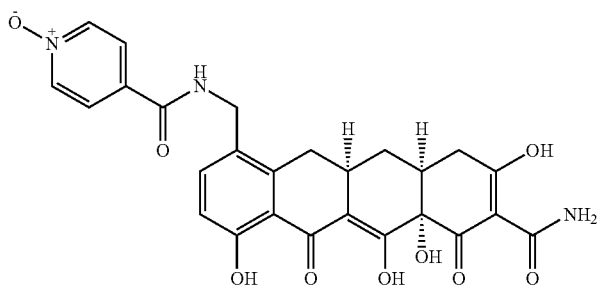
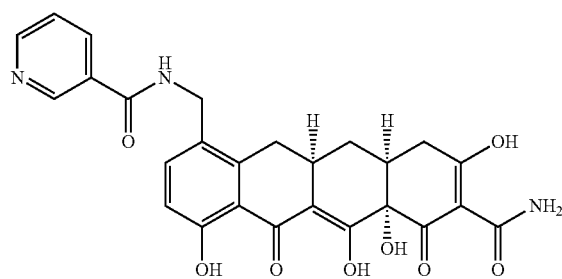 [SMILES: NC(=O)C1=C(O)C[C@@H]2C[C@@H]3Cc4c(CNC(=O)c5cccnc5)ccc(O)c4C(=O)C3=C(O)[C@]2(O)C1=O]
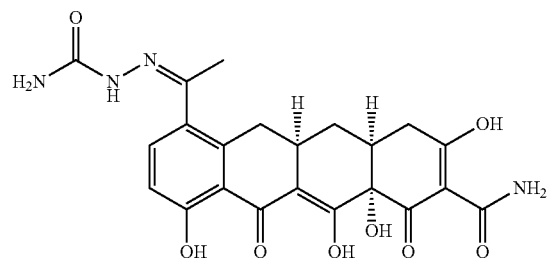 [SMILES: C/C(=N/NC(N)=O)c1ccc(O)c2c1C[C@H]1C[C@H]3CC(O)=C(C(N)=O)C(=O)[C@@]3(O)C(O)=C1C2=O]

TABLE 2-continued
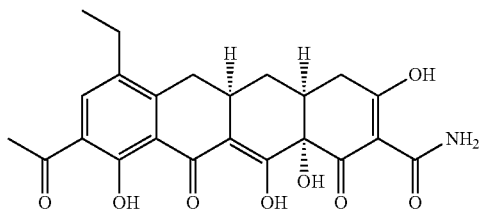 [SMILES: CCc1cc(C(C)=O)c(O)c2c1C[C@H]1C[C@H]3CC(O)=C(C(N)=O)C(=O)[C@@]3(O)C(O)=C1C2=O]
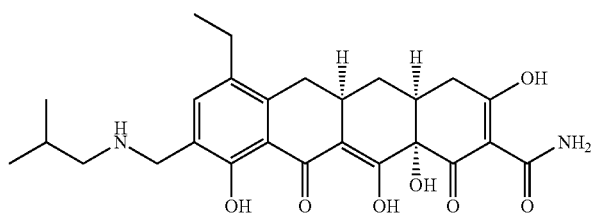 [SMILES: CCc1cc(CNCC(C)C)c(O)c2c1C[C@H]1C[C@H]3CC(O)=C(C(N)=O)C(=O)[C@@]3(O)C(O)=C1C2=O]
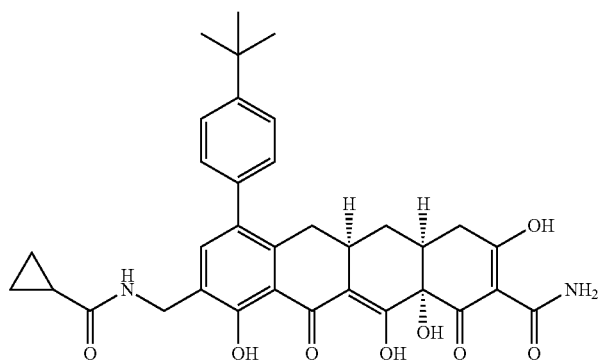 [SMILES: CC(C)(C)c1ccc(-c2cc(CNC(=O)C3CC3)c(O)c3c2C[C@H]2C[C@H]4CC(O)=C(C(N)=O)C(=O)[C@@]4(O)C(O)=C2C3=O)cc1]
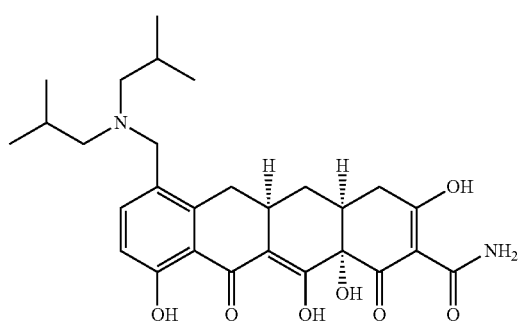 [SMILES: CC(C)CN(Cc1ccc(O)c2c1C[C@H]1C[C@H]3CC(O)=C(C(N)=O)C(=O)[C@@]3(O)C(O)=C1C2=O)CC(C)C]
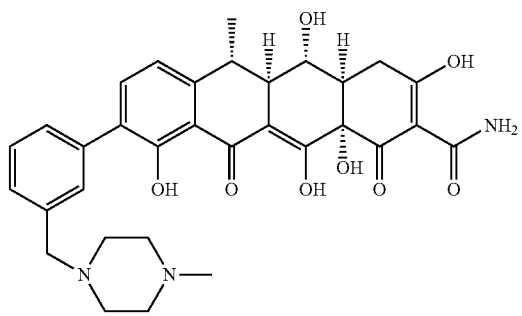 [SMILES: C[C@H]1c2ccc(-c3cccc(CN4CCN(C)CC4)c3)c(O)c2C(=O)C2=C(O)[C@]3(O)C(=O)C(C(N)=O)=C(O)C[C@@H]3[C@@H](O)[C@@H]21]

TABLE 2-continued
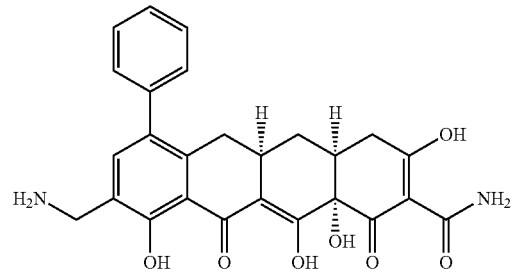 [SMILES: NCc1cc(-c2ccccc2)c2c(c1O)C(=O)C1=C(O)[C@]3(O)C(=O)C(C(N)=O)=C(O)C[C@@H]3C[C@@H]1C2]
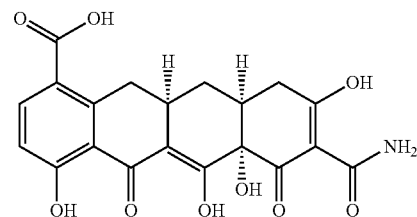 [SMILES: NC(=O)C1=C(O)C[C@@H]2C[C@@H]3Cc4c(C(=O)O)ccc(O)c4C(=O)C3=C(O)[C@]2(O)C1=O]
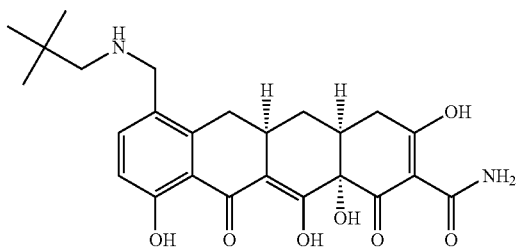 [SMILES: CC(C)(C)CNCc1ccc(O)c2c1C[C@H]1C[C@H]3CC(O)=C(C(N)=O)C(=O)[C@@]3(O)C(O)=C1C2=O]
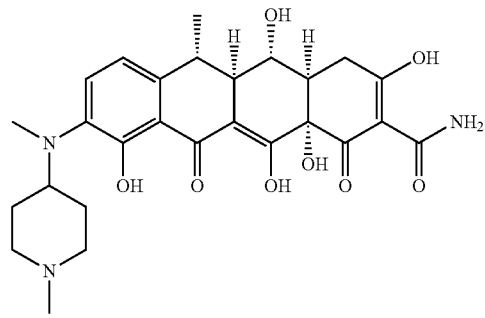 [SMILES: C[C@H]1c2ccc(N(C)C3CCN(C)CC3)c(O)c2C(=O)C2=C(O)[C@]3(O)C(=O)C(C(N)=O)=C(O)C[C@@H]3[C@@H](O)[C@@H]21]
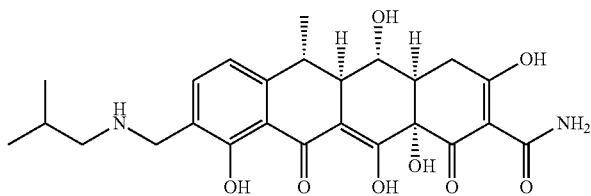 [SMILES: CC(C)CNCc1ccc2c(c1O)C(=O)C1=C(O)[C@]3(O)C(=O)C(C(N)=O)=C(O)C[C@@H]3[C@@H](O)[C@@H]1[C@H]2C]
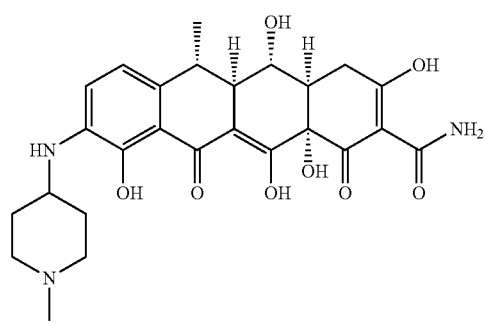 [SMILES: C[C@H]1c2ccc(NC3CCN(C)CC3)c(O)c2C(=O)C2=C(O)[C@]3(O)C(=O)C(C(N)=O)=C(O)C[C@@H]3[C@@H](O)[C@@H]21]

TABLE 2-continued
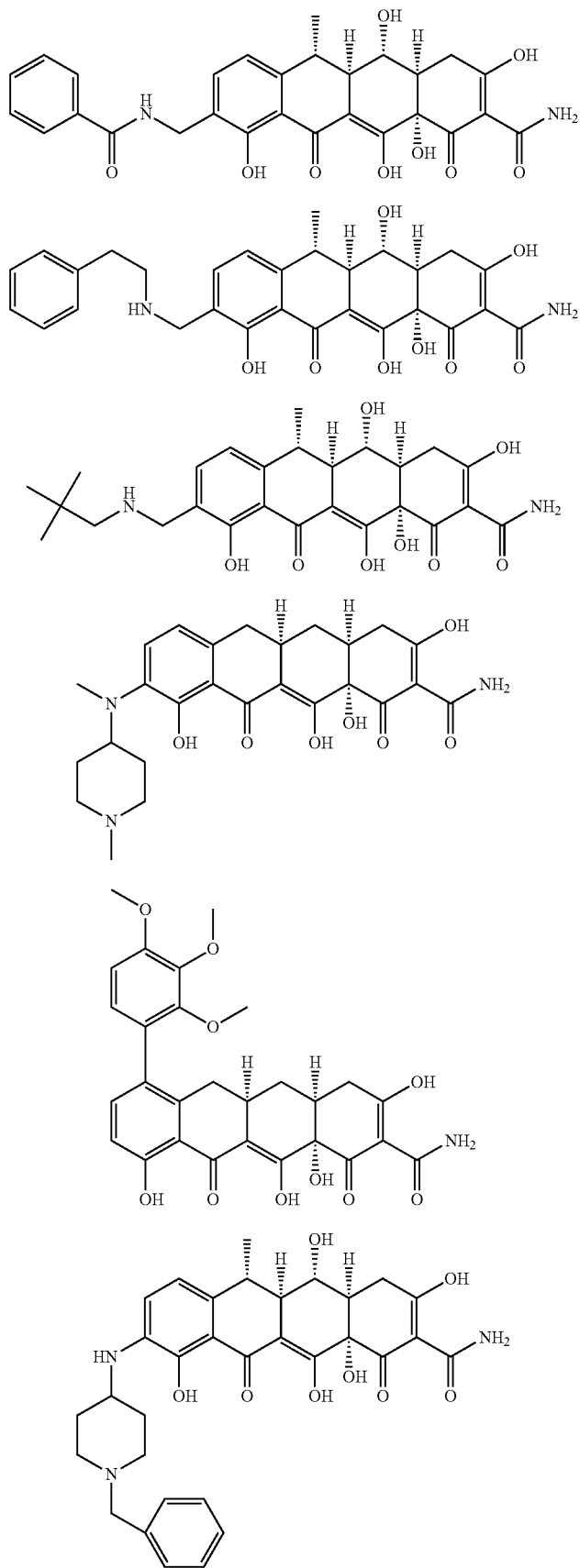

TABLE 2-continued
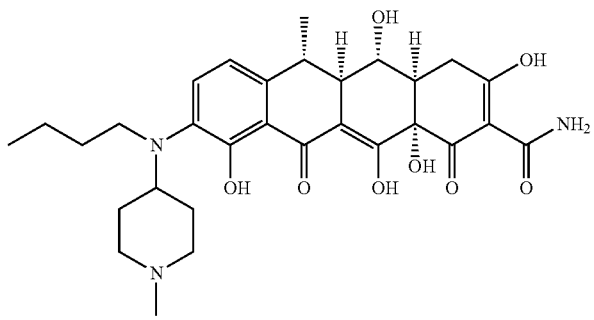 [SMILES: CCCCN(c1ccc2c(c1O)C(=O)C1=C(O)[C@]3(O)C(=O)C(C(N)=O)=C(O)C[C@@H]3[C@@H](O)[C@@H]1[C@H]2C)C1CCN(C)CC1]
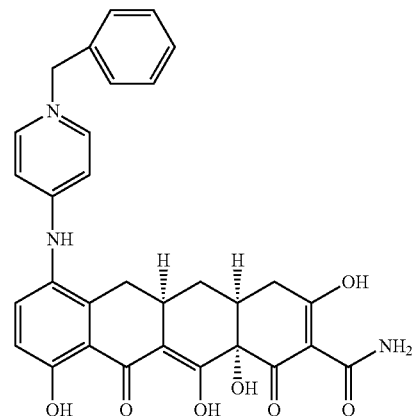
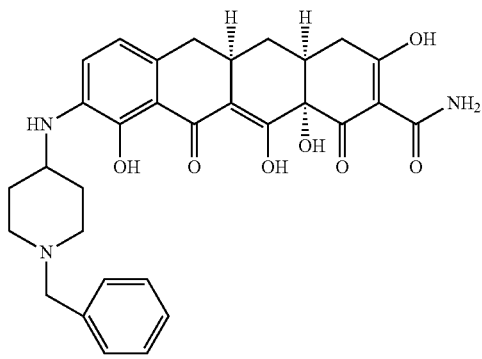 [SMILES: NC(=O)C1=C(O)C[C@@H]2C[C@@H]3Cc4ccc(NC5CCN(Cc6ccccc6)CC5)c(O)c4C(=O)C3=C(O)[C@]2(O)C1=O]
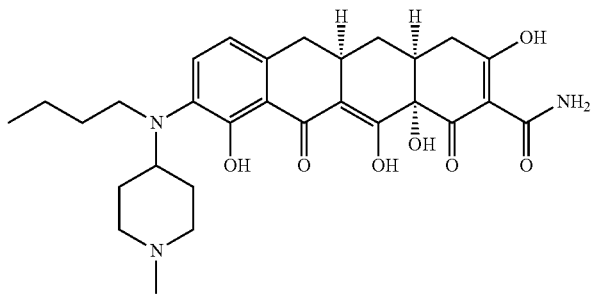 [SMILES: CCCCN(c1ccc2c(c1O)C(=O)C1=C(O)[C@]3(O)C(=O)C(C(N)=O)=C(O)C[C@@H]3C[C@@H]1C2)C1CCN(C)CC1]
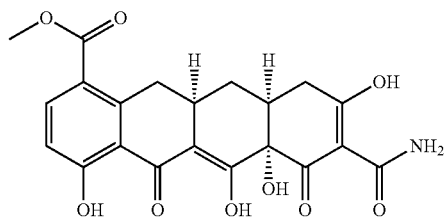 [SMILES: COC(=O)c1ccc(O)c2c1C[C@H]1C[C@H]3CC(O)=C(C(N)=O)C(=O)[C@@]3(O)C(O)=C1C2=O]

TABLE 2-continued
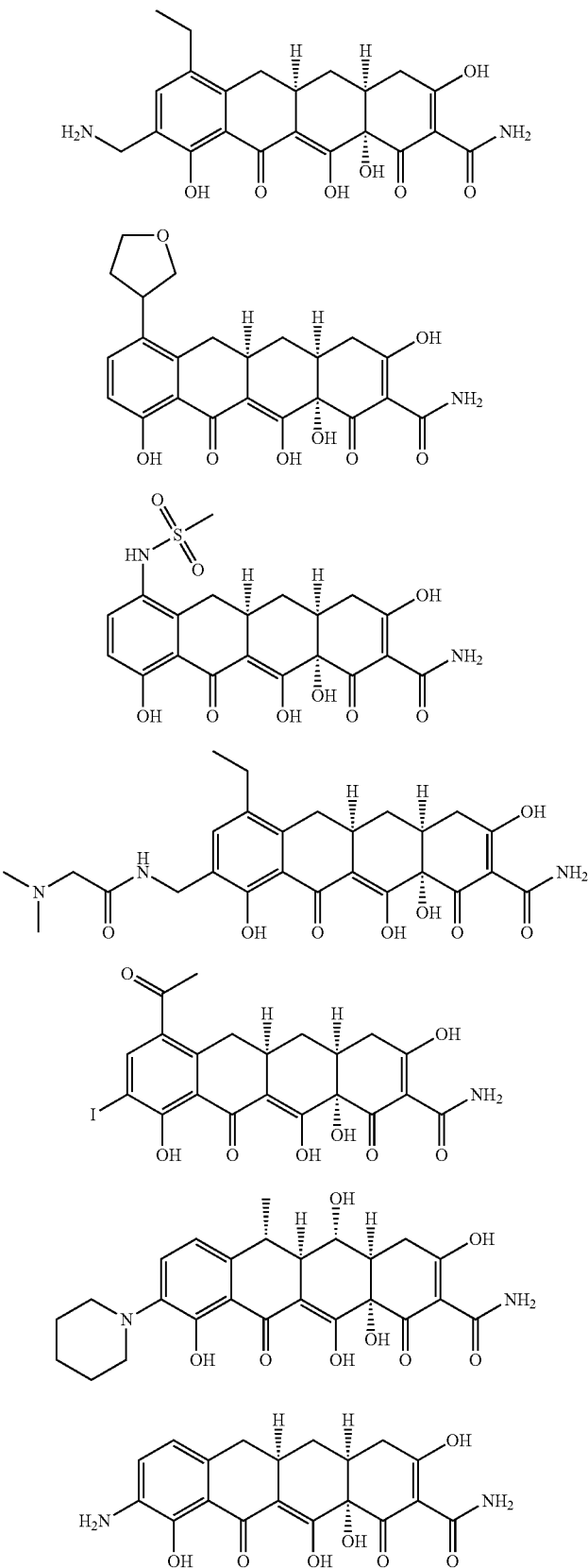

TABLE 2-continued
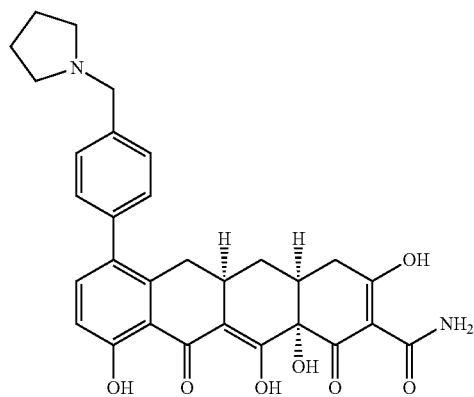 [SMILES: NC(=O)C1=C(O)C[C@@H]2C[C@@H]3Cc4c(-c5ccc(CN6CCCC6)cc5)ccc(O)c4C(=O)C3=C(O)[C@]2(O)C1=O]
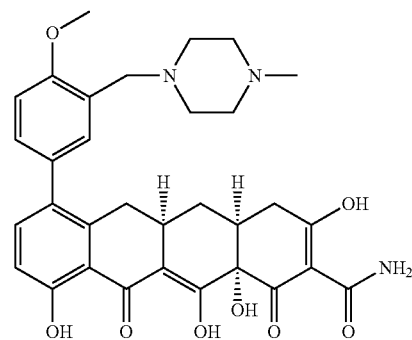 [SMILES: COc1ccc(-c2ccc(O)c3c2C[C@H]2C[C@H]4CC(O)=C(C(N)=O)C(=O)[C@@]4(O)C(O)=C2C3=O)cc1CN1CCN(C)CC1]
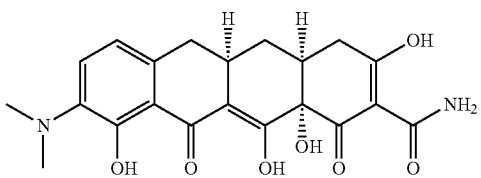 [SMILES: CN(C)c1ccc2c(c1O)C(=O)C1=C(O)[C@]3(O)C(=O)C(C(N)=O)=C(O)C[C@@H]3C[C@@H]1C2]
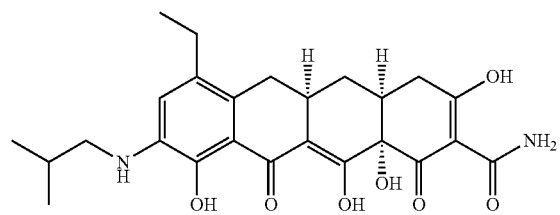 [SMILES: CCc1cc(NCC(C)C)c(O)c2c1C[C@H]1C[C@H]3CC(O)=C(C(N)=O)C(=O)[C@@]3(O)C(O)=C1C2=O]
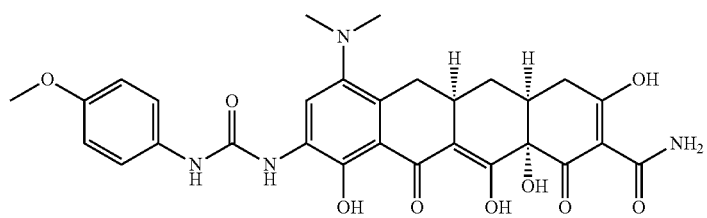 [SMILES: COc1ccc(NC(=O)Nc2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
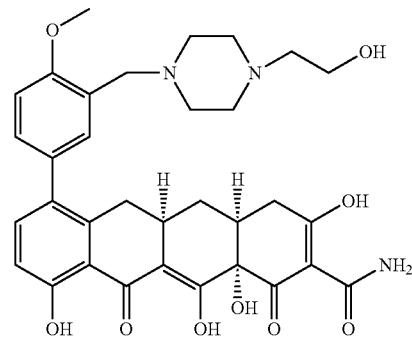 [SMILES: COc1ccc(-c2ccc(O)c3c2C[C@H]2C[C@H]4CC(O)=C(C(N)=O)C(=O)[C@@]4(O)C(O)=C2C3=O)cc1CN1CCN(CCO)CC1]
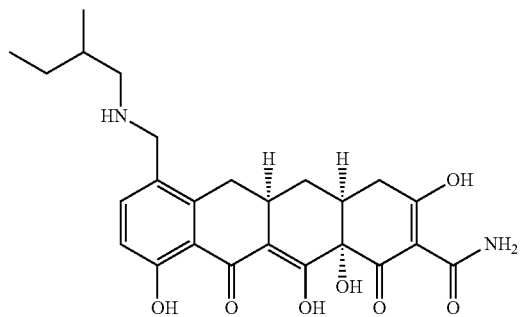 [SMILES: CCC(C)CNCc1ccc(O)c2c1C[C@H]1C[C@H]3CC(O)=C(C(N)=O)C(=O)[C@@]3(O)C(O)=C1C2=O]
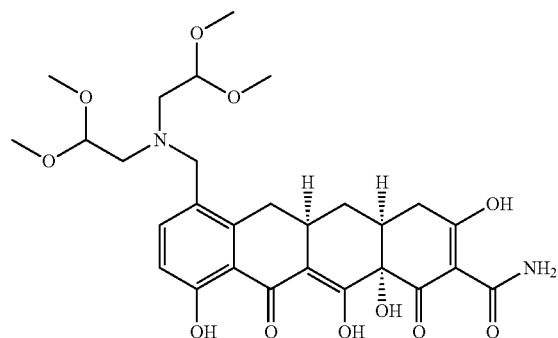 [SMILES: COC(CN(Cc1ccc(O)c2c1C[C@H]1C[C@H]3CC(O)=C(C(N)=O)C(=O)[C@@]3(O)C(O)=C1C2=O)CC(OC)OC)OC]
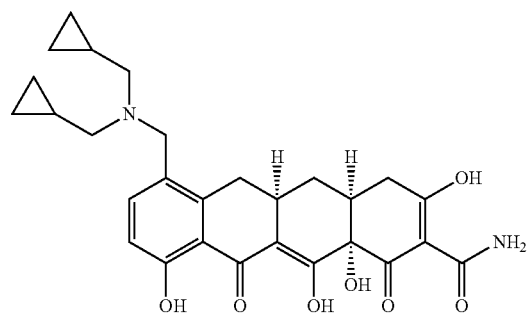 [SMILES: NC(=O)C1=C(O)C[C@@H]2C[C@@H]3Cc4c(CN(CC5CC5)CC5CC5)ccc(O)c4C(=O)C3=C(O)[C@]2(O)C1=O]
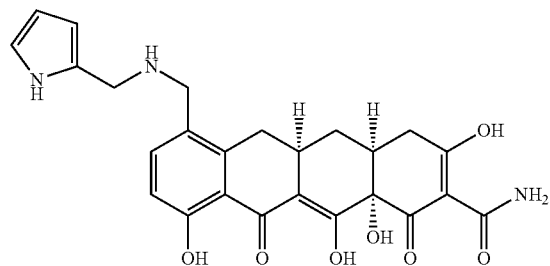 [SMILES: NC(=O)C1=C(O)C[C@@H]2C[C@@H]3Cc4c(CNCc5ccc[nH]5)ccc(O)c4C(=O)C3=C(O)[C@]2(O)C1=O]

TABLE 2-continued
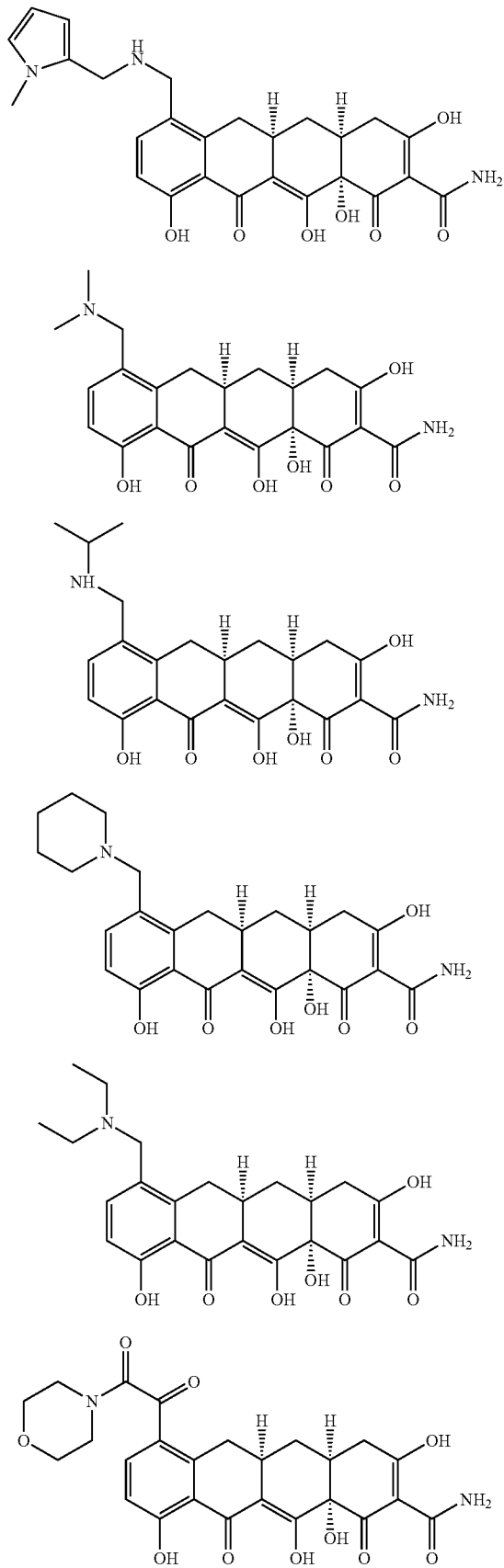

TABLE 2-continued
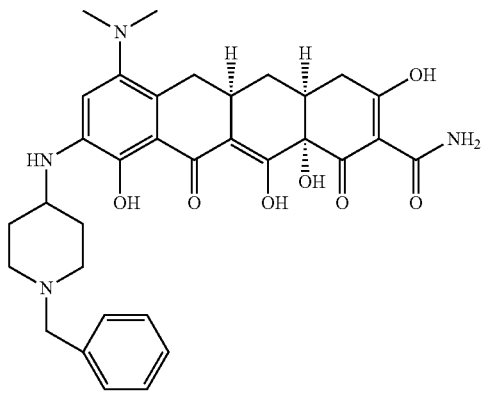 [SMILES: CN(C)c1cc(NC2CCN(Cc3ccccc3)CC2)c(O)c2c1C[C@H]1C[C@H]3CC(O)=C(C(N)=O)C(=O)[C@@]3(O)C(O)=C1C2=O]
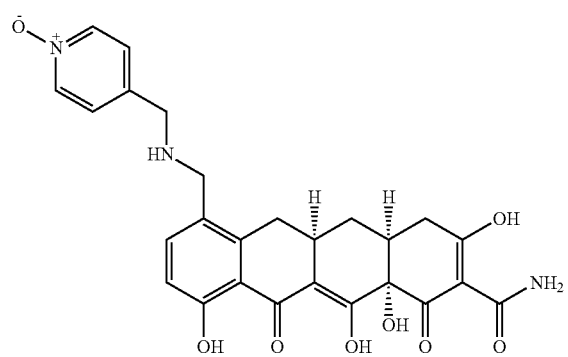
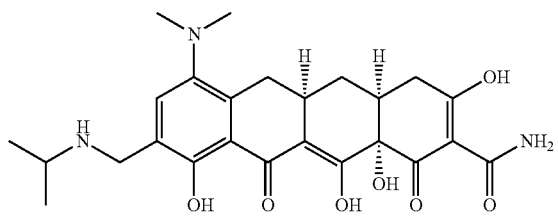
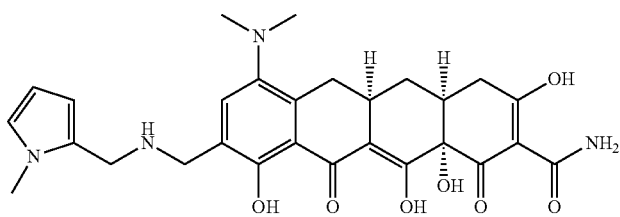 [SMILES: CN(C)c1cc(CNCc2cccn2C)c(O)c2c1C[C@H]1C[C@H]3CC(O)=C(C(N)=O)C(=O)[C@@]3(O)C(O)=C1C2=O]
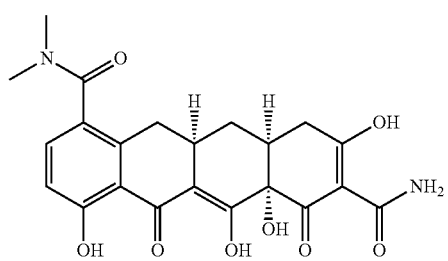 [SMILES: CN(C)C(=O)c1ccc(O)c2c1C[C@H]1C[C@H]3CC(O)=C(C(N)=O)C(=O)[C@@]3(O)C(O)=C1C2=O]

TABLE 2-continued
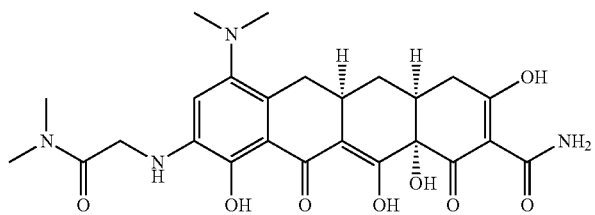 [SMILES: CN(C)C(=O)CNc1cc(N(C)C)c2c(c1O)C(=O)C1=C(O)[C@]3(O)C(=O)C(C(N)=O)=C(O)C[C@@H]3C[C@@H]1C2]
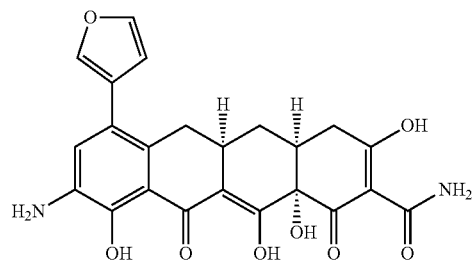 [SMILES: NC(=O)C1=C(O)C[C@@H]2C[C@@H]3Cc4c(-c5ccoc5)cc(N)c(O)c4C(=O)C3=C(O)[C@]2(O)C1=O]
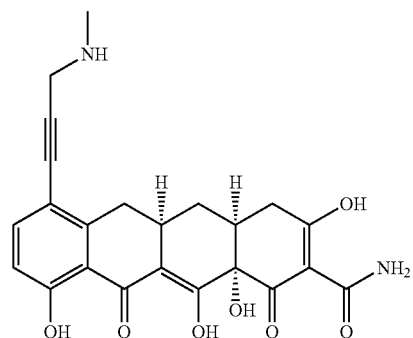 [SMILES: CNCC#Cc1ccc(O)c2c1C[C@H]1C[C@H]3CC(O)=C(C(N)=O)C(=O)[C@@]3(O)C(O)=C1C2=O]
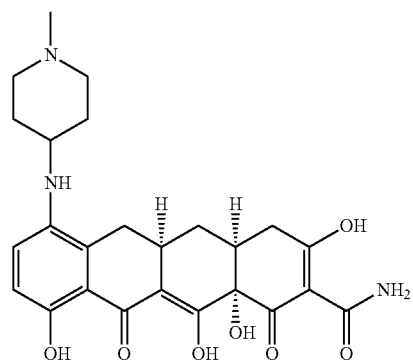 [SMILES: CN1CCC(Nc2ccc(O)c3c2C[C@H]2C[C@H]4CC(O)=C(C(N)=O)C(=O)[C@@]4(O)C(O)=C2C3=O)CC1]
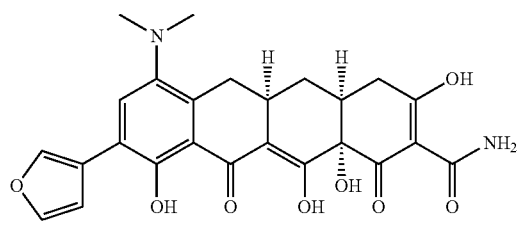 [SMILES: CN(C)c1cc(-c2ccoc2)c(O)c2c1C[C@H]1C[C@H]3CC(O)=C(C(N)=O)C(=O)[C@@]3(O)C(O)=C1C2=O]
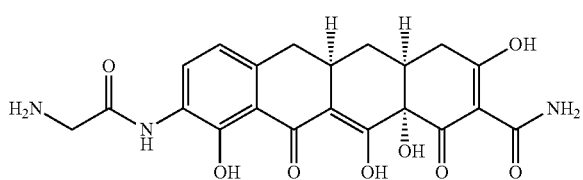 [SMILES: NCC(=O)Nc1ccc2c(c1O)C(=O)C1=C(O)[C@]3(O)C(=O)C(C(N)=O)=C(O)C[C@@H]3C[C@@H]1C2]

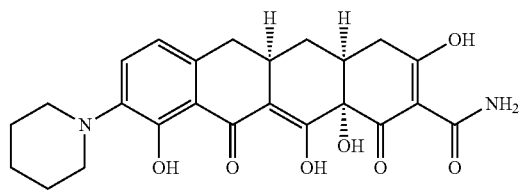 [SMILES: NC(=O)C1=C(O)C[C@@H]2C[C@@H]3Cc4ccc(N5CCCCC5)c(O)c4C(=O)C3=C(O)[C@]2(O)C1=O]
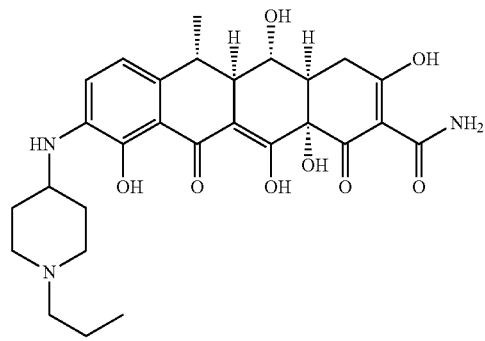 [SMILES: CCCN1CCC(Nc2ccc3c(c2O)C(=O)C2=C(O)[C@]4(O)C(=O)C(C(N)=O)=C(O)C[C@@H]4[C@@H](O)[C@@H]2[C@H]3C)CC1]
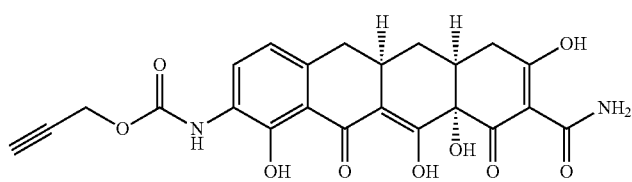 [SMILES: C#CCOC(=O)Nc1ccc2c(c1O)C(=O)C1=C(O)[C@]3(O)C(=O)C(C(N)=O)=C(O)C[C@@H]3C[C@@H]1C2]
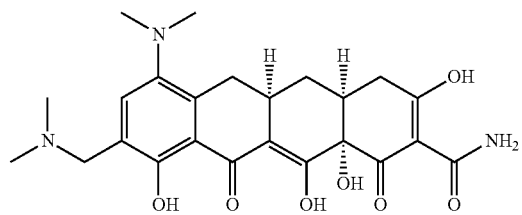
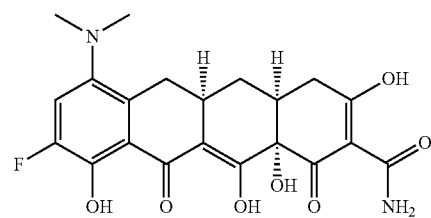 [SMILES: CN(C)c1cc(F)c(O)c2c1C[C@H]1C[C@H]3CC(O)=C(C(N)=O)C(=O)[C@@]3(O)C(O)=C1C2=O]
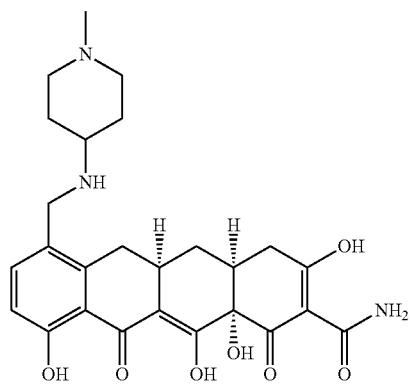 [SMILES: CN1CCC(NCc2ccc(O)c3c2C[C@H]2C[C@H]4CC(O)=C(C(N)=O)C(=O)[C@@]4(O)C(O)=C2C3=O)CC1]

TABLE 2-continued
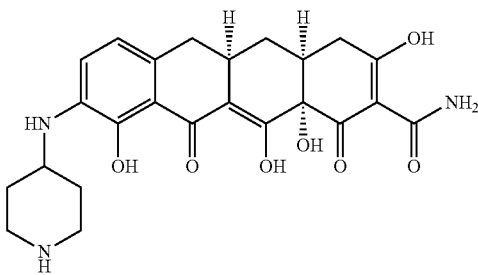 [SMILES: NC(=O)C1=C(O)C[C@@H]2C[C@@H]3Cc4ccc(NC5CCNCC5)c(O)c4C(=O)C3=C(O)[C@]2(O)C1=O]
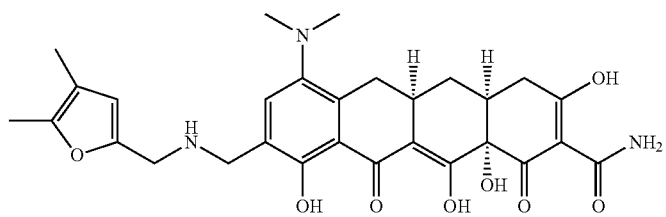 [SMILES: Cc1cc(CNCc2cc(N(C)C)c3c(c2O)C(=O)C2=C(O)[C@]4(O)C(=O)C(C(N)=O)=C(O)C[C@@H]4C[C@@H]2C3)oc1C]
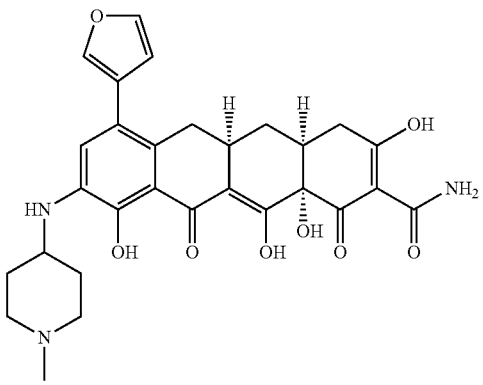 [SMILES: CN1CCC(Nc2cc(-c3ccoc3)c3c(c2O)C(=O)C2=C(O)[C@]4(O)C(=O)C(C(N)=O)=C(O)C[C@@H]4C[C@@H]2C3)CC1]
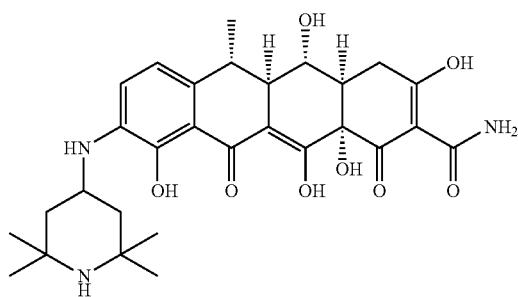 [SMILES: C[C@H]1c2ccc(NC3CC(C)(C)NC(C)(C)C3)c(O)c2C(=O)C2=C(O)[C@]3(O)C(=O)C(C(N)=O)=C(O)C[C@@H]3[C@@H](O)[C@@H]21]
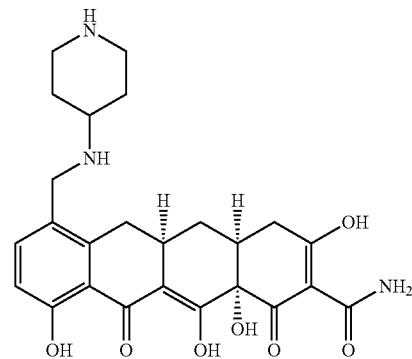 [SMILES: NC(=O)C1=C(O)C[C@@H]2C[C@@H]3Cc4c(CNC5CCNCC5)ccc(O)c4C(=O)C3=C(O)[C@]2(O)C1=O]

TABLE 2-continued
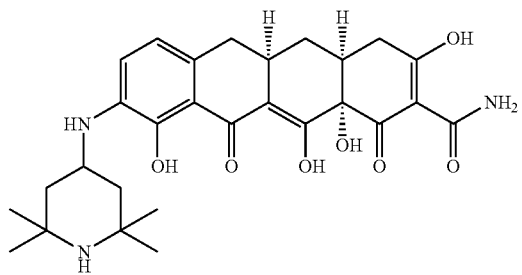 [SMILES: CC1(C)CC(Nc2ccc3c(c2O)C(=O)C2=C(O)[C@]4(O)C(=O)C(C(N)=O)=C(O)C[C@@H]4C[C@@H]2C3)CC(C)(C)N1]
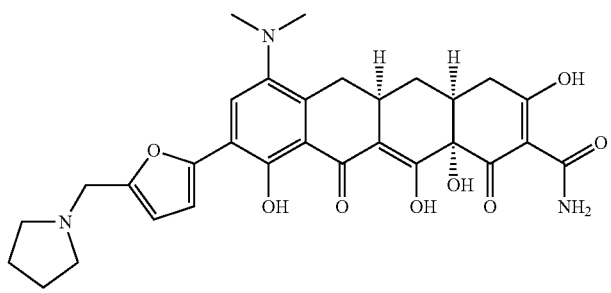 [SMILES: CN(C)c1cc(-c2ccc(CN3CCCC3)o2)c(O)c2c1C[C@H]1C[C@H]3CC(O)=C(C(N)=O)C(=O)[C@@]3(O)C(O)=C1C2=O]
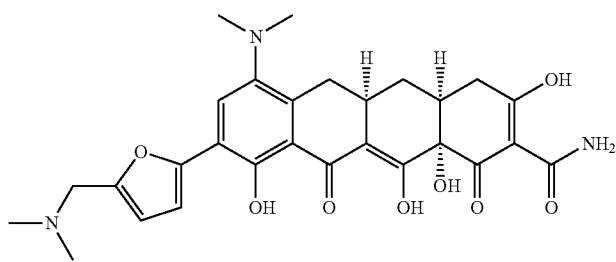 [SMILES: CN(C)Cc1ccc(-c2cc(N(C)C)c3c(c2O)C(=O)C2=C(O)[C@]4(O)C(=O)C(C(N)=O)=C(O)C[C@@H]4C[C@@H]2C3)o1]
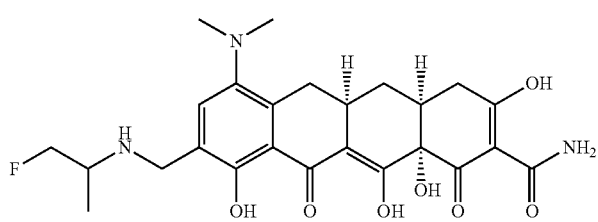 [SMILES: CC(CF)NCc1cc(N(C)C)c2c(c1O)C(=O)C1=C(O)[C@]3(O)C(=O)C(C(N)=O)=C(O)C[C@@H]3C[C@@H]1C2]
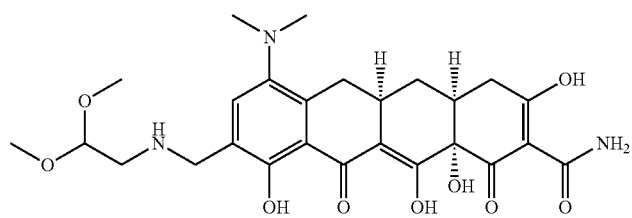 [SMILES: COC(CNCc1cc(N(C)C)c2c(c1O)C(=O)C1=C(O)[C@]3(O)C(=O)C(C(N)=O)=C(O)C[C@@H]3C[C@@H]1C2)OC]

TABLE 2-continued
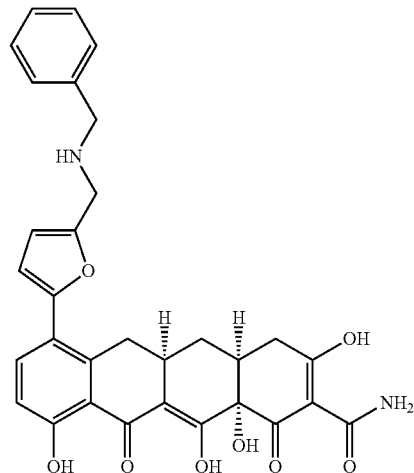 [SMILES: NC(=O)C1=C(O)C[C@@H]2C[C@@H]3Cc4c(-c5ccc(CNCc6ccccc6)o5)ccc(O)c4C(=O)C3=C(O)[C@]2(O)C1=O]
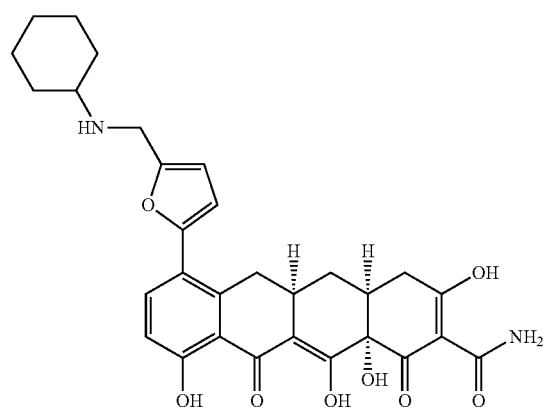 [SMILES: NC(=O)C1=C(O)C[C@@H]2C[C@@H]3Cc4c(-c5ccc(CNC6CCCCC6)o5)ccc(O)c4C(=O)C3=C(O)[C@]2(O)C1=O]
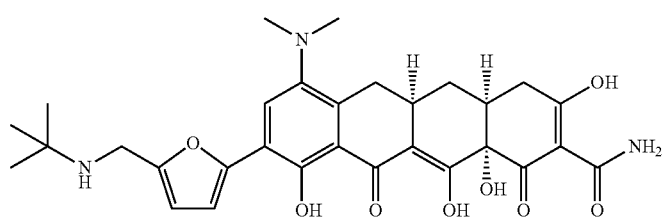 [SMILES: CN(C)c1cc(-c2ccc(CNC(C)(C)C)o2)c(O)c2c1C[C@H]1C[C@H]3CC(O)=C(C(N)=O)C(=O)[C@@]3(O)C(O)=C1C2=O]
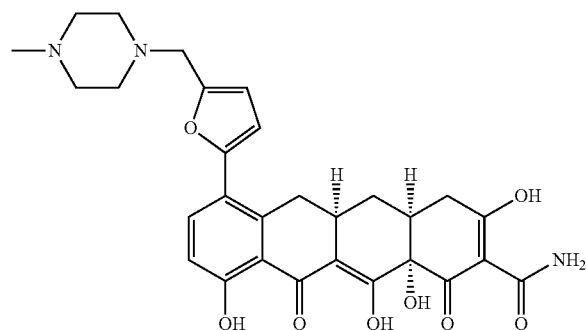 [SMILES: CN1CCN(Cc2ccc(-c3ccc(O)c4c3C[C@H]3C[C@H]5CC(O)=C(C(N)=O)C(=O)[C@@]5(O)C(O)=C3C4=O)o2)CC1]

TABLE 2-continued
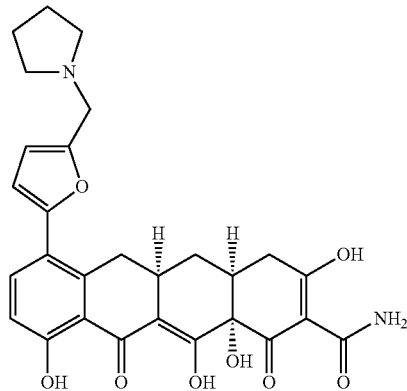 [SMILES: NC(=O)C1=C(O)C[C@@H]2C[C@@H]3Cc4c(-c5ccc(CN6CCCC6)o5)ccc(O)c4C(=O)C3=C(O)[C@]2(O)C1=O]
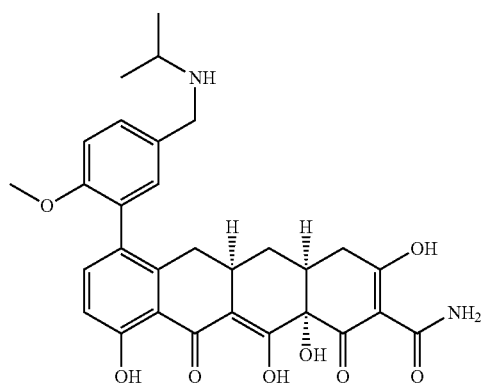 [SMILES: COc1ccc(CNC(C)C)cc1-c1ccc(O)c2c1C[C@H]1C[C@H]3CC(O)=C(C(N)=O)C(=O)[C@@]3(O)C(O)=C1C2=O]
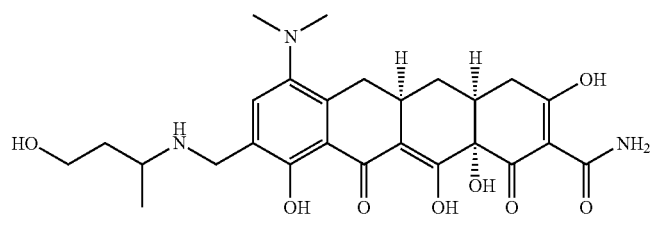 [SMILES: CC(CCO)NCc1cc(N(C)C)c2c(c1O)C(=O)C1=C(O)[C@]3(O)C(=O)C(C(N)=O)=C(O)C[C@@H]3C[C@@H]1C2]
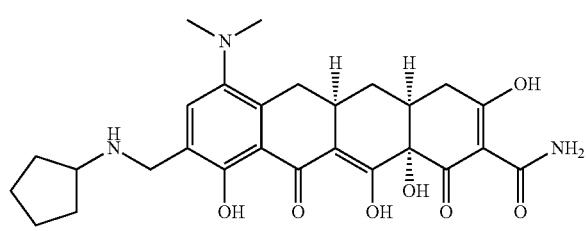 [SMILES: CN(C)c1cc(CNC2CCCC2)c(O)c2c1C[C@H]1C[C@H]3CC(O)=C(C(N)=O)C(=O)[C@@]3(O)C(O)=C1C2=O]
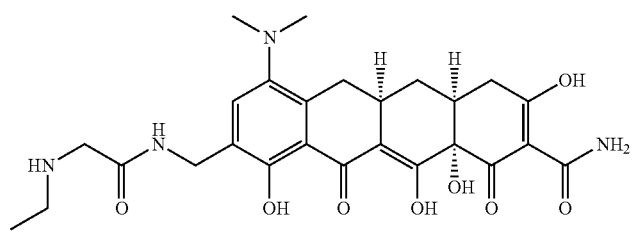 [SMILES: CCNCC(=O)NCc1cc(N(C)C)c2c(c1O)C(=O)C1=C(O)[C@]3(O)C(=O)C(C(N)=O)=C(O)C[C@@H]3C[C@@H]1C2]

TABLE 2-continued
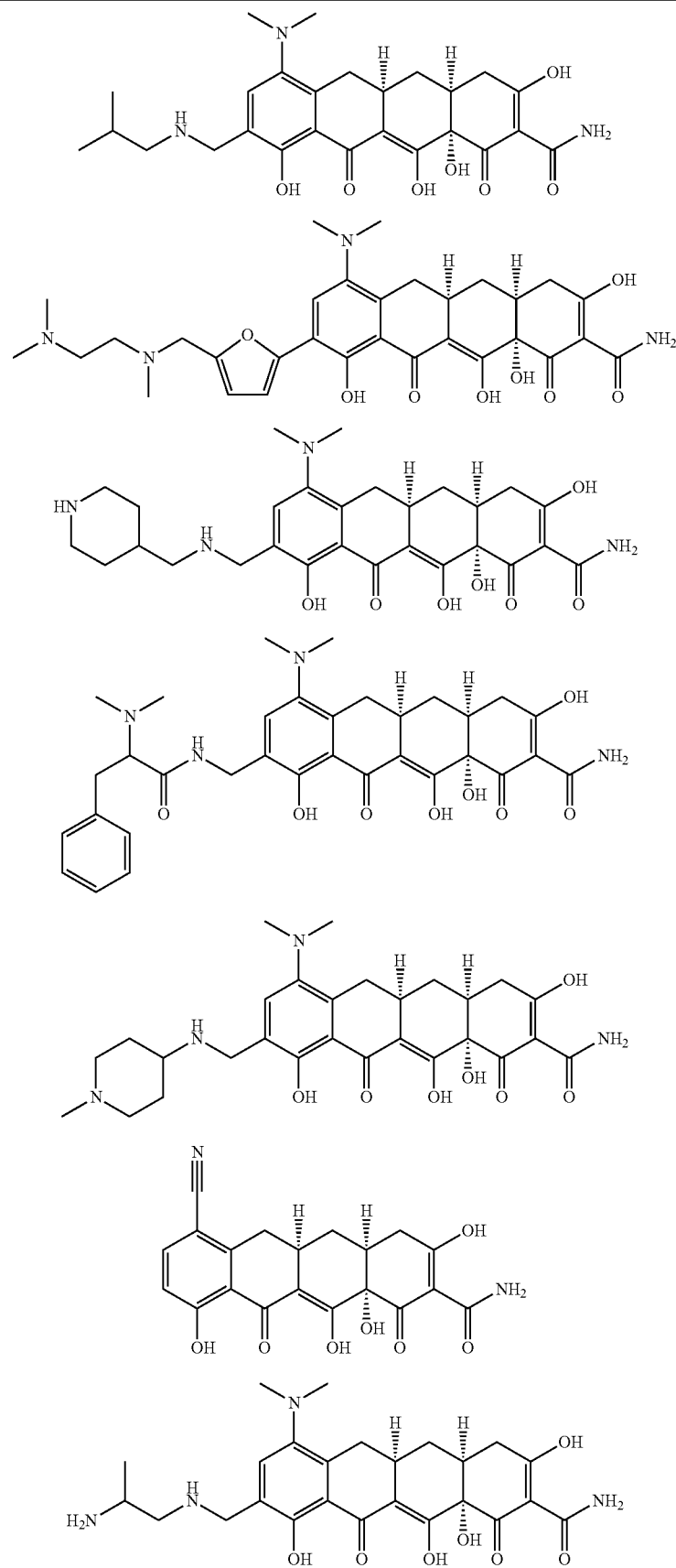

TABLE 2-continued
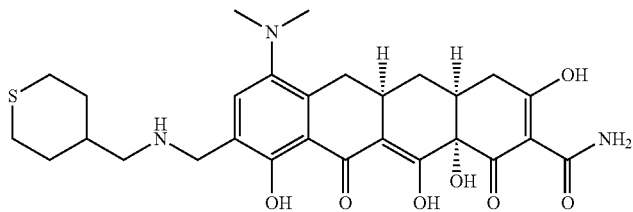 [SMILES: CN(C)c1cc(CNCC2CCSCC2)c(O)c2c1C[C@H]1C[C@H]3CC(O)=C(C(N)=O)C(=O)[C@@]3(O)C(O)=C1C2=O]
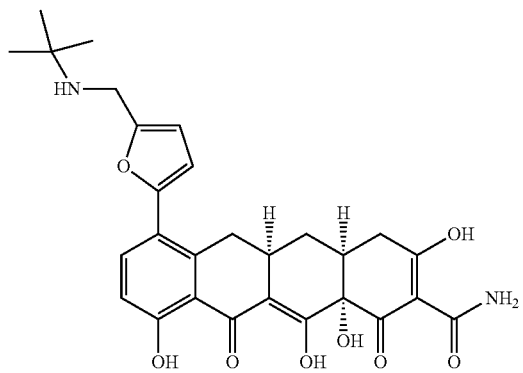 [SMILES: CC(C)(C)NCc1ccc(-c2ccc(O)c3c2C[C@H]2C[C@H]4CC(O)=C(C(N)=O)C(=O)[C@@]4(O)C(O)=C2C3=O)o1]
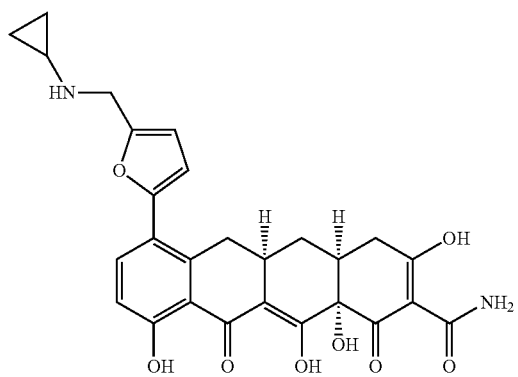 [SMILES: NC(=O)C1=C(O)C[C@@H]2C[C@@H]3Cc4c(-c5ccc(CNC6CC6)o5)ccc(O)c4C(=O)C3=C(O)[C@]2(O)C1=O]
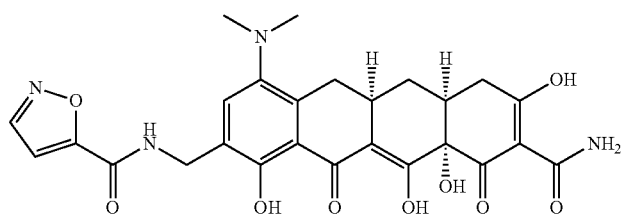 [SMILES: CN(C)c1cc(CNC(=O)c2ccno2)c(O)c2c1C[C@H]1C[C@H]3CC(O)=C(C(N)=O)C(=O)[C@@]3(O)C(O)=C1C2=O]
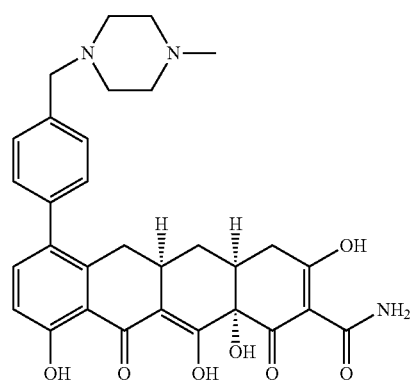 [SMILES: CN1CCN(Cc2ccc(-c3ccc(O)c4c3C[C@H]3C[C@H]5CC(O)=C(C(N)=O)C(=O)[C@@]5(O)C(O)=C3C4=O)cc2)CC1]

TABLE 2-continued
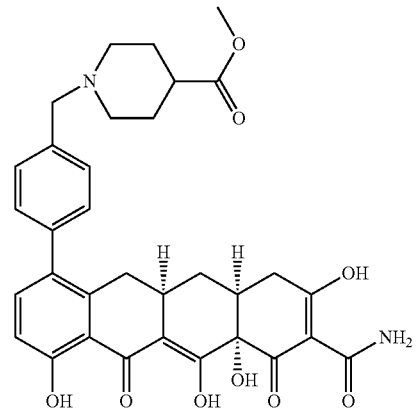 [SMILES: COC(=O)C1CCN(Cc2ccc(-c3ccc(O)c4c3C[C@H]3C[C@H]5CC(O)=C(C(N)=O)C(=O)[C@@]5(O)C(O)=C3C4=O)cc2)CC1]
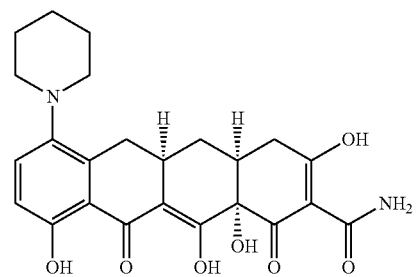 [SMILES: NC(=O)C1=C(O)C[C@@H]2C[C@@H]3Cc4c(N5CCCCC5)ccc(O)c4C(=O)C3=C(O)[C@]2(O)C1=O]
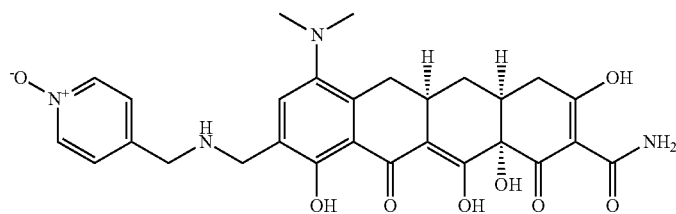
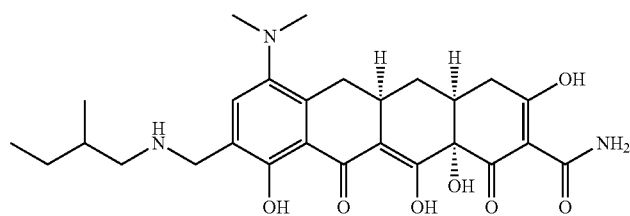
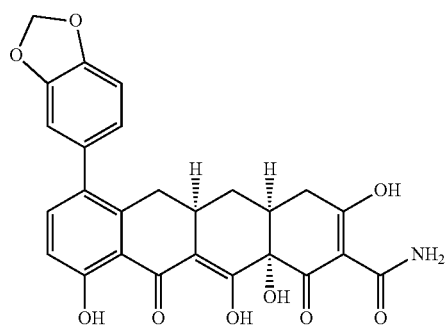 [SMILES: NC(=O)C1=C(O)C[C@@H]2C[C@@H]3Cc4c(-c5ccc6c(c5)OCO6)ccc(O)c4C(=O)C3=C(O)[C@]2(O)C1=O]

TABLE 2-continued
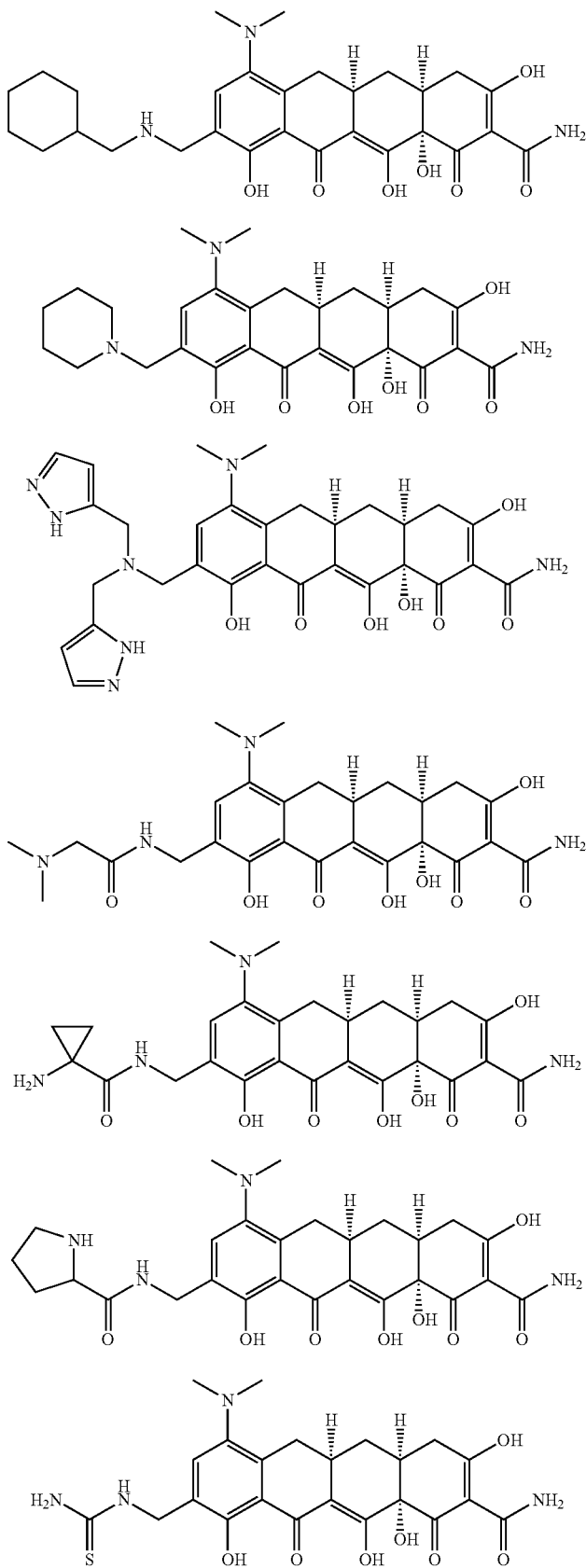

TABLE 2-continued
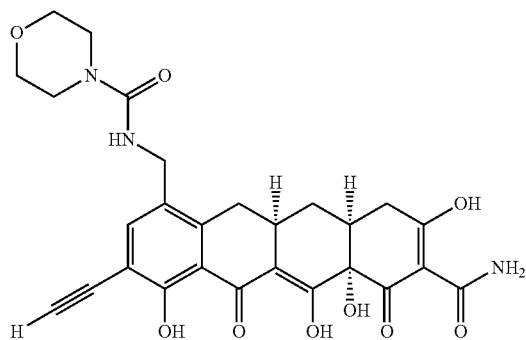 [SMILES: C#Cc1cc(CNC(=O)N2CCOCC2)c2c(c1O)C(=O)C1=C(O)[C@]3(O)C(=O)C(C(N)=O)=C(O)C[C@@H]3C[C@@H]1C2]
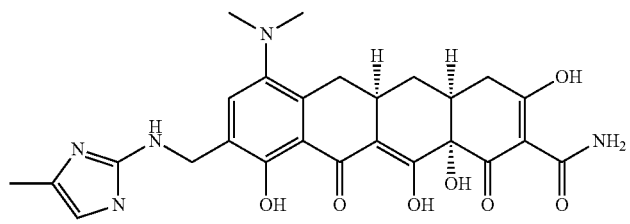 [SMILES: Cc1c[nH]c(NCc2cc(N(C)C)c3c(c2O)C(=O)C2=C(O)[C@]4(O)C(=O)C(C(N)=O)=C(O)C[C@@H]4C[C@@H]2C3)n1]
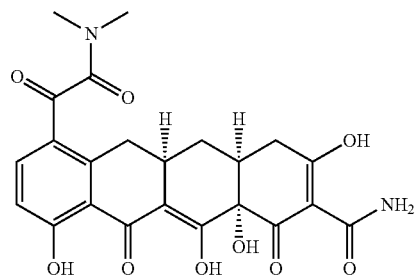 [SMILES: CN(C)C(=O)C(=O)c1ccc(O)c2c1C[C@H]1C[C@H]3CC(O)=C(C(N)=O)C(=O)[C@@]3(O)C(O)=C1C2=O]
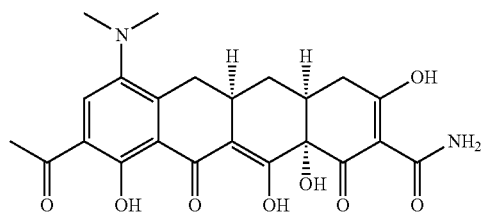 [SMILES: CC(=O)c1cc(N(C)C)c2c(c1O)C(=O)C1=C(O)[C@]3(O)C(=O)C(C(N)=O)=C(O)C[C@@H]3C[C@@H]1C2]
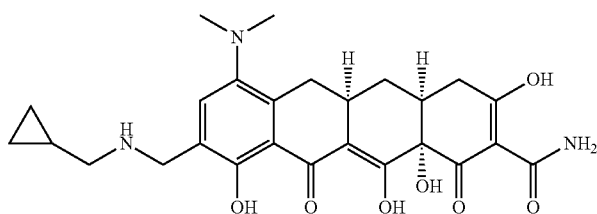 [SMILES: CN(C)c1cc(CNCC2CC2)c(O)c2c1C[C@H]1C[C@H]3CC(O)=C(C(N)=O)C(=O)[C@@]3(O)C(O)=C1C2=O]
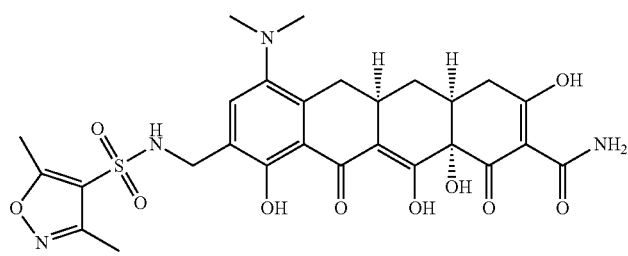 [SMILES: Cc1noc(C)c1S(=O)(=O)NCc1cc(N(C)C)c2c(c1O)C(=O)C1=C(O)[C@]3(O)C(=O)C(C(N)=O)=C(O)C[C@@H]3C[C@@H]1C2]

TABLE 2-continued
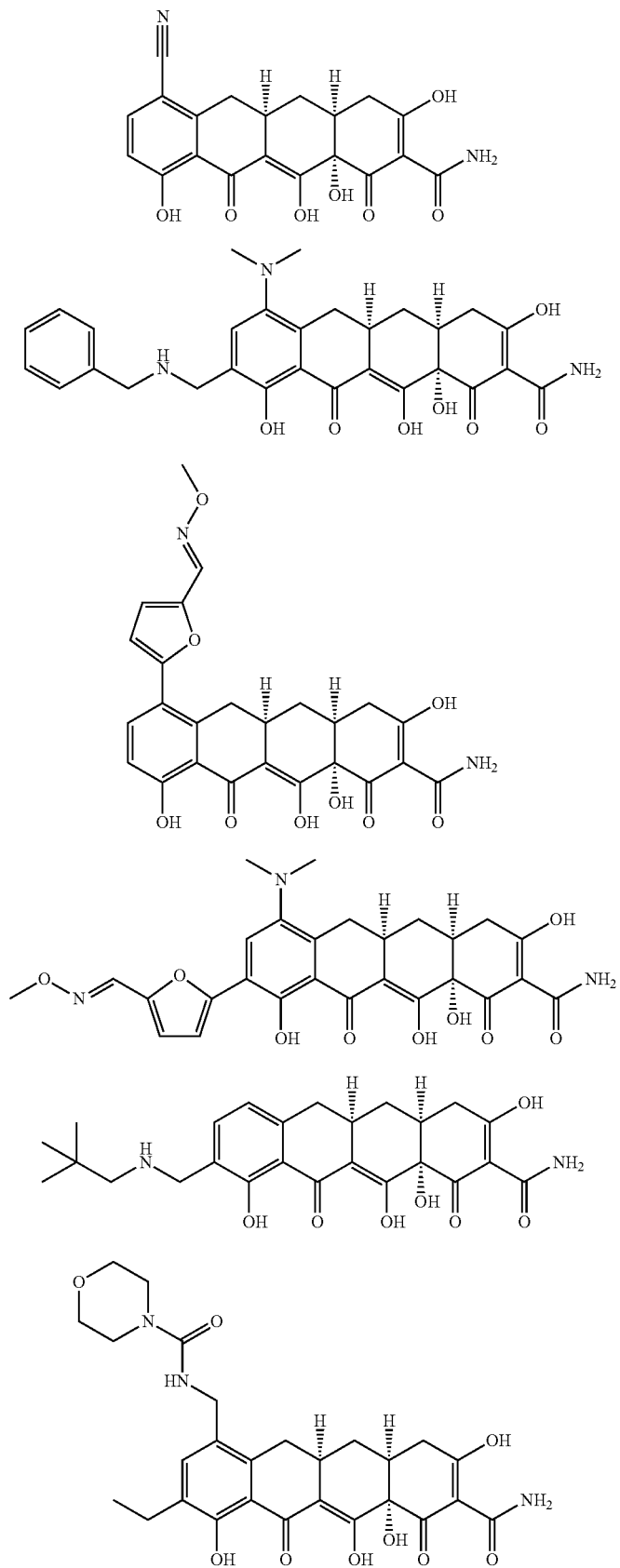

TABLE 2-continued
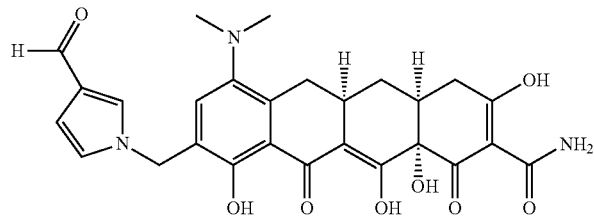 [SMILES: CN(C)c1cc(Cn2ccc(C=O)c2)c(O)c2c1C[C@H]1C[C@H]3CC(O)=C(C(N)=O)C(=O)[C@@]3(O)C(O)=C1C2=O]
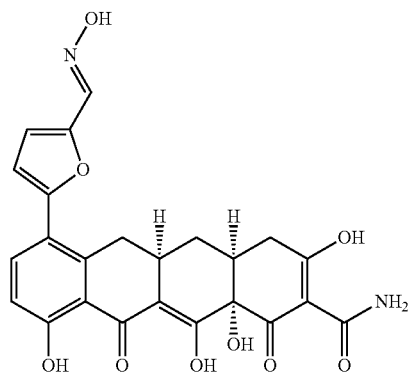 [SMILES: NC(=O)C1=C(O)C[C@@H]2C[C@@H]3Cc4c(-c5ccc(/C=N/O)o5)ccc(O)c4C(=O)C3=C(O)[C@]2(O)C1=O]
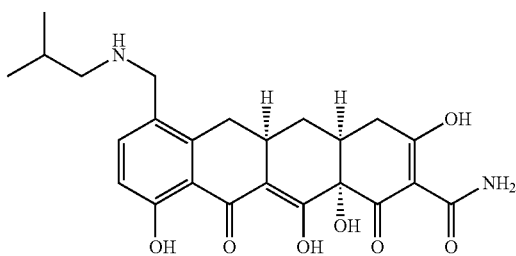 [SMILES: CC(C)CNCc1ccc(O)c2c1C[C@H]1C[C@H]3CC(O)=C(C(N)=O)C(=O)[C@@]3(O)C(O)=C1C2=O]
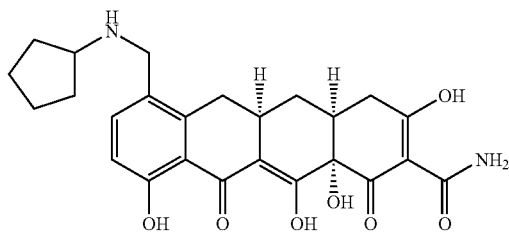 [SMILES: NC(=O)C1=C(O)C[C@@H]2C[C@@H]3Cc4c(CNC5CCCC5)ccc(O)c4C(=O)C3=C(O)[C@]2(O)C1=O]
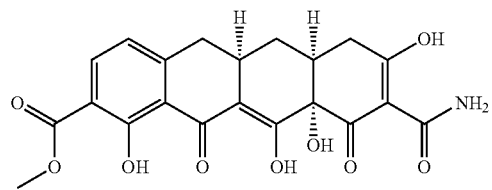 [SMILES: COC(=O)c1ccc2c(c1O)C(=O)C1=C(O)[C@]3(O)C(=O)C(C(N)=O)=C(O)C[C@@H]3C[C@@H]1C2]
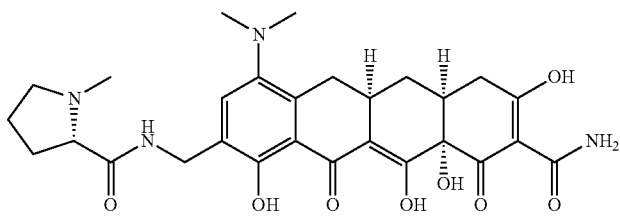 [SMILES: CN(C)c1cc(CNC(=O)[C@@H]2CCCN2C)c(O)c2c1C[C@H]1C[C@H]3CC(O)=C(C(N)=O)C(=O)[C@@]3(O)C(O)=C1C2=O]

TABLE 2-continued
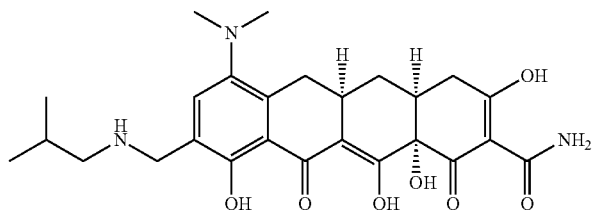 [SMILES: CC(C)CNCc1cc(N(C)C)c2c(c1O)C(=O)C1=C(O)[C@]3(O)C(=O)C(C(N)=O)=C(O)C[C@@H]3C[C@@H]1C2]
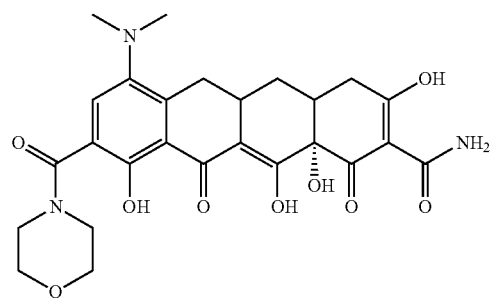 [SMILES: CN(C)c1cc(C(=O)N2CCOCC2)c(O)c2c1CC1CC3CC(O)=C(C(N)=O)C(=O)[C@@]3(O)C(O)=C1C2=O]
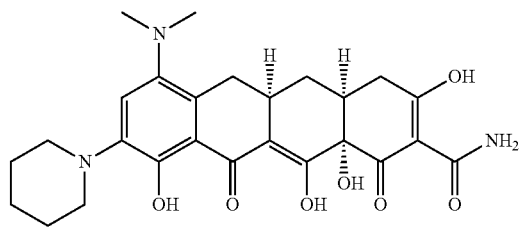 [SMILES: CN(C)c1cc(N2CCCCC2)c(O)c2c1C[C@H]1C[C@H]3CC(O)=C(C(N)=O)C(=O)[C@@]3(O)C(O)=C1C2=O]
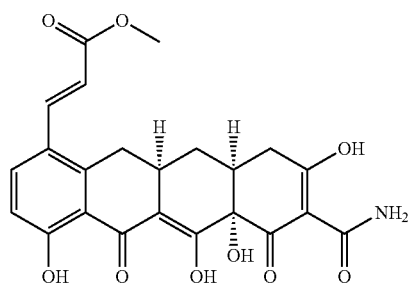 [SMILES: COC(=O)/C=C/c1ccc(O)c2c1C[C@H]1C[C@H]3CC(O)=C(C(N)=O)C(=O)[C@@]3(O)C(O)=C1C2=O]
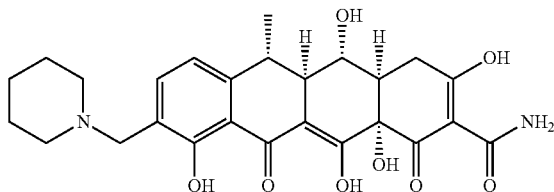 [SMILES: C[C@H]1c2ccc(CN3CCCCC3)c(O)c2C(=O)C2=C(O)[C@]3(O)C(=O)C(C(N)=O)=C(O)C[C@@H]3[C@@H](O)[C@@H]21]
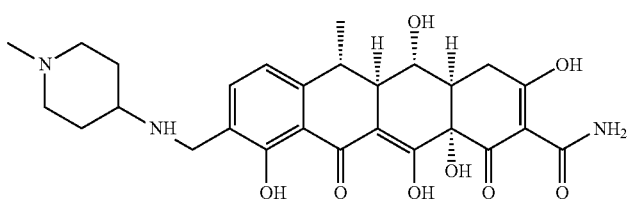 [SMILES: C[C@H]1c2ccc(CNC3CCN(C)CC3)c(O)c2C(=O)C2=C(O)[C@]3(O)C(=O)C(C(N)=O)=C(O)C[C@@H]3[C@@H](O)[C@@H]21]

TABLE 2-continued
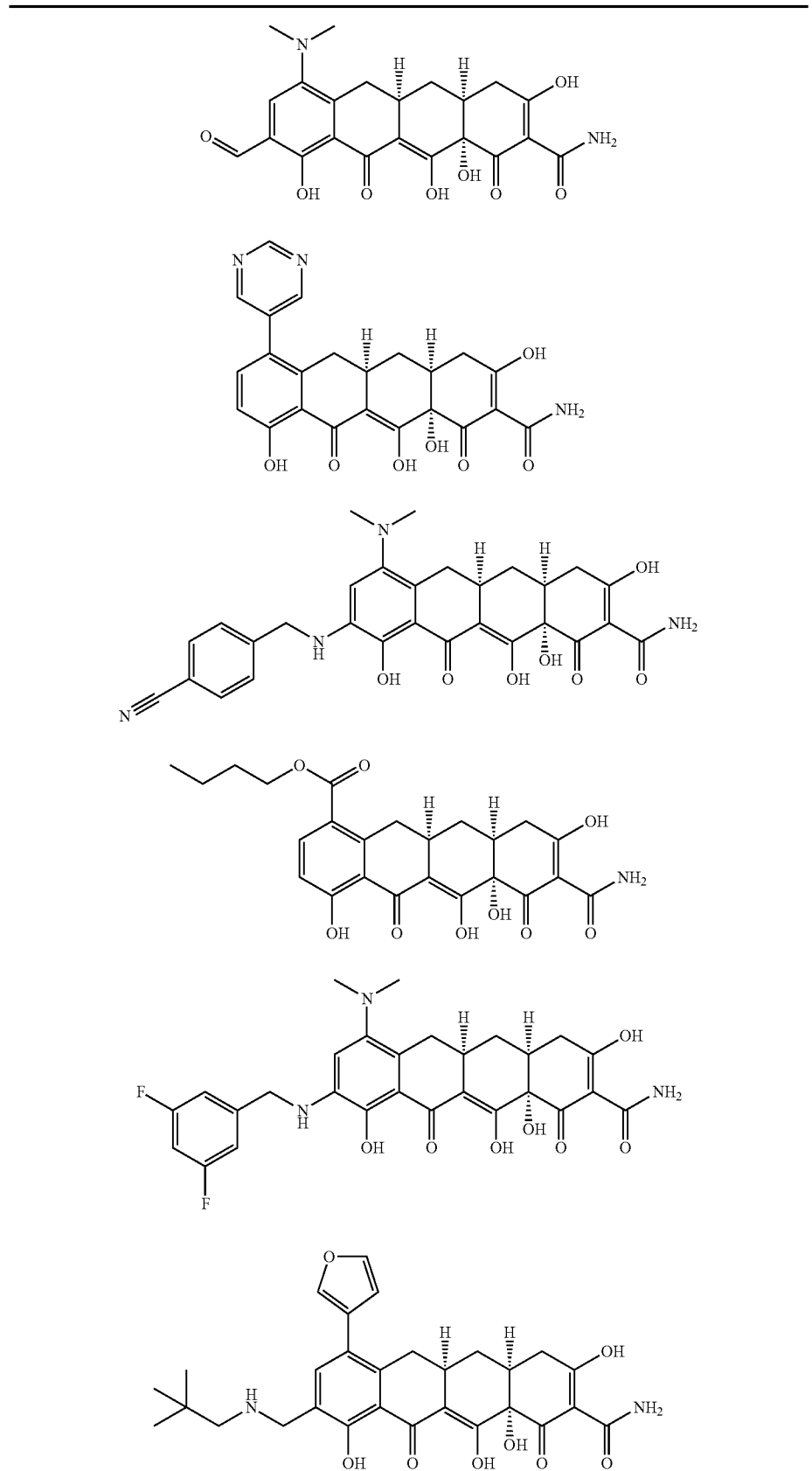

TABLE 2-continued
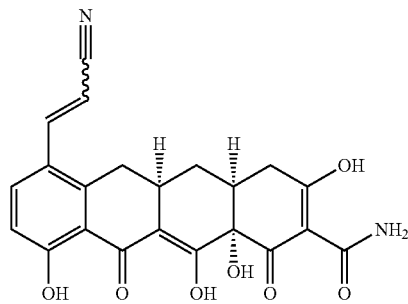 [SMILES: N#CC=Cc1ccc(O)c2c1C[C@H]1C[C@H]3CC(O)=C(C(N)=O)C(=O)[C@@]3(O)C(O)=C1C2=O]
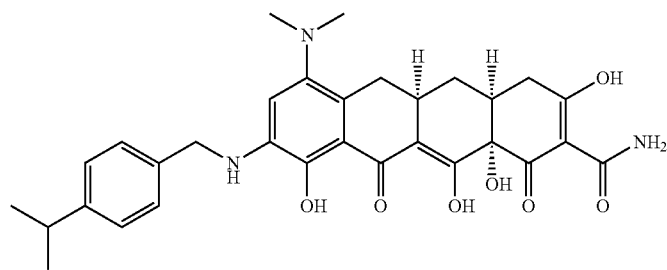 [SMILES: CC(C)c1ccc(CNc2cc(N(C)C)c3c(c2O)C(=O)C2=C(O)[C@]4(O)C(=O)C(C(N)=O)=C(O)C[C@@H]4C[C@@H]2C3)cc1]
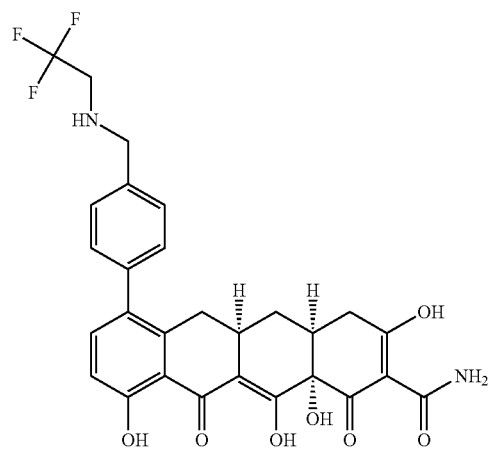 [SMILES: NC(=O)C1=C(O)C[C@@H]2C[C@@H]3Cc4c(-c5ccc(CNCC(F)(F)F)cc5)ccc(O)c4C(=O)C3=C(O)[C@]2(O)C1=O]
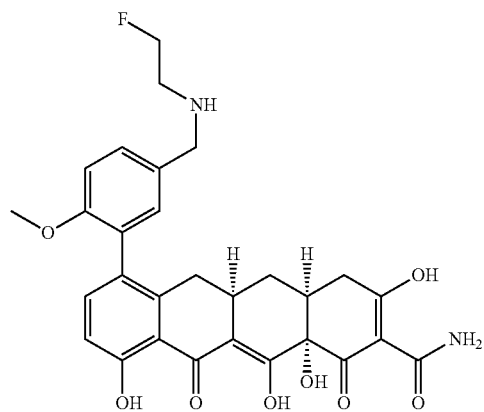 [SMILES: COc1ccc(CNCCF)cc1-c1ccc(O)c2c1C[C@H]1C[C@H]3CC(O)=C(C(N)=O)C(=O)[C@@]3(O)C(O)=C1C2=O]

TABLE 2-continued
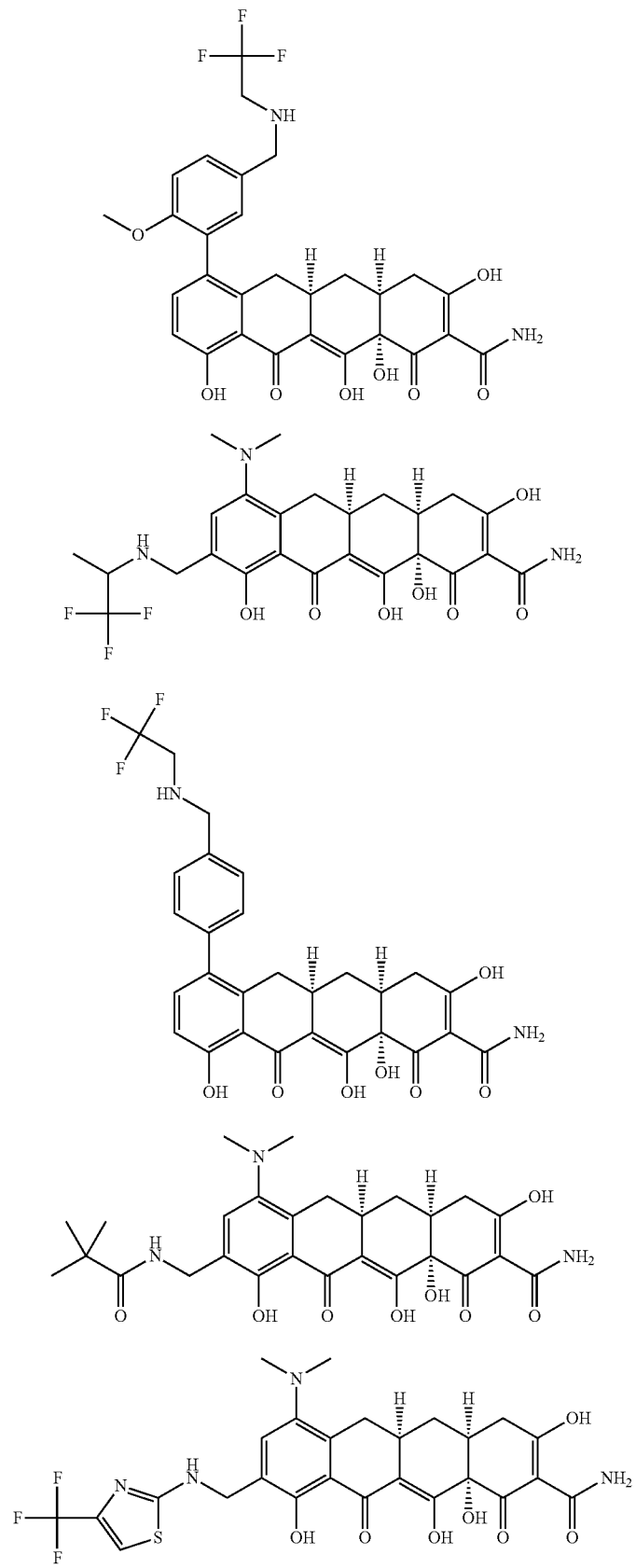

TABLE 2-continued
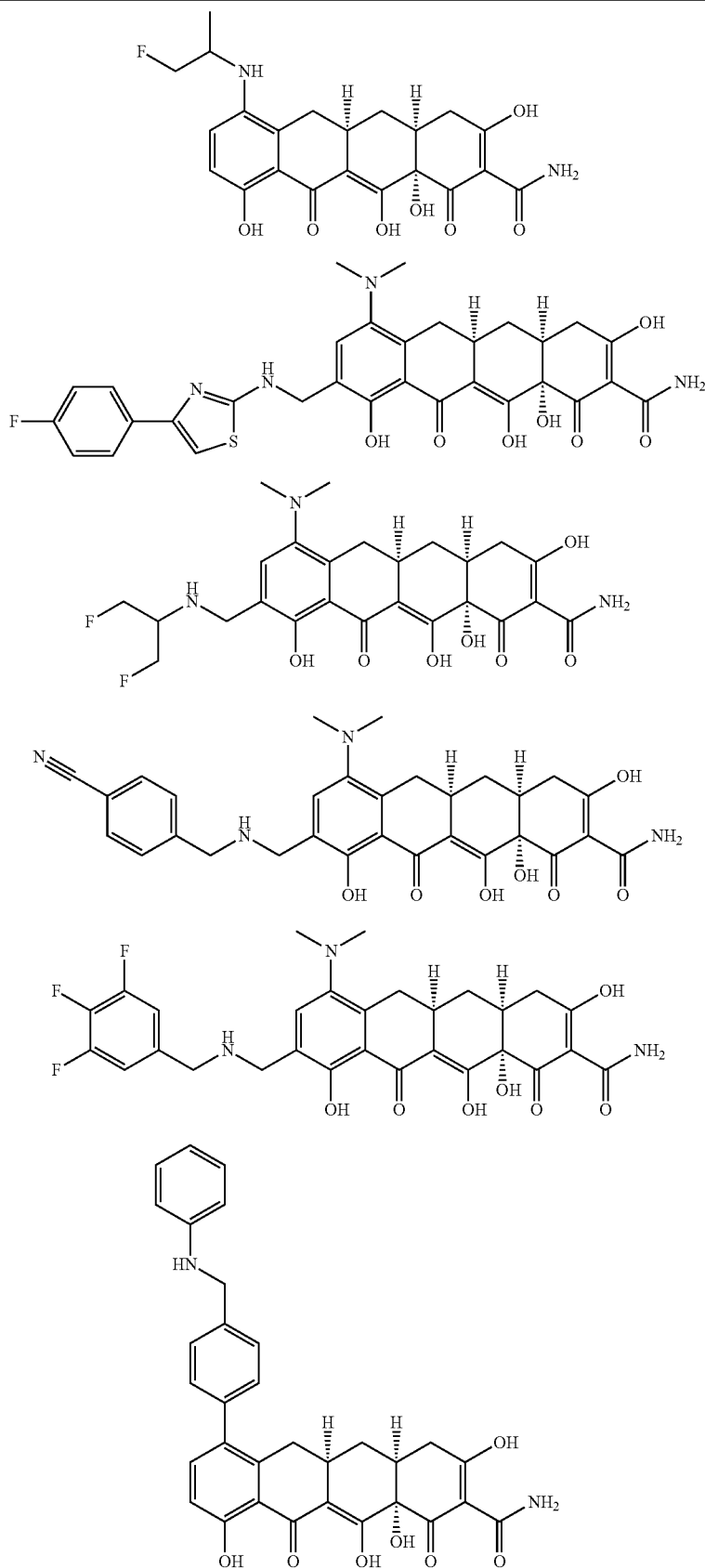

TABLE 2-continued
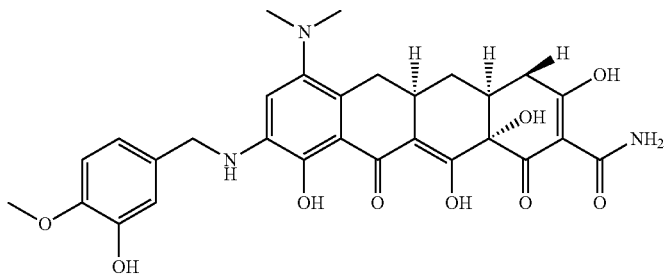
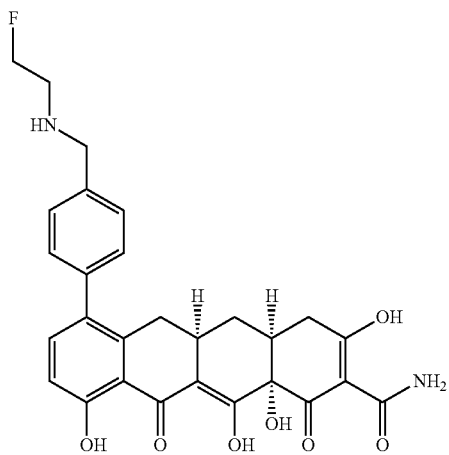 [SMILES: NC(=O)C1=C(O)C[C@@H]2C[C@@H]3Cc4c(-c5ccc(CNCCF)cc5)ccc(O)c4C(=O)C3=C(O)[C@]2(O)C1=O]
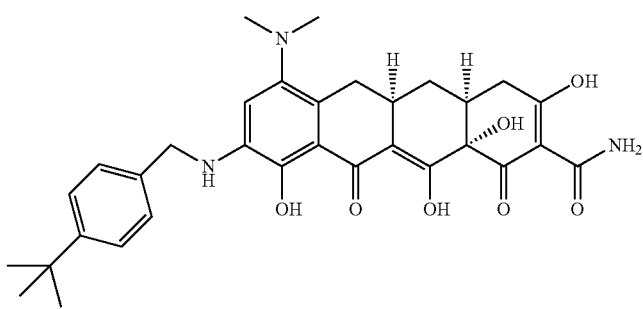
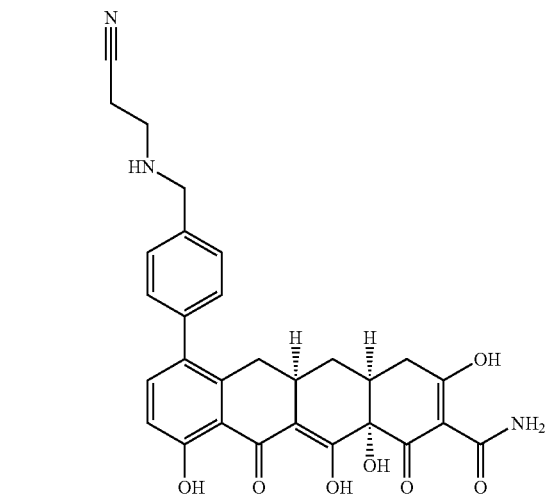 [SMILES: N#CCCNCc1ccc(-c2ccc(O)c3c2C[C@H]2C[C@H]4CC(O)=C(C(N)=O)C(=O)[C@@]4(O)C(O)=C2C3=O)cc1]

TABLE 2-continued
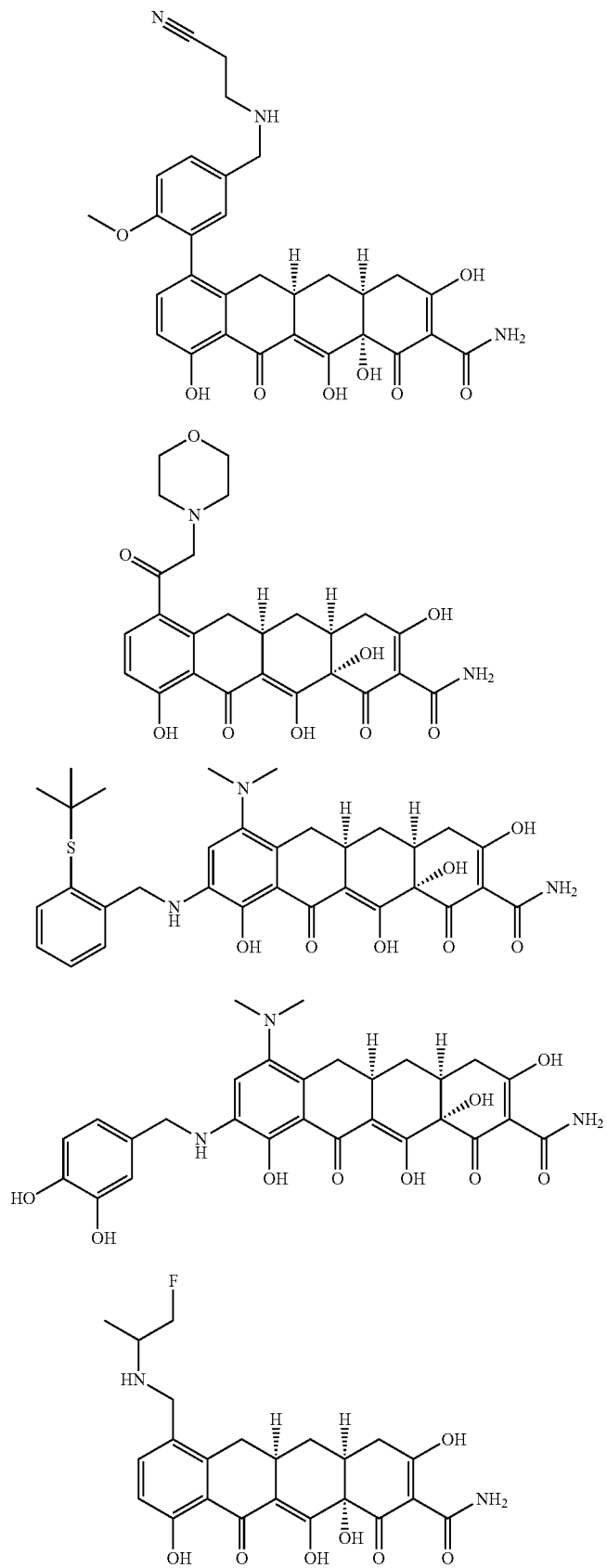

TABLE 2-continued
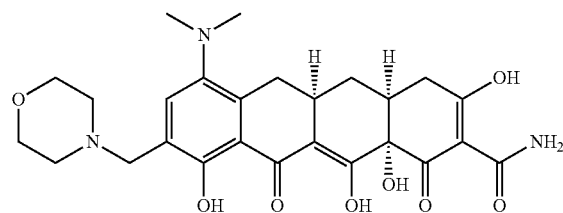 [SMILES: CN(C)c1cc(CN2CCOCC2)c(O)c2c1C[C@H]1C[C@H]3CC(O)=C(C(N)=O)C(=O)[C@@]3(O)C(O)=C1C2=O]
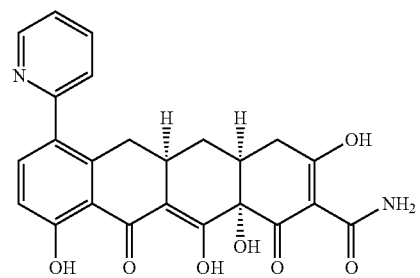
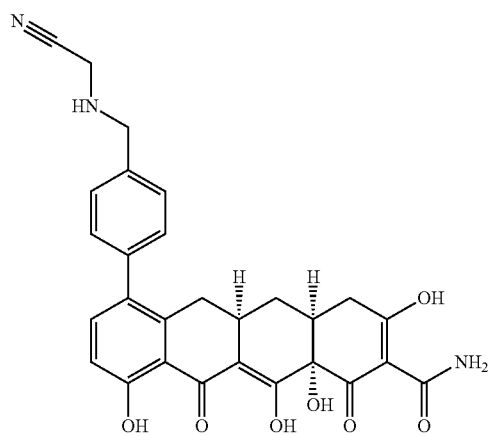 [SMILES: N#CCNCc1ccc(-c2ccc(O)c3c2C[C@H]2C[C@H]4CC(O)=C(C(N)=O)C(=O)[C@@]4(O)C(O)=C2C3=O)cc1]
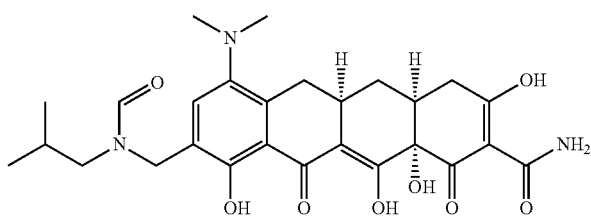 [SMILES: CC(C)CN(C=O)Cc1cc(N(C)C)c2c(c1O)C(=O)C1=C(O)[C@]3(O)C(=O)C(C(N)=O)=C(O)C[C@@H]3C[C@@H]1C2]
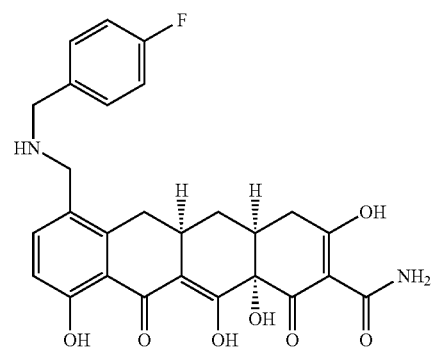 [SMILES: NC(=O)C1=C(O)C[C@@H]2C[C@@H]3Cc4c(CNCc5ccc(F)cc5)ccc(O)c4C(=O)C3=C(O)[C@]2(O)C1=O]

TABLE 2-continued
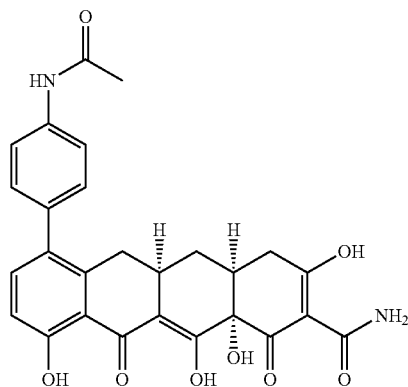 [SMILES: CC(=O)Nc1ccc(-c2ccc(O)c3c2C[C@H]2C[C@H]4CC(O)=C(C(N)=O)C(=O)[C@@]4(O)C(O)=C2C3=O)cc1]
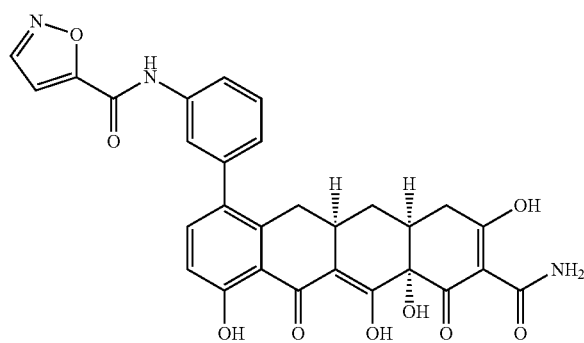 [SMILES: NC(=O)C1=C(O)C[C@@H]2C[C@@H]3Cc4c(-c5cccc(NC(=O)c6ccno6)c5)ccc(O)c4C(=O)C3=C(O)[C@]2(O)C1=O]
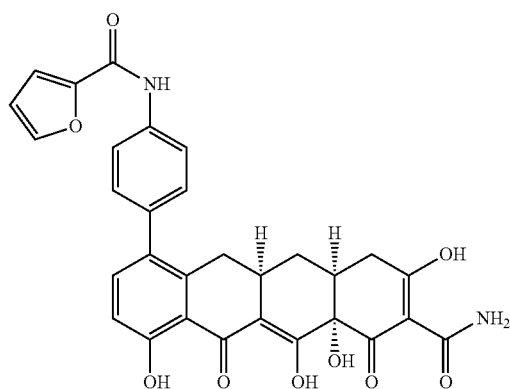 [SMILES: NC(=O)C1=C(O)C[C@@H]2C[C@@H]3Cc4c(-c5ccc(NC(=O)c6ccco6)cc5)ccc(O)c4C(=O)C3=C(O)[C@]2(O)C1=O]
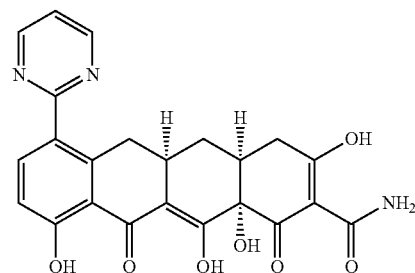 [SMILES: NC(=O)C1=C(O)C[C@@H]2C[C@@H]3Cc4c(-c5ncccn5)ccc(O)c4C(=O)C3=C(O)[C@]2(O)C1=O]

TABLE 2-continued
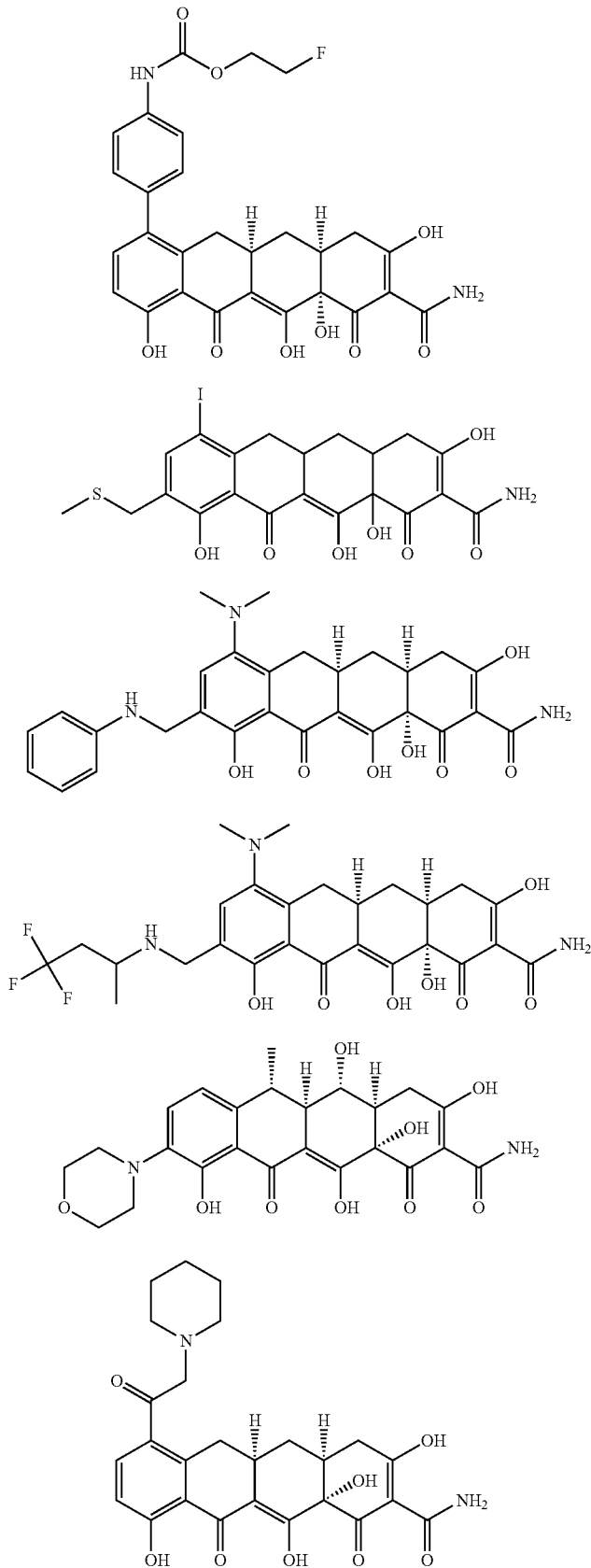

TABLE 2-continued
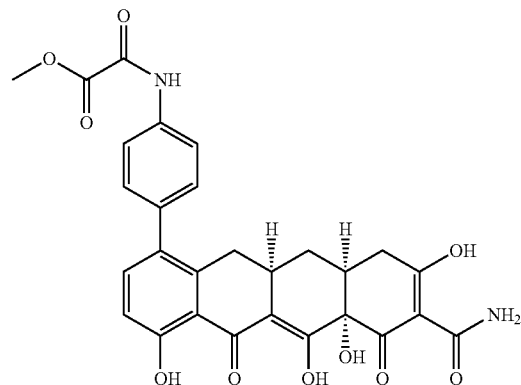 [SMILES: COC(=O)C(=O)Nc1ccc(-c2ccc(O)c3c2C[C@H]2C[C@H]4CC(O)=C(C(N)=O)C(=O)[C@@]4(O)C(O)=C2C3=O)cc1]
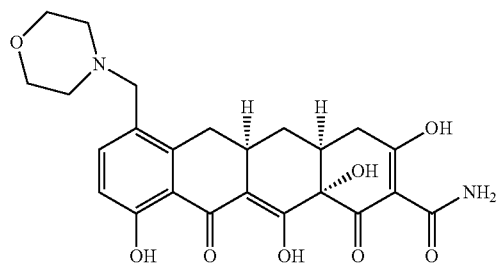
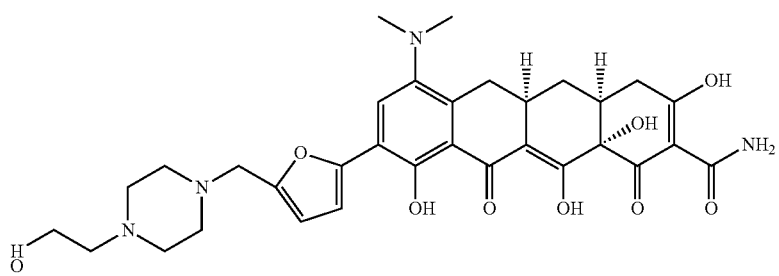
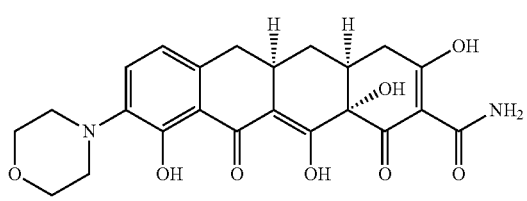
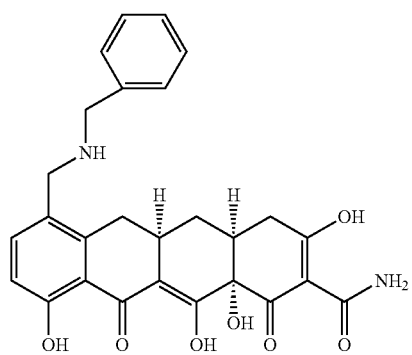 [SMILES: NC(=O)C1=C(O)C[C@@H]2C[C@@H]3Cc4c(CNCc5ccccc5)ccc(O)c4C(=O)C3=C(O)[C@]2(O)C1=O]

TABLE 2-continued
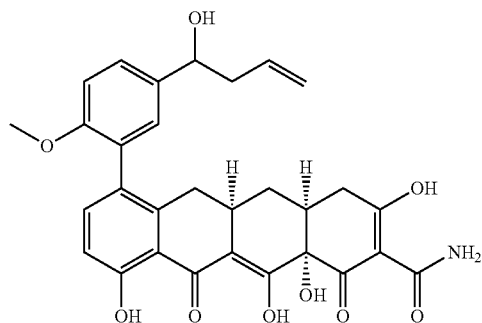 [SMILES: C=CCC(O)c1ccc(OC)c(-c2ccc(O)c3c2C[C@H]2C[C@H]4CC(O)=C(C(N)=O)C(=O)[C@@]4(O)C(O)=C2C3=O)c1]
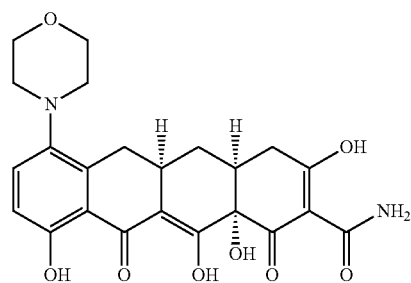 [SMILES: NC(=O)C1=C(O)C[C@@H]2C[C@@H]3Cc4c(N5CCOCC5)ccc(O)c4C(=O)C3=C(O)[C@]2(O)C1=O]
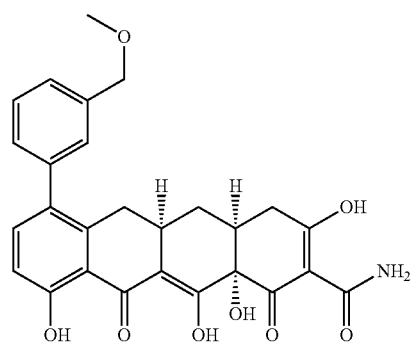 [SMILES: COCc1cccc(-c2ccc(O)c3c2C[C@H]2C[C@H]4CC(O)=C(C(N)=O)C(=O)[C@@]4(O)C(O)=C2C3=O)c1]
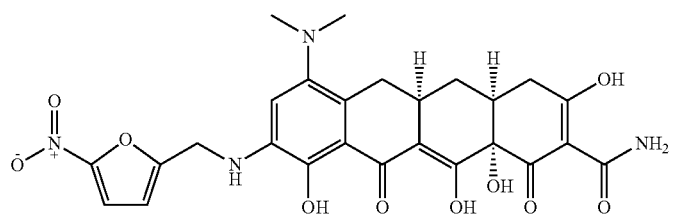
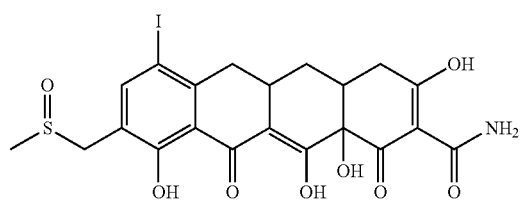 [SMILES: CS(=O)Cc1cc(I)c2c(c1O)C(=O)C1=C(O)C3(O)C(=O)C(C(N)=O)=C(O)CC3CC1C2]

TABLE 2-continued
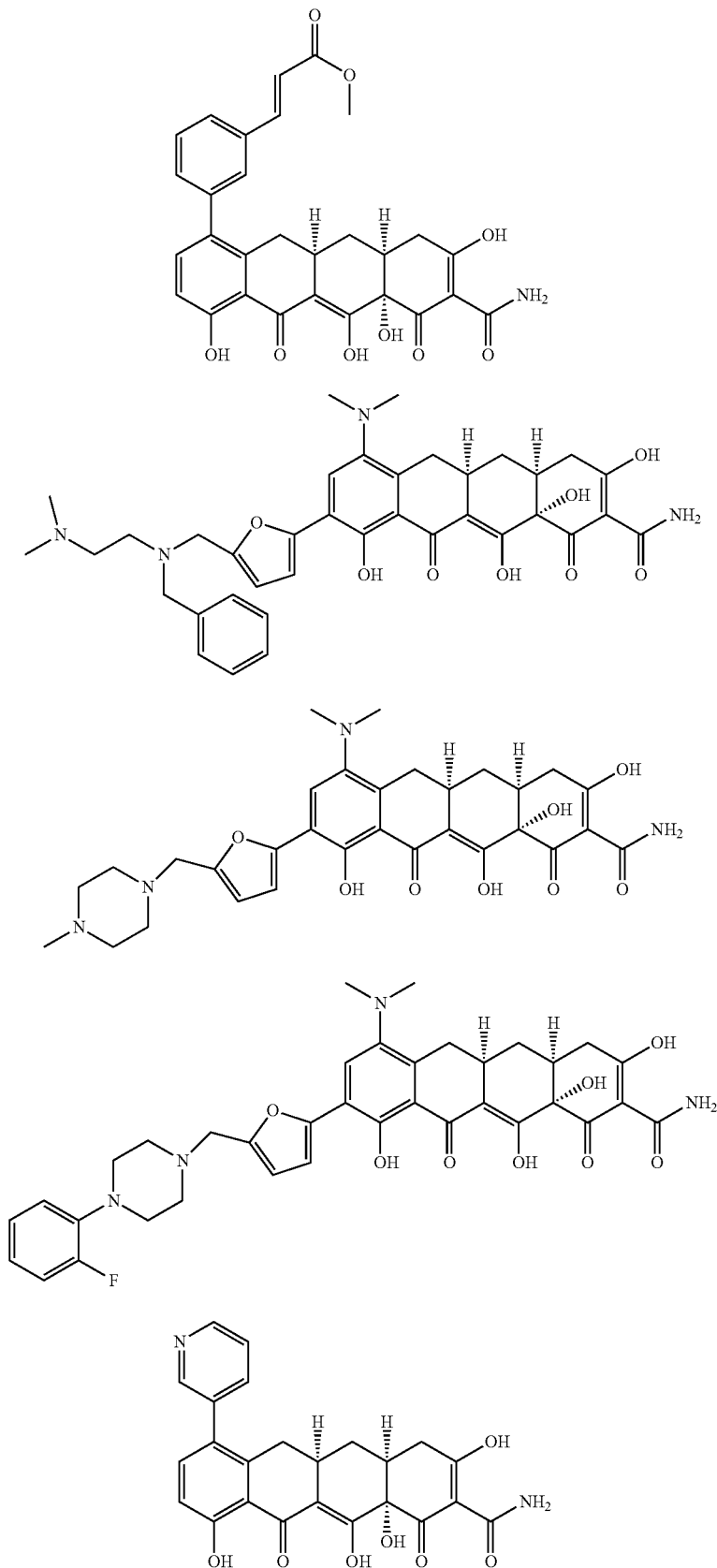

TABLE 2-continued
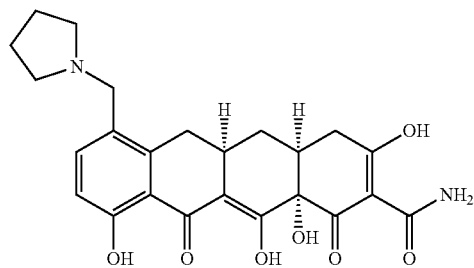 [SMILES: NC(=O)C1=C(O)C[C@@H]2C[C@@H]3Cc4c(CN5CCCC5)ccc(O)c4C(=O)C3=C(O)[C@]2(O)C1=O]
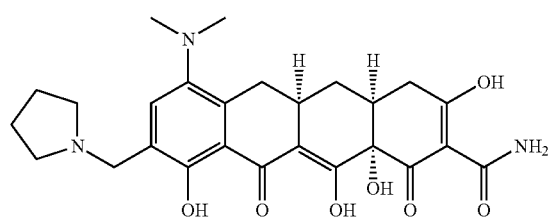 [SMILES: CN(C)c1cc(CN2CCCC2)c(O)c2c1C[C@H]1C[C@H]3CC(O)=C(C(N)=O)C(=O)[C@@]3(O)C(O)=C1C2=O]
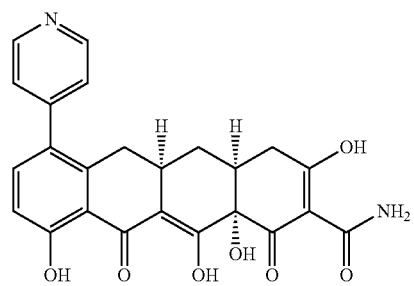 [SMILES: NC(=O)C1=C(O)C[C@@H]2C[C@@H]3Cc4c(-c5ccncc5)ccc(O)c4C(=O)C3=C(O)[C@]2(O)C1=O]
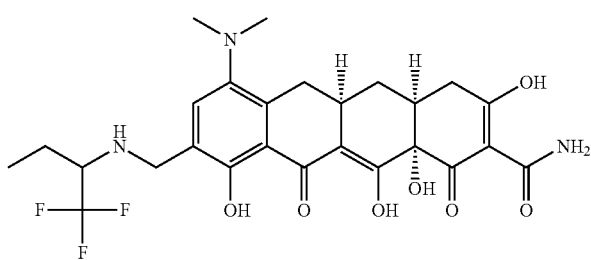 [SMILES: CCC(NCc1cc(N(C)C)c2c(c1O)C(=O)C1=C(O)[C@]3(O)C(=O)C(C(N)=O)=C(O)C[C@@H]3C[C@@H]1C2)C(F)(F)F]
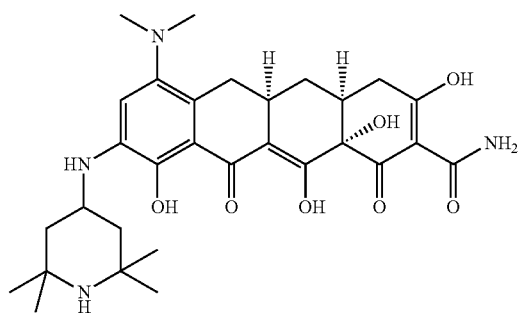

TABLE 2-continued
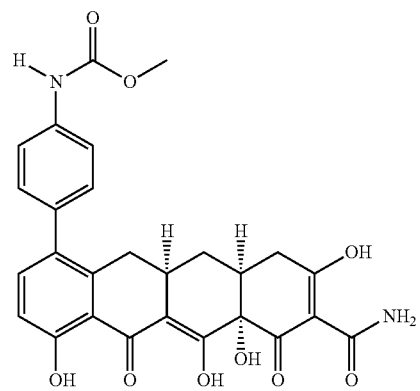 [SMILES: COC(=O)Nc1ccc(-c2ccc(O)c3c2C[C@H]2C[C@H]4CC(O)=C(C(N)=O)C(=O)[C@@]4(O)C(O)=C2C3=O)cc1]
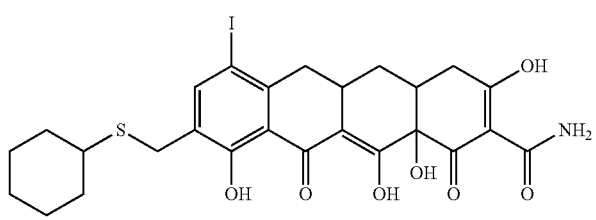 [SMILES: NC(=O)C1=C(O)CC2CC3Cc4c(I)cc(CSC5CCCCC5)c(O)c4C(=O)C3=C(O)C2(O)C1=O]
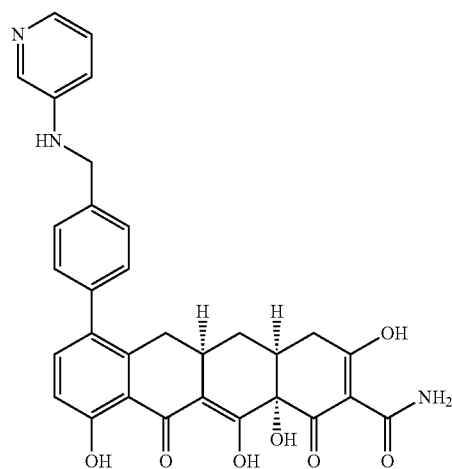 [SMILES: NC(=O)C1=C(O)C[C@@H]2C[C@@H]3Cc4c(-c5ccc(CNc6cccnc6)cc5)ccc(O)c4C(=O)C3=C(O)[C@]2(O)C1=O]
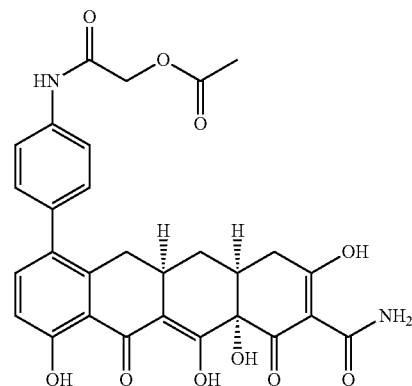 [SMILES: CC(=O)OCC(=O)Nc1ccc(-c2ccc(O)c3c2C[C@H]2C[C@H]4CC(O)=C(C(N)=O)C(=O)[C@@]4(O)C(O)=C2C3=O)cc1]

TABLE 2-continued
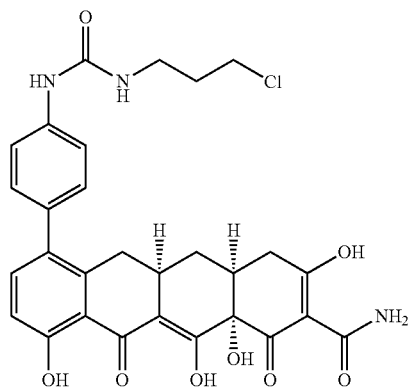 [SMILES: NC(=O)C1=C(O)C[C@@H]2C[C@@H]3Cc4c(-c5ccc(NC(=O)NCCCCl)cc5)ccc(O)c4C(=O)C3=C(O)[C@]2(O)C1=O]
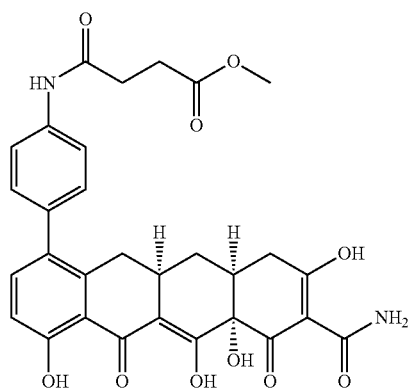 [SMILES: COC(=O)CCC(=O)Nc1ccc(-c2ccc(O)c3c2C[C@H]2C[C@H]4CC(O)=C(C(N)=O)C(=O)[C@@]4(O)C(O)=C2C3=O)cc1]
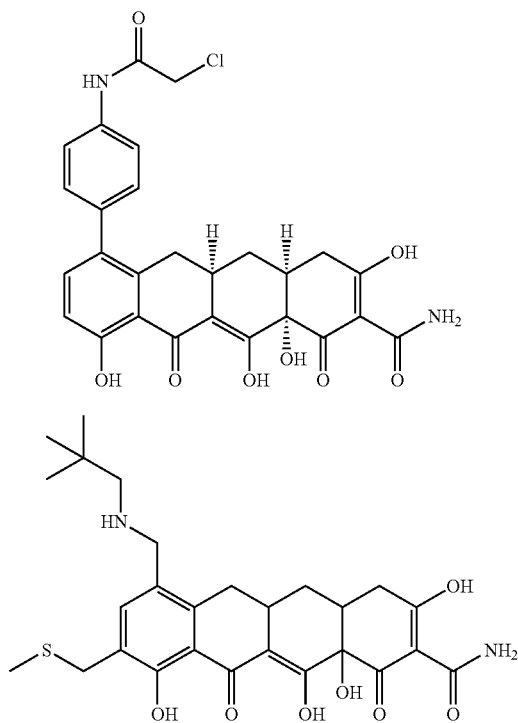

TABLE 2-continued
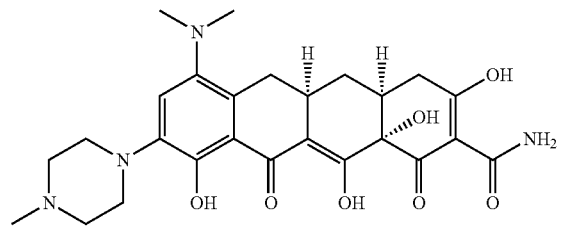
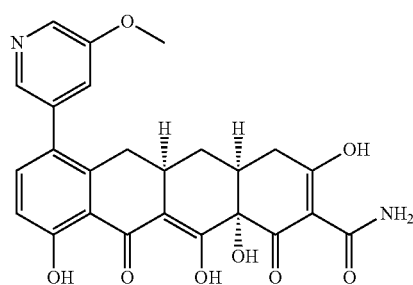 [SMILES: COc1cncc(-c2ccc(O)c3c2C[C@H]2C[C@H]4CC(O)=C(C(N)=O)C(=O)[C@@]4(O)C(O)=C2C3=O)c1]
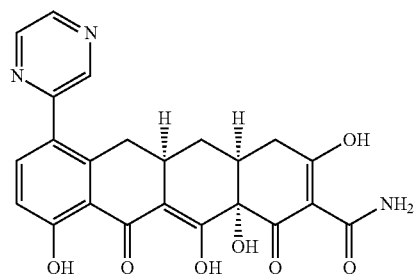 [SMILES: NC(=O)C1=C(O)C[C@@H]2C[C@@H]3Cc4c(-c5cnccn5)ccc(O)c4C(=O)C3=C(O)[C@]2(O)C1=O]
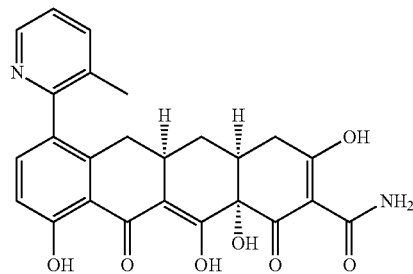 [SMILES: Cc1cccnc1-c1ccc(O)c2c1C[C@H]1C[C@H]3CC(O)=C(C(N)=O)C(=O)[C@@]3(O)C(O)=C1C2=O]
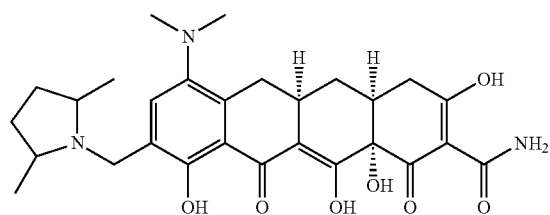 [SMILES: CC1CCC(C)N1Cc1cc(N(C)C)c2c(c1O)C(=O)C1=C(O)[C@]3(O)C(=O)C(C(N)=O)=C(O)C[C@@H]3C[C@@H]1C2]

TABLE 2-continued
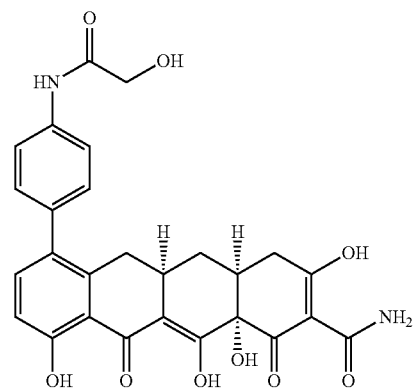 [SMILES: NC(=O)C1=C(O)C[C@@H]2C[C@@H]3Cc4c(-c5ccc(NC(=O)CO)cc5)ccc(O)c4C(=O)C3=C(O)[C@]2(O)C1=O]
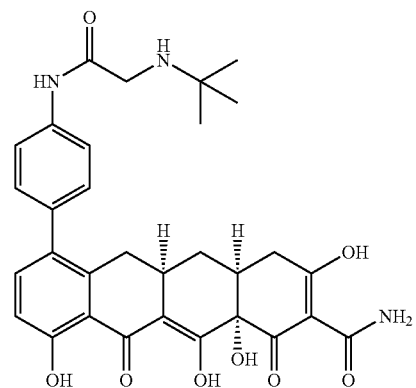 [SMILES: CC(C)(C)NCC(=O)Nc1ccc(-c2ccc(O)c3c2C[C@H]2C[C@H]4CC(O)=C(C(N)=O)C(=O)[C@@]4(O)C(O)=C2C3=O)cc1]
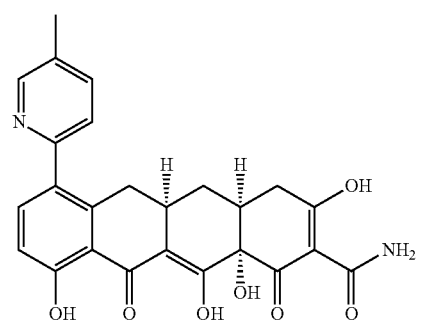 [SMILES: Cc1ccc(-c2ccc(O)c3c2C[C@H]2C[C@H]4CC(O)=C(C(N)=O)C(=O)[C@@]4(O)C(O)=C2C3=O)nc1]
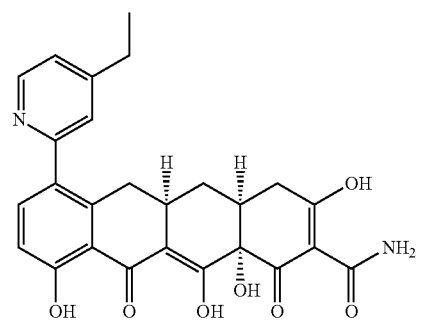 [SMILES: CCc1ccnc(-c2ccc(O)c3c2C[C@H]2C[C@H]4CC(O)=C(C(N)=O)C(=O)[C@@]4(O)C(O)=C2C3=O)c1]

TABLE 2-continued
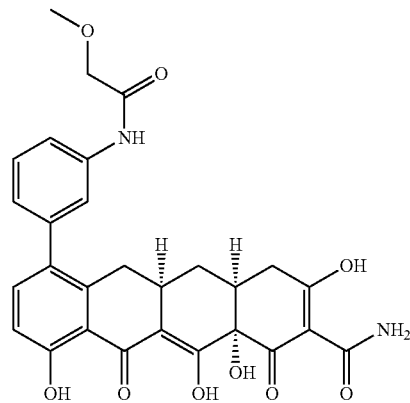 [SMILES: COCC(=O)Nc1cccc(-c2ccc(O)c3c2C[C@H]2C[C@H]4CC(O)=C(C(N)=O)C(=O)[C@@]4(O)C(O)=C2C3=O)c1]
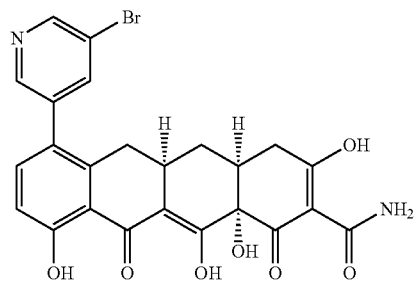 [SMILES: NC(=O)C1=C(O)C[C@@H]2C[C@@H]3Cc4c(-c5cncc(Br)c5)ccc(O)c4C(=O)C3=C(O)[C@]2(O)C1=O]
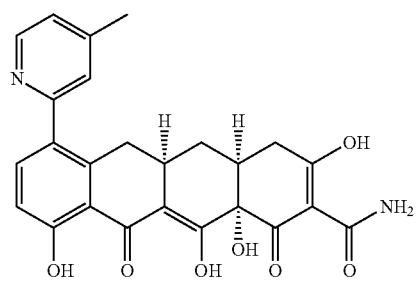 [SMILES: Cc1ccnc(-c2ccc(O)c3c2C[C@H]2C[C@H]4CC(O)=C(C(N)=O)C(=O)[C@@]4(O)C(O)=C2C3=O)c1]
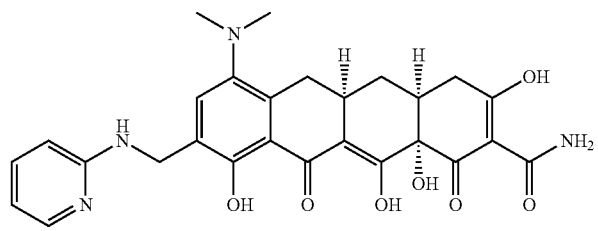 [SMILES: CN(C)c1cc(CNc2ccccn2)c(O)c2c1C[C@H]1C[C@H]3CC(O)=C(C(N)=O)C(=O)[C@@]3(O)C(O)=C1C2=O]
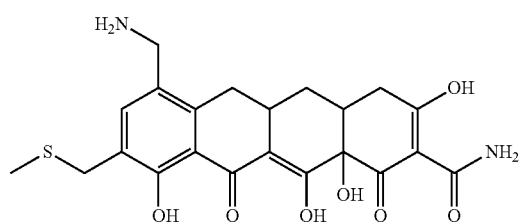 [SMILES: CSCc1cc(CN)c2c(c1O)C(=O)C1=C(O)C3(O)C(=O)C(C(N)=O)=C(O)CC3CC1C2]

TABLE 2-continued
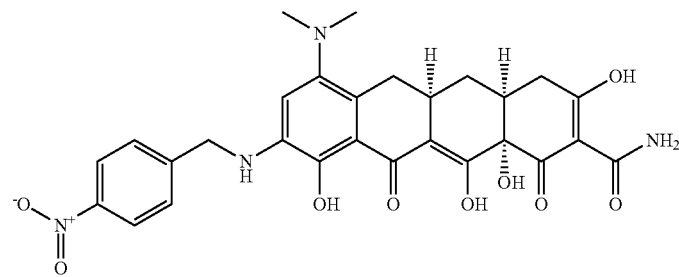
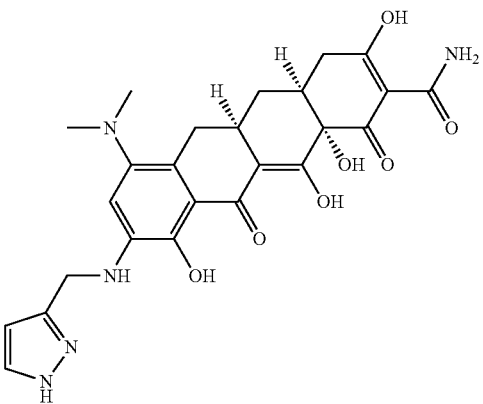 [SMILES: CN(C)c1cc(NCc2cc[nH]n2)c(O)c2c1C[C@H]1C[C@H]3CC(O)=C(C(N)=O)C(=O)[C@@]3(O)C(O)=C1C2=O]
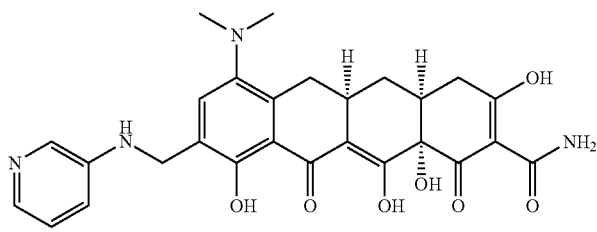 [SMILES: CN(C)c1cc(CNc2cccnc2)c(O)c2c1C[C@H]1C[C@H]3CC(O)=C(C(N)=O)C(=O)[C@@]3(O)C(O)=C1C2=O]
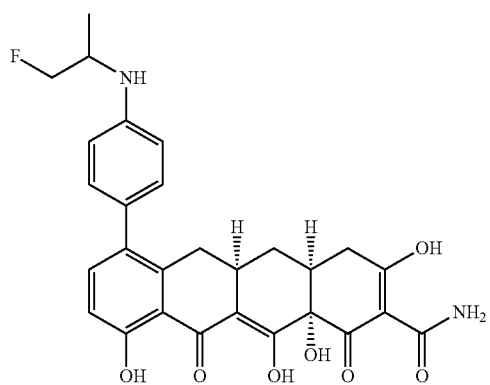 [SMILES: CC(CF)Nc1ccc(-c2ccc(O)c3c2C[C@H]2C[C@H]4CC(O)=C(C(N)=O)C(=O)[C@@]4(O)C(O)=C2C3=O)cc1]
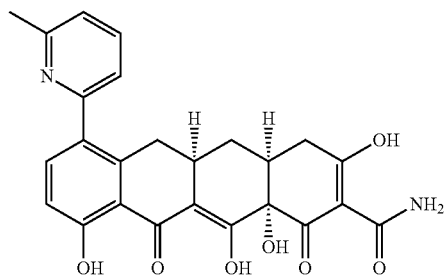 [SMILES: Cc1cccc(-c2ccc(O)c3c2C[C@H]2C[C@H]4CC(O)=C(C(N)=O)C(=O)[C@@]4(O)C(O)=C2C3=O)n1]

TABLE 2-continued
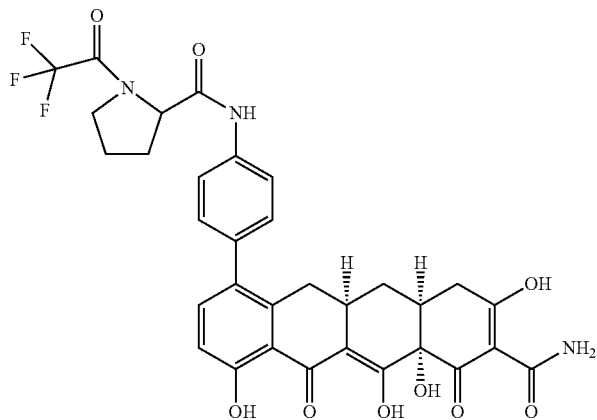 [SMILES: NC(=O)C1=C(O)C[C@@H]2C[C@@H]3Cc4c(-c5ccc(NC(=O)C6CCCN6C(=O)C(F)(F)F)cc5)ccc(O)c4C(=O)C3=C(O)[C@]2(O)C1=O]
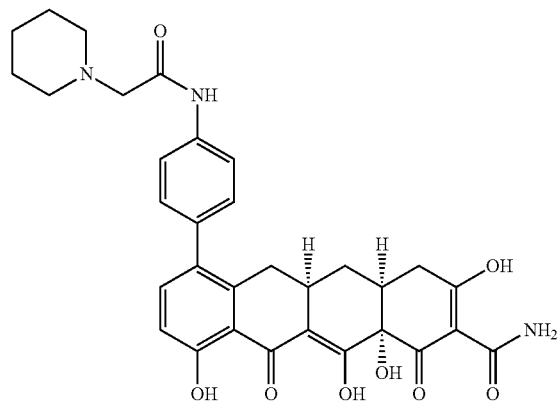 [SMILES: NC(=O)C1=C(O)C[C@@H]2C[C@@H]3Cc4c(-c5ccc(NC(=O)CN6CCCCC6)cc5)ccc(O)c4C(=O)C3=C(O)[C@]2(O)C1=O]
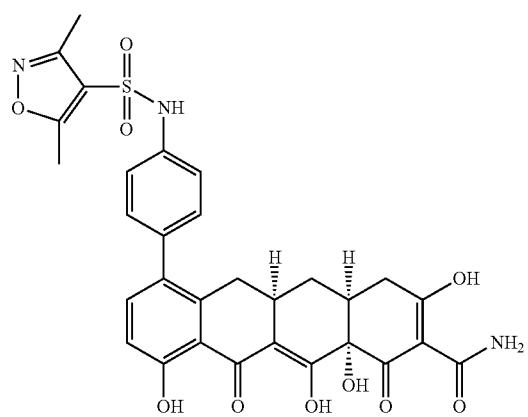 [SMILES: Cc1noc(C)c1S(=O)(=O)Nc1ccc(-c2ccc(O)c3c2C[C@H]2C[C@H]4CC(O)=C(C(N)=O)C(=O)[C@@]4(O)C(O)=C2C3=O)cc1]
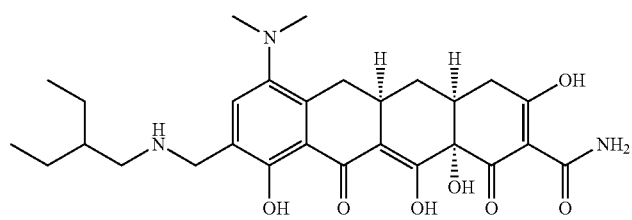 [SMILES: CCC(CC)CNCc1cc(N(C)C)c2c(c1O)C(=O)C1=C(O)[C@]3(O)C(=O)C(C(N)=O)=C(O)C[C@@H]3C[C@@H]1C2]

TABLE 2-continued
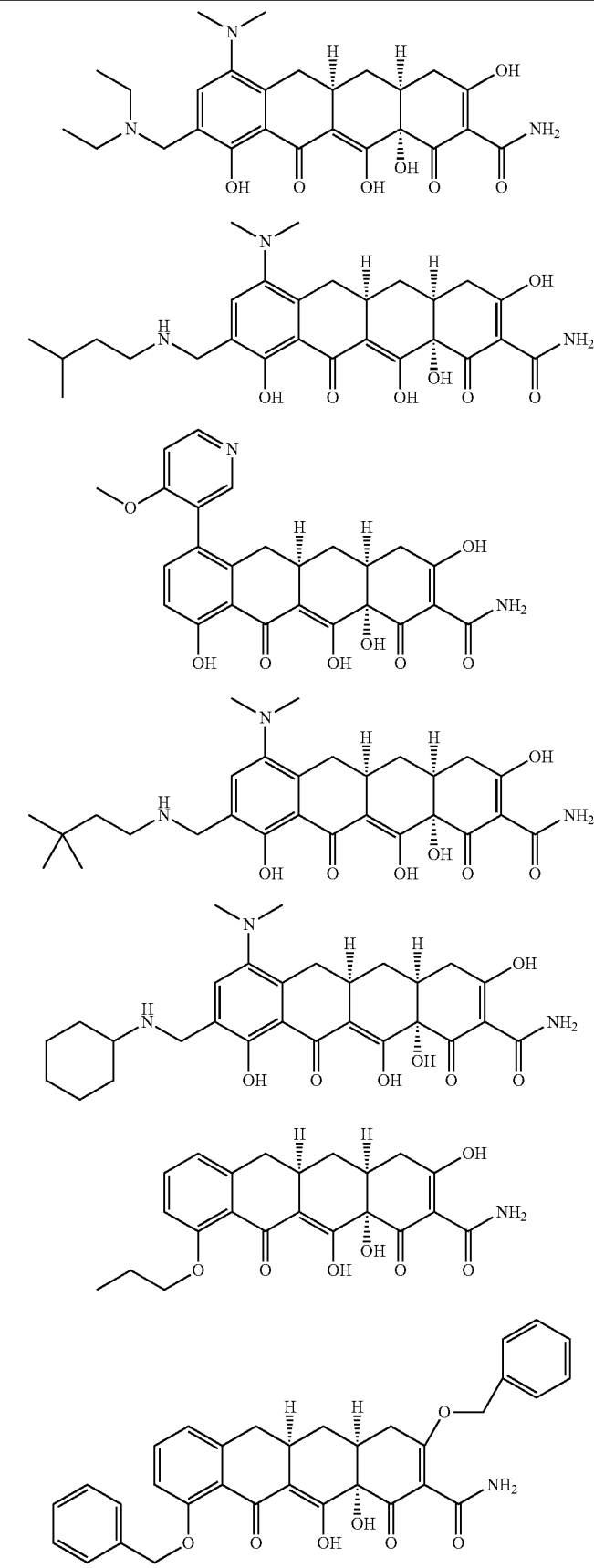

TABLE 2-continued
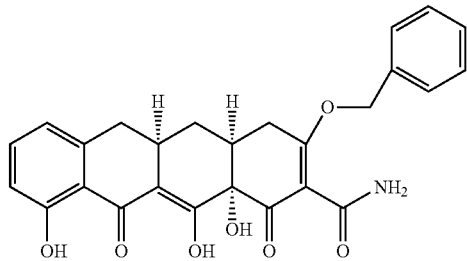 [SMILES: NC(=O)C1=C(OCc2ccccc2)C[C@@H]2C[C@@H]3Cc4cccc(O)c4C(=O)C3=C(O)[C@]2(O)C1=O]
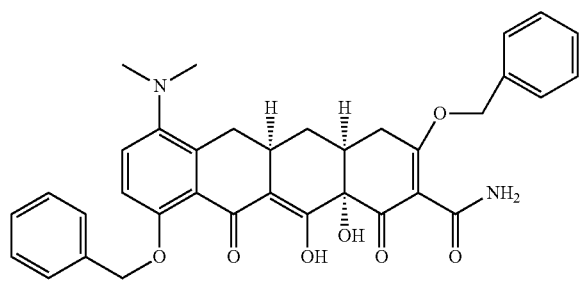 [SMILES: CN(C)c1ccc(OCc2ccccc2)c2c1C[C@H]1C[C@H]3CC(OCc4ccccc4)=C(C(N)=O)C(=O)[C@@]3(O)C(O)=C1C2=O]
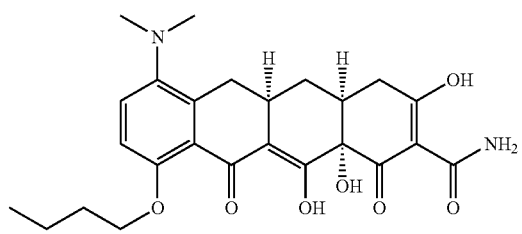 [SMILES: CCCCOc1ccc(N(C)C)c2c1C(=O)C1=C(O)[C@]3(O)C(=O)C(C(N)=O)=C(O)C[C@@H]3C[C@@H]1C2]
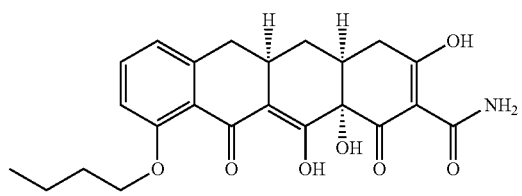 [SMILES: CCCCOc1cccc2c1C(=O)C1=C(O)[C@]3(O)C(=O)C(C(N)=O)=C(O)C[C@@H]3C[C@@H]1C2]
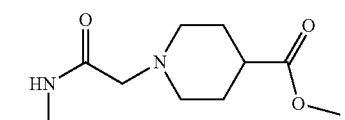
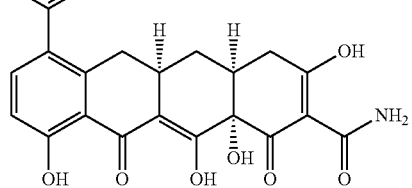

TABLE 2-continued
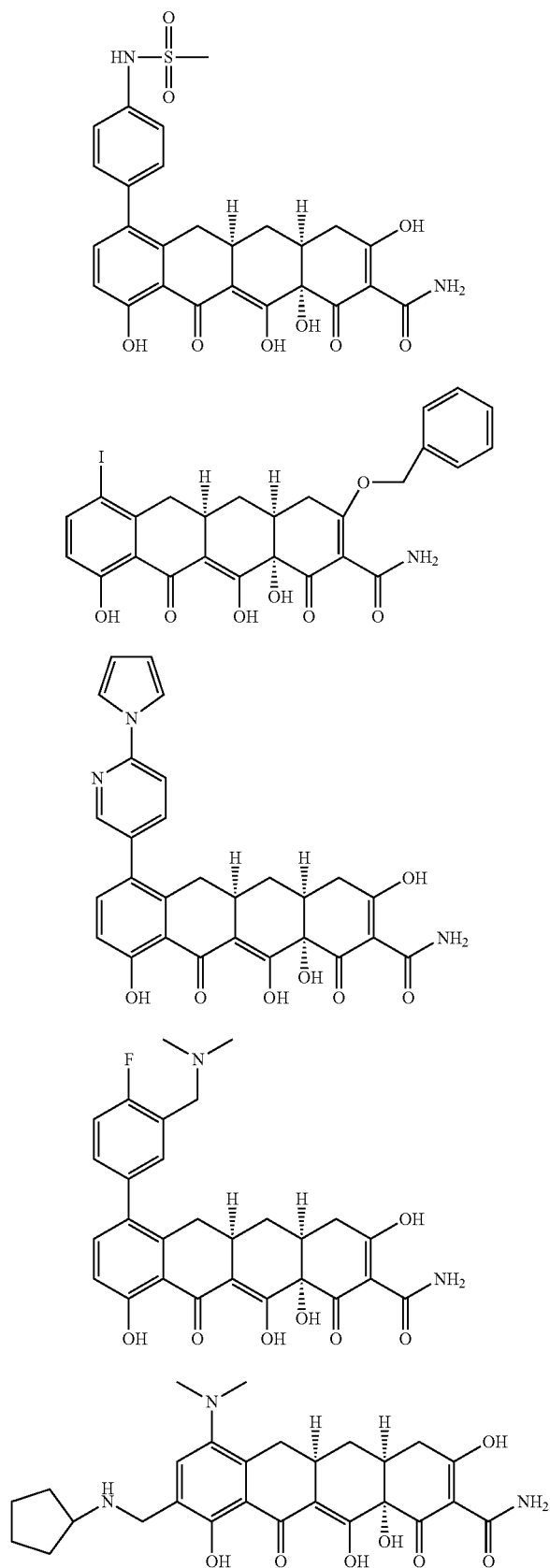

TABLE 2-continued
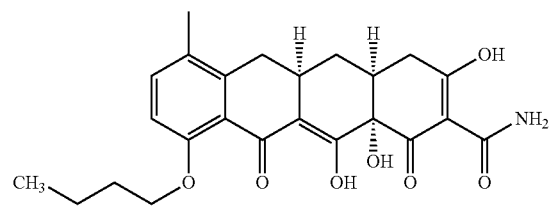 [SMILES: CCCCOc1ccc(C)c2c1C(=O)C1=C(O)[C@]3(O)C(=O)C(C(N)=O)=C(O)C[C@@H]3C[C@@H]1C2]
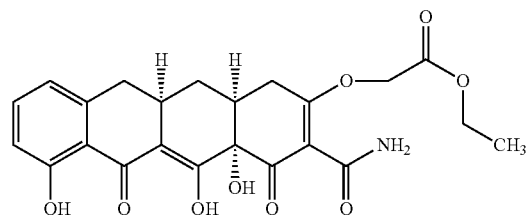 [SMILES: CCOC(=O)COC1=C(C(N)=O)C(=O)[C@@]2(O)C(O)=C3C(=O)c4c(O)cccc4C[C@H]3C[C@H]2C1]
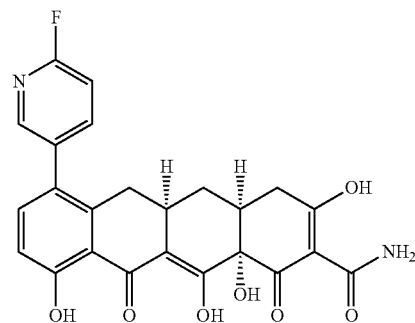
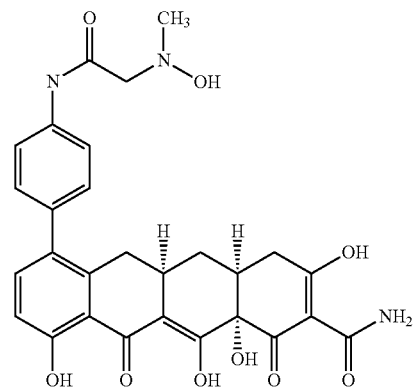 [SMILES: CN(O)CC(=O)Nc1ccc(-c2ccc(O)c3c2C[C@H]2C[C@H]4CC(O)=C(C(N)=O)C(=O)[C@@]4(O)C(O)=C2C3=O)cc1]
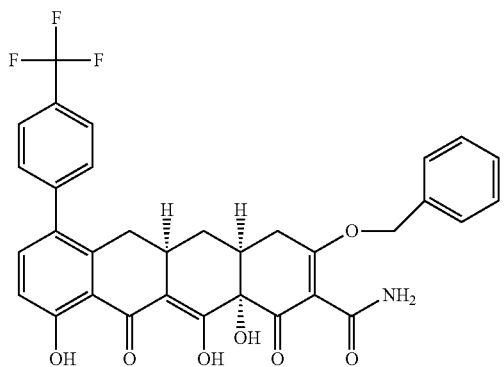 [SMILES: NC(=O)C1=C(OCc2ccccc2)C[C@@H]2C[C@@H]3Cc4c(-c5ccc(C(F)(F)F)cc5)ccc(O)c4C(=O)C3=C(O)[C@]2(O)C1=O]

TABLE 2-continued
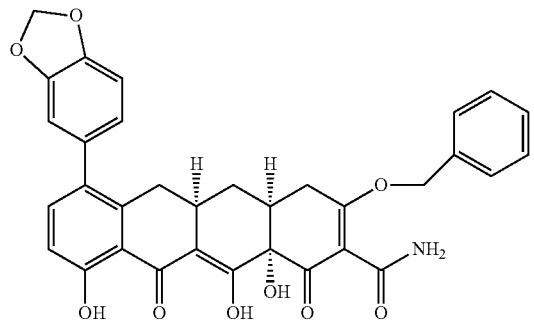 [SMILES: NC(=O)C1=C(OCc2ccccc2)C[C@@H]2C[C@@H]3Cc4c(-c5ccc6c(c5)OCO6)ccc(O)c4C(=O)C3=C(O)[C@]2(O)C1=O]
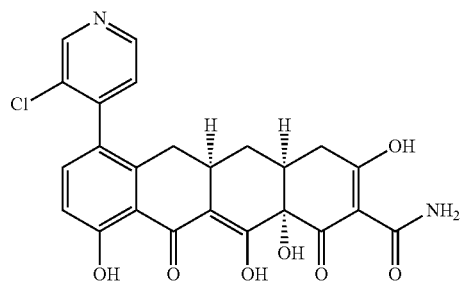 [SMILES: NC(=O)C1=C(O)C[C@@H]2C[C@@H]3Cc4c(-c5ccncc5Cl)ccc(O)c4C(=O)C3=C(O)[C@]2(O)C1=O]
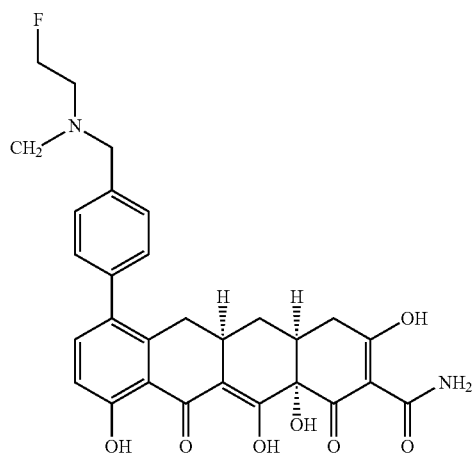 [SMILES: CN(CCF)Cc1ccc(-c2ccc(O)c3c2C[C@H]2C[C@H]4CC(O)=C(C(N)=O)C(=O)[C@@]4(O)C(O)=C2C3=O)cc1]
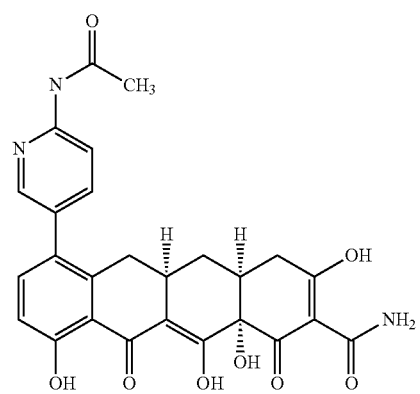 [SMILES: CC(=O)Nc1ccc(-c2ccc(O)c3c2C[C@H]2C[C@H]4CC(O)=C(C(N)=O)C(=O)[C@@]4(O)C(O)=C2C3=O)cn1]

TABLE 2-continued
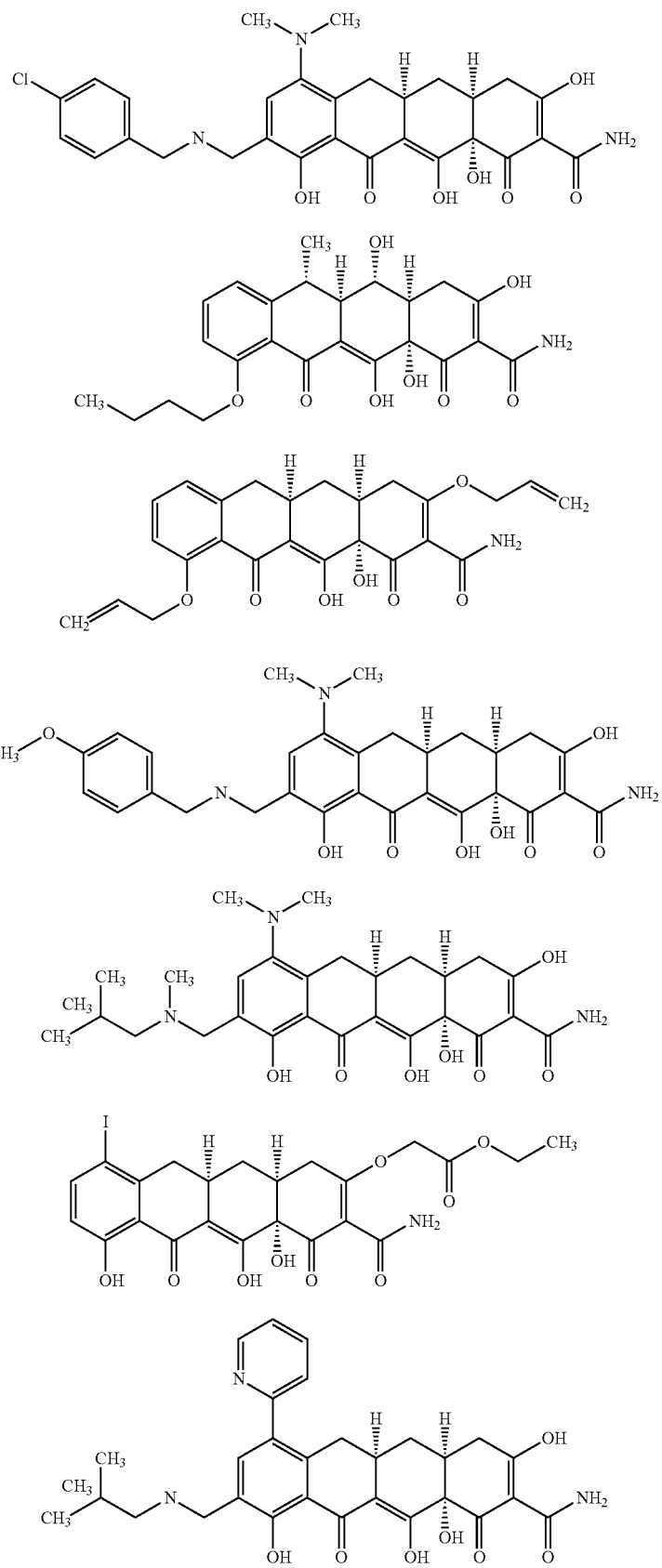

TABLE 2-continued
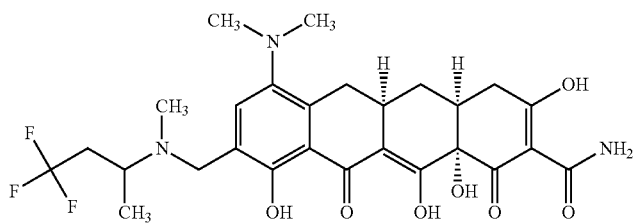 [SMILES: CC(CC(F)(F)F)N(C)Cc1cc(N(C)C)c2c(c1O)C(=O)C1=C(O)[C@]3(O)C(=O)C(C(N)=O)=C(O)C[C@@H]3C[C@@H]1C2]
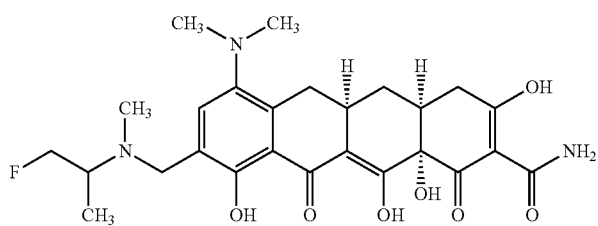 [SMILES: CC(CF)N(C)Cc1cc(N(C)C)c2c(c1O)C(=O)C1=C(O)[C@]3(O)C(=O)C(C(N)=O)=C(O)C[C@@H]3C[C@@H]1C2]
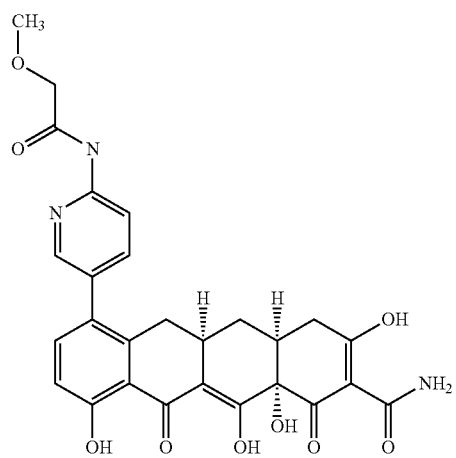 [SMILES: COCC(=O)Nc1ccc(-c2ccc(O)c3c2C[C@H]2C[C@H]4CC(O)=C(C(N)=O)C(=O)[C@@]4(O)C(O)=C2C3=O)cn1]
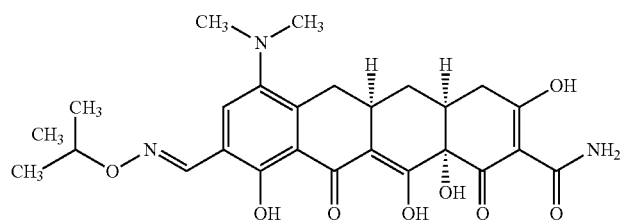
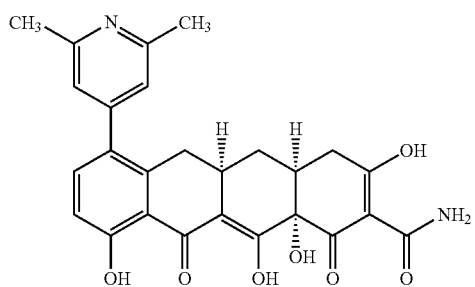 [SMILES: Cc1cc(-c2ccc(O)c3c2C[C@H]2C[C@H]4CC(O)=C(C(N)=O)C(=O)[C@@]4(O)C(O)=C2C3=O)cc(C)n1]

TABLE 2-continued
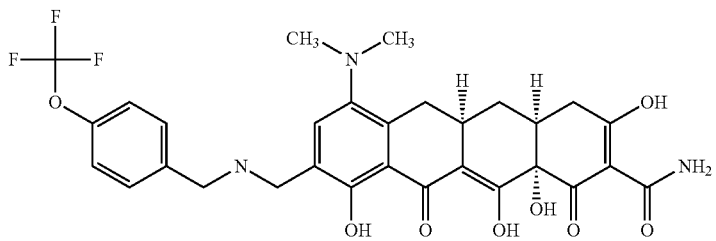 [SMILES: CN(C)c1cc(CNCc2ccc(OC(F)(F)F)cc2)c(O)c2c1C[C@H]1C[C@H]3CC(O)=C(C(N)=O)C(=O)[C@@]3(O)C(O)=C1C2=O]
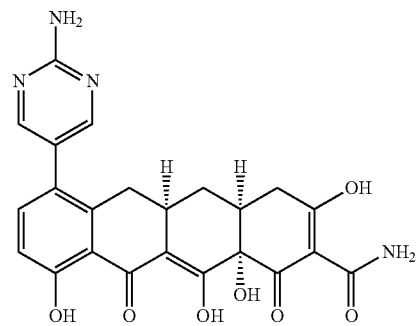
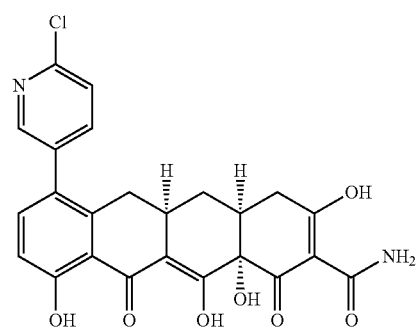
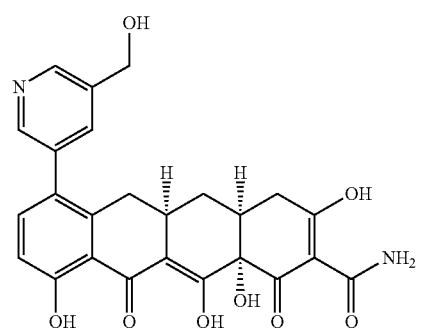 [SMILES: NC(=O)C1=C(O)C[C@@H]2C[C@@H]3Cc4c(-c5cncc(CO)c5)ccc(O)c4C(=O)C3=C(O)[C@]2(O)C1=O]
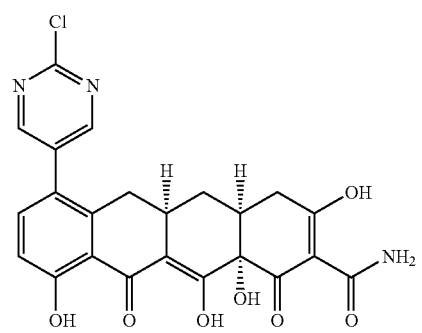

TABLE 2-continued
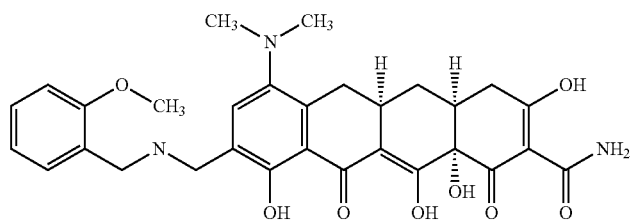 [SMILES: COc1ccccc1CNCc1cc(N(C)C)c2c(c1O)C(=O)C1=C(O)[C@]3(O)C(=O)C(C(N)=O)=C(O)C[C@@H]3C[C@@H]1C2]
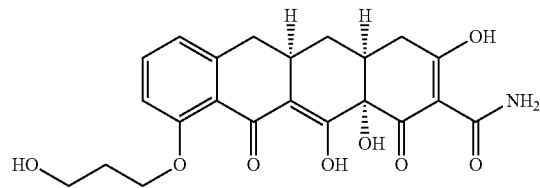 [SMILES: NC(=O)C1=C(O)C[C@@H]2C[C@@H]3Cc4cccc(OCCCO)c4C(=O)C3=C(O)[C@]2(O)C1=O]
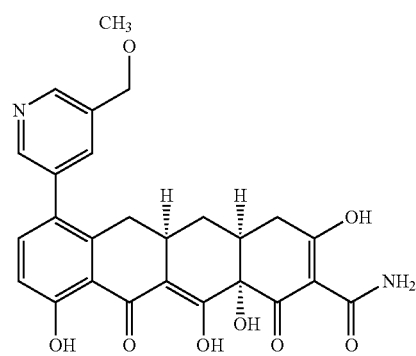
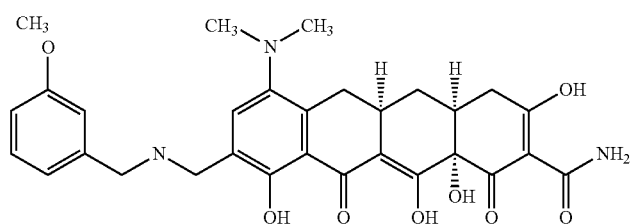
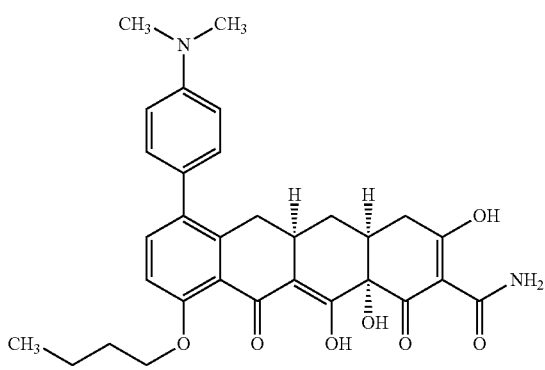 [SMILES: CCCCOc1ccc(-c2ccc(N(C)C)cc2)c2c1C(=O)C1=C(O)[C@]3(O)C(=O)C(C(N)=O)=C(O)C[C@@H]3C[C@@H]1C2]

TABLE 2-continued
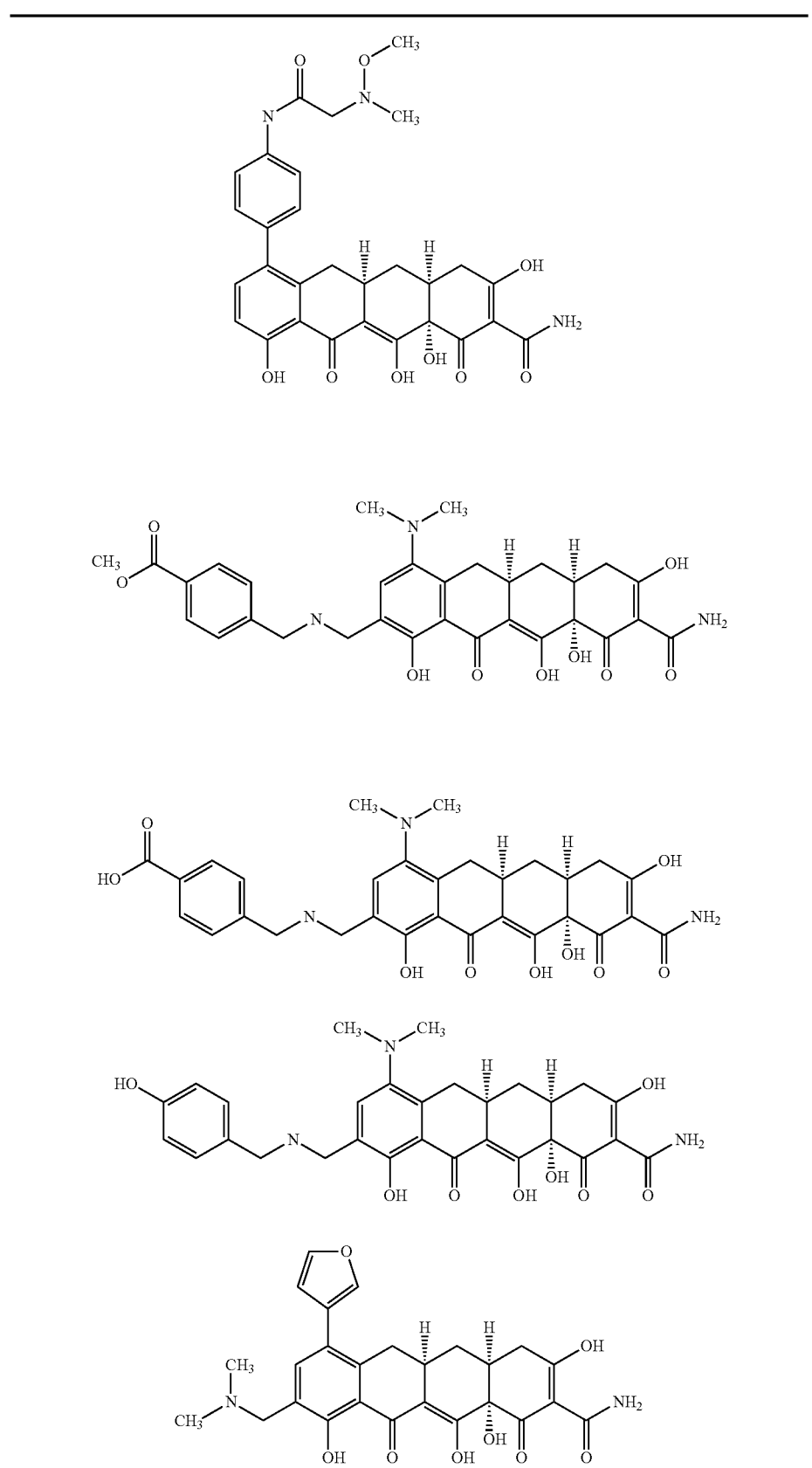

TABLE 2-continued
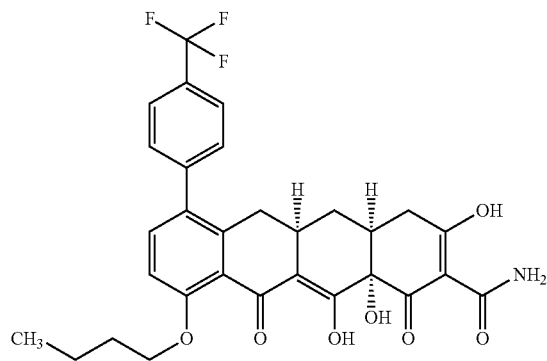 [SMILES: CCCCOc1ccc(-c2ccc(C(F)(F)F)cc2)c2c1C(=O)C1=C(O)[C@]3(O)C(=O)C(C(N)=O)=C(O)C[C@@H]3C[C@@H]1C2]
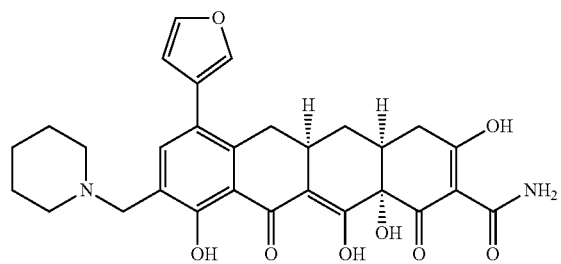 [SMILES: NC(=O)C1=C(O)C[C@@H]2C[C@@H]3Cc4c(-c5ccoc5)cc(CN5CCCCC5)c(O)c4C(=O)C3=C(O)[C@]2(O)C1=O]
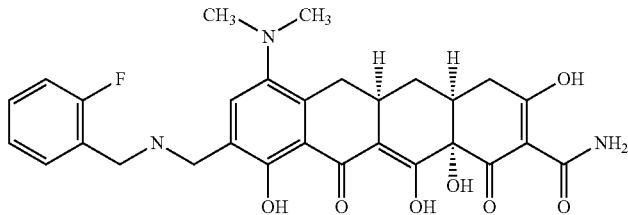 [SMILES: CN(C)c1cc(CNCc2ccccc2F)c(O)c2c1C[C@H]1C[C@H]3CC(O)=C(C(N)=O)C(=O)[C@@]3(O)C(O)=C1C2=O]
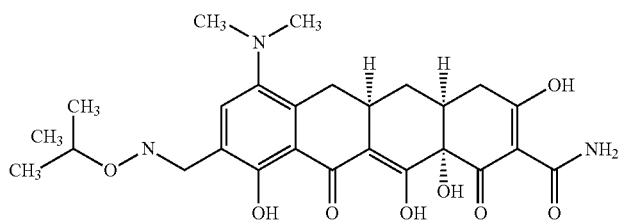
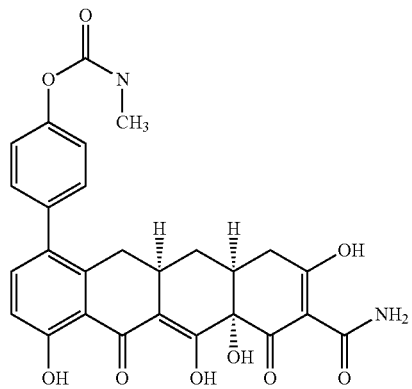 [SMILES: CNC(=O)Oc1ccc(-c2ccc(O)c3c2C[C@H]2C[C@H]4CC(O)=C(C(N)=O)C(=O)[C@@]4(O)C(O)=C2C3=O)cc1]

TABLE 2-continued
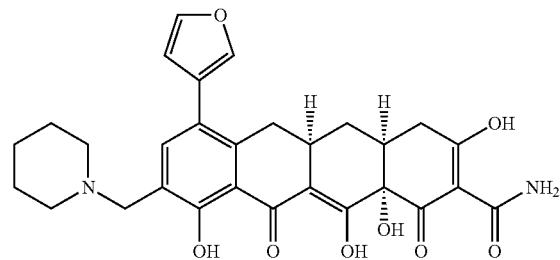 [SMILES: NC(=O)C1=C(O)C[C@@H]2C[C@@H]3Cc4c(-c5ccoc5)cc(CN5CCCCC5)c(O)c4C(=O)C3=C(O)[C@]2(O)C1=O]
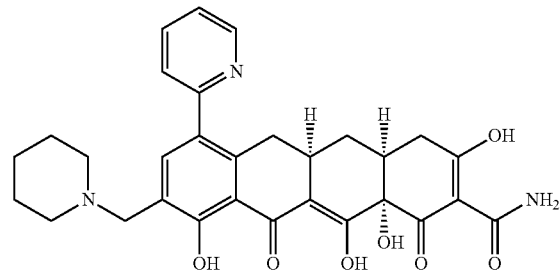 [SMILES: NC(=O)C1=C(O)C[C@@H]2C[C@@H]3Cc4c(-c5ccccn5)cc(CN5CCCCC5)c(O)c4C(=O)C3=C(O)[C@]2(O)C1=O]
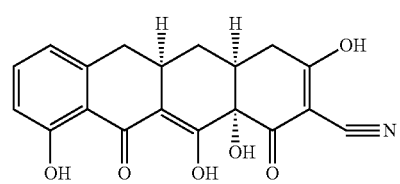 [SMILES: N#CC1=C(O)C[C@@H]2C[C@@H]3Cc4cccc(O)c4C(=O)C3=C(O)[C@]2(O)C1=O]
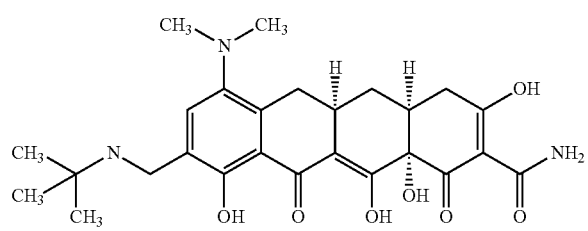 [SMILES: CN(C)c1cc(CNC(C)(C)C)c(O)c2c1C[C@H]1C[C@H]3CC(O)=C(C(N)=O)C(=O)[C@@]3(O)C(O)=C1C2=O]
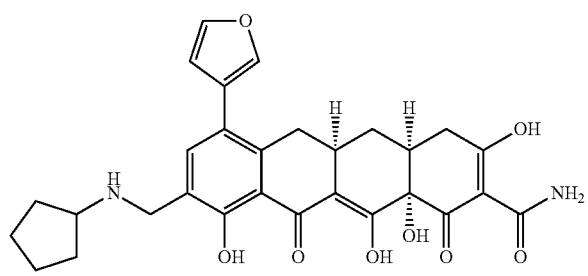 [SMILES: NC(=O)C1=C(O)C[C@@H]2C[C@@H]3Cc4c(-c5ccoc5)cc(CNC5CCCC5)c(O)c4C(=O)C3=C(O)[C@]2(O)C1=O]
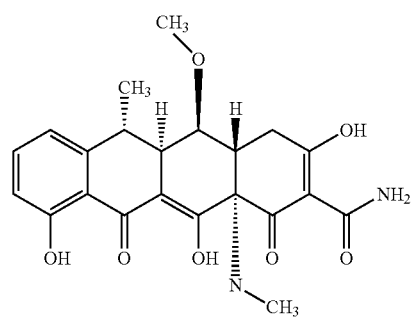 [SMILES: CN[C@@]12C(=O)C(C(N)=O)=C(O)C[C@H]1[C@H](OC)[C@H]1C(=C2O)C(=O)c2c(O)cccc2[C@@H]1C]

TABLE 2-continued
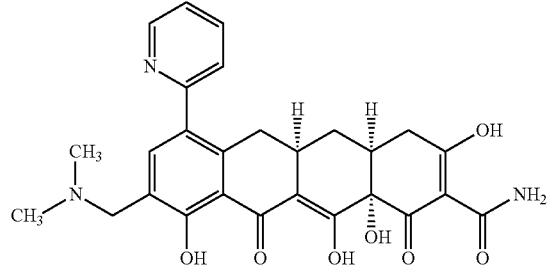 [SMILES: CN(C)Cc1cc(-c2ccccn2)c2c(c1O)C(=O)C1=C(O)[C@]3(O)C(=O)C(C(N)=O)=C(O)C[C@@H]3C[C@@H]1C2]
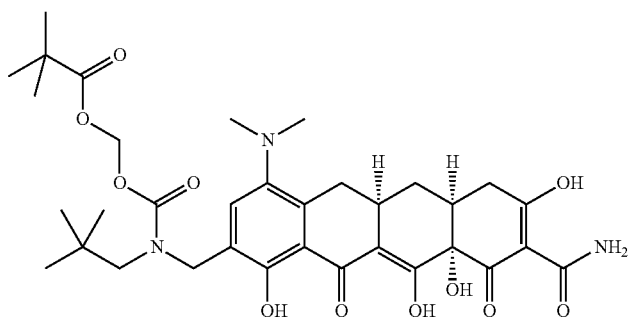 [SMILES: CN(C)c1cc(CN(CC(C)(C)C)C(=O)OCOC(=O)C(C)(C)C)c(O)c2c1C[C@H]1C[C@H]3CC(O)=C(C(N)=O)C(=O)[C@@]3(O)C(O)=C1C2=O]
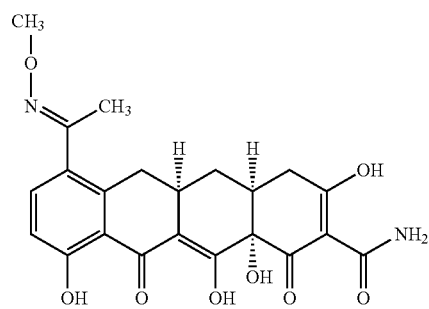 [SMILES: CO/N=C(\C)c1ccc(O)c2c1C[C@H]1C[C@H]3CC(O)=C(C(N)=O)C(=O)[C@@]3(O)C(O)=C1C2=O]
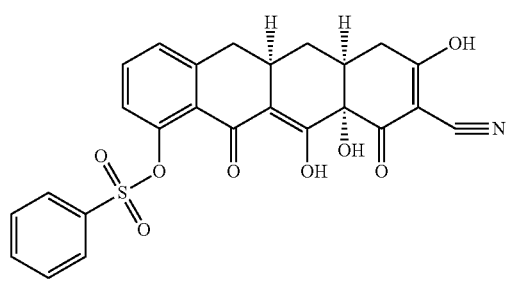 [SMILES: N#CC1=C(O)C[C@@H]2C[C@@H]3Cc4cccc(OS(=O)(=O)c5ccccc5)c4C(=O)C3=C(O)[C@]2(O)C1=O]
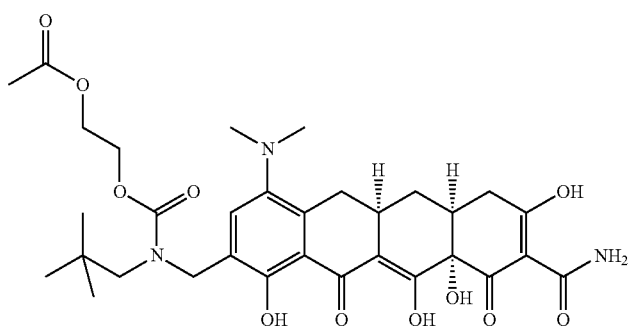 [SMILES: CC(=O)OCCOC(=O)N(Cc1cc(N(C)C)c2c(c1O)C(=O)C1=C(O)[C@]3(O)C(=O)C(C(N)=O)=C(O)C[C@@H]3C[C@@H]1C2)CC(C)(C)C]

TABLE 2-continued
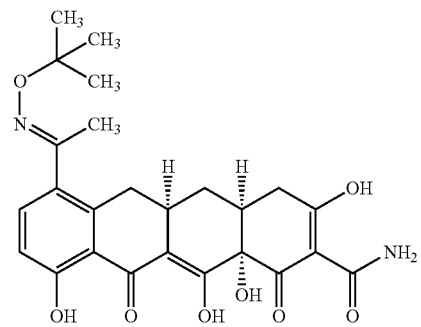 [SMILES: C/C(=N\OC(C)(C)C)c1ccc(O)c2c1C[C@H]1C[C@H]3CC(O)=C(C(N)=O)C(=O)[C@@]3(O)C(O)=C1C2=O]
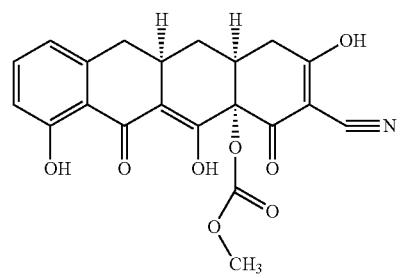 [SMILES: COC(=O)O[C@@]12C(=O)C(C#N)=C(O)C[C@@H]1C[C@@H]1Cc3cccc(O)c3C(=O)C1=C2O]
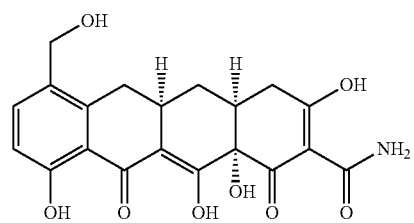
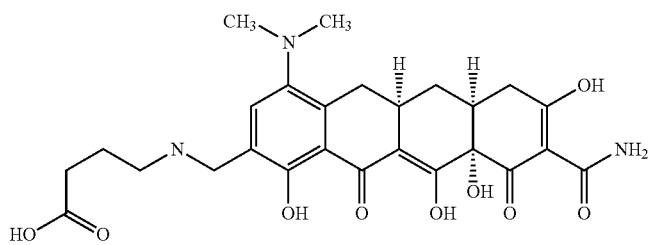 [SMILES: CN(C)c1cc(CNCCCC(=O)O)c(O)c2c1C[C@H]1C[C@H]3CC(O)=C(C(N)=O)C(=O)[C@@]3(O)C(O)=C1C2=O]
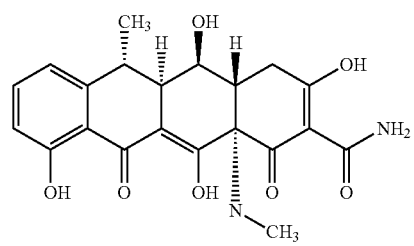 [SMILES: CN[C@@]12C(=O)C(C(N)=O)=C(O)C[C@H]1[C@H](O)[C@H]1C(=C2O)C(=O)c2c(O)cccc2[C@@H]1C]
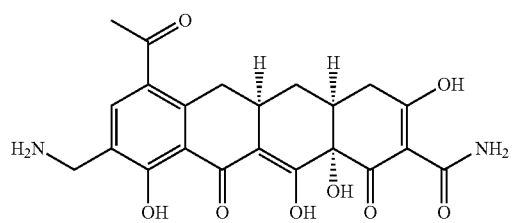 [SMILES: CC(=O)c1cc(CN)c(O)c2c1C[C@H]1C[C@H]3CC(O)=C(C(N)=O)C(=O)[C@@]3(O)C(O)=C1C2=O]

TABLE 2-continued
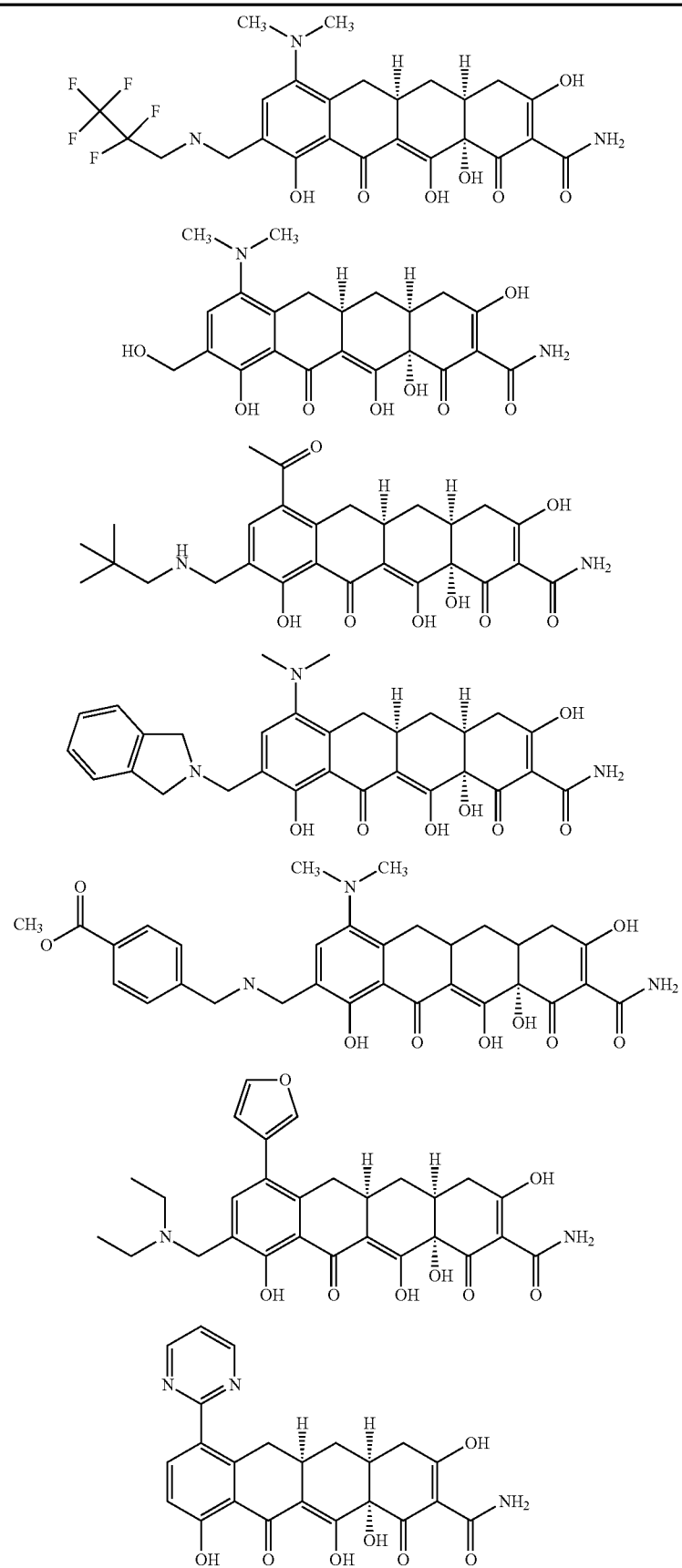

TABLE 2-continued
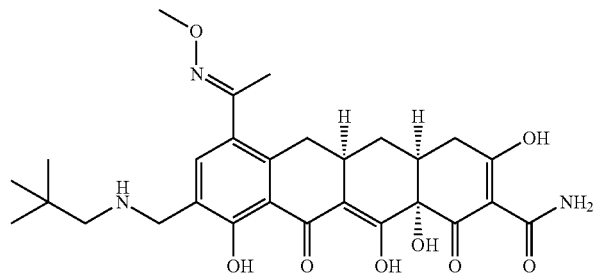 [SMILES: CO/N=C(\C)c1cc(CNCC(C)(C)C)c(O)c2c1C[C@H]1C[C@H]3CC(O)=C(C(N)=O)C(=O)[C@@]3(O)C(O)=C1C2=O]
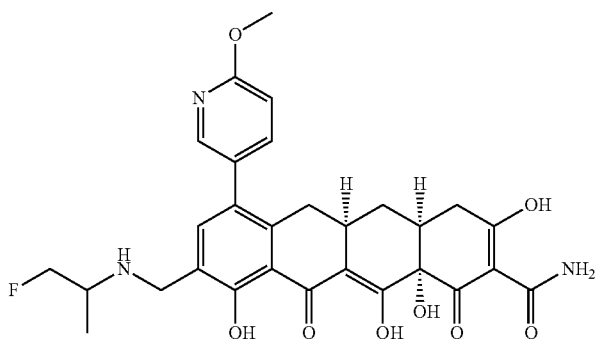 [SMILES: COc1ccc(-c2cc(CNC(C)CF)c(O)c3c2C[C@H]2C[C@H]4CC(O)=C(C(N)=O)C(=O)[C@@]4(O)C(O)=C2C3=O)cn1]
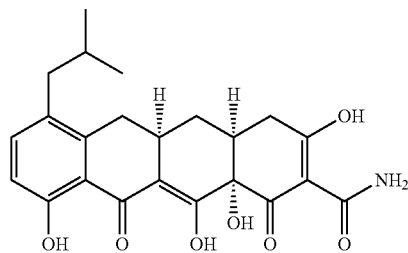 [SMILES: CC(C)Cc1ccc(O)c2c1C[C@H]1C[C@H]3CC(O)=C(C(N)=O)C(=O)[C@@]3(O)C(O)=C1C2=O]
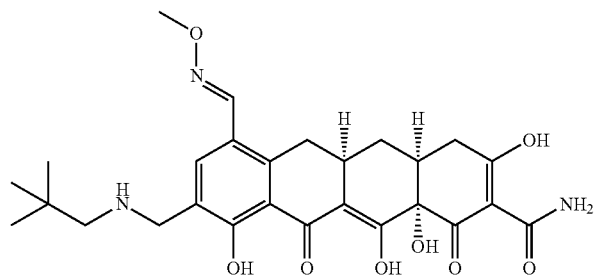 [SMILES: CO/N=C/c1cc(CNCC(C)(C)C)c(O)c2c1C[C@H]1C[C@H]3CC(O)=C(C(N)=O)C(=O)[C@@]3(O)C(O)=C1C2=O]
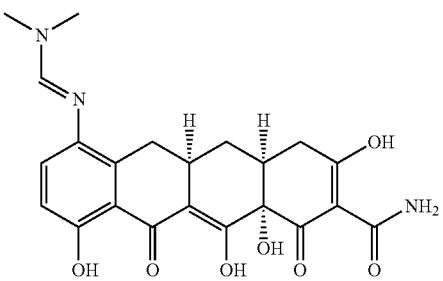 [SMILES: CN(C)/C=N/c1ccc(O)c2c1C[C@H]1C[C@H]3CC(O)=C(C(N)=O)C(=O)[C@@]3(O)C(O)=C1C2=O]

TABLE 2-continued
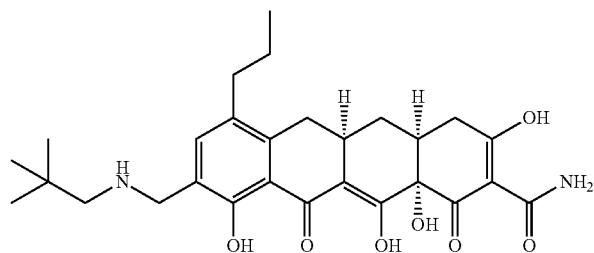 [SMILES: CCCc1cc(CNCC(C)(C)C)c(O)c2c1C[C@H]1C[C@H]3CC(O)=C(C(N)=O)C(=O)[C@@]3(O)C(O)=C1C2=O]
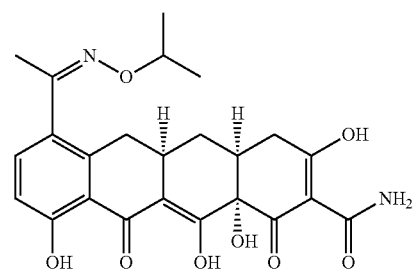 [SMILES: C/C(=N/OC(C)C)c1ccc(O)c2c1C[C@H]1C[C@H]3CC(O)=C(C(N)=O)C(=O)[C@@]3(O)C(O)=C1C2=O]
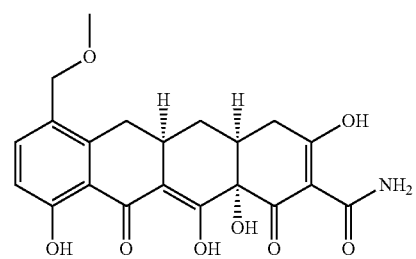 [SMILES: COCc1ccc(O)c2c1C[C@H]1C[C@H]3CC(O)=C(C(N)=O)C(=O)[C@@]3(O)C(O)=C1C2=O]
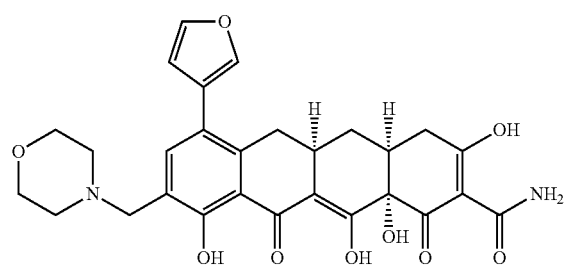 [SMILES: NC(=O)C1=C(O)C[C@@H]2C[C@@H]3Cc4c(-c5ccoc5)cc(CN5CCOCC5)c(O)c4C(=O)C3=C(O)[C@]2(O)C1=O]
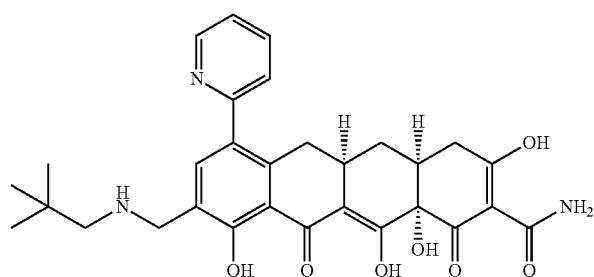 [SMILES: CC(C)(C)CNCc1cc(-c2ccccn2)c2c(c1O)C(=O)C1=C(O)[C@]3(O)C(=O)C(C(N)=O)=C(O)C[C@@H]3C[C@@H]1C2]
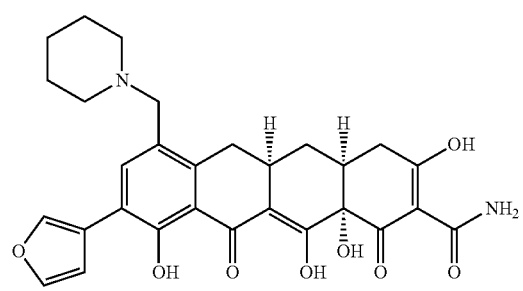 [SMILES: NC(=O)C1=C(O)C[C@@H]2C[C@@H]3Cc4c(CN5CCCCC5)cc(-c5ccoc5)c(O)c4C(=O)C3=C(O)[C@]2(O)C1=O]

TABLE 2-continued
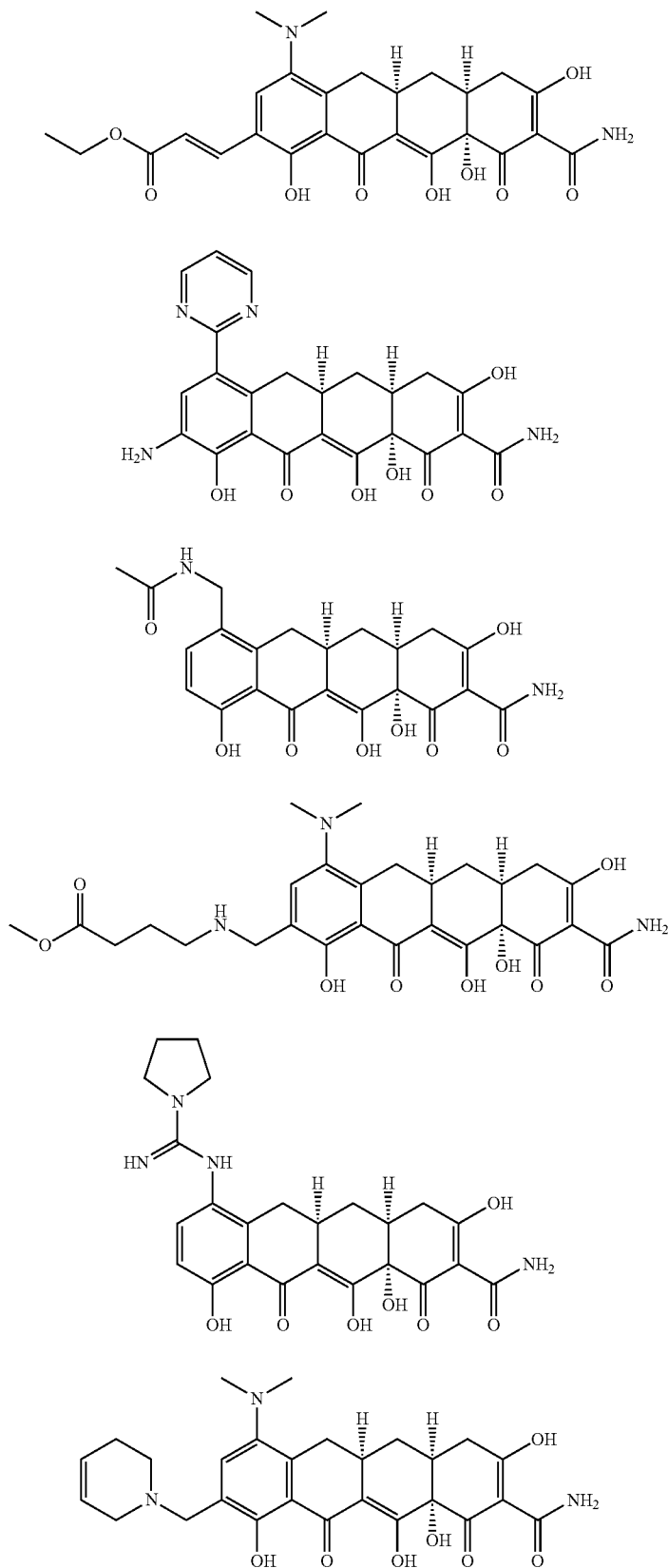

TABLE 2-continued
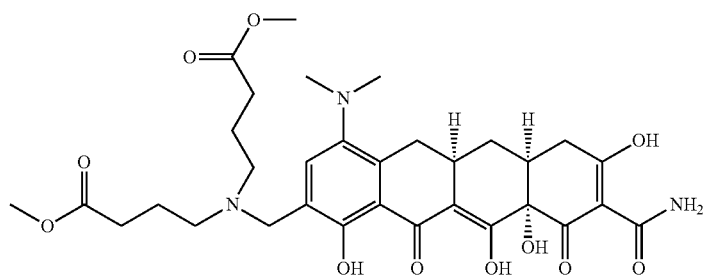 [SMILES: COC(=O)CCCN(CCCC(=O)OC)Cc1cc(N(C)C)c2c(c1O)C(=O)C1=C(O)[C@]3(O)C(=O)C(C(N)=O)=C(O)C[C@@H]3C[C@@H]1C2]
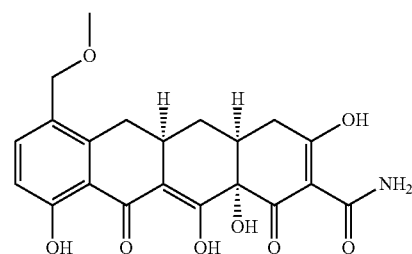
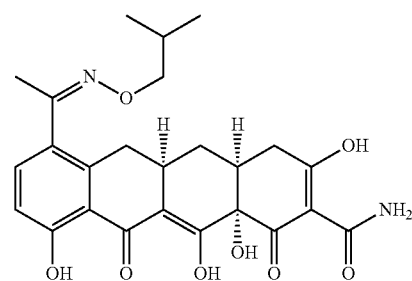 [SMILES: C/C(=N/OCC(C)C)c1ccc(O)c2c1C[C@H]1C[C@H]3CC(O)=C(C(N)=O)C(=O)[C@@]3(O)C(O)=C1C2=O]
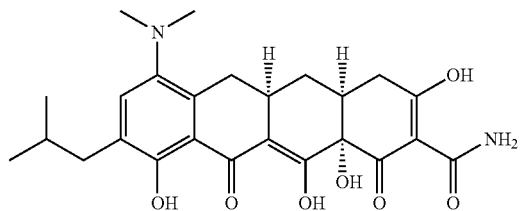 [SMILES: CC(C)Cc1cc(N(C)C)c2c(c1O)C(=O)C1=C(O)[C@]3(O)C(=O)C(C(N)=O)=C(O)C[C@@H]3C[C@@H]1C2]
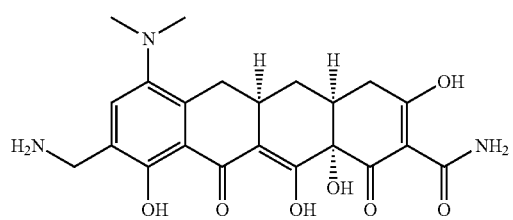 [SMILES: CN(C)c1cc(CN)c(O)c2c1C[C@H]1C[C@H]3CC(O)=C(C(N)=O)C(=O)[C@@]3(O)C(O)=C1C2=O]
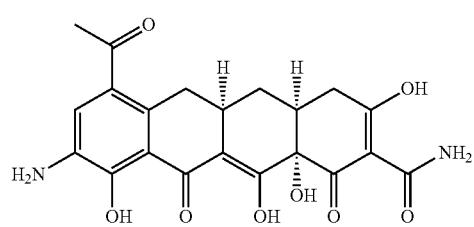 [SMILES: CC(=O)c1cc(N)c(O)c2c1C[C@H]1C[C@H]3CC(O)=C(C(N)=O)C(=O)[C@@]3(O)C(O)=C1C2=O]

TABLE 2-continued
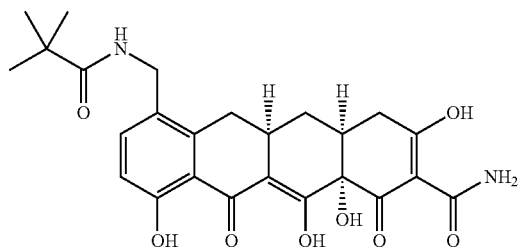 [SMILES: CC(C)(C)C(=O)NCc1ccc(O)c2c1C[C@H]1C[C@H]3CC(O)=C(C(N)=O)C(=O)[C@@]3(O)C(O)=C1C2=O]
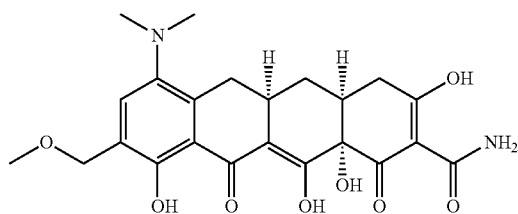 [SMILES: COCc1cc(N(C)C)c2c(c1O)C(=O)C1=C(O)[C@]3(O)C(=O)C(C(N)=O)=C(O)C[C@@H]3C[C@@H]1C2]
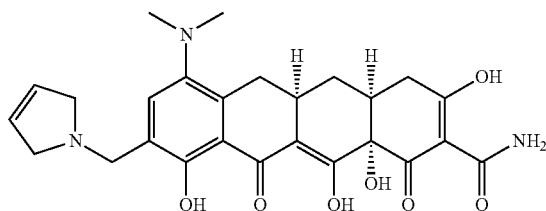 [SMILES: CN(C)c1cc(CN2CC=CC2)c(O)c2c1C[C@H]1C[C@H]3CC(O)=C(C(N)=O)C(=O)[C@@]3(O)C(O)=C1C2=O]
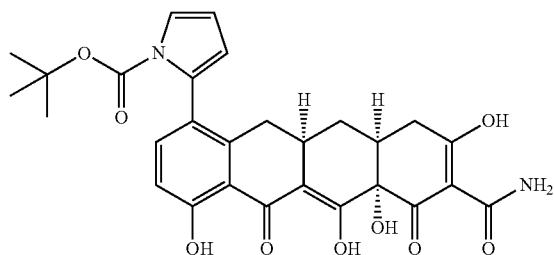 [SMILES: CC(C)(C)OC(=O)n1cccc1-c1ccc(O)c2c1C[C@H]1C[C@H]3CC(O)=C(C(N)=O)C(=O)[C@@]3(O)C(O)=C1C2=O]
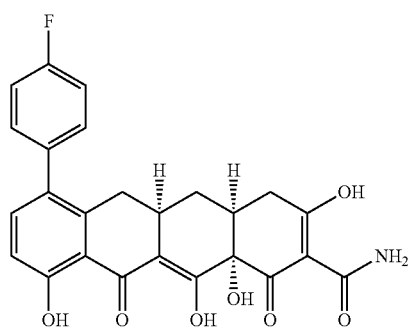 [SMILES: NC(=O)C1=C(O)C[C@@H]2C[C@@H]3Cc4c(-c5ccc(F)cc5)ccc(O)c4C(=O)C3=C(O)[C@]2(O)C1=O]
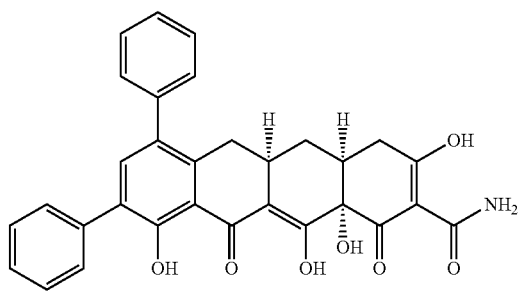 [SMILES: NC(=O)C1=C(O)C[C@@H]2C[C@@H]3Cc4c(-c5ccccc5)cc(-c5ccccc5)c(O)c4C(=O)C3=C(O)[C@]2(O)C1=O]

TABLE 2-continued
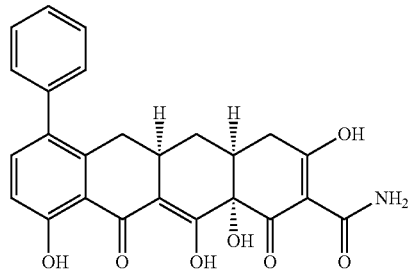 [SMILES: NC(=O)C1=C(O)C[C@@H]2C[C@@H]3Cc4c(-c5ccccc5)ccc(O)c4C(=O)C3=C(O)[C@]2(O)C1=O]
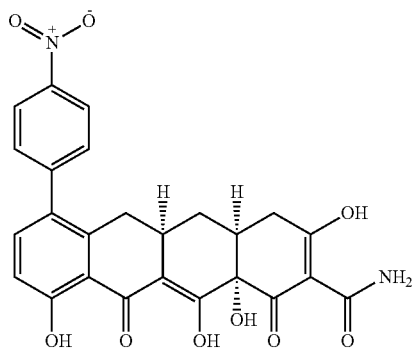
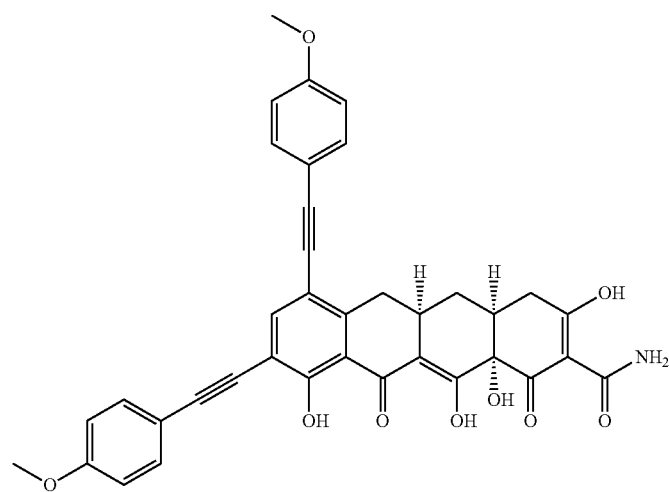 [SMILES: COc1ccc(C#Cc2cc(C#Cc3ccc(OC)cc3)c3c(c2O)C(=O)C2=C(O)[C@]4(O)C(=O)C(C(N)=O)=C(O)C[C@@H]4C[C@@H]2C3)cc1]
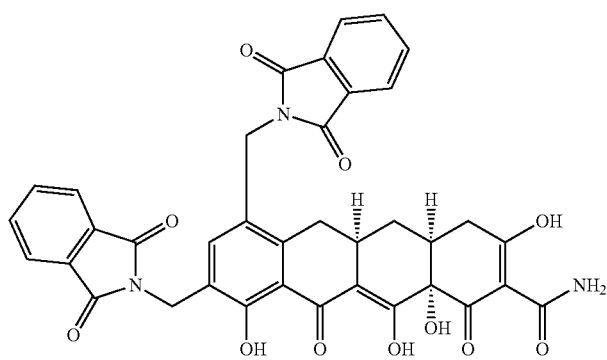 [SMILES: NC(=O)C1=C(O)C[C@@H]2C[C@@H]3Cc4c(CN5C(=O)c6ccccc6C5=O)cc(CN5C(=O)c6ccccc6C5=O)c(O)c4C(=O)C3=C(O)[C@]2(O)C1=O]

TABLE 2-continued
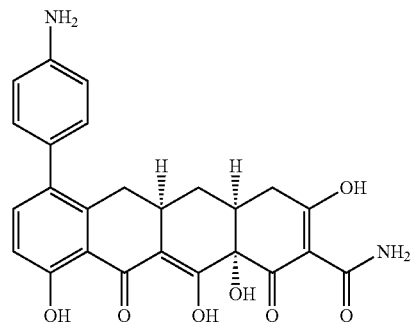 [SMILES: NC(=O)C1=C(O)C[C@@H]2C[C@@H]3Cc4c(-c5ccc(N)cc5)ccc(O)c4C(=O)C3=C(O)[C@]2(O)C1=O]
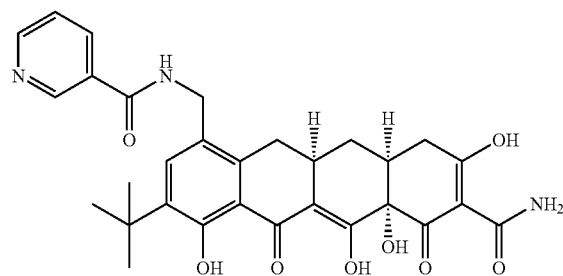 [SMILES: CC(C)(C)c1cc(CNC(=O)c2cccnc2)c2c(c1O)C(=O)C1=C(O)[C@]3(O)C(=O)C(C(N)=O)=C(O)C[C@@H]3C[C@@H]1C2]
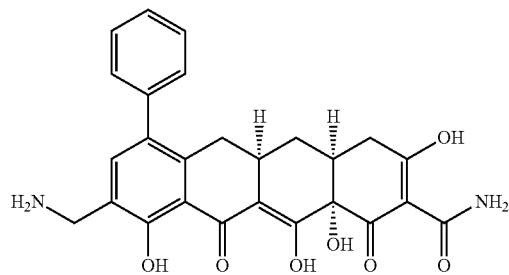 [SMILES: NCc1cc(-c2ccccc2)c2c(c1O)C(=O)C1=C(O)[C@]3(O)C(=O)C(C(N)=O)=C(O)C[C@@H]3C[C@@H]1C2]
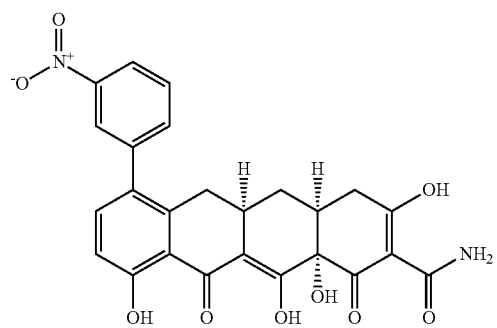
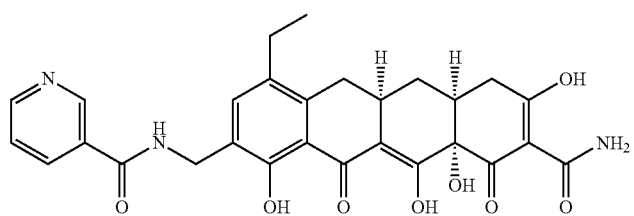 [SMILES: CCc1cc(CNC(=O)c2cccnc2)c(O)c2c1C[C@H]1C[C@H]3CC(O)=C(C(N)=O)C(=O)[C@@]3(O)C(O)=C1C2=O]

TABLE 2-continued
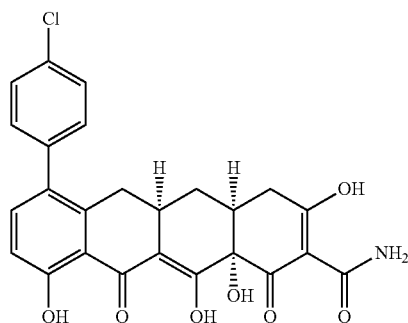 [SMILES: NC(=O)C1=C(O)C[C@@H]2C[C@@H]3Cc4c(-c5ccc(Cl)cc5)ccc(O)c4C(=O)C3=C(O)[C@]2(O)C1=O]
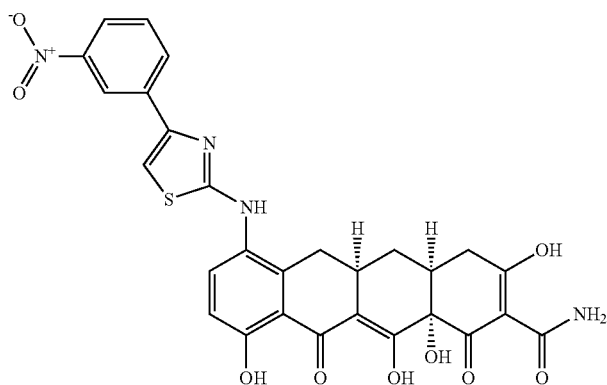
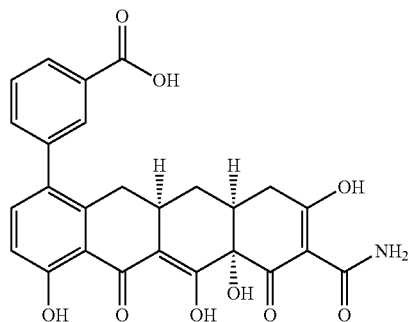 [SMILES: NC(=O)C1=C(O)C[C@@H]2C[C@@H]3Cc4c(-c5cccc(C(=O)O)c5)ccc(O)c4C(=O)C3=C(O)[C@]2(O)C1=O]
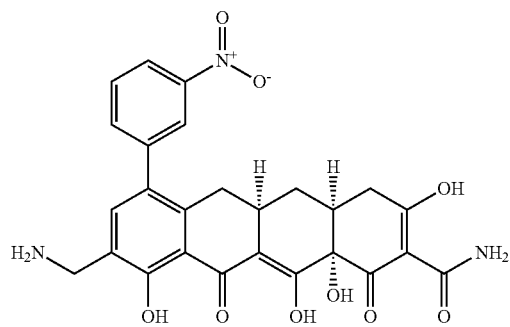 [SMILES: NCc1cc(-c2cccc([N+](=O)[O-])c2)c2c(c1O)C(=O)C1=C(O)[C@]3(O)C(=O)C(C(N)=O)=C(O)C[C@@H]3C[C@@H]1C2]

TABLE 2-continued
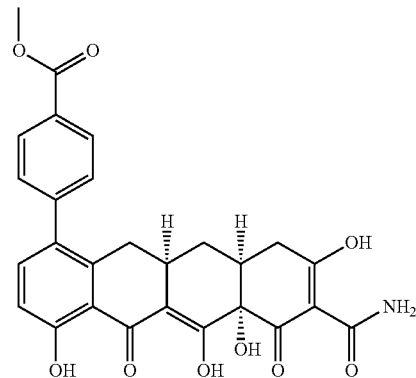 [SMILES: COC(=O)c1ccc(-c2ccc(O)c3c2C[C@H]2C[C@H]4CC(O)=C(C(N)=O)C(=O)[C@@]4(O)C(O)=C2C3=O)cc1]
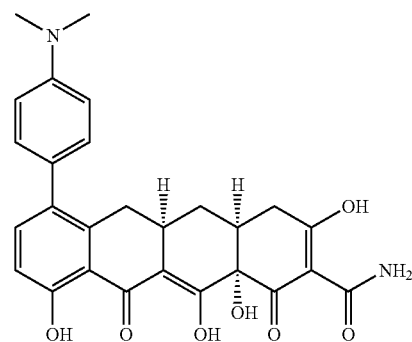 [SMILES: CN(C)c1ccc(-c2ccc(O)c3c2C[C@H]2C[C@H]4CC(O)=C(C(N)=O)C(=O)[C@@]4(O)C(O)=C2C3=O)cc1]
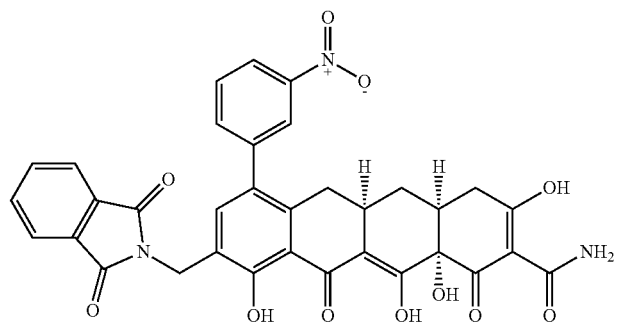
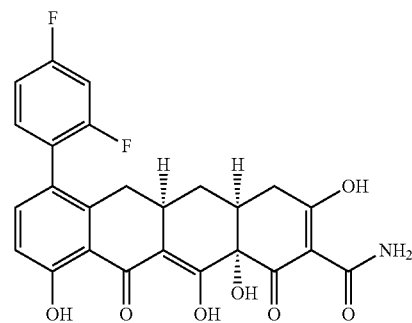 [SMILES: NC(=O)C1=C(O)C[C@@H]2C[C@@H]3Cc4c(-c5ccc(F)cc5F)ccc(O)c4C(=O)C3=C(O)[C@]2(O)C1=O]

TABLE 2-continued
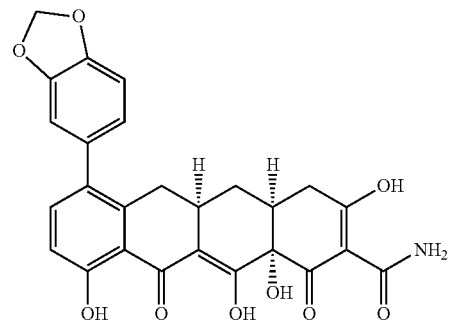 [SMILES: NC(=O)C1=C(O)C[C@@H]2C[C@@H]3Cc4c(-c5ccc6c(c5)OCO6)ccc(O)c4C(=O)C3=C(O)[C@]2(O)C1=O]
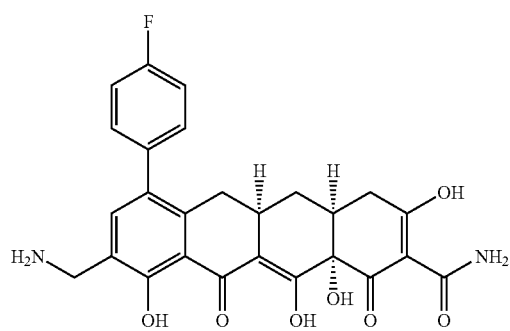 [SMILES: NCc1cc(-c2ccc(F)cc2)c2c(c1O)C(=O)C1=C(O)[C@]3(O)C(=O)C(C(N)=O)=C(O)C[C@@H]3C[C@@H]1C2]
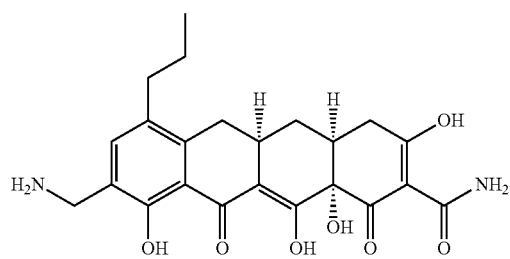 [SMILES: CCCc1cc(CN)c(O)c2c1C[C@H]1C[C@H]3CC(O)=C(C(N)=O)C(=O)[C@@]3(O)C(O)=C1C2=O]
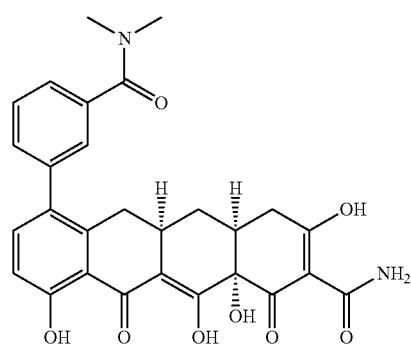 [SMILES: CN(C)C(=O)c1cccc(-c2ccc(O)c3c2C[C@H]2C[C@H]4CC(O)=C(C(N)=O)C(=O)[C@@]4(O)C(O)=C2C3=O)c1]
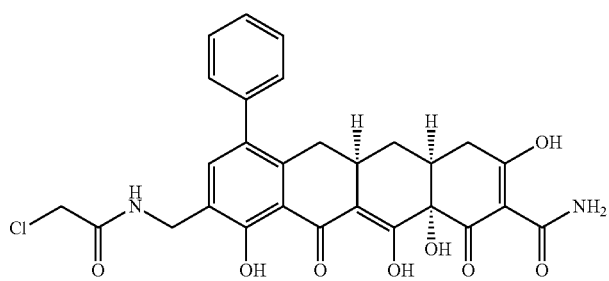 [SMILES: NC(=O)C1=C(O)C[C@@H]2C[C@@H]3Cc4c(-c5ccccc5)cc(CNC(=O)CCl)c(O)c4C(=O)C3=C(O)[C@]2(O)C1=O]

TABLE 2-continued
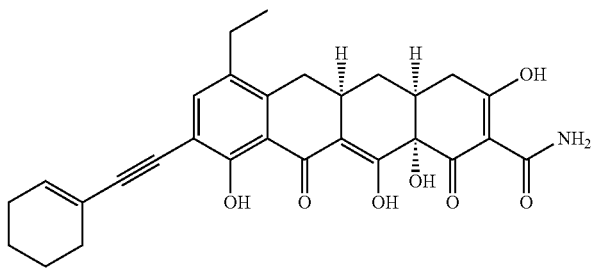 [SMILES: CCc1cc(C#CC2=CCCCC2)c(O)c2c1C[C@H]1C[C@H]3CC(O)=C(C(N)=O)C(=O)[C@@]3(O)C(O)=C1C2=O]
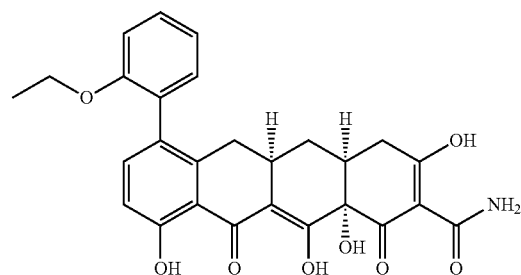 [SMILES: CCOc1ccccc1-c1ccc(O)c2c1C[C@H]1C[C@H]3CC(O)=C(C(N)=O)C(=O)[C@@]3(O)C(O)=C1C2=O]
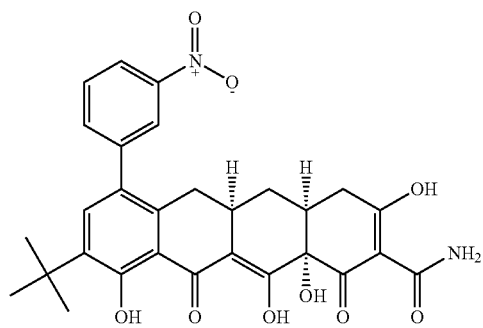
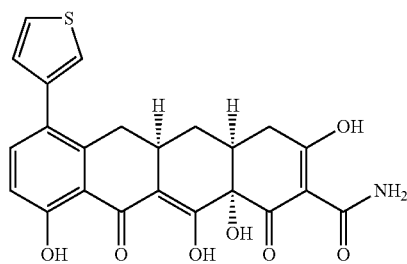 [SMILES: NC(=O)C1=C(O)C[C@@H]2C[C@@H]3Cc4c(-c5ccsc5)ccc(O)c4C(=O)C3=C(O)[C@]2(O)C1=O]
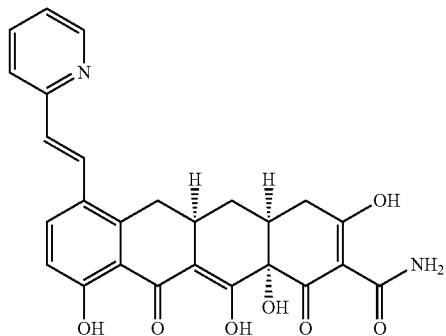 [SMILES: NC(=O)C1=C(O)C[C@@H]2C[C@@H]3Cc4c(/C=C/c5ccccn5)ccc(O)c4C(=O)C3=C(O)[C@]2(O)C1=O]

TABLE 2-continued
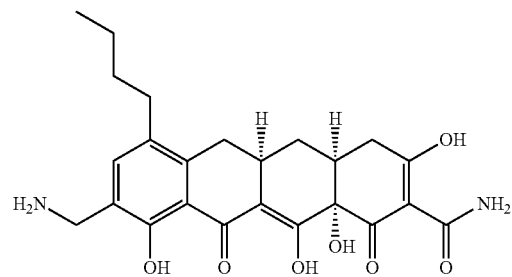 [SMILES: CCCCc1cc(CN)c(O)c2c1C[C@H]1C[C@H]3CC(O)=C(C(N)=O)C(=O)[C@@]3(O)C(O)=C1C2=O]
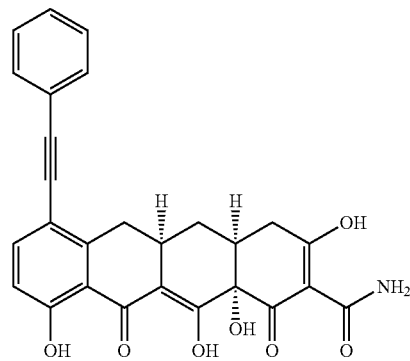 [SMILES: NC(=O)C1=C(O)C[C@@H]2C[C@@H]3Cc4c(C#Cc5ccccc5)ccc(O)c4C(=O)C3=C(O)[C@]2(O)C1=O]
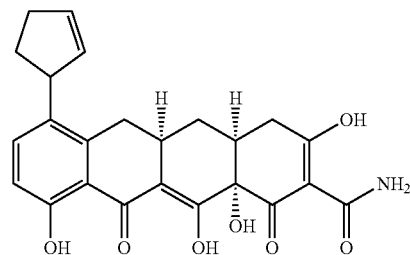 [SMILES: NC(=O)C1=C(O)C[C@@H]2C[C@@H]3Cc4c(C5C=CCC5)ccc(O)c4C(=O)C3=C(O)[C@]2(O)C1=O]
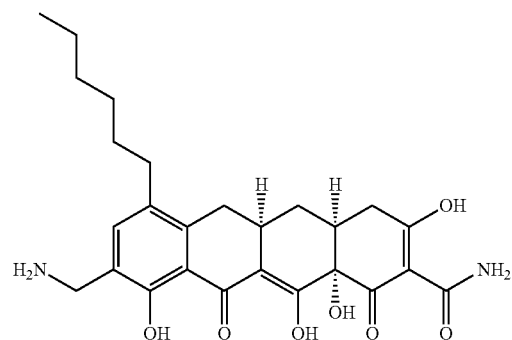 [SMILES: CCCCCCc1cc(CN)c(O)c2c1C[C@H]1C[C@H]3CC(O)=C(C(N)=O)C(=O)[C@@]3(O)C(O)=C1C2=O]
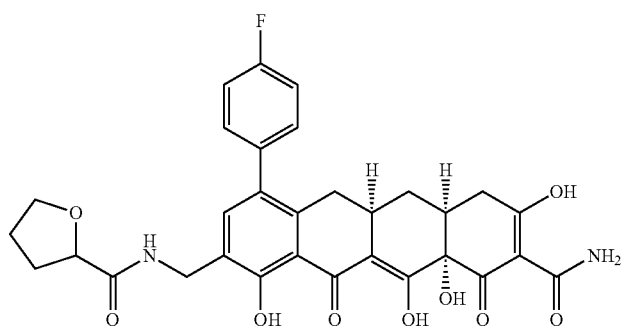 [SMILES: NC(=O)C1=C(O)C[C@@H]2C[C@@H]3Cc4c(-c5ccc(F)cc5)cc(CNC(=O)C5CCCO5)c(O)c4C(=O)C3=C(O)[C@]2(O)C1=O]

TABLE 2-continued
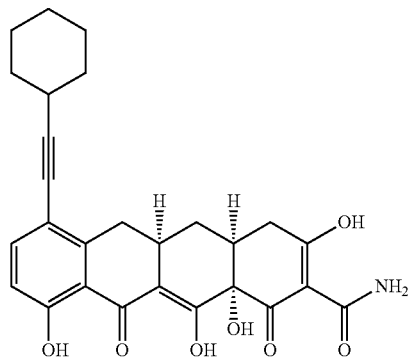 [SMILES: NC(=O)C1=C(O)C[C@@H]2C[C@@H]3Cc4c(C#CC5CCCCC5)ccc(O)c4C(=O)C3=C(O)[C@]2(O)C1=O]
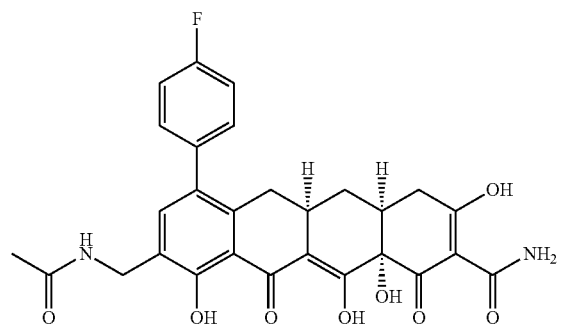 [SMILES: CC(=O)NCc1cc(-c2ccc(F)cc2)c2c(c1O)C(=O)C1=C(O)[C@]3(O)C(=O)C(C(N)=O)=C(O)C[C@@H]3C[C@@H]1C2]
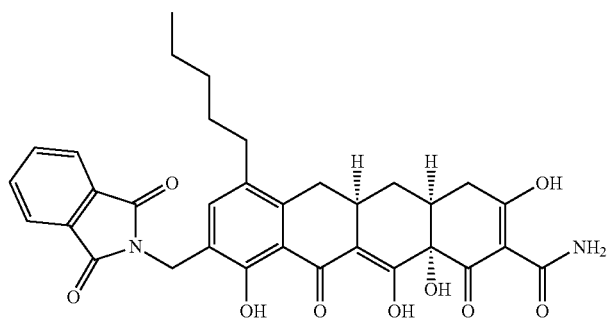 [SMILES: CCCCCc1cc(CN2C(=O)c3ccccc3C2=O)c(O)c2c1C[C@H]1C[C@H]3CC(O)=C(C(N)=O)C(=O)[C@@]3(O)C(O)=C1C2=O]
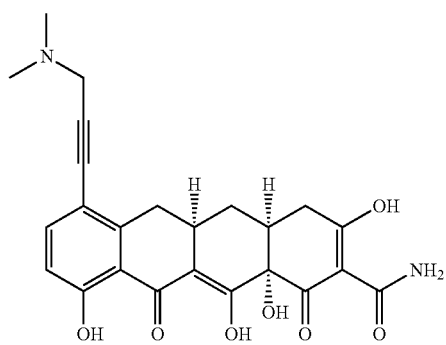 [SMILES: CN(C)CC#Cc1ccc(O)c2c1C[C@H]1C[C@H]3CC(O)=C(C(N)=O)C(=O)[C@@]3(O)C(O)=C1C2=O]
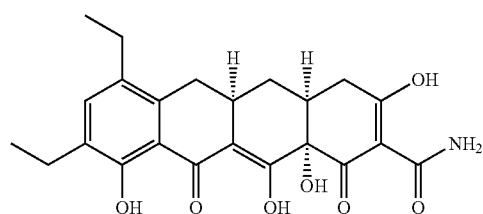 [SMILES: CCc1cc(CC)c2c(c1O)C(=O)C1=C(O)[C@]3(O)C(=O)C(C(N)=O)=C(O)C[C@@H]3C[C@@H]1C2]

TABLE 2-continued
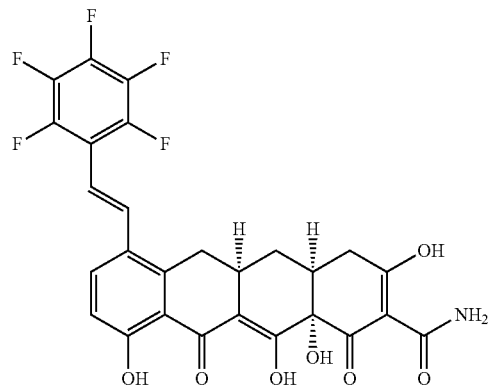 [SMILES: NC(=O)C1=C(O)C[C@@H]2C[C@@H]3Cc4c(/C=C/c5c(F)c(F)c(F)c(F)c5F)ccc(O)c4C(=O)C3=C(O)[C@]2(O)C1=O]
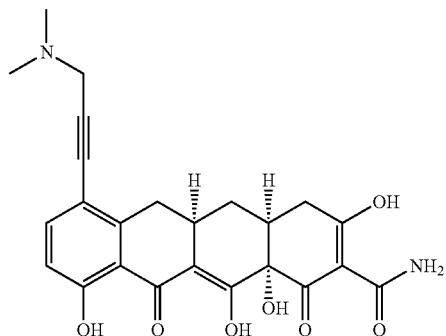 [SMILES: CN(C)CC#Cc1ccc(O)c2c1C[C@H]1C[C@H]3CC(O)=C(C(N)=O)C(=O)[C@@]3(O)C(O)=C1C2=O]
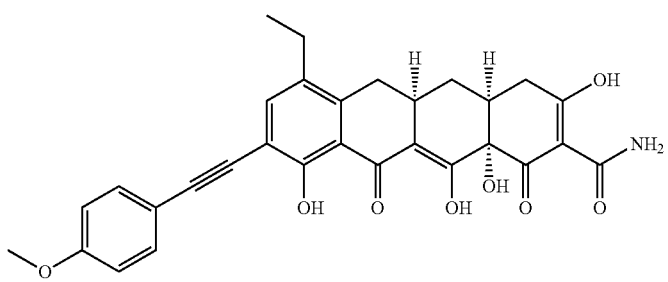 [SMILES: CCc1cc(C#Cc2ccc(OC)cc2)c(O)c2c1C[C@H]1C[C@H]3CC(O)=C(C(N)=O)C(=O)[C@@]3(O)C(O)=C1C2=O]
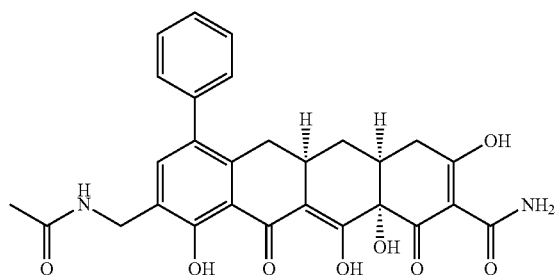 [SMILES: CC(=O)NCc1cc(-c2ccccc2)c2c(c1O)C(=O)C1=C(O)[C@]3(O)C(=O)C(C(N)=O)=C(O)C[C@@H]3C[C@@H]1C2]
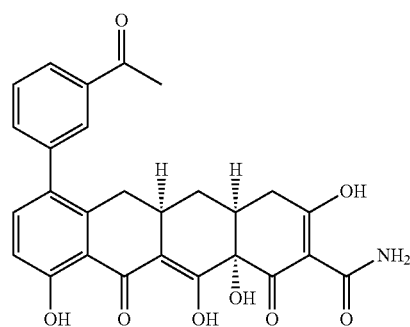 [SMILES: CC(=O)c1cccc(-c2ccc(O)c3c2C[C@H]2C[C@H]4CC(O)=C(C(N)=O)C(=O)[C@@]4(O)C(O)=C2C3=O)c1]

TABLE 2-continued
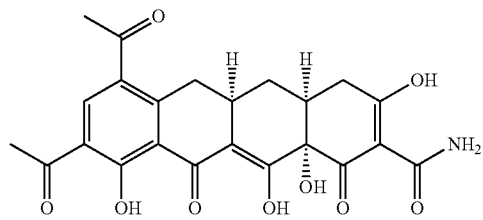 [SMILES: CC(=O)c1cc(C(C)=O)c2c(c1O)C(=O)C1=C(O)[C@]3(O)C(=O)C(C(N)=O)=C(O)C[C@@H]3C[C@@H]1C2]
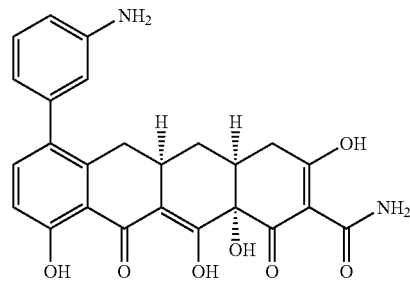 [SMILES: NC(=O)C1=C(O)C[C@@H]2C[C@@H]3Cc4c(-c5cccc(N)c5)ccc(O)c4C(=O)C3=C(O)[C@]2(O)C1=O]
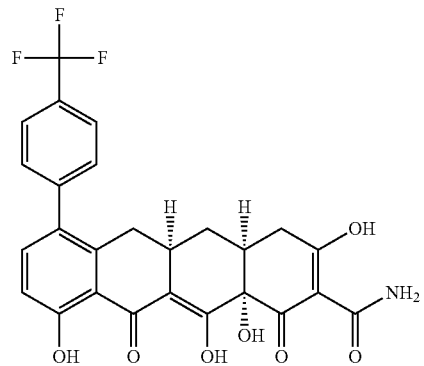 [SMILES: NC(=O)C1=C(O)C[C@@H]2C[C@@H]3Cc4c(-c5ccc(C(F)(F)F)cc5)ccc(O)c4C(=O)C3=C(O)[C@]2(O)C1=O]
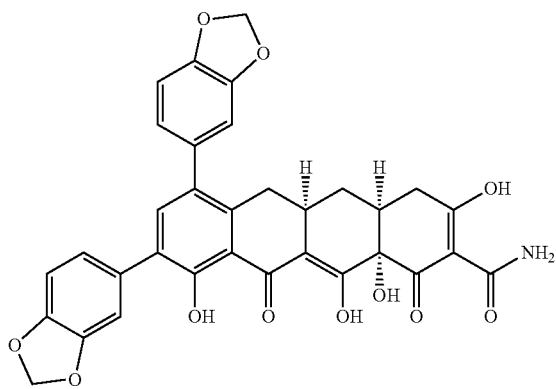 [SMILES: NC(=O)C1=C(O)C[C@@H]2C[C@@H]3Cc4c(-c5ccc6c(c5)OCO6)cc(-c5ccc6c(c5)OCO6)c(O)c4C(=O)C3=C(O)[C@]2(O)C1=O]
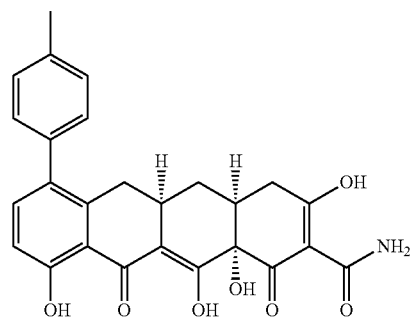 [SMILES: Cc1ccc(-c2ccc(O)c3c2C[C@H]2C[C@H]4CC(O)=C(C(N)=O)C(=O)[C@@]4(O)C(O)=C2C3=O)cc1]

TABLE 2-continued
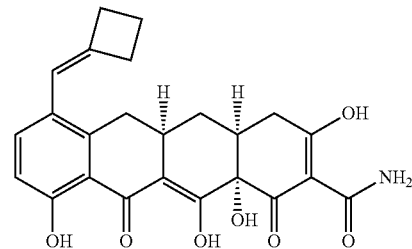 [SMILES: NC(=O)C1=C(O)C[C@@H]2C[C@@H]3Cc4c(C=C5CCC5)ccc(O)c4C(=O)C3=C(O)[C@]2(O)C1=O]
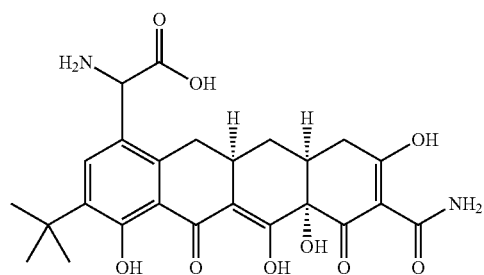 [SMILES: CC(C)(C)c1cc(C(N)C(=O)O)c2c(c1O)C(=O)C1=C(O)[C@]3(O)C(=O)C(C(N)=O)=C(O)C[C@@H]3C[C@@H]1C2]
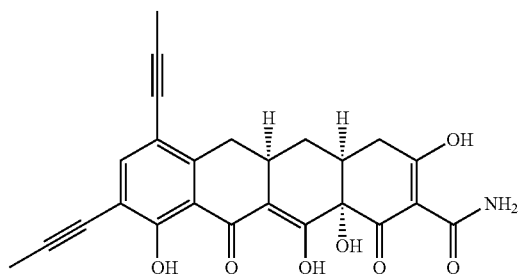 [SMILES: CC#Cc1cc(C#CC)c2c(c1O)C(=O)C1=C(O)[C@]3(O)C(=O)C(C(N)=O)=C(O)C[C@@H]3C[C@@H]1C2]
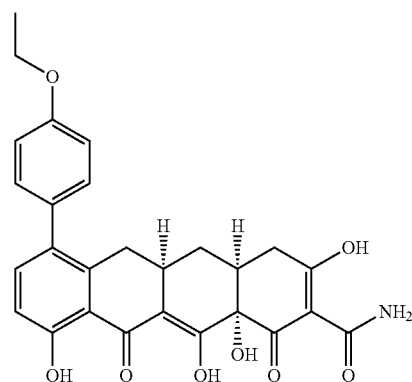 [SMILES: CCOc1ccc(-c2ccc(O)c3c2C[C@H]2C[C@H]4CC(O)=C(C(N)=O)C(=O)[C@@]4(O)C(O)=C2C3=O)cc1]
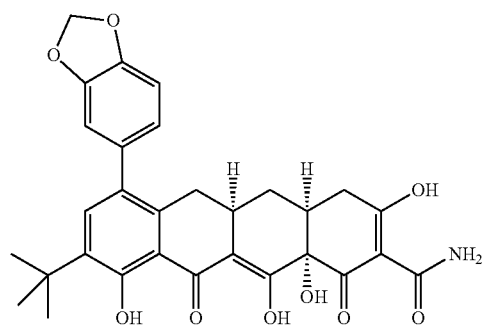 [SMILES: CC(C)(C)c1cc(-c2ccc3c(c2)OCO3)c2c(c1O)C(=O)C1=C(O)[C@]3(O)C(=O)C(C(N)=O)=C(O)C[C@@H]3C[C@@H]1C2]

TABLE 2-continued
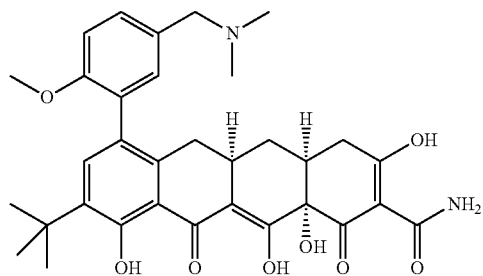 [SMILES: COc1ccc(CN(C)C)cc1-c1cc(C(C)(C)C)c(O)c2c1C[C@H]1C[C@H]3CC(O)=C(C(N)=O)C(=O)[C@@]3(O)C(O)=C1C2=O]
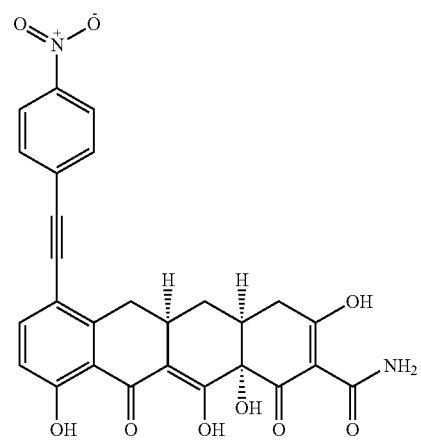
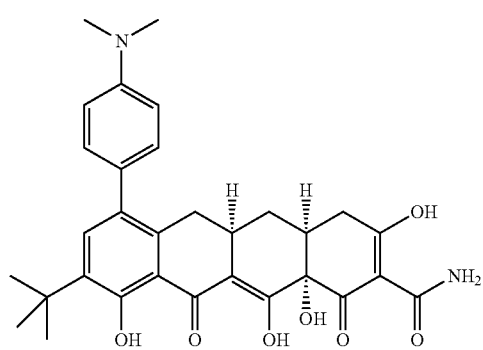 [SMILES: CN(C)c1ccc(-c2cc(C(C)(C)C)c(O)c3c2C[C@H]2C[C@H]4CC(O)=C(C(N)=O)C(=O)[C@@]4(O)C(O)=C2C3=O)cc1]
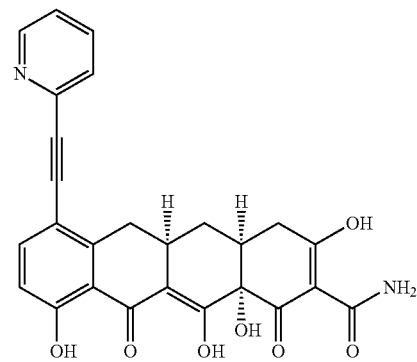 [SMILES: NC(=O)C1=C(O)C[C@@H]2C[C@@H]3Cc4c(C#Cc5ccccn5)ccc(O)c4C(=O)C3=C(O)[C@]2(O)C1=O]

TABLE 2-continued
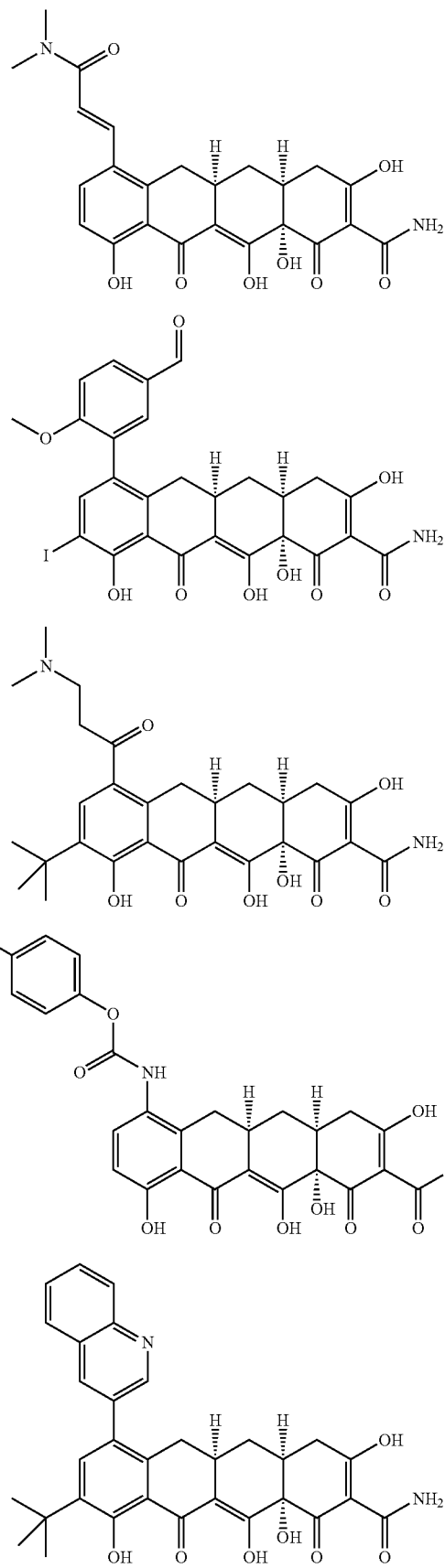

TABLE 2-continued
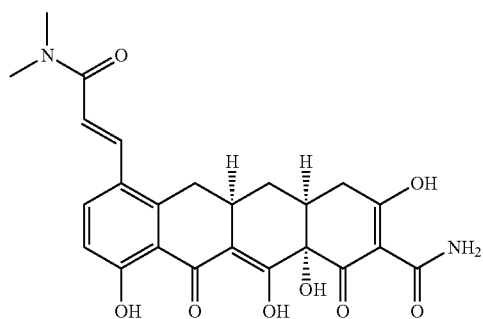 [SMILES: CN(C)C(=O)/C=C/c1ccc(O)c2c1C[C@H]1C[C@H]3CC(O)=C(C(N)=O)C(=O)[C@@]3(O)C(O)=C1C2=O]
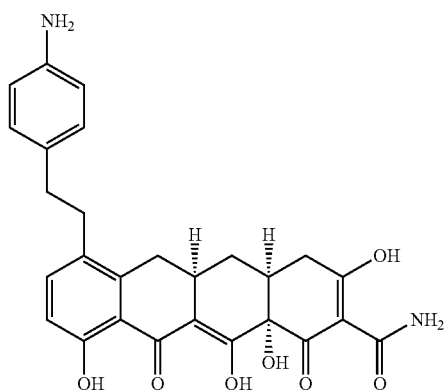 [SMILES: NC(=O)C1=C(O)C[C@@H]2C[C@@H]3Cc4c(CCc5ccc(N)cc5)ccc(O)c4C(=O)C3=C(O)[C@]2(O)C1=O]
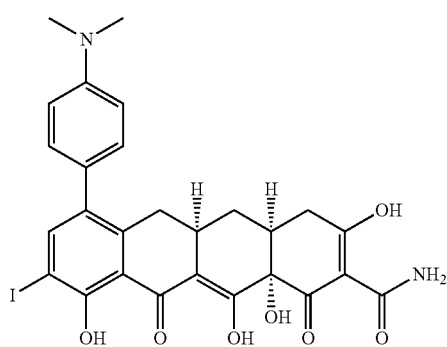 [SMILES: CN(C)c1ccc(-c2cc(I)c(O)c3c2C[C@H]2C[C@H]4CC(O)=C(C(N)=O)C(=O)[C@@]4(O)C(O)=C2C3=O)cc1]
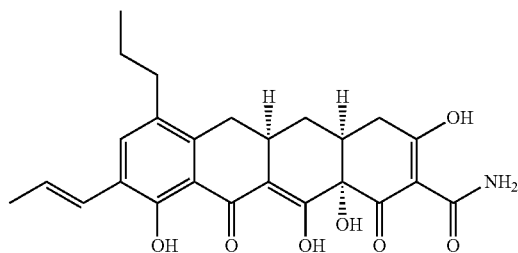 [SMILES: C/C=C/c1cc(CCC)c2c(c1O)C(=O)C1=C(O)[C@]3(O)C(=O)C(C(N)=O)=C(O)C[C@@H]3C[C@@H]1C2]

TABLE 2-continued
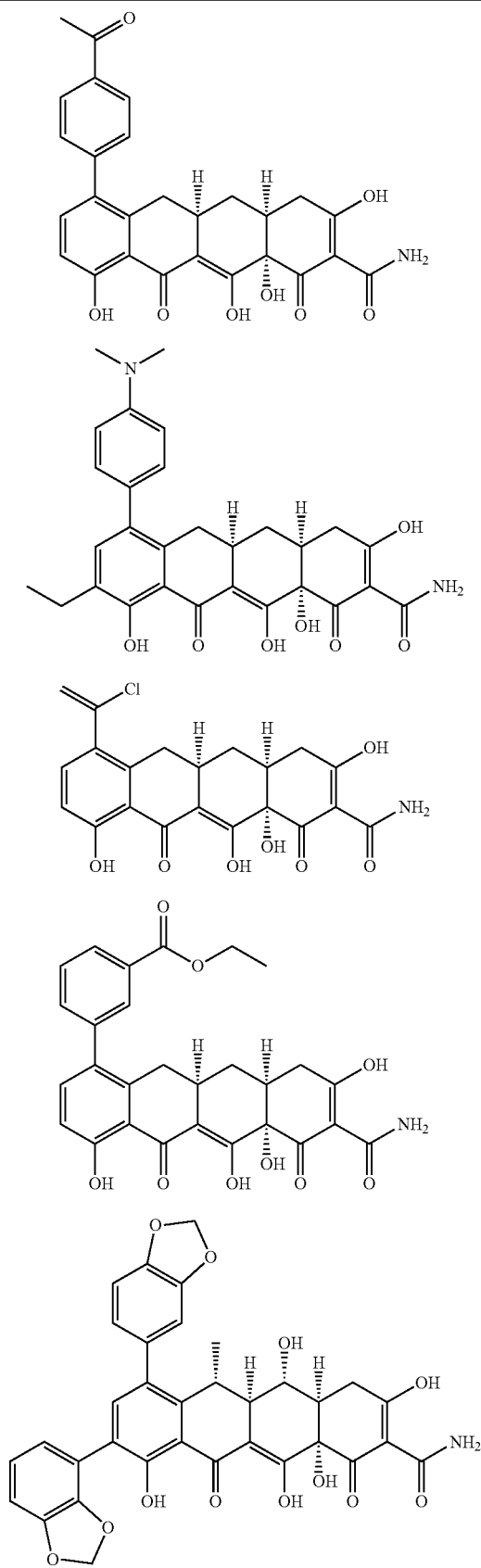

TABLE 2-continued
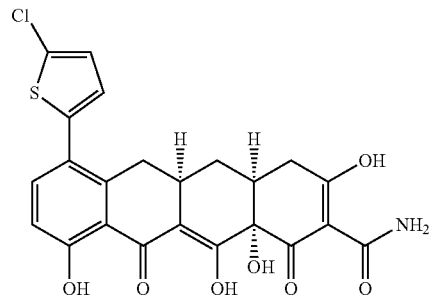 [SMILES: NC(=O)C1=C(O)C[C@@H]2C[C@@H]3Cc4c(-c5ccc(Cl)s5)ccc(O)c4C(=O)C3=C(O)[C@]2(O)C1=O]
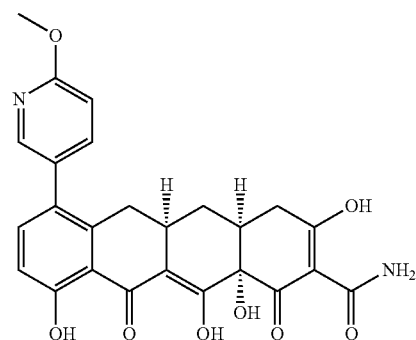 [SMILES: COc1ccc(-c2ccc(O)c3c2C[C@H]2C[C@H]4CC(O)=C(C(N)=O)C(=O)[C@@]4(O)C(O)=C2C3=O)cn1]
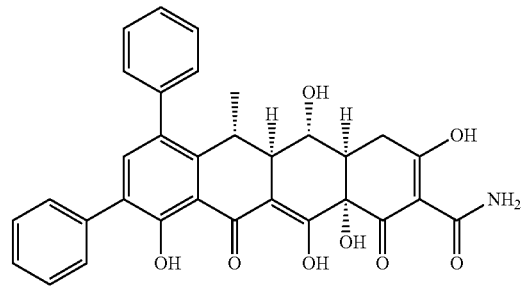 [SMILES: C[C@H]1c2c(-c3ccccc3)cc(-c3ccccc3)c(O)c2C(=O)C2=C(O)[C@]3(O)C(=O)C(C(N)=O)=C(O)C[C@@H]3[C@@H](O)[C@@H]21]
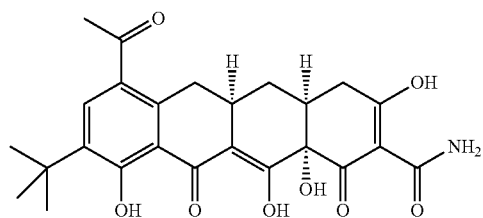 [SMILES: CC(=O)c1cc(C(C)(C)C)c(O)c2c1C[C@H]1C[C@H]3CC(O)=C(C(N)=O)C(=O)[C@@]3(O)C(O)=C1C2=O]
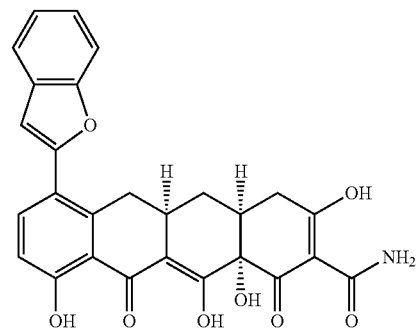 [SMILES: NC(=O)C1=C(O)C[C@@H]2C[C@@H]3Cc4c(-c5cc6ccccc6o5)ccc(O)c4C(=O)C3=C(O)[C@]2(O)C1=O]

TABLE 2-continued
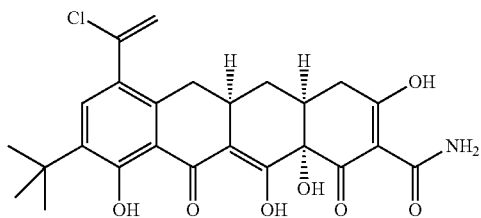 [SMILES: C=C(Cl)c1cc(C(C)(C)C)c(O)c2c1C[C@H]1C[C@H]3CC(O)=C(C(N)=O)C(=O)[C@@]3(O)C(O)=C1C2=O]
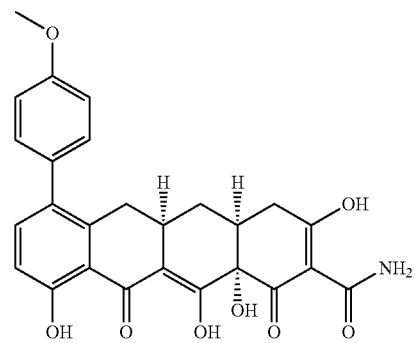 [SMILES: COc1ccc(-c2ccc(O)c3c2C[C@H]2C[C@H]4CC(O)=C(C(N)=O)C(=O)[C@@]4(O)C(O)=C2C3=O)cc1]
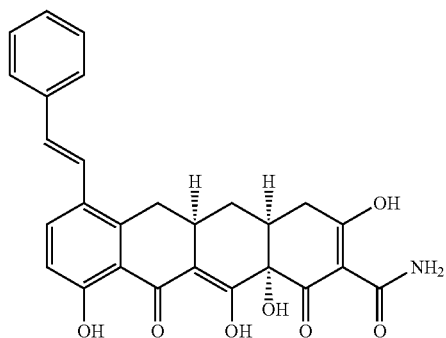 [SMILES: NC(=O)C1=C(O)C[C@@H]2C[C@@H]3Cc4c(/C=C/c5ccccc5)ccc(O)c4C(=O)C3=C(O)[C@]2(O)C1=O]
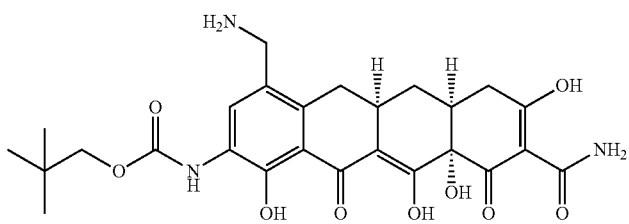 [SMILES: CC(C)(C)COC(=O)Nc1cc(CN)c2c(c1O)C(=O)C1=C(O)[C@]3(O)C(=O)C(C(N)=O)=C(O)C[C@@H]3C[C@@H]1C2]
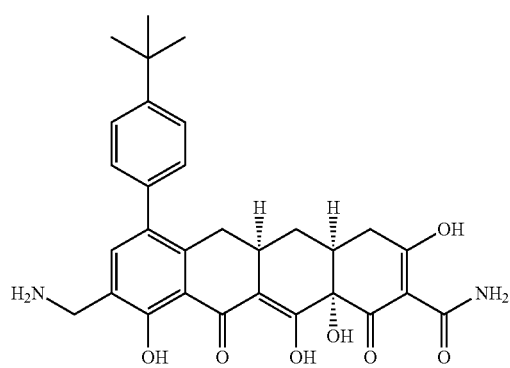 [SMILES: CC(C)(C)c1ccc(-c2cc(CN)c(O)c3c2C[C@H]2C[C@H]4CC(O)=C(C(N)=O)C(=O)[C@@]4(O)C(O)=C2C3=O)cc1]

TABLE 2-continued
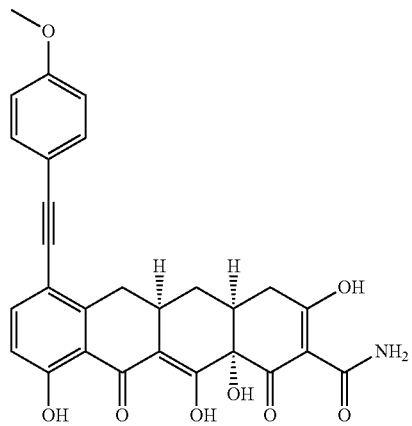 [SMILES: COc1ccc(C#Cc2ccc(O)c3c2C[C@H]2C[C@H]4CC(O)=C(C(N)=O)C(=O)[C@@]4(O)C(O)=C2C3=O)cc1]
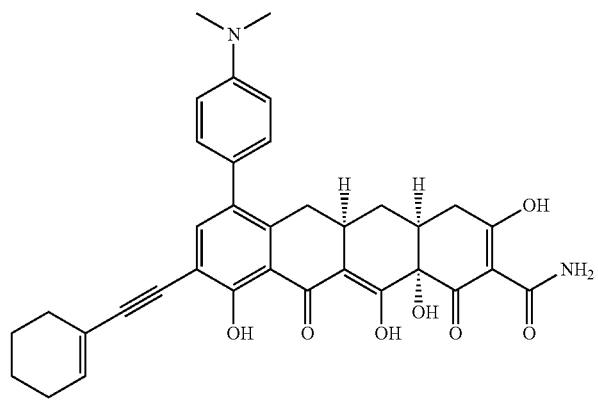 [SMILES: CN(C)c1ccc(-c2cc(C#CC3=CCCCC3)c(O)c3c2C[C@H]2C[C@H]4CC(O)=C(C(N)=O)C(=O)[C@@]4(O)C(O)=C2C3=O)cc1]
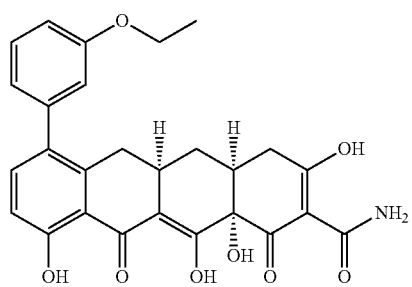 [SMILES: CCOc1cccc(-c2ccc(O)c3c2C[C@H]2C[C@H]4CC(O)=C(C(N)=O)C(=O)[C@@]4(O)C(O)=C2C3=O)c1]
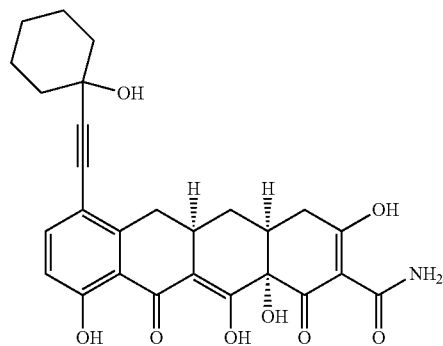 [SMILES: NC(=O)C1=C(O)C[C@@H]2C[C@@H]3Cc4c(C#CC5(O)CCCCC5)ccc(O)c4C(=O)C3=C(O)[C@]2(O)C1=O]

TABLE 2-continued
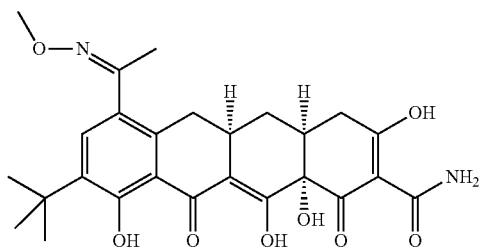 [SMILES: CO/N=C(/C)c1cc(C(C)(C)C)c(O)c2c1C[C@H]1C[C@H]3CC(O)=C(C(N)=O)C(=O)[C@@]3(O)C(O)=C1C2=O]
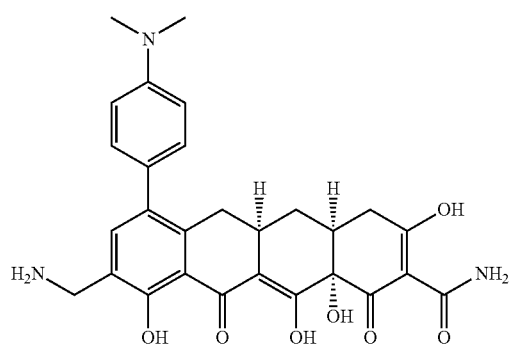 [SMILES: CN(C)c1ccc(-c2cc(CN)c(O)c3c2C[C@H]2C[C@H]4CC(O)=C(C(N)=O)C(=O)[C@@]4(O)C(O)=C2C3=O)cc1]
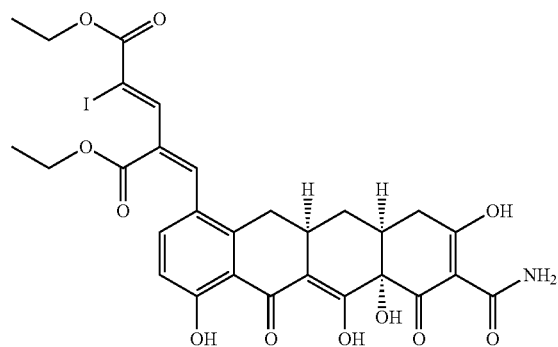 [SMILES: CCOC(=O)/C(I)=C/C(=C/c1ccc(O)c2c1C[C@H]1C[C@H]3CC(O)=C(C(N)=O)C(=O)[C@@]3(O)C(O)=C1C2=O)C(=O)OCC]
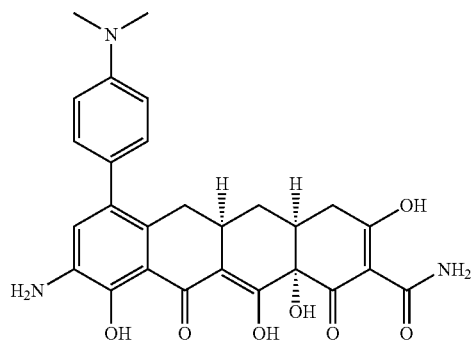 [SMILES: CN(C)c1ccc(-c2cc(N)c(O)c3c2C[C@H]2C[C@H]4CC(O)=C(C(N)=O)C(=O)[C@@]4(O)C(O)=C2C3=O)cc1]
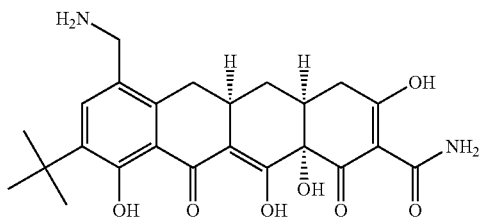 [SMILES: CC(C)(C)c1cc(CN)c2c(c1O)C(=O)C1=C(O)[C@]3(O)C(=O)C(C(N)=O)=C(O)C[C@@H]3C[C@@H]1C2]

TABLE 2-continued
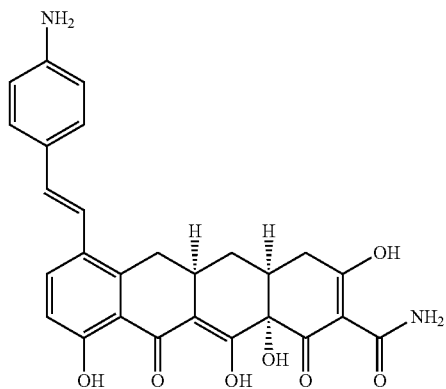 [SMILES: NC(=O)C1=C(O)C[C@@H]2C[C@@H]3Cc4c(/C=C/c5ccc(N)cc5)ccc(O)c4C(=O)C3=C(O)[C@]2(O)C1=O]
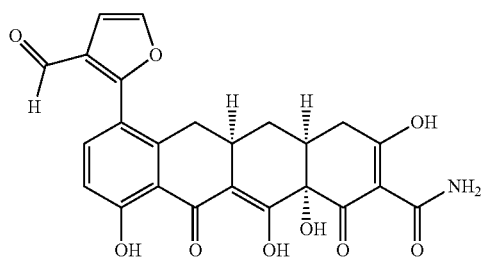 [SMILES: NC(=O)C1=C(O)C[C@@H]2C[C@@H]3Cc4c(-c5occc5C=O)ccc(O)c4C(=O)C3=C(O)[C@]2(O)C1=O]
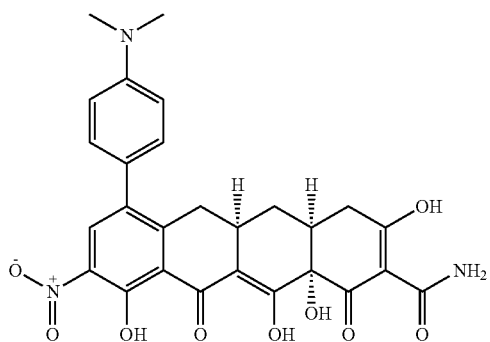
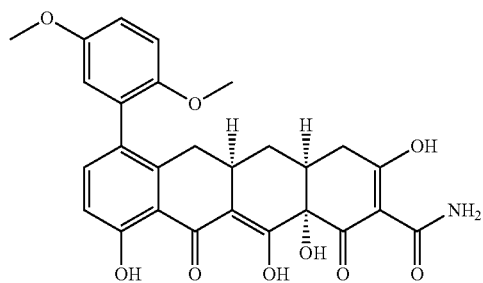 [SMILES: COc1ccc(OC)c(-c2ccc(O)c3c2C[C@H]2C[C@H]4CC(O)=C(C(N)=O)C(=O)[C@@]4(O)C(O)=C2C3=O)c1]
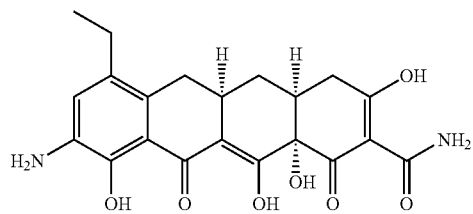 [SMILES: CCc1cc(N)c(O)c2c1C[C@H]1C[C@H]3CC(O)=C(C(N)=O)C(=O)[C@@]3(O)C(O)=C1C2=O]

TABLE 2-continued
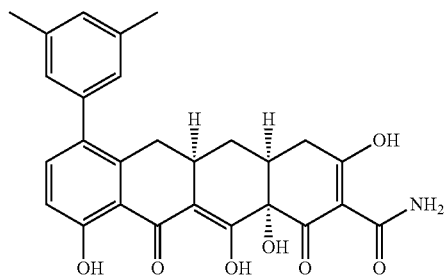 [SMILES: Cc1cc(C)cc(-c2ccc(O)c3c2C[C@H]2C[C@H]4CC(O)=C(C(N)=O)C(=O)[C@@]4(O)C(O)=C2C3=O)c1]
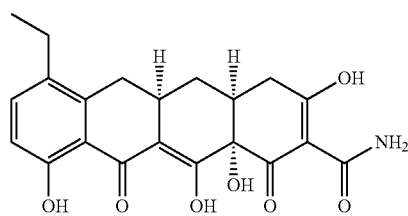 [SMILES: CCc1ccc(O)c2c1C[C@H]1C[C@H]3CC(O)=C(C(N)=O)C(=O)[C@@]3(O)C(O)=C1C2=O]
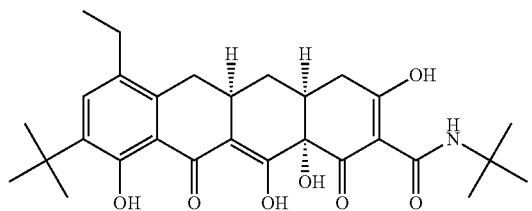 [SMILES: CCc1cc(C(C)(C)C)c(O)c2c1C[C@H]1C[C@H]3CC(O)=C(C(=O)NC(C)(C)C)C(=O)[C@@]3(O)C(O)=C1C2=O]
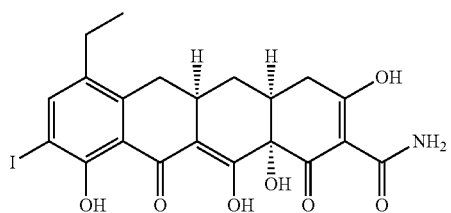 [SMILES: CCc1cc(I)c(O)c2c1C[C@H]1C[C@H]3CC(O)=C(C(N)=O)C(=O)[C@@]3(O)C(O)=C1C2=O]
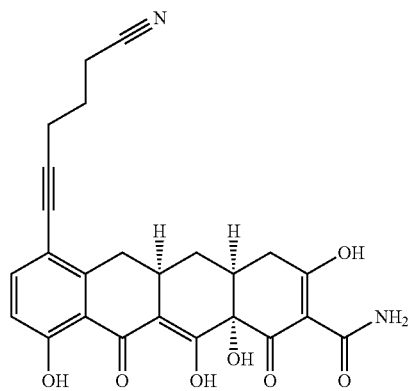 [SMILES: N#CCCCC#Cc1ccc(O)c2c1C[C@H]1C[C@H]3CC(O)=C(C(N)=O)C(=O)[C@@]3(O)C(O)=C1C2=O]
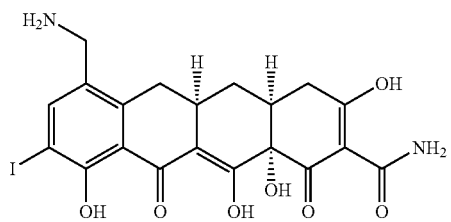 [SMILES: NCc1cc(I)c(O)c2c1C[C@H]1C[C@H]3CC(O)=C(C(N)=O)C(=O)[C@@]3(O)C(O)=C1C2=O]

TABLE 2-continued
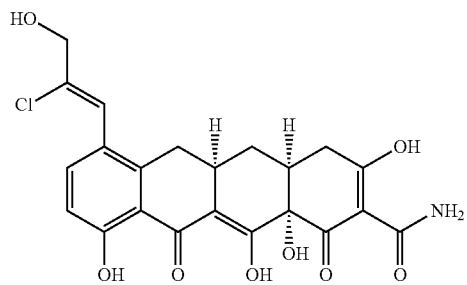 [SMILES: NC(=O)C1=C(O)C[C@@H]2C[C@@H]3Cc4c(/C=C(\Cl)CO)ccc(O)c4C(=O)C3=C(O)[C@]2(O)C1=O]
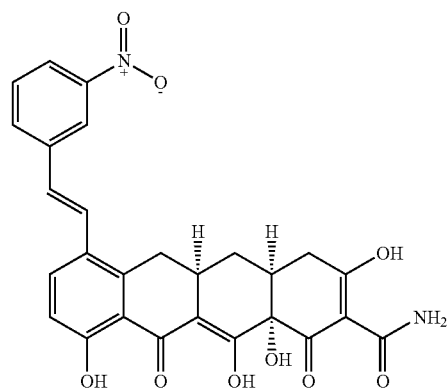
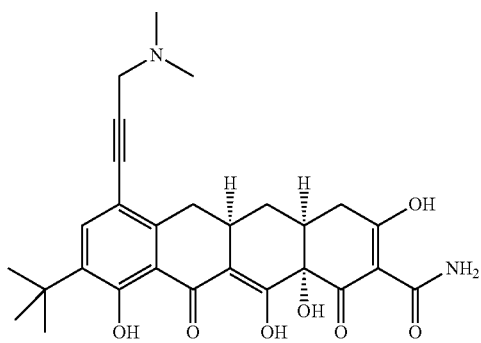 [SMILES: CN(C)CC#Cc1cc(C(C)(C)C)c(O)c2c1C[C@H]1C[C@H]3CC(O)=C(C(N)=O)C(=O)[C@@]3(O)C(O)=C1C2=O]
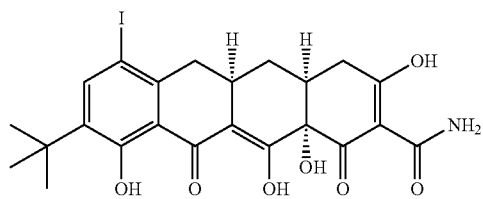 [SMILES: CC(C)(C)c1cc(I)c2c(c1O)C(=O)C1=C(O)[C@]3(O)C(=O)C(C(N)=O)=C(O)C[C@@H]3C[C@@H]1C2]
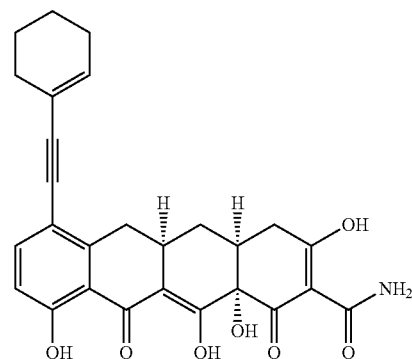 [SMILES: NC(=O)C1=C(O)C[C@@H]2C[C@@H]3Cc4c(C#CC5=CCCCC5)ccc(O)c4C(=O)C3=C(O)[C@]2(O)C1=O]

TABLE 2-continued
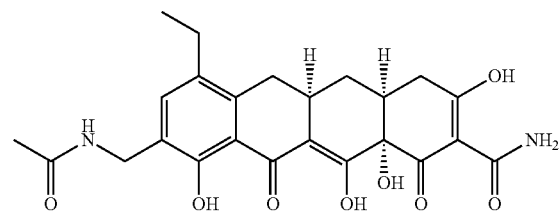 [SMILES: CCc1cc(CNC(C)=O)c(O)c2c1C[C@H]1C[C@H]3CC(O)=C(C(N)=O)C(=O)[C@@]3(O)C(O)=C1C2=O]
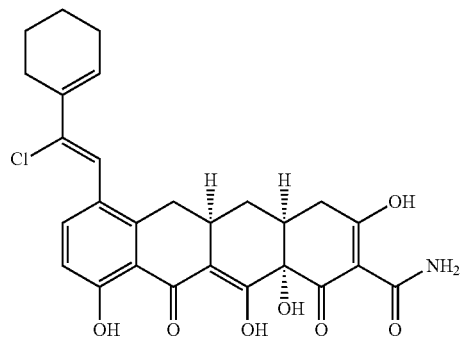 [SMILES: NC(=O)C1=C(O)C[C@@H]2C[C@@H]3Cc4c(/C=C(\Cl)C5=CCCCC5)ccc(O)c4C(=O)C3=C(O)[C@]2(O)C1=O]
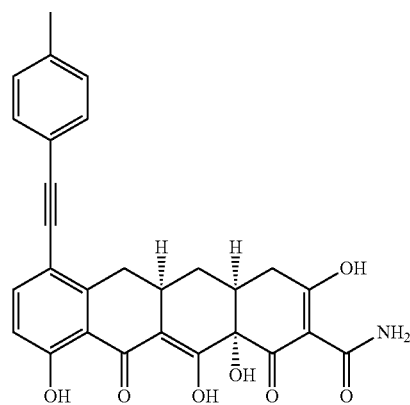 [SMILES: Cc1ccc(C#Cc2ccc(O)c3c2C[C@H]2C[C@H]4CC(O)=C(C(N)=O)C(=O)[C@@]4(O)C(O)=C2C3=O)cc1]
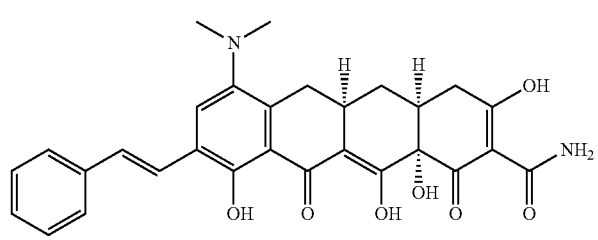 [SMILES: CN(C)c1cc(/C=C/c2ccccc2)c(O)c2c1C[C@H]1C[C@H]3CC(O)=C(C(N)=O)C(=O)[C@@]3(O)C(O)=C1C2=O]
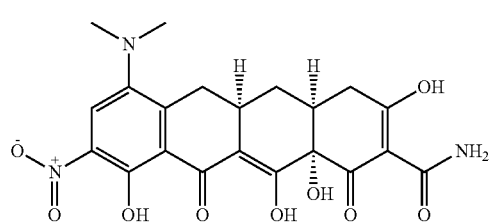

TABLE 2-continued
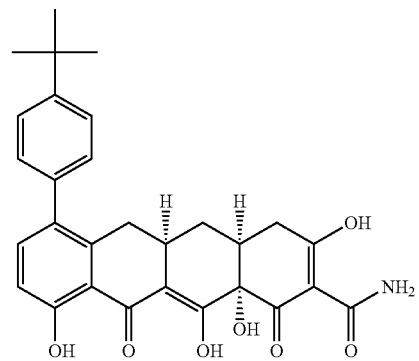 [SMILES: CC(C)(C)c1ccc(-c2ccc(O)c3c2C[C@H]2C[C@H]4CC(O)=C(C(N)=O)C(=O)[C@@]4(O)C(O)=C2C3=O)cc1]
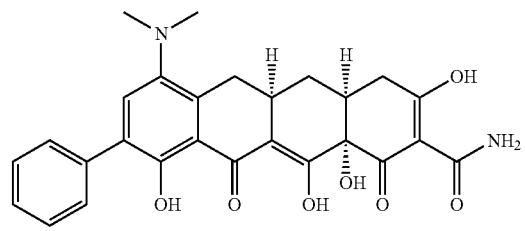 [SMILES: CN(C)c1cc(-c2ccccc2)c(O)c2c1C[C@H]1C[C@H]3CC(O)=C(C(N)=O)C(=O)[C@@]3(O)C(O)=C1C2=O]
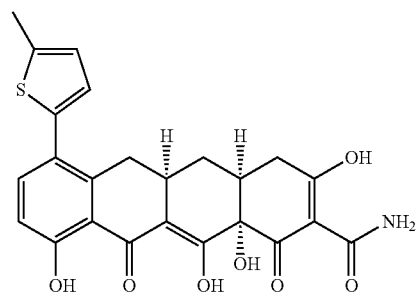 [SMILES: Cc1ccc(-c2ccc(O)c3c2C[C@H]2C[C@H]4CC(O)=C(C(N)=O)C(=O)[C@@]4(O)C(O)=C2C3=O)s1]
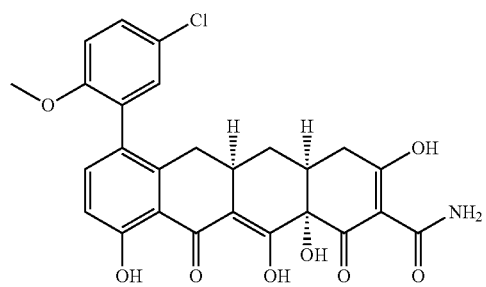 [SMILES: COc1ccc(Cl)cc1-c1ccc(O)c2c1C[C@H]1C[C@H]3CC(O)=C(C(N)=O)C(=O)[C@@]3(O)C(O)=C1C2=O]
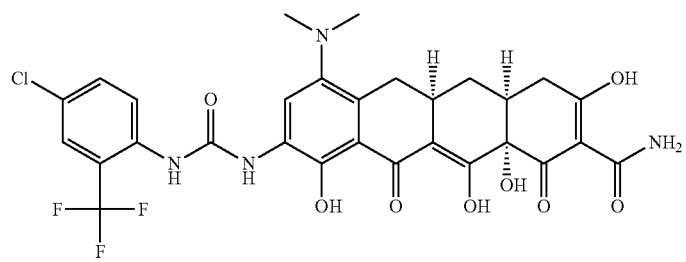 [SMILES: CN(C)c1cc(NC(=O)Nc2ccc(Cl)cc2C(F)(F)F)c(O)c2c1C[C@H]1C[C@H]3CC(O)=C(C(N)=O)C(=O)[C@@]3(O)C(O)=C1C2=O]

TABLE 2-continued
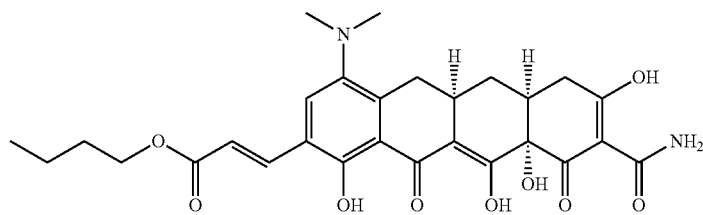 [SMILES: CCCCOC(=O)/C=C/c1cc(N(C)C)c2c(c1O)C(=O)C1=C(O)[C@]3(O)C(=O)C(C(N)=O)=C(O)C[C@@H]3C[C@@H]1C2]
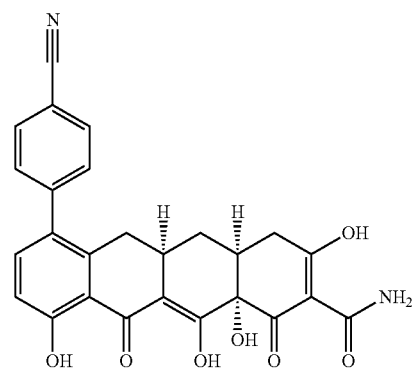 [SMILES: N#Cc1ccc(-c2ccc(O)c3c2C[C@H]2C[C@H]4CC(O)=C(C(N)=O)C(=O)[C@@]4(O)C(O)=C2C3=O)cc1]
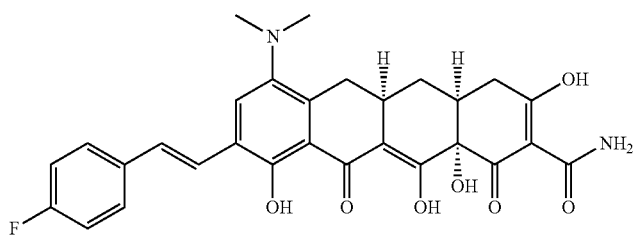 [SMILES: CN(C)c1cc(/C=C/c2ccc(F)cc2)c(O)c2c1C[C@H]1C[C@H]3CC(O)=C(C(N)=O)C(=O)[C@@]3(O)C(O)=C1C2=O]
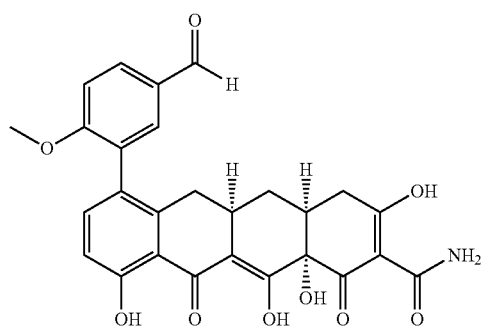 [SMILES: COc1ccc(C=O)cc1-c1ccc(O)c2c1C[C@H]1C[C@H]3CC(O)=C(C(N)=O)C(=O)[C@@]3(O)C(O)=C1C2=O]
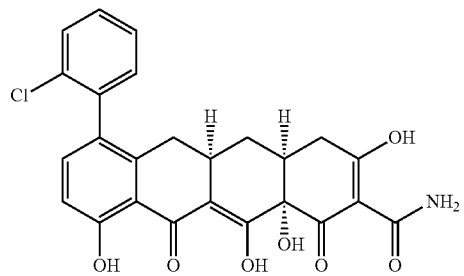 [SMILES: NC(=O)C1=C(O)C[C@@H]2C[C@@H]3Cc4c(-c5ccccc5Cl)ccc(O)c4C(=O)C3=C(O)[C@]2(O)C1=O]

TABLE 2-continued
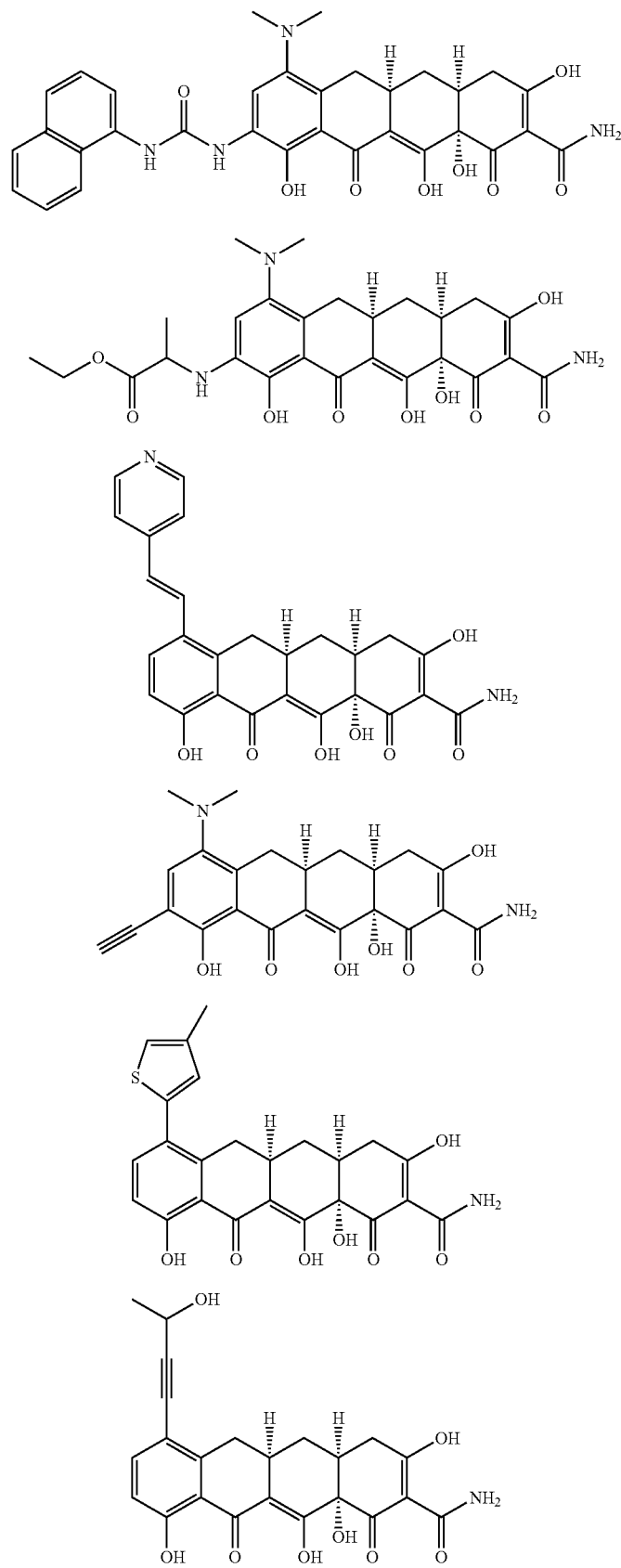

TABLE 2-continued
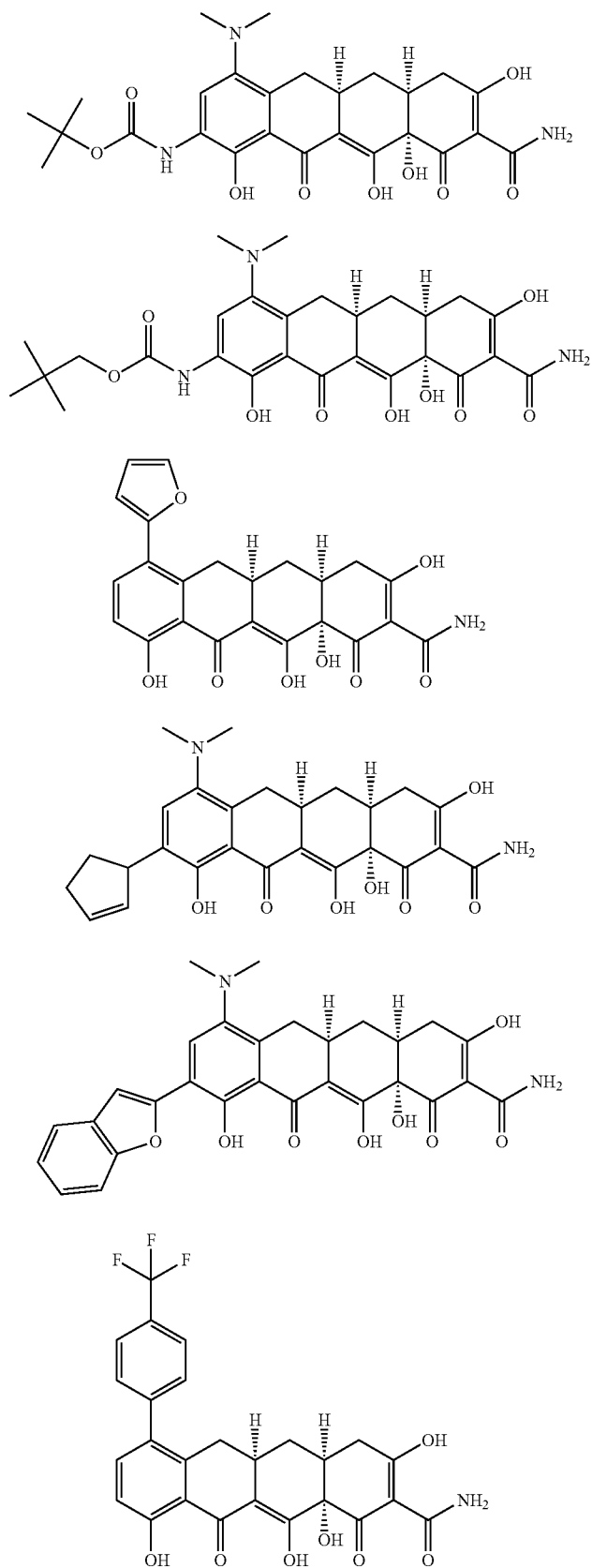

TABLE 2-continued
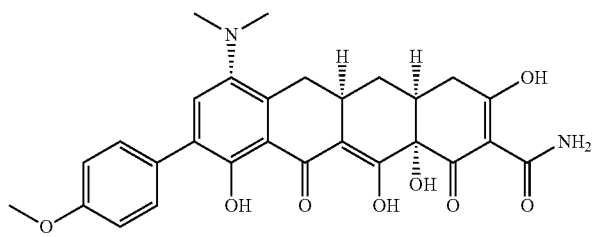
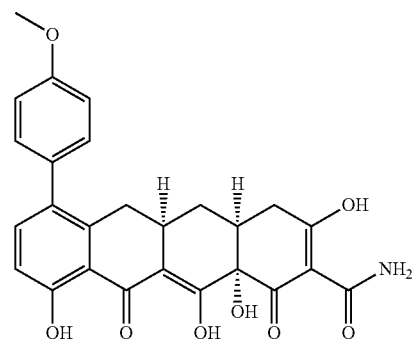 [SMILES: COc1ccc(-c2ccc(O)c3c2C[C@H]2C[C@H]4CC(O)=C(C(N)=O)C(=O)[C@@]4(O)C(O)=C2C3=O)cc1]
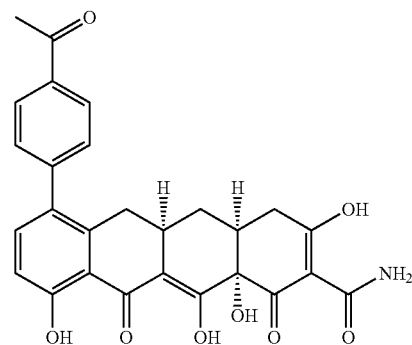 [SMILES: CC(=O)c1ccc(-c2ccc(O)c3c2C[C@H]2C[C@H]4CC(O)=C(C(N)=O)C(=O)[C@@]4(O)C(O)=C2C3=O)cc1]
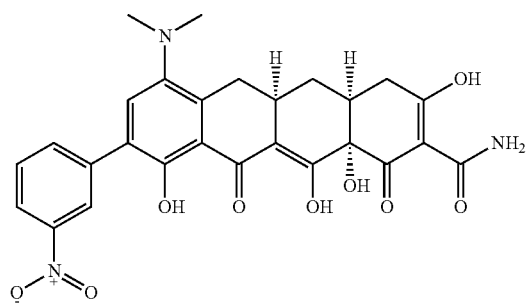
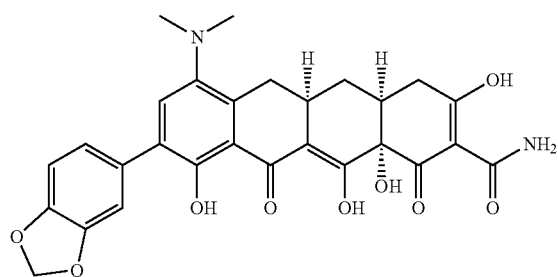 [SMILES: CN(C)c1cc(-c2ccc3c(c2)OCO3)c(O)c2c1C[C@H]1C[C@H]3CC(O)=C(C(N)=O)C(=O)[C@@]3(O)C(O)=C1C2=O]

TABLE 2-continued
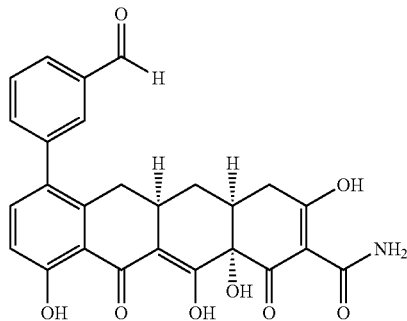
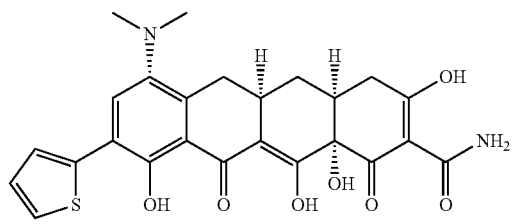
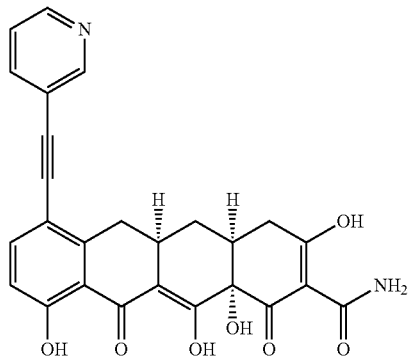
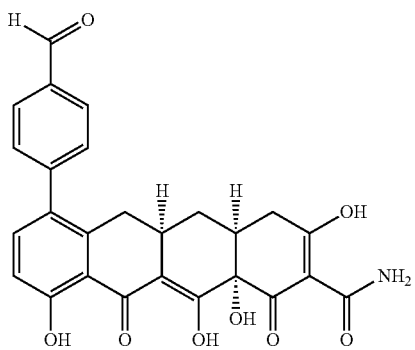 [SMILES: NC(=O)C1=C(O)C[C@@H]2C[C@@H]3Cc4c(-c5ccc(C=O)cc5)ccc(O)c4C(=O)C3=C(O)[C@]2(O)C1=O]
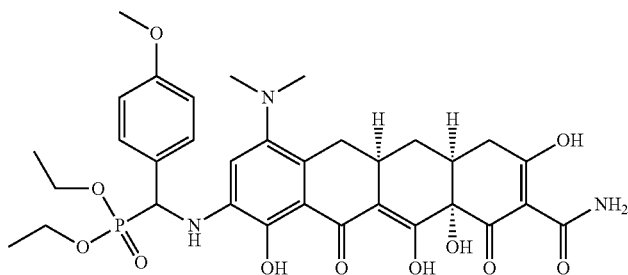 [SMILES: CCOP(=O)(OCC)C(Nc1cc(N(C)C)c2c(c1O)C(=O)C1=C(O)[C@]3(O)C(=O)C(C(N)=O)=C(O)C[C@@H]3C[C@@H]1C2)c1ccc(OC)cc1]

TABLE 2-continued
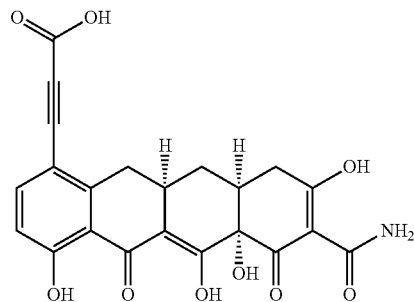 [SMILES: NC(=O)C1=C(O)C[C@@H]2C[C@@H]3Cc4c(C#CC(=O)O)ccc(O)c4C(=O)C3=C(O)[C@]2(O)C1=O]
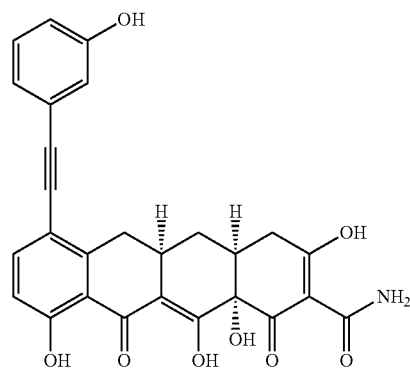 [SMILES: NC(=O)C1=C(O)C[C@@H]2C[C@@H]3Cc4c(C#Cc5cccc(O)c5)ccc(O)c4C(=O)C3=C(O)[C@]2(O)C1=O]
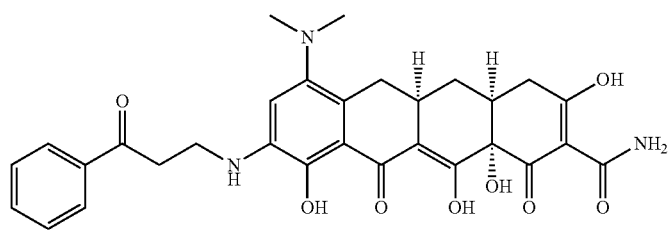 [SMILES: CN(C)c1cc(NCCC(=O)c2ccccc2)c(O)c2c1C[C@H]1C[C@H]3CC(O)=C(C(N)=O)C(=O)[C@@]3(O)C(O)=C1C2=O]
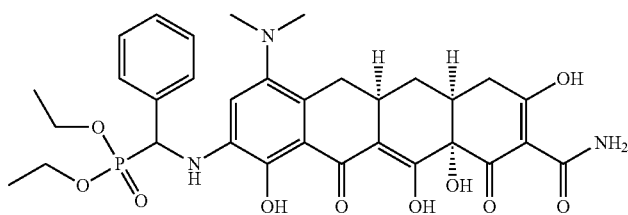 [SMILES: CCOP(=O)(OCC)C(Nc1cc(N(C)C)c2c(c1O)C(=O)C1=C(O)[C@]3(O)C(=O)C(C(N)=O)=C(O)C[C@@H]3C[C@@H]1C2)c1ccccc1]
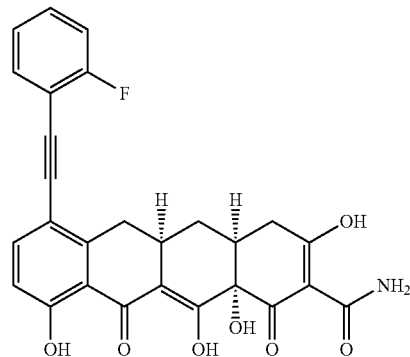 [SMILES: NC(=O)C1=C(O)C[C@@H]2C[C@@H]3Cc4c(C#Cc5ccccc5F)ccc(O)c4C(=O)C3=C(O)[C@]2(O)C1=O]

TABLE 2-continued
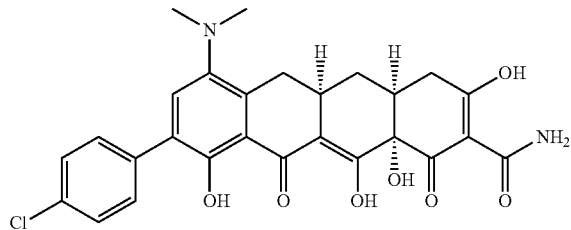 [SMILES: CN(C)c1cc(-c2ccc(Cl)cc2)c(O)c2c1C[C@H]1C[C@H]3CC(O)=C(C(N)=O)C(=O)[C@@]3(O)C(O)=C1C2=O]
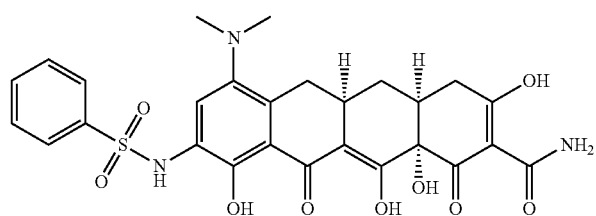 [SMILES: CN(C)c1cc(NS(=O)(=O)c2ccccc2)c(O)c2c1C[C@H]1C[C@H]3CC(O)=C(C(N)=O)C(=O)[C@@]3(O)C(O)=C1C2=O]
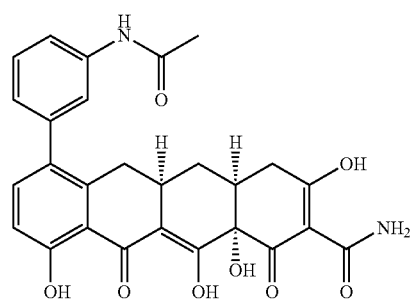 [SMILES: CC(=O)Nc1cccc(-c2ccc(O)c3c2C[C@H]2C[C@H]4CC(O)=C(C(N)=O)C(=O)[C@@]4(O)C(O)=C2C3=O)c1]
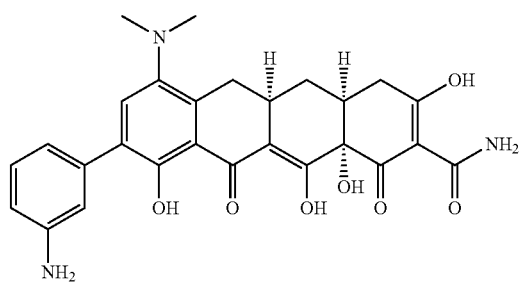 [SMILES: CN(C)c1cc(-c2cccc(N)c2)c(O)c2c1C[C@H]1C[C@H]3CC(O)=C(C(N)=O)C(=O)[C@@]3(O)C(O)=C1C2=O]
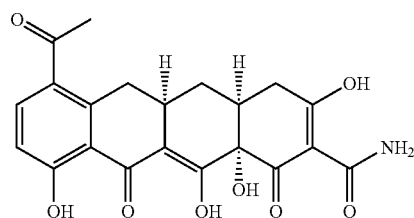 [SMILES: CC(=O)c1ccc(O)c2c1C[C@H]1C[C@H]3CC(O)=C(C(N)=O)C(=O)[C@@]3(O)C(O)=C1C2=O]

TABLE 2-continued
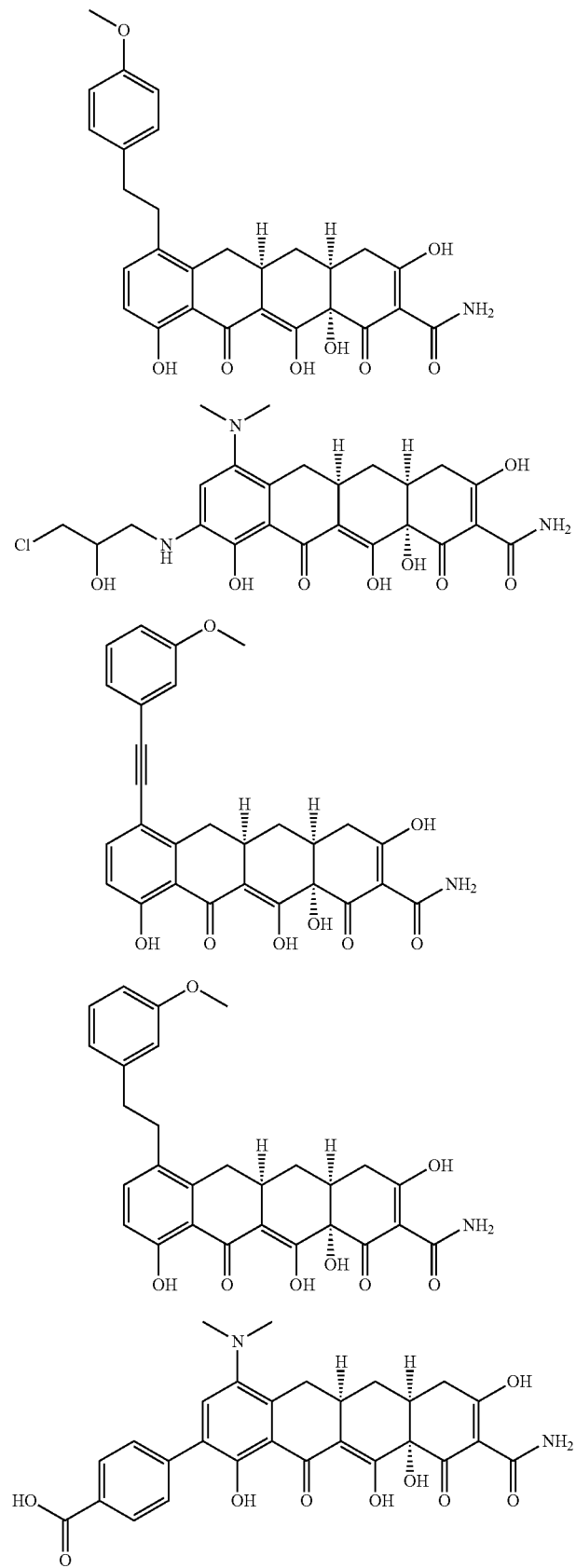

TABLE 2-continued
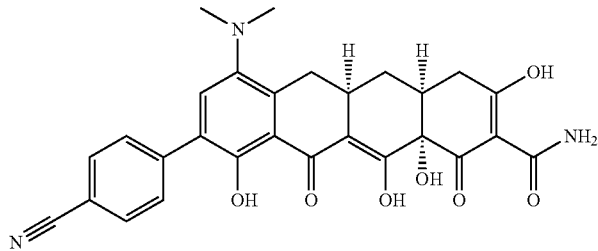 [SMILES: CN(C)c1cc(-c2ccc(C#N)cc2)c(O)c2c1C[C@H]1C[C@H]3CC(O)=C(C(N)=O)C(=O)[C@@]3(O)C(O)=C1C2=O]
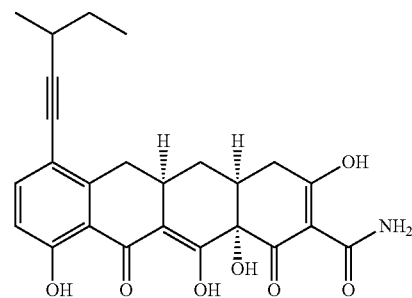 [SMILES: CCC(C)C#Cc1ccc(O)c2c1C[C@H]1C[C@H]3CC(O)=C(C(N)=O)C(=O)[C@@]3(O)C(O)=C1C2=O]
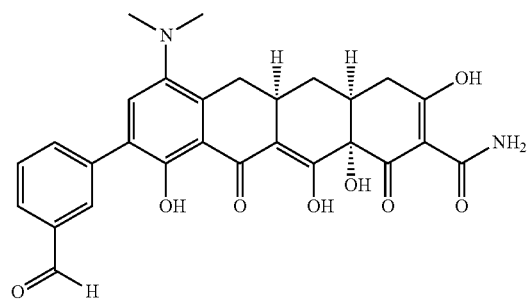 [SMILES: CN(C)c1cc(-c2cccc(C=O)c2)c(O)c2c1C[C@H]1C[C@H]3CC(O)=C(C(N)=O)C(=O)[C@@]3(O)C(O)=C1C2=O]
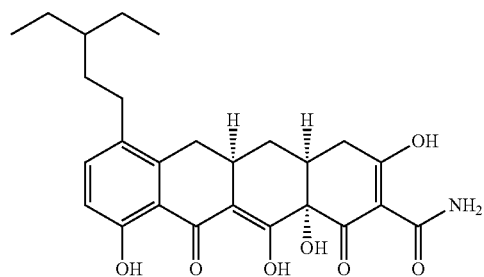 [SMILES: CCC(CC)CCc1ccc(O)c2c1C[C@H]1C[C@H]3CC(O)=C(C(N)=O)C(=O)[C@@]3(O)C(O)=C1C2=O]

TABLE 2-continued
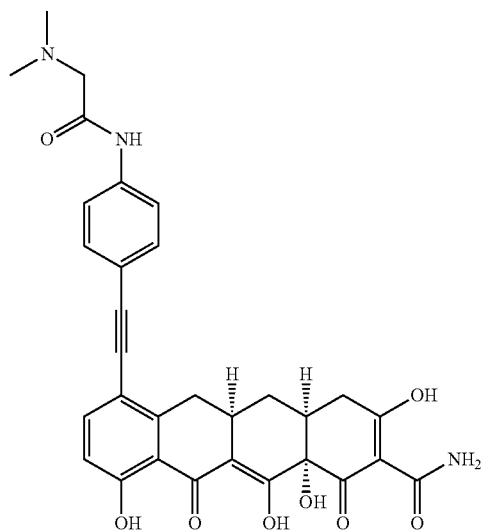 [SMILES: CN(C)CC(=O)Nc1ccc(C#Cc2ccc(O)c3c2C[C@H]2C[C@H]4CC(O)=C(C(N)=O)C(=O)[C@@]4(O)C(O)=C2C3=O)cc1]
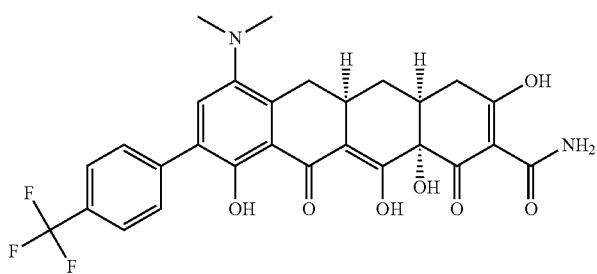 [SMILES: CN(C)c1cc(-c2ccc(C(F)(F)F)cc2)c(O)c2c1C[C@H]1C[C@H]3CC(O)=C(C(N)=O)C(=O)[C@@]3(O)C(O)=C1C2=O]
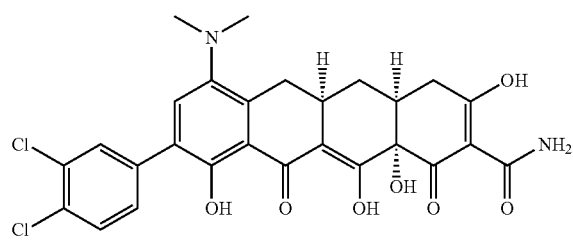 [SMILES: CN(C)c1cc(-c2ccc(Cl)c(Cl)c2)c(O)c2c1C[C@H]1C[C@H]3CC(O)=C(C(N)=O)C(=O)[C@@]3(O)C(O)=C1C2=O]
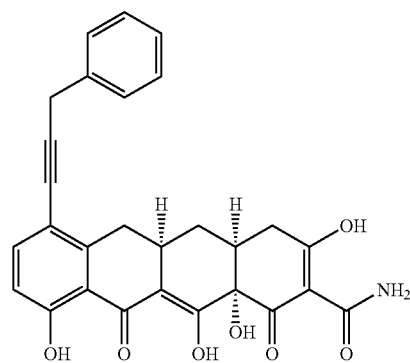 [SMILES: NC(=O)C1=C(O)C[C@@H]2C[C@@H]3Cc4c(C#CCc5ccccc5)ccc(O)c4C(=O)C3=C(O)[C@]2(O)C1=O]

TABLE 2-continued
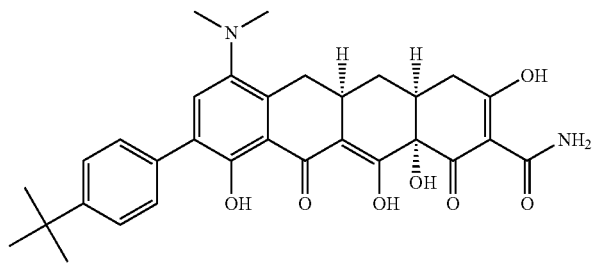 [SMILES: CN(C)c1cc(-c2ccc(C(C)(C)C)cc2)c(O)c2c1C[C@H]1C[C@H]3CC(O)=C(C(N)=O)C(=O)[C@@]3(O)C(O)=C1C2=O]
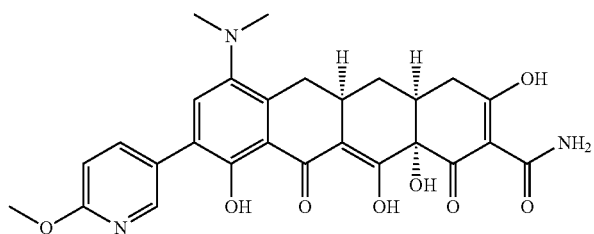 [SMILES: COc1ccc(-c2cc(N(C)C)c3c(c2O)C(=O)C2=C(O)[C@]4(O)C(=O)C(C(N)=O)=C(O)C[C@@H]4C[C@@H]2C3)cn1]
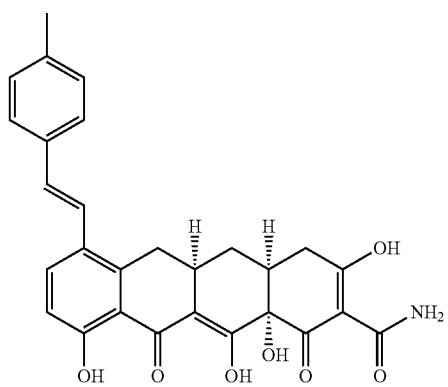 [SMILES: Cc1ccc(/C=C/c2ccc(O)c3c2C[C@H]2C[C@H]4CC(O)=C(C(N)=O)C(=O)[C@@]4(O)C(O)=C2C3=O)cc1]
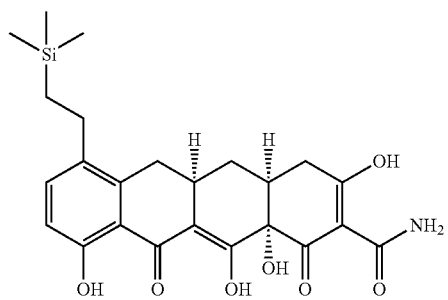 [SMILES: C[Si](C)(C)CCc1ccc(O)c2c1C[C@H]1C[C@H]3CC(O)=C(C(N)=O)C(=O)[C@@]3(O)C(O)=C1C2=O]
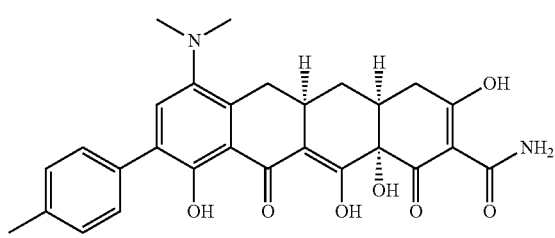 [SMILES: Cc1ccc(-c2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
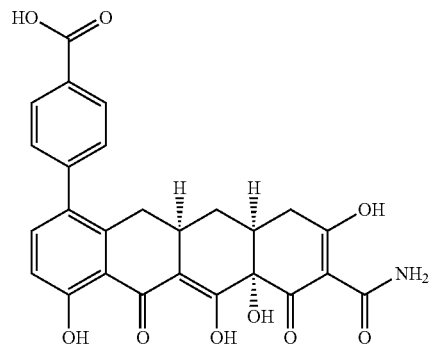 [SMILES: NC(=O)C1=C(O)C[C@@H]2C[C@@H]3Cc4c(-c5ccc(C(=O)O)cc5)ccc(O)c4C(=O)C3=C(O)[C@]2(O)C1=O]
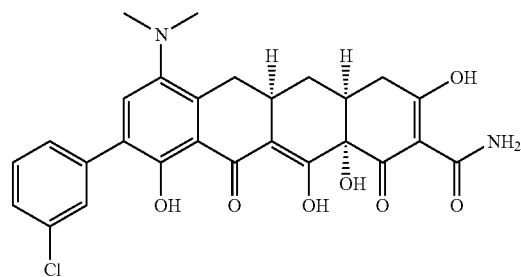 [SMILES: CN(C)c1cc(-c2cccc(Cl)c2)c(O)c2c1C[C@H]1C[C@H]3CC(O)=C(C(N)=O)C(=O)[C@@]3(O)C(O)=C1C2=O]
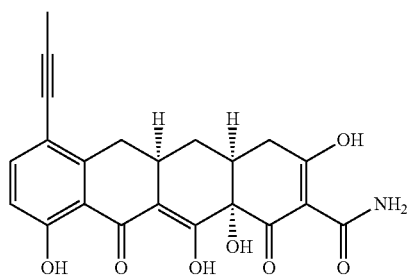 [SMILES: CC#Cc1ccc(O)c2c1C[C@H]1C[C@H]3CC(O)=C(C(N)=O)C(=O)[C@@]3(O)C(O)=C1C2=O]
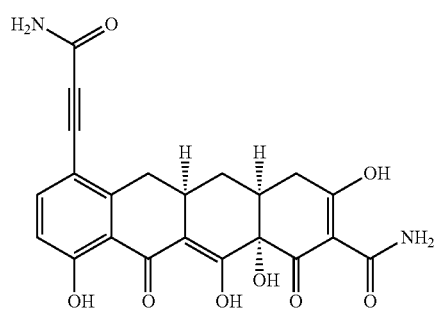 [SMILES: NC(=O)C#Cc1ccc(O)c2c1C[C@H]1C[C@H]3CC(O)=C(C(N)=O)C(=O)[C@@]3(O)C(O)=C1C2=O]
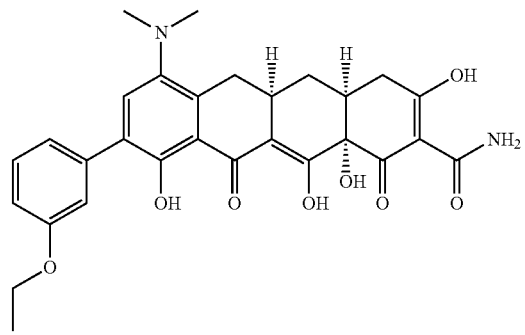 [SMILES: CCOc1cccc(-c2cc(N(C)C)c3c(c2O)C(=O)C2=C(O)[C@]4(O)C(=O)C(C(N)=O)=C(O)C[C@@H]4C[C@@H]2C3)c1]

TABLE 2-continued
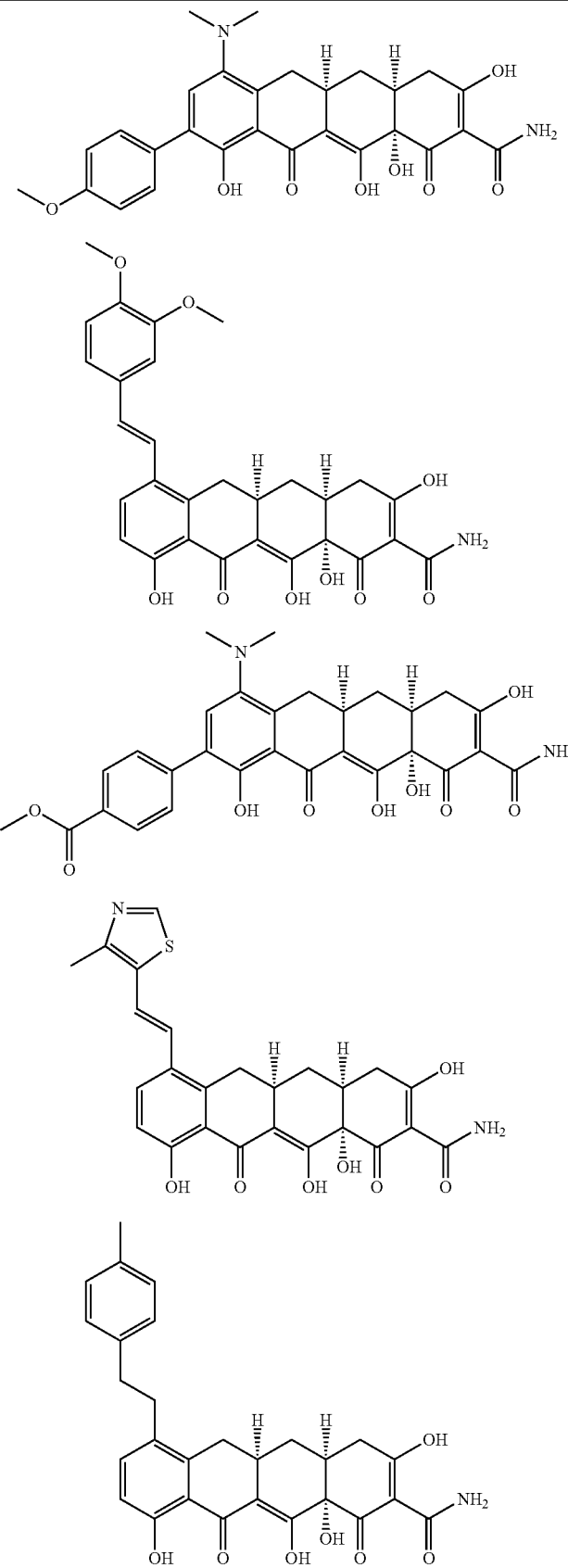

TABLE 2-continued
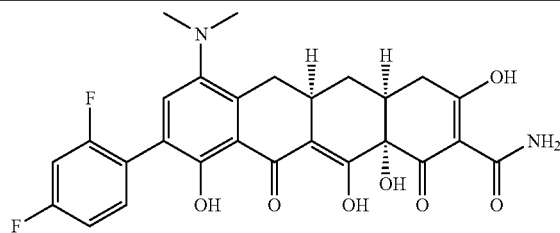
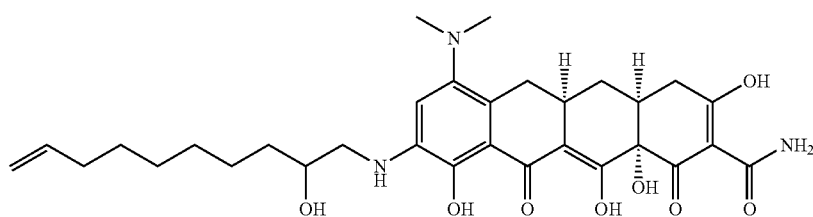 [SMILES: C=CCCCCCCC(O)CNc1cc(N(C)C)c2c(c1O)C(=O)C1=C(O)[C@]3(O)C(=O)C(C(N)=O)=C(O)C[C@@H]3C[C@@H]1C2]
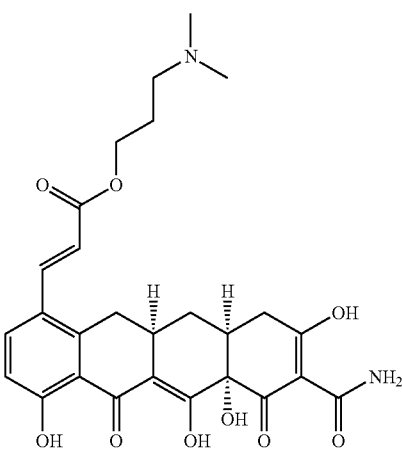 [SMILES: CN(C)CCCOC(=O)/C=C/c1ccc(O)c2c1C[C@H]1C[C@H]3CC(O)=C(C(N)=O)C(=O)[C@@]3(O)C(O)=C1C2=O]
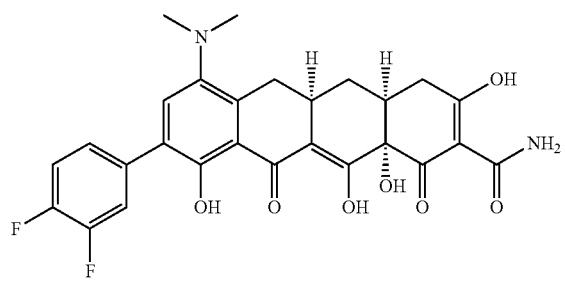 [SMILES: CN(C)c1cc(-c2ccc(F)c(F)c2)c(O)c2c1C[C@H]1C[C@H]3CC(O)=C(C(N)=O)C(=O)[C@@]3(O)C(O)=C1C2=O]
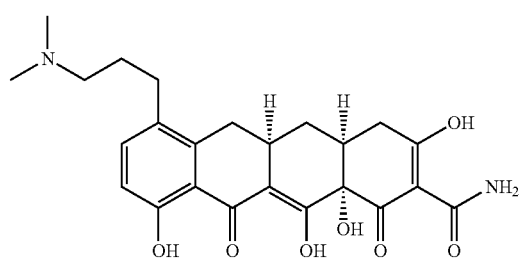 [SMILES: CN(C)CCCc1ccc(O)c2c1C[C@H]1C[C@H]3CC(O)=C(C(N)=O)C(=O)[C@@]3(O)C(O)=C1C2=O]

TABLE 2-continued
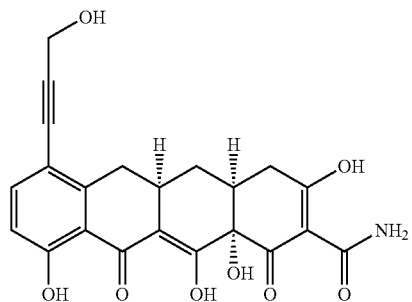 [SMILES: NC(=O)C1=C(O)C[C@@H]2C[C@@H]3Cc4c(C#CCO)ccc(O)c4C(=O)C3=C(O)[C@]2(O)C1=O]
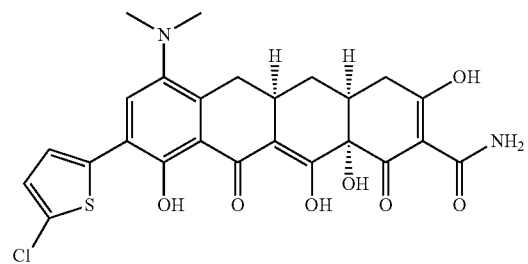 [SMILES: CN(C)c1cc(-c2ccc(Cl)s2)c(O)c2c1C[C@H]1C[C@H]3CC(O)=C(C(N)=O)C(=O)[C@@]3(O)C(O)=C1C2=O]
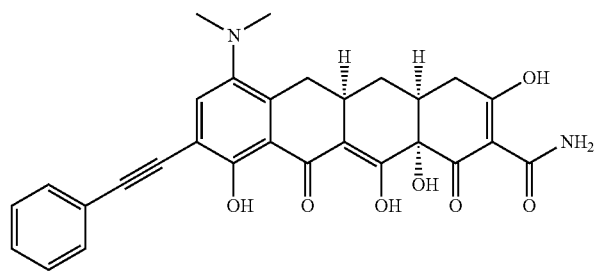
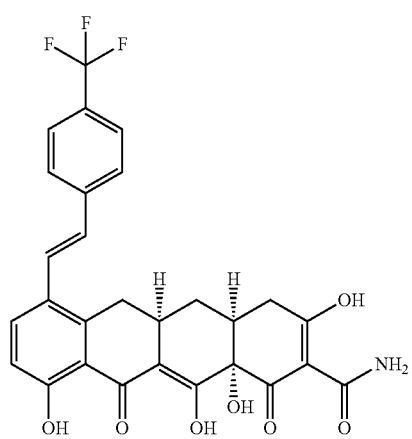 [SMILES: NC(=O)C1=C(O)C[C@@H]2C[C@@H]3Cc4c(/C=C/c5ccc(C(F)(F)F)cc5)ccc(O)c4C(=O)C3=C(O)[C@]2(O)C1=O]
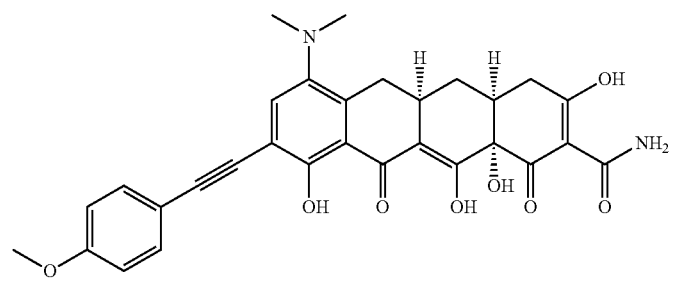 [SMILES: COc1ccc(C#Cc2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
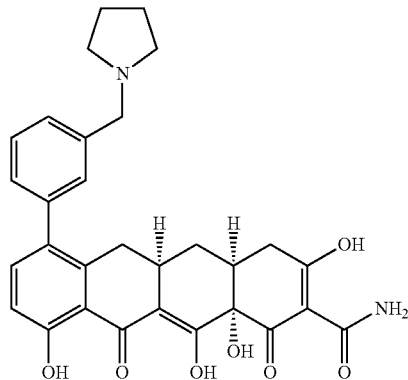 [SMILES: NC(=O)C1=C(O)C[C@@H]2C[C@@H]3Cc4c(-c5cccc(CN6CCCC6)c5)ccc(O)c4C(=O)C3=C(O)[C@]2(O)C1=O]
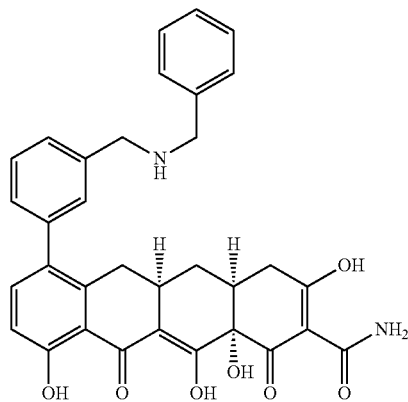 [SMILES: NC(=O)C1=C(O)C[C@@H]2C[C@@H]3Cc4c(-c5cccc(CNCc6ccccc6)c5)ccc(O)c4C(=O)C3=C(O)[C@]2(O)C1=O]
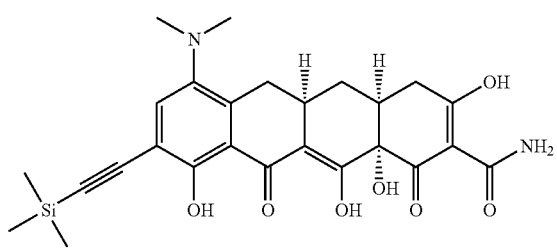
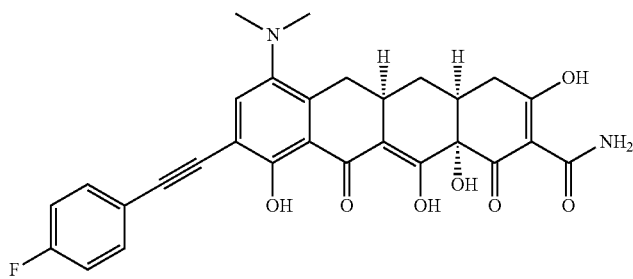 [SMILES: CN(C)c1cc(C#Cc2ccc(F)cc2)c(O)c2c1C[C@H]1C[C@H]3CC(O)=C(C(N)=O)C(=O)[C@@]3(O)C(O)=C1C2=O]

TABLE 2-continued
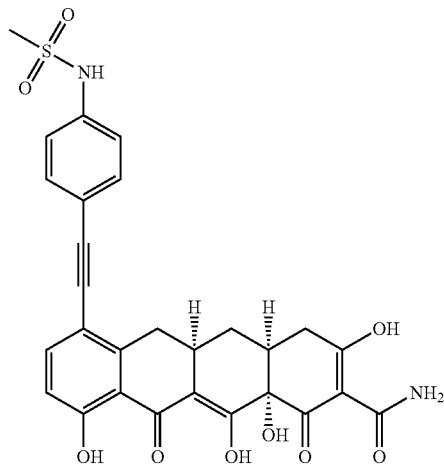 [SMILES: CS(=O)(=O)Nc1ccc(C#Cc2ccc(O)c3c2C[C@H]2C[C@H]4CC(O)=C(C(N)=O)C(=O)[C@@]4(O)C(O)=C2C3=O)cc1]
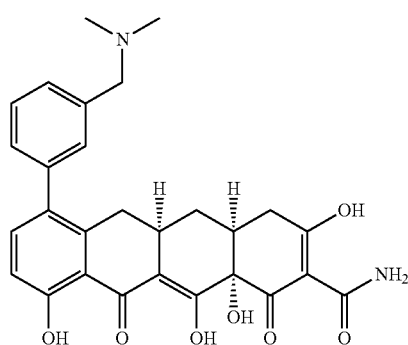
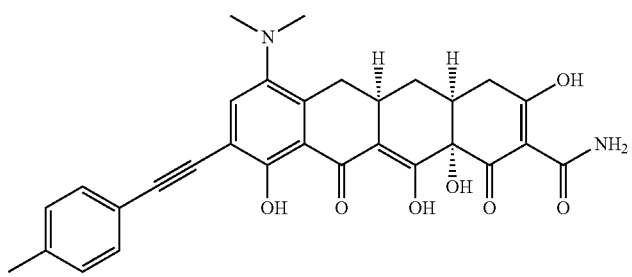 [SMILES: Cc1ccc(C#Cc2cc(N(C)C)c3c(c2O)C(=O)C2=C(O)[C@]4(O)C(=O)C(C(N)=O)=C(O)C[C@@H]4C[C@@H]2C3)cc1]
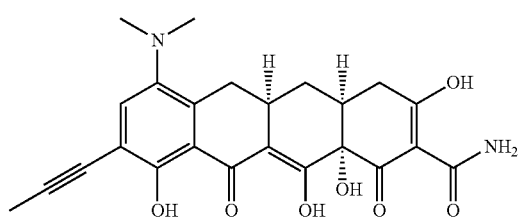 [SMILES: CC#Cc1cc(N(C)C)c2c(c1O)C(=O)C1=C(O)[C@]3(O)C(=O)C(C(N)=O)=C(O)C[C@@H]3C[C@@H]1C2]

TABLE 2-continued
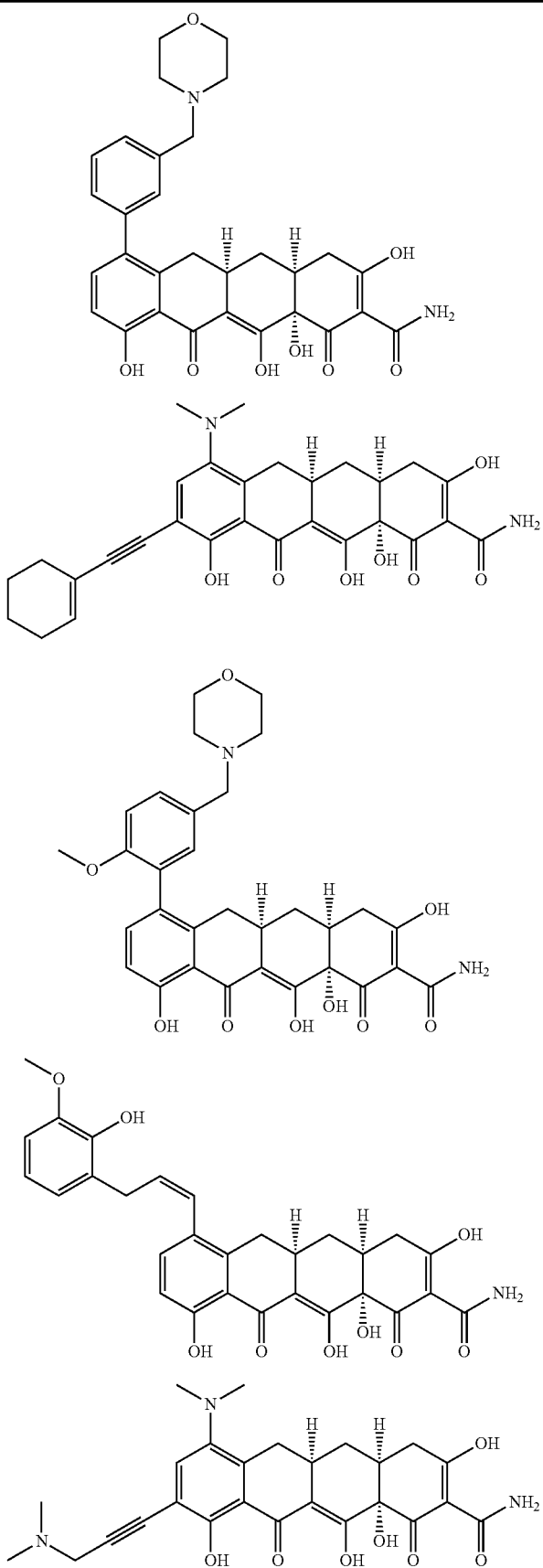

TABLE 2-continued
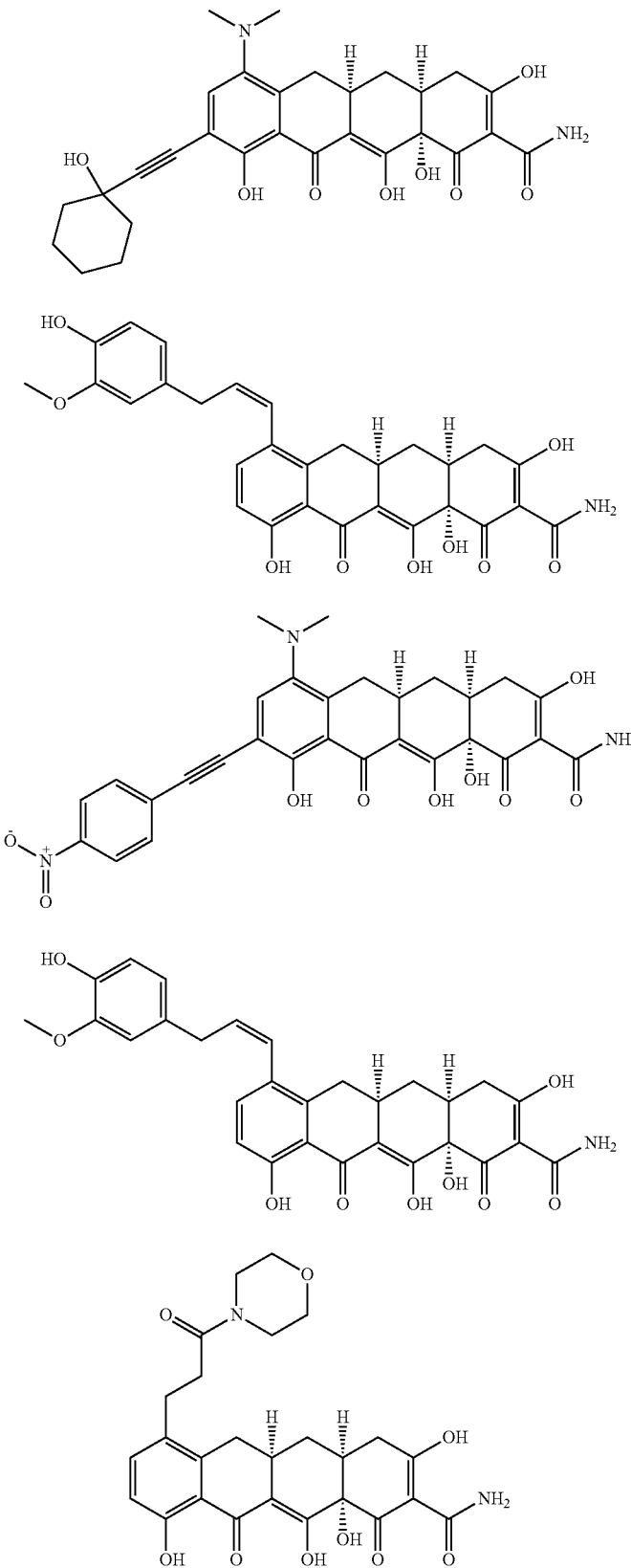

TABLE 2-continued
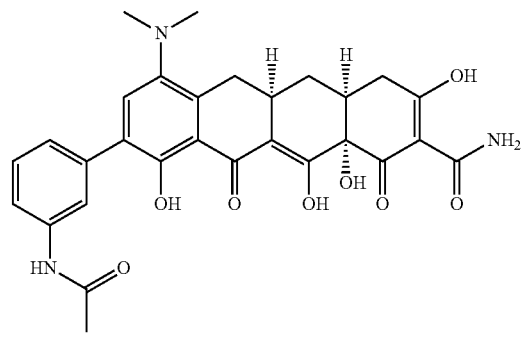 [SMILES: CC(=O)Nc1cccc(-c2cc(N(C)C)c3c(c2O)C(=O)C2=C(O)[C@]4(O)C(=O)C(C(N)=O)=C(O)C[C@@H]4C[C@@H]2C3)c1]
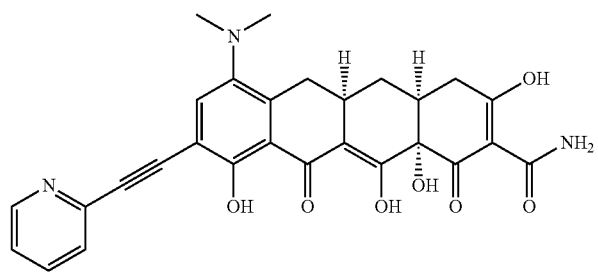 [SMILES: CN(C)c1cc(C#Cc2ccccn2)c(O)c2c1C[C@H]1C[C@H]3CC(O)=C(C(N)=O)C(=O)[C@@]3(O)C(O)=C1C2=O]
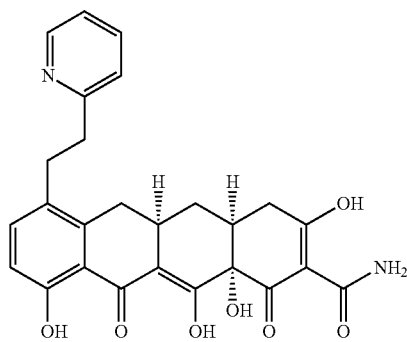 [SMILES: NC(=O)C1=C(O)C[C@@H]2C[C@@H]3Cc4c(CCc5ccccn5)ccc(O)c4C(=O)C3=C(O)[C@]2(O)C1=O]
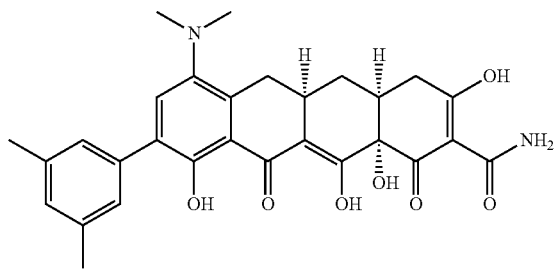 [SMILES: Cc1cc(C)cc(-c2cc(N(C)C)c3c(c2O)C(=O)C2=C(O)[C@]4(O)C(=O)C(C(N)=O)=C(O)C[C@@H]4C[C@@H]2C3)c1]
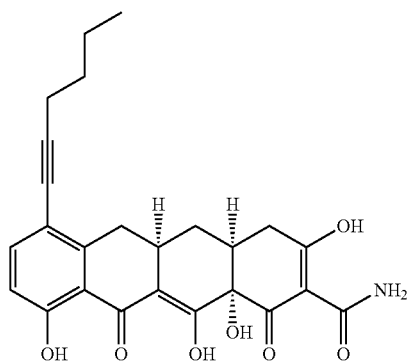 [SMILES: CCCCC#Cc1ccc(O)c2c1C[C@H]1C[C@H]3CC(O)=C(C(N)=O)C(=O)[C@@]3(O)C(O)=C1C2=O]

TABLE 2-continued
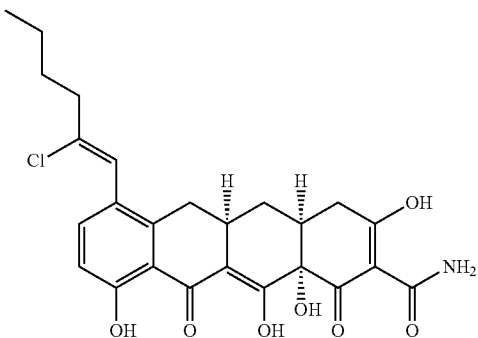 [SMILES: CCCC/C(Cl)=C/c1ccc(O)c2c1C[C@H]1C[C@H]3CC(O)=C(C(N)=O)C(=O)[C@@]3(O)C(O)=C1C2=O]
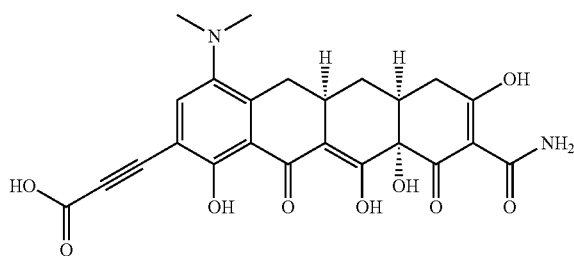 [SMILES: CN(C)c1cc(C#CC(=O)O)c(O)c2c1C[C@H]1C[C@H]3CC(O)=C(C(N)=O)C(=O)[C@@]3(O)C(O)=C1C2=O]
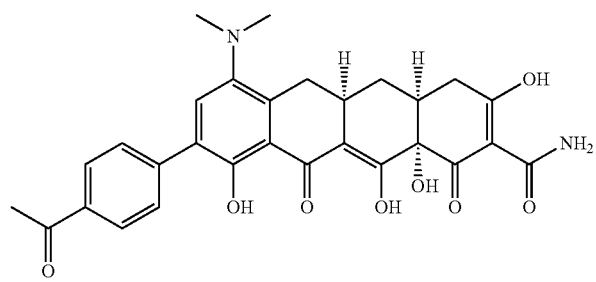 [SMILES: CC(=O)c1ccc(-c2cc(N(C)C)c3c(c2O)C(=O)C2=C(O)[C@]4(O)C(=O)C(C(N)=O)=C(O)C[C@@H]4C[C@@H]2C3)cc1]
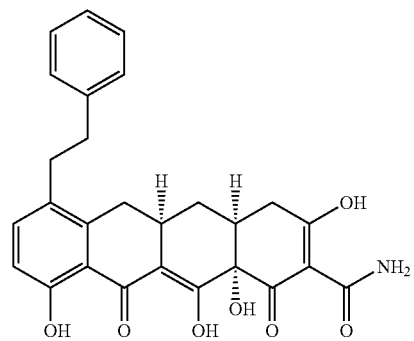
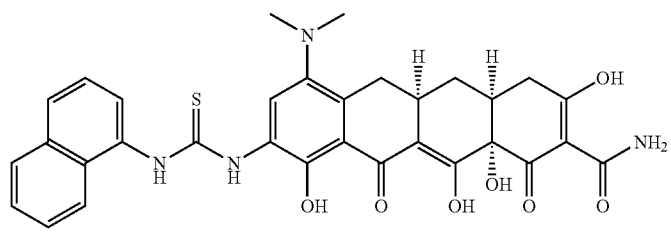

TABLE 2-continued
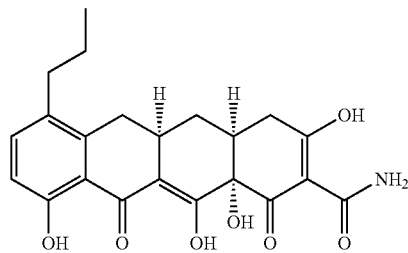
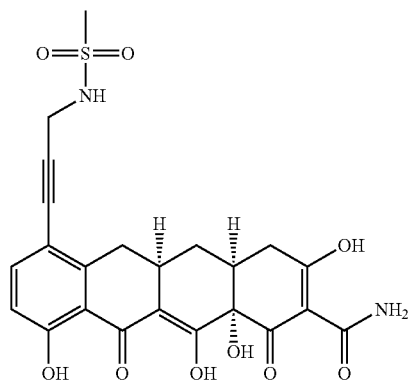 [SMILES: CS(=O)(=O)NCC#Cc1ccc(O)c2c1C[C@H]1C[C@H]3CC(O)=C(C(N)=O)C(=O)[C@@]3(O)C(O)=C1C2=O]
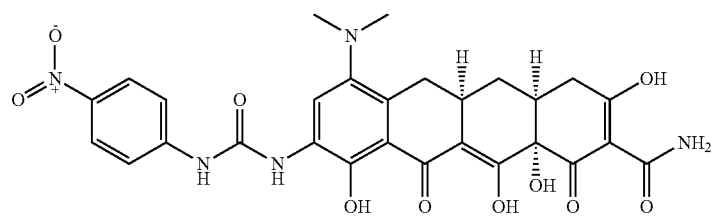
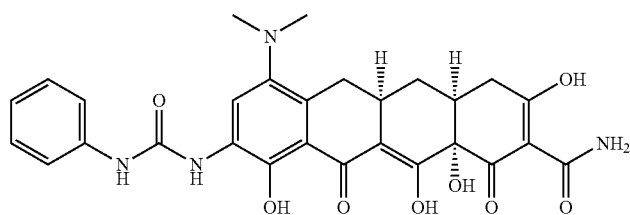 [SMILES: CN(C)c1cc(NC(=O)Nc2ccccc2)c(O)c2c1C[C@H]1C[C@H]3CC(O)=C(C(N)=O)C(=O)[C@@]3(O)C(O)=C1C2=O]
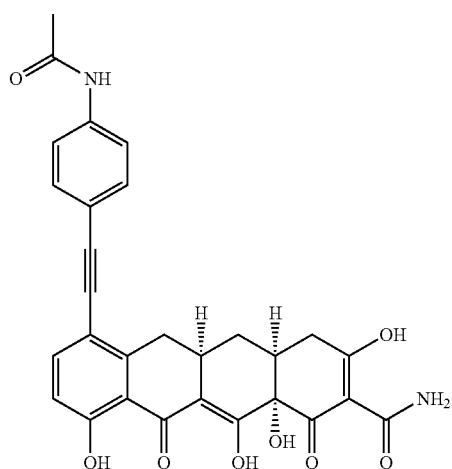 [SMILES: CC(=O)Nc1ccc(C#Cc2ccc(O)c3c2C[C@H]2C[C@H]4CC(O)=C(C(N)=O)C(=O)[C@@]4(O)C(O)=C2C3=O)cc1]

TABLE 2-continued
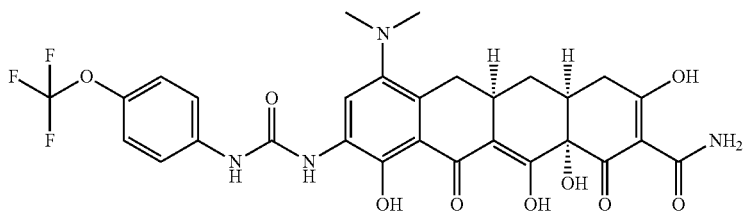 [SMILES: CN(C)c1cc(NC(=O)Nc2ccc(OC(F)(F)F)cc2)c(O)c2c1C[C@H]1C[C@H]3CC(O)=C(C(N)=O)C(=O)[C@@]3(O)C(O)=C1C2=O]
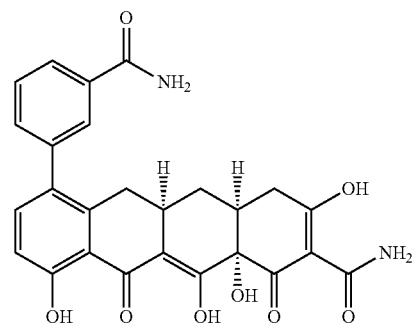 [SMILES: NC(=O)C1=C(O)C[C@@H]2C[C@@H]3Cc4c(-c5cccc(C(N)=O)c5)ccc(O)c4C(=O)C3=C(O)[C@]2(O)C1=O]
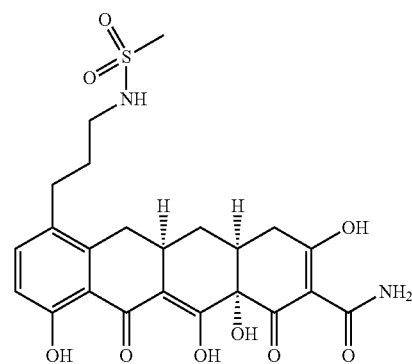 [SMILES: CS(=O)(=O)NCCCc1ccc(O)c2c1C[C@H]1C[C@H]3CC(O)=C(C(N)=O)C(=O)[C@@]3(O)C(O)=C1C2=O]
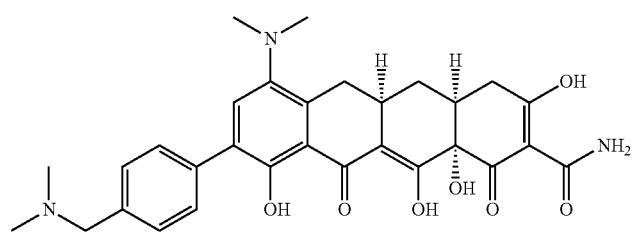 [SMILES: CN(C)Cc1ccc(-c2cc(N(C)C)c3c(c2O)C(=O)C2=C(O)[C@]4(O)C(=O)C(C(N)=O)=C(O)C[C@@H]4C[C@@H]2C3)cc1]
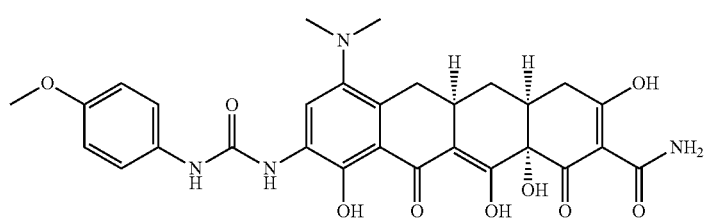 [SMILES: COc1ccc(NC(=O)Nc2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
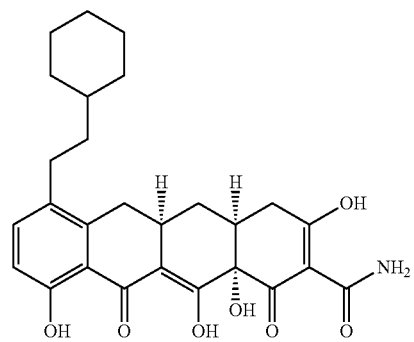 [SMILES: NC(=O)C1=C(O)C[C@@H]2C[C@@H]3Cc4c(CCC5CCCCC5)ccc(O)c4C(=O)C3=C(O)[C@]2(O)C1=O]
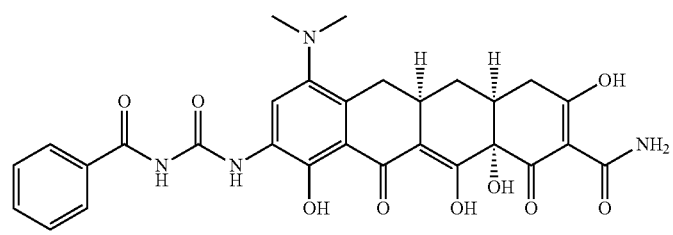 [SMILES: CN(C)c1cc(NC(=O)NC(=O)c2ccccc2)c(O)c2c1C[C@H]1C[C@H]3CC(O)=C(C(N)=O)C(=O)[C@@]3(O)C(O)=C1C2=O]
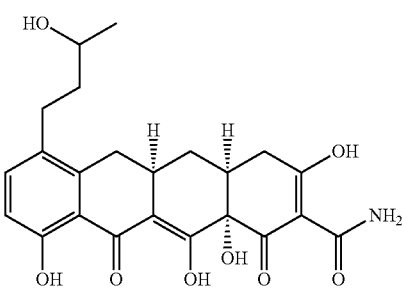 [SMILES: CC(O)CCc1ccc(O)c2c1C[C@H]1C[C@H]3CC(O)=C(C(N)=O)C(=O)[C@@]3(O)C(O)=C1C2=O]
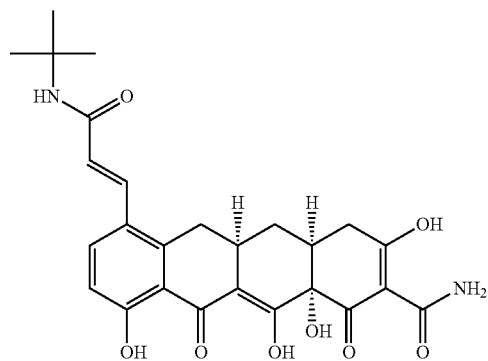 [SMILES: CC(C)(C)NC(=O)/C=C/c1ccc(O)c2c1C[C@H]1C[C@H]3CC(O)=C(C(N)=O)C(=O)[C@@]3(O)C(O)=C1C2=O]
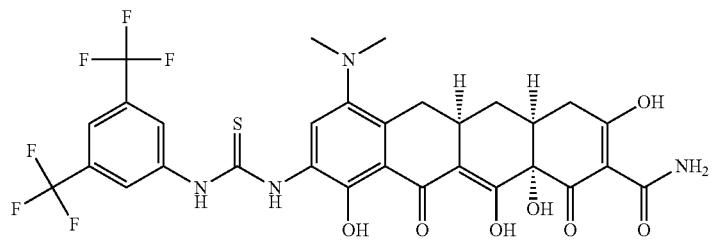 [SMILES: CN(C)c1cc(NC(=S)Nc2cc(C(F)(F)F)cc(C(F)(F)F)c2)c(O)c2c1C[C@H]1C[C@H]3CC(O)=C(C(N)=O)C(=O)[C@@]3(O)C(O)=C1C2=O]

TABLE 2-continued
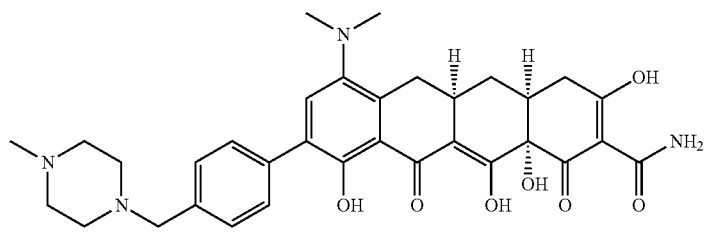 [SMILES: CN1CCN(Cc2ccc(-c3cc(N(C)C)c4c(c3O)C(=O)C3=C(O)[C@]5(O)C(=O)C(C(N)=O)=C(O)C[C@@H]5C[C@@H]3C4)cc2)CC1]
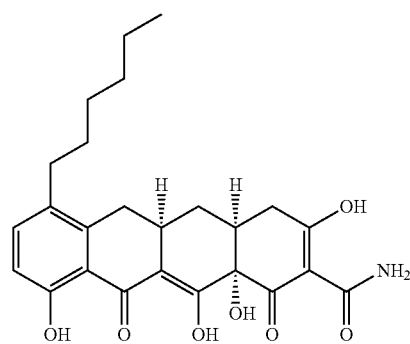 [SMILES: CCCCCCc1ccc(O)c2c1C[C@H]1C[C@H]3CC(O)=C(C(N)=O)C(=O)[C@@]3(O)C(O)=C1C2=O]
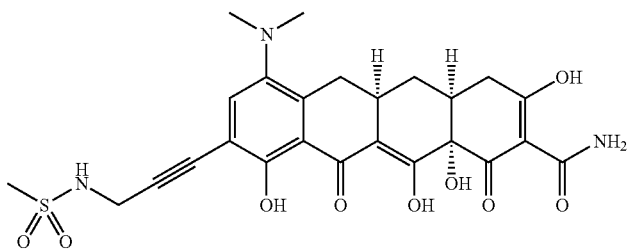 [SMILES: CN(C)c1cc(C#CCNS(C)(=O)=O)c(O)c2c1C[C@H]1C[C@H]3CC(O)=C(C(N)=O)C(=O)[C@@]3(O)C(O)=C1C2=O]
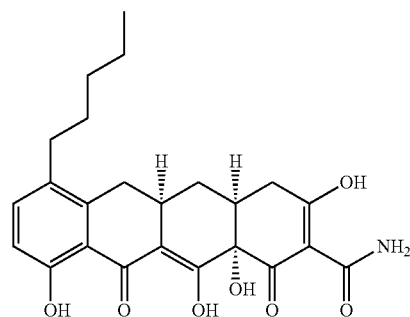 [SMILES: CCCCCc1ccc(O)c2c1C[C@H]1C[C@H]3CC(O)=C(C(N)=O)C(=O)[C@@]3(O)C(O)=C1C2=O]
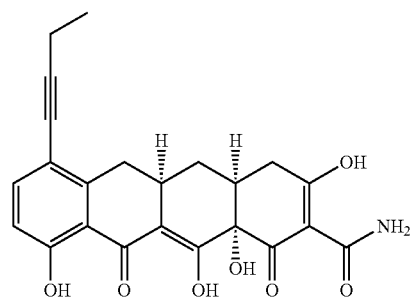 [SMILES: CCC#Cc1ccc(O)c2c1C[C@H]1C[C@H]3CC(O)=C(C(N)=O)C(=O)[C@@]3(O)C(O)=C1C2=O]

TABLE 2-continued
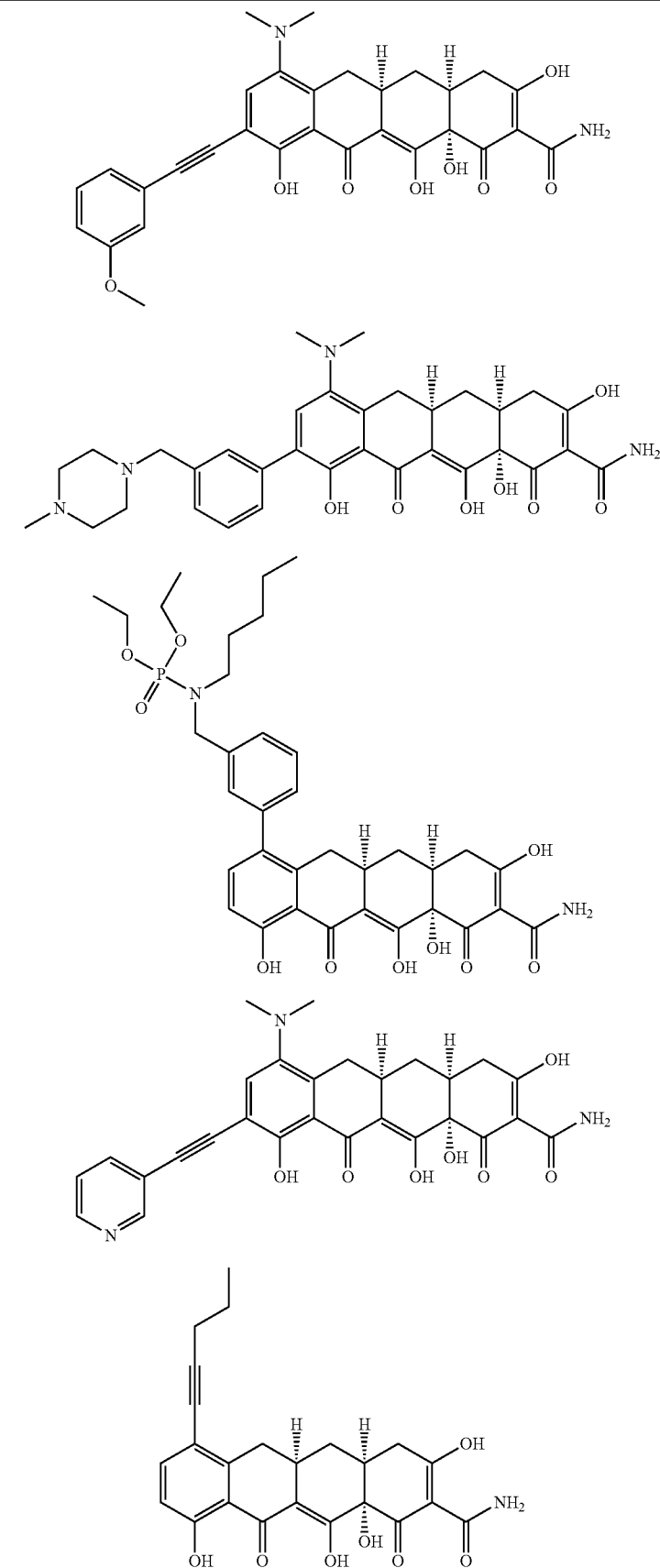

TABLE 2-continued
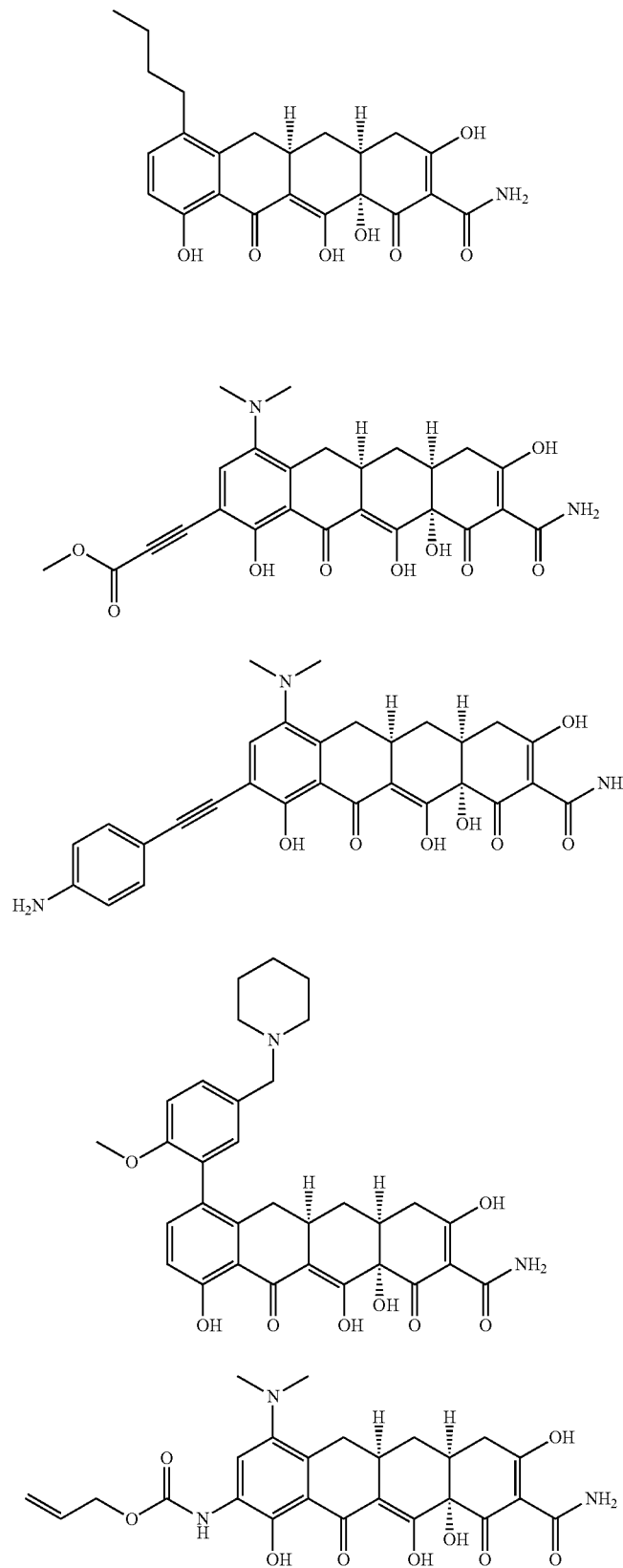

TABLE 2-continued
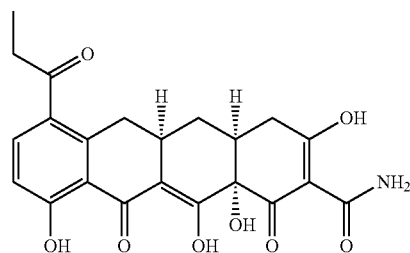 [SMILES: CCC(=O)c1ccc(O)c2c1C[C@H]1C[C@H]3CC(O)=C(C(N)=O)C(=O)[C@@]3(O)C(O)=C1C2=O]
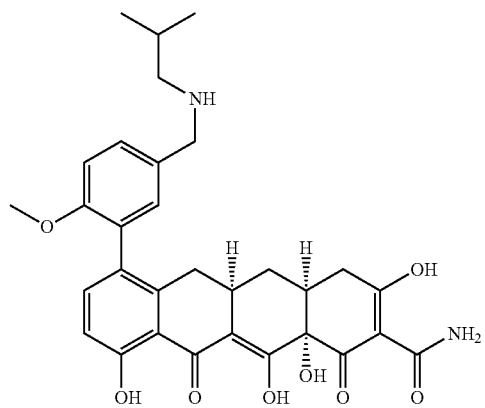 [SMILES: COc1ccc(CNCC(C)C)cc1-c1ccc(O)c2c1C[C@H]1C[C@H]3CC(O)=C(C(N)=O)C(=O)[C@@]3(O)C(O)=C1C2=O]
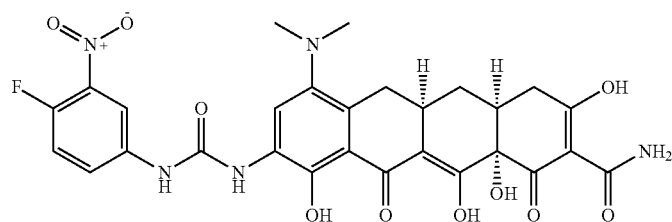
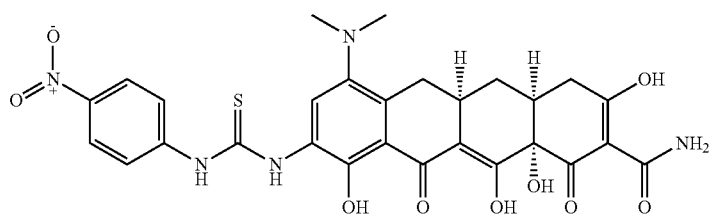
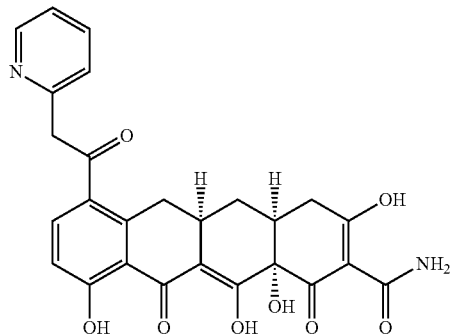 [SMILES: NC(=O)C1=C(O)C[C@@H]2C[C@@H]3Cc4c(C(=O)Cc5ccccn5)ccc(O)c4C(=O)C3=C(O)[C@]2(O)C1=O]

TABLE 2-continued
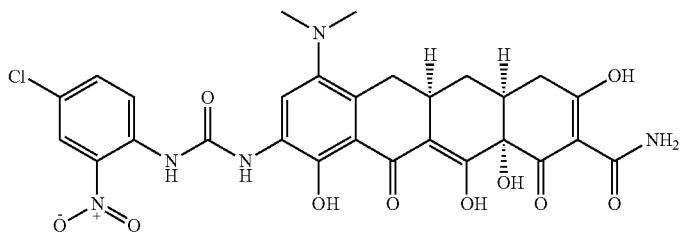
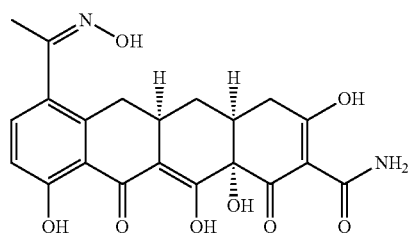 [SMILES: C/C(=N/O)c1ccc(O)c2c1C[C@H]1C[C@H]3CC(O)=C(C(N)=O)C(=O)[C@@]3(O)C(O)=C1C2=O]
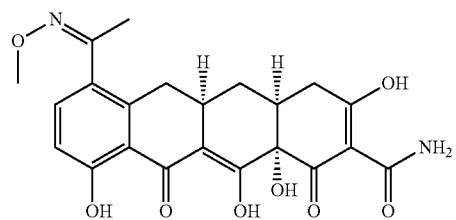 [SMILES: CO/N=C(/C)c1ccc(O)c2c1C[C@H]1C[C@H]3CC(O)=C(C(N)=O)C(=O)[C@@]3(O)C(O)=C1C2=O]
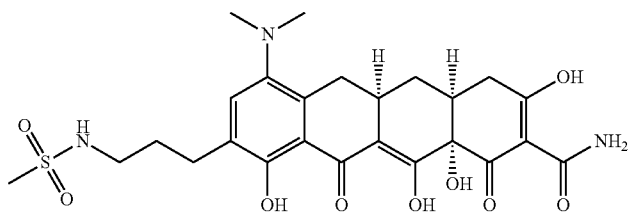 [SMILES: CN(C)c1cc(CCCNS(C)(=O)=O)c(O)c2c1C[C@H]1C[C@H]3CC(O)=C(C(N)=O)C(=O)[C@@]3(O)C(O)=C1C2=O]
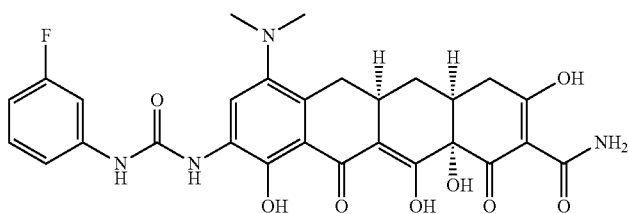 [SMILES: CN(C)c1cc(NC(=O)Nc2cccc(F)c2)c(O)c2c1C[C@H]1C[C@H]3CC(O)=C(C(N)=O)C(=O)[C@@]3(O)C(O)=C1C2=O]
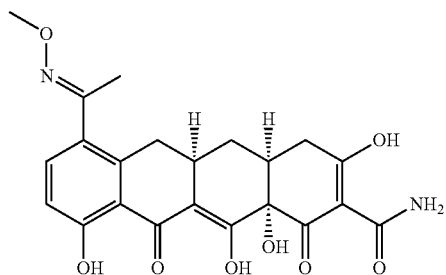 [SMILES: CO/N=C(\C)c1ccc(O)c2c1C[C@H]1C[C@H]3CC(O)=C(C(N)=O)C(=O)[C@@]3(O)C(O)=C1C2=O]

TABLE 2-continued
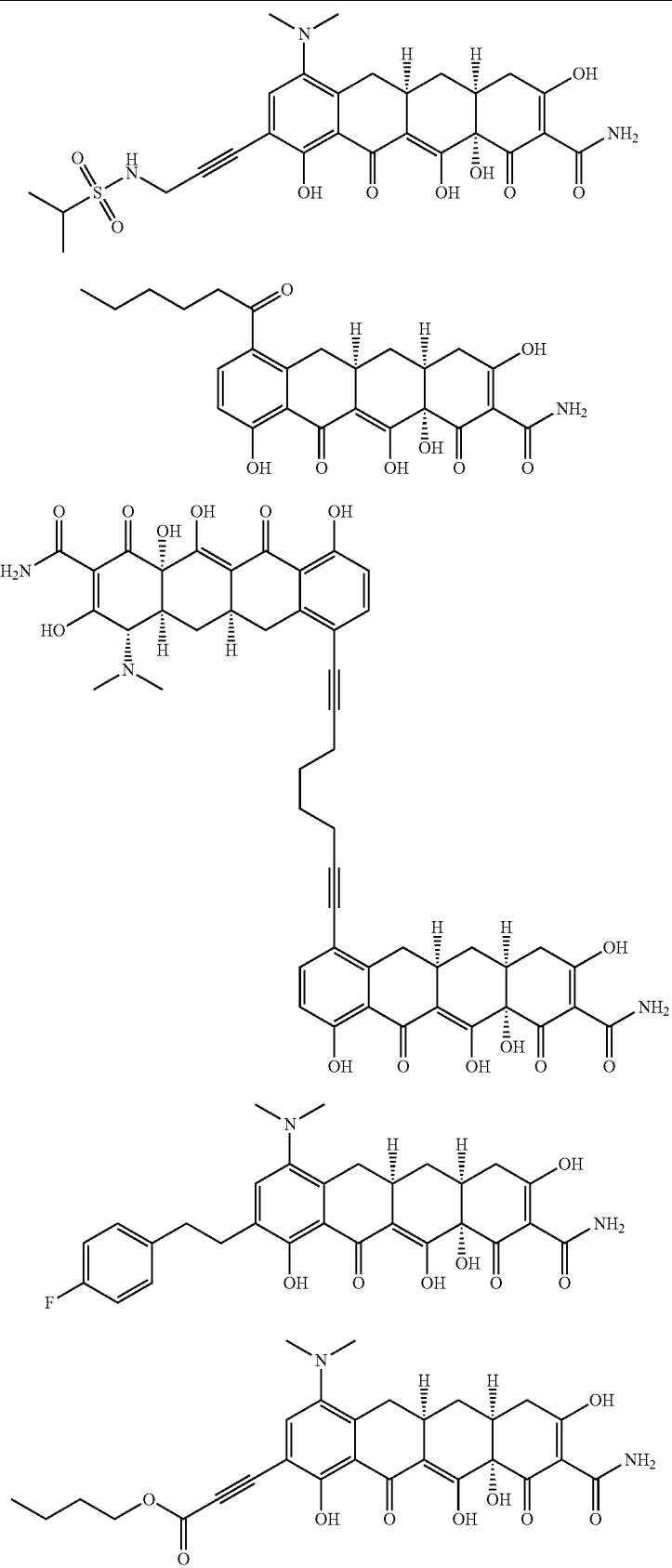

TABLE 2-continued
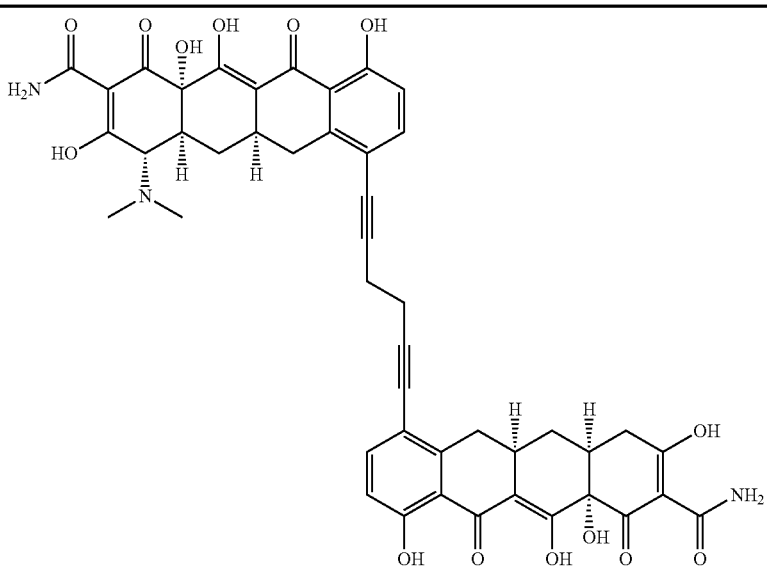
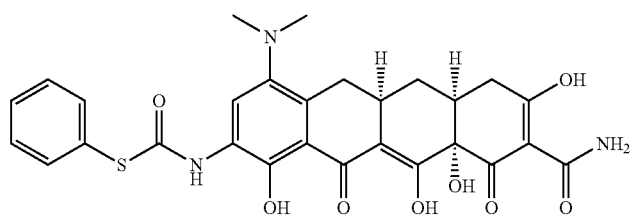 [SMILES: CN(C)c1cc(NC(=O)Sc2ccccc2)c(O)c2c1C[C@H]1C[C@H]3CC(O)=C(C(N)=O)C(=O)[C@@]3(O)C(O)=C1C2=O]
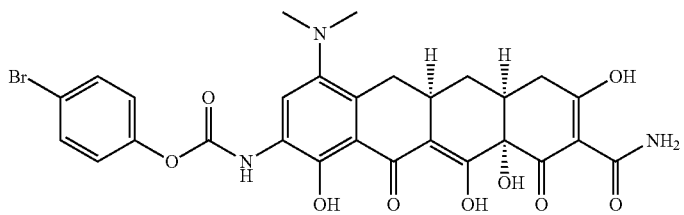
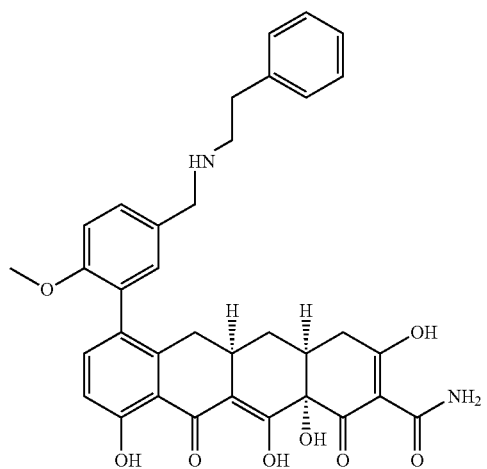 [SMILES: COc1ccc(CNCCc2ccccc2)cc1-c1ccc(O)c2c1C[C@H]1C[C@H]3CC(O)=C(C(N)=O)C(=O)[C@@]3(O)C(O)=C1C2=O]

TABLE 2-continued
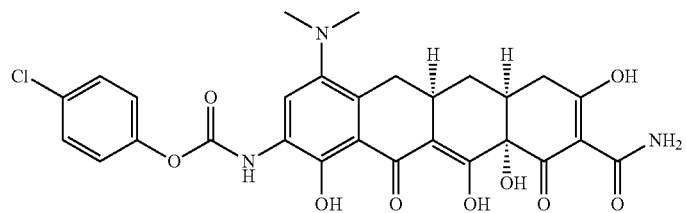 [SMILES: CN(C)c1cc(NC(=O)Oc2ccc(Cl)cc2)c(O)c2c1C[C@H]1C[C@H]3CC(O)=C(C(N)=O)C(=O)[C@@]3(O)C(O)=C1C2=O]
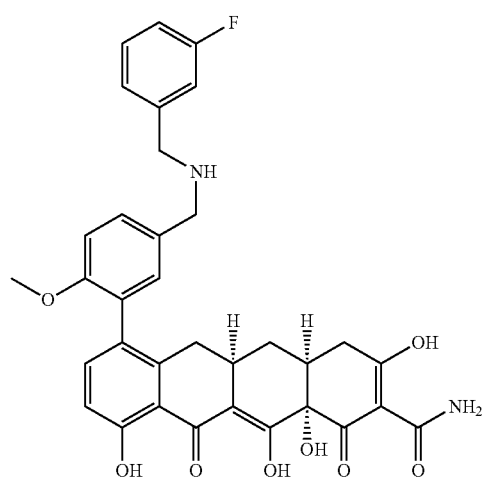 [SMILES: COc1ccc(CNCc2cccc(F)c2)cc1-c1ccc(O)c2c1C[C@H]1C[C@H]3CC(O)=C(C(N)=O)C(=O)[C@@]3(O)C(O)=C1C2=O]
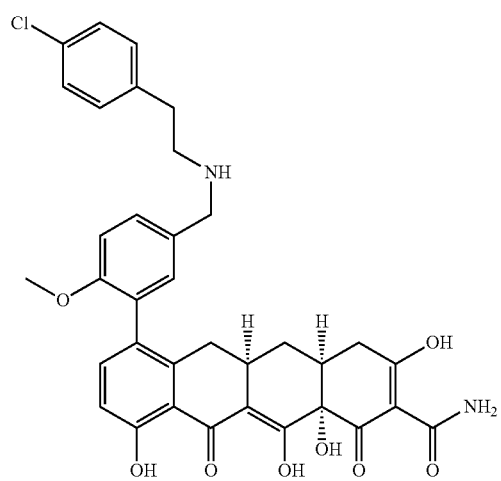 [SMILES: COc1ccc(CNCCc2ccc(Cl)cc2)cc1-c1ccc(O)c2c1C[C@H]1C[C@H]3CC(O)=C(C(N)=O)C(=O)[C@@]3(O)C(O)=C1C2=O]
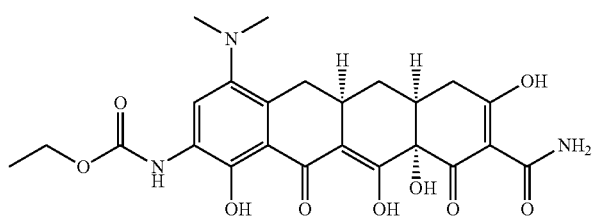 [SMILES: CCOC(=O)Nc1cc(N(C)C)c2c(c1O)C(=O)C1=C(O)[C@]3(O)C(=O)C(C(N)=O)=C(O)C[C@@H]3C[C@@H]1C2]

TABLE 2-continued
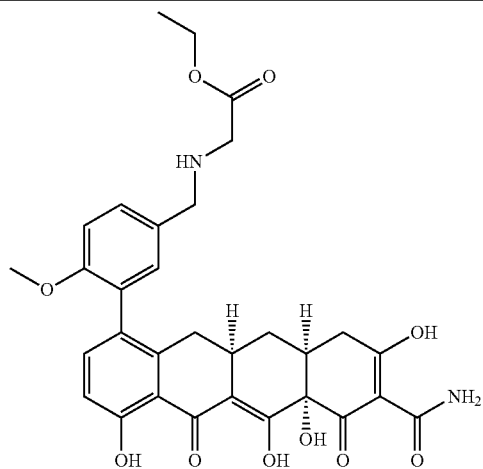
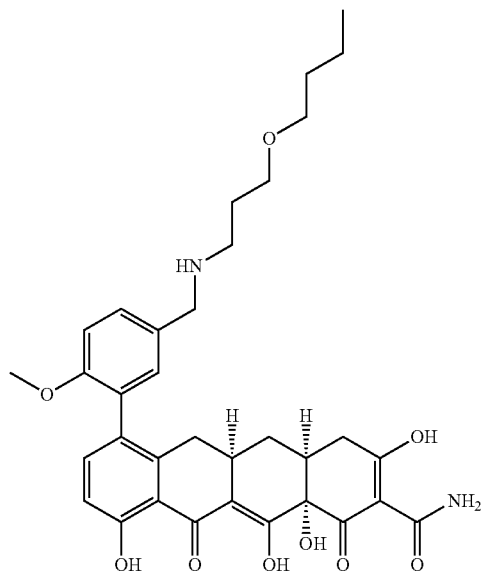 [SMILES: CCCCOCCCNCc1ccc(OC)c(-c2ccc(O)c3c2C[C@H]2C[C@H]4CC(O)=C(C(N)=O)C(=O)[C@@]4(O)C(O)=C2C3=O)c1]
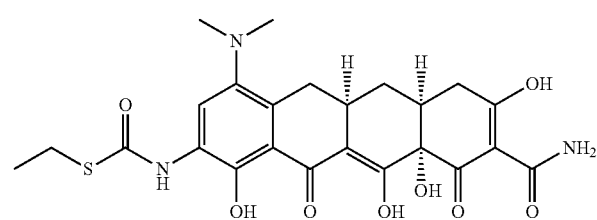
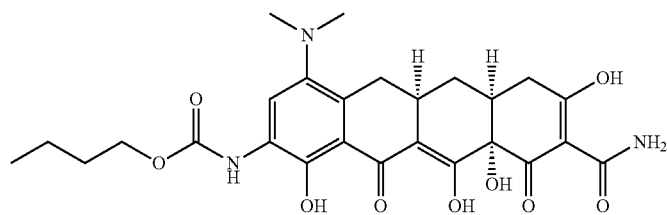 [SMILES: CCCCOC(=O)Nc1cc(N(C)C)c2c(c1O)C(=O)C1=C(O)[C@]3(O)C(=O)C(C(N)=O)=C(O)C[C@@H]3C[C@@H]1C2]

TABLE 2-continued
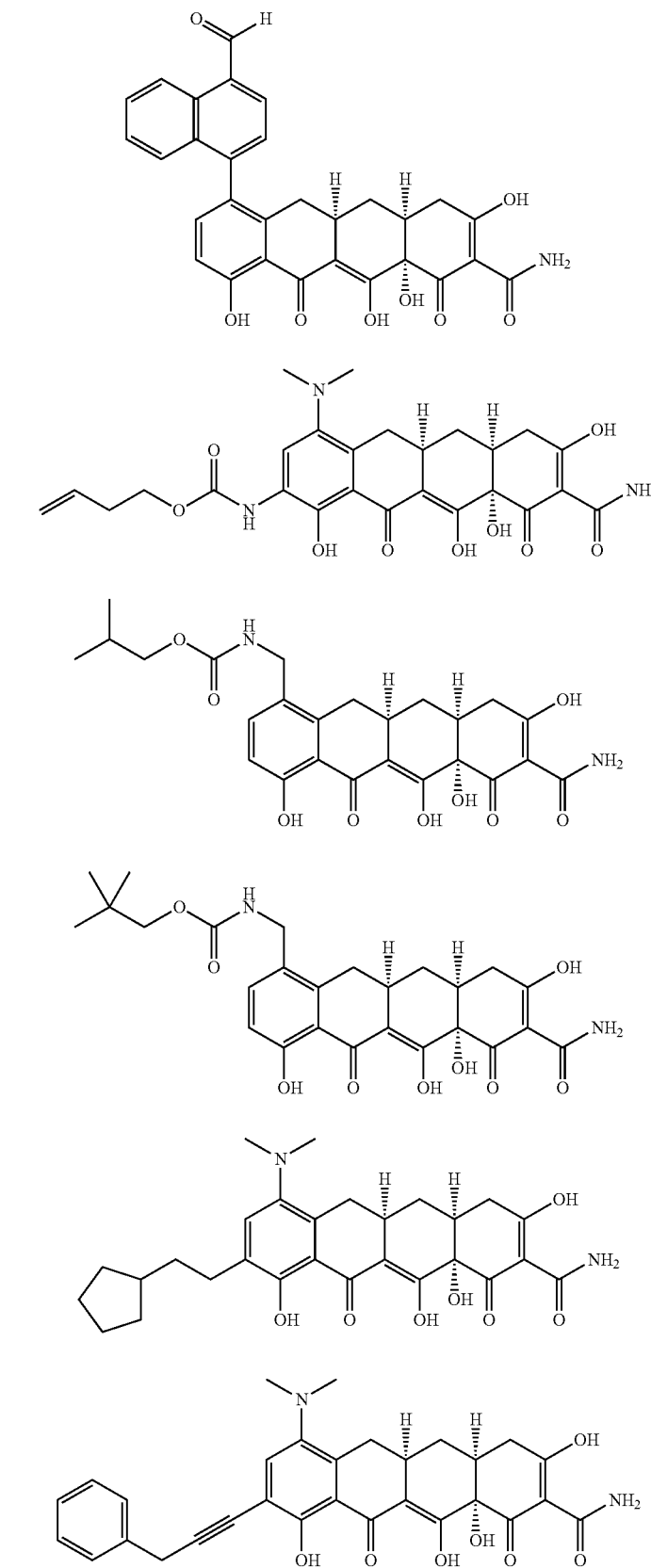

TABLE 2-continued
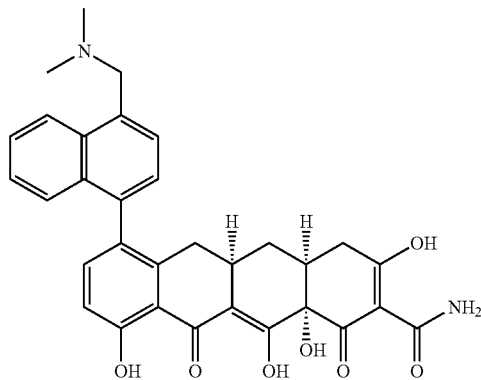 [SMILES: CN(C)Cc1ccc(-c2ccc(O)c3c2C[C@H]2C[C@H]4CC(O)=C(C(N)=O)C(=O)[C@@]4(O)C(O)=C2C3=O)c2ccccc12]
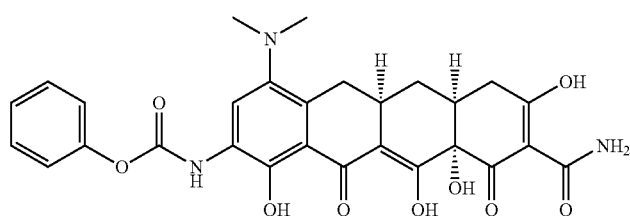
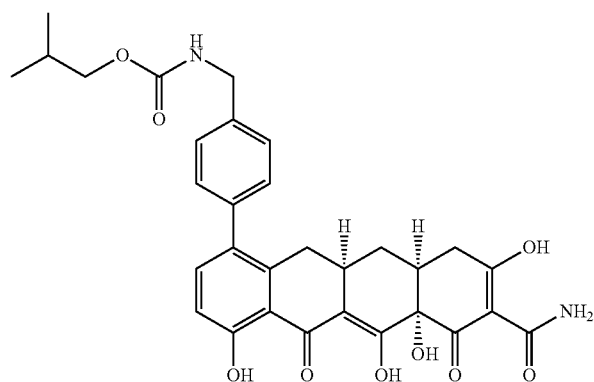 [SMILES: CC(C)COC(=O)NCc1ccc(-c2ccc(O)c3c2C[C@H]2C[C@H]4CC(O)=C(C(N)=O)C(=O)[C@@]4(O)C(O)=C2C3=O)cc1]
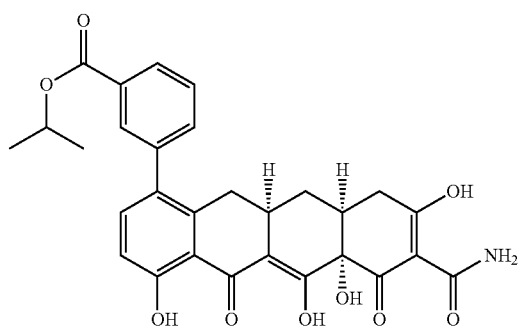 [SMILES: CC(C)OC(=O)c1cccc(-c2ccc(O)c3c2C[C@H]2C[C@H]4CC(O)=C(C(N)=O)C(=O)[C@@]4(O)C(O)=C2C3=O)c1]
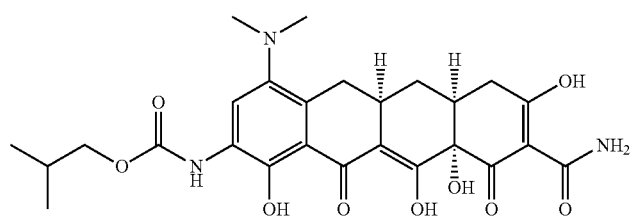 [SMILES: CC(C)COC(=O)Nc1cc(N(C)C)c2c(c1O)C(=O)C1=C(O)[C@]3(O)C(=O)C(C(N)=O)=C(O)C[C@@H]3C[C@@H]1C2]

TABLE 2-continued
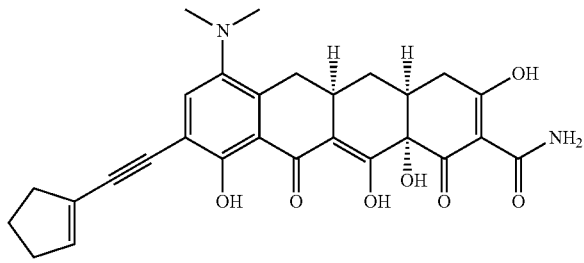 [SMILES: CN(C)c1cc(C#CC2=CCCC2)c(O)c2c1C[C@H]1C[C@H]3CC(O)=C(C(N)=O)C(=O)[C@@]3(O)C(O)=C1C2=O]
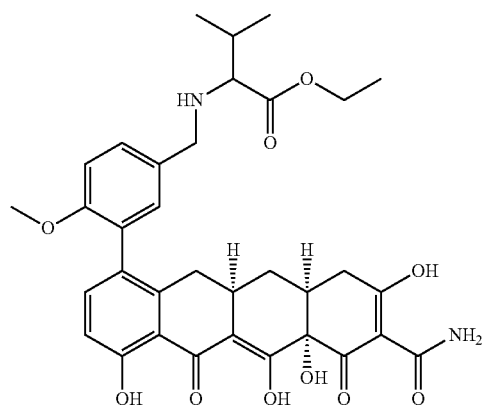 [SMILES: CCOC(=O)C(NCc1ccc(OC)c(-c2ccc(O)c3c2C[C@H]2C[C@H]4CC(O)=C(C(N)=O)C(=O)[C@@]4(O)C(O)=C2C3=O)c1)C(C)C]
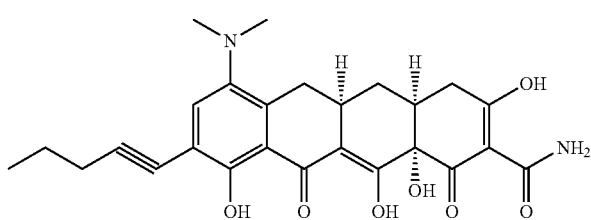 [SMILES: CCCC#Cc1cc(N(C)C)c2c(c1O)C(=O)C1=C(O)[C@]3(O)C(=O)C(C(N)=O)=C(O)C[C@@H]3C[C@@H]1C2]
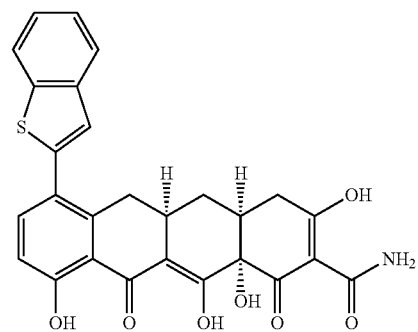 [SMILES: NC(=O)C1=C(O)C[C@@H]2C[C@@H]3Cc4c(-c5cc6ccccc6s5)ccc(O)c4C(=O)C3=C(O)[C@]2(O)C1=O]

TABLE 2-continued
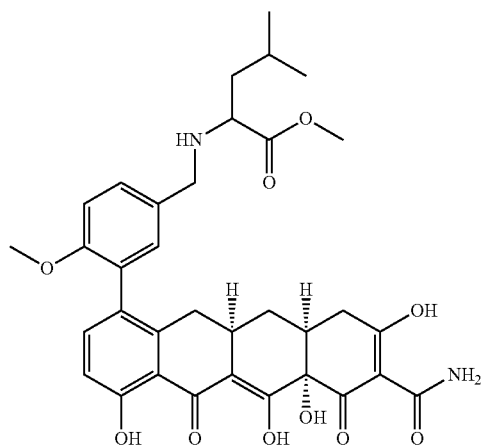 [SMILES: COC(=O)C(CC(C)C)NCc1ccc(OC)c(-c2ccc(O)c3c2C[C@H]2C[C@H]4CC(O)=C(C(N)=O)C(=O)[C@@]4(O)C(O)=C2C3=O)c1]
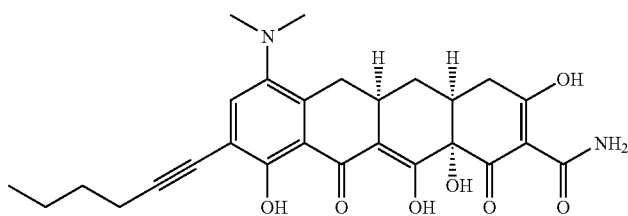 [SMILES: CCCCC#Cc1cc(N(C)C)c2c(c1O)C(=O)C1=C(O)[C@]3(O)C(=O)C(C(N)=O)=C(O)C[C@@H]3C[C@@H]1C2]
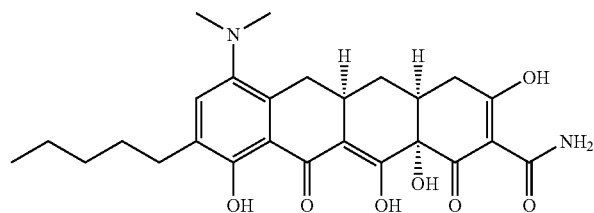 [SMILES: CCCCCc1cc(N(C)C)c2c(c1O)C(=O)C1=C(O)[C@]3(O)C(=O)C(C(N)=O)=C(O)C[C@@H]3C[C@@H]1C2]
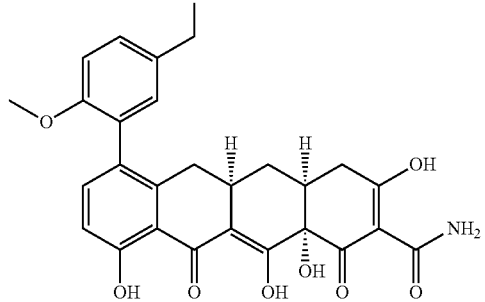
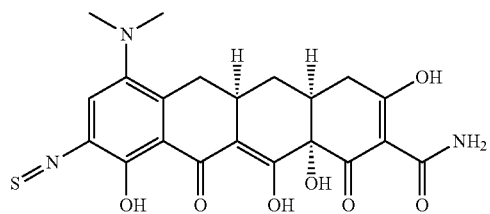 [SMILES: CN(C)c1cc(N=S)c(O)c2c1C[C@H]1C[C@H]3CC(O)=C(C(N)=O)C(=O)[C@@]3(O)C(O)=C1C2=O]

TABLE 2-continued
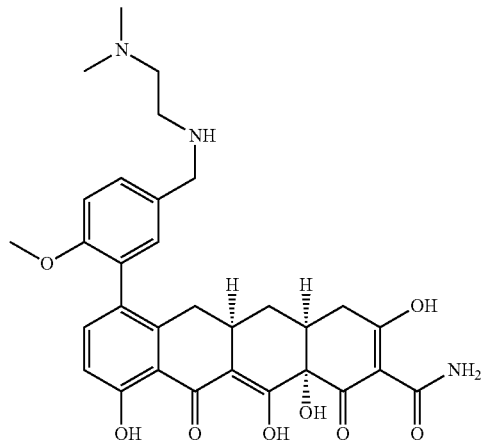 [SMILES: COc1ccc(CNCCN(C)C)cc1-c1ccc(O)c2c1C[C@H]1C[C@H]3CC(O)=C(C(N)=O)C(=O)[C@@]3(O)C(O)=C1C2=O]
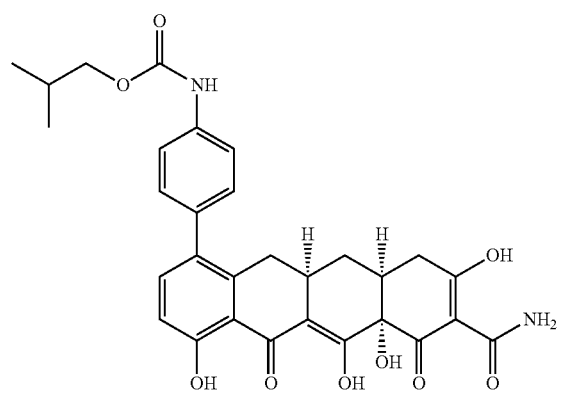 [SMILES: CC(C)COC(=O)Nc1ccc(-c2ccc(O)c3c2C[C@H]2C[C@H]4CC(O)=C(C(N)=O)C(=O)[C@@]4(O)C(O)=C2C3=O)cc1]
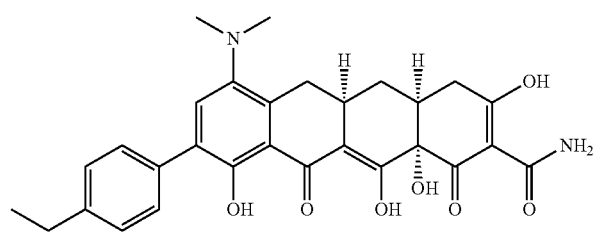 [SMILES: CCc1ccc(-c2cc(N(C)C)c3c(c2O)C(=O)C2=C(O)[C@]4(O)C(=O)C(C(N)=O)=C(O)C[C@@H]4C[C@@H]2C3)cc1]
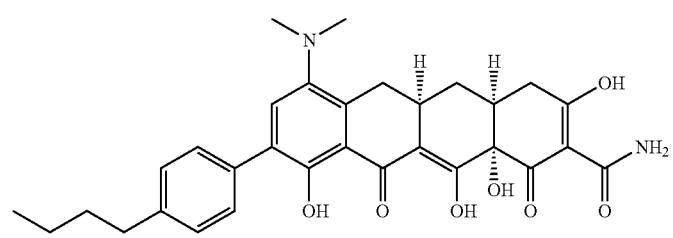 [SMILES: CCCCc1ccc(-c2cc(N(C)C)c3c(c2O)C(=O)C2=C(O)[C@]4(O)C(=O)C(C(N)=O)=C(O)C[C@@H]4C[C@@H]2C3)cc1]

TABLE 2-continued
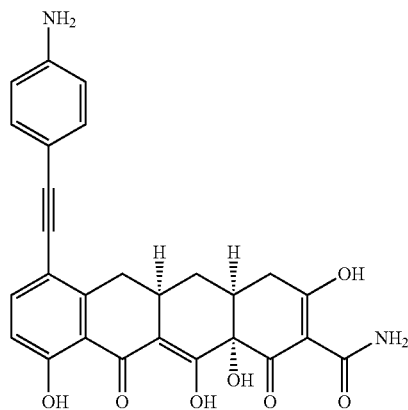 [SMILES: NC(=O)C1=C(O)C[C@@H]2C[C@@H]3Cc4c(C#Cc5ccc(N)cc5)ccc(O)c4C(=O)C3=C(O)[C@]2(O)C1=O]
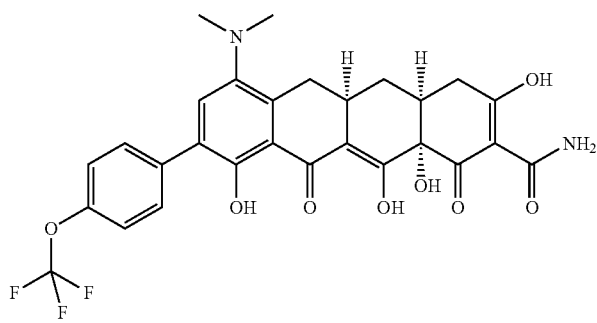 [SMILES: CN(C)c1cc(-c2ccc(OC(F)(F)F)cc2)c(O)c2c1C[C@H]1C[C@H]3CC(O)=C(C(N)=O)C(=O)[C@@]3(O)C(O)=C1C2=O]
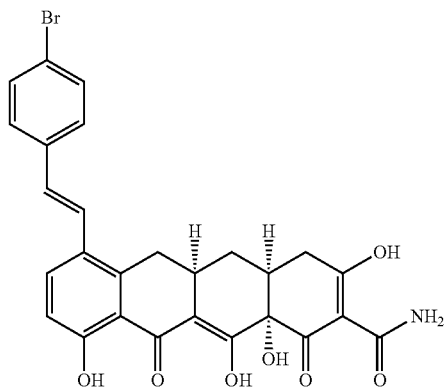 [SMILES: NC(=O)C1=C(O)C[C@@H]2C[C@@H]3Cc4c(/C=C/c5ccc(Br)cc5)ccc(O)c4C(=O)C3=C(O)[C@]2(O)C1=O]
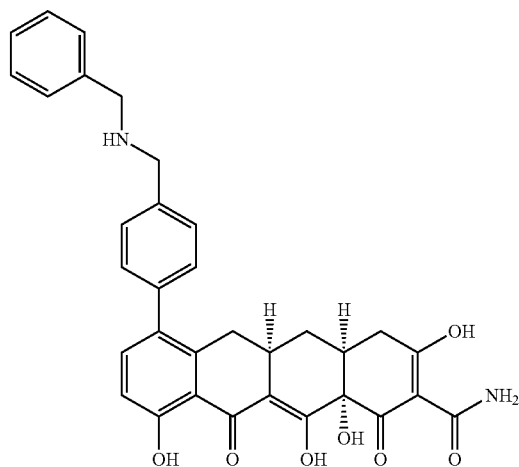 [SMILES: NC(=O)C1=C(O)C[C@@H]2C[C@@H]3Cc4c(-c5ccc(CNCc6ccccc6)cc5)ccc(O)c4C(=O)C3=C(O)[C@]2(O)C1=O]

TABLE 2-continued
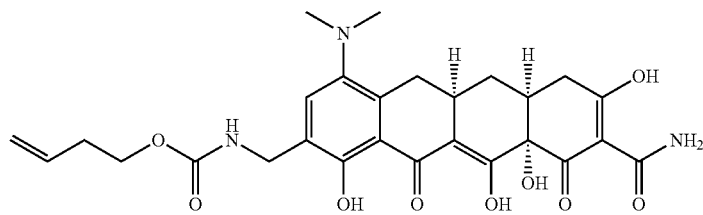 [SMILES: C=CCCOC(=O)NCc1cc(N(C)C)c2c(c1O)C(=O)C1=C(O)[C@]3(O)C(=O)C(C(N)=O)=C(O)C[C@@H]3C[C@@H]1C2]
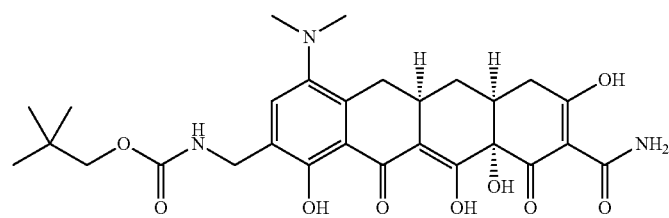 [SMILES: CN(C)c1cc(CNC(=O)OCC(C)(C)C)c(O)c2c1C[C@H]1C[C@H]3CC(O)=C(C(N)=O)C(=O)[C@@]3(O)C(O)=C1C2=O]
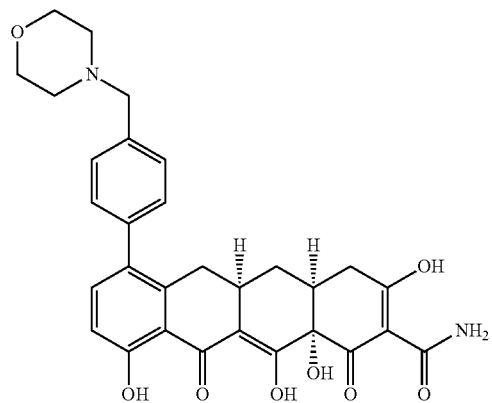 [SMILES: NC(=O)C1=C(O)C[C@@H]2C[C@@H]3Cc4c(-c5ccc(CN6CCOCC6)cc5)ccc(O)c4C(=O)C3=C(O)[C@]2(O)C1=O]
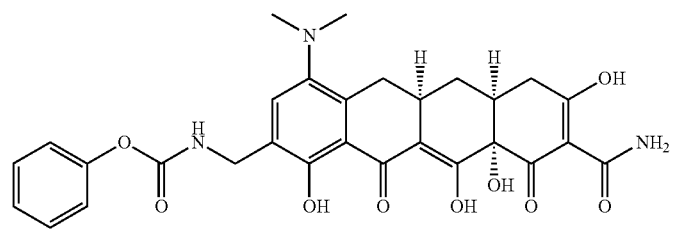 [SMILES: CN(C)c1cc(CNC(=O)Oc2ccccc2)c(O)c2c1C[C@H]1C[C@H]3CC(O)=C(C(N)=O)C(=O)[C@@]3(O)C(O)=C1C2=O]
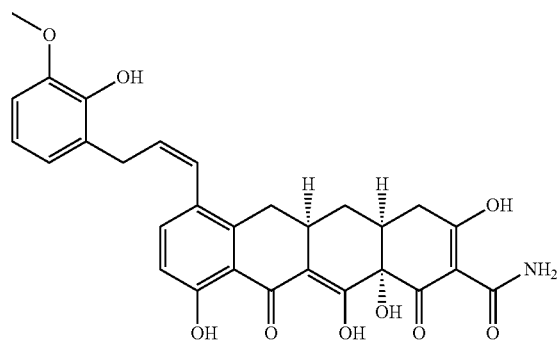 [SMILES: COc1cccc(C/C=C\c2ccc(O)c3c2C[C@H]2C[C@H]4CC(O)=C(C(N)=O)C(=O)[C@@]4(O)C(O)=C2C3=O)c1O]

TABLE 2-continued
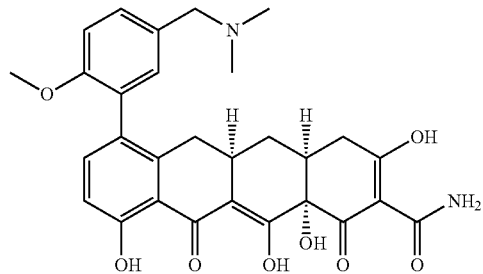 [SMILES: COc1ccc(CN(C)C)cc1-c1ccc(O)c2c1C[C@H]1C[C@H]3CC(O)=C(C(N)=O)C(=O)[C@@]3(O)C(O)=C1C2=O]
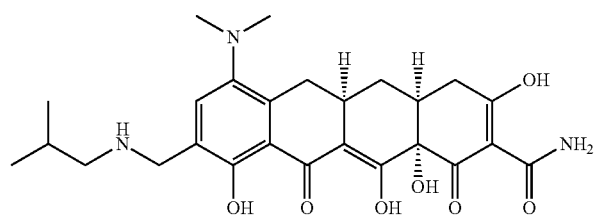 [SMILES: CC(C)CNCc1cc(N(C)C)c2c(c1O)C(=O)C1=C(O)[C@]3(O)C(=O)C(C(N)=O)=C(O)C[C@@H]3C[C@@H]1C2]
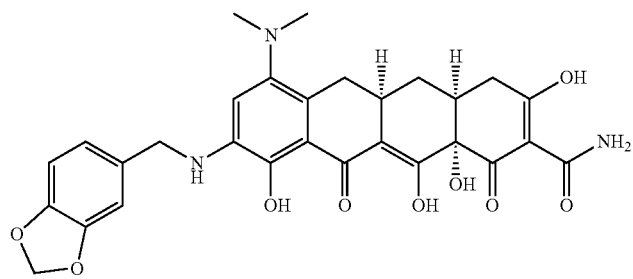 [SMILES: CN(C)c1cc(NCc2ccc3c(c2)OCO3)c(O)c2c1C[C@H]1C[C@H]3CC(O)=C(C(N)=O)C(=O)[C@@]3(O)C(O)=C1C2=O]
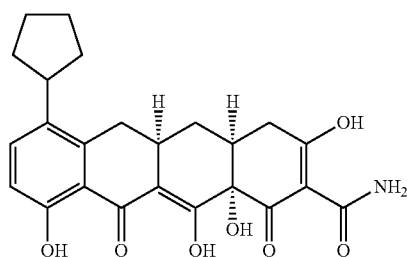 [SMILES: NC(=O)C1=C(O)C[C@@H]2C[C@@H]3Cc4c(C5CCCC5)ccc(O)c4C(=O)C3=C(O)[C@]2(O)C1=O]
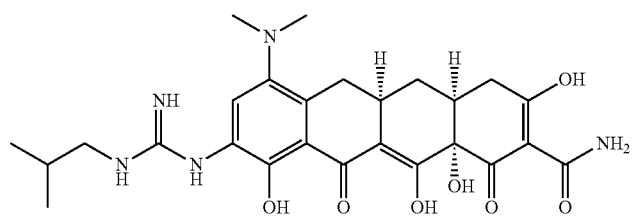 [SMILES: CC(C)CNC(=N)Nc1cc(N(C)C)c2c(c1O)C(=O)C1=C(O)[C@]3(O)C(=O)C(C(N)=O)=C(O)C[C@@H]3C[C@@H]1C2]

TABLE 2-continued
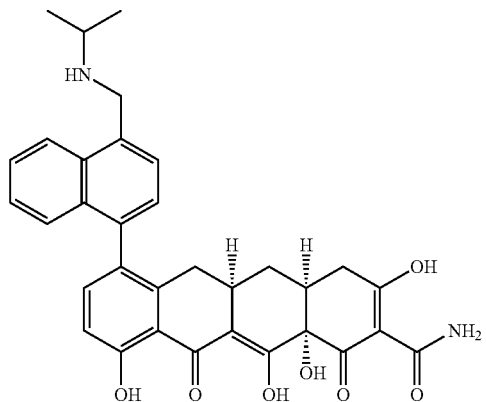 [SMILES: CC(C)NCc1ccc(-c2ccc(O)c3c2C[C@H]2C[C@H]4CC(O)=C(C(N)=O)C(=O)[C@@]4(O)C(O)=C2C3=O)c2ccccc12]
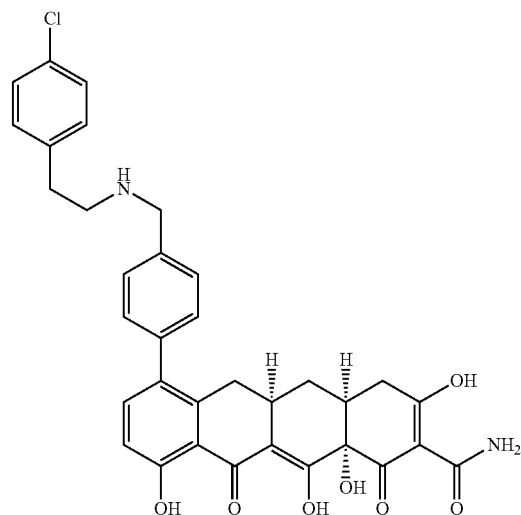 [SMILES: NC(=O)C1=C(O)C[C@@H]2C[C@@H]3Cc4c(-c5ccc(CNCCc6ccc(Cl)cc6)cc5)ccc(O)c4C(=O)C3=C(O)[C@]2(O)C1=O]
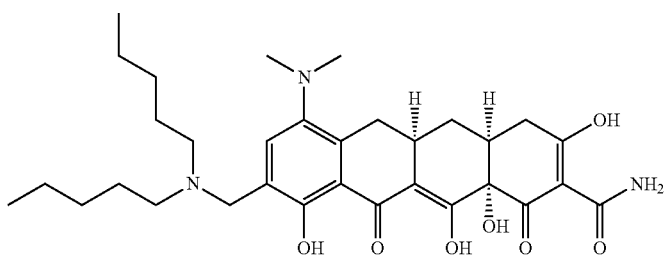 [SMILES: CCCCCN(CCCCC)Cc1cc(N(C)C)c2c(c1O)C(=O)C1=C(O)[C@]3(O)C(=O)C(C(N)=O)=C(O)C[C@@H]3C[C@@H]1C2]
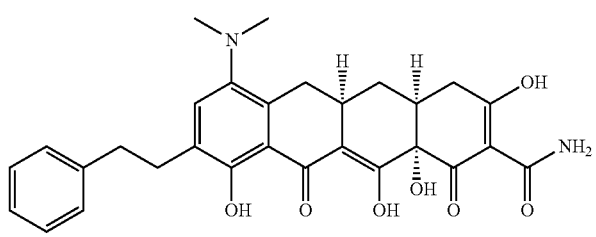 [SMILES: CN(C)c1cc(CCc2ccccc2)c(O)c2c1C[C@H]1C[C@H]3CC(O)=C(C(N)=O)C(=O)[C@@]3(O)C(O)=C1C2=O]

TABLE 2-continued
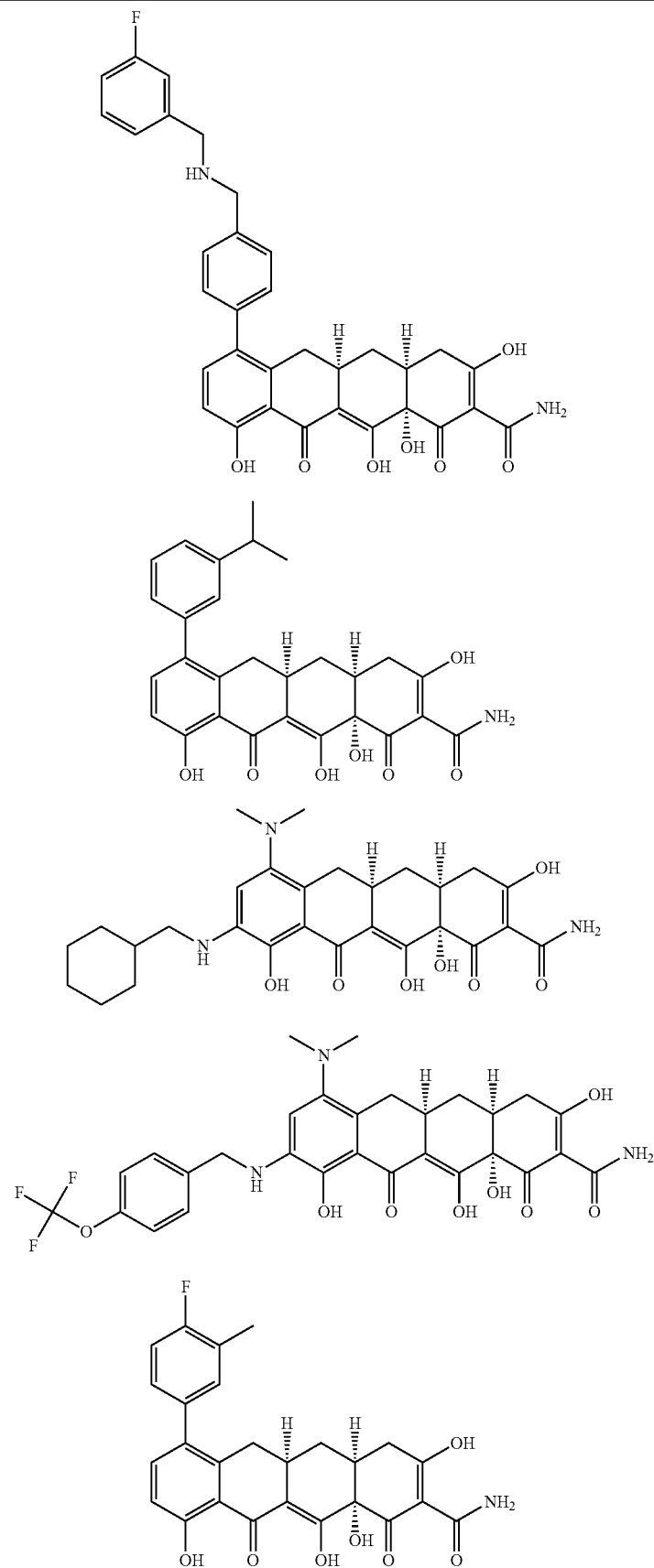

TABLE 2-continued
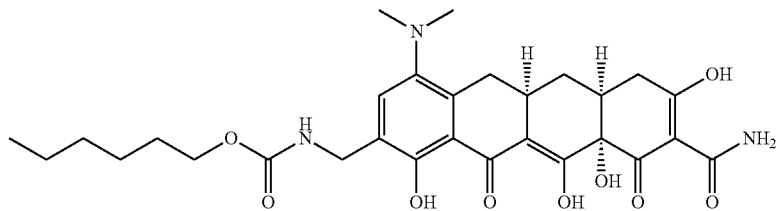 [SMILES: CCCCCCOC(=O)NCc1cc(N(C)C)c2c(c1O)C(=O)C1=C(O)[C@]3(O)C(=O)C(C(N)=O)=C(O)C[C@@H]3C[C@@H]1C2]
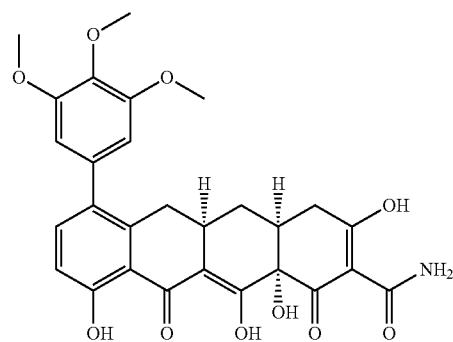 [SMILES: COc1cc(-c2ccc(O)c3c2C[C@H]2C[C@H]4CC(O)=C(C(N)=O)C(=O)[C@@]4(O)C(O)=C2C3=O)cc(OC)c1OC]
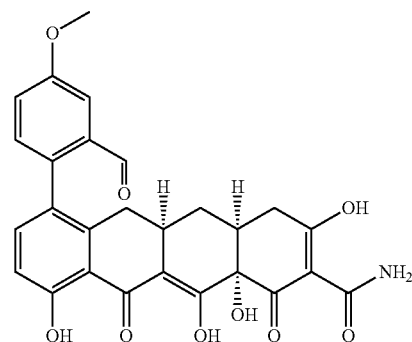 [SMILES: COc1ccc(-c2ccc(O)c3c2C[C@H]2C[C@H]4CC(O)=C(C(N)=O)C(=O)[C@@]4(O)C(O)=C2C3=O)c(C=O)c1]
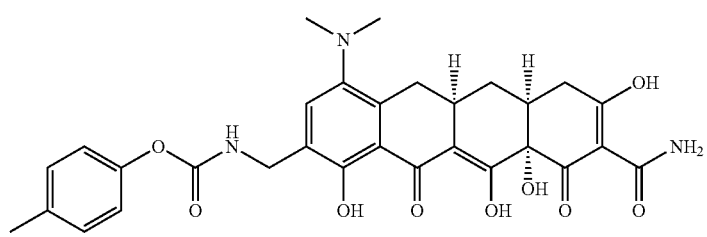 [SMILES: Cc1ccc(OC(=O)NCc2cc(N(C)C)c3c(c2O)C(=O)C2=C(O)[C@]4(O)C(=O)C(C(N)=O)=C(O)C[C@@H]4C[C@@H]2C3)cc1]
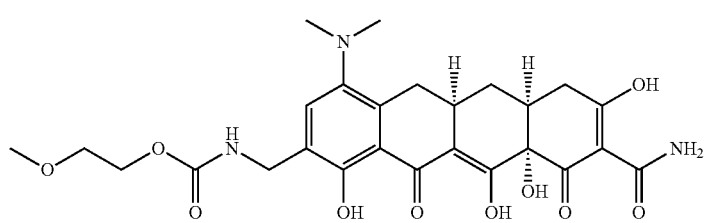

TABLE 2-continued
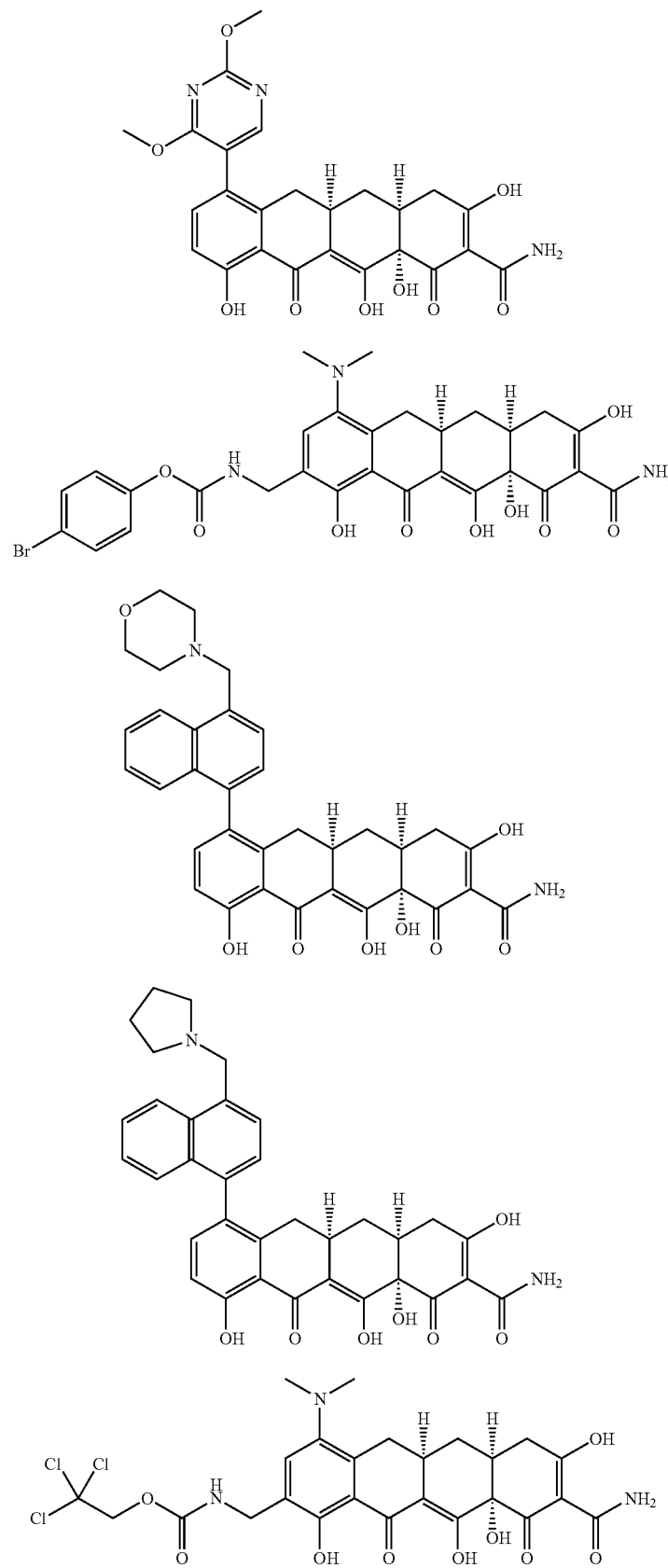

TABLE 2-continued
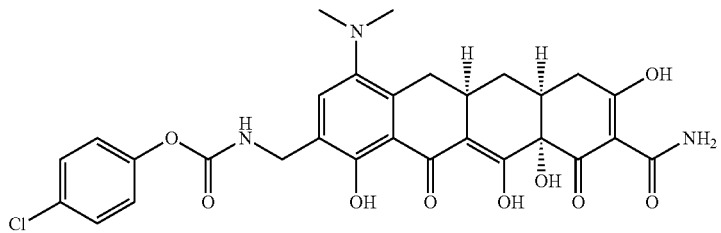 [SMILES: CN(C)c1cc(CNC(=O)Oc2ccc(Cl)cc2)c(O)c2c1C[C@H]1C[C@H]3CC(O)=C(C(N)=O)C(=O)[C@@]3(O)C(O)=C1C2=O]
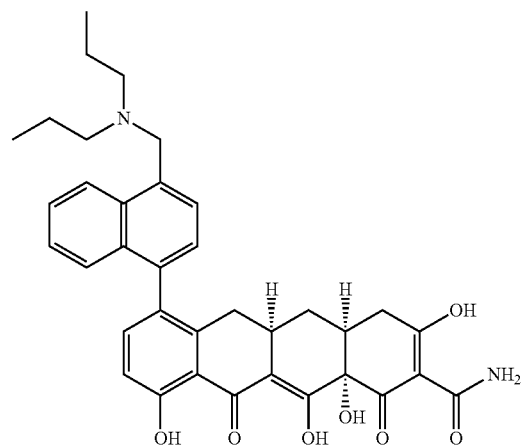 [SMILES: CCCN(CCC)Cc1ccc(-c2ccc(O)c3c2C[C@H]2C[C@H]4CC(O)=C(C(N)=O)C(=O)[C@@]4(O)C(O)=C2C3=O)c2ccccc12]
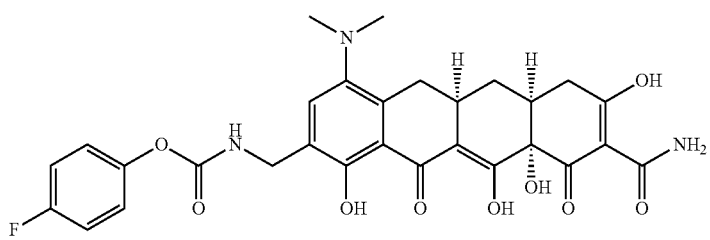 [SMILES: CN(C)c1cc(CNC(=O)Oc2ccc(F)cc2)c(O)c2c1C[C@H]1C[C@H]3CC(O)=C(C(N)=O)C(=O)[C@@]3(O)C(O)=C1C2=O]
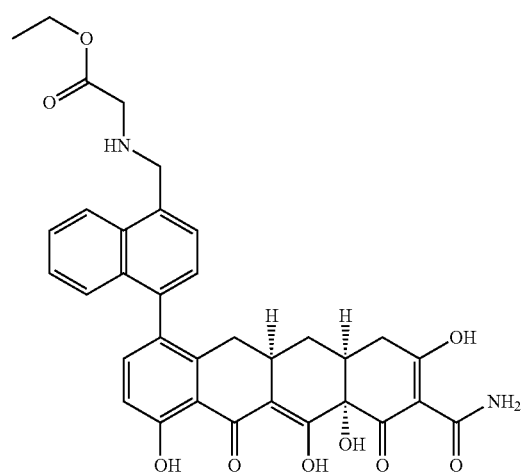 [SMILES: CCOC(=O)CNCc1ccc(-c2ccc(O)c3c2C[C@H]2C[C@H]4CC(O)=C(C(N)=O)C(=O)[C@@]4(O)C(O)=C2C3=O)c2ccccc12]

TABLE 2-continued
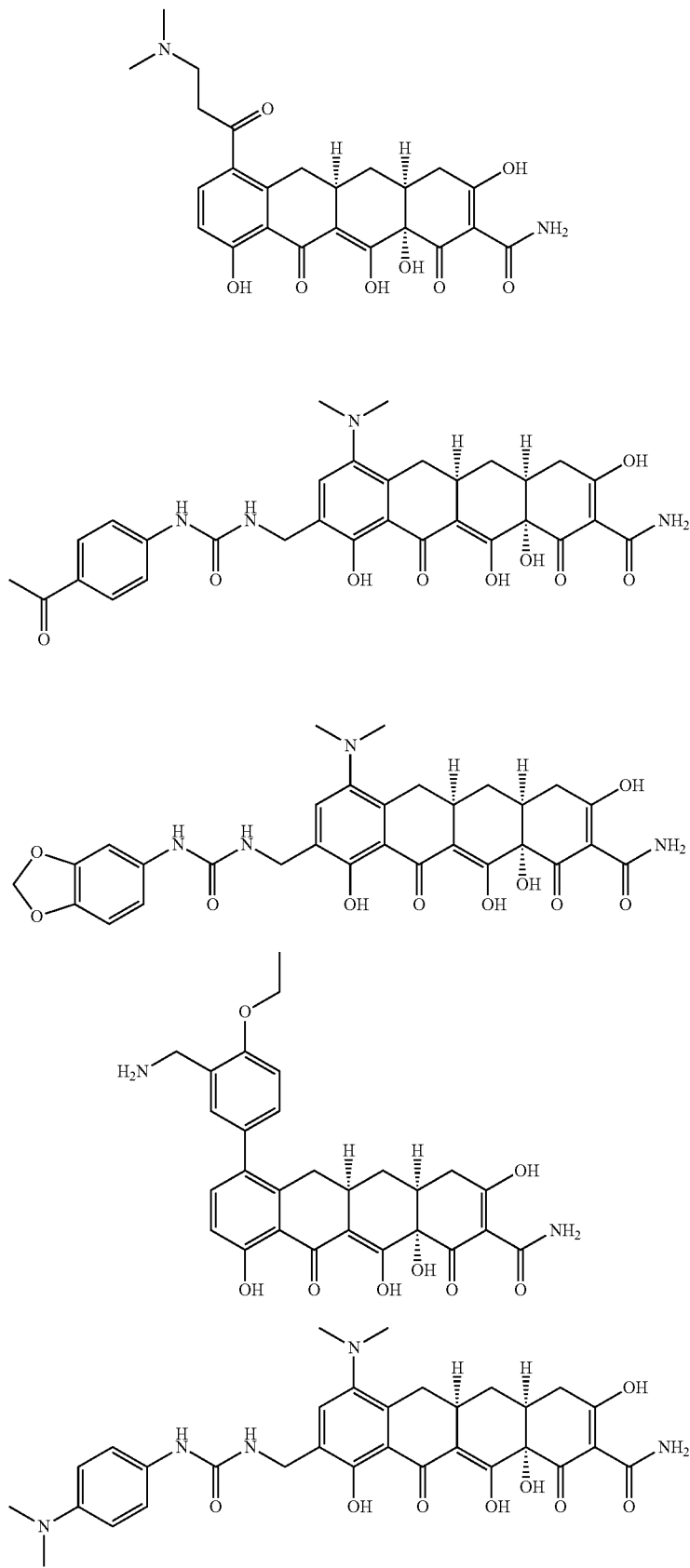

TABLE 2-continued
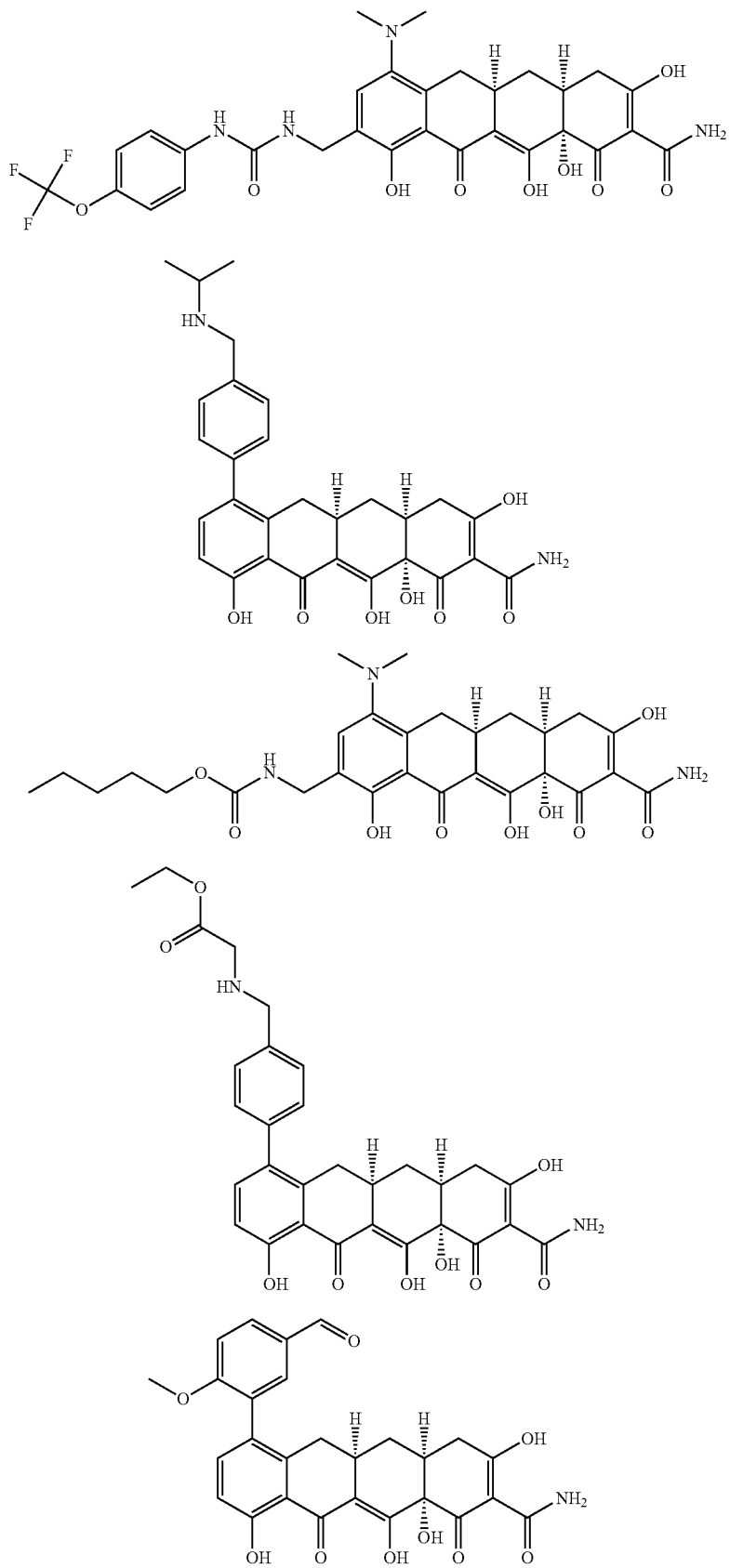

TABLE 2-continued
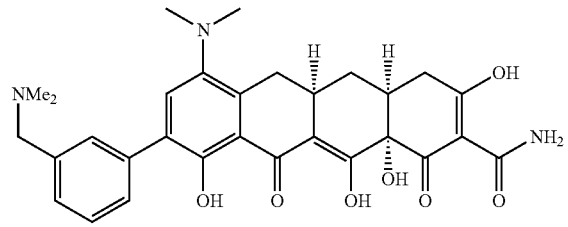 [SMILES: CN(C)Cc1cccc(-c2cc(N(C)C)c3c(c2O)C(=O)C2=C(O)[C@]4(O)C(=O)C(C(N)=O)=C(O)C[C@@H]4C[C@@H]2C3)c1]
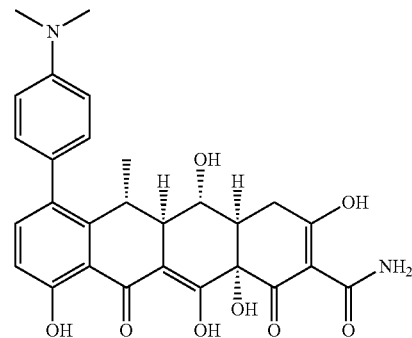 [SMILES: C[C@H]1c2c(-c3ccc(N(C)C)cc3)ccc(O)c2C(=O)C2=C(O)[C@]3(O)C(=O)C(C(N)=O)=C(O)C[C@@H]3[C@@H](O)[C@@H]21]
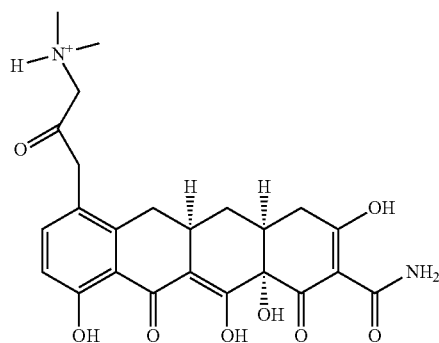 [SMILES: C[NH+](C)CC(=O)Cc1ccc(O)c2c1C[C@H]1C[C@H]3CC(O)=C(C(N)=O)C(=O)[C@@]3(O)C(O)=C1C2=O]
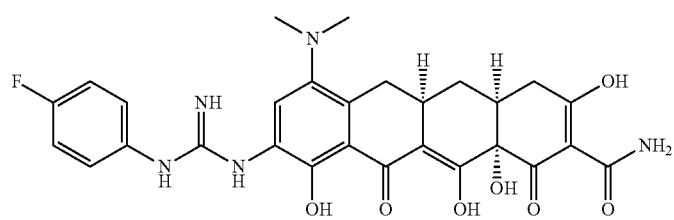 [SMILES: CN(C)c1cc(NC(=N)Nc2ccc(F)cc2)c(O)c2c1C[C@H]1C[C@H]3CC(O)=C(C(N)=O)C(=O)[C@@]3(O)C(O)=C1C2=O]
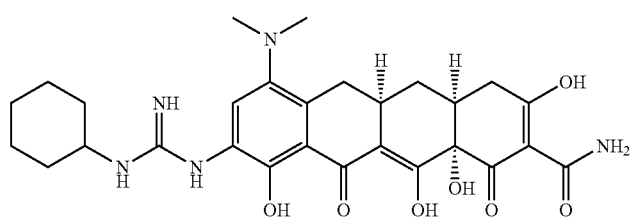 [SMILES: CN(C)c1cc(NC(=N)NC2CCCCC2)c(O)c2c1C[C@H]1C[C@H]3CC(O)=C(C(N)=O)C(=O)[C@@]3(O)C(O)=C1C2=O]

TABLE 2-continued
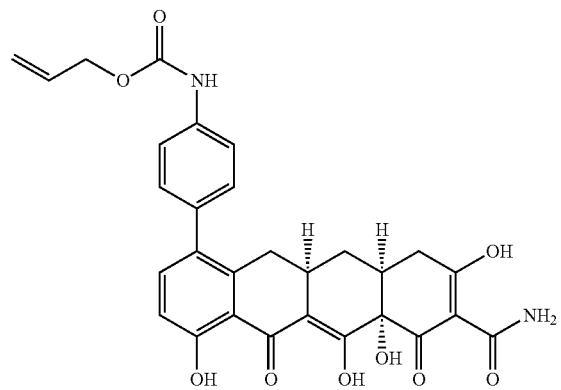 [SMILES: C=CCOC(=O)Nc1ccc(-c2ccc(O)c3c2C[C@H]2C[C@H]4CC(O)=C(C(N)=O)C(=O)[C@@]4(O)C(O)=C2C3=O)cc1]
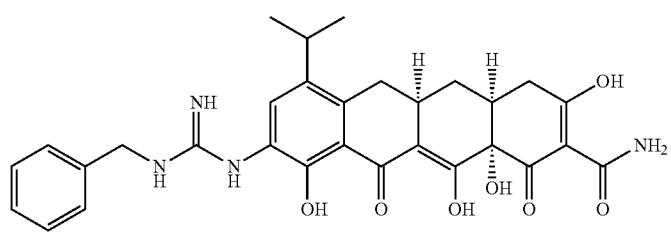
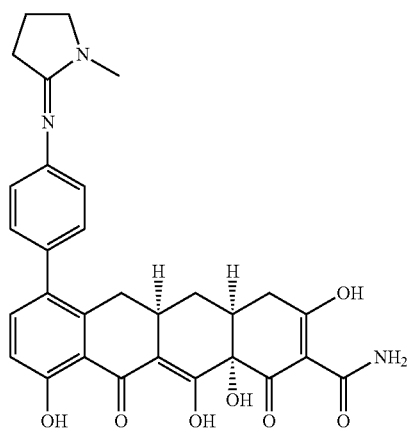 [SMILES: CN1CCCC1=Nc1ccc(-c2ccc(O)c3c2C[C@H]2C[C@H]4CC(O)=C(C(N)=O)C(=O)[C@@]4(O)C(O)=C2C3=O)cc1]
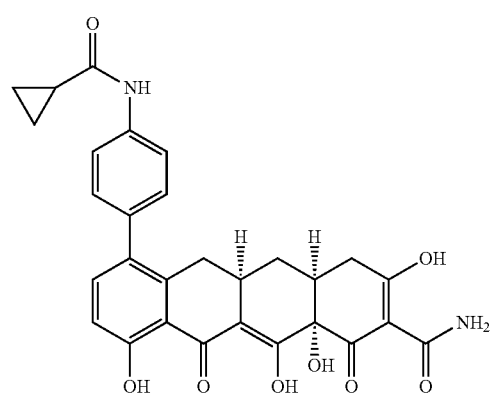 [SMILES: NC(=O)C1=C(O)C[C@@H]2C[C@@H]3Cc4c(-c5ccc(NC(=O)C6CC6)cc5)ccc(O)c4C(=O)C3=C(O)[C@]2(O)C1=O]

TABLE 2-continued
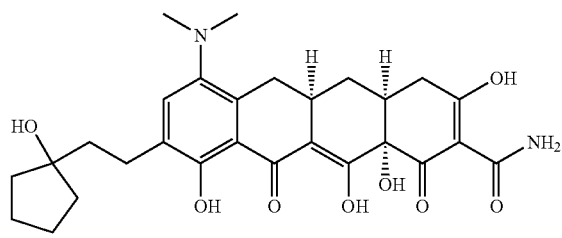 [SMILES: CN(C)c1cc(CCC2(O)CCCC2)c(O)c2c1C[C@H]1C[C@H]3CC(O)=C(C(N)=O)C(=O)[C@@]3(O)C(O)=C1C2=O]
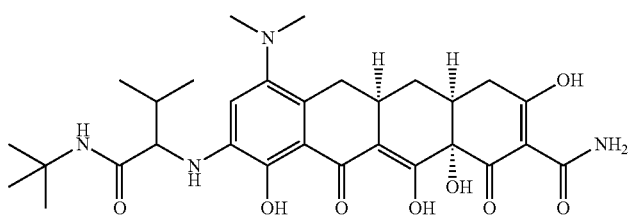 [SMILES: CC(C)C(Nc1cc(N(C)C)c2c(c1O)C(=O)C1=C(O)[C@]3(O)C(=O)C(C(N)=O)=C(O)C[C@@H]3C[C@@H]1C2)C(=O)NC(C)(C)C]
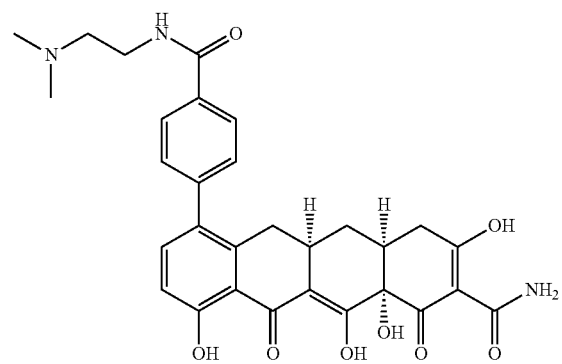 [SMILES: CN(C)CCNC(=O)c1ccc(-c2ccc(O)c3c2C[C@H]2C[C@H]4CC(O)=C(C(N)=O)C(=O)[C@@]4(O)C(O)=C2C3=O)cc1]
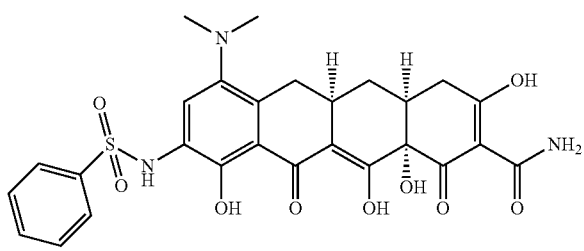 [SMILES: CN(C)c1cc(NS(=O)(=O)c2ccccc2)c(O)c2c1C[C@H]1C[C@H]3CC(O)=C(C(N)=O)C(=O)[C@@]3(O)C(O)=C1C2=O]
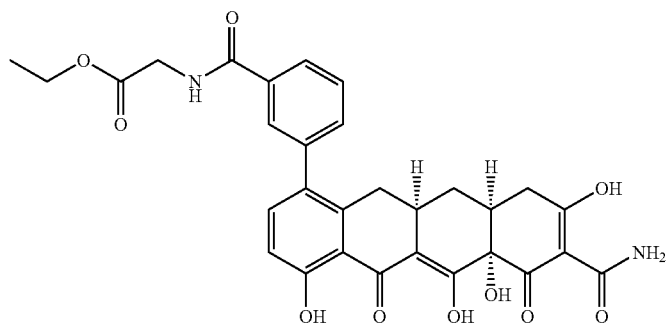 [SMILES: CCOC(=O)CNC(=O)c1cccc(-c2ccc(O)c3c2C[C@H]2C[C@H]4CC(O)=C(C(N)=O)C(=O)[C@@]4(O)C(O)=C2C3=O)c1]

TABLE 2-continued
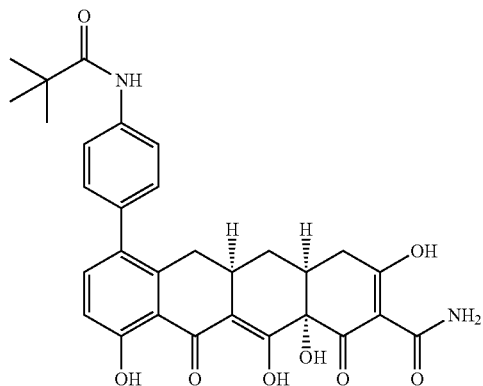 [SMILES: CC(C)(C)C(=O)Nc1ccc(-c2ccc(O)c3c2C[C@H]2C[C@H]4CC(O)=C(C(N)=O)C(=O)[C@@]4(O)C(O)=C2C3=O)cc1]
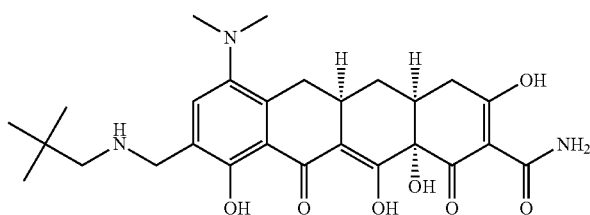 [SMILES: CN(C)c1cc(CNCC(C)(C)C)c(O)c2c1C[C@H]1C[C@H]3CC(O)=C(C(N)=O)C(=O)[C@@]3(O)C(O)=C1C2=O]
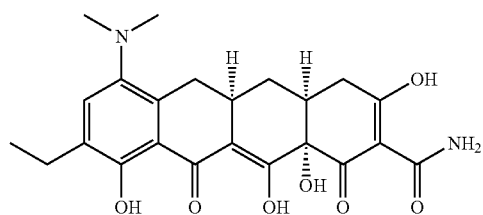 [SMILES: CCc1cc(N(C)C)c2c(c1O)C(=O)C1=C(O)[C@]3(O)C(=O)C(C(N)=O)=C(O)C[C@@H]3C[C@@H]1C2]
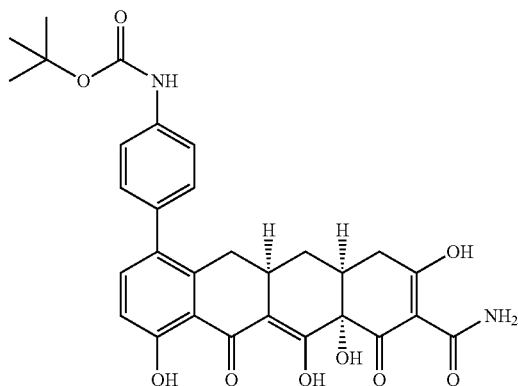 [SMILES: CC(C)(C)OC(=O)Nc1ccc(-c2ccc(O)c3c2C[C@H]2C[C@H]4CC(O)=C(C(N)=O)C(=O)[C@@]4(O)C(O)=C2C3=O)cc1]
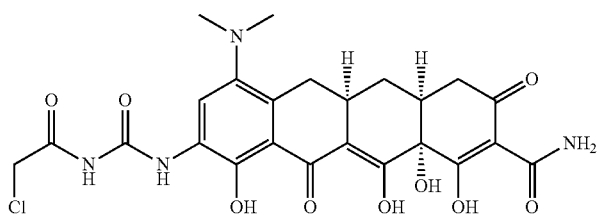 [SMILES: CN(C)c1cc(NC(=O)NC(=O)CCl)c(O)c2c1C[C@H]1C[C@H]3CC(=O)C(C(N)=O)=C(O)[C@@]3(O)C(O)=C1C2=O]

TABLE 2-continued
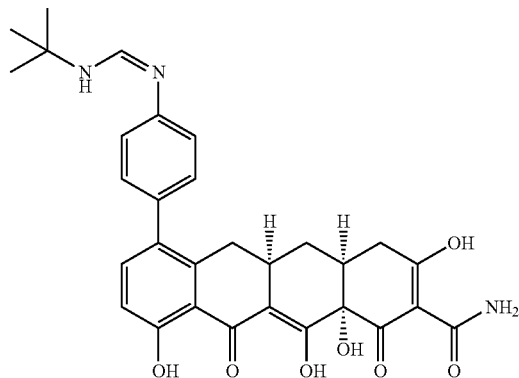 [SMILES: CC(C)(C)N/C=N\c1ccc(-c2ccc(O)c3c2C[C@H]2C[C@H]4CC(O)=C(C(N)=O)C(=O)[C@@]4(O)C(O)=C2C3=O)cc1]
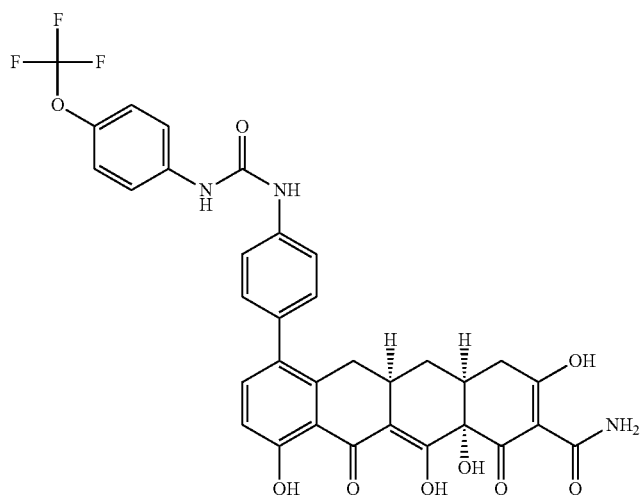 [SMILES: NC(=O)C1=C(O)C[C@@H]2C[C@@H]3Cc4c(-c5ccc(NC(=O)Nc6ccc(OC(F)(F)F)cc6)cc5)ccc(O)c4C(=O)C3=C(O)[C@]2(O)C1=O]
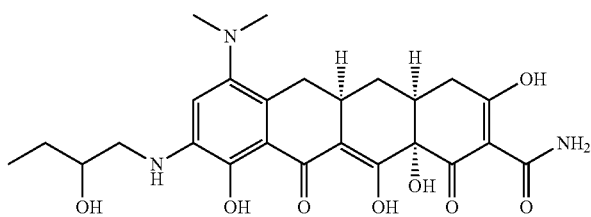 [SMILES: CCC(O)CNc1cc(N(C)C)c2c(c1O)C(=O)C1=C(O)[C@]3(O)C(=O)C(C(N)=O)=C(O)C[C@@H]3C[C@@H]1C2]
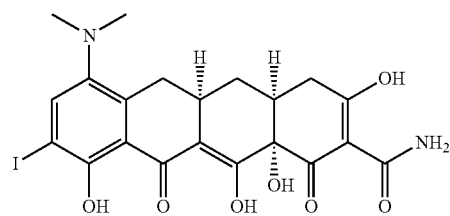 [SMILES: CN(C)c1cc(I)c(O)c2c1C[C@H]1C[C@H]3CC(O)=C(C(N)=O)C(=O)[C@@]3(O)C(O)=C1C2=O]

TABLE 2-continued
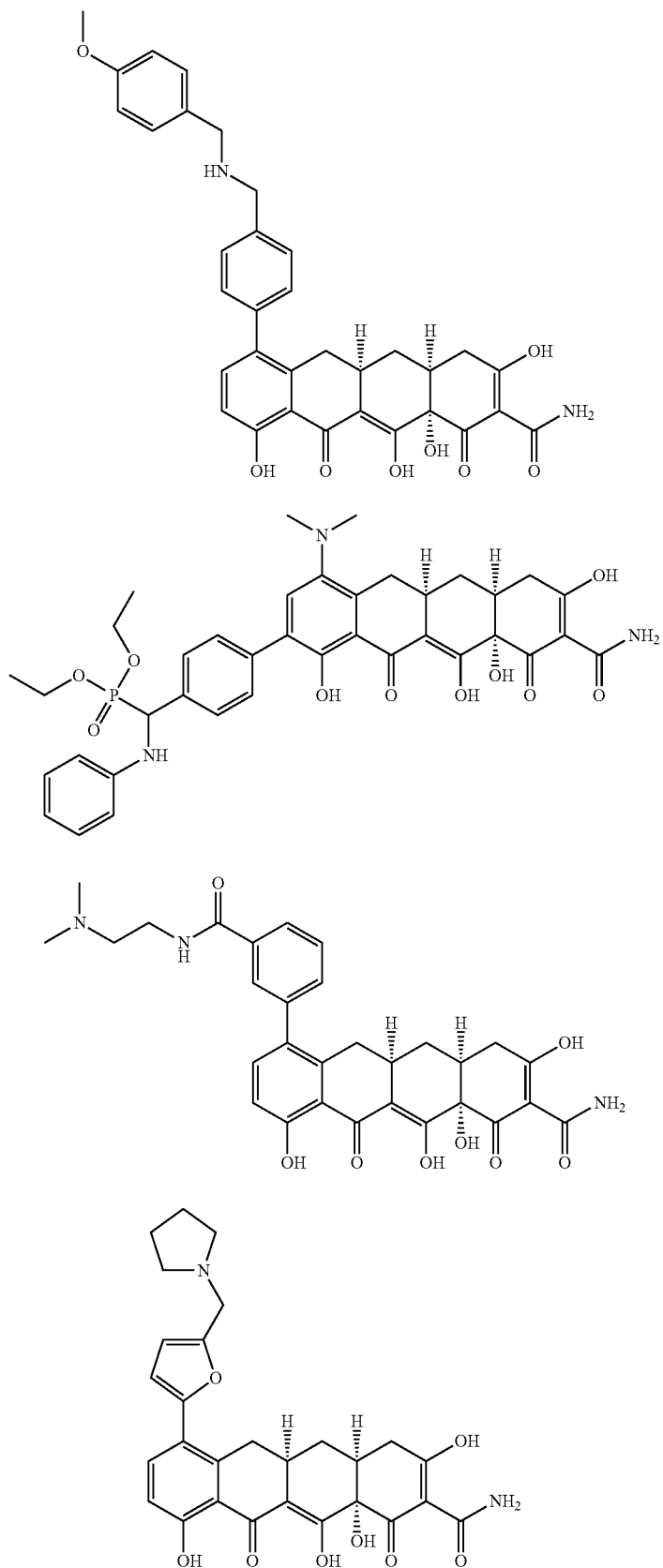

TABLE 2-continued
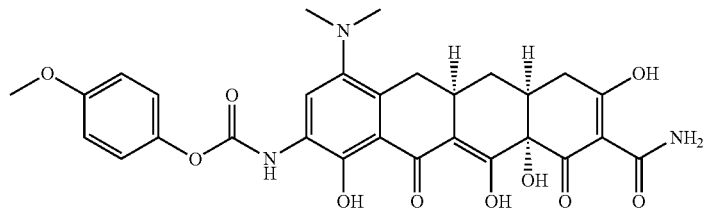 [SMILES: COc1ccc(OC(=O)Nc2cc(N(C)C)c3c(c2O)C(=O)C2=C(O)[C@]4(O)C(=O)C(C(N)=O)=C(O)C[C@@H]4C[C@@H]2C3)cc1]
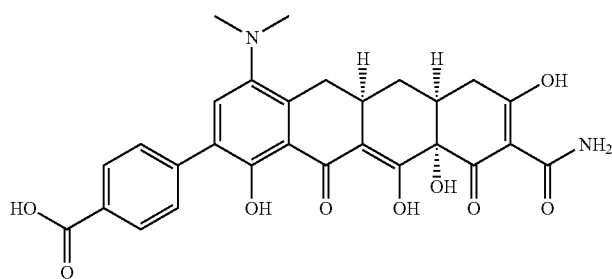 [SMILES: CN(C)c1cc(-c2ccc(C(=O)O)cc2)c(O)c2c1C[C@H]1C[C@H]3CC(O)=C(C(N)=O)C(=O)[C@@]3(O)C(O)=C1C2=O]
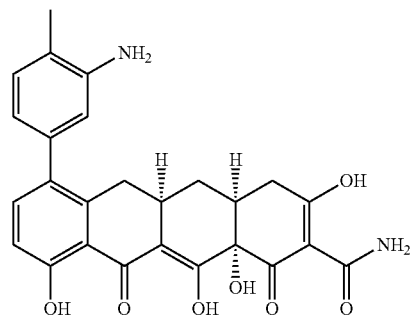 [SMILES: Cc1ccc(-c2ccc(O)c3c2C[C@H]2C[C@H]4CC(O)=C(C(N)=O)C(=O)[C@@]4(O)C(O)=C2C3=O)cc1N]
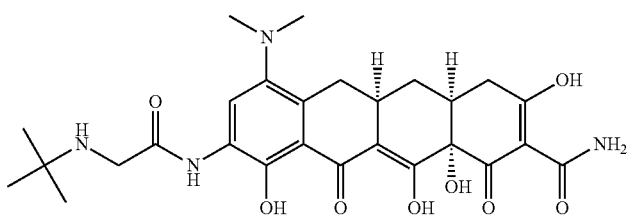 [SMILES: CN(C)c1cc(NC(=O)CNC(C)(C)C)c(O)c2c1C[C@H]1C[C@H]3CC(O)=C(C(N)=O)C(=O)[C@@]3(O)C(O)=C1C2=O]
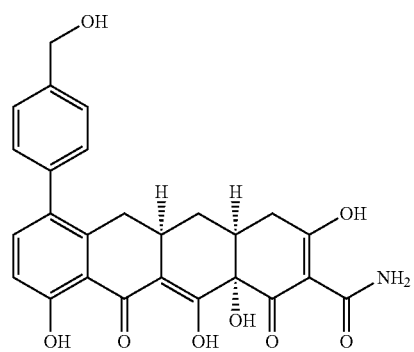 [SMILES: NC(=O)C1=C(O)C[C@@H]2C[C@@H]3Cc4c(-c5ccc(CO)cc5)ccc(O)c4C(=O)C3=C(O)[C@]2(O)C1=O]

TABLE 2-continued
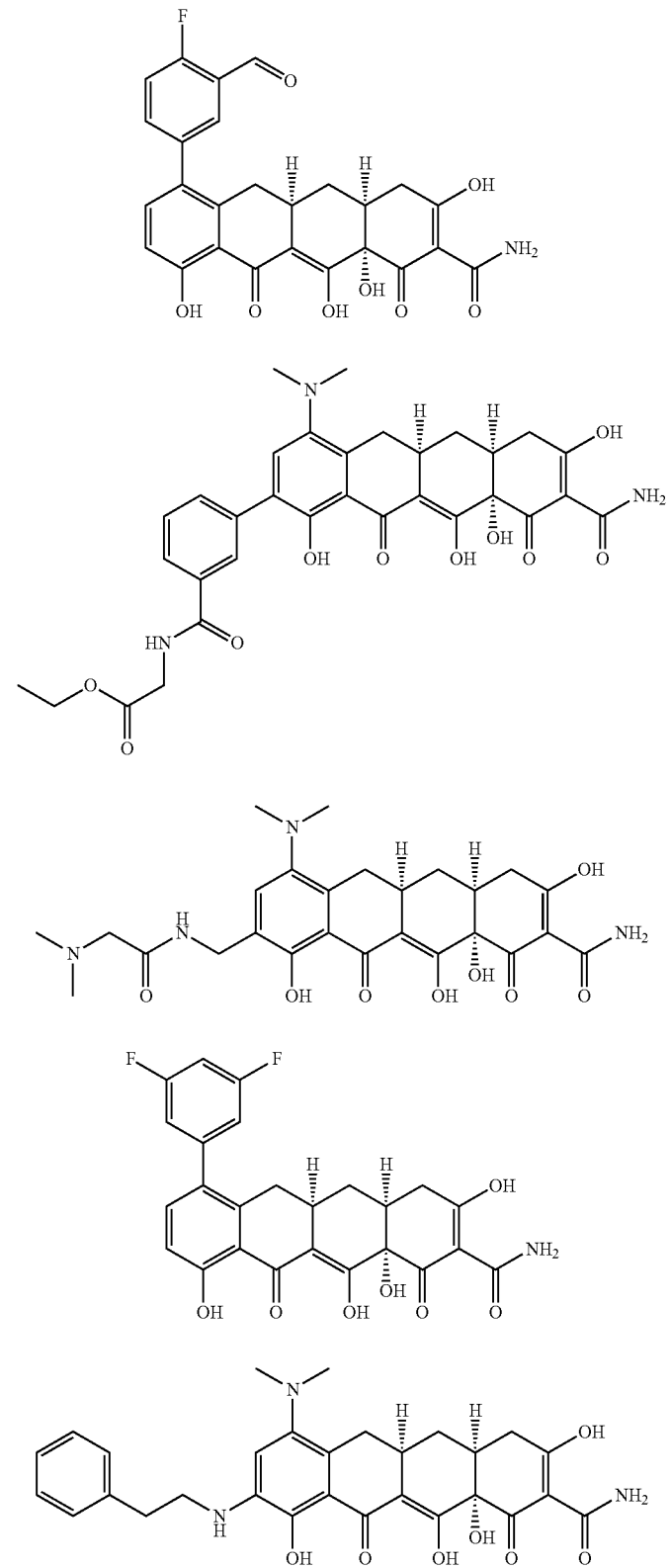

TABLE 2-continued
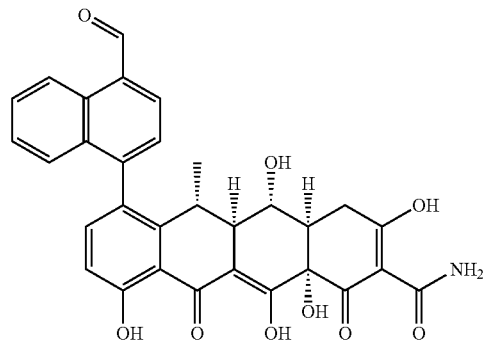 [SMILES: C[C@H]1c2c(-c3ccc(C=O)c4ccccc34)ccc(O)c2C(=O)C2=C(O)[C@]3(O)C(=O)C(C(N)=O)=C(O)C[C@@H]3[C@@H](O)[C@@H]21]
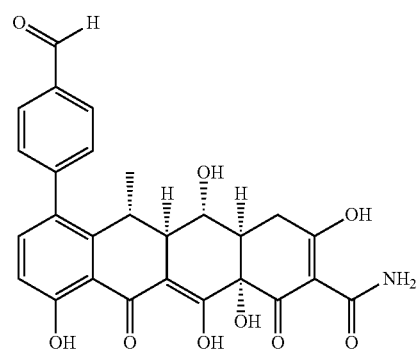 [SMILES: C[C@H]1c2c(-c3ccc(C=O)cc3)ccc(O)c2C(=O)C2=C(O)[C@]3(O)C(=O)C(C(N)=O)=C(O)C[C@@H]3[C@@H](O)[C@@H]21]
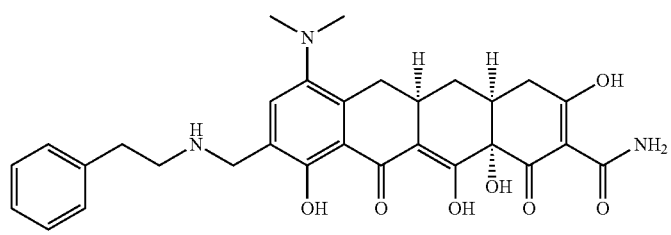 [SMILES: CN(C)c1cc(CNCCc2ccccc2)c(O)c2c1C[C@H]1C[C@H]3CC(O)=C(C(N)=O)C(=O)[C@@]3(O)C(O)=C1C2=O]
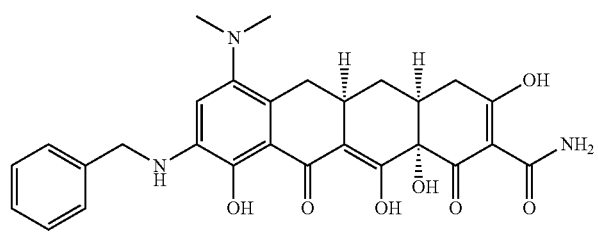 [SMILES: CN(C)c1cc(NCc2ccccc2)c(O)c2c1C[C@H]1C[C@H]3CC(O)=C(C(N)=O)C(=O)[C@@]3(O)C(O)=C1C2=O]
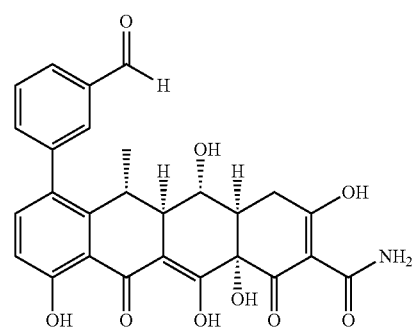 [SMILES: C[C@H]1c2c(-c3cccc(C=O)c3)ccc(O)c2C(=O)C2=C(O)[C@]3(O)C(=O)C(C(N)=O)=C(O)C[C@@H]3[C@@H](O)[C@@H]21]

TABLE 2-continued
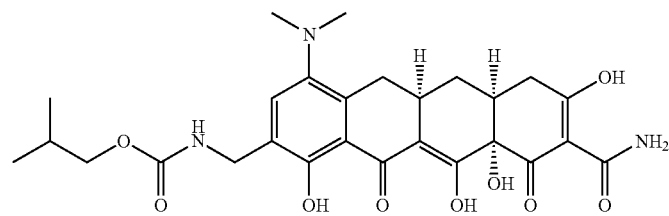 [SMILES: CC(C)COC(=O)NCc1cc(N(C)C)c2c(c1O)C(=O)C1=C(O)[C@]3(O)C(=O)C(C(N)=O)=C(O)C[C@@H]3C[C@@H]1C2]
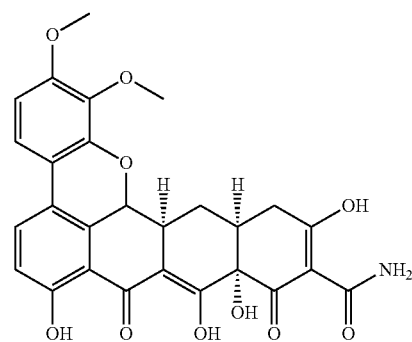 [SMILES: COc1ccc2c(c1OC)OC1c3c-2ccc(O)c3C(=O)C2=C(O)[C@]3(O)C(=O)C(C(N)=O)=C(O)C[C@@H]3C[C@@H]21]
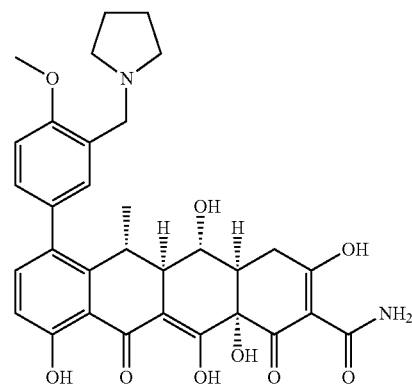 [SMILES: COc1ccc(-c2ccc(O)c3c2[C@H](C)[C@@H]2C(=C(O)[C@]4(O)C(=O)C(C(N)=O)=C(O)C[C@@H]4[C@H]2O)C3=O)cc1CN1CCCC1]
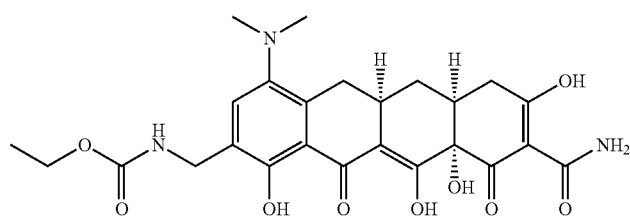 [SMILES: CCOC(=O)NCc1cc(N(C)C)c2c(c1O)C(=O)C1=C(O)[C@]3(O)C(=O)C(C(N)=O)=C(O)C[C@@H]3C[C@@H]1C2]
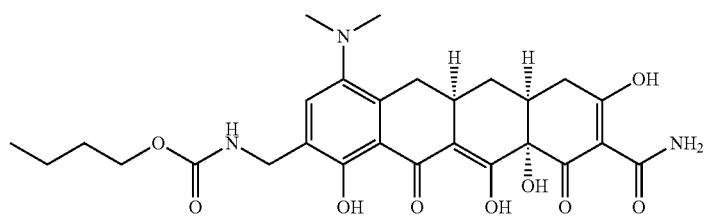 [SMILES: CCCCOC(=O)NCc1cc(N(C)C)c2c(c1O)C(=O)C1=C(O)[C@]3(O)C(=O)C(C(N)=O)=C(O)C[C@@H]3C[C@@H]1C2]

TABLE 2-continued
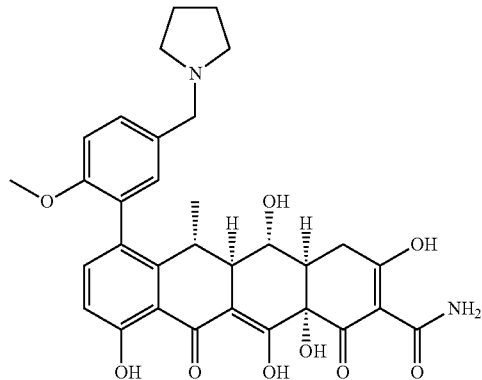 [SMILES: COc1ccc(CN2CCCC2)cc1-c1ccc(O)c2c1[C@H](C)[C@@H]1C(=C(O)[C@]3(O)C(=O)C(C(N)=O)=C(O)C[C@@H]3[C@H]1O)C2=O]
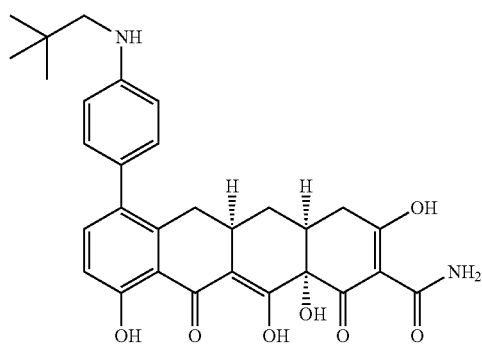 [SMILES: CC(C)(C)CNc1ccc(-c2ccc(O)c3c2C[C@H]2C[C@H]4CC(O)=C(C(N)=O)C(=O)[C@@]4(O)C(O)=C2C3=O)cc1]
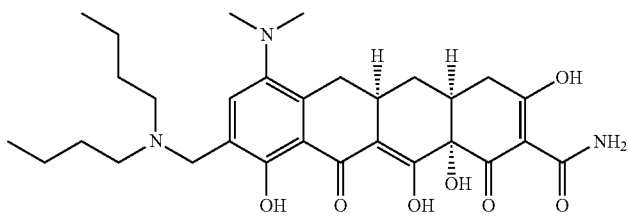 [SMILES: CCCCN(CCCC)Cc1cc(N(C)C)c2c(c1O)C(=O)C1=C(O)[C@]3(O)C(=O)C(C(N)=O)=C(O)C[C@@H]3C[C@@H]1C2]
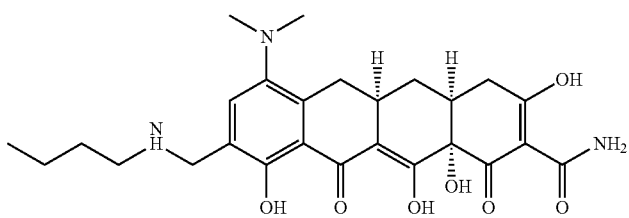 [SMILES: CCCCNCc1cc(N(C)C)c2c(c1O)C(=O)C1=C(O)[C@]3(O)C(=O)C(C(N)=O)=C(O)C[C@@H]3C[C@@H]1C2]
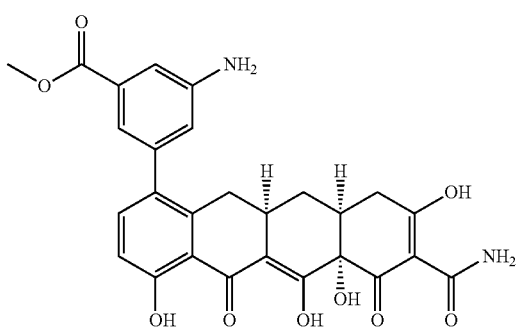 [SMILES: COC(=O)c1cc(N)cc(-c2ccc(O)c3c2C[C@H]2C[C@H]4CC(O)=C(C(N)=O)C(=O)[C@@]4(O)C(O)=C2C3=O)c1]

TABLE 2-continued
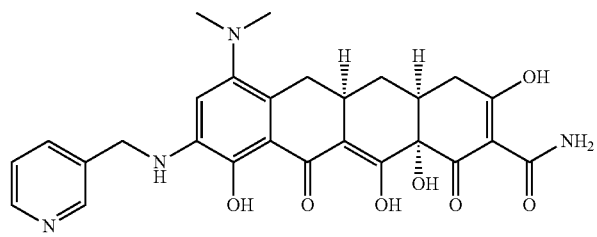 [SMILES: CN(C)c1cc(NCc2cccnc2)c(O)c2c1C[C@H]1C[C@H]3CC(O)=C(C(N)=O)C(=O)[C@@]3(O)C(O)=C1C2=O]
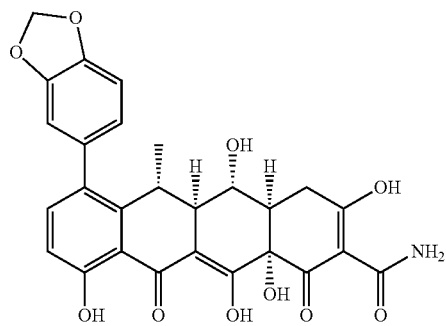 [SMILES: C[C@H]1c2c(-c3ccc4c(c3)OCO4)ccc(O)c2C(=O)C2=C(O)[C@]3(O)C(=O)C(C(N)=O)=C(O)C[C@@H]3[C@@H](O)[C@@H]21]
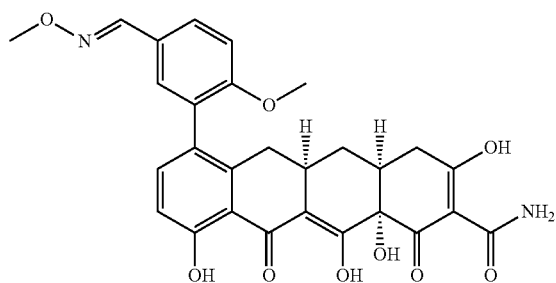 [SMILES: CO/N=C/c1ccc(OC)c(-c2ccc(O)c3c2C[C@H]2C[C@H]4CC(O)=C(C(N)=O)C(=O)[C@@]4(O)C(O)=C2C3=O)c1]
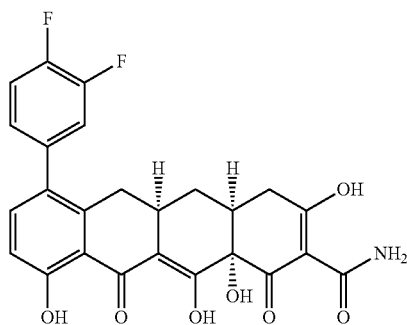
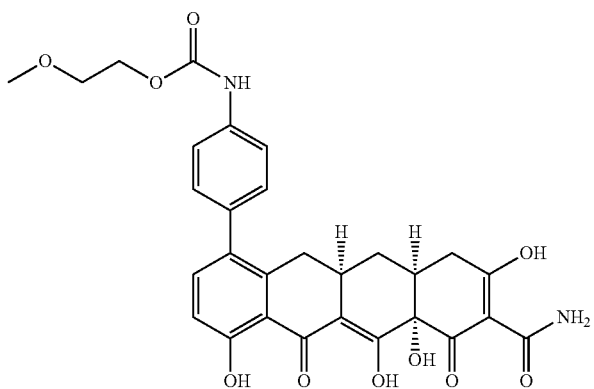 [SMILES: COCCOC(=O)Nc1ccc(-c2ccc(O)c3c2C[C@H]2C[C@H]4CC(O)=C(C(N)=O)C(=O)[C@@]4(O)C(O)=C2C3=O)cc1]

TABLE 2-continued
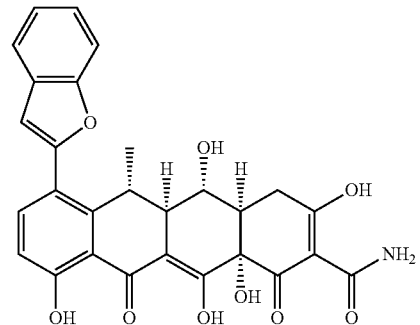 [SMILES: C[C@H]1c2c(-c3cc4ccccc4o3)ccc(O)c2C(=O)C2=C(O)[C@]3(O)C(=O)C(C(N)=O)=C(O)C[C@@H]3[C@@H](O)[C@@H]21]
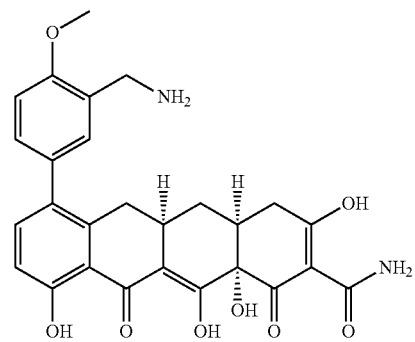 [SMILES: COc1ccc(-c2ccc(O)c3c2C[C@H]2C[C@H]4CC(O)=C(C(N)=O)C(=O)[C@@]4(O)C(O)=C2C3=O)cc1CN]
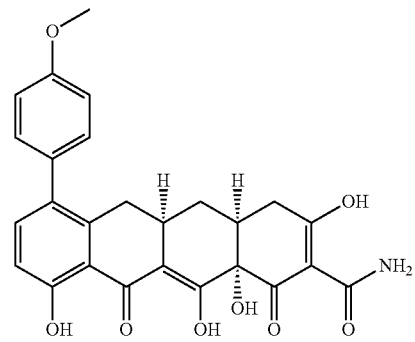 [SMILES: COc1ccc(-c2ccc(O)c3c2C[C@H]2C[C@H]4CC(O)=C(C(N)=O)C(=O)[C@@]4(O)C(O)=C2C3=O)cc1]
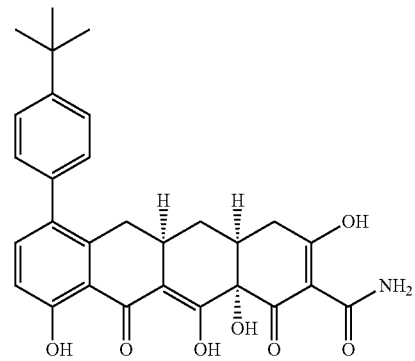 [SMILES: CC(C)(C)c1ccc(-c2ccc(O)c3c2C[C@H]2C[C@H]4CC(O)=C(C(N)=O)C(=O)[C@@]4(O)C(O)=C2C3=O)cc1]

TABLE 2-continued
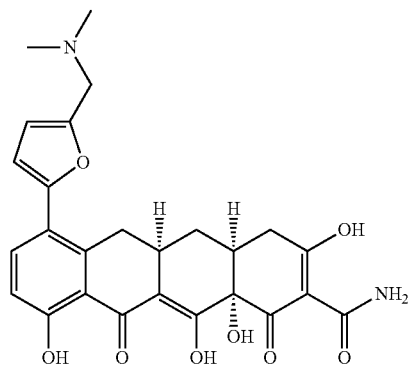 [SMILES: CN(C)Cc1ccc(-c2ccc(O)c3c2C[C@H]2C[C@H]4CC(O)=C(C(N)=O)C(=O)[C@@]4(O)C(O)=C2C3=O)o1]
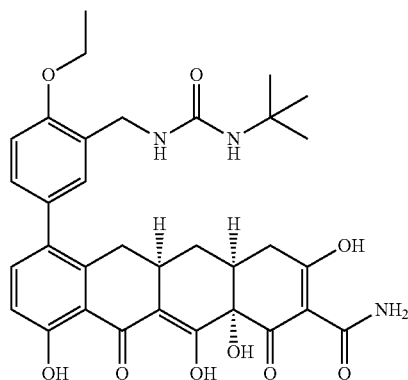 [SMILES: CCOc1ccc(-c2ccc(O)c3c2C[C@H]2C[C@H]4CC(O)=C(C(N)=O)C(=O)[C@@]4(O)C(O)=C2C3=O)cc1CNC(=O)NC(C)(C)C]
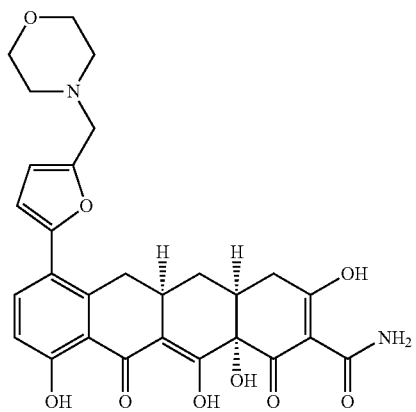 [SMILES: NC(=O)C1=C(O)C[C@@H]2C[C@@H]3Cc4c(-c5ccc(CN6CCOCC6)o5)ccc(O)c4C(=O)C3=C(O)[C@]2(O)C1=O]
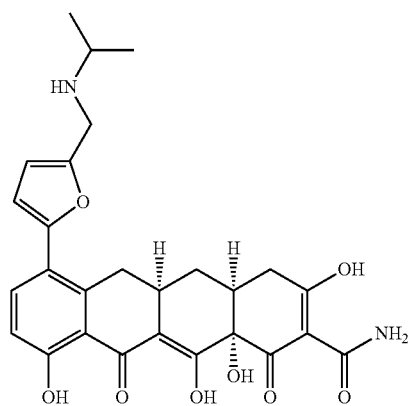 [SMILES: CC(C)NCc1ccc(-c2ccc(O)c3c2C[C@H]2C[C@H]4CC(O)=C(C(N)=O)C(=O)[C@@]4(O)C(O)=C2C3=O)o1]

TABLE 2-continued
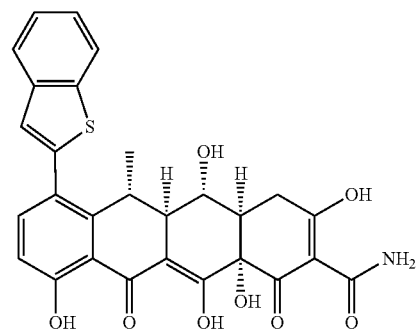
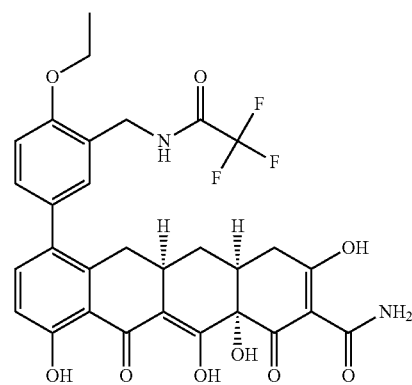 [SMILES: CCOc1ccc(-c2ccc(O)c3c2C[C@H]2C[C@H]4CC(O)=C(C(N)=O)C(=O)[C@@]4(O)C(O)=C2C3=O)cc1CNC(=O)C(F)(F)F]
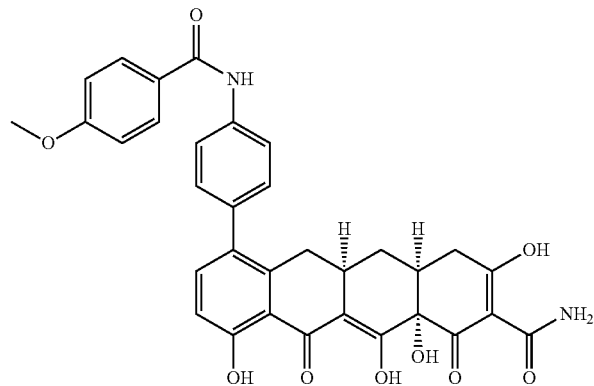 [SMILES: COc1ccc(C(=O)Nc2ccc(-c3ccc(O)c4c3C[C@H]3C[C@H]5CC(O)=C(C(N)=O)C(=O)[C@@]5(O)C(O)=C3C4=O)cc2)cc1]
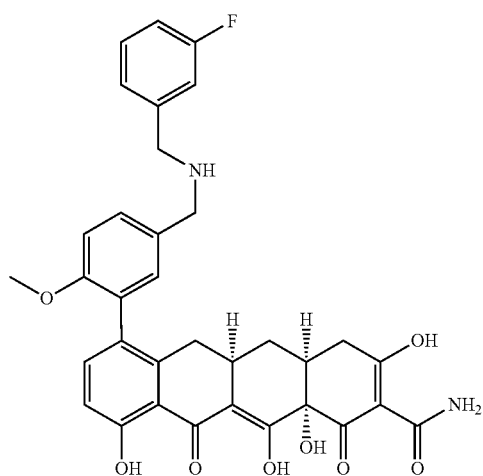 [SMILES: COc1ccc(CNCc2cccc(F)c2)cc1-c1ccc(O)c2c1C[C@H]1C[C@H]3CC(O)=C(C(N)=O)C(=O)[C@@]3(O)C(O)=C1C2=O]

TABLE 2-continued
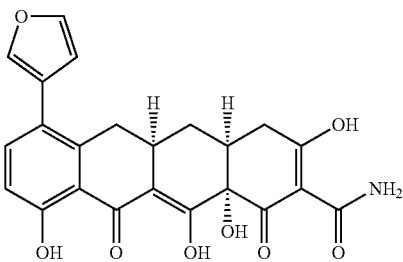 [SMILES: NC(=O)C1=C(O)C[C@@H]2C[C@@H]3Cc4c(-c5ccoc5)ccc(O)c4C(=O)C3=C(O)[C@]2(O)C1=O]
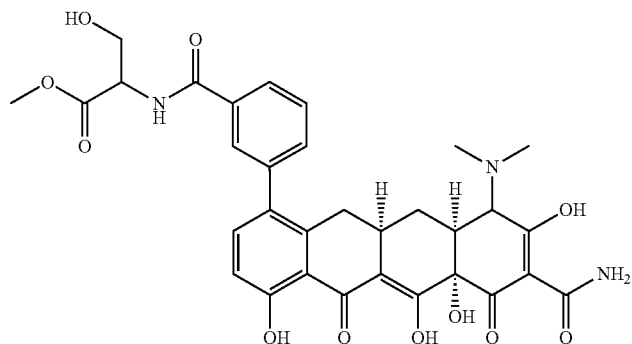 [SMILES: COC(=O)C(CO)NC(=O)c1cccc(-c2ccc(O)c3c2C[C@H]2C[C@H]4C(N(C)C)C(O)=C(C(N)=O)C(=O)[C@@]4(O)C(O)=C2C3=O)c1]
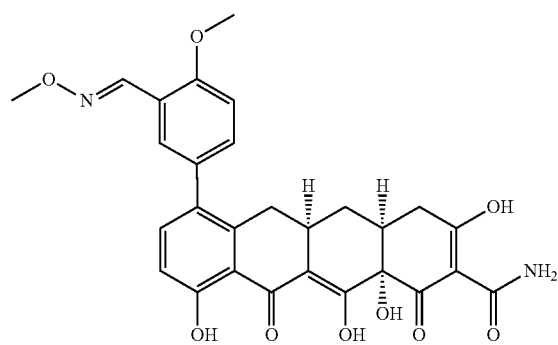 [SMILES: CO/N=C/c1cc(-c2ccc(O)c3c2C[C@H]2C[C@H]4CC(O)=C(C(N)=O)C(=O)[C@@]4(O)C(O)=C2C3=O)ccc1OC]
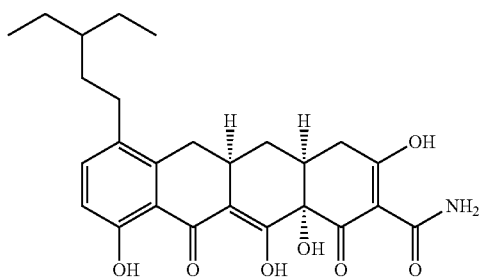 [SMILES: CCC(CC)CCc1ccc(O)c2c1C[C@H]1C[C@H]3CC(O)=C(C(N)=O)C(=O)[C@@]3(O)C(O)=C1C2=O]
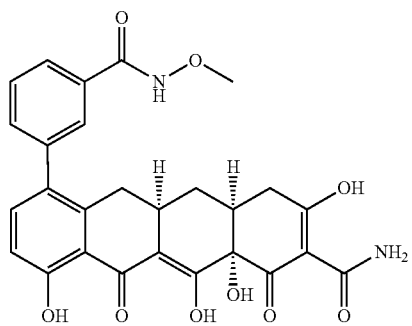 [SMILES: CONC(=O)c1cccc(-c2ccc(O)c3c2C[C@H]2C[C@H]4CC(O)=C(C(N)=O)C(=O)[C@@]4(O)C(O)=C2C3=O)c1]

TABLE 2-continued
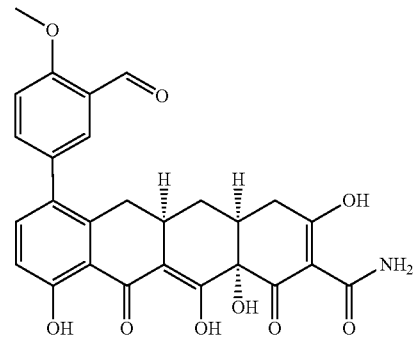 [SMILES: COc1ccc(-c2ccc(O)c3c2C[C@H]2C[C@H]4CC(O)=C(C(N)=O)C(=O)[C@@]4(O)C(O)=C2C3=O)cc1C=O]
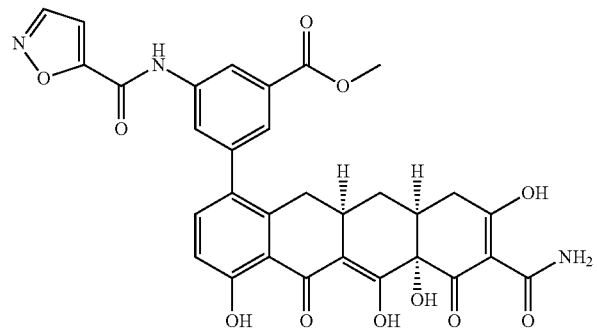 [SMILES: COC(=O)c1cc(NC(=O)c2ccno2)cc(-c2ccc(O)c3c2C[C@H]2C[C@H]4CC(O)=C(C(N)=O)C(=O)[C@@]4(O)C(O)=C2C3=O)c1]
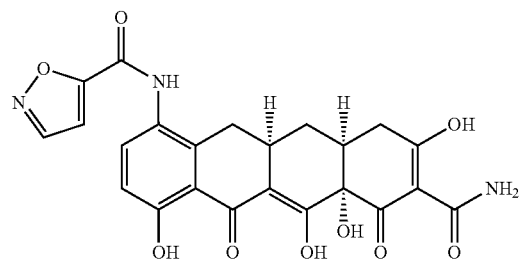 [SMILES: NC(=O)C1=C(O)C[C@@H]2C[C@@H]3Cc4c(NC(=O)c5ccno5)ccc(O)c4C(=O)C3=C(O)[C@]2(O)C1=O]
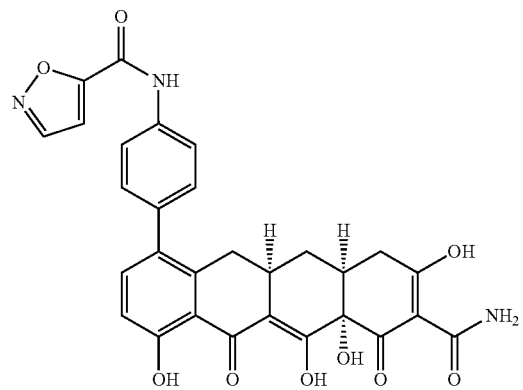 [SMILES: NC(=O)C1=C(O)C[C@@H]2C[C@@H]3Cc4c(-c5ccc(NC(=O)c6ccno6)cc5)ccc(O)c4C(=O)C3=C(O)[C@]2(O)C1=O]
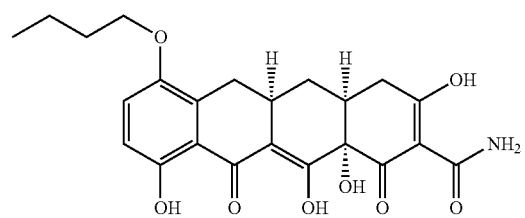 [SMILES: CCCCOc1ccc(O)c2c1C[C@H]1C[C@H]3CC(O)=C(C(N)=O)C(=O)[C@@]3(O)C(O)=C1C2=O]

TABLE 2-continued
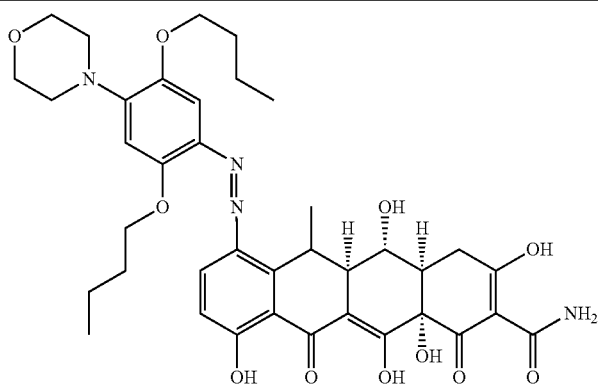
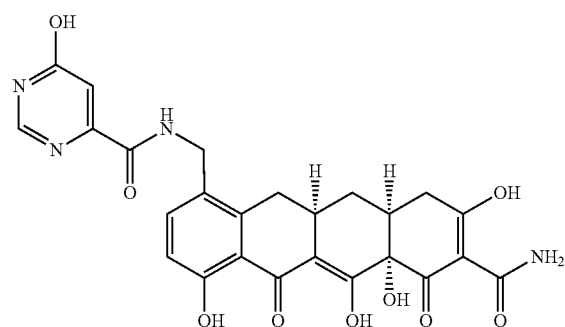 [SMILES: NC(=O)C1=C(O)C[C@@H]2C[C@@H]3Cc4c(CNC(=O)c5cc(O)ncn5)ccc(O)c4C(=O)C3=C(O)[C@]2(O)C1=O]
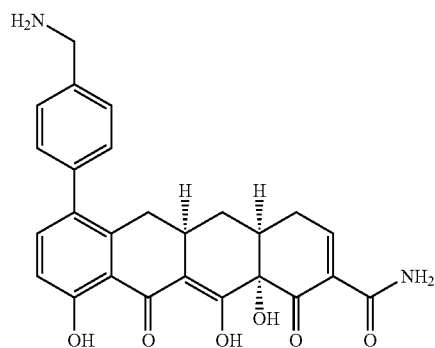 [SMILES: NCc1ccc(-c2ccc(O)c3c2C[C@H]2C[C@H]4CC=C(C(N)=O)C(=O)[C@@]4(O)C(O)=C2C3=O)cc1]
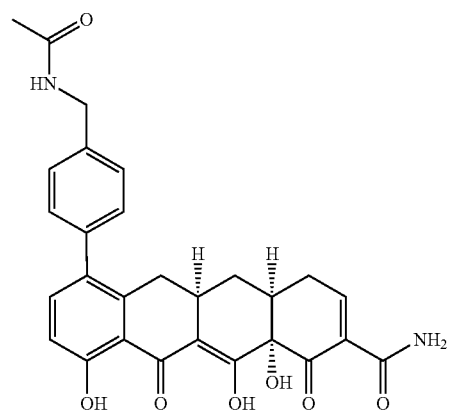 [SMILES: CC(=O)NCc1ccc(-c2ccc(O)c3c2C[C@H]2C[C@H]4CC=C(C(N)=O)C(=O)[C@@]4(O)C(O)=C2C3=O)cc1]

TABLE 2-continued
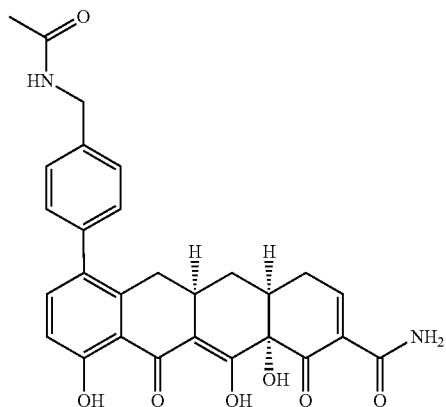 [SMILES: CC(=O)NCc1ccc(-c2ccc(O)c3c2C[C@H]2C[C@H]4CC=C(C(N)=O)C(=O)[C@@]4(O)C(O)=C2C3=O)cc1]
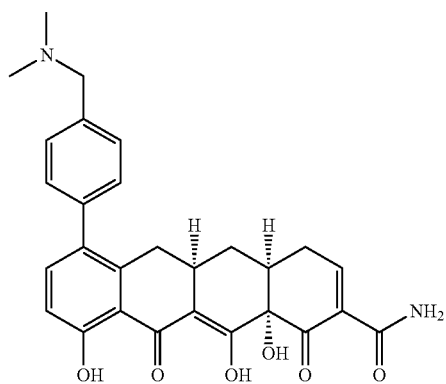 [SMILES: CN(C)Cc1ccc(-c2ccc(O)c3c2C[C@H]2C[C@H]4CC=C(C(N)=O)C(=O)[C@@]4(O)C(O)=C2C3=O)cc1]
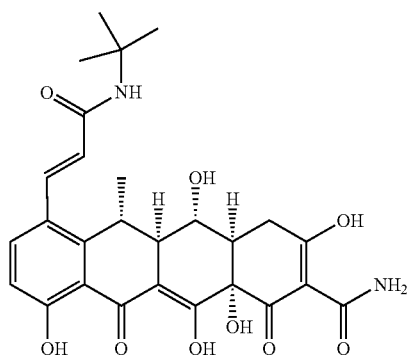 [SMILES: C[C@H]1c2c(/C=C/C(=O)NC(C)(C)C)ccc(O)c2C(=O)C2=C(O)[C@]3(O)C(=O)C(C(N)=O)=C(O)C[C@@H]3[C@@H](O)[C@@H]21]
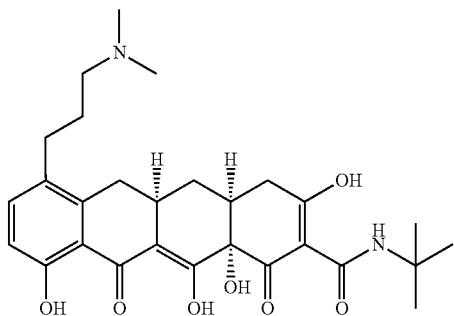 [SMILES: CN(C)CCCc1ccc(O)c2c1C[C@H]1C[C@H]3CC(O)=C(C(=O)NC(C)(C)C)C(=O)[C@@]3(O)C(O)=C1C2=O]

TABLE 2-continued
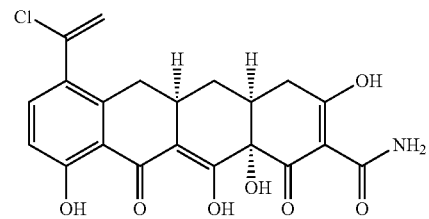 [SMILES: C=C(Cl)c1ccc(O)c2c1C[C@H]1C[C@H]3CC(O)=C(C(N)=O)C(=O)[C@@]3(O)C(O)=C1C2=O]
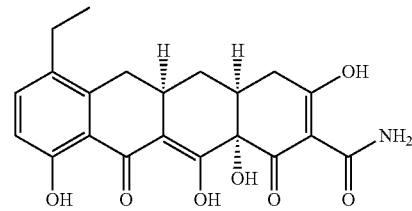 [SMILES: CCc1ccc(O)c2c1C[C@H]1C[C@H]3CC(O)=C(C(N)=O)C(=O)[C@@]3(O)C(O)=C1C2=O]
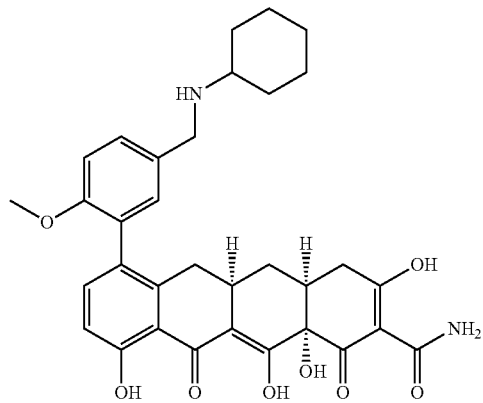 [SMILES: COc1ccc(CNC2CCCCC2)cc1-c1ccc(O)c2c1C[C@H]1C[C@H]3CC(O)=C(C(N)=O)C(=O)[C@@]3(O)C(O)=C1C2=O]
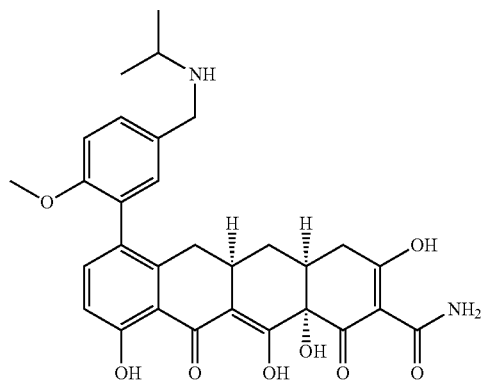 [SMILES: COc1ccc(CNC(C)C)cc1-c1ccc(O)c2c1C[C@H]1C[C@H]3CC(O)=C(C(N)=O)C(=O)[C@@]3(O)C(O)=C1C2=O]
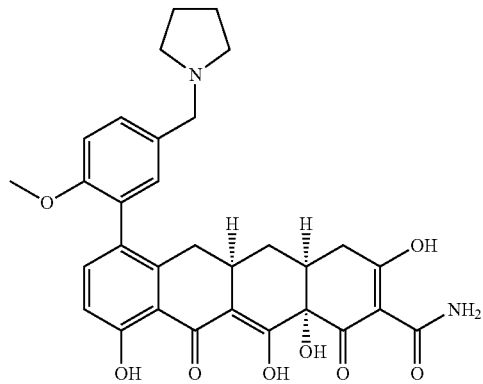 [SMILES: COc1ccc(CN2CCCC2)cc1-c1ccc(O)c2c1C[C@H]1C[C@H]3CC(O)=C(C(N)=O)C(=O)[C@@]3(O)C(O)=C1C2=O]

TABLE 2-continued
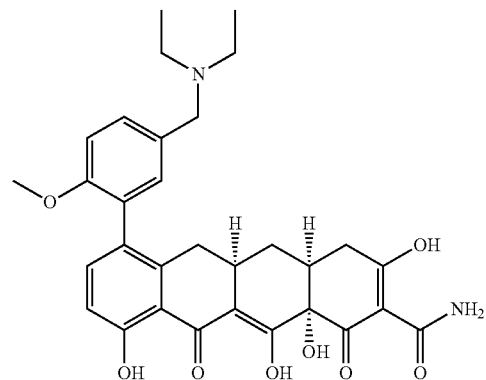 [SMILES: CCN(CC)Cc1ccc(OC)c(-c2ccc(O)c3c2C[C@H]2C[C@H]4CC(O)=C(C(N)=O)C(=O)[C@@]4(O)C(O)=C2C3=O)c1]
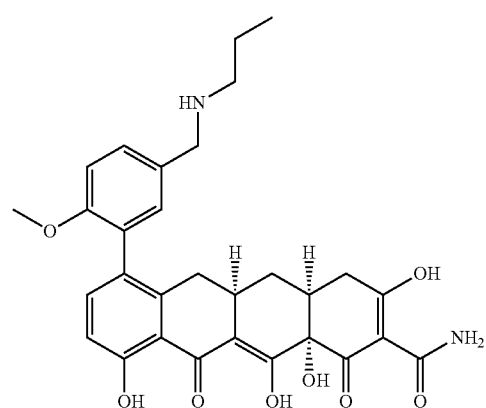 [SMILES: CCCNCc1ccc(OC)c(-c2ccc(O)c3c2C[C@H]2C[C@H]4CC(O)=C(C(N)=O)C(=O)[C@@]4(O)C(O)=C2C3=O)c1]
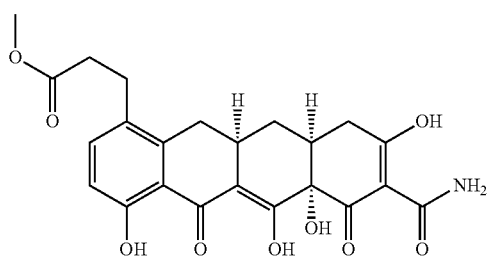 [SMILES: COC(=O)CCc1ccc(O)c2c1C[C@H]1C[C@H]3CC(O)=C(C(N)=O)C(=O)[C@@]3(O)C(O)=C1C2=O]
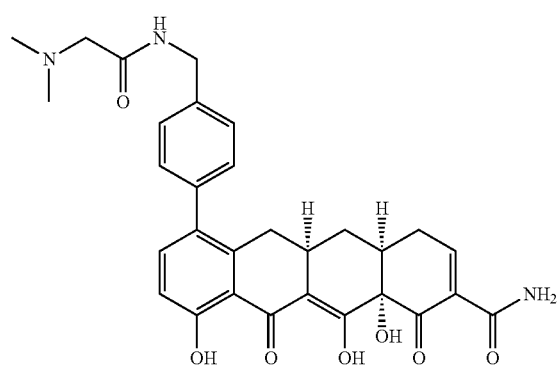 [SMILES: CN(C)CC(=O)NCc1ccc(-c2ccc(O)c3c2C[C@H]2C[C@H]4CC=C(C(N)=O)C(=O)[C@@]4(O)C(O)=C2C3=O)cc1]
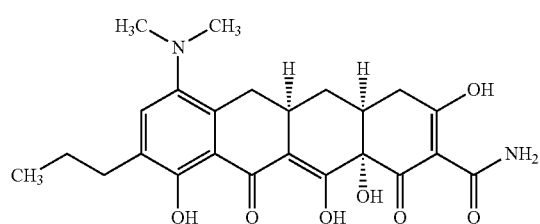 [SMILES: CCCc1cc(N(C)C)c2c(c1O)C(=O)C1=C(O)[C@]3(O)C(=O)C(C(N)=O)=C(O)C[C@@H]3C[C@@H]1C2]

TABLE 2-continued
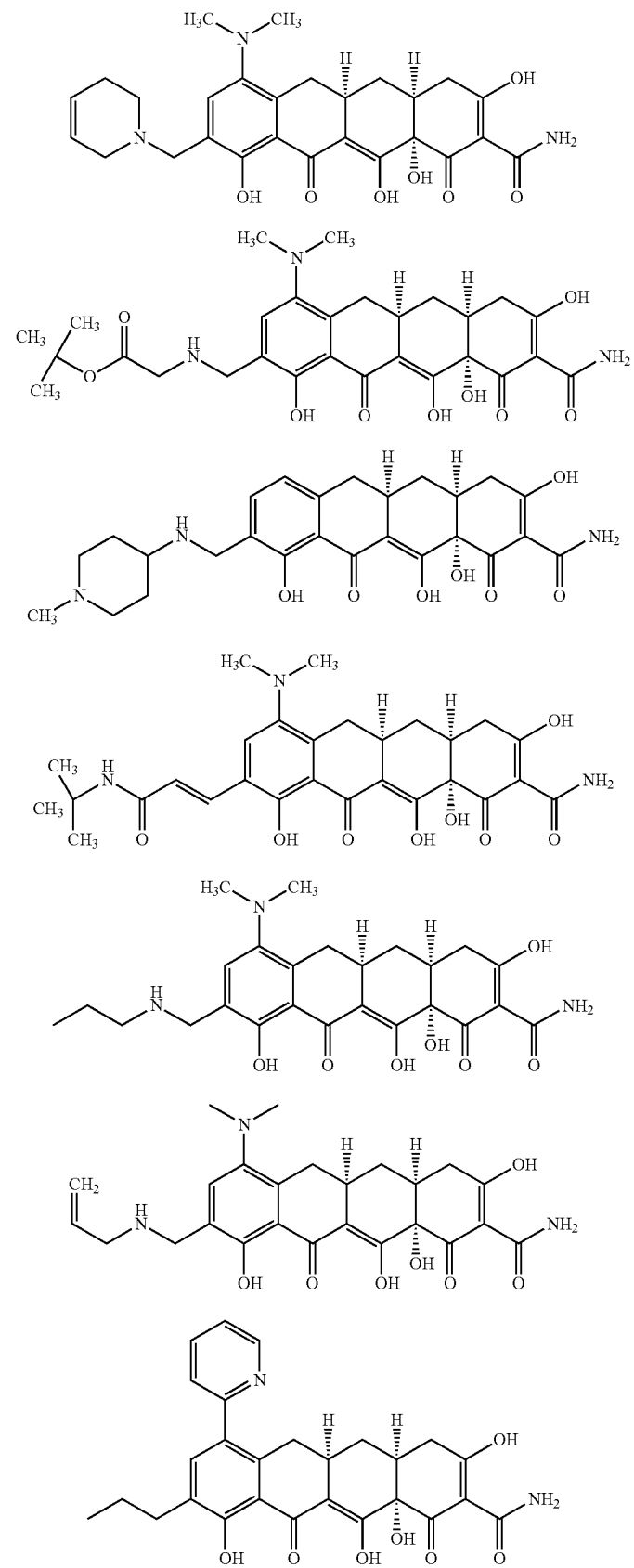

TABLE 2-continued
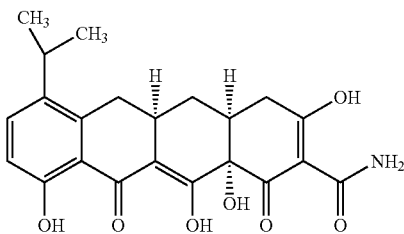 [SMILES: CC(C)c1ccc(O)c2c1C[C@H]1C[C@H]3CC(O)=C(C(N)=O)C(=O)[C@@]3(O)C(O)=C1C2=O]
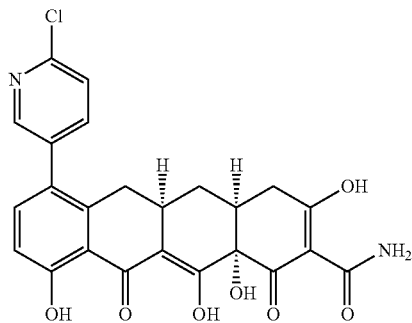 [SMILES: NC(=O)C1=C(O)C[C@@H]2C[C@@H]3Cc4c(-c5ccc(Cl)nc5)ccc(O)c4C(=O)C3=C(O)[C@]2(O)C1=O]
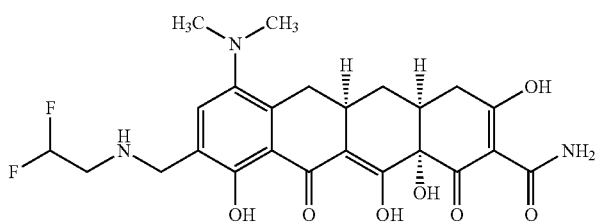 [SMILES: CN(C)c1cc(CNCC(F)F)c(O)c2c1C[C@H]1C[C@H]3CC(O)=C(C(N)=O)C(=O)[C@@]3(O)C(O)=C1C2=O]
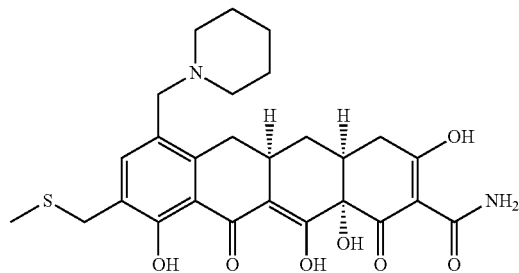 [SMILES: CSCc1cc(CN2CCCCC2)c2c(c1O)C(=O)C1=C(O)[C@]3(O)C(=O)C(C(N)=O)=C(O)C[C@@H]3C[C@@H]1C2]
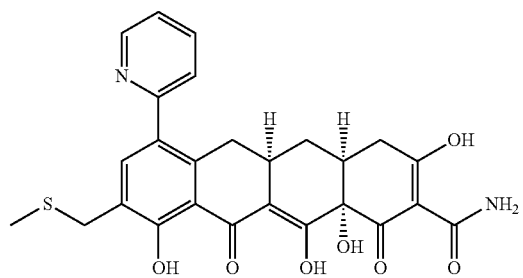
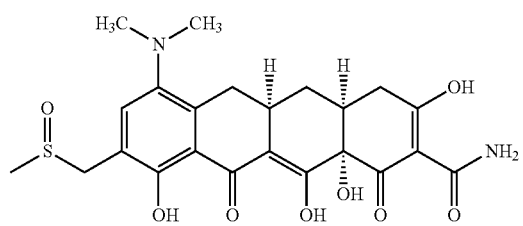 [SMILES: CN(C)c1cc(CS(C)=O)c(O)c2c1C[C@H]1C[C@H]3CC(O)=C(C(N)=O)C(=O)[C@@]3(O)C(O)=C1C2=O]

TABLE 2-continued
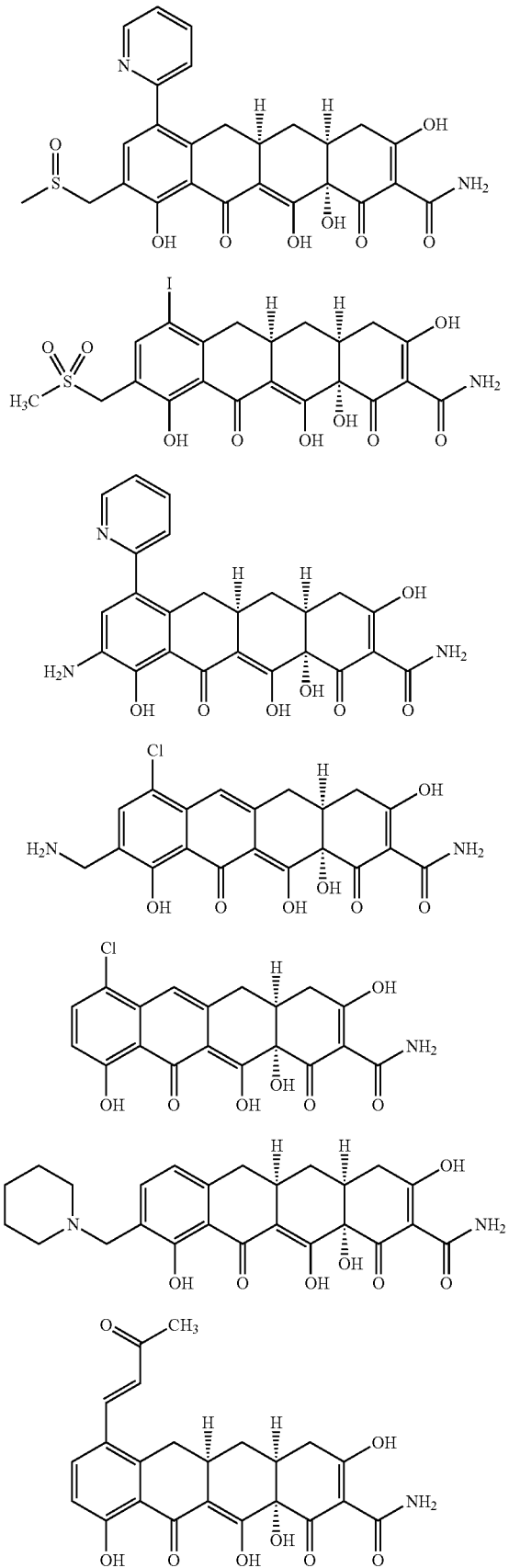

TABLE 2-continued
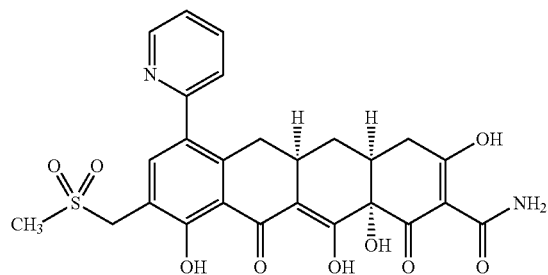 [SMILES: CS(=O)(=O)Cc1cc(-c2ccccn2)c2c(c1O)C(=O)C1=C(O)[C@]3(O)C(=O)C(C(N)=O)=C(O)C[C@@H]3C[C@@H]1C2]
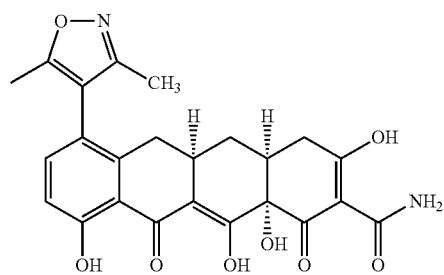 [SMILES: Cc1noc(C)c1-c1ccc(O)c2c1C[C@H]1C[C@H]3CC(O)=C(C(N)=O)C(=O)[C@@]3(O)C(O)=C1C2=O]
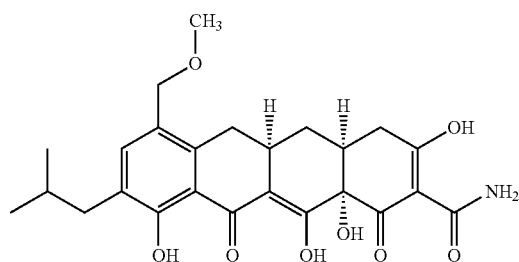 [SMILES: COCc1cc(CC(C)C)c(O)c2c1C[C@H]1C[C@H]3CC(O)=C(C(N)=O)C(=O)[C@@]3(O)C(O)=C1C2=O]
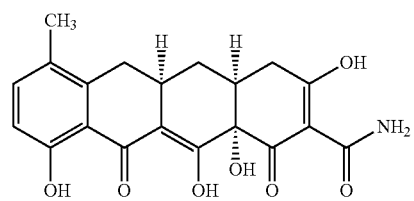 [SMILES: Cc1ccc(O)c2c1C[C@H]1C[C@H]3CC(O)=C(C(N)=O)C(=O)[C@@]3(O)C(O)=C1C2=O]
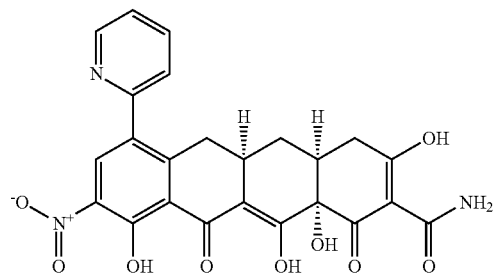

TABLE 2-continued
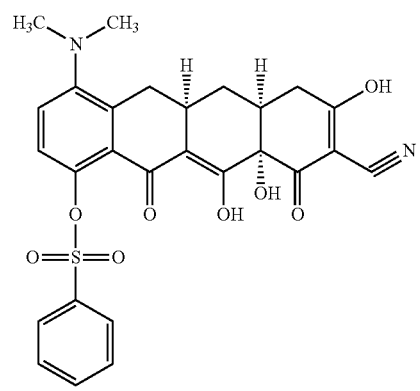 [SMILES: CN(C)c1ccc(OS(=O)(=O)c2ccccc2)c2c1C[C@H]1C[C@H]3CC(O)=C(C#N)C(=O)[C@@]3(O)C(O)=C1C2=O]
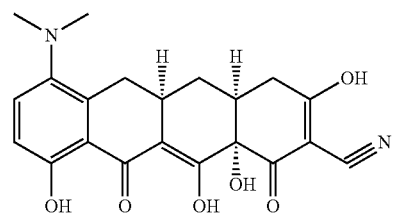 [SMILES: CN(C)c1ccc(O)c2c1C[C@H]1C[C@H]3CC(O)=C(C#N)C(=O)[C@@]3(O)C(O)=C1C2=O]
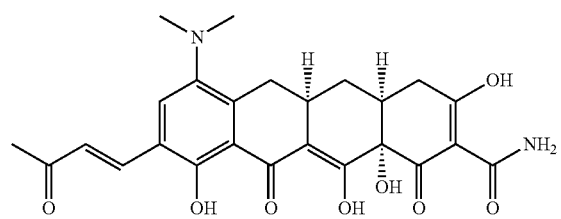 [SMILES: CC(=O)/C=C/c1cc(N(C)C)c2c(c1O)C(=O)C1=C(O)[C@]3(O)C(=O)C(C(N)=O)=C(O)C[C@@H]3C[C@@H]1C2]
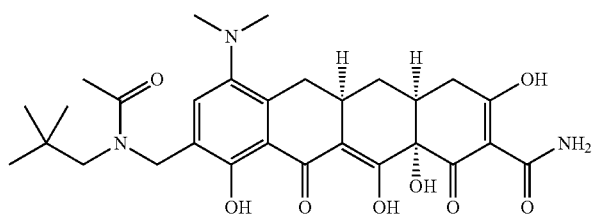 [SMILES: CC(=O)N(Cc1cc(N(C)C)c2c(c1O)C(=O)C1=C(O)[C@]3(O)C(=O)C(C(N)=O)=C(O)C[C@@H]3C[C@@H]1C2)CC(C)(C)C]
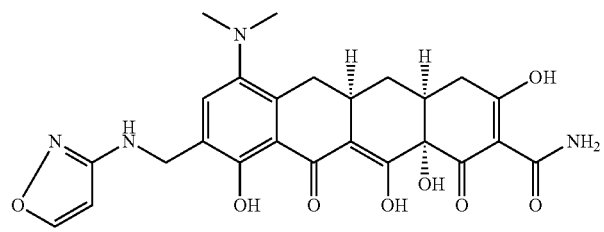 [SMILES: CN(C)c1cc(CNc2ccon2)c(O)c2c1C[C@H]1C[C@H]3CC(O)=C(C(N)=O)C(=O)[C@@]3(O)C(O)=C1C2=O]
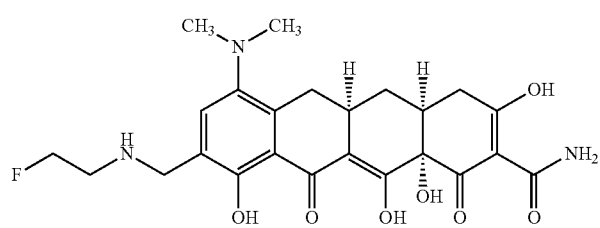 [SMILES: CN(C)c1cc(CNCCF)c(O)c2c1C[C@H]1C[C@H]3CC(O)=C(C(N)=O)C(=O)[C@@]3(O)C(O)=C1C2=O]

TABLE 2-continued
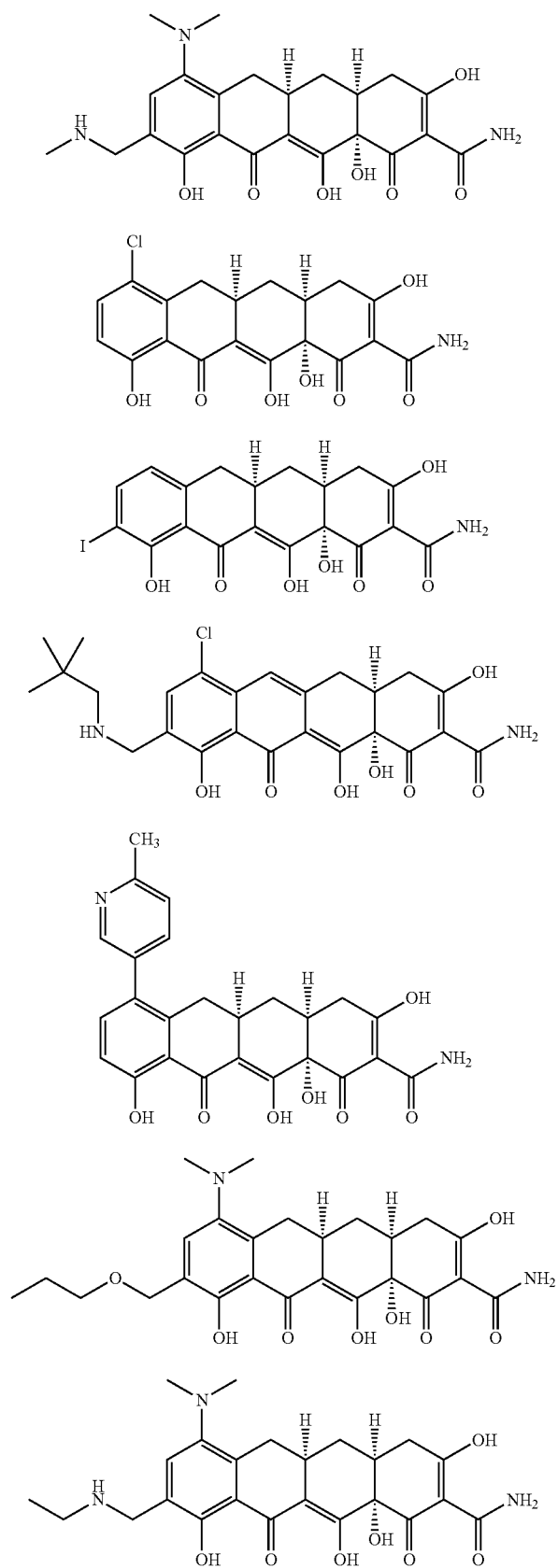

TABLE 2-continued
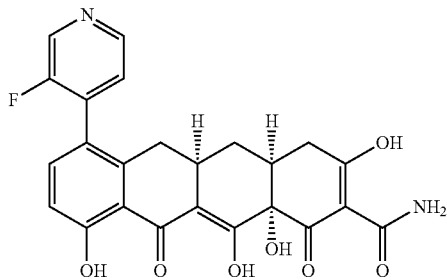 [SMILES: NC(=O)C1=C(O)C[C@@H]2C[C@@H]3Cc4c(-c5ccncc5F)ccc(O)c4C(=O)C3=C(O)[C@]2(O)C1=O]
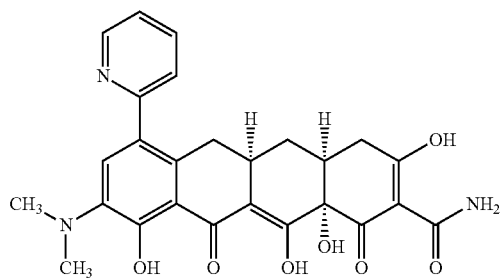 [SMILES: CN(C)c1cc(-c2ccccn2)c2c(c1O)C(=O)C1=C(O)[C@]3(O)C(=O)C(C(N)=O)=C(O)C[C@@H]3C[C@@H]1C2]
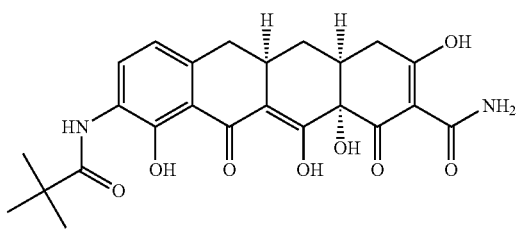 [SMILES: CC(C)(C)C(=O)Nc1ccc2c(c1O)C(=O)C1=C(O)[C@]3(O)C(=O)C(C(N)=O)=C(O)C[C@@H]3C[C@@H]1C2]
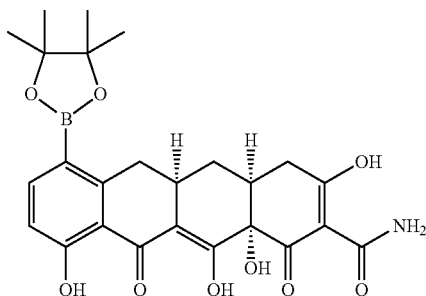 [SMILES: CC1(C)OB(c2ccc(O)c3c2C[C@H]2C[C@H]4CC(O)=C(C(N)=O)C(=O)[C@@]4(O)C(O)=C2C3=O)OC1(C)C]
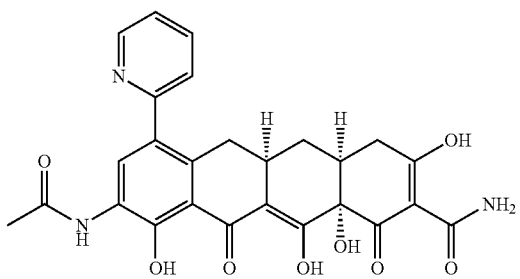 [SMILES: CC(=O)Nc1cc(-c2ccccn2)c2c(c1O)C(=O)C1=C(O)[C@]3(O)C(=O)C(C(N)=O)=C(O)C[C@@H]3C[C@@H]1C2]

TABLE 2-continued
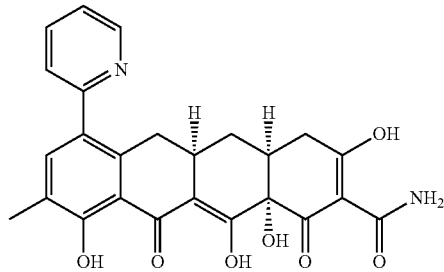 [SMILES: Cc1cc(-c2ccccn2)c2c(c1O)C(=O)C1=C(O)[C@]3(O)C(=O)C(C(N)=O)=C(O)C[C@@H]3C[C@@H]1C2]
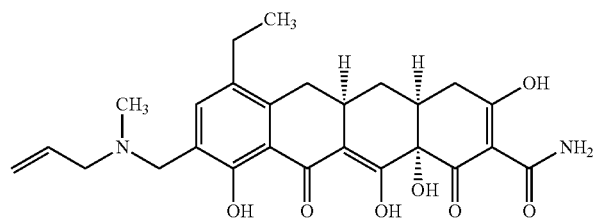 [SMILES: C=CCN(C)Cc1cc(CC)c2c(c1O)C(=O)C1=C(O)[C@]3(O)C(=O)C(C(N)=O)=C(O)C[C@@H]3C[C@@H]1C2]
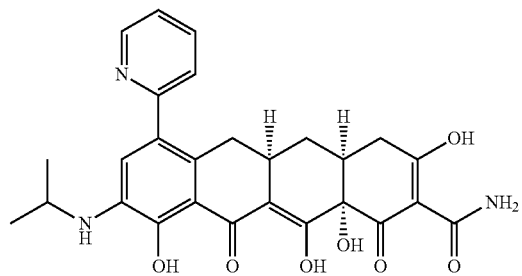 [SMILES: CC(C)Nc1cc(-c2ccccn2)c2c(c1O)C(=O)C1=C(O)[C@]3(O)C(=O)C(C(N)=O)=C(O)C[C@@H]3C[C@@H]1C2]
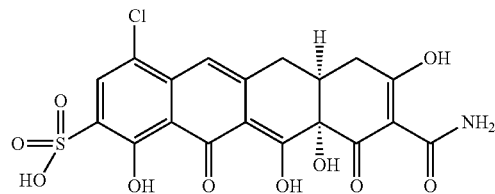 [SMILES: NC(=O)C1=C(O)C[C@@H]2CC3=Cc4c(Cl)cc(S(=O)(=O)O)c(O)c4C(=O)C3=C(O)[C@]2(O)C1=O]
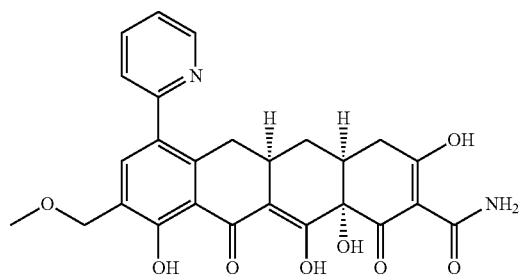
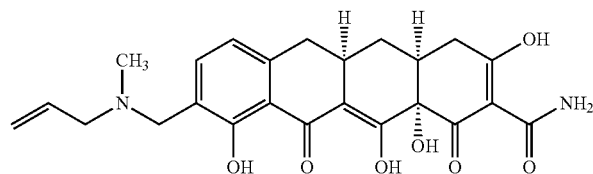 [SMILES: C=CCN(C)Cc1ccc2c(c1O)C(=O)C1=C(O)[C@]3(O)C(=O)C(C(N)=O)=C(O)C[C@@H]3C[C@@H]1C2]

TABLE 2-continued
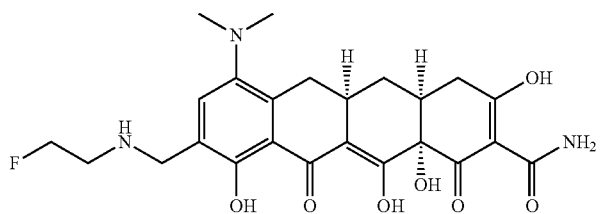 [SMILES: CN(C)c1cc(CNCCF)c(O)c2c1C[C@H]1C[C@H]3CC(O)=C(C(N)=O)C(=O)[C@@]3(O)C(O)=C1C2=O]
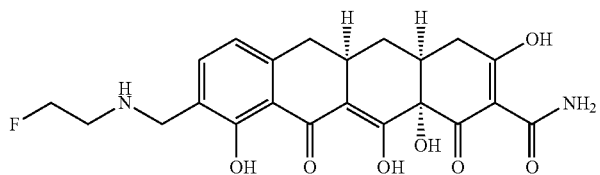 [SMILES: NC(=O)C1=C(O)C[C@@H]2C[C@@H]3Cc4ccc(CNCCF)c(O)c4C(=O)C3=C(O)[C@]2(O)C1=O]
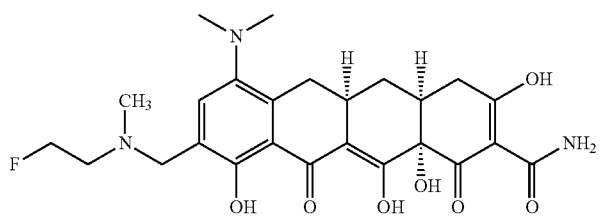 [SMILES: CN(CCF)Cc1cc(N(C)C)c2c(c1O)C(=O)C1=C(O)[C@]3(O)C(=O)C(C(N)=O)=C(O)C[C@@H]3C[C@@H]1C2]
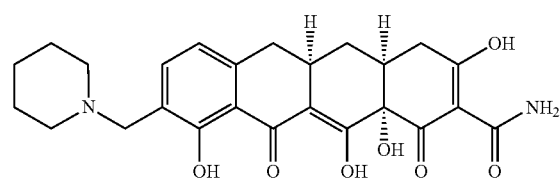 [SMILES: NC(=O)C1=C(O)C[C@@H]2C[C@@H]3Cc4ccc(CN5CCCCC5)c(O)c4C(=O)C3=C(O)[C@]2(O)C1=O]
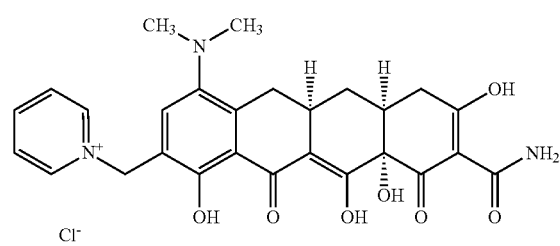 [SMILES: CN(C)c1cc(C[n+]2ccccc2)c(O)c2c1C[C@H]1C[C@H]3CC(O)=C(C(N)=O)C(=O)[C@@]3(O)C(O)=C1C2=O ; [Cl-]]
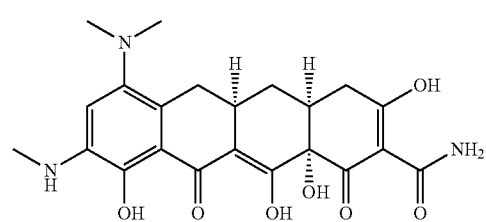 [SMILES: CNc1cc(N(C)C)c2c(c1O)C(=O)C1=C(O)[C@]3(O)C(=O)C(C(N)=O)=C(O)C[C@@H]3C[C@@H]1C2]
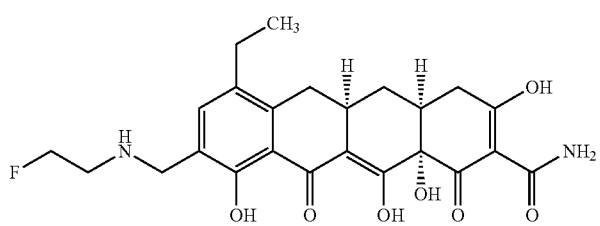 [SMILES: CCc1cc(CNCCF)c(O)c2c1C[C@H]1C[C@H]3CC(O)=C(C(N)=O)C(=O)[C@@]3(O)C(O)=C1C2=O]

TABLE 2-continued
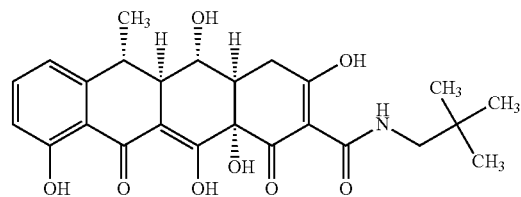 [SMILES: C[C@H]1c2cccc(O)c2C(=O)C2=C(O)[C@]3(O)C(=O)C(C(=O)NCC(C)(C)C)=C(O)C[C@@H]3[C@@H](O)[C@@H]21]
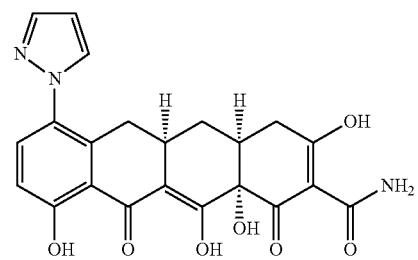 [SMILES: NC(=O)C1=C(O)C[C@@H]2C[C@@H]3Cc4c(-n5cccn5)ccc(O)c4C(=O)C3=C(O)[C@]2(O)C1=O]
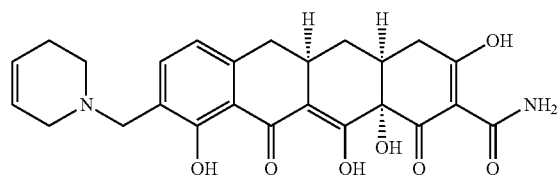 [SMILES: NC(=O)C1=C(O)C[C@@H]2C[C@@H]3Cc4ccc(CN5CC=CCC5)c(O)c4C(=O)C3=C(O)[C@]2(O)C1=O]
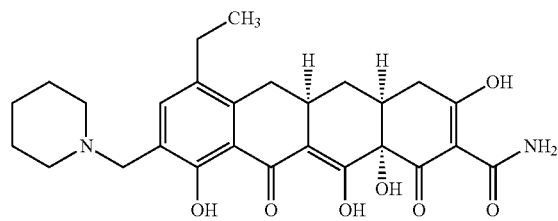
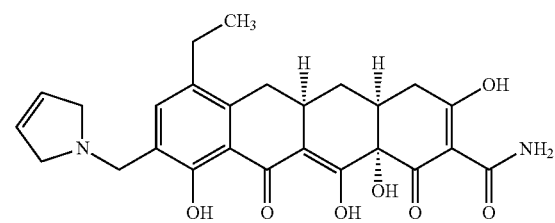 [SMILES: CCc1cc(CN2CC=CC2)c(O)c2c1C[C@H]1C[C@H]3CC(O)=C(C(N)=O)C(=O)[C@@]3(O)C(O)=C1C2=O]
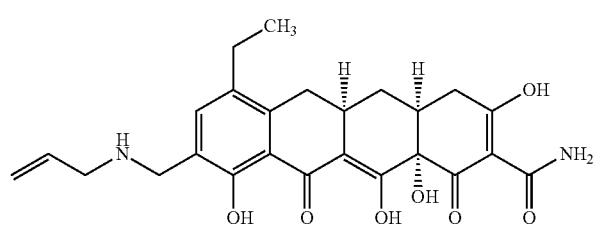 [SMILES: C=CCNCc1cc(CC)c2c(c1O)C(=O)C1=C(O)[C@]3(O)C(=O)C(C(N)=O)=C(O)C[C@@H]3C[C@@H]1C2]
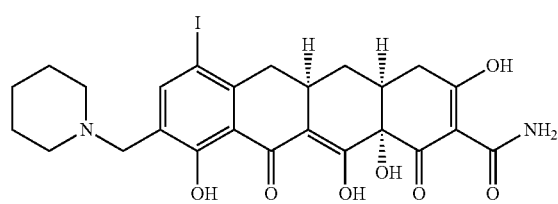 [SMILES: NC(=O)C1=C(O)C[C@@H]2C[C@@H]3Cc4c(I)cc(CN5CCCCC5)c(O)c4C(=O)C3=C(O)[C@]2(O)C1=O]

TABLE 2-continued
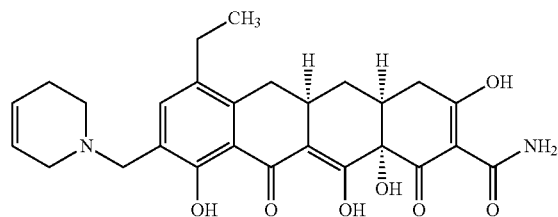 [SMILES: CCc1cc(CN2CC=CCC2)c(O)c2c1C[C@H]1C[C@H]3CC(O)=C(C(N)=O)C(=O)[C@@]3(O)C(O)=C1C2=O]
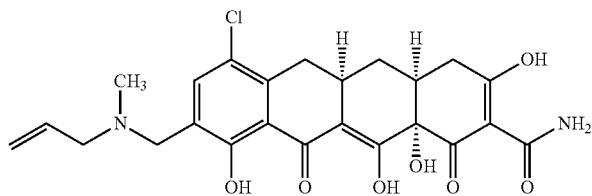 [SMILES: C=CCN(C)Cc1cc(Cl)c2c(c1O)C(=O)C1=C(O)[C@]3(O)C(=O)C(C(N)=O)=C(O)C[C@@H]3C[C@@H]1C2]
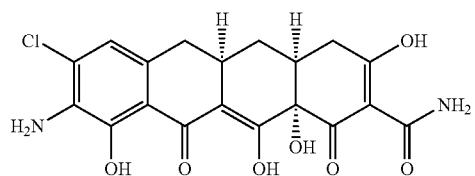 [SMILES: NC(=O)C1=C(O)C[C@@H]2C[C@@H]3Cc4cc(Cl)c(N)c(O)c4C(=O)C3=C(O)[C@]2(O)C1=O]
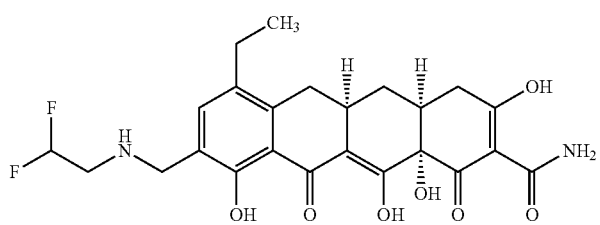 [SMILES: CCc1cc(CNCC(F)F)c(O)c2c1C[C@H]1C[C@H]3CC(O)=C(C(N)=O)C(=O)[C@@]3(O)C(O)=C1C2=O]
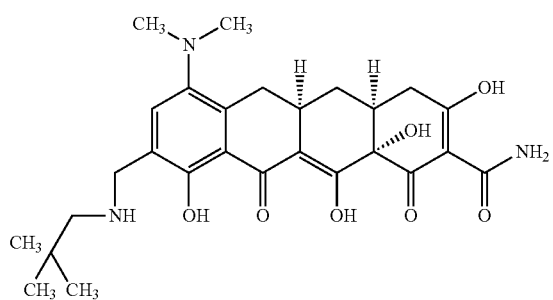
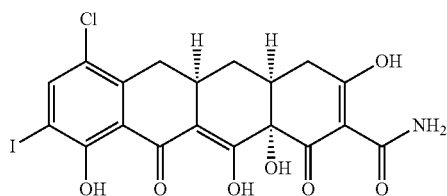 [SMILES: NC(=O)C1=C(O)C[C@@H]2C[C@@H]3Cc4c(Cl)cc(I)c(O)c4C(=O)C3=C(O)[C@]2(O)C1=O]

TABLE 2-continued

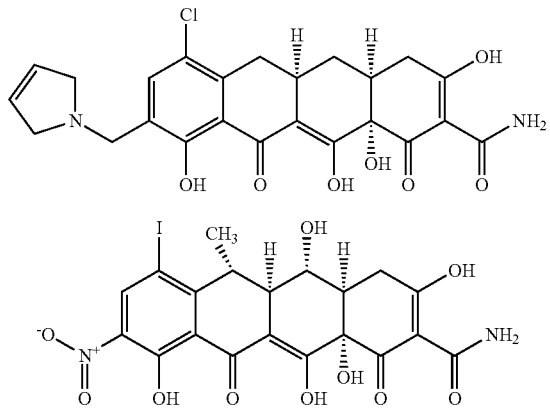

VI. Synthetic Methods for the Synthesis of Tetracycline Compounds

The tetracycline compounds of this invention can be synthesized using the methods described in the Schemes and Examples below.

Certain substituted 4-dedimethylamino tetracycline compounds can be synthesized by the method shown in Scheme 1. Although in each scheme sancycline is used as the tetracycline compound, one of skill in the art will appreciate that the methodology can also be applied to other tetracycline compounds such as tetracycline and doxycycline. In addition, similar methodology can be used to synthesize 9-substituted 4-dedimethylamino tetracycline compounds.

SCHEME 1

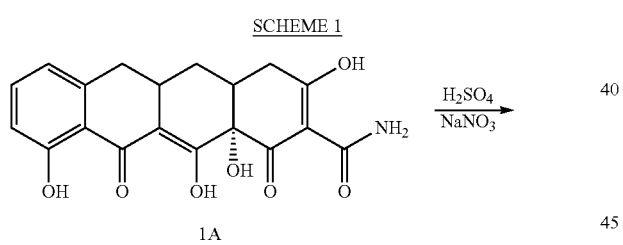

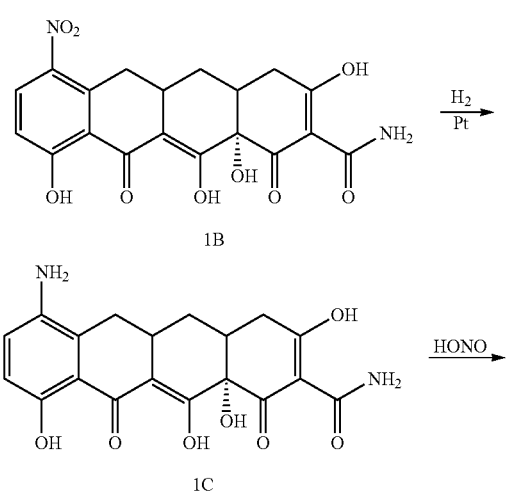

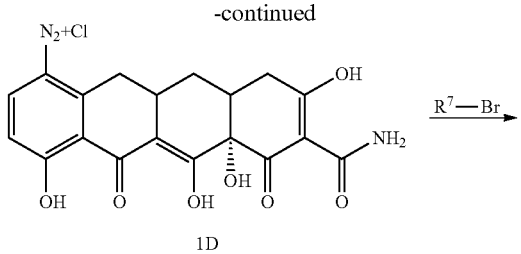

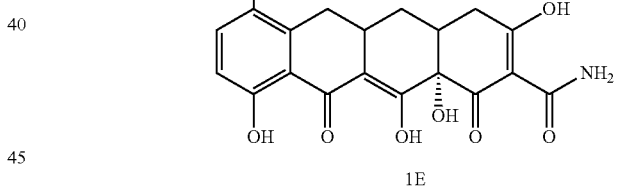

Generally, substituted 4-dedimethylamino tetracycline compounds can be synthesized as shown in Scheme 1 for 4-dedimethylamino sancycline. 4-Dedimethylamino sancycline (1A) is treated with sulfuric acid and sodium nitrate. The resulting product is 7-nitro (1B) 4-dedimethylamino sancycline (in a mixture with the 9-position isomers). The nitro 4-dedimethylamino sancycline compound is then treated with hydrogen gas and a platinum catalyst to yield the 7-amino 4-dedimethylamino sancycline compound, 1C. To synthesize 7 derivatives, the 7-amino 4-dedimethylamino sancycline compound is treated with HONO, to yield the diazonium salt (1D). The salt can subsequently be treated with numerous compounds possessing an alkene or n bond functional group such as alkenes, aryls, and alkynyls (e.g., $R^7Br$) yielding the 7-substituted sancycline compound (1E).

SCHEME 2

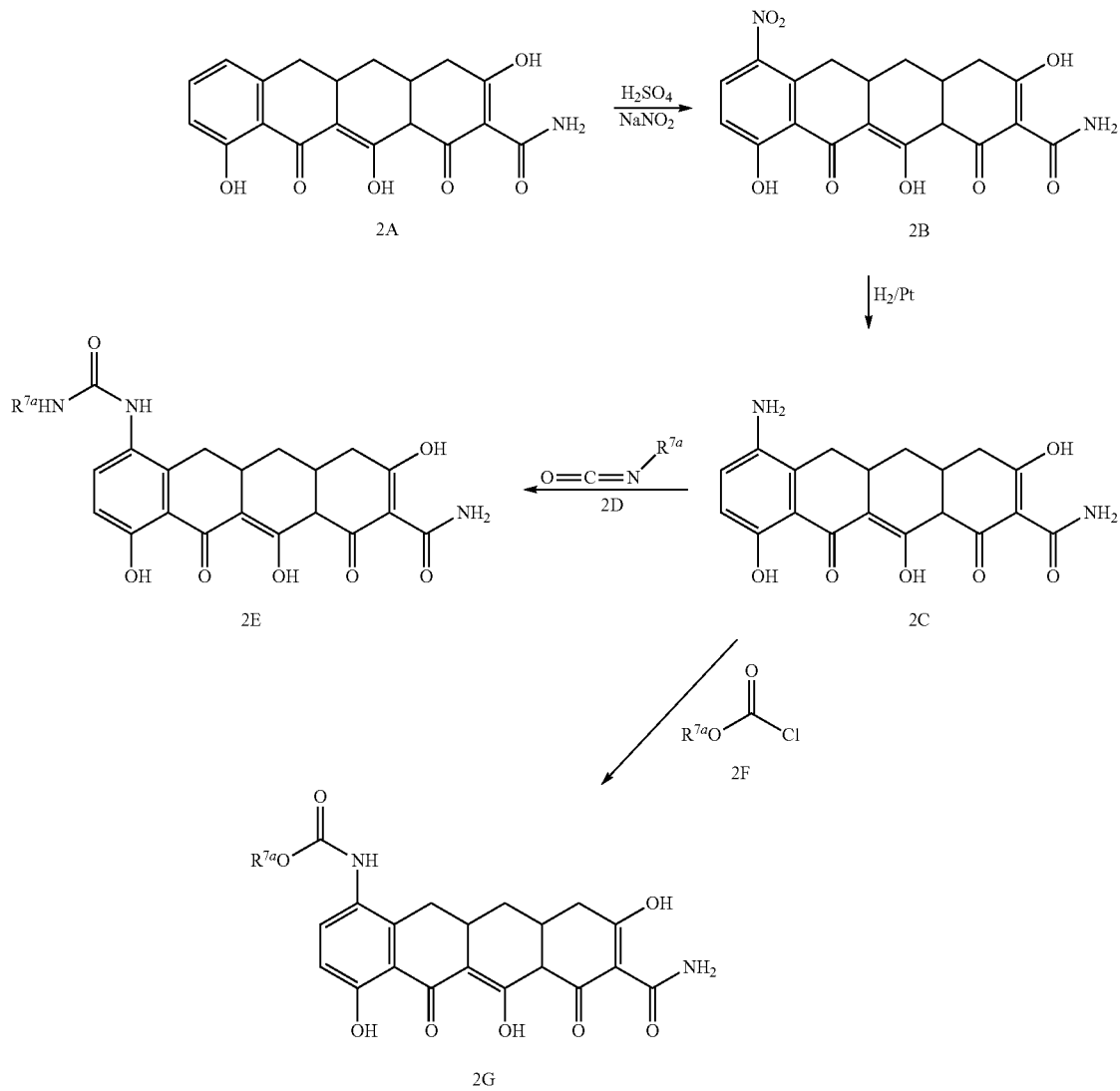

As shown in Scheme 2,4-dedimethylamino tetracycline compounds of the invention wherein $R^7$ is a carbamate or a urea derivative can be synthesized using the following protocol. 4-Dedimethylamino sancycline (2A) is treated with NaNO$_2$ under acidic conditions forming 7-nitro 4-dedimethylamino sancycline (2B) in a mixture of positional isomers. 7-nitro 4-dedimethylamino sancycline (2B) is then treated with H$_2$ gas and a platinum catalyst to form the 7-amino 4-dedimethylamino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

SCHEME 3

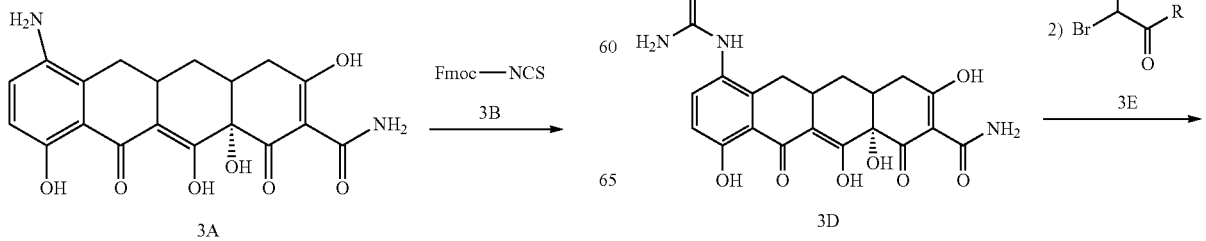

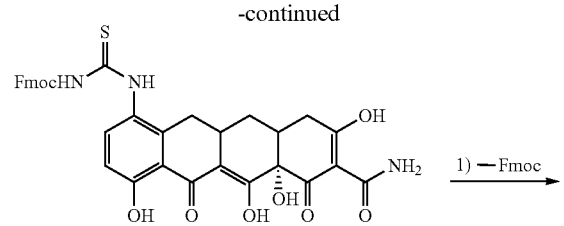

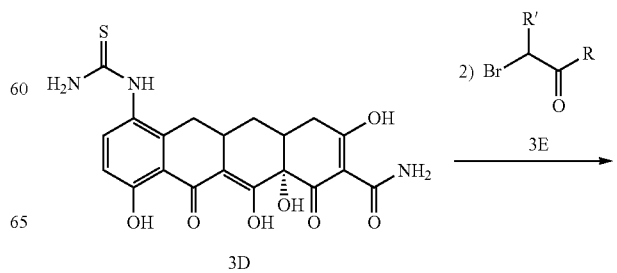

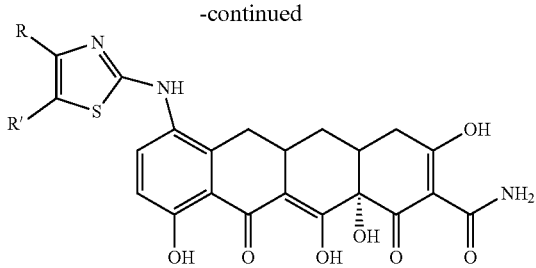

3F

As shown in Scheme 3, 4-dedimethylamino tetracycline compounds of the invention, wherein $R^7$ is a heterocyclic (i.e. thiazole) substituted amino group can be synthesized using the above protocol. 7-amino 4-dedimethylamino sancycline (3A) is reacted with Fmoc-isothiocyanate (3B) to produce the protected thiourea (3C). The protected thiourea (3C) is then deprotected yielding the active 4-dedimethylamino sancycline thiourea (3D) compound. The 4-dedimethylamino sancycline thiourea (3D) is reacted with an α-haloketone (3E) to produce a thiazole substituted 7-amino 4-dedimethylamino sancycline (3F).

SCHEME 4

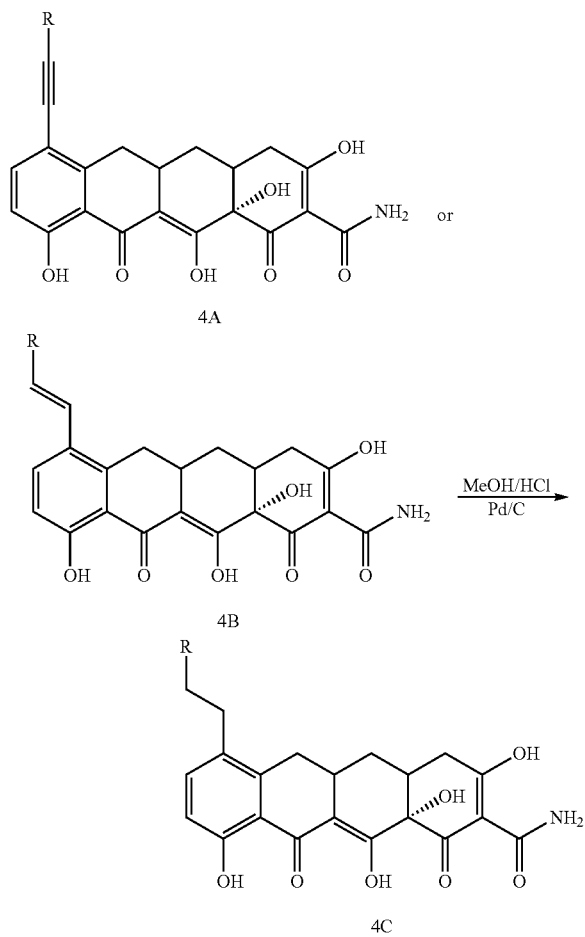

Alkenyl substituted 4-dedimethylamino tetracycline compounds, such as 7-alkynyl 4-dedimethylamino sancycline (4A) and 7-alkenyl 4-dedimethylamino sancycline (4B), can be hydrogenated to form alkyl substituted 4-dedimethylamino tetracycline compounds (e.g., 7-alkyl 4-dedimethylamino sancycline, 4C). Scheme 4 depicts the selective hydrogenation of the 7-position double or triple bond, in saturated methanol and hydrochloric acid solution with a palladium/carbon catalyst under pressure, to yield the product. A 9-position double or triple bond can be treated in a similar manner.

SCHEME 5

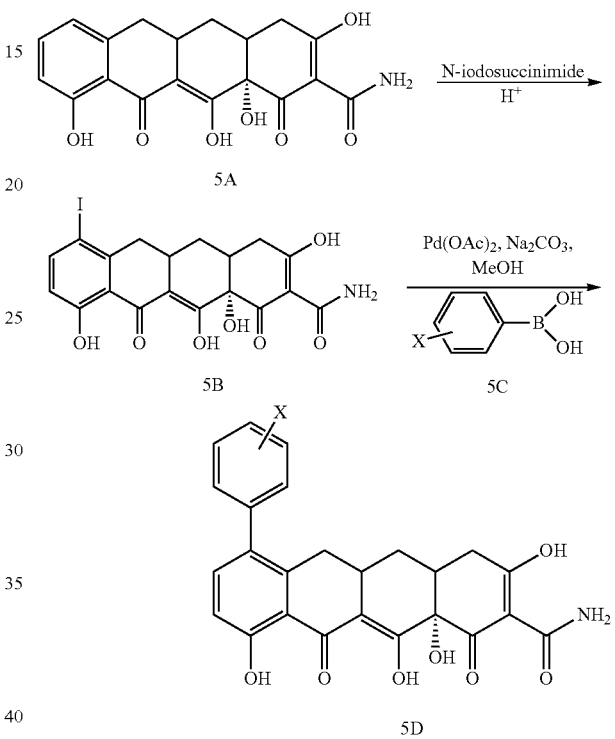

In Scheme 5, a general synthetic scheme for synthesizing 7-position aryl derivatives is shown. Similar methodology can be used to synthesize 9-position aryl derivatives. A Suzuki coupling of an aryl boronic acid with an iodosancycline compound is shown. An iodo 4-dedimethylamino sancycline compound (5B) can be synthesized from 4-dedimethylamino sancycline by treating 4-dedimethylamino sancycline (5A) with at least one equivalent N-iodosuccinimide (NIS) under acidic conditions. The reaction is quenched, and the resulting 7-iodo 4-dedimethylamino sancycline (5B) can then be purified using standard techniques known in the art. To form the aryl derivative, 7-iodo 4-dedimethylamino sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl and alkynyl tetracycline compounds can be synthesized using similar protocols.

The substituted 4-dedimethylamino tetracycline compounds of the invention can also be synthesized using Stile cross couplings. Stille cross couplings can be performed using an appropriate tin reagent (e.g., R—SnBu$_3$) and a halogenated 4-dedimethylamino tetracycline compound, (e.g., 7-iodo 4-dedimethylamino sancycline). The tin reagent and the iodo 4-dedimethylamino sancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

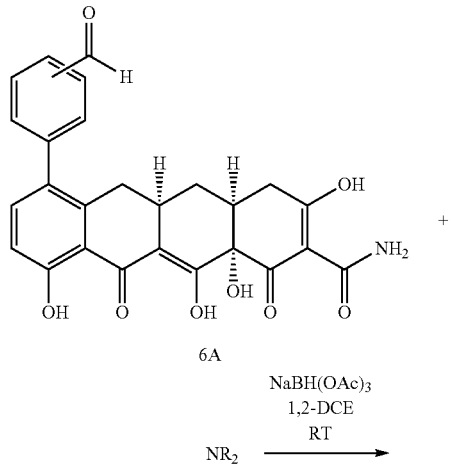

6A

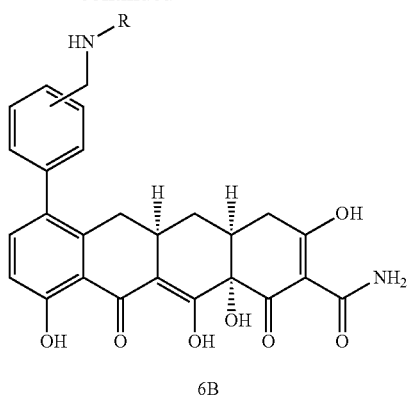

6B

The aryl derivatives formed by Suzuki or Stille couplings, can be further derivatized. For example in Scheme 6, a formyl aryl 4-dedimethylamino sancycline (6A), an amine, and a solvent (e.g., 1,2 dichloroethane) are combined in a reaction flask. A reducing agent is then added (e.g., NaBH(OAc)$_3$. and the reaction is allowed to proceed to completion to yield the product (6B). The product is purified and characterized using standard methods.

SCHEME 7

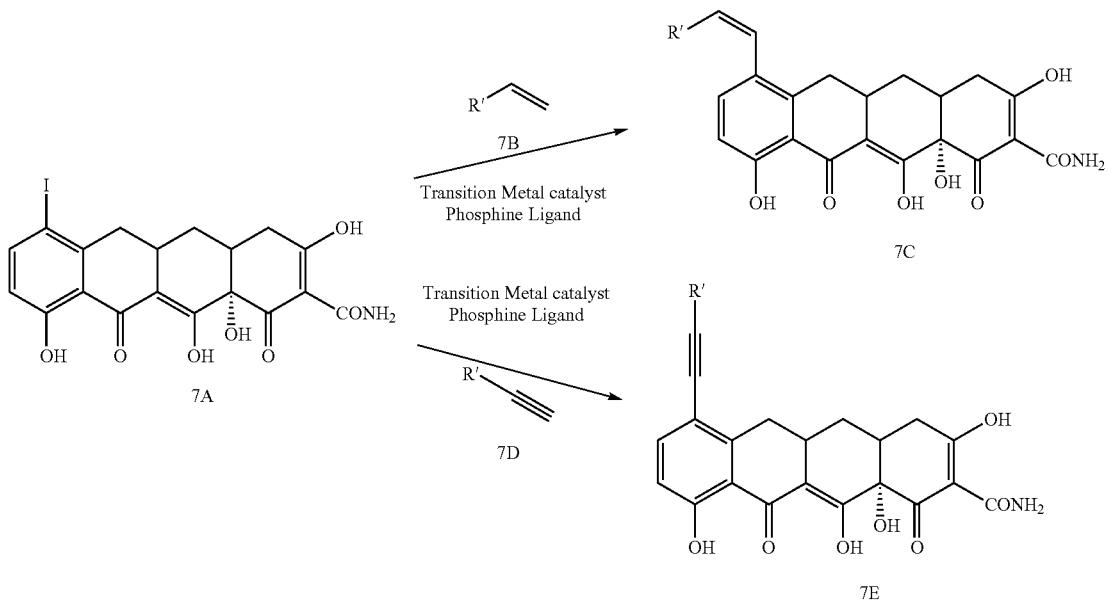

The compounds of the invention can also be synthesized using Heck-type cross coupling reactions. As shown in Scheme 7, Heck-type cross-couplings can be performed by suspending a halogenated tetracycline compound (e.g., 7-iodo 4-dedimethylamino sancycline, 7A) and an appropriate palladium or other transition metal catalyst (e.g., Pd(OAc)$_2$ and CuI) in an appropriate solvent (e.g., degassed acetonitrile). The substrate, a reactive alkene (7B) or alkyne (7D), and triethylamine are then added and the mixture is heated for several hours, before being cooled to room temperature. The resulting 7-substituted alkenyl (7C) or 7-substituted alkynyl (7E) 4-dedimethylamino tetracycline compound can then be purified using techniques known in the art.

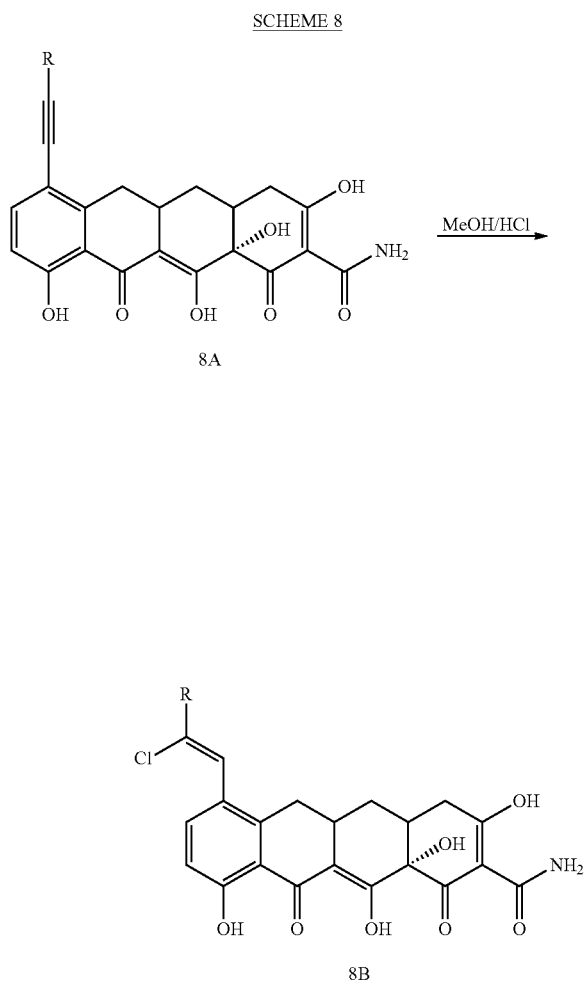

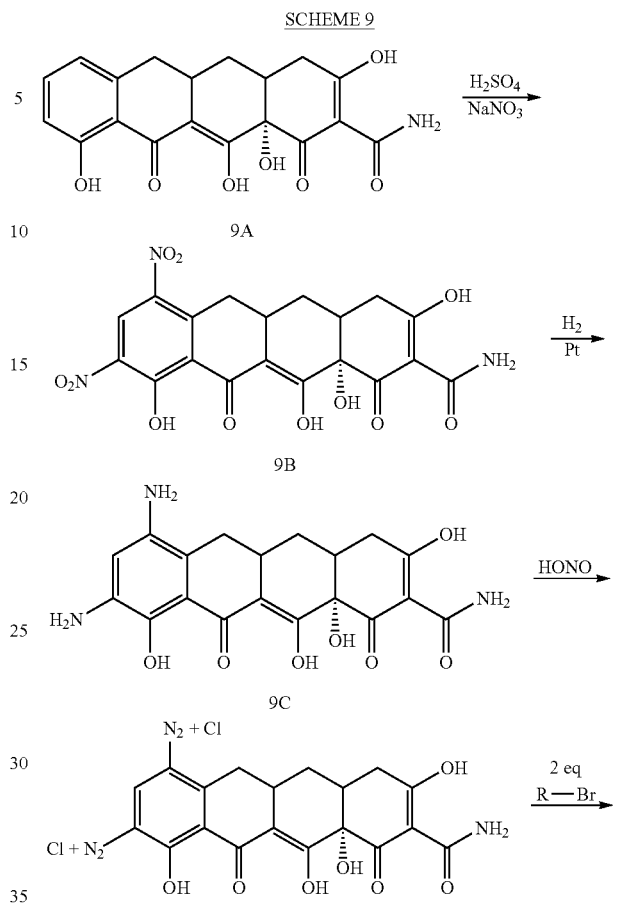

Generally, 7,9-substituted 4-dedimethylamino tetracycline compounds can be synthesized as shown in Scheme 9 for 4-dedimethylamino sancycline. 4-Dedimethylamino sancycline (9A) is treated with sulfuric acid and sodium nitrate. The resulting product is 7,9-nitro 4-dedimethylamino sancycline (9B). The nitro 4-dedimethylamino sancycline compound is then treated with hydrogen gas and a platinum catalyst to yield the 7,9-amino 4-dedimethylamino sancycline compound, 9C. To synthesize derivatives, the 7,9-amino 4-dedimethylamino sancycline compound is treated with HONO, to yield the diazonium salt (9D). The salt can subsequently be treated with numerous compounds possessing an alkene or n bond functional group such as alkenes, aryls, and alkynyls (e.g., RBr) yielding the 7,9-substituted 4-dedimethylamino sancycline compound (9E).

The 13-substituted 4-dedimethylamino methacycline compounds of the invention can be synthesized by methods known in the art and/or as described herein. In Scheme 10, a general synthetic scheme for the synthesis of 13-substituted 4-dedimethylamino methacycline compounds is shown. In this reaction, 4-dedimethylamino methacycline is coupled with a boronic acid in the presence of a transition metal catalyst. Furthermore, other aryl coupling reactions known in the art may also be used.

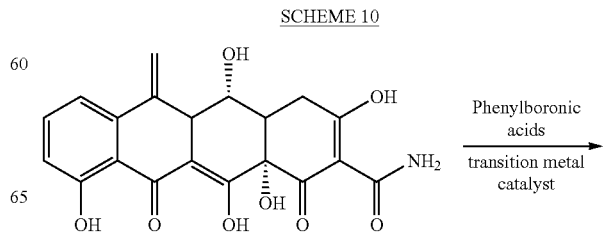

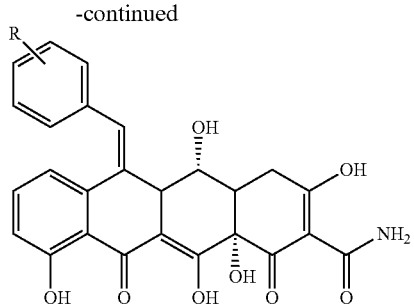

As shown in Scheme 10, the 4-dedimethylamino methacycline is reacted with a phenylboronic acid in the presence of a palladium catalyst such as $Pd(OAc)_2$. The resulting compound can then be purified using techniques known in the art such as preparative HPLC and characterized. The synthesis of the compounds of the invention are described in more detail in Example 4.

13-substituted 4-dedimethylamino methacycline compounds wherein $R^6$ is an alkyl group can be synthesized using a tertiary alcohol and an acid catalyst as shown in Scheme 11.

SCHEME 11

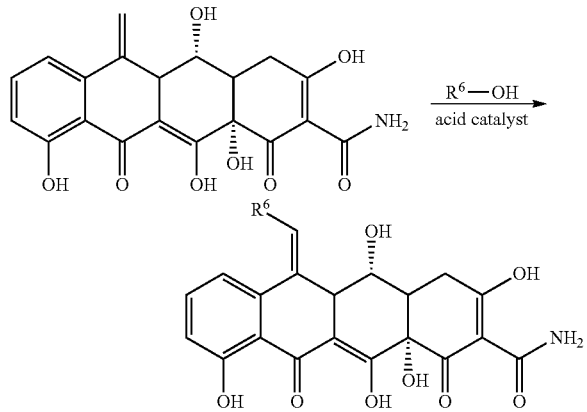

To prepare 7-(2'-Chloro-alkenyl) 4-dedimethylamino tetracycline compounds, the following procedure can be used. 7-(alkynyl) 4-dedimethylamino sancycline is dissolved in saturated methanol and hydrochloric acid and stirred. The solvent is then removed to yield the product.

8-Substituted 4-dedimethylamino tetracycline compounds of the invention can be synthesized by transition metal catalyzed coupling of tetracyclines halogenated at the 8-position. For example, many reactions between aryl halides and various reactive species have been developed using transition metal catalysis. Coupling of aryl halides or triflates with main group organometallics with oxidate addition-transmetallation-reductive elimination reactions has been developed and occurs using a wide range of catalysts, such as $Pd(Pd_3)_4$, $Pd(dba)_2$, $PdCl_2$, $Pd(OAc)_2$, and $PdCl_2(CH_3CN)_2$. Ligands such as $PPh_3$ or $AsPh_3$ may be added to form catalysts in situ with palladium species such as $Pd(dba)_2$ or $PdCl_2$. Furthermore, copper salts, such as CuCN or CuI may also be added to further enhance the reaction. An example of a coupling using a halogenated tetracycline compound is shown in Scheme 12. In Scheme 12, X is bromine or chlorine.

SCHEME 12

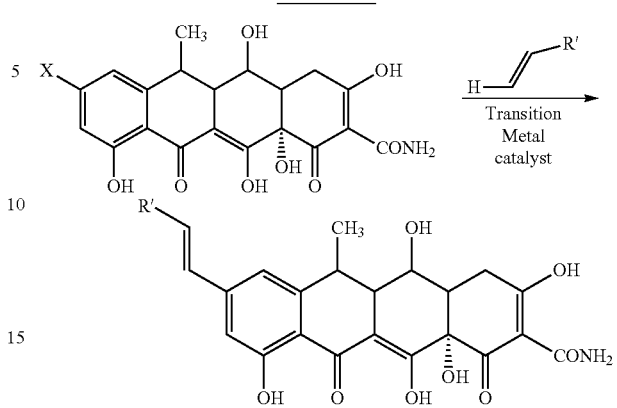

The substituted tetracycline compounds of the invention can be synthesized using organotin reagents, halogenated or triflate tetracycline compounds, and an appropriate catalyst (e.g., palladium). Examples of tin reagents include, for example, ethenyl tributyltin, ethynyl tributyltin, phenyl tributyltin, ethenyl trimethyl tin, ethynyl trimethyl tin, etc. These Stille type couplings are run by adding the transition metal (e.g., palladium) catalyst to a solution of the halogenated or triflate tetracycline compound and the organotin reagent in polar solvents. Stille type couplings with alkynyl and alkenyl tin reagents are shown in Scheme 13, wherein X is a halogen or a triflate group.

SCHEME 13

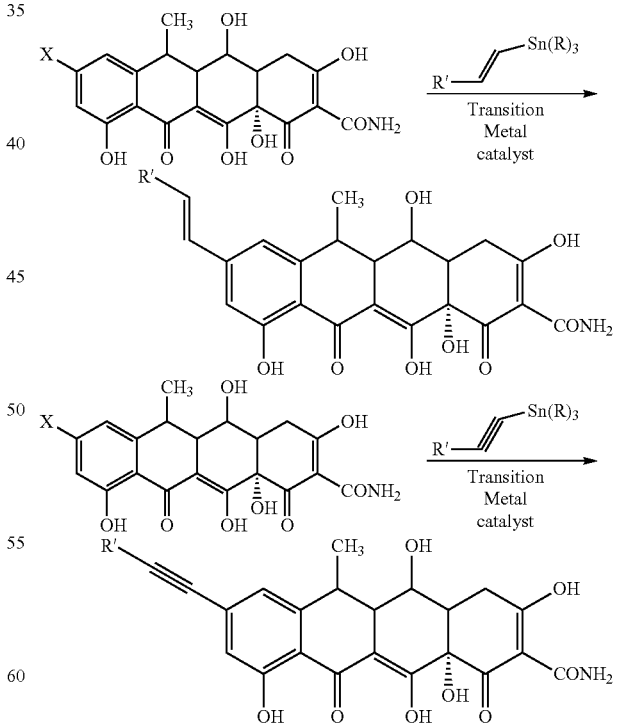

Other methods of synthesizing the 8-substituted tetracycline compounds of the invention include coupling halogenated tetracycline compounds to boronic acids using Suzuki type couplings (M. J. Sharp et al. *Tetrahedron Lett.* 28 (1987)

5093; W. Cheng, et al. *Tetrahedron Lett.* 28 (1987) 5097; Alves, A. B. et al. *Tetrahedron Lett.* 29 (1988) 2135; D. Muller, et al. *Tetrahedron Lett.* 32 (1991) 2135), Grignard reagents (K. Tamao et al. *Bull. Chem. Soc. Jpn.* 49 (1976) 1958), or organolithium reagents (S.-I. Murahashi et al., *J. Org. Chem* 44 (1979) 2408) and a transition metal catalyst, as shown in Scheme 14.

SCHEME 14

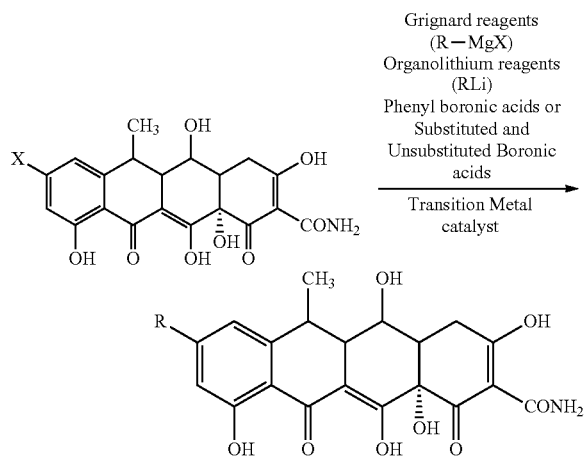

8-halogenated 4-dedimethyl amino tetracycline compounds can be synthesized via azidotetracyclines. The protonolysis of the aryl azides produces 8-halo-9-amino 4-dedimethylamino tetracycline in good yield.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkylaminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiothiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido; nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide."Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

VI. Methods for Treating Tetracycline Responsive States

The invention also pertains to methods for treating a tetracycline responsive states in subjects, by administering to a subject an effective amount of a 4-dedimethylamino tetracycline compound of the invention (e.g., of Formula I, II, III, IV, V, VI, VII, VIII or Table 2), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a 4-dedimethylamino tetracycline compound (e.g., of Formula I, II, III, IV, V, VI, VII, VIII or Table 2). Tetracycline compound responsive states include bacterial infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). Other examples of tetracycline associated states are described in U.S. Ser. Nos. 10/196,010 and 60/421,248, which are incorporated herein by reference.

In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 6).

Tetracycline compound responsive states also include inflammatory process associated states (IPAF). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention (e.g., of Formula I, II, III, IV, V, VI, VII, VIII or Table 2). In certain embodiments, the invention includes 7-substituted 4-dedimethylamino tetracyclines. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (re-perfusion-associated injury following infarction), juvenile diabetes, inflammatory disorders, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., 4-dedimethylamino tetracycline compounds such as those described herein (e.g., of Formula I, II, III, IV, V, VI, VII, VIII or Table 2).

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphesema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,83915, 459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

VII. Pharmaceutical Compositions

The invention also pertains to pharmaceutical compositions comprising a therapeutically effective amount of a 4-dedimethylamino tetracycline compound (e.g., a compound of Formula I, II, III, IV, V, VI, VII, VIII or Table 2) and, optionally; a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of Formula I, II, III, IV, V, VI, VII, VIII or Table 2 for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below, with modifications to the procedure below within the skill of those of ordinary skill in the art.

Example 1

Synthesis of 7-Substituted 4-Dedimethylamino Sancyclines

7 Iodo 4-Dedimethylamino Sancycline

One gram of 4-dedimethylamino sancycline is dissolved in 25 mL of TFA (trifluoroacetic acid) that was cooled to 0 C (on ice). 1.2 equivalents of N-iodosuccinimide (NIS) is added to the reaction mixture and reacted for forty minutes. The reaction is removed from the ice bath and allowed to react at room temperature for an additional five hours. The mixture is then analyzed by HPLC and TLC, and driven to completion by the stepwise addition of NIS. After completion of the reaction, the TFA is removed in vacuo and 3 mL of MeOH is added to dissolve the residue. The methanolic solution is added slowly to a rapidly stirring solution of the product in diethyl ether to form a greenish brown precipitate. The 7-iodo isomer of 4-dedimethylamino sancycline is purified by treating the 7-iodo 4-dedimethylamino product with activated charcoal, filtering through Celite, and subsequent removal of the solvent in vacuo to produce the 7-isomer compound as a pure solid.

(7-Phenyl) 4-Dedimethylamino Sancycline)

7-iodo 4-dedimethylamino sancycline, 150 mg (0.28 mM), Pd(OAc)$_2$ and 10 mL of MeOH are added to a flask with a stir bar and the system degassed three times using argon. Na$_2$CO$_3$ (87 mg, 0.8 mM) dissolved in water and argon degassed is added via syringe and is added along with phenylboronic acid (68 mg, 0.55 mM) in MeOH that was also degassed. The reaction is followed by HPLC for 2 hours and then the reaction mixture is cooled to room temperature. The solution is filtered, and dried to produce a crude mixture. The solid is dissolved in dimethylformamide and injected onto a preparative HPLC system using C18 reverse-phase silica. The product fraction is isolated, and the solvent is removed in vacuo to yield the product.

7-(4'-Chlorophenyl) 4-Dedimethylamino Sancycline 7-iodo 4-dedimethylamino sancycline, 500 mg (0.91 mM), Pd(OAc)$_2$ 21 mg, and 20 mL of MeOH are added to a flask with a stir bar and the system is degassed 3× using argon. Na$_2$CO$_3$ (293 mg, 2.8 mM) dissolved in water and argon degassed is added via syringe and is added along with 4-Cl-phenylboronic acid (289 mg, 1.85 mM) in MeOH that was also degassed. The reaction is followed by HPLC for 45 minutes and the reaction mixture is cooled to room temperature. The solution is filtered, and dried to produce a crude mixture. The solid is dissolved in dimethylformamide and injected onto a preparative HPLC system using C18 reverse-phase silica. The fraction at 39 minutes is isolated, and the solvent is removed in vacuo to yield the product.

7-(4'-Fluorophenyl) 4-Dedimethylamino Sancycline 7-iodo 4-dedimethylamino sancycline, 200 mg (0.3 mM), Pd(OAc)$_2$ 8.3 mg, and 10 mL of MeOH are added to a flask with a stir bar and the system is degassed 3× using argon. Na$_2$CO$_3$ (104 mg, 1.1 mM) (dissolved in water) and argon (degassed) are added via syringe along with 4-F-phenylboronic acid (104 mg, 0.7 mM) in MeOH which was also previously degassed. The reaction is followed by HPLC for 20 minutes and the mixture is cooled to room temperature. The solution is filtered, and dried to produce a crude mixture. The solid is dissolved in dimethylformamide and injected onto a preparative HPLC system using C18 reverse-phase silica. The fraction containing the product is isolated.

7-(4'-Iodo-1',3'-carboethoxy-1',3'-butadiene) 4-Dedimethylamino Sancycline

7-I-4-dedimethylamino sancycline (1.86 mmol) is dissolved in 25 mL of acetonitrile that was previously degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) are added and purged with nitrogen. Ethyl propiolate (1 mL) and triethylamine (1 mL) are added to the suspension. The reaction mixture is then heated to 70 degrees C. for two hours. Progress of the reaction is monitored by HPLC. It is then cooled down to room temperature and filtered through celite. Evaporation of the solvent gives the product, which is purified on preparative HPLC.

7-(2'-Chloroethenyl)-4-Dedimethylamino Sancycline

To a solution/suspension of (1 mmol) of 7-iodo 4-dedimethylamino sancycline, 0.05 g tetrakis triphenyl phosphinato palladate, 0.012 g palladium acetate, 0.05 g copper (I) iodide in 10 mL acetonitrile, 2 mL triethylamine and 0.5 g trimethylsilyl acetylene are added at room temperature. The reaction is allowed to proceed for two hours before being filtered through a celite bed and concentrated. The crude product is purified by preparative HPLC. The collected fractions are concentrated and the residue is taken up in about 1 mL of methanol and 2 mL of HCl saturated methanol. The product is precipitated with ether. The solids are filtered off and dried under reduced pressure.

7-(4'-aminophenyl) 4-Dedimethylamino Sancycline

To a solution of 200 mg of 7-(4-nitrophenyl) 4-dedimethylamino sancycline in 50 mL methanol, 10 mg of 10% palladium on charcoal catalyst is added. The reaction mixture is shaken under 40 psi hydrogen pressure for 2 hours and is then filtered followed by concentration. The residue is further purified by preparative HPLC.

1,8-Di-7-4-Dedimethylamino Sancyclinyl-1,8-Heptyne

SCHEME 15

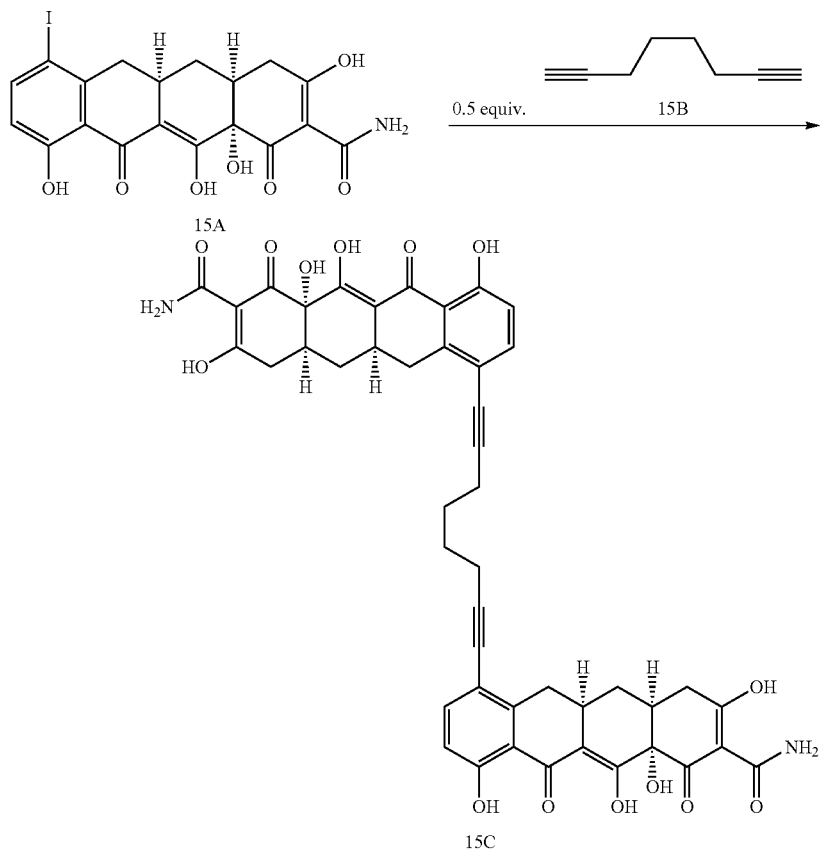

A flask was charged with 7-iodo 4-dedimethylamino sancycline (3.0 g, 4.57 mmol, 15A), Pd(OAc)$_2$ (0.102 g, 0.46 mmol), CuI (0.044 g, 0.23 mmol), and P(o-Tol)$_3$ (0.278 g, 0.91 mmol) and the contents are suspended in anhydrous acetonitrile. After purging this mixture with dinitrogen at 60° C. (bath temperature), 1,7-octadiyne (0.305 mL, 2.29 mmol, 15B) is added to it, followed by the addition of triethylamine. The solution is stirred at 60° C. for 3 h, filtered through a bed of celite, and dried. A methanol:DMF:TFA (90:8:2) solution of the product (15C) is purified on preparative HPLC column.

7-(N,N-Dimethylpropynyl)-4-Dedimethylamino Sancycline

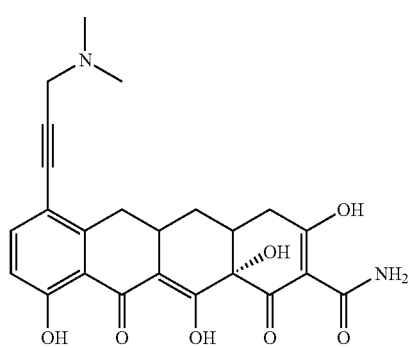

7-I-4-dedimethylamino sancycline (1 gm, 1.86 mmol), taken in 25 mL of acetonitrile, is degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) are added and purged with nitrogen for few minutes. N,N-Dimethylpropyne (308 mg, 3.72 mmol) and triethylamine (1 mL) are added to the suspension. The reaction mixture is then heated to 70° C. for 3 hours. Progress of the reaction is monitored by HPLC. It is then cooled down to room temperature and filtered through celite. Evaporation of the solvent gives the product, which is then purified on preparative HPLC.

7-(2'-Chloro-3-Hydroxypropenyl)-4-Dedimethylamino Sancycline

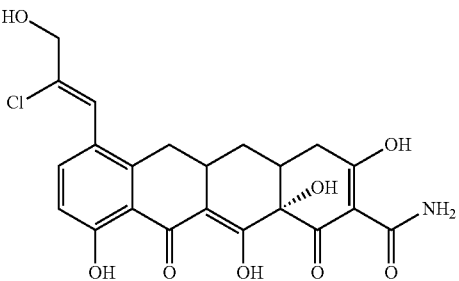

7-(alkynyl)-4-dedimethylamino sancycline (100 mg) is taken in 20 ml of saturated MeOH/HCl and stirred for 20 min. The solvent is then evaporated to give the product.

7-(3'Methoxyphenylethyl)-4-Dedimethylamino Sancycline

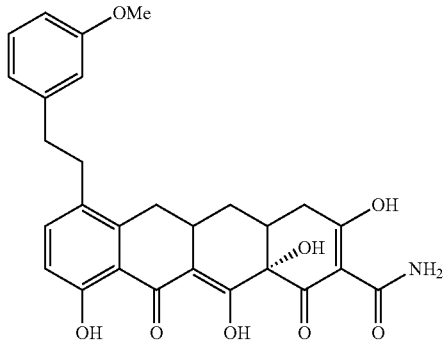

7-(3'-Methoxyphenylethynyl)-4-dedimethylamino sancycline (1 mmol)/is taken in saturated solution of MeOH/HCl. To this solution 10% Pd/C is added and is subjected to hydrogenation at 50 psi for 12 hrs. It is then filtered through celite. The solvent is evaporated, and the product is precipitated from MeOH/diethylether.

(2-Dimethylamino-Acetylamino)-4-Dedimethylamino Sancycline

SCHEME 16

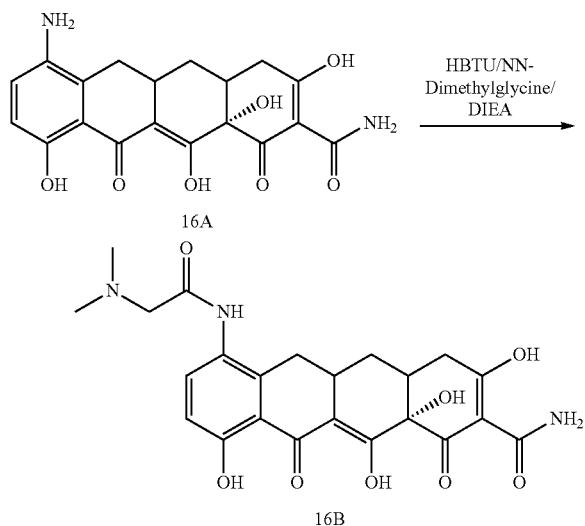

N,N-Dimethylglycine (1.2 mmol) is dissolved in DMF (5 mL) and O-Benzotriazol-1-yl-N,N,N',N',-tetramethyluronium hexafluorophosphate (HBTU, 1.2 mmol) was added. The solution is then stirred for 5 minutes at room temperature. To this solution, 7-amino 4-dedimethylamino sancycline (1 mmol, 16A) was added, followed by the addition of diisopropylethyl amine (DIEA, 1.2 mmol). The reaction is then stirred at room temperature for 2 hours. The solvent, DMF, is removed on vacuum. The crude material is dissolved in 5 mL of MeOH and filtered using autovials and purified using preparative HPLC.

7-(N-Methylsulphonamidopropargylamine) 4-Dedimethylamino Sancycline

SCHEME 17

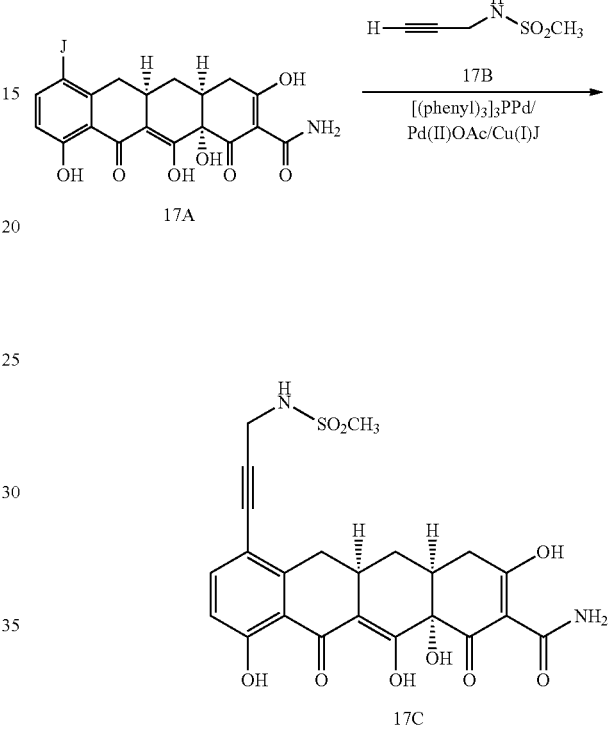

To a mixture of 7-iodo 4-dedimethylamino sancycline mono trifluoroacetic acid salt (1 g; 1.53 mmoles, 17A), palladium II acetate (17.2 mg; 0.076 mmoles), tetrakis triphenylphosphine palladium (176.8 mg; 0.153 mmoles), and copper (I) iodide (49 mg; 0.228 mmoles) is added 15 ml of reagent grade acetonitrile in a clean dry 2 necked round bottom flask. The reaction is purged with a slow steam of argon gas, with stirring, for 5 minutes before the addition (in one portion as a solid) of N-methylsulphonamidopropargyl amine (17B). The sulphonamide is prepared by a method known in the art (J. Med. Chem 31(3) 1988; 577-82). This is followed by one milliliter of triethylamine (1 ml; 0.726 mg; 7.175 mmoles) and the reaction is stirred, under an argon atmosphere, for approximately 1.0 hour at ambient temperature. The reaction mixture is suctioned filtered through a pad of diatomaceous earth and washed with acetonitrile. The filtrates are reduced to dryness under vacuo and the residue is treated with a dilute solution of trifluororoacetic acid in acetonitrile to adjust the pH to approximately 2. The residue is treated with more dilute trifluoroacetic acid in acetonitrile, resulting in the formation of a precipitate, which is removed via suction filtration. The crude filtrates are purified utilizing reverse phase HPLC with DVB as the solid phase; and a gradient of 1:1 methanol/acetonitrile 1% trifluoroacetic acid and 1% trifluoroacetic acid in water. The appropriate fractions are reduced to dryness under reduced pressure and solid collected. The product is characterized via ¹H NMR, mass spectrogram and LC reverse phase.

7-(2'-methoxy-5'-formylphenyl) 4-dedimethylamino sancycline

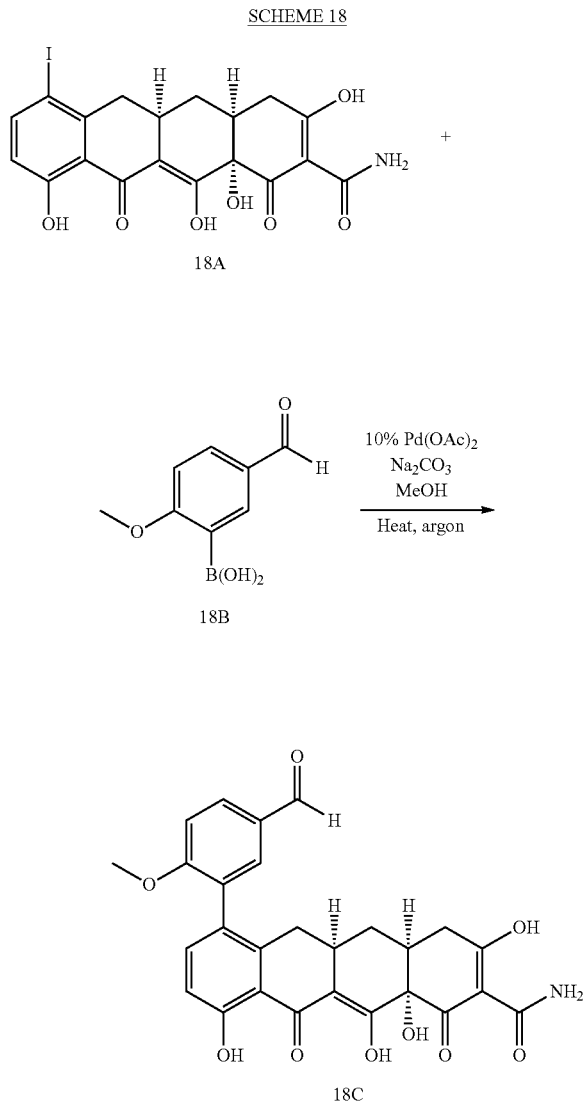

SCHEME 18

7-iodo-4-dedimethylamino sancycline (18A, 1 g, 1.53 mmol), Pd(OAc)₂ (34 mg, 0.153 mmol), and MeOH (50 mL) are combined in a 250 mL 2 neck round bottom flask equipped with a condenser and argon line. The solution is then purged with argon (15 min) while heated in an oil bath to approximately 70° C. Sodium carbonate (482 mg, 4.58 mmol) is dissolved in water (3-5 mL) and added to reaction flask. The flask is then purged with argon for another 5 minutes. 2-Methoxy-5-formylphenyl boronic acid (18B, 333 mg, 1.83 mmol) is dissolved in MeOH (5 mL) and added to reaction flask. The flask is then purged again with argon for 10 minutes. The reaction is monitored to completion within 3 hours. The contents of the flask are filtered through filter paper and the remaining solvent is evacuated. To make the hydrochloric acid salt, the residue is dissolved in MeOH (sat. HCl). The solution is then filtered and the solvent was evacuated. The product is then characterized by ¹H NMR, LC-MS.

7-(2'-Methoxy-5'-N,N'-Dimethylaminomethylphenyl) 4-Dedimethylamino Sancycline

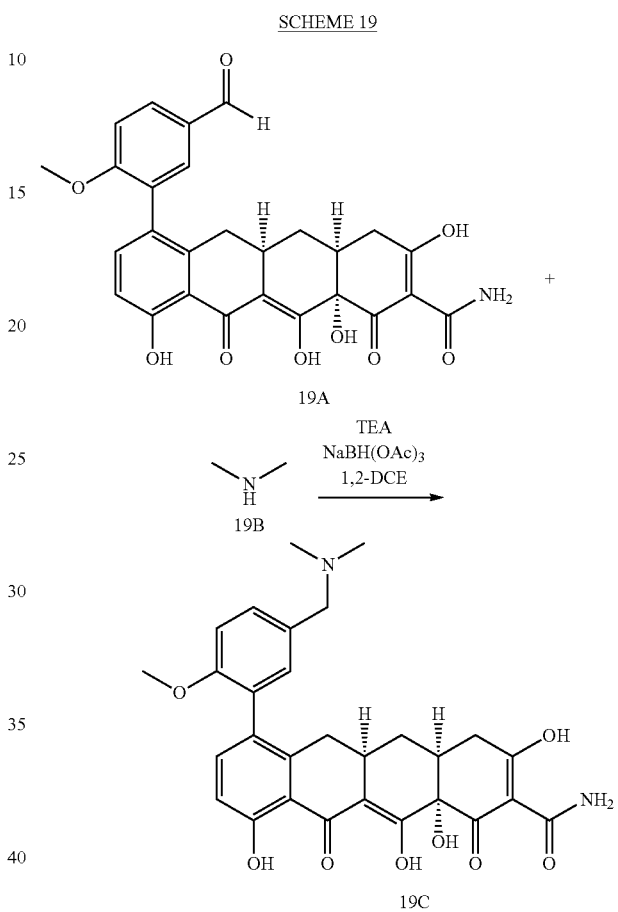

SCHEME 19

The aldehyde (19A, 1 g, 1.82 mmol), dimethylamine HCl (19B, 297 mg, 3.64 mmol), triethylamine (506 μL, 3.64 mmol), and 1,2-DCE (7 mL) are combined in a 40 mL vial. The contents are dissolved within several minutes of shaking or stirring. Sodium triacetoxyborohydride (772 mg, 3.64 mmol) is then added as a solid. The reaction is monitored by HPLC and LC-MS and is complete within 3 hours. The reaction is quenched with MeOH (20 mL) and the solvent is subsequently evacuated. The residue is redissolved in 3 mL DMF and separated on a C-18 column. Fractions from the prep column dried down in-vacuo and the HCl salt are made by dissolving contents in methanol (sat. HCl). The solvent is reduced and the product is obtained and characterized by ¹H NMR, LC-MS, HPLC.

Example 2

Synthesis of 7,9-Substituted 4-Dedimethylamino Tetracycline Compounds 7,9-Diiodo 4-dedimethylamino Sancyline 30.0 mL of concentrated sulfuric acid is added to 1.00 g of 4-dedimethylamino sancycline with stirring and the solution is then cooled to 0° C. 1.09 g of N-iodosuccinimide is added portionwise to the solution over one hour and the reaction mixture monitored by HPLC and TLC. The reaction mixture is poured into 250 mL of ice water, extracted three times with n-butanol, and the solvent is removed under reduced pressure. The crude residue is purified by preparative HPLC yielding 7-iodosancycline and 7,9-diiodosancycline.

7,9-Bis(3,4-Methylenedioxyphenyl)-Sancycline

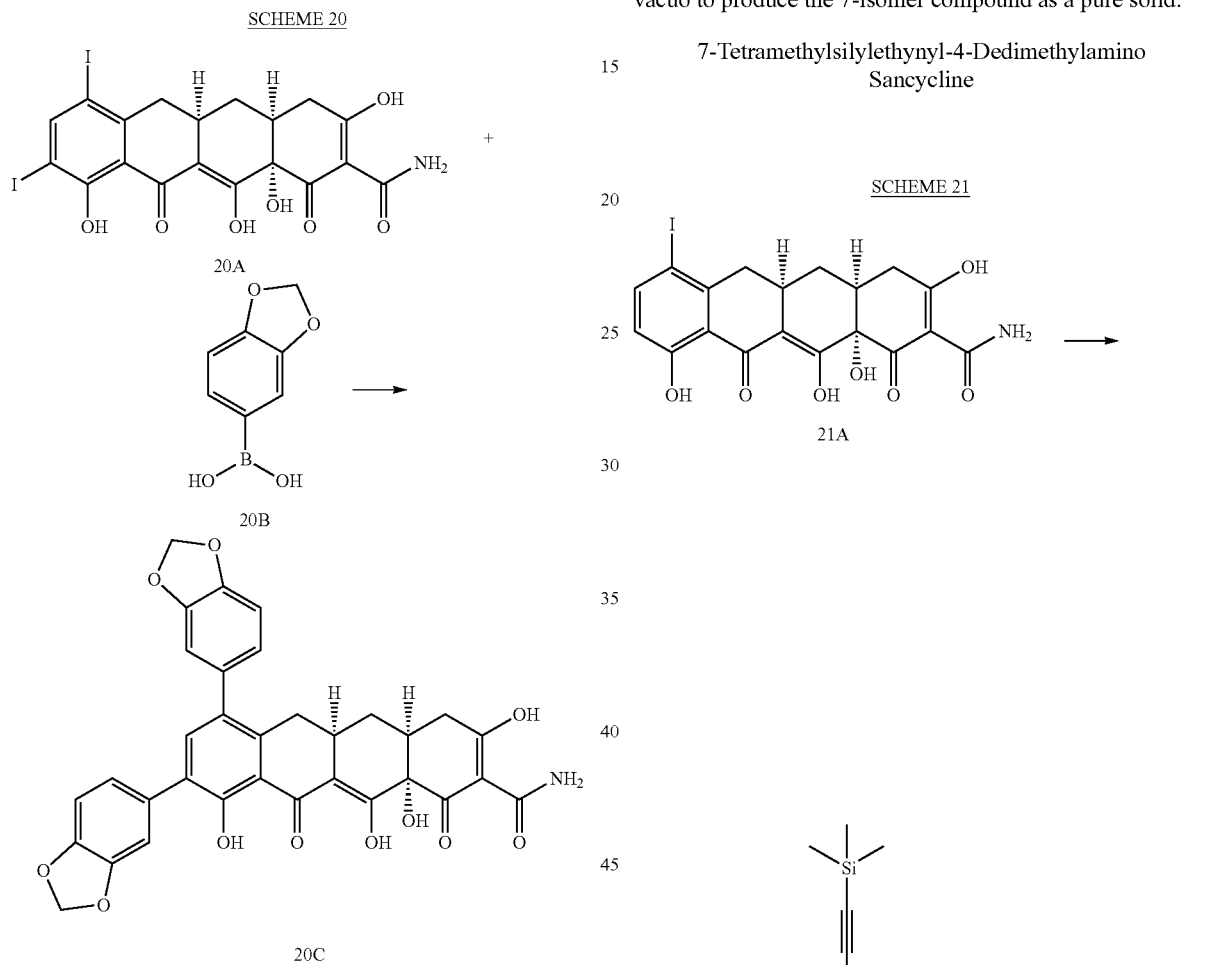

0.74 mmol of 7,9-diiodo 4-dedimethylamino sancycline (20C.) and 8.3 mg (0.37 mmol) palladium acetate are dissolved in 25 ml methanol, under a nitrogen atmosphere. The solution is warmed to 60° C. After stirring for ten minutes 234 mg (2.22 mmol), sodium carbonate is added followed by 246 mg (1.48 mmol) of 3,4-methylenedioxyphenyl boronic acid (20B). After the reaction is complete, the reaction mixture is filtered through a celite bed and concentrated under reduced pressure. This crude product is purified by preparative liquid chromatography using a $C_{18}$ stationary phase with eluent A: 0.1% TFA in water and eluent B: 0.1% TFA in acetonitrile.

7 Iodo 4-Dedimethylamino Sancycline

One gram of 4-dedimethylamino sancycline is dissolved in 25 mL of TFA (trifluoroacetic acid) that was cooled to 0 C. (on ice). 1.2 equivalents of N-iodosuccinimide (NIS) is added to the reaction mixture and reacted for forty minutes. The reaction is removed from the ice bath and is then allowed to react at room temperature for an additional five hours. The mixture is then analyzed by HPLC and TLC, driven to completion by the stepwise addition of NIS. After completion of the reaction, the TFA is removed in vacuo and 3 mL of MeOH is added to dissolve the residue. The methanolic solution is then added slowly to a rapidly stirring solution of diethyl ether to form a precipitate. The 7-iodo isomer of sancycline is purified by treating the 7-iodo product with activated charcoal, filtering through Celite, and subsequent removal of the solvent in vacuo to produce the 7-isomer compound as a pure solid.

7-Tetramethylsilylethynyl-4-Dedimethylamino Sancycline

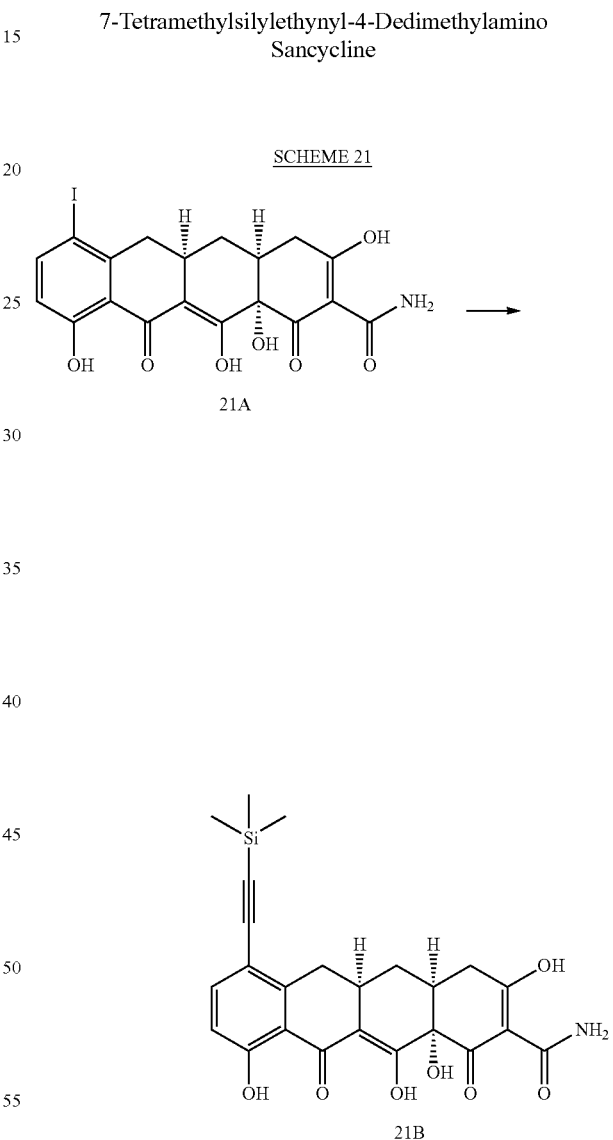

To a solution of 10 mmol of 7-iodo-4-dedimethylamino-sancycline trifluoroacetate 500 mg tetrakis-triphenylphosphino-palladate, 500 mg copper(I) iodide, 100 mg palladium acetate and 30 ml triethylamine 3 ml trimethylsilyl-acetylene is added. The reaction mixture is stirred at room temperature for two hours than filtered through a celite bed and concentrated. The dry material is picked up in methanol, and the insolubles are filtered out. The solution is then concentrated to recover the product (21B).

7-Ethynyl-4-Dedimethylamino Sancycline

SCHEME 22

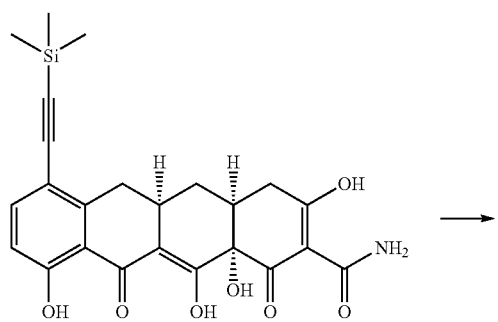

7-Tetramethylsilylethynyl-4-dedimethylamino-sancycline (21B) is dissolved in 300 ml methanol, and stirred at 40° C. with 6.8 g potassium carbonate. When no starting material is detected by HPLC (~3 hours), the reaction mixture is cooled in an ice/water bath and solids are removed by filtration. The structure of the alkyne (22B) is confirmed by LCMS. 8B is then used without further purification in the next step.

7-Ethyl-4-Dedimethylamino Sancycline

SCHEME 23

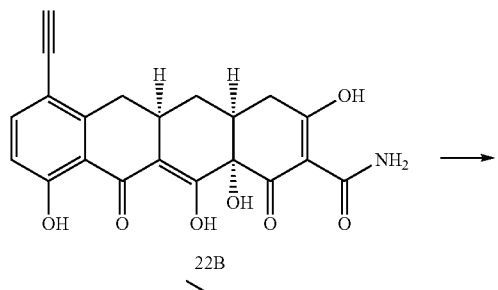

10% palladium catalyst on charcoal (1 g) is added to 7-ethynyl 4-dedimethylamino sancycline (22B) in a saturated methanol hydrochloric acid solvent. The mixture is placed in a hydrogenator under 50 psi hydrogen pressure. After the reaction is complete, the catalyst is filtered off, and the resulting solution is concentrated. The crude product is purified by preparative liquid chromatography using a $C_{18}$ stationary phase with eluent A: 0.1% TFA in water and eluent B: 0.1% TFA in acetonitrile. The combined clean fractions are concentrated and hydrochloric acid saturated isopropanol added. The pure product is precipitated by addition of diethylether and filtered off.

7-Ethyl-9-Iodo-4-Dedimethylamino Sancycline

SCHEME 24

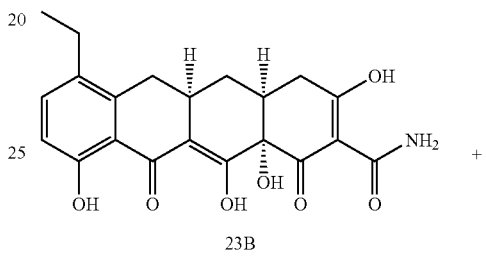

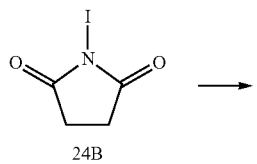

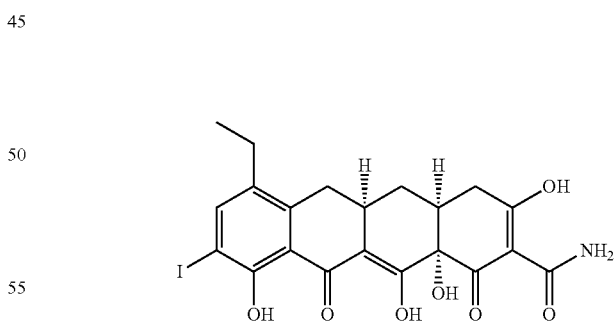

7-Ethyl-4-dedimethylamino sancycline (23B, 6.7 mmol, 3.2 g) is dissolved in 75 ml methanesulfonic acid at room temperature. N-iodo succinimide (24B, 13.5 mmol, 3.05 g) is added over two hours in 6 portions. After two hours diethyl ether is added, and the precipitate is filtered off and dried. The crude product is purified by preparative liquid chromatography using a $C_{18}$ stationary phase with eluent A: 0.1% TFA in water and eluent B: 0.1% TFA in acetonitrile.

7-Ethyl-9-Cyclohexenylethynyl-4-Dedimethylamino Sancycline

SCHEME 25

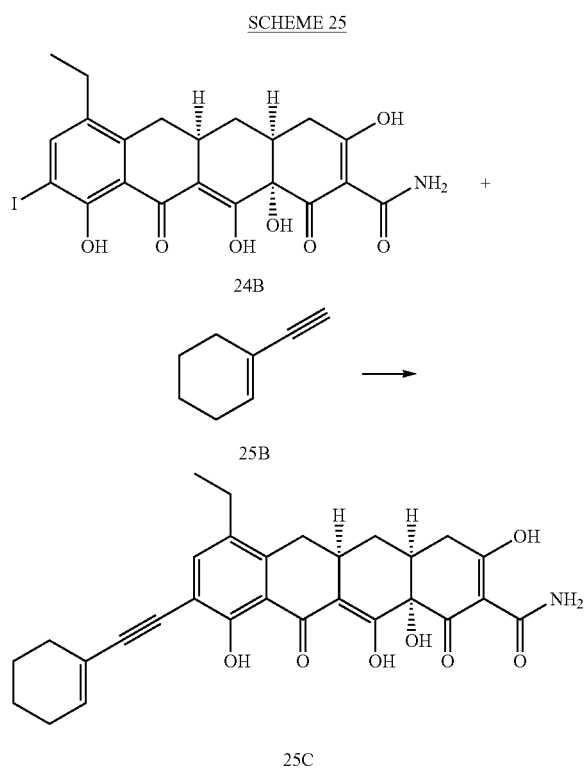

To a solution of 7-ethyl-4-dedimethylamino sancycline (1.13 mmol), 50 mg tetrakis-triphenylphosphino-palladate, 50 mg copper(I) iodide, 10 mg palladium acetate and 3 ml triethylamine 0.1 ml cyclohexenyl-acetylene was added. The reaction mixture is stirred at 60° C. for one hour, filtered through a celite bed and concentrated. The dry material is dissolved in methanol and filtered. The solution is then concentrated and purified using preparative liquid chromatography. The preparative liquid chromatography used a $C_{18}$ stationary phase with eluent A: 0.1% TFA in water and eluent B: 0.1% TFA in acetonitrile.

7-Iodo-9-t-Butyl-4-Dedimethylamino Sancycline

SCHEME 26

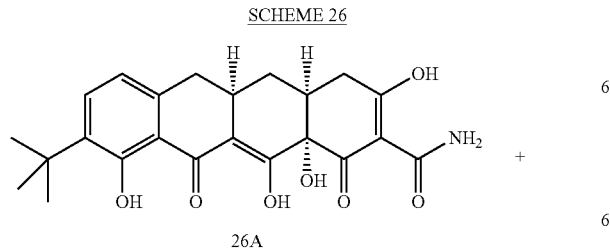

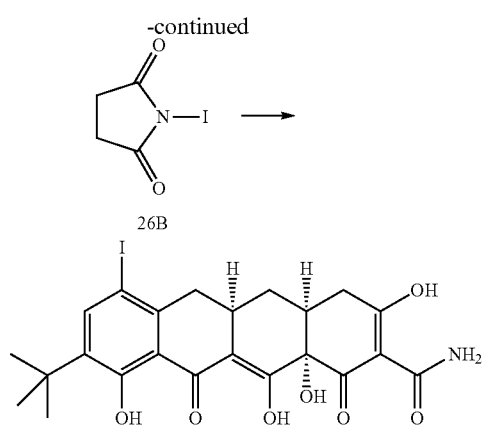

9-t-butyl-4-dedimethylamino sancycline (26A, 1.13 g, 2 mmol) is dissolved in 5 ml methanesulfonic acid (0.448, 2 mmol). N-iodosuccinimide (26B) is added at room temperature over one hour in four portions. The product (26C) is precipitated with diethyl ether, filtered off and used in other reaction without further purification.

7-(2-Methoxy-5-Dimethylaminomethylphenyl)-9-t-Butyl-4-Dedimethylamino Sancycline

SCHEME 27

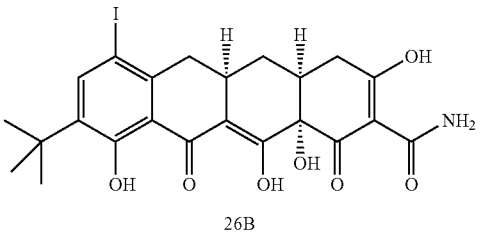

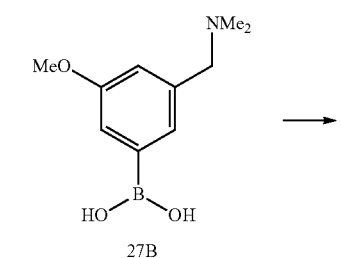

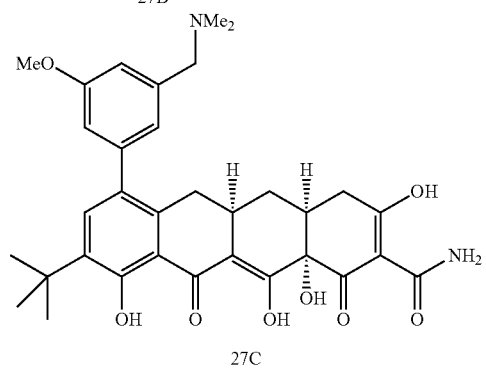

7-Iodo-9-t-butyl-4-dedimethylamino sancycline (26B, 710 mg, 1.0 mmol) and palladium acetate (22.4 mg, 0.1 mmol) are dissolved in 25 ml of methanol under a nitrogen atmosphere. Cesium carbonate (3.25 g, 10 mmol) and 2-methoxy-5-dimethylaminomethylphenyl-boronic acid (27B, 0.435 g, 0.15 mmol) are added. The reaction mixture is stirred at 60° C. for two hours and then filtered through a celite bed and concentrated under reduced pressure. The crude product is purified by preparative liquid chromatography using a $C_{18}$ stationary phase with eluent A: 0.1% TFA in water and eluent B: 0.1% TFA in acetonitrile.

Example 3

Preparation of 9-Substituted 4-Dedimethylamino Tetracycline Compounds

Preparation of 9-Iodo 4-dedimethylamino Minocycline

To 200 ml of 97% methanesulfonic acid is slowly added, at ambient temperature, portionwise [56.56 mM] of 4-dedimethylamino minocycline-hydrochloride salt. The dark solution is then stirred at ambient temperature while [38 g; 169.7 mM] of N-iodosuccinimide is added, in six equal portions, over 3.0 hours time. The reaction is monitored via analytical LC, noting the disappearance of the starting material. The reaction is slowly quenched into 2 L of ice cold water containing [17.88 g; 1134.1 mM] of sodium thiosulfate with rapid stirring. This quench is stirred for approximately 30 minutes at ambient temperature. The aqueous layer is then extracted with 6×200 ml of ethyl acetate before the aqueous was poured onto [259.8 g; 3.08M] of sodium hydrogen carbonate containing 300 ml of n-butanol. The phases are split and the aqueous extracted with 4×250 ml of n-butanol. The organic fractions are combined and washed with 3×250 ml of water and once with 250 ml of saturated brine. The resulting organic phase is reduced to dryness under reduced pressure. The residue is suspended in methanol (~600 ml) and anhydrous HCl gas is bubbled into this mixture until solution occurred This solution is reduced to dryness under reduced pressure. The filtrates are reduced to dryness under reduced pressure. The resulting material is triturated with 300 ml of methyl t-butyl ether and isolated via filtration. This material is redissolved in 300 ml of methanol and treated with 0.5 g of wood carbon, filtered and filtrates reduced to dryness under reduced pressure. The material is again powdered under methyl t-butyl ether, isolated via suction filtration and washed with more ether, and finally hexanes. The material is vacuum dried to give the product.

General Procedure For Preparation of 9-Alkynyl 4-Dedimethylamino Minocycline Compounds 1 mmol 9-iodo 4-dedimethylamino minocycline, 50 mg tetrakis tripenylphosphinato palladate, 12 mg palladium acetate, 32 mg copper (I) iodide are dissolved/suspended in 10 ml acetonitrile. 2 to 5 ml triethylamine and 3 to 5 mmol alkynyl 4-dedimethylamino minocycline derivative is added. The reaction mixture is vigorously stirred between ambient temperature to 70° C. The reaction time is 2-24 hours. When the reaction is completed the dark suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

General Procedure For Preparation of 9-Aryl 4-Dedimethylamino Minocycline Compounds 0.15 mmol of 9-iodo 4-dedimethylamino minocycline, PdOAc (3.2 mg), 229 µl 2M $Na_2CO_3$ and 2 equivalents of phenyl boronic acid are dissolved/suspended in 10 ml methanol. The reaction flask is purged with argon and the reaction is run for a minimum of four hours or until HPLC monitoring shows consumption of starting material and/or the appearance of products. The suspension is filtered through celite, and subject to purification by prep HPLC on a divinylbenzene column.

9-(4-Trifluoromethoxyphenylureido)-Methyl Minocycline

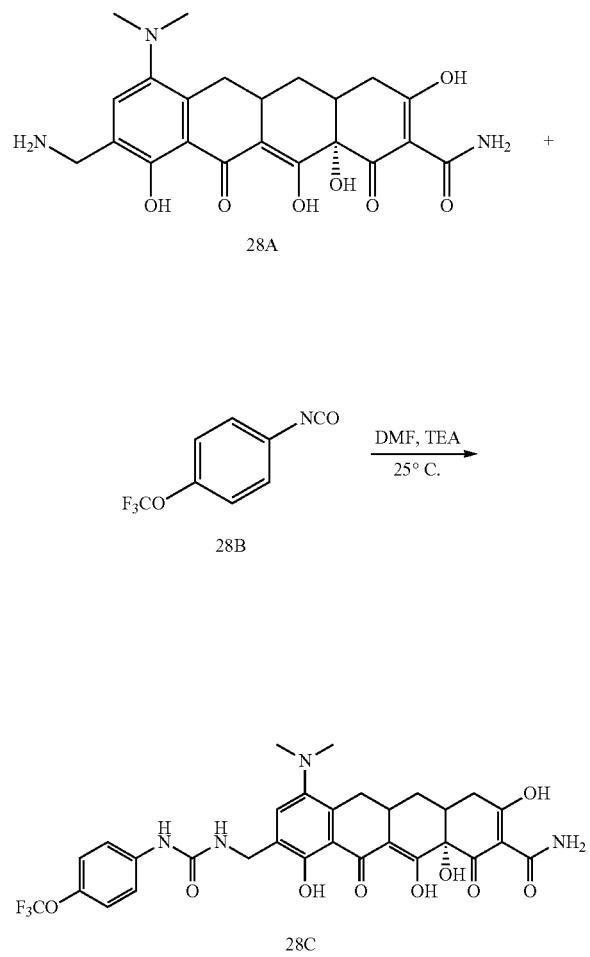

To 3 mL of dimethylformamide is added 150 mg (0.25 mmol) of 9-methyl amino 4-dedimethylamino minocyline trihydrochloride and 67 mL (0.50 mmol) of triethylamine at 25° C. With stirring, 75 mL (0.50 mmol) of 4-trifluoromethoxyphenylisocyanate is added and the resulting reaction mixture is stirred at 25° C. for two hours. The reaction is monitored by analytical HPLC (4.6×50 mm reversed phase Luna C18 column, 5 minute linear gradient 1-100% B buffer, A buffer is water with 0.1% trifluoroacetic acid, B buffer is acetonitrile with 0.1% trifluoroacetic acid). Upon completion, the reaction is quenched with 1 mL of water and the pH

9-(4'Carboxy phenyl) 4-Dedimethylamino Minocycline

SCHEME 29

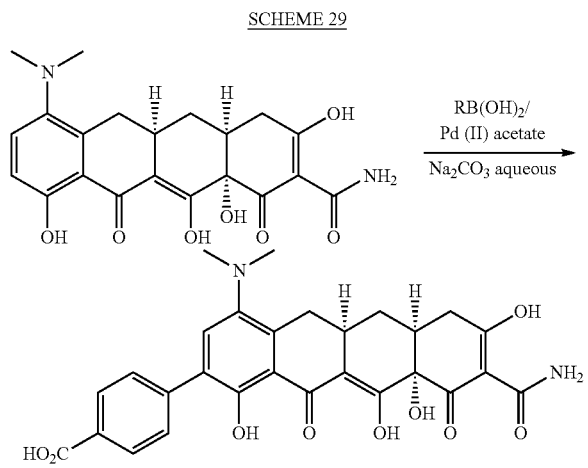

In a clean, dry reaction vessel, is placed 9-iodo 4-dedimethylamino minocycline [0.762 mmoles]bis HCl salt, palladium (II) acetate [17.2 mg; 0.076 mmoles] along with 10 ml of reagent grade methanol. The solution is immediately purged, with stirring, with a stream of argon gas for approximately 5 minutes. The reaction vessel is brought to reflux and to it is sequentially added via syringe 2M potassium carbonate solution [1.91 ml; 3.81 mmoles], followed by a solution of p-carboxyphenyl boronic acid [238.3 mg; 1.53 mmoles] in 5 ml of reagent DMF. Both of these solutions are previously degassed with argon gas for approximately 5 minutes. The reaction is heated for 45 minutes, the progress is monitored via reverse phase HPLC. The reaction is suctioned filtered through a pad of diatomaceous earth and the pad is washed with DMF. The filtrates are reduced to an oil under vacuum and residue is treated with t-butylmethyl ether. Crude material is purified via reverse phase HPLC on DVB utilizing a gradient of water and methanol/acetonitrile containing 1.0% trifluoroacetic acid.

Example 4

Synthesis of 13-Substituted 4-Dedimethylamino Methacycline Compounds

General Procedure for Phenyl Boronic Acid Derivitization of 4-Dedimethylamino Methacycline 4-Dedimethylamino methacycline (1 equiv.), $PdCl_2$ (0.14 equiv.), and $CuCl_2$ (0.90 equiv.) are dissolved in 20 ml of MeOH and heated under nitrogen atmosphere. After 1 hour, the boronic acid (2 equiv.) is added and the reaction mixture is heated for another 6-10 hours. The reactions are monitored by TLC or analytical HPLC. The reaction mixture is then cooled to room temperature and passed through a bed of celite. Evaporation of the solvent generally gives a yellow-brown solid, which is purified using preparative HPLC ($CH_3CN$:MeOH:$H_2O$). The solvent is then evaporated from the product giving a yellow solid, which is then dissolved in MeOH and purged with HCl gas. After evaporation of MeOH, the yellow material is dried under vacuum for several hours.

Synthesis of 5-propionyl-13-(4'-chlorophenyl) 4-dedimethylamino Methacycline 500 mg of 13-(4'-Cl phenyl) 4-dedimethylamino methacycline is dissolved in 20 ml of anhydrous HF. 3 ml of propionic acid is added and the reaction left for 2 days at room temperature. The HF is removed under a steady stream of $N_2$, and the residue is triturated with $Et_2O$ to yield a dark yellow solid. The solid is dissolved in MeOH, and chromatographed on a divinyl benzene resin using an acetonitrile gradient from 30% to 100% with a primary solvent system of 0.1% formic acid. The corresponding fractions are collected and dried in vacuo to yield the product. The yellow solid is dissolved in MeOH and HCl gas is bubbled in to produce the product as a yellow solid HCl salt.

Synthesis of 9,13-di-t-butyl 4-Dedimethylamino Methacycline 1.0 g of 4-dedimethylamino methacycline is added to 15 ml of concentrated $H_2SO_4$. 5 ml of isobutylene or t-butanol is added and the reaction is stirred for 6 hours at room temperature. The reaction is neutralized with $Na_2CO_3$ (8 grams) and 40 ml of water, and the aqueous layer is extracted 3× with 100 ml of N-butanol. The extracts are combined and dried to yield 69% of product as a light yellow solid. An analytical sample is obtained by the chromatography on divinyl benzene using a gradient of acetonitrile from 30-100% over 30 minutes against a primary solvent of 0.1% formic acid.

Example 5

Synthesis of 8-Substituted 4-Dedimethylamino Tetracycline Compounds

9-$NO_2$ 4-Dedimethylamino Doxycycline 1.0 g of 4-dedimethylamino doxycycline HCl is dissolved in concentrated $H_2SO_4$ (5 ml) and $NaNO_3$ (1.1 eq) is added over 1 minute. The reaction is stirred for 1 hour and subsequently dripped into cold, rapidly stirred ether (500 ml). The precipitate is washed with ether and dried in vacuum to yield 9-$NO_2$ 4-dedimethylamino doxycycline without further purification.

9-$NH_2$ 4-Dedimethylamino Doxycycline

9-$NO_2$ 4-dedimethylamino doxycycline (1 g) is dissolved in methanol (50 ml) and poured into a Parr apparatus with 100 mg of 10% Pd/C. The reaction is charged with $H_2$ and shaken for 2 hours. The 9-amino 4-dedimethylamino doxycycline is separated by preparative apic purification to produce 9-$NH_2$ 4-dedimethylamino doxycycline and 7-$NH_2$ 4-dedimethylamino doxycycline.

9-$N_2$ 4-Dedimethylamino Doxycycline

9-$NH_2$ 4-dedimethylamino doxycycline (1.5 g) is dissolved in 50 ml of 0.1N methanol HCl and 2.2 ml of butyl nitrate is subsequently added. The reaction is stirred for 1 hour, then the product is precipitated in 400 mL of dry ether to produce the 9-diazonium salt of 4-dedimethylamino doxycycline

9-Azido 4-Dedimethylamino Doxycycline

Sodium azide (0.126 g) is added to a warm 0.1 N methanol/HCl solution of the 9-diazonium salt (1 g). The mixture is then stirred at room temperature for 4 hours and the product is obtained by precipitation into diethyl ether.

9-NH$_2$-8-Bromo 4-Dedimethylamino Doxycycline 0.5 g of 9-azido 4-dedimethylamino doxycycline is added to 10 mL of HBr in acetic acid (30 wt %) and the reaction is stirred at room temperature for 1 hour. The product is obtained by preparative C18 HPLC.

8-Bromo 4-Dedimethylamino Doxycycline 100 mg of 9-amino-8-bromo 4-dedimethylamino doxycycline is reacted with 1.1 g of butyl nitrate in 0.1N HCl to produce the 9-diazonium salt of the 8-bromo 4-dedimethylamino doxycycline. The reaction is treated with phosphoric acid to yield the product as crude solid. Preparative HPLC is used to purify the product.

8-Phenyl-4-Dedimethylamino Doxycycline 8-bromo 4-dedimethylamino doxycycline, 150 mg, Pd(OAc)$_2$ and 10 mL of MeOH are added to a flask with a stir bar and the system degassed three times using argon. Na$_2$CO$_3$ (87 mg, 0.8 mM) dissolved in water and argon degassed is added via syringe and is added along with phenylboronic acid (68 mg, 0.55 mM) in MeOH that was also degassed. The reaction is followed by HPLC for 2 hours and then the reaction mixture is cooled to room temperature. The solution is filtered, and dried to produce a crude mixture. The solid is dissolved in dimethylformamide and injected onto a preparative HPLC system using C18 reverse-phase silica. The product fraction is isolated, and the solvent is removed in vacuo to yield the product.

8-Ethynyl-4-Dedimethylamino Doxycycline 1 mmol 8-bromo 4-dedimethylamino doxycycline, 50 mg tetrakis tripenylphosphinato palladate, 12 mg palladium acetate, 32 mg copper (I) iodide are dissolved/suspended in 10 ml acetonitrile. 2 to 5 ml triethylamine and 3 to 5 mmol ethyne is added. The reaction mixture is vigorously stirred between ambient temperature to 70° C. The reaction time is 2-24 hours. When the reaction is completed the suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

8-Ethenyl-4-Dedimethylamino Doxycycline 1 mmol 8-bromo 4-dedimethylamino doxycycline, 50 mg tetrakis tripenylphosphinato palladate, 12 mg palladium acetate, 32 mg copper (I) iodide are dissolved/suspended in 10 ml acetonitrile. 2 to 5 ml triethylamine and 3 to 5 mmol ethene is added. The reaction mixture is vigorously stirred between ambient temperature to 70° C. The reaction time is 2-24 hours. When the reaction is completed the suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

Example 6

In Vitro Minimum Inhibitory Concentration (MIC) Assay

The following assay is used to determine the efficacy of the tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of 1×10$^6$ CFU/ml. At OD=1, cell densities for different genera should be approximately:

| | |
|---|---|
| E. coli | 1 × 10$^9$ CFU/ml |
| S. aureus | 5 × 10$^8$ CFU/ml |
| Enterococcus sp. | 2.5 × 10$^9$ CFU/ml |

50 µl of the cell suspensions are added to each well of microtiter plates. The final cell density should be approximately 5×10$^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

This application is related to U.S. patent application Ser. No. 09/895,812, entitled "7-Substituted Tetracycline Compounds," filed Jun. 29, 2001; U.S. Provisional Patent Application Ser. No. 60/275,576, entitled "7-Substituted Tetracycline Compounds" filed Mar. 13, 2001, and U.S. Provisional Patent Application Ser. No. 60/216,760, entitled "7-Substituted Sancycline Compounds" filed on Jul. 7, 2000; the entire contents of each of these applications are hereby incorporated herein by reference.

This application is also related to U.S. patent application Ser. No. 09/895,797, entitled "7,9-Substituted Tetracycline Compounds," filed on Jun. 29, 2001; and U.S. Provisional Patent Application Ser. No. 60/275,620, entitled "7,9-Substituted Tetracycline Compounds," filed on Mar. 13, 2001. The entire contents of each of these applications are hereby incorporated herein by reference.

This application is also related to U.S. patent application Ser. No. 09/895,857, entitled "9-Substituted Minocycline Compounds," filed on Jun. 29, 2001; U.S. Provisional Patent Application Ser. No. 60/275,621, entitled "9-Substituted Minocycline Compounds," filed on Mar. 13, 2001, and U.S.

Provisional Patent Application Ser. No. 60/216,659, entitled "9-Substituted Minocycline Compounds," filed on Jul. 7, 2000, the entire contents of each of which are incorporated herein by reference.

This application is also related to U.S. patent application Ser. No. 09/895,796, filed on Jun. 29, 2001; U.S. Provisional Application Ser. No. 60/216,580, filed on Jul. 7, 2000; U.S. Provisional Application No. 60/154,701, filed on Sep. 14, 1999; U.S. Provisional Application No. 60/193,972, filed on Mar. 31, 2000; U.S. Provisional Application No. 60/193,879, filed on Mar. 31, 2000; U.S. Provisional Application No. 60/204,158, filed on May 15, 2000; U.S. Provisional Application No. 60/212,030, filed Jun. 16, 2000; and U.S. Provisional Application No. 60/212,471, filed Jun. 16, 2000, the entire contents of each of these applications are hereby incorporated herein by reference.

This application is related to U.S. patent application Ser. No. 09/894,805, entitled "7, 8, and 9 Substituted Tetracycline Compounds," filed on Jun. 29, 2001; U.S. Provisional Patent Application Ser. No. 60/216,656, entitled "7, 8 and 9-Substituted Tetracycline Compounds," filed on Jul. 7, 2000; and International Patent Application Serial No.: PCT/US00/21366, entitled, "8-Substituted Tetracycline Compounds," filed on Aug. 4, 2000. The application is also related to U.S. Ser. No. 60/395,696, filed Jul. 12, 2002. The entire contents of each of these applications are hereby incorporated herein by reference.

The invention claimed is:

1. A method for ameliorating rheumatoid arthritis in a subject in need thereof, the method comprising administering to said subject an effective amount of a tetracycline compound of the following structural formula:

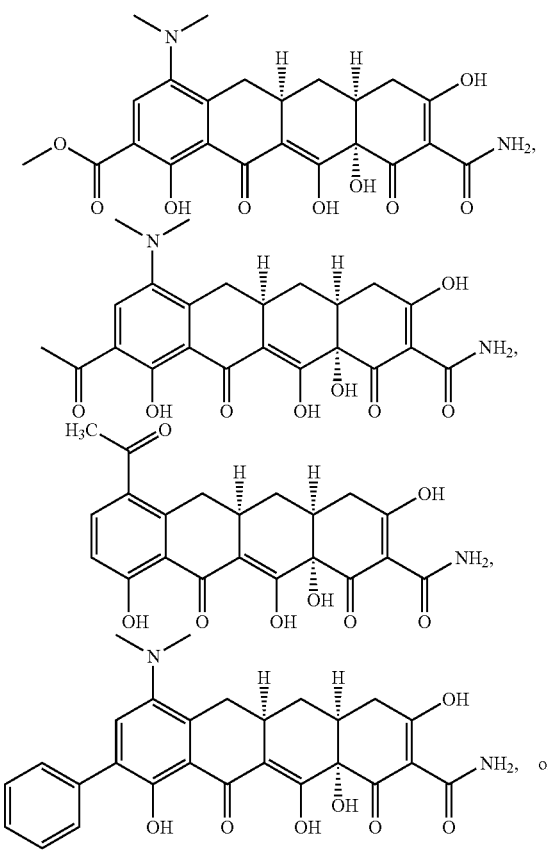

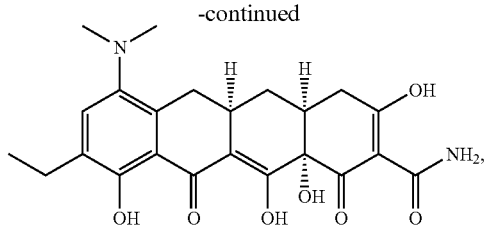

or a pharmaceutically acceptable salt thereof, such that said rheumatoid arthritis in said subject is ameliorated.

2. The method of claim 1, wherein said subject is a human.

3. The method of claim 1, wherein said tetracycline compound is of the following structural formula:

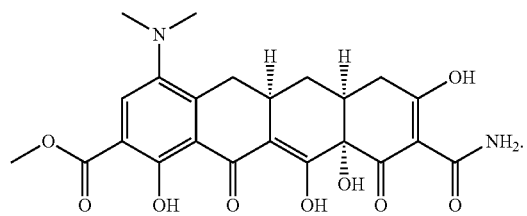 [SMILES: COC(=O)c1cc(N(C)C)c2c(c1O)C(=O)C1=C(O)[C@]3(O)C(=O)C(C(N)=O)=C(O)C[C@@H]3C[C@@H]1C2]

4. The method of claim 1, wherein said tetracycline compound is of the following structural formula:

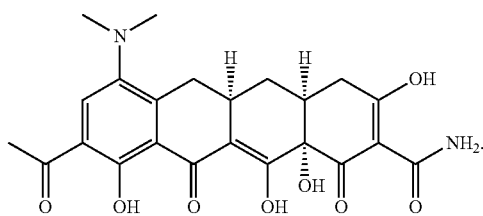 [SMILES: CC(=O)c1cc(N(C)C)c2c(c1O)C(=O)C1=C(O)[C@]3(O)C(=O)C(C(N)=O)=C(O)C[C@@H]3C[C@@H]1C2]

5. The method of claim 1, wherein said tetracycline compound is of the following structural formula:

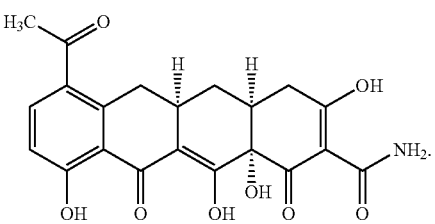 [SMILES: CC(=O)c1ccc(O)c2c1C[C@H]1C[C@H]3CC(O)=C(C(N)=O)C(=O)[C@@]3(O)C(O)=C1C2=O]

6. The method of claim 1, wherein said tetracycline compound is of the following structural formula:

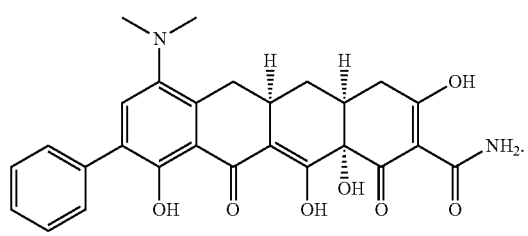 [SMILES: CN(C)c1cc(-c2ccccc2)c(O)c2c1C[C@H]1C[C@H]3CC(O)=C(C(N)=O)C(=O)[C@@]3(O)C(O)=C1C2=O]

7. The method of claim 1, wherein said tetracycline compound is of the following structural formula:

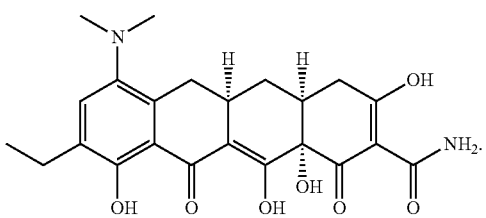 [SMILES: CCc1cc(N(C)C)c2c(c1O)C(=O)C1=C(O)[C@]3(O)C(=O)C(C(N)=O)=C(O)C[C@@H]3C[C@@H]1C2]

8. A method for ameliorating rheumatoid arthritis in a subject in need thereof, the method comprising administering to said subject an effective amount of a pharmaceutical composition comprising a tetracycline compound of the following structural formula:

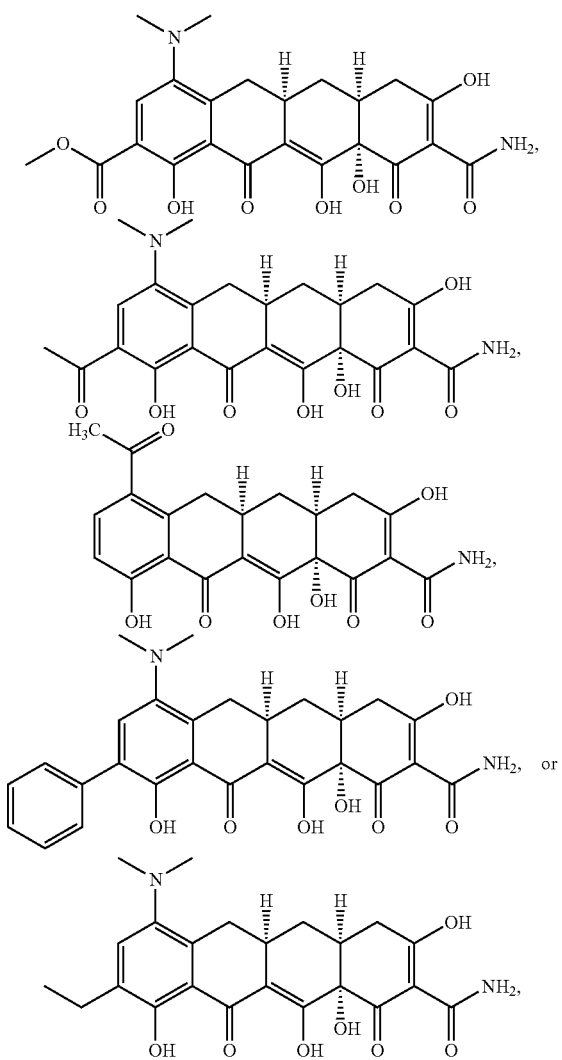

or a pharmaceutically acceptable salt thereof, and a pharmaceutically acceptable carrier, such that said rheumatoid arthritis in said subject is ameliorated.

9. The method of claim 8, wherein said subject is a human.

10. The method of claim 8, wherein said tetracycline compound is of the following structural formula:

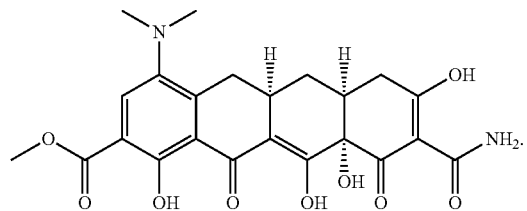 [SMILES: COC(=O)c1cc(N(C)C)c2c(c1O)C(=O)C1=C(O)[C@]3(O)C(=O)C(C(N)=O)=C(O)C[C@@H]3C[C@@H]1C2]

11. The method of claim 8, wherein said tetracycline compound is of the following structural formula:

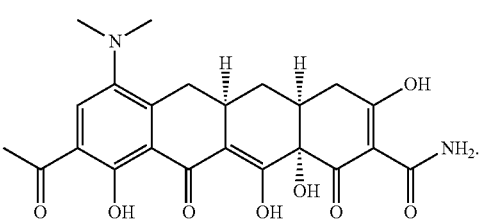 [SMILES: CC(=O)c1cc(N(C)C)c2c(c1O)C(=O)C1=C(O)[C@]3(O)C(=O)C(C(N)=O)=C(O)C[C@@H]3C[C@@H]1C2]

12. The method of claim 8, wherein said tetracycline compound is of the following structural formula:

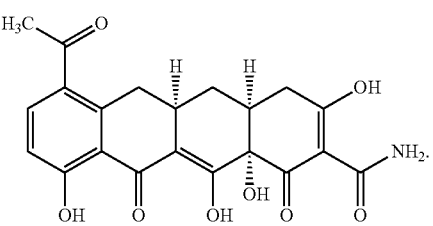 [SMILES: CC(=O)c1ccc(O)c2c1C[C@H]1C[C@H]3CC(O)=C(C(N)=O)C(=O)[C@@]3(O)C(O)=C1C2=O]

13. The method of claim 8, wherein said tetracycline compound is of the following structural formula:

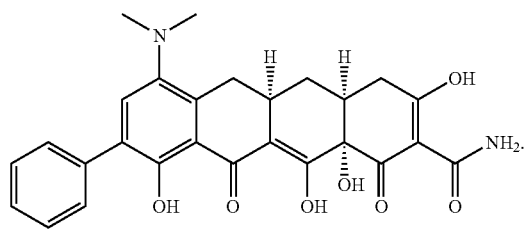 [SMILES: CN(C)c1cc(-c2ccccc2)c(O)c2c1C[C@H]1C[C@H]3CC(O)=C(C(N)=O)C(=O)[C@@]3(O)C(O)=C1C2=O]

14. The method of claim 8, wherein said tetracycline compound is of the following structural formula:

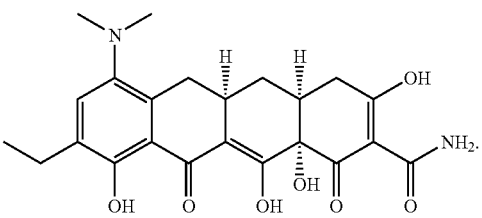 [SMILES: CCc1cc(N(C)C)c2c(c1O)C(=O)C1=C(O)[C@]3(O)C(=O)C(C(N)=O)=C(O)C[C@@H]3C[C@@H]1C2]

* * * * *